(12) United States Patent
Claremon et al.

(10) Patent No.: US 8,569,292 B2
(45) Date of Patent: Oct. 29, 2013

(54) CYCLIC INHIBITORS OF 11β-HYDROXYSTEROID DEHYDROGENASE 1

(75) Inventors: David A. Claremon, Maple Glen, PA (US); Linghang Zhuang, Chalfont, PA (US); Katerina Leftheris, San Diego, CA (US); Colin M. Tice, Ambler, PA (US); Zhenrong Xu, Horsham, PA (US); Yuanjie Ye, Ambler, PA (US); Suresh B. Singh, Kendall Park, NJ (US); Salvacion Cacatian, Blue Bell, PA (US); Frank Himmelsbach, Mittelbiberach (DE); Matthias Eckhardt, Ingelheim am Rhein (DE); Wei Zhao, Eagleville, PA (US)

(73) Assignees: Vitae Pharmaceuticals, Inc., Fort Washington, PA (US); Boehringer Ingelheim International GmbH, Ingelheim am Rhein (DE)

( * ) Notice: Subject to any disclaimer, the term of this patent is extended or adjusted under 35 U.S.C. 154(b) by 33 days.

(21) Appl. No.: 12/990,306

(22) PCT Filed: Apr. 30, 2009

(86) PCT No.: PCT/US2009/002641
§ 371 (c)(1),
(2), (4) Date: Jun. 6, 2011

(87) PCT Pub. No.: WO2009/134392
PCT Pub. Date: Nov. 5, 2009

(65) Prior Publication Data
US 2011/0263584 A1    Oct. 27, 2011

Related U.S. Application Data

(60) Provisional application No. 61/049,650, filed on May 1, 2008, provisional application No. 61/137,148, filed on Jul. 25, 2008, provisional application No. 61/206,775, filed on Feb. 4, 2009.

(30) Foreign Application Priority Data

Jul. 25, 2008  (WO) ................ PCT/US2008/009017

(51) Int. Cl.
C07D 413/10  (2006.01)
C07D 413/14  (2006.01)
A61K 31/5355  (2006.01)
(52) U.S. Cl.
USPC ........................................ 514/228.8; 544/96
(58) Field of Classification Search
USPC ........................................ 544/96; 514/228.8
See application file for complete search history.

(56) References Cited

U.S. PATENT DOCUMENTS

| | | |
|---|---|---|
| 3,341,538 A | 9/1967 | Block et al. |
| 3,378,587 A | 4/1968 | Reinhardt |
| 3,681,349 A | 8/1972 | Schwan et al. |
| 3,703,529 A | 11/1972 | Frederick et al. |
| 3,919,047 A | 11/1975 | Vidic et al. |
| 4,009,171 A | 2/1977 | Albertson |
| 4,043,927 A | 8/1977 | Duling et al. |
| 4,108,857 A | 8/1978 | Albertson |
| 4,136,145 A | 1/1979 | Fuchs et al. |
| 4,136,162 A | 1/1979 | Fuchs et al. |
| 5,089,506 A | 2/1992 | Gray et al. |
| 5,098,916 A | 3/1992 | Gray et al. |
| 5,215,992 A | 6/1993 | Gray et al. |
| 5,393,735 A | 2/1995 | Lange et al. |
| 5,410,081 A | 4/1995 | Kunde et al. |
| 5,432,175 A | 7/1995 | Piwinski et al. |
| 5,480,899 A | 1/1996 | Yano et al. |
| 5,502,027 A | 3/1996 | Lange et al. |
| 5,631,209 A | 5/1997 | Lange et al. |
| 5,776,959 A | 7/1998 | Covey et al. |
| 5,780,466 A | 7/1998 | Emonds-Alt et al. |
| 5,811,422 A | 9/1998 | Lam et al. |
| 5,856,273 A | 1/1999 | Kay et al. |
| 5,866,702 A | 2/1999 | Mackman et al. |
| 5,936,124 A | 8/1999 | Hilborn et al. |
| 5,981,436 A | 11/1999 | Drewes et al. |
| 6,066,666 A | 5/2000 | Covey et al. |
| 6,159,990 A | 12/2000 | Lagu et al. |

(Continued)

FOREIGN PATENT DOCUMENTS

DE    1801556 A1    5/1970
DE    2 105 743 A1   8/1972

(Continued)

OTHER PUBLICATIONS

Office Action for U.S. Appl. No. 12/741,532, date of mailing Dec. 15, 2010.
Office Action for U.S. Appl. No. 12/771,499, date of mailing Dec. 21, 2010.
CA 154 : 284276, dated Aug. 10, 2009.
CA 1267843-31-1, dated Aug. 10, 2009.
Sullivan, John M. and Efner, Howard F., "The Preparation of 6-Aryltetrahydro-1,3-oxazin-2-ones and Their Hydrolysis to 3-Substituted Propylamines," *The Journal of Organic Chemistry*, 33 (5): 2134-2136 (1968).

(Continued)

*Primary Examiner* — Kahsay Habte
(74) *Attorney, Agent, or Firm* — McCarter & English LLP; Steven G. Davis; Michael J. DeGrazia

(57) ABSTRACT

This invention relates to novel compounds of the Formula I, Ik, $Iq^{1-21}$, $Ir^{1-21}$, $Is^{1-21}$, $It^{1-7}$, pharmaceutically acceptable salts thereof, and pharmaceutical compositions thereof, which are useful for the therapeutic treatment of diseases associated with the modulation or inhibition of 11 β-HSD1 in mammals. The invention further relates to pharmaceutical compositions of the novel compounds and methods for their use in the reduction or control of the production of cortisol in a cell or the inhibition of the conversion of cortisone to cortisol in a cell.

7 Claims, No Drawings

(56) References Cited

U.S. PATENT DOCUMENTS

| | | |
|---|---|---|
| 6,242,637 B1 | 6/2001 | Emonds-Alt et al. |
| 6,251,897 B1 | 6/2001 | Ina et al. |
| 6,368,816 B2 | 4/2002 | Walker et al. |
| 6,559,163 B2 | 5/2003 | Cai et al. |
| 6,620,815 B1 | 9/2003 | Lagu et al. |
| 6,635,630 B2 | 10/2003 | Shih et al. |
| 6,638,935 B2 | 10/2003 | Emig et al. |
| 6,653,315 B2 | 11/2003 | Tulshian et al. |
| 6,706,722 B2 | 3/2004 | Emig et al. |
| 6,794,390 B2 | 9/2004 | Lum et al. |
| 6,838,253 B2 | 1/2005 | Walker et al. |
| 6,841,671 B2 | 1/2005 | Noe et al. |
| 6,890,926 B2 | 5/2005 | Emig et al. |
| 6,900,201 B2 | 5/2005 | Noe et al. |
| 6,916,807 B2 | 7/2005 | Freeman-Cook et al. |
| 6,936,615 B2 | 8/2005 | Emig et al. |
| 6,946,487 B2 | 9/2005 | Walker et al. |
| 7,026,310 B2 | 4/2006 | Emig et al. |
| 7,056,912 B2 | 6/2006 | Emig et al. |
| 7,087,400 B2 | 8/2006 | Walker et al. |
| 7,122,531 B2 | 10/2006 | Walker et al. |
| 7,122,532 B2 | 10/2006 | Walker et al. |
| 7,129,231 B2 | 10/2006 | Walker et al. |
| 7,132,551 B2 | 11/2006 | Aquila et al. |
| 7,186,844 B2 | 3/2007 | Ikemoto |
| 7,208,487 B2 | 4/2007 | Bergnes et al. |
| 7,253,198 B2 | 8/2007 | Demont et al. |
| 7,256,005 B2 | 8/2007 | Zitzmann et al. |
| 7,262,212 B2 | 8/2007 | Tsubouchi et al. |
| 7,294,637 B2 | 11/2007 | Aquila et al. |
| 7,417,045 B2 | 8/2008 | Anilkumar et al. |
| 7,566,718 B2 | 7/2009 | Wong et al. |
| 7,652,049 B2 | 1/2010 | Ali et al. |
| 7,897,773 B2 | 3/2011 | Aletru et al. |
| 8,114,868 B2 | 2/2012 | Himmelsbach |
| 8,138,178 B2 | 3/2012 | Claremon et al. |
| 2001/0039286 A1 | 11/2001 | Dinnell et al. |
| 2006/0063819 A1 | 3/2006 | Lanter et al. |
| 2006/0089349 A1 | 4/2006 | Gundertofte et al. |
| 2006/0116382 A1 | 6/2006 | Yao et al. |
| 2006/0194780 A1 | 8/2006 | Nargund et al. |
| 2006/0276457 A1 | 12/2006 | Yu et al. |
| 2006/0276479 A1 | 12/2006 | Kim et al. |
| 2006/0276480 A1 | 12/2006 | Wong et al. |
| 2007/0021611 A1 | 1/2007 | McGuinness et al. |
| 2007/0054919 A1 | 3/2007 | Rosenblum et al. |
| 2007/0082913 A1 | 4/2007 | Kim et al. |
| 2007/0129345 A1 | 6/2007 | Zhuo et al. |
| 2007/0208001 A1 | 9/2007 | Zhuo et al. |
| 2007/0219182 A1 | 9/2007 | Lubisch et al. |
| 2007/0254875 A1 | 11/2007 | Zhi et al. |
| 2007/0254901 A1 | 11/2007 | Bilodeau et al. |
| 2007/0259891 A1 | 11/2007 | Strobel et al. |
| 2008/0004300 A1 | 1/2008 | Strobel et al. |
| 2008/0021029 A1 | 1/2008 | Strobel et al. |
| 2008/0045518 A1 | 2/2008 | Commons et al. |
| 2008/0045578 A1 | 2/2008 | Commons et al. |
| 2008/0045579 A1 | 2/2008 | Commons et al. |
| 2008/0124384 A1 | 5/2008 | Blum |
| 2008/0188482 A1 | 8/2008 | Rice et al. |
| 2008/0249087 A1 | 10/2008 | Rotstein et al. |
| 2008/0269295 A1 | 10/2008 | Haurand et al. |
| 2008/0280933 A1 | 11/2008 | Efremov et al. |
| 2008/0312271 A1 | 12/2008 | Efremov et al. |
| 2009/0018054 A1 | 1/2009 | Ali et al. |
| 2009/0170894 A1 | 7/2009 | Aletru et al. |
| 2009/0264650 A1 | 10/2009 | Cho et al. |
| 2010/0025636 A1 | 2/2010 | Gelbin et al. |
| 2010/0041637 A1 | 2/2010 | Claremon et al. |
| 2010/0197675 A1 | 8/2010 | Claremon et al. |
| 2010/0256363 A1 | 10/2010 | Xu |
| 2010/0324045 A1 | 12/2010 | Claremon et al. |
| 2011/0009402 A1 | 1/2011 | Himmelsbach |
| 2011/0015157 A1 | 1/2011 | Claremon et al. |
| 2011/0019643 A1 | 1/2011 | Kim et al. |
| 2011/0021512 A1 | 1/2011 | Claremon et al. |
| 2011/0028445 A1 | 2/2011 | Eckhardt et al. |
| 2011/0071139 A1 | 3/2011 | Claremon et al. |
| 2011/0098320 A1 | 4/2011 | Claremon et al. |
| 2011/0105504 A1 | 5/2011 | Claremon et al. |
| 2011/0112062 A1 | 5/2011 | Claremon et al. |
| 2011/0112082 A1 | 5/2011 | Claremon et al. |
| 2011/0124635 A1 | 5/2011 | Claremon et al. |
| 2011/0136800 A1 | 6/2011 | Eckhardt et al. |
| 2011/0190262 A1 | 8/2011 | Himmelsbach et al. |
| 2011/0224242 A1 | 9/2011 | Giethlen et al. |
| 2011/0263583 A1 | 10/2011 | Claremon et al. |
| 2011/0269736 A1 | 11/2011 | Eckhardt et al. |
| 2011/0269791 A1 | 11/2011 | Peters et al. |
| 2011/0269957 A1 | 11/2011 | Fandrick et al. |
| 2011/0275595 A1 | 11/2011 | Eckhardt et al. |
| 2012/0040973 A1 | 2/2012 | Claremon et al. |
| 2012/0108578 A1 | 5/2012 | Himmelsbach et al. |
| 2012/0108579 A1 | 5/2012 | Renz et al. |
| 2012/0115853 A1 | 5/2012 | Eckhardt et al. |
| 2012/0172357 A1 | 7/2012 | Himmelsbach |
| 2012/0178746 A1 | 7/2012 | Claremon et al. |
| 2012/0184549 A1 | 7/2012 | Himmelsbach |

FOREIGN PATENT DOCUMENTS

| | | |
|---|---|---|
| DE | 2 108 954 A1 | 9/1972 |
| DE | 2 229 695 A1 | 1/1974 |
| DE | 23 38 369 A1 | 2/1975 |
| DE | 23 54 002 A1 | 5/1975 |
| DE | 2 411 382 A1 | 9/1975 |
| DE | 2 437 610 A1 | 2/1976 |
| DE | 2 828 039 A1 | 1/1980 |
| DE | 19918725 A1 | 10/2000 |
| DE | 19929348 A1 | 12/2000 |
| DE | 100 34 623 | 1/2002 |
| DE | 100 34 623 A1 | 1/2002 |
| DE | 10034623 | 1/2002 |
| EP | 0415642 A1 | 3/1991 |
| EP | 0454444 A | 10/1991 |
| EP | 0640594 A1 | 3/1995 |
| EP | 0645387 A | 3/1995 |
| EP | 0471591 B1 | 5/1995 |
| EP | 0 847 275 A1 | 6/1998 |
| EP | 0928789 A1 | 7/1999 |
| EP | 1156049 A | 11/2001 |
| EP | 1270724 A2 | 1/2003 |
| EP | 1852425 A | 11/2007 |
| EP | 1 864 971 A1 | 12/2007 |
| EP | 1864971 A | 12/2007 |
| EP | 1935420 | 6/2008 |
| GB | 1077711 | 8/1967 |
| JP | 6092945 A | 4/1994 |
| JP | 7157681 | 6/1995 |
| JP | 2009110842 A2 | 4/1997 |
| JP | 09151179 | 6/1997 |
| JP | 2002179572 A2 | 6/2002 |
| JP | 2003096058 | 4/2003 |
| JP | 2003300884 A2 | 10/2003 |
| JP | 2005-206503 A | 8/2005 |
| JP | 2005239670 | 9/2005 |
| JP | 2005272321 A | 10/2005 |
| JP | 2007 140188 | 6/2007 |
| JP | 2007 254409 | 10/2007 |
| JP | 2011519374 A | 7/2011 |
| WO | WO 92/07838 | 5/1992 |
| WO | WO 93/07128 | 4/1993 |
| WO | WO 93/13103 | 7/1993 |
| WO | WO 95/31440 | 11/1995 |
| WO | WO 96/14297 A | 5/1996 |
| WO | WO 96/23787 | 8/1996 |
| WO | 96/37494 A1 | 11/1996 |
| WO | 97/07789 A1 | 3/1997 |
| WO | WO 97/36605 | 10/1997 |
| WO | 98/22462 A1 | 5/1998 |
| WO | WO 98/57940 | 12/1998 |
| WO | WO 99/05125 | 2/1999 |
| WO | WO 99/06395 | 2/1999 |
| WO | WO 01/00595 A1 | 1/2001 |

(56) References Cited

FOREIGN PATENT DOCUMENTS

| | | |
|---|---|---|
| WO | WO 01/44200 A2 | 6/2001 |
| WO | WO 2001/055063 | 8/2001 |
| WO | WO 02/06244 A1 | 1/2002 |
| WO | WO 02/06277 A1 | 1/2002 |
| WO | WO 02/22572 A2 | 3/2002 |
| WO | WO 03/043988 A1 | 5/2003 |
| WO | WO 03/057673 A | 7/2003 |
| WO | 03/097608 A2 | 11/2003 |
| WO | WO 03/093261 A1 | 11/2003 |
| WO | WO 2004/004722 A1 | 1/2004 |
| WO | WO 2004/009559 A2 | 1/2004 |
| WO | WO 2004/014859 A2 | 2/2004 |
| WO | WO 2004/046137 A1 | 6/2004 |
| WO | 2004/089896 A1 | 10/2004 |
| WO | WO 2004/094375 A | 11/2004 |
| WO | WO 2005/000845 | 1/2005 |
| WO | WO 2005/086700 A2 | 9/2005 |
| WO | WO 2005/108361 | 11/2005 |
| WO | WO 2005/108361 A | 11/2005 |
| WO | WO 2005/113525 A1 | 12/2005 |
| WO | WO 2006/003494 A2 | 1/2006 |
| WO | WO 2006/014357 A | 2/2006 |
| WO | WO 2006/024627 A2 | 3/2006 |
| WO | WO 2006/024628 A | 3/2006 |
| WO | WO 2006/031715 A | 3/2006 |
| WO | WO 2006/040329 | 4/2006 |
| WO | WO 2006/044174 | 4/2006 |
| WO | WO 2006/049952 A | 5/2006 |
| WO | WO 2006/066924 A2 | 6/2006 |
| WO | WO 2006/066948 A1 | 6/2006 |
| WO | WO 2006/090792 A1 | 8/2006 |
| WO | WO 2006/104280 A | 10/2006 |
| WO | WO 2006/109056 A1 | 10/2006 |
| WO | WO 2007/008529 A2 | 1/2007 |
| WO | 2007/022371 A2 | 2/2007 |
| WO | WO 2007/048595 A1 | 5/2007 |
| WO | WO 2007/051810 | 5/2007 |
| WO | WO 2007/061661 A2 | 5/2007 |
| WO | WO 2007/068330 A1 | 6/2007 |
| WO | 2007/076055 A2 | 7/2007 |
| WO | WO 2007/079186 A2 | 7/2007 |
| WO | WO 2007/081569 A2 | 7/2007 |
| WO | WO 2007/081570 A | 7/2007 |
| WO | WO 2007/081571 A2 | 7/2007 |
| WO | WO 2007/084314 A2 | 7/2007 |
| WO | WO 2007/109456 A2 | 9/2007 |
| WO | WO 2007/118185 A2 | 10/2007 |
| WO | 2007/127763 A2 | 11/2007 |
| WO | 2007123853 A2 | 11/2007 |
| WO | WO 2007/124254 | 11/2007 |
| WO | WO 2007/124329 A | 11/2007 |
| WO | WO 2007/124337 | 11/2007 |
| WO | WO 2007/127693 A | 11/2007 |
| WO | WO 2008/000951 | 1/2008 |
| WO | WO 2008/031227 A1 | 3/2008 |
| WO | WO 2008/036715 A1 | 3/2008 |
| WO | 2008/046578 A2 | 4/2008 |
| WO | WO 2008/046758 A | 4/2008 |
| WO | WO 2008/059948 A | 5/2008 |
| WO | WO 2008/106128 | 9/2008 |
| WO | WO 2008/106128 A | 9/2008 |
| WO | WO 2008/118332 A2 | 10/2008 |
| WO | WO 2009/017664 | 2/2009 |
| WO | WO 2009/017664 A1 | 2/2009 |
| WO | WO 2009/017671 | 2/2009 |
| WO | WO 2009/061498 | 5/2009 |
| WO | WO 2009/063061 | 5/2009 |
| WO | WO 2009/075835 | 6/2009 |
| WO | WO 2009/088997 | 7/2009 |
| WO | WO 2009/094169 A | 7/2009 |
| WO | WO 2009/100872 | 8/2009 |
| WO | WO 2009/102428 | 8/2009 |
| WO | WO 2009/102460 | 8/2009 |
| WO | 2009/107664 A1 | 9/2009 |
| WO | WO 2009/117109 | 9/2009 |
| WO | WO 2009/134384 | 11/2009 |
| WO | WO 2009/134387 | 11/2009 |
| WO | WO 2009/134392 | 11/2009 |
| WO | WO 2009/134400 | 11/2009 |
| WO | WO 2009/138386 | 11/2009 |
| WO | WO 2010/010149 | 1/2010 |
| WO | WO 2010/010150 A1 | 1/2010 |
| WO | WO 2010/010157 | 1/2010 |
| WO | WO 2010/010174 | 1/2010 |
| WO | WO 2010/011314 | 1/2010 |
| WO | WO 2010/023161 | 3/2010 |
| WO | WO 2010/046445 | 4/2010 |
| WO | WO 2010/091067 | 8/2010 |
| WO | WO 2010/127237 | 11/2010 |
| WO | 2010/139673 A1 | 12/2010 |
| WO | 2011/057054 A1 | 5/2011 |

OTHER PUBLICATIONS

Wolfling, Janos et al., "Neighboring Group Participation Part 15. Stereoselective Synthesis of Some Steroidal Tetrahydrooxaziin-2-ones, as Novel Presumed Inhibitors of Human 5α-Reductase," Steroids, 69: 451-460 (2004).
Office Action for U.S. Appl. No. 12/741,522 (U.S. Patent No. 8,138,178), date of mailing Dec. 15, 2010.
Office Action dated Apr. 3, 2012 for corresponding U.S. Appl. No. 13/318,271.
Office Action dated May 3, 2012 for corresponding U.S. Appl. No. 13/347,799.
Office Action dated Jun. 14, 2012 for corresponding U.S. Appl. No. 13/347,784.
Chemical Abstracts, Registry No. 351443-37-3 (Available on Aug. 15, 2001.).
Souillac et al., Characterization of Delivery Systems, Differential Scanning Calorimetry, pp. 217-218 (in Encyclopedia of Controlled Drug Delivery, 1999, John Wiley & Sons, pp. 212-227).
Morissette et al. Advanced Drug Deliery Reviews 2004, 56, 275-300.
Examiner Interview Summary dated May 2, 2011, in U.S. Appl. No. 12/741,522 (U.S. Patent No. 8,138,178).
Chalmers (TIPS vol. 17, pp. 166-172 Apr. 1996).
Anderson, (Chem and Biol 10:787-797, 2003).
Thiel (Nature Biotechnol 2:513-519, 2004).
International Search Report for PCT/EP2009/063913 mailed May 6, 2010.
Gutkowska et al.: Acta Poloniae Pharmaceutica 1986, 43, p. 403-405.
Gutkowska et al.: Acta Polonaie Pharmaceutica 1987, 39, p. 411-414.
DeMarinis R.M. et.al. Journal of Medicinal Chemistry 1981, vol. 24, No. 12, pp. 1432-1437.
Rosenstock et.al. Diabetes Care Jul. 2010, LNKDPUBMED: 20413513, vol. 33, No. 7, pp. 1516-1522.
Vidic et al.: Chem. Ber. 1976, 109, p. 2657-2669.
Bosch et al.: Heterocycles 1980, 14, p. 1983-1988.
Ma et al.: Tetrahedron 2007, 63, p. 7523-7531.
Ma et al.: Synthesis 2007, p. 161-163.
Yokoyama et al.: J. Med. Chem. 1979, 22, p. 537-553.
Harno et.al. Trends in Endocrinology and Metabolism, Elsevier Science Publishing, New York 2010, vol. 21, No. 10, pp. 619-627.
Taddayon et.al. Expert opinion on Investigational Drugs, Ashley Publication Ltd. 2003, vol. 12, No. 3, pp. 307-324.
Hughes, K.A. et al., "11-beta-hydroxysteroid dehydrogenase type 1 (11b-HSD1) inhibitors in Type 2 diabetes mellitus and obesity". Expert Opinion, Investig. Drugs, 17(4), 2008, pp. 481-496.
Gutkowska et al.: Acta Poloniae Pharmaceutica, 1982, vol. 39, p. 61-64.
Olesen et al.: Current Opin Drug Dis Dev, 2001, vol. 4, No. 4, p. 471-478.
Thornber et al.: Chem Soc Rev, 1979, vol. 8, p. 563-580.
Caplus—133:4656—Anantanarayan, A. el. al., "Preparation of heteroarylpyrazoles as P38 kinase inhibitors". 2000.
Caplus—147:134403, Hembrough, TA, et al., Composition and methods comprising proteinase activated receptor 2 antagonists for treatment of angiogenesis and inflammatory disorders and cancer. 2007.
Caplus—77:5360, Helsley, G. C. "Antispasmodic 8-carbamoyl-3-phenylnortropanes". 1972.

(56) References Cited

OTHER PUBLICATIONS

International Search Report and Written Opinion for PCT/US2012/050679 mailed Oct. 31, 2012.
U.S. Appl. No. 12/670,205, filed Jul. 25, 2005, Vitae Pharmaceuticals, Inc.
U.S. Appl. No. 12/670,209, filed Jul. 25, 2008, Vitae Pharmaceuticals, Inc.
U.S. Appl. No. 12/741,522, filed Apr. 30, 2009, Vitae Pharmaceuticals, Inc.
U.S. Appl. No. 12/990,309, filed Apr. 30, 2009, Vitae Pharmaceuticals, Inc.
U.S. Appl. No. 12/990,296, filed Apr. 30, 2009, Vitae Pharmaceuticals, Inc.
U.S. Appl. No. 12/745,663, filed Nov. 7, 2008, Vitae Pharmaceuticals, Inc.
U.S. Appl. No. 12/811,577, filed Jan. 7, 2009, Vitae Pharmaceuticals, Inc.
U.S. Appl. No. 12/747,391, filed Dec. 10, 2008, Vitae Pharmaceuticals, Inc.
U.S. Appl. No. 12/863,634, filed Jan. 21, 2009, Vitae Pharmaceuticals, Inc.
U.S. Appl. No. 12/867,374, filed Feb. 13, 2009, Vitae Pharmaceuticals, Inc.
U.S. Appl. No. 12/741,532, filed Sep. 27, 2010, Vitae Pharmaceuticals, Inc.
U.S. Appl. No. 12/771,499, filed Apr. 30, 2010, Vitae Pharmaceuticals, Inc.
U.S. Appl. No. 12/933,027, filed Mar. 18, 2009, Vitae Pharmaceuticals, Inc.
Ms Bitar, "Glucocorticoid Dynamics and Impaired Wound Healing in Diabetes Mellitus", Am J Pathol., 1998, vol. 152, pp. 547-554.
Ms Bitar, et al., "Heat-Shock Protein 72/73 and Impaired Wound Healing in Diabetic and Hypercortisolemic States", Sugery, 1999, vol. 125, pp. 594-601.
Ms Bitar, et al., "Glucocorticoid-Dependent Impairment of Wound Healing in Experimental Diabetes: Amelioration by Adrenalectomy and RU 486", J Surg Res., 1999, vol. 82, pp. 234-243.
Ms Bitar, "Insulin and Glucocorticoid-Dependent Suppression of the IGF-I System in Diabetic Wounds", Sugery, 2000, vol. 127, pp. 687-695.
Database Caplus []Online] Chemical Abstracts Service, Mallard et al., "Spiroheterocyclic Cycloalkane Compounds. II. Synthesis of 6-Substituted-Tetrahydro-2H-1,3-Oxazine-2-Ones", XP002516521, retrieved from STN Database accession No. 1969:68280 CAS RN: 20057-45-8 abstract.
Chimica Therapeutica, 1968, vol. 3(5), pp. 321-324, 1968.
Database Caplus [Online Chemical Abstracts Service, Slyusarenko et al., "Synthesis based on Thionylamides.IV. 2-Alkoxy-5,6-Dihydro-1,3-Oxazines", XP002516522, retrieved from STN Database accession No. 1978:563520 CAS RN: 67868-26-2 abstract.
Zhurnal Organicheskoi Khimii, 1978, vol. 14(5), pp. 1092-1094.
Database CA [Online], Chemica Abstracts Service, Fukushima et al., "Preparation of Imidazolidinone Derviatives as 11.beta.-HSD1 Inhibitors", 2007, XP 002531878.
"Khimiia Elementoorganicheskikh Soedineni", 1982, vol. 1982 pp. 22-26.
"Zhurnal Organicheskoi Khimii", 1982, vol. 18, PT 11, p. 2468.
Chemical Abstracts, vol. 98, No. 11, 1983, Columbus, Ohio, US; abstract No. 89280k, Lapkin, et al., "Synthesis of 1,3-oxazin-2,4-diones", p. 552, col. 1, XP002504063 abstract.
Chemical Abstracts, vol. 99, No. 23, 1983, Columbus, Ohio, US; abstract No. 1985067b, Saitkulova, et al., "Synthesis involving bromozinc alcoholates of carboxylic acid esters", p. 764 col. 1, XP002504063 abstract.
Goubet, et al., "Conversion of a Thiohydantoin to the Corresponding Hydantoin via a Ring-Opening/Ring Closure Mechanism", Tetrahedron Letters, Elsevier, Amsterdam, 1996, vol. 37, pp. 7727-7730.
Ho-Jane Shue et al., "Cyclic Urea Derivatives as Potent NK1 Selective Antagonists". Bioorganic & Medicinal Chemistry Letters, 2005, vol. 15, pp. 3896-3899.
Ho-Jane Shue et al., "Cyclic Urea Derivatives as Potent NK1 Selective Antagonists. Part II: Effects of Fluoro and Benzylic Methyl Substitutions", Bioorganic & Medicinal Chemistry Letters, 2006, vol. 16, pp. 1065-1069.
Kashima, et al., "Preparation of N-Aryl-2,4-diaminopentanes by the Ring Opening Reaction of 1-Aryl-3,4,5,6-tetrahydro-2-(1H)pyrimidinones", Journal of Heterocyclic Chemistry, vol. 18, 1981, pp. 1595-1596, XP002517485.
Lohray et al., "Enantiospecific Synthesis of 6-Substituted N-Aryl-1,3-Oxazin-2-Ones", Tetrahedron Letters, 1998, vol. 39, pp. 6555-6556.
Malgorzata Wamil and Jonathan R. Seckl, "Inhibition of 11β-hydroxysteroid Dehydrogenase Type 1 as a Promising Therapeutic Target", Drug Discovery Today, 2007, vol. 12, pp. 504-520.
Muehlstadt, et al., "Cyclisation reactions of beta, gamma-unsaturated derivatives of carbonic acid. IX.", Journal Fuer Praktische Chemie, vol. 328, 1986, pp. 163-172, XP002504062 p. 164, compound 4j.
Schoellkopf, et al., "Umsetzungen Alphametallierter Isocyanide Mit Einigen 1,3-Dipolen//Reactions of Alpha-Metaiated Osicyanides with Some 1,3-Dipoles", Liebigs Annalen Der Chemie, Verlag Chemie GMBH. Weinheim, DE, 1980, vol. 4, pp. 600-610.
Suga, Seiji et al., ""N-Acyliminium Ion Pool" as a Heterodiene in [4+2] Cycloaddition Reaction", Organic Letters, 2003, vol. 5, pp. 945-947.
Suga, Seiji et al., "Cycloaddition of "N-Acyliminium Ion Pools" with Carbon-Carbon Multiple Bonds". Bulletin of the Chemical Society of Japan, Chemical Society of Japan, 2005, vol. 78, pp. 1206-1217.
Tamaru et al., "Urea as the Most Reactive and Versatile Nitrogen Nucleophile for the Palladium(2+)-Catalyzed Cyclization of Unsaturated Amines", Journal of the American Chemical Society, 1988, vol. 110, pp. 3994-4002.
Yoshida, Masaaki et al., "Selective synthesis of five- and six-membered cyclic carbamates by the reaction of 2-(1-haloalkyl)oxiranes with carbon dioxide and aliphatic primary amines", Heterocycles, Elsevier Science Ltd., 1993, vol. 35 (2), pp. 623-626.
Yoshinao Tamaru, "Palladium(2+)-Catalyzed Intramolecular Aminocarbonylation of 3-Hydroxy-4-pentenylamines and 4-Hydroxy-5-hexenylamines", J. Org. Chem., 1988, pp. 5731-5741.
International Search Report & Written Opinion—(PCT/US2008/009017) Date of Mailing Apr. 12, 2008.
International Search Report & Written Opinion—(PCT/US2008/002517) Date of Mailing Dec. 29, 2008.
International Search Report—(PCT/US2009/002653) Date of Mailing Jul. 3, 2009.
International Search Report—(PCT/US2009/002641) Date of Mailing Jul. 3, 2009.
International Search Report—(PCT/US2009/002629) Date of Mailing Jul. 3, 2009.
International Search Report—(PCT/US2009/002633) Date of Mailing Jul. 3, 2009.
International Search Report—(PCT/US2008/012618) Date of Mailing Dec. 3, 2009.
International Search Report—(PCT/US2009/000057) Date of Mailing Mar. 25, 2009.
International Search Report—(PCT/US2008/013539) Date of Mailing Mar. 19, 2009.
International Search Report—(PCT/US2009/000853) Date of Mailing Sep. 2, 2009.
International Search Report—(PCT/US2009/000421) Date of Mailing Apr. 15, 2009.
International Search Report—(PCT/US2009/000908) Date of Mailing Sep. 17, 2009.
International Search Report—(PCT/US2009/001712) Date of Mailing Jul. 14, 2009.
Database File Registry [Online], Chemical Abstracts Service, Columbus, Ohio, US, 2007, Database accession No. 958700-63-5, Abstract, XP002556893.
Database File Registry [Online], Chemical Abstracts Service, Columbus, Ohio, US, 2007, Database accession No. 958696-39-4, Abstract, XP002556894.
Database File Registry [Online], Chemical Abstracts Service, Columbus, Ohio, US, 2007, Database accession No. 958696-32-7, Abstract, XP002556895.

(56) References Cited

OTHER PUBLICATIONS

Database File Registry [Online], Chemical Abstracts Service, Columbus, Ohio, US, 2007, Database accession No. 958629-39-5, Abstract, XP002556896.
Database File Registry [Online], Chemical Abstracts Service, Columbus, Ohio, US, 2007, Database accession No. 958629-22-6, Abstract, XP002556897.
Database File Registry [Online], Chemical Abstracts Service, Columbus, Ohio, US, 2007, Database accession No. 958629-14-6, Abstract, XP002556898.
Database File Registry [Online], Chemical Abstracts Service, Columbus, Ohio, US, 2007, Database accession No. 958625-83-7, Abstract, XP002556899.
Database File Registry [Online], Chemical Abstracts Service, Columbus, Ohio, US, 2007, Database accession No. 958599-31-10, Abstract, XP002556900.
International Search Report—(PCT/US2010/023021) Date of Mailing Aug. 5, 2010.
International Search Report—(PCT/US2008/009048) Date of Mailing Dec. 4, 2008.
International Search Report—(PCT/US2009/004261) Date of Mailing Oct. 21, 2009.
Shibata, et al., "Cycloaddition of Ocetanes with Heterocumulenes Catalysed by Organotin Iodine-Lewis Base Complex", Journal of Heterocyclic Chemistry, vol. 24, 1987, pp. 361-363.
Gavezzotti, "Are Crystal Structures Predictable?", Accounts of Chemical Research, 1994, vol. 27, pp. 309-314.
Vippagunta, et al., "Crystalline Solids", Advanced Drug Deliver Reviews, 2001, vol. 48, pp. 3-26.

CYCLIC INHIBITORS OF 11β-HYDROXYSTEROID DEHYDROGENASE 1

RELATED APPLICATIONS

This application is the U.S. National Stage of PCT International Application Number PCT/US2009/002641, filed Apr. 30, 2009, which claims the benefit of U.S. Provisional Application No. 61/206,775, filed on Feb. 4, 2009, U.S. Provisional Application No. 61/137,148, filed on Jul. 25, 2008, and U.S. Provisional Application No. 61/049,650, filed May 1, 2000.

PCT/US2009/002641 also claims priority to International Application No. PCT/US2008/009017, which designated the United States and was filed on Jul. 25, 2008, published in English, which claims the benefit of U.S. Provisional Application No. 61/049,650, filed May 1, 2008.

The entire teachings of the above applications are incorporated herein by reference.

FIELD OF THE INVENTION

The present invention relates to inhibitors of 11β-hydroxysteroid dehydrogenase type 1 (11β-HSD1), pharmaceutical compositions thereof and methods of using the same.

BACKGROUND OF THE INVENTION

Glucocorticoids, such as cortisol (hydrocortisone), are steroid hormones that regulate fat metabolism, function and distribution, and play a role in carbohydrate, protein and fat metabolism. Glucocorticoids are also known to have physiological effects on development, neurobiology, inflammation, blood pressure, metabolism, and programmed cell death. Cortisol and other corticosteroids bind both the glucocorticoid receptor (GR) and the mineralocorticoid receptor (MR), which are members of the nuclear hormone receptor superfamily and have been shown to mediate cortisol function in vivo. These receptors directly modulate transcription via DNA-binding zinc finger domains and transcriptional activation domains.

Until recently, the major determinants of glucocorticoid action were attributed to three primary factors: (1) circulating levels of glucocorticoid (driven primarily by the hypothalamic-pituitary-adrenal (HPA) axis); (2) protein binding of glucocorticoids in circulation; and (3) intracellular receptor density inside target tissues. Recently, a fourth determinant of glucocorticoid function has been identified: tissue-specific pre-receptor metabolism by glucocorticoid-activating and -inactivating enzymes. These 11β-hydroxysteroid dehydrogenase (11β-HSD) pre-receptor control enzymes modulate activation of GR and MR by regulation of glucocorticoid hormones. To date, two distinct isozymes of 11-beta-HSD have been cloned and characterized: 11β-HSD1 (also known as 11-beta-HSD type 1, 11betaHSD1, HSD11B1, HDL, and HSD11L) and 11β-HSD2. 11β-HSD1 is a bi-directional oxidoreductase that regenerates active cortisol from inactive 11-keto forms, whereas 11β-HSD2 is a unidirectional dehydrogenase that inactivates biologically active cortisol by converting it into cortisone.

The two isoforms are expressed in a distinct tissue-specific fashion, consistent with the differences in their physiological roles. 11β-HSD1 is widely distributed in rat and human tissues; expression of the enzyme and corresponding mRNA have been detected in human liver, adipose tissue, lung, testis, bone and ciliary epithelium. In adipose tissue, increased cortisol concentrations stimulate adipocyte differentiation and may play a role in promoting visceral obesity. In the eye, 11β-HSD1 may regulate intraocular pressure and may contribute to glaucoma; some data suggest that inhibition of 11β-HSD1 may cause a drop in intraocular pressure in patients with intraocular hypertension (Kotelevstev et al. (1997), Proc. Natl. Acad. Sci. USA 94(26):14924-9). Although 11β-HSD1 catalyzes both 11-beta-dehydrogenation and the reverse 11-oxoreduction reaction, 11β-HSD1 acts predominantly as a NADPH-dependent oxoreductase in intact cells and tissues, catalyzing the formation of active cortisol from inert cortisone (Low et al. (1994) J. Mol. Endocrin. 13: 167-174). In contradistinction, 11β-HSD2 expression is found mainly in mineralocorticoid target tissues such as kidney (cortex and medulla), placenta, sigmoid and rectal colon, salivary gland and colonic epithelial cell lines. 11β-HSD2 acts as an NAD-dependent dehydrogenase catalyzing the inactivation of cortisol to cortisone (Albiston et al. (1994) Mol. Cell. Endocrin. 105: R11-R17), and has been shown to protect the MR from glucocorticoid excess (e.g., high levels of receptor-active cortisol) (Blum, et al. (2003) Prog. Nucl. Acid Res. Mol. Biol. 75:173-216).

Mutations in either the 11β-HSD1 or the 11β-HSD2 genes result in human pathology. For example, individuals with mutations in 11β-HSD2 are deficient in this cortisol-inactivation activity and, as a result, present with a syndrome of apparent mineralocorticoid excess (also referred to as 'SAME') characterized by hypertension, hypokalemia, and sodium retention (Edwards et al. (1988) Lancet 2: 986-989; Wilson et al. (1998) Proc. Natl. Acad. Sci. 95: 10200-10205). Similarly, mutations in 11β-HSD1 and in the gene encoding a co-localized NADPH-generating enzyme, hexose 6-phosphate dehydrogenase (H6PD), can result in cortisone reductase deficiency (CRD); these individuals present with ACTH-mediated androgen excess (hirsutism, menstrual irregularity, hyperandrogenism), a phenotype resembling polycystic ovary syndrome (PCOS) (Draper et al. (2003) Nat. Genet. 34: 434-439).

Notably, disruption of homeostasis in the HPA axis by either deficient or excess secretion or action results in Cushing's syndrome or Addison's disease, respectively (Miller and Chrousos (2001) Endocrinology and Metabolism, eds. Felig and Frohman (McGraw-Hill, New York), 4$^{th}$ Ed.: 387-524). Patients with Cushing's syndrome or receiving glucocorticoid therapy develop reversible visceral fat obesity. The phenotype of Cushing's syndrome patients closely resembles that of Reaven's metabolic syndrome (also known as Syndrome X or insulin resistance syndrome), the symptoms of which include visceral obesity, glucose intolerance, insulin resistance, hypertension, type 2 diabetes and hyperlipidemia (Reaven (1993) Ann. Rev. Med. 44: 121-131). Although the role of glucocorticoids in human obesity is not fully characterized, there is mounting evidence that 11β-HSD1 activity plays an important role in obesity and metabolic syndrome (Bujalska et al. (1997) Lancet 349: 1210-1213); (Livingstone et al. (2000) Endocrinology 131: 560-563; Rask et al. (2001) J. Clin. Endocrinol. Metab. 86: 1418-1421; Lindsay et al. (2003) J. Clin. Endocrinol. Metab. 88: 2738-2744; Wake et al. (2003) J. Clin. Endocrinol. Metab. 88: 3983-3988).

Data from studies in mouse transgenic models supports the hypothesis that adipocyte 11β-HSD1 activity plays a central role in visceral obesity and metabolic syndrome (Alberts et al. (2002) Diabetologia. 45(11): 1526-32). Over-expression in adipose tissue of 11β-HSD1 under the control of the aP2 promoter in transgenic mice produced a phenotype remarkably similar to human metabolic syndrome (Masuzaki et al. (2001) Science 294: 2166-2170; Masuzaki et al. (2003) J.

Clinical Invest. 112: 83-90). Moreover, the increased activity of 11β-HSD1 in these mice is very similar to that observed in human obesity (Rask et al. (2001) J. Clin. Endocrinol. Metab. 86: 1418-1421). In addition, data from studies with 11β-HSD1-deficient mice produced by homologous recombination demonstrate that the loss of 11β-HSD1 leads to an increase in insulin sensitivity and glucose tolerance due to a tissue-specific deficiency in active glucocorticoid levels (Kotelevstev et al. (1997) Proc. Natl. Acad. Sci. 94: 14924-14929; Morton et al. (2001) J. Biol. Chem. 276: 41293-41300; Morton et al. (2004) Diabetes 53: 931-938).

The published data supports the hypothesis that increased expression of 11β-HSD1 contributes to increased local conversion of cortisone to cortisol in adipose tissue and hence that 11β-HSD1 plays a role in the pathogenesis of central obesity and the appearance of the metabolic syndrome in humans (Engeli, et al., (2004) Obes. Res. 12: 9-17). Therefore, 11β-HSD1 is a promising pharmaceutical target for the treatment of the metabolic syndrome (Masuzaki, et al., (2003) Curr. Drug Targets Immune Endocr. Metabol. Disord. 3: 255-62). Furthermore, inhibition of 11β-HSD1 activity may prove beneficial in treating numerous glucocorticoid-related disorders. For example, 11β-HSD1 inhibitors could be effective in combating obesity and/or aspects of the metabolic syndrome cluster, including glucose intolerance, insulin resistance, hyperglycemia, hypertension, and/or hyperlipidemia (Kotelevstev et al. (1997) Proc. Natl. Acad. Sci. 94: 14924-14929; Morton et al. (2001) J. Biol. Chem. 276: 41293-41300; Morton et al. (2004) Diabetes 53: 931-938). In addition, inhibition of 11β-HSD1 activity may have beneficial effects on the pancreas, including the enhancement of glucose-stimulated insulin release (Billaudel and Sutter (1979) Horm. Metab. Res. 11: 555-560; Ogawa et al. (1992) J. Clin. Invest. 90: 497-504; Davani et al. (2000) J. Biol. Chem. 275: 34841-34844).

Furthermore, given that inter-individual differences in general cognitive function have been linked to variability in the long-term exposure to glucocorticoids (Lupien et al. (1998) Nat. Neurosci. 1: 69-73) and dysregulation of the HPA axis resulting in chronic exposure to glucocorticoid excess in certain brain subregions has been theorized to contribute to the decline of cognitive function (McEwen and Sapolsky (1995) Curr. Opin. Neurobiol. 5: 205-216), one might predict that inhibition of 11β-HSD1 could reduce exposure to glucocorticoids in the brain and thereby protect against deleterious glucocorticoid effects on neuronal function, including cognitive impairment, dementia, and/or depression. Notably, it is known that stress and glucocorticoids influence cognitive function (de Quervain et al. (1998) Nature 394: 787-790); and it has been shown that 11β-HSD1, through its control of glucocorticoid action in the brain, may have effects on neurotoxicity (Rajan et al. (1996) Neuroscience 16: 65-70; Seckl (2000) Neuroendocrinol. 18:49-99).

There is also evidence that glucocorticoids and 11β-HSD1 play a role in regulation of in intra-ocular pressure (IOP) (Stokes et al. (2000) Invest. Ophthalmol. Vis. Sci. 41: 1629-1683; Rauz et al. (2001) Invest. Ophthalmol. Vis. Sci. 42: 2037-2042); if left untreated, elevated IOP can lead to partial visual field loss and eventually blindness. Thus, inhibition of 11β-HSD1 in the eye could reduce local glucocorticoid concentrations and IOP, and 11β-HSD1 hence could potentially be used to treat glaucoma and other visual disorders.

Transgenic aP2-11βHSD1 mice exhibit high arterial blood pressure and have increased sensitivity to dietary salt. Moreover, plasma angiotensinogen levels are elevated in the transgenic mice, as are angiotensin II and aldosterone; and treatment of the mice with an angiotensin II antagonist alleviates the hypertension (Masuzaki et al. (2003) J. Clinical Invest. 112: 83-90). This suggests that hypertension may be caused or exacerbated by 11β-HSD1 activity. Thus, 11β-HSD1 inhibitors may be useful for treatment of hypertension and hypertension-related cardiovascular disorders. Inhibition of 11β-HSD1 in mature adipocytes is also expected to attenuate secretion of plasminogen activator inhibitor 1 (PAI-1), which is an independent cardiovascular risk factor (Halleux et al. (1999) J. Clin. Endocrinol. Metabl. 84: 4097-4105).

Glucocorticoids can have adverse effects on skeletal tissues; and prolonged exposure to even moderate glucocorticoid doses can result in osteoporosis (Cannalis (1996) J. Clin. Endocrinol. Metab. 81: 3441-3447). In addition, 11β-HSD1 has been shown to be present in cultures of human primary osteoblasts as well as cells from adult bone (Cooper et al. (2000) Bone 27: 375-381), and the 11β-HSD1 inhibitor carbenoxolone has been shown to attenuate the negative effects of glucocorticoids on bone nodule formation (Bellows et al. (1998) Bone 23: 119-125). Thus, inhibition of 11β-HSD1 is predicted to decrease the local glucocorticoid concentration within osteoblasts and osteoclasts, thereby producing beneficial effects in various forms of bone disease, including osteoporosis.

11β-HSD1 inhibitors may also be useful for immunomodulation. Although glucocorticoids are perceived to suppress the immune system, in actuality, there is a complex, dynamic interaction between the HPA axis and the immune system (Rook (1999) Baillier's Clin. Endocrinol. Metabl. 13: 576-581). Glucocorticoids play a role in modulating the balance between cell-mediated and humoral immune response, with high glucocorticoid activity normally associated with a humoral response. Inhibition of 11β-HSD1 therefore can be used a means of shifting the immune response towards a cell-mediated response. Certain disease states, such as tuberculosis, leprosy (Hansen's disease) and psoriasis, trigger immune responses that are biased towards a humoral response whereas the more effective immune response may be a cell-mediated response. Hence, 11β-HSD1 inhibitors may be useful for treating such diseases.

It has been reported that glucocorticoids inhibit wound healing, especially in diabetic patients with ulcers (Bitar et al. (1999) J. Surg. Res. 82: 234-243; Bitar et al. (1999) Surgery 125: 594-601; Bitar (2000) Surgery 127: 687-695; Bitar (1998) Am. J. Pathol. 152: 547-554). Patients that exhibit impaired glucose tolerance and/or type 2 diabetes often also have impaired wound healing. Glucocorticoids have been shown to increase the risk of infection and delay wound healing (Anstead (1998) Adv. Wound Care 11:277-285). Moreover, there is a correlation between elevated levels of cortisol in wound fluid and non-healing wounds (EP Patent App. No. 0 902 288). Recent published patent applications have suggested that certain 11β-HSD1 inhibitors may be useful for promoting wound healing (PCT/US2006/043, 951).

As evidenced herein, there is a continuing need for new and improved drugs that inhibit 11β-HSD1. The novel compounds of the instant invention are effective inhibitors of 11β-HSD1.

SUMMARY OF THE INVENTION

It has now been found that compounds of Formula I or pharmaceutically acceptable salts thereof, are effective inhibitors of 11β-HSD1.

The invention is a compound represented by Formula (I)

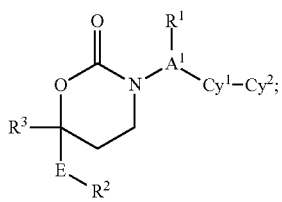

(I)

or a pharmaceutically acceptable salt, enantiomer or diastereomer thereof.

In a first embodiment of the invention, Formula I and its constituent members are defined herein as follows:

$R^1$ is (a) absent or (b) is selected from $(C_1-C_6)$alkyl, $(C_2-C_6)$alkenyl, $(C_2-C_6)$alkynyl, $(C_1-C_3)$alkoxy$(C_1-C_3)$alkoxy, or $(C_1-C_3)$alkoxy$(C_1-C_3)$alkyl and is optionally substituted with up to four groups independently selected from fluorine, cyano, oxo, $R^4$, $R^4O$—, $(R^4)_2N$—, $R^4O_2C$—, $R^4S$, $R^4S(\!=\!O)$—, $R^4S(\!=\!O)_2$—, $R^4C(\!=\!O)NR^4$—, $(R^4)_2NC(\!=\!O)$—, $(R^4)_2NC(\!=\!O)O$—, $(R^4)_2NC(\!=\!O)NR^4$—, $R^4OC(\!=\!O)NR^4$—, $(R^4)_2NC(\!=\!NCN)NR^4$—, $(R^4O)_2P(\!=\!O)O$—, $(R^4O)_2P(\!=\!O)NR^4$—, $R^4OS(\!=\!O)_2NR^4$—, $(R^4)_2NS(\!=\!O)_2O$—, $(R^4)_2NS(\!=\!O)_2NR^4$—, $R^4S(\!=\!O)_2NR^4$—, $R^4S(\!=\!O)_2NHC(\!=\!O)$—, $R^4S(\!=\!O)_2NHC(\!=\!O)O$—, $R^4S(\!=\!O)_2NHC(\!=\!O)NR^4$—, $R^4OS(\!=\!O)_2NHC(\!=\!O)$—, $R^4OS(\!=\!O)_2NHC(\!=\!O)O$—, $R^4OS(\!=\!O)_2NHC(\!=\!O)NR^4$—, $(R^4)_2NS(\!=\!O)_2NHC(\!=\!O)$—, $(R^4)_2NS(\!=\!O)_2NHC(\!=\!O)O$—, $(R^4)_2NS(\!=\!O)_2NHC(\!=\!O)NR^4$—, $R^4C(\!=\!O)NHS(\!=\!O)_2$—, $R^4C(\!=\!O)NHS(\!=\!O)_2O$—, $R^4C(\!=\!O)NHS(\!=\!O)_2NR^4$—, $R^4OC(\!=\!O)NHS(\!=\!O)_2$—, $R^4OC(\!=\!O)NHS(\!=\!O)_2O$—, $R^4OC(\!=\!O)NHS(\!=\!O)_2NR^4$—, $(R^4)_2NC(\!=\!O)NHS(\!=\!O)_2$—, $(R^4)_2NC(\!=\!O)NHS(\!=\!O)_2O$—, $(R^4)_2NC(\!=\!O)NHS(\!=\!O)_2NR^4$—, heterocyclyl, heteroaryl, arylamino and heteroarylamino;

$A^1$ is (a) a bond, or (b) $(C_1-C_3)$alkylene, $CH_2CH_2O$, wherein the oxygen is attached to $Cy^1$, or $CH_2C(\!=\!O)$, wherein the carbonyl carbon is attached to $Cy^1$;

$Cy^1$ is aryl, heteroaryl, monocyclic cycloalkyl or monocyclic heterocyclyl and is optionally substituted with 1 to 4 groups independently selected from fluorine, chlorine, bromine, iodine, cyano, nitro, amino, hydroxy, carboxy, $(C_1-C_6)$alkyl, hydroxy$(C_1-C_6)$alkyl, $(C_3-C_6)$cycloalkyl, hydroxy$(C_3-C_6)$cycloalkyl, $(C_4-C_7)$cycloalkylalkyl, $(C_2-C_6)$alkenyl, halo$(C_2-C_6)$alkenyl, hydroxy$(C_2-C_6)$alkenyl, $(C_2-C_6)$alkynyl, $(C_3-C_6)$cycloalkyl$(C_2-C_4)$alkynyl, halo$(C_1-C_6)$alkyl, halo$(C_3-C_6)$cycloalkyl, halo$(C_4-C_7)$cycloalkylalkyl, $(C_1-C_6)$alkoxy, $(C_3-C_6)$cycloalkoxy, $(C_4-C_7)$cycloalkylalkoxy, halo$(C_1-C_6)$alkoxy, halo$(C_3-C_6)$cycloalkoxy, halo$(C_4-C_7)$cycloalkylalkoxy, $(C_1-C_6)$alkylthio, $(C_3-C_6)$cycloalkythio, $(C_4-C_7)$cycloalkylalkylthio, halo$(C_1-C_6)$alkylthio, halo$(C_3-C_6)$cycloalkythio, halo$(C_4-C_7)$cycloalkylalkylthio, $(C_1-C_6)$alkanesulfinyl, $(C_3-C_6)$cycloalkanesulfinyl, $(C_4-C_7)$cycloalkylalkanesulfinyl, halo$(C_1-C_6)$alkanesulfinyl, halo$(C_3-C_6)$cycloalkanesulfinyl, halo$(C_4-C_7)$cycloalkylalkanesulfinyl, $(C_1-C_6)$alkanesulfonyl, $(C_3-C_6)$cycloalkanesulfonyl, $(C_4-C_7)$cycloalkyl-alkanesulfonyl, halo$(C_1-C_6)$alkanesulfonyl, halo$(C_3-C_6)$cycloalkanesulfonyl, halo$(C_4-C_7)$cycloalkyl-alkanesulfonyl, $(C_1-C_6)$alkylamino, di$(C_1-C_6)$alkylamino, $(C_1-C_6)$alkoxy$(C_1-C_6)$alkoxy, halo$(C_1-C_6)$alkoxy$(C_1-C_6)$alkoxy, $(C_1-C_6)$alkoxycarbonyl, $H_2NCO$, $H_2NSO_2$, $(C_1-C_6)$alkylaminocarbonyl, di$(C_1-C_6)$alkylaminocarbonyl, $(C_1-C_3)$alkoxy$(C_1-C_3)$alkylaminocarbonyl, heterocyclylcarbonyl, $(C_1-C_6)$alkylaminosulfonyl, di$(C_1-C_6)$alkylaminosulfonyl, heterocyclylsulfonyl, $(C_1-C_6)$alkylcarbonylamino, $(C_1-C_6)$alkylcarbonylamino$(C_1-C_6)$alkyl, $(C_1-C_6)$alkylsulfonylamino, $(C_1-C_6)$alkylsulfonylamino$(C_1-C_6)$alkyl, $(C_1-C_6)$alkoxycarbonyl$(C_1-C_6)$alkoxy, $(C_1-C_6)$alkoxy$(C_1-C_6)$alkyl, halo$(C_1-C_6)$alkoxy$(C_1-C_6)$alkyl, hydroxy$(C_1-C_6)$alkoxy, heteroaryl oxo, amino$(C_1-C_6)$alkyl, $(C_1-C_6)$alkylamino$(C_1-C_6)$alkyl, di$(C_1-C_6)$alkylamino$(C_1-C_6)$alkyl amino$(C_2-C_6)$alkoxy, $(C_1-C_6)$alkylamino$(C_2-C_6)$alkoxy, di$(C_1-C_6)$alkylamino$(C_2-C_6)$alkoxy, $(C_1-C_6)$alkylcarbonyl, $(C_3-C_6)$cycloalkylcarbonyl, $(C_3-C_6)$cycloalkylaminocarbonyl, $\{(C_3-C_6)$cycloalkyl$\}\{(C_1-C_6)$alkyl$\}$aminocarbonyl, di$(C_3-C_6)$cycloalkylaminocarbonyl, $(C_3-C_6)$cycloalkylaminosulfonyl, $\{(C_3-C_6)$cycloalkyl$\}\{(C_1-C_6)$alkyl$\}$aminosulfonyl, di$(C_3-C_6)$cycloalkylaminosulfonyl, cyano$(C_1-C_6)$alkyl, aminocarbonyl$(C_1-C_6)$alkyl, $(C_1-C_6)$alkylaminocarbonyl$(C_1-C_6)$alkyl, di$(C_1-C_6)$alkylaminocarbonyl$(C_1-C_6)$alkyl, $(C_3-C_6)$cycloalkylaminocarbonyl$(C_1-C_6)$alkyl, $\{(C_3-C_6)$cycloalkyl$\}\{(C_1-C_6)$alkyl$\}$aminocarbonyl$(C_1-C_6)$alkyl and di$(C_3-C_6)$cycloalkylaminocarbonyl$(C_1-C_6)$alkyl;

$Cy^2$ in Formula I is pyridyl, pyridazinyl, pyrimidinyl, pyrazinyl, pyrazolyl, thiazolyl or thiadiazoly and is optionally substituted with 1 to 4 groups independently selected from fluorine, chlorine, bromine, iodine, cyano, nitro, amino, hydroxy, carboxy, $(C_1-C_6)$alkyl, hydroxy$(C_1-C_6)$alkyl, $(C_3-C_6)$cycloalkyl, hydroxy$(C_3-C_6)$cycloalkyl, $(C_4-C_7)$cycloalkylalkyl, $(C_2-C_6)$alkenyl, halo$(C_2-C_6)$alkenyl, hydroxy$(C_2-C_6)$alkenyl, $(C_2-C_6)$alkynyl, $(C_3-C_6)$cycloalkyl$(C_2-C_4)$alkynyl, halo$(C_1-C_6)$alkyl, halo$(C_3-C_6)$cycloalkyl, halo$(C_4-C_7)$cycloalkylalkyl, $(C_1-C_6)$alkoxy, $(C_3-C_6)$cycloalkoxy, $(C_4-C_7)$cycloalkylalkoxy, halo$(C_1-C_6)$alkoxy, halo$(C_3-C_6)$cycloalkoxy, halo$(C_4-C_7)$cycloalkylalkoxy, $(C_1-C_6)$alkylthio, $(C_3-C_6)$cycloalkythio, $(C_4-C_7)$cycloalkylalkylthio, halo$(C_1-C_6)$alkylthio, halo$(C_3-C_6)$cycloalkythio, halo$(C_4-C_7)$cycloalkylalkylthio, $(C_1-C_6)$alkanesulfinyl, $(C_3-C_6)$cycloalkanesulfinyl, $(C_4-C_7)$cycloalkylalkanesulfinyl, halo$(C_1-C_6)$alkanesulfinyl, halo$(C_3-C_6)$cycloalkanesulfinyl, halo$(C_4-C_7)$cycloalkylalkanesulfinyl, $(C_1-C_6)$alkanesulfonyl, $(C_3-C_6)$cycloalkanesulfonyl, $(C_4-C_7)$cycloalkyl-alkanesulfonyl, halo$(C_1-C_6)$alkanesulfonyl, halo$(C_3-C_6)$cycloalkanesulfonyl, halo$(C_4-C_7)$cycloalkyl-alkanesulfonyl, $(C_1-C_6)$alkylamino, di$(C_1-C_6)$alkylamino, $(C_1-C_6)$alkoxy$(C_1-C_6)$alkoxy, halo$(C_1-C_6)$alkoxy$(C_1-C_6)$alkoxy, $(C_1-C_6)$alkoxycarbonyl, $H_2NCO$, $H_2NSO_2$, $(C_1-C_6)$alkylaminocarbonyl, di$(C_1-C_6)$alkylaminocarbonyl, $(C_1-C_3)$alkoxy$(C_1-C_3)$alkylaminocarbonyl, heterocyclylcarbonyl, $(C_1-C_6)$alkylaminosulfonyl, di$(C_1-C_6)$alkylaminosulfonyl, heterocyclylsulfonyl, $(C_1-C_6)$alkylcarbonylamino, $(C_1-C_6)$alkylcarbonylamino$(C_1-C_6)$alkyl, $(C_1-C_6)$alkylsulfonylamino, $(C_1-C_6)$alkylsulfonylamino$(C_1-C_6)$alkyl, $(C_1-C_6)$alkoxycarbonyl$(C_1-C_6)$alkoxy, $(C_1-C_6)$alkoxy$(C_1-C_6)$alkyl, halo$(C_1-C_6)$alkoxy$(C_1-C_6)$alkyl, hydroxy$(C_1-C_6)$alkoxy, heteroaryl, oxo, amino$(C_1-C_6)$alkyl, $(C_1-C_6)$alkylamino$(C_1-C_6)$alkyl, di$(C_1-C_6)$alkylamino$(C_1-C_6)$alkyl amino$(C_2-C_6)$alkoxy, $(C_1-C_6)$alkylamino$(C_2-C_6)$alkoxy, di$(C_1-C_6)$alkylamino$(C_2-C_6)$alkoxy, $(C_1-C_6)$alkylcarbonyl, $(C_3-C_6)$cycloalkylcarbonyl, $(C_3-C_6)$cycloalkylaminocarbonyl, $\{(C_3-C_6)$cycloalkyl$\}\{(C_1-C_6)$alkyl$\}$aminocarbonyl, di$(C_3-C_6)$cycloalkylaminocarbonyl, $(C_3-C_6)$cycloalkylaminosulfonyl, $\{(C_3-C_6)$cycloalkyl$\}\{(C_1-C_6)$alkyl$\}$aminosulfonyl, di$(C_3-C_6)$cycloalkylaminosulfonyl, cyano$(C_1-C_6)$alkyl, aminocarbonyl$(C_1-C_6)$alkyl, $(C_1-C_6)$alkylaminocarbonyl$(C_1-C_6)$alkyl, di$(C_1-C_6)$alkylaminocarbonyl$(C_1-C_6)$alkyl, $(C_3-C_6)$cycloalkylaminocarbonyl$(C_1-C_6)$alkyl, $\{(C_3-C_6)$cycloalkyl$\}\{(C_1-C_6)$alkyl$\}$aminocarbonyl$(C_1-C_6)$alkyl and di$(C_3-C_6)$cycloalkylaminocarbonyl$(C_1-C_6)$alkyl;

E is (a) a bond or (b) $(C_1-C_3)$alkylene or $(C_1-C_2)$alkylenyloxy, wherein the O is attached to $R^2$, each of which is optionally substituted with 1 to 4 groups independently selected from methyl, ethyl, trifluoromethyl or oxo;

$R^2$ is $(C_1-C_6)$alkyl, aryl, heteroaryl, cycloalkyl or heterocyclyl and is optionally substituted with up to 4 groups independently selected from fluorine, chlorine, bromine, iodine, cyano, nitro, amino, hydroxy, carboxy, $(C_1-C_6)$alkyl, hydroxy$(C_1-C_6)$alkyl, $(C_3-C_6)$cycloalkyl, hydroxy$(C_3-C_6)$cycloalkyl, $(C_4-C_7)$cycloalkylalkyl, $(C_2-C_6)$alkenyl, halo$(C_2-C_6)$alkenyl, hydroxy$(C_2-C_6)$alkenyl, $(C_2-C_6)$alkynyl, $(C_3-C_6)$cycloalkyl$(C_2-C_4)$alkynyl, halo$(C_1-C_6)$alkyl, halo$(C_3-C_6)$cycloalkyl, halo$(C_4-C_7)$cycloalkylalkyl, $(C_1-C_6)$alkoxy, $(C_3-C_6)$cycloalkoxy, $(C_4-C_7)$cycloalkylalkoxy, halo$(C_1-C_6)$alkoxy, halo$(C_3-C_6)$cycloalkoxy, halo$(C_4-C_7)$cycloalkylalkoxy, $(C_1-C_6)$alkylthio, $(C_3-C_6)$cycloalkythio, $(C_4-C_7)$cycloalkylalkylthio, halo$(C_1-C_6)$alkylthio, halo$(C_3-C_6)$cycloalkythio, halo$(C_4-C_7)$cycloalkylalkylthio, $(C_1-C_6)$alkanesulfinyl, $(C_3-C_6)$cycloalkanesulfinyl, $(C_4-C_7)$cycloalkylalkanesulfinyl, halo$(C_1-C_6)$alkanesulfinyl, halo$(C_3-C_6)$cycloalkanesulfinyl, halo$(C_4-C_7)$cycloalkylalkanesulfinyl, $(C_1-C_6)$alkanesulfonyl, $(C_3-C_6)$cycloalkanesulfonyl, $(C_4-C_7)$cycloalkylalkanesulfonyl, halo$(C_1-C_6)$alkanesulfonyl, halo$(C_3-C_6)$cycloalkanesulfonyl, halo$(C_4-C_7)$cyclo-alkylalkanesulfonyl, $(C_1-C_6)$alkylamino, di$(C_1-C_6)$alkylamino, $(C_1-C_6)$alkoxy$(C_1-C_6)$alkoxy, halo$(C_1-C_6)$alkoxy$(C_1-C_6)$alkoxy, $(C_1-C_6)$alkoxycarbonyl, $H_2NCO$, $H_2NSO_2$, $(C_1-C_6)$alkylaminocarbonyl, di$(C_1-C_6)$alkylaminocarbonyl, $(C_1-C_3)$alkoxy$(C_1-C_3)$alkylaminocarbonyl, heterocyclylcarbonyl, $(C_1-C_6)$alkylaminosulfonyl, di$(C_1-C_6)$alkylaminosulfonyl, heterocyclylsulfonyl, $(C_1-C_6)$alkylcarbonylamino, $(C_1-C_6)$alkylcarbonylamino$(C_1-C_6)$alkyl, $(C_1-C_6)$alkylsulfonylamino, $(C_1-C_6)$alkylsulfonylamino$(C_1-C_6)$alkyl, $(C_1-C_6)$alkoxycarbonyl$(C_1-C_6)$alkoxy, $(C_1-C_6)$alkoxy$(C_1-C_6)$alkyl, halo$(C_1-C_6)$alkoxy$(C_1-C_6)$alkyl, hydroxy$(C_1-C_6)$alkoxy, heteroaryl, oxo, amino$(C_1-C_6)$alkyl, $(C_1-C_6)$alkylamino$(C_1-C_6)$alkyl, di$(C_1-C_6)$alkylamino$(C_1-C_6)$alkyl amino$(C_2-C_6)$alkoxy, $(C_1-C_6)$alkylamino$(C_2-C_6)$alkoxy, di$(C_1-C_6)$alkylamino$(C_2-C_6)$alkoxy, $(C_1-C_6)$alkylcarbonyl, $(C_3-C_6)$cycloalkylcarbonyl, $(C_3-C_6)$cycloalkylaminocarbonyl, $\{(C_3-C_6)$cycloalkyl$\}\{(C_1-C_6)$alkyl$\}$aminocarbonyl, di$(C_3-C_6)$cycloalkylaminocarbonyl, $(C_3-C_6)$cycloalkylaminosulfonyl, $\{(C_3-C_6)$cycloalkyl$\}\{(C_1-C_6)$alkyl$\}$aminosulfonyl, di$(C_3-C_6)$cycloalkylaminosulfonyl, cyano$(C_1-C_6)$alkyl, aminocarbonyl$(C_1-C_6)$alkyl, $(C_1-C_6)$alkylaminocarbonyl$(C_1-C_6)$alkyl, di$(C_1-C_6)$alkylaminocarbonyl$(C_1-C_6)$alkyl, $(C_3-C_6)$cycloalkylaminocarbonyl$(C_1-C_6)$alkyl, $\{(C_3-C_6)$cycloalkyl$\}\{(C_1-C_6)$alkyl$\}$aminocarbonyl$(C_1-C_6)$alkyl and di$(C_3-C_6)$cycloalkylaminocarbonyl$(C_1-C_6)$alkyl;

$R^3$ is selected from $(C_1-C_6)$alkyl, $(C_2-C_6)$alkenyl, $(C_2-C_6)$alkynyl, $(C_3-C_5)$cycloalkyl$(C_1-C_4)$alkyl, $(C_1-C_3)$alkoxy$(C_1-C_3)$alkoxy, or $(C_1-C_3)$alkoxy$(C_1-C_3)$alkyl and is optionally substituted with up to four groups independently selected from fluorine, cyano, oxo, $R^4$, $R^4O—$, $(R^4)_2N—$, $R^4O_2C—$, $R^4C(=O)O—$, $R^4S$, $R^4S(=O)—$, $R^4S(=O)_2—$, $R^4C(=O)NR^4—$, $(R^4)_2NC(=O)—$, $(R^4)_2NC(=O)O—$, $(R^4)_2NC(=O)NR^4—$, $R^4OC(=O)NR^4—$, $(R^4)_2NC(=NCN)NR^4—$, $(R^4O)_2P(=O)O—$, $(R^4O)_2P(=O)NR^4—$, $R^4OS(=O)_2NR^4—$, $(R^4)_2NS(=O)_2O—$, $(R^4)_2NS(=O)_2NR^4—$, $R^4S(=O)_2NR^4—$, $R^4S(=O)_2NHC(=O)—$, $R^4S(=O)_2NHC(=O)O—$, $R^4S(=O)_2NHC(=O)NR^4—$, $R^4OS(=O)_2NHC(=O)—$, $R^4OS(=O)_2NHC(=O)O—$, $R^4OS(=O)_2NHC(=O)NR^4—$, $(R^4)_2NS(=O)_2NHC(=O)—$, $(R^4)_2NS(=O)_2NHC(=O)O—$, $(R^4)_2NS(=O)_2NHC(=O)NR^4—$, $R^4C(=O)NHS(=O)_2—$, $R^4C(=O)NHS(=O)_2O—$, $R^4C(=O)NHS(=O)_2NR^4—$, $R^4OC(=O)NHS(=O)_2—$, $R^4OC(=O)NHS(=O)_2O—$, $R^4OC(=O)NHS(=O)_2NR^4—$, $(R^4)_2NC(=O)NHS(=O)_2—$, $(R^4)_2NC(=O)NHS(=O)_2O—$, $(R^4)_2NC(=O)NHS(=O)_2NR^4—$, spirocycloalkyl; heterocyclyl (which in turn may be optionally substituted with alkyl, haloalkyl, halogen or oxo), heteroaryl (which in turn may be optionally substituted with alkyl, haloalkyl, alkoxy, alkylthio, alkylsulfonyl, halogen, trifluoromethyl, dialkylamino, nitro, cyano, $CO_2H$, $CONH_2$, N-monoalkyl-substituted amido, N,N-dialkyl-substituted amido, or oxo), arylamino (which in turn may be optionally substituted with alkyl, alkoxy, alkylthio, alkylsulfonyl, halogen, trifluoromethyl, dialkylamino, nitro, cyano, $CO_2H$, $CONH_2$, N-monoalkyl-substituted amido and N,N-dialkyl-substituted amido) and heteroarylamino (which in turn may be optionally substituted with alkyl, haloalkyl, alkoxy, alkylthio, alkylsulfonyl, halogen, trifluoromethyl, dialkylamino, nitro, cyano, $CO_2H$, $CONH_2$, N-monoalkyl-substituted amido, N,N-dialkyl-substituted amido, or oxo); and $R^4$ is independently selected from H, $(C_1-C_6)$alkyl, halo$(C_1-C_6)$alkyl, amino$(C_1-C_6)$alkyl, $(C_1-C_6)$alkylamino$(C_1-C_6)$alkyl, di$(C_1-C_6)$alkylamino$(C_1-C_6)$alkyl, hydroxy$(C_1-C_6)$alkyl and $(C_1-C_6)$alkoxy$(C_1-C_6)$alkyl.

Alternatively, the first embodiment above excludes the compounds of structural formulas PR-205, PR-211, PR-214, PR-222, PR-225, PR-235, PR-236, PR-281, PR-292, PR-295, PR-298, PR-300, PR-302, PR-305, PR-304, PR-306, PR-307, PR-210, PR-296, PR-311, PR-230, PR-244, PR-258 and PR-291 or a pharmaceutically acceptable salt, enantiomer or diastereomer thereof.

Alternatively, the first embodiment above excludes the compounds of structural formulas PR-205, PR-211, PR-214, PR-222, PR-225, PR-235, PR-236, PR-281, PR-292, PR-295, PR-298, PR-300, PR-302, PR-305, PR-304, PR-306, PR-307, PR-210, PR-296, PR-311, PR-230, PR-244, PR-258 and PR-291, or a pharmaceutically acceptable salt, enantiomer or diastereomer thereof, and the compound of Example 32, Example 33, (R)-6-allyl-3-((S)-1-(4-(6-aminopyridin-3-yl)phenyl)ethyl)-6-phenyl-1,3-oxazinan-2-one, (R)-3-((S)-1-(4-(6-aminopyridin-3-yl)phenyl)ethyl)-6-(3-hydroxypropyl)-6-phenyl-1,3-oxazinan-2-one, (R)-6-(3-hydroxypropyl)-3-((S)-1-(4-(6-oxo-1,6-dihydropyridin-3-yl)phenyl)ethyl)-6-phenyl-1,3-oxazinan-2-one, (R)-6-allyl-6-(4-fluorophenyl)-3-((S)-1-(4-(pyridin-3-yl)phenyl)ethyl)-1,3-oxazinan-2-one, (R)-6-(2-aminoethyl)-6-phenyl-3-((S)-1-(4-(pyridin-3-yl)phenyl)ethyl)-1,3-oxazinan-2-one and (R)-6-(3-hydroxypropyl)-3-((S)-1-(4-(1-methyl-6-oxo-1,6-dihydropyridin-3-yl)phenyl)ethyl)-6-phenyl-1,3-oxazinan-2-one, (R)-6-allyl-6-phenyl-3-((S)-1-(4-(pyridin-3-yl)phenyl)ethyl)-1,3-oxazinan-2-one, (R)-6-allyl-6-(4-fluorophenyl)-3-((S)-1-(4-(pyridin-3-yl)phenyl)ethyl)-1,3-oxazinan-2-one, 3-((R)-6-(4-fluorophenyl)-2-oxo-3-((S)-1-(4-(pyridin-3-yl)phenyl)ethyl)-1,3-oxazinan-6-yl)propanoic acid, 3-((R)-2-oxo-6-phenyl-3-((S)-1-(4-(pyridin-4-yl)phenyl)ethyl)-1,3-oxazinan-6-yl)propanoic acid, (R)-6-allyl-6-phenyl-3-((S)-1-(4-(pyridin-4-yl)phenyl)ethyl)-1,3-oxazinan-2-one, (R)-6-allyl-3-((S)-1-(4-(6-methoxypyridin-3-yl)phenyl)ethyl)-6-phenyl-1,3-oxazinan-2-one, (R)-3-((S)-1-(4-(1H-pyrazol-3-yl)phenyl)ethyl)-6-allyl-6-phenyl-1,3-oxazinan-2-one, or a pharmaceutically acceptable salt, enantiomer or diastereomer thereof.

Another embodiment of the invention is a pharmaceutical composition comprising i) a pharmaceutically acceptable carrier or diluent, and ii) a compound of Formulas I, Ik, $Iq^{1-21}$, $Ir^{1-21}$, $Is^{1-21}$ or $It^{1-7}$, or a pharmaceutically acceptable salt, enantiomer or diastereomer thereof.

Another embodiment of the invention is a method of inhibiting 11β-HSD1 activity comprising the step of administering to a mammal in need of such treatment an effective amount of a compound of Formulas I, Ik, $Iq^{1-21}$, $Ir^{1-21}$, $Is^{1-21}$ or $It^{1-7}$, or a pharmaceutically acceptable salt, enantiomer or diastereomer thereof.

Another embodiment of the invention is a method of treating a subject with a disease associated with the activity or expression of 11β-HSD1, comprising the step of administering to the subject an effective amount of a compound of Formulas I, Ik, Iq$^{1-21}$, Ir$^{1-21}$, Is$^{1-21}$ or It$^{1-7}$, or a pharmaceutically acceptable salt, enantiomer or diastereomer thereof.

Another embodiment of the invention is the use of a compound of Formulas I, Ik, Iq$^{1-21}$, Ir$^{1-21}$, Is$^{1-21}$ or It$^{1-7}$, or a pharmaceutically acceptable salt, enantiomer or diastereomer thereof for the manufacture of a medicament for inhibiting 11β-HSD1 activity in a mammal in need of such treatment.

Another embodiment of the invention is the use of a compound of Formulas I, Ik, Iq$^{1-21}$, Ir$^{1-21}$, Is$^{1-21}$ or It$^{1-7}$, or a pharmaceutically acceptable salt, enantiomer or diastereomer thereof for the manufacture of a medicament for treating a subject with a disease associated with the activity or expression of 11β-HSD1.

Another embodiment of the invention is a compound of Formulas I, Ik, Iq$^{1-21}$, Ir$^{1-21}$, Is$^{1-21}$ or It$^{1-7}$, or a pharmaceutically acceptable salt, enantiomer or diastereomer thereof for use in inhibiting 11β-HSD1 activity in a mammal in need of such treatment.

Another embodiment of the invention is a compound of I, Ik, Iq$^{1-21}$, Ir$^{1-21}$, Is$^{1-21}$ or It$^{1-7}$, or a pharmaceutically acceptable salt, enantiomer or diastereomer thereof for use in for treating a subject with a disease associated with the activity or expression of 11β-HSD1.

DETAILED DESCRIPTION OF THE INVENTION

Another embodiment of the invention is a compound of Formula Ik:

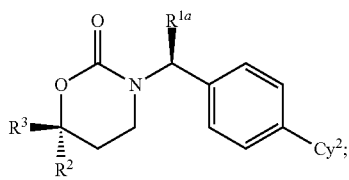

Ik or a pharmaceutically acceptable salt thereof;

$R^{1a}$ is absent or is methyl or ethyl;

$Cy^2$ is pyridyl, thiazolyl or pyrazolyl and is optionally substituted by 1 to 4 groups independently selected from halo, hydroxy, methoxy, hydroxymethyl, methoxycarbonyl, amino, carbamoyl, methylcarbamoyl, dimethylcarbamoyl, (2-methoxyethyl)aminocarbonyl, acetylaminomethyl, methylsulfonyl, methylsulfonylamino, methylaminosulfonyl, isopropylaminosulfonyl, dimethylaminosulfonyl, pyrrolidine-1-sulfonyl, methylsulfonylaminomethyl, tetrazolyl, methyl, trifluoromethyl, acetyl, 2-hydroxyethyl and 1-aminoethyl;

$R^2$ is phenyl, thienyl, pyridyl or isopropyl each optionally substituted with halo, methyl, methylthio or (4-morpholino)methyl; and $R^3$ is methyl, ethyl, propyl, butyl, vinyl, allyl or ethoxyethyl each optionally substituted with up to two groups independently selected from Methyl, HO—, MeO—, H$_2$N—, MeC(═O)NH—, MeS(═O)$_2$NH—, H$_2$NC(═O)—, MeNHC(═O)—, HO$_2$C—, (HO)$_2$P(═O)O—, H$_2$NS(═O)$_2$O—, H$_2$NS(═O)$_2$NH—, MeNHC(═O)NH—, MeNHC(═O)O—, oxo, cyano, HO$_2$C—, HOCH$_2$CH$_2$NH—, 4-morpholino, HOCH$_2$C(═O)NH—, H$_2$NCH$_2$C(═O)NH—, EtNHC(═O)NH, MeOC(═O)NH—, MeNHC(═NC≡N)NH—, Me-, MeS—, MeSO$_2$— MeSO$_2$N(Me)—, MeS(═O)$_2$ NHC(═O)—, imidazolylamino-, imidazolyl, tetrazolyl, H$_2$NCONH—, H$_2$NCO$_2$—, HOCH$_2$CH$_2$O—, MeNH—, Me$_2$N— and MeCONMe.

Another embodiment of the invention is a compound of Formula Ik, or a pharmaceutically acceptable salt, enantiomer or diastereomer thereof; $R^{1a}$ is absent or is methyl or ethyl; $Cy^2$ is optionally substituted pyridazinyl or pyrimidinyl; $R^2$ is (C$_1$-C$_6$)alkyl, aryl, heteroaryl, cycloalkyl or heterocyclyl and is optionally substituted with up to 4 groups independently selected from fluorine, chlorine, bromine, iodine, cyano, nitro, amino, hydroxy, carboxy, (C$_1$-C$_6$)alkyl, hydroxy(C$_1$-C$_6$)alkyl, (C$_3$-C$_6$)cycloalkyl, hydroxy(C$_3$-C$_6$)cycloalkyl, (C$_4$-C$_7$)cycloalkylalkyl, (C$_2$-C$_6$)alkenyl, halo(C$_2$-C$_6$)alkenyl, hydroxy(C$_2$-C$_6$)alkenyl, (C$_2$-C$_6$)alkynyl, (C$_3$-C$_6$)cycloalkyl(C$_2$-C$_4$)alkynyl, halo(C$_1$-C$_6$)alkyl, halo(C$_3$-C$_6$)cycloalkyl, halo(C$_4$-C$_7$)cycloalkylalkyl, (C$_1$-C$_6$)alkoxy, (C$_3$-C$_6$)cycloalkoxy, (C$_4$-C$_7$)cycloalkylalkoxy, halo(C$_1$-C$_6$)alkoxy, halo(C$_3$-C$_6$)cycloalkoxy, halo(C$_4$-C$_7$)cycloalkylalkoxy, (C$_1$-C$_6$)alkylthio, (C$_3$-C$_6$)cycloalkythio, (C$_4$-C$_7$)cycloalkylalkylthio, halo(C$_1$-C$_6$)alkylthio, halo(C$_3$-C$_6$)cycloalkythio, halo(C$_4$-C$_7$)cycloalkylalkylthio, (C$_1$-C$_6$)alkanesulfinyl, (C$_3$-C$_6$)cycloalkanesulfinyl, (C$_4$-C$_7$)cycloalkylalkanesulfinyl, halo(C$_1$-C$_6$)alkanesulfinyl, halo(C$_3$-C$_6$)cycloalkanesulfinyl, halo(C$_4$-C$_7$)cycloalkylalkanesulfinyl, (C$_1$-C$_6$)alkanesulfonyl, (C$_3$-C$_6$)cycloalkanesulfonyl, (C$_4$-C$_7$)cycloalkyl-alkanesulfonyl, halo(C$_1$-C$_6$)alkanesulfonyl, halo(C$_3$-C$_6$)cycloalkanesulfonyl, halo(C$_4$-C$_7$)cyclo-alkylalkanesulfonyl, (C$_1$-C$_6$)alkylamino, di(C$_1$-C$_6$)alkylamino, (C$_1$-C$_6$)alkoxy(C$_1$-C$_6$)alkoxy, halo(C$_1$-C$_6$)alkoxy(C$_1$-C$_6$)alkoxy, (C$_1$-C$_6$)alkoxycarbonyl, H$_2$NCO, H$_2$NSO$_2$, (C$_1$-C$_6$)alkylaminocarbonyl, di(C$_1$-C$_6$)alkylaminocarbonyl, (C$_1$-C$_3$)alkoxy(C$_1$-C$_3$)alkylaminocarbonyl, heterocyclylcarbonyl, (C$_1$-C$_6$)alkylaminosulfonyl, di(C$_1$-C$_6$)alkylaminosulfonyl, heterocyclylsulfonyl, (C$_1$-C$_6$)alkylcarbonylamino, (C$_1$-C$_6$)alkylcarbonylamino(C$_1$-C$_6$)alkyl, (C$_1$-C$_6$)alkylsulfonylamino, (C$_1$-C$_6$)alkylsulfonylamino(C$_1$-C$_6$)alkyl, (C$_1$-C$_6$)alkoxycarbonyl(C$_1$-C$_6$)alkoxy, (C$_1$-C$_6$)alkoxy(C$_1$-C$_6$)alkyl, halo(C$_1$-C$_6$)alkoxy(C$_1$-C$_6$)alkyl, hydroxy(C$_1$-C$_6$)alkoxy, heteroaryl, oxo, amino(C$_1$-C$_6$)alkyl, (C$_1$-C$_6$)alkylamino(C$_1$-C$_6$)alkyl, di(C$_1$-C$_6$)alkylamino(C$_1$-C$_6$)alkyl amino(C$_2$-C$_6$)alkoxy, (C$_1$-C$_6$)alkylamino(C$_2$-C$_6$)alkoxy, di(C$_1$-C$_6$)alkylamino(C$_2$-C$_6$)alkoxy and (C$_1$-C$_6$)alkylcarbonyl; and $R^3$ is as defined above in the first embodiment.

Another embodiment of the invention is a compound of any one of Formulas Iq$^{1-21}$ or a pharmaceutically acceptable salt, enantiomer or diastereomer thereof:

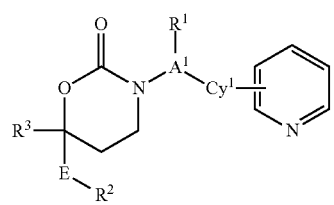

Iq$^1$

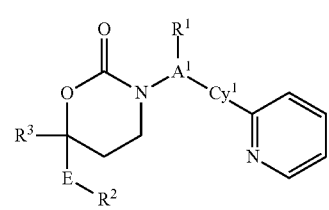

Iq$^2$

-continued
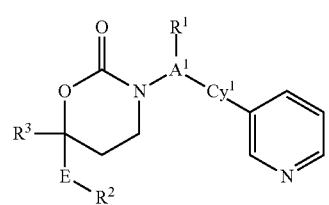
Iq³
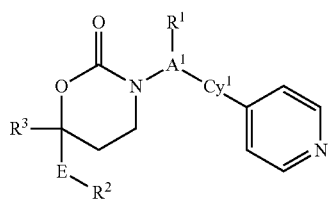
Iq⁴
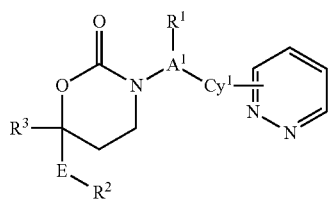
Iq⁵
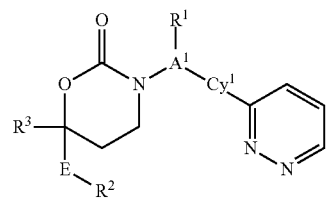
Iq⁶
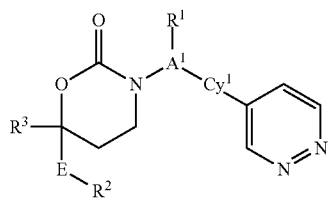
Iq⁷
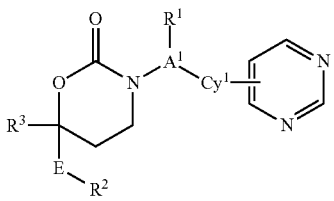
Iq⁸
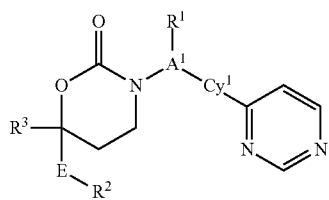
Iq⁹
-continued
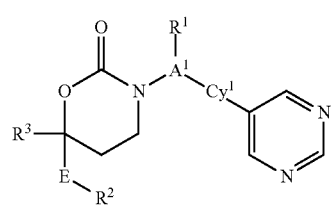
Iq¹⁰
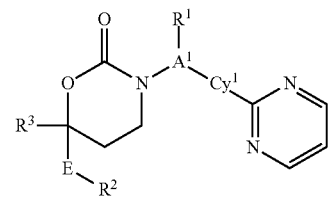
Iq¹¹
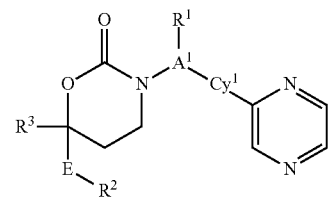
Iq¹²
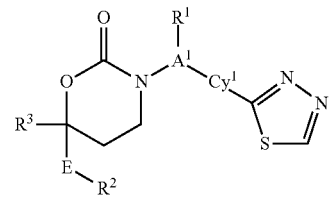
Iq¹³
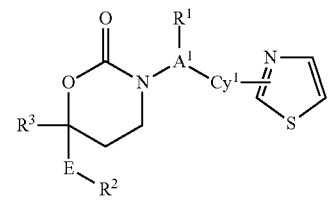
Iq¹⁴
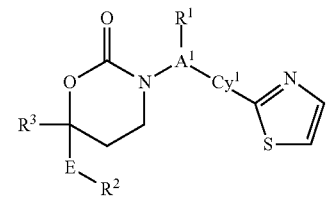
Iq¹⁵
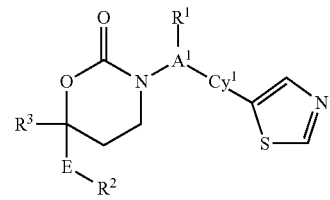
Iq¹⁶

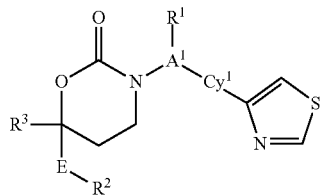

Iq17

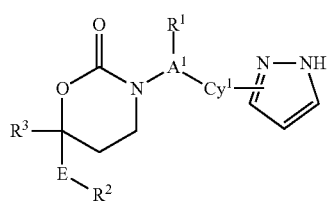

Iq18

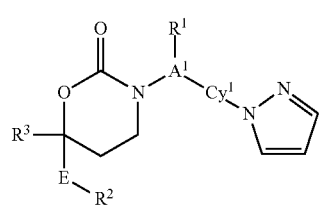

Iq19

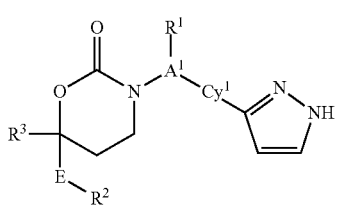

Iq20

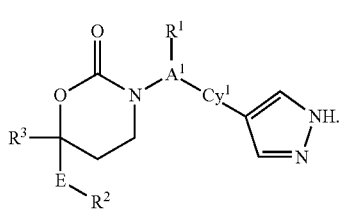

Iq21

In Formulas Iq$^{1-21}$, the pyridine, pyridazine, pyrimidine, pyrazine, pyrazole, thiazole and thiadiazole rings are optionally substituted (substitution at ring carbons bonded to hydrogen and ring nitrogen atoms bonded to hydrogen atoms are encompassed, i.e., a "substitutable ring nitrogen atom") with up to four substituents as described for Cy$^2$ in the first embodiment. Suitable substituents for Cy$^2$ and suitable values for R$^1$, R$^2$, R$^3$, A$^1$, Cy$^1$ and E are as defined above in the first embodiment. Alternatively, suitable substituents for Cy$^1$ and the pyridine, pyridazine, pyrimidine, pyrazine, pyrazole, thiazole and thiadiazole rings in Formulas Iq$^{1-21}$ are independently fluorine, chlorine, bromine, iodine, cyano, nitro, amino, hydroxy, carboxy, (C$_1$-C$_6$)alkyl, hydroxy(C$_1$-C$_6$)alkyl, (C$_3$-C$_6$)cycloalkyl, hydroxy(C$_3$-C$_6$)cycloalkyl, (C$_4$-C$_7$)cycloalkylalkyl, (C$_2$-C$_6$)alkenyl, halo(C$_2$-C$_6$)alkenyl, hydroxy(C$_2$-C$_6$)alkenyl, (C$_2$-C$_6$)alkynyl, (C$_3$-C$_6$)cycloalkyl (C$_2$-C$_4$)alkynyl, halo(C$_1$-C$_6$)alkyl, halo(C$_3$-C$_6$)cycloalkyl, halo(C$_4$-C$_7$)cycloalkylalkyl, (C$_1$-C$_6$)alkoxy, (C$_3$-C$_6$)cycloalkoxy, (C$_4$-C$_7$)cycloalkylalkoxy, halo(C$_1$-C$_6$)alkoxy, halo(C$_3$-C$_6$)cycloalkoxy, halo(C$_4$-C$_7$)cycloalkylalkoxy, (C$_1$-C$_6$)alkylthio, (C$_3$-C$_6$)cycloalkythio, (C$_4$-C$_7$)cycloalkylalkylthio, halo(C$_1$-C$_6$)alkylthio, halo(C$_3$-C$_6$)cycloalkythio, halo(C$_4$-C$_7$)cycloalkylalkylthio, (C$_1$-C$_6$)alkanesulfinyl, (C$_3$-C$_6$)cycloalkanesulfinyl, (C$_4$-C$_7$)cycloalkylalkanesulfinyl, halo(C$_1$-C$_6$)alkanesulfinyl, halo(C$_3$-C$_6$)cycloalkanesulfinyl, halo(C$_4$-C$_7$)cycloalkylalkanesulfinyl, (C$_1$-C$_6$)alkanesulfonyl, (C$_3$-C$_6$)cycloalkanesulfonyl, (C$_4$-C$_7$)cycloalkyl-alkanesulfonyl, halo(C$_1$-C$_6$)alkanesulfonyl, halo(C$_3$-C$_6$)cycloalkanesulfonyl, halo(C$_4$-C$_7$)cyclo-alkylalkanesulfonyl, (C$_1$-C$_6$)alkylamino, di(C$_1$-C$_6$)alkylamino, (C$_1$-C$_6$)alkoxy(C$_1$-C$_6$)alkoxy, halo(C$_1$-C$_6$)alkoxy(C$_1$-C$_6$)alkoxy, (C$_1$-C$_6$)alkoxycarbonyl, H$_2$NCO, H$_2$NSO$_2$, (C$_1$-C$_6$)alkylaminocarbonyl, di(C$_1$-C$_6$)alkylaminocarbonyl, (C$_1$-C$_3$)alkoxy(C$_1$-C$_3$)alkylaminocarbonyl, heterocyclylcarbonyl, (C$_1$-C$_6$)alkylaminosulfonyl, di(C$_1$-C$_6$)alkylaminosulfonyl, heterocyclylsulfonyl, (C$_1$-C$_6$)alkylcarbonylamino, (C$_1$-C$_6$)alkylcarbonylamino(C$_1$-C$_6$)alkyl, (C$_1$-C$_6$)alkylsulfonylamino, (C$_1$-C$_6$)alkylsulfonylamino(C$_1$-C$_6$)alkyl, (C$_1$-C$_6$)alkoxycarbonyl(C$_1$-C$_6$)alkoxy, (C$_1$-C$_6$)alkoxy(C$_1$-C$_6$)alkyl, halo(C$_1$-C$_6$)alkoxy(C$_1$-C$_6$)alkyl, hydroxy(C$_1$-C$_6$)alkoxy, heteroaryl, amino(C$_1$-C$_6$)alkyl, (C$_1$-C$_6$)alkylamino(C$_1$-C$_6$)alkyl, di(C$_1$-C$_6$)alkylamino(C$_1$-C$_6$)alkyl amino(C$_2$-C$_6$)alkoxy, (C$_1$-C$_6$)alkylamino(C$_2$-C$_6$)alkoxy, di(C$_1$-C$_6$)alkylamino(C$_2$-C$_6$)alkoxy, (C$_1$-C$_6$)alkylcarbonyl, (C$_3$-C$_6$)cycloalkylcarbonyl, (C$_3$-C$_6$)cycloalkylaminocarbonyl, {(C$_3$-C$_6$)cycloalkyl}{(C$_1$-C$_6$)alkyl}aminocarbonyl, di(C$_3$-C$_6$)cycloalkylaminocarbonyl, (C$_3$-C$_6$)cycloalkylaminosulfonyl, {(C$_3$-C$_6$)cycloalkyl}{(C$_1$-C$_6$)alkyl}aminosulfonyl, di(C$_3$-C$_6$)cycloalkylaminosulfonyl, cyano(C$_1$-C$_6$)alkyl, aminocarbonyl(C$_1$-C$_6$)alkyl, (C$_1$-C$_6$)alkylaminocarbonyl(C$_1$-C$_6$)alkyl, di(C$_1$-C$_6$)alkylaminocarbonyl(C$_1$-C$_6$)alkyl, (C$_3$-C$_6$)cycloalkylaminocarbonyl(C$_1$-C$_6$)alkyl, {(C$_3$-C$_6$)cycloalkyl}{(C$_1$-C$_6$)alkyl}aminocarbonyl(C$_1$-C$_6$)alkyl and di(C$_3$-C$_6$)cycloalkylaminocarbonyl(C$_1$-C$_6$)alkyl; and values for R$^1$, R$^2$, R$^3$, A$^1$, Cy$^1$ and E are as defined above in the first embodiment. Alternatively, suitable substituents for Cy$^1$ include (C$_1$-C$_4$)alkyl, (C$_1$-C$_4$)alkoxy, (C$_1$-C$_4$)haloalkyl, (C$_1$-C$_4$)haloalkoxy, halogen, cyano and nitro; suitable substituents for a substitutable ring nitrogen atom in the pyrazole rings in Formulas Iq$^{18}$, Iq$^{20}$ and Iq$^{21}$ include (C$_1$-C$_4$)alkyl, (C$_3$-C$_4$)cycloalkyl, (C$_3$-C$_4$)cycloalkyl(C$_1$-C$_2$)alkyl, and (C$_1$-C$_4$)haloalkyl; suitable substituents for a ring carbon atom in the pyridine, pyridazine, pyrimidine, pyrazine, pyrazole, thiazole and thiadiazole rings in Formulas Iq$^{1-21}$ include fluorine, chlorine, cyano, amino, (C$_1$-C$_4$)alkyl, (C$_3$-C$_4$)cycloalkyl, (C$_3$-C$_4$)cycloalkyl(C$_1$-C$_2$)alkyl, halo(C$_1$-C$_4$)alkyl, (C$_1$-C$_4$)alkoxy, (C$_1$-C$_4$)haloalkoxy, CONH$_2$, (C$_1$-C$_4$)alkylaminocarbonyl, di(C$_1$-C$_4$)alkylaminocarbonyl, (C$_3$-C$_4$)cycloalkylaminocarbonyl, {(C$_1$-C$_4$)alkyl}{(C$_3$-C$_4$)cycloalkyl}aminocarbonyl and (C$_1$-C$_4$)alkylcarbonylamino; the ring nitrogen in the pyridine rings in Formulas Iq$^{1-4}$ is optionally substituted by oxo; and suitable values for R$^1$, R$^2$, R$^3$, A$^1$, Cy$^1$ and E are as defined the first embodiment. In another alternative, the embodiments in this paragraph exclude the following compounds:

15

(S)-6-(2-hydroxyethyl)-6-phenyl-3-((S)-1-(4-(pyridin-3-yl)phenyl)ethyl)-1,3-oxazinan-2-one (PR-205)

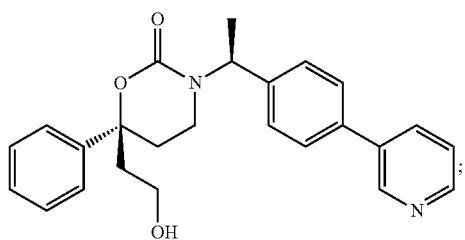

(R)-6-(3-hydroxypropyl)-6-phenyl-3-((S)-1-(4-(pyridin-3-yl)phenyl)ethyl)-1,3-oxazinan-2-one (PR-211)

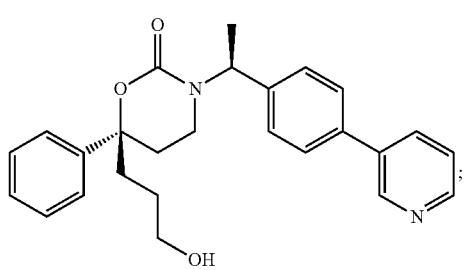

(S)-6-(4-fluorophenyl)-6-(2-hydroxyethyl)-3-((S)-1-(4-(pyridin-3-yl)phenyl)ethyl)-1,3-oxazinan-2-one (PR-214)

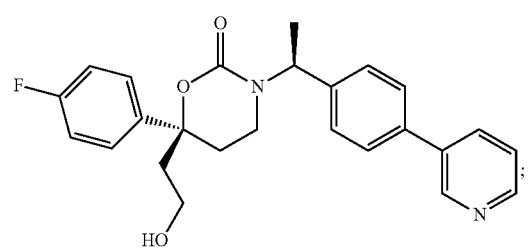

16

3-(4-((S)-1-((R)-6-(3-hydroxypropyl)-2-oxo-6-phenyl-1,3-oxazinan-3-yl)ethyl)phenyl)pyridine 1-oxide (PR-222)

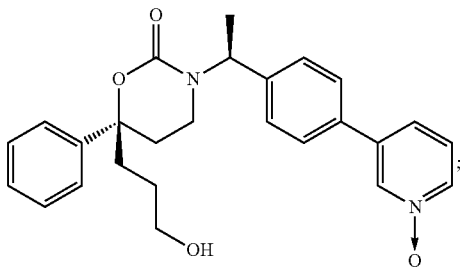

(R)-6-(4-fluorophenyl)-6-(3-hydroxypropyl)-3-((S)-1-(4-(pyridin-3-yl)phenyl)ethyl)-1,3

(PR-225)

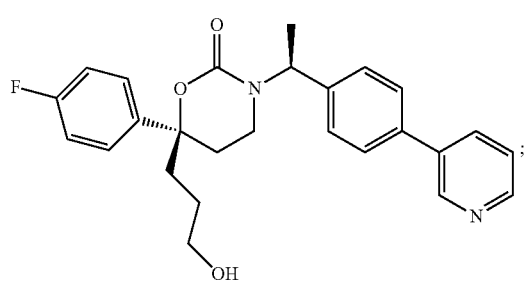

(R)-6-(3-hydroxypropyl)-3-((S)-1-(4-(6-methoxypyridin-3-yl)phenyl)ethyl)-6-phenyl-1,3-oxazinan-2-one (PR-235)

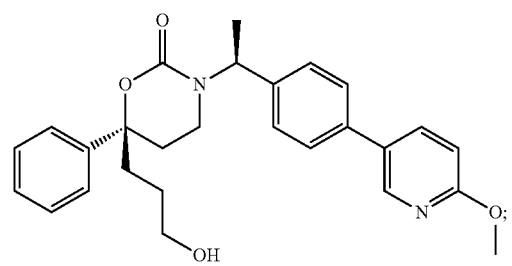

| 17 | 18 |

3-((R)-6-(4-fluorophenyl)-2-oxo-3-((S)-1-(4-(pyridin-3-yl)phenyl)ethyl)-1,3-oxazinan-6-yl)propanamide 3-((R)-2-oxo-6-phenyl-3-((S)-1-(4-(pyridin-3-yl)phenyl)ethyl)-1,3-oxazinan-6-yl)propanamide (PR-236)

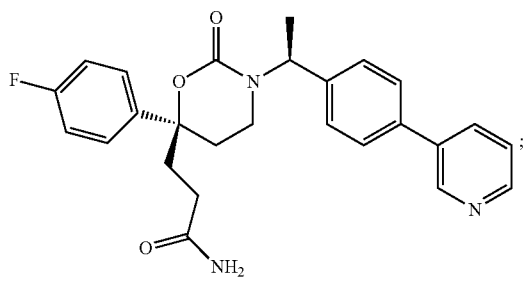

(PR-295)

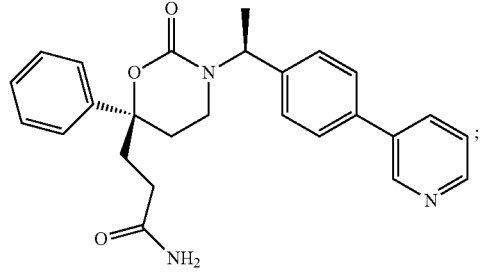

(R)-6-(4-fluorophenyl)-6-(3-hydroxypropyl)-3-((S)-1-(4-(6-(trifluoromethyl)pyridin-3-yl)phenyl)ethyl)-1,3-oxazinan-2-one (R)-3-((S)-1-(4-(5-fluoropyridin-3-yl)phenyl)ethyl)-6-(3-hydroxypropyl)-6-phenyl-1,3-oxazinan-2-one (PR-281)

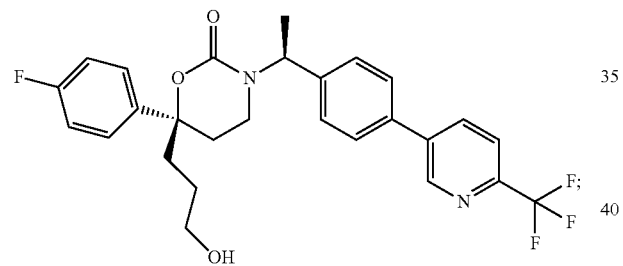

(PR-298)

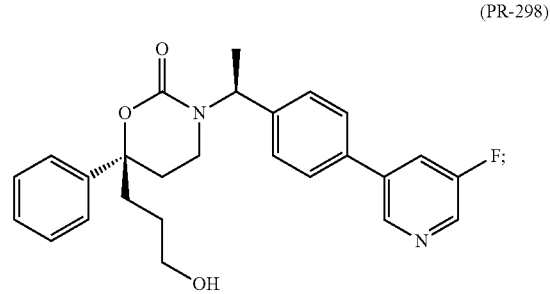 [SMILES: C[C@@H](c1ccc(-c2cncc(F)c2)cc1)N1CC[C@](CCCO)(c2ccccc2)OC1=O]

(R)-6-allyl-3-((S)-1-(4-(5-fluoropyridin-3-yl)phenyl)ethyl)-6-phenyl-1,3-oxazinan-2-one 3-(4-((S)-1-((R)-6-(3-amino-3-oxopropyl)-2-oxo-6-phenyl-1,3-oxazinan-3-yl)ethyl)phenyl)pyridine 1-oxide (PR-292)

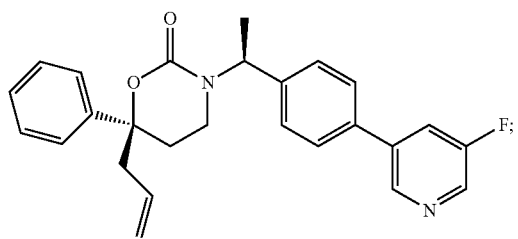

(PR-300)

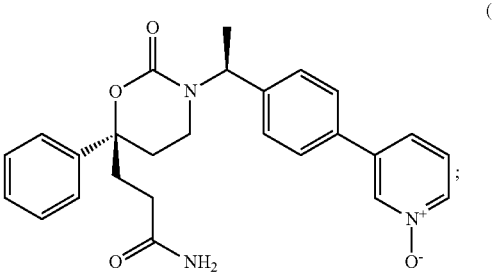

19

(R)-6-allyl-6-(4-fluorophenyl)-3-((S)-1-(4-(5-fluoro-pyridin-3-yl)phenyl)ethyl)-1,3-oxazinan-2-one (PR-302)

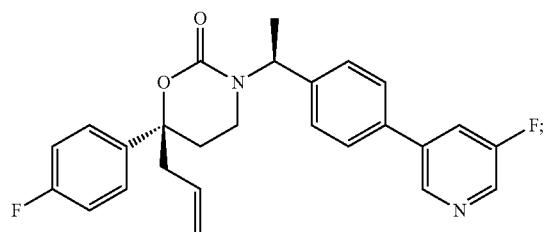

20

(R)-6-allyl-3-((S)-1-(4-(5-chloropyridin-3-yl)phenyl)ethyl)-6-(4-fluorophenyl)-1,3-oxazinan-2-one (PR-306)

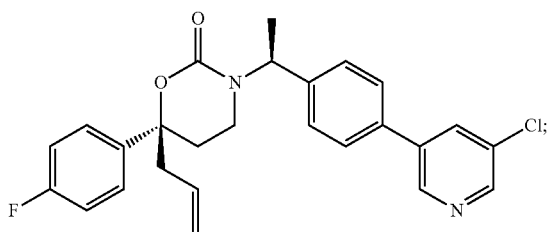

(R)-6-(4-fluorophenyl)-6-(3-hydroxypropyl)-3-((S)-1-(4-(5-methoxypyridin-3-yl)phenyl)ethyl)-1,3-oxazinan-2-one

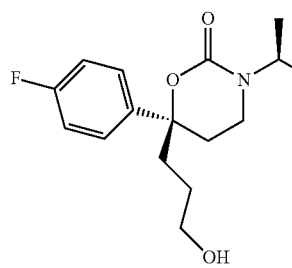

N-(2-((S)-2-oxo-6-phenyl-3-((S)-1-(4-(pyridin-3-yl)phenyl)ethyl)-1,3-oxazinan-6-yl)ethyl)methanesulfonamide (PR-307)

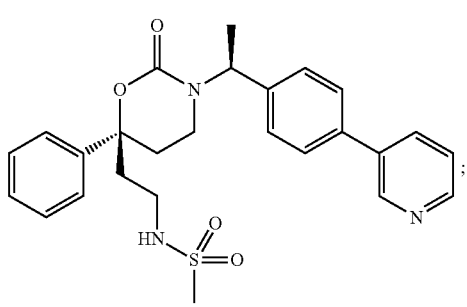

3-((R)-3-((S)-1-(4-(6-methoxypyridin-3-yl)phenyl)ethyl)-2-oxo-6-phenyl-1,3-oxazinan-6-yl)propanamide (PR-304)

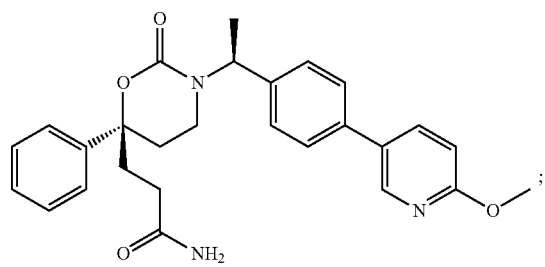

(R)-6-(3-hydroxypropyl)-6-phenyl-3-((S)-1-(4-(pyridin-4-yl)phenyl)ethyl)-1,3-oxazinan-2-one (PR-210)

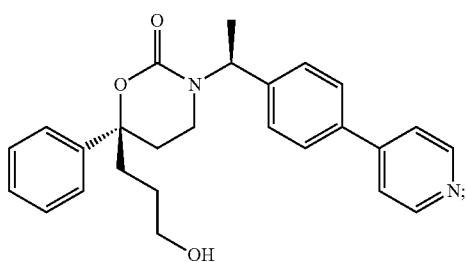

21

3-((R)-2-oxo-6-phenyl-3-((S)-1-(4-(pyridin-4-yl)
phenyl)ethyl)-1,3-oxazinan-6-yl)propanamide (PR-296)

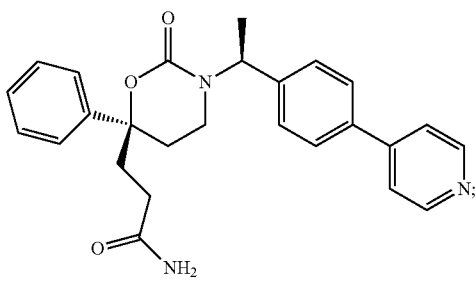

(R)-6-(4-fluorophenyl)-6-(3-hydroxypropyl)-3-((S)-
1-(4-(2-methylpyridin-4-yl)phenyl)ethyl)-1,3-oxazi-
nan-2-one (PR-311)

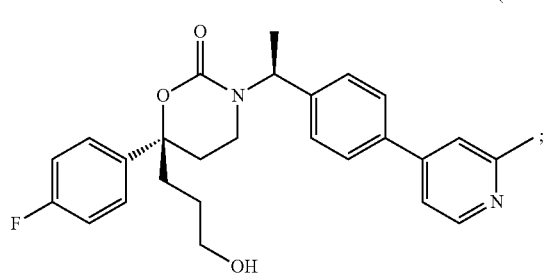

(R)-6-allyl-6-(4-fluorophenyl)-3-((S)-1-(4-(5-me-
thyl-1,3,4-thiadiazol-2-yl)phenyl)ethyl)-1,3-oxazi-
nan-2-one (PR-230)

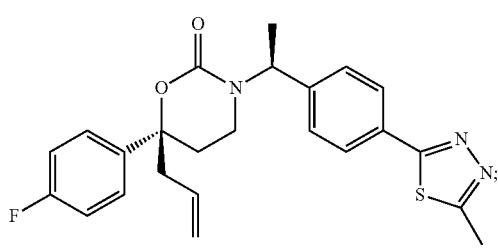

wz293-78

22

(R)-6-allyl-3-((S)-1-(4-(2,4-dimethylthiazol-5-yl)
phenyl)ethyl)-6-(4-fluorophenyl)-1,3-oxazinan-2-one (PR-244)

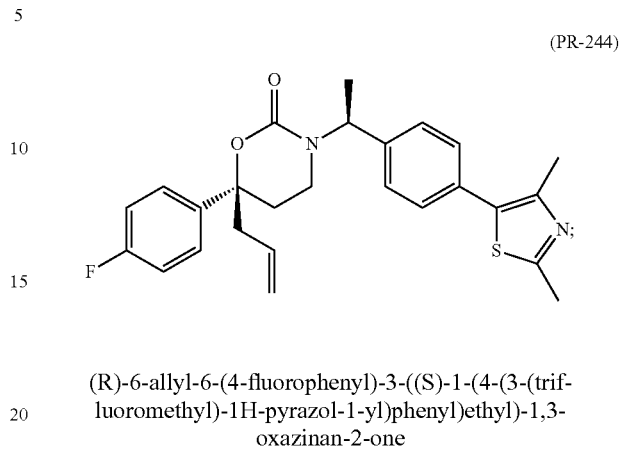

(R)-6-allyl-6-(4-fluorophenyl)-3-((S)-1-(4-(3-(trif-
luoromethyl)-1H-pyrazol-1-yl)phenyl)ethyl)-1,3-
oxazinan-2-one (PR-258)

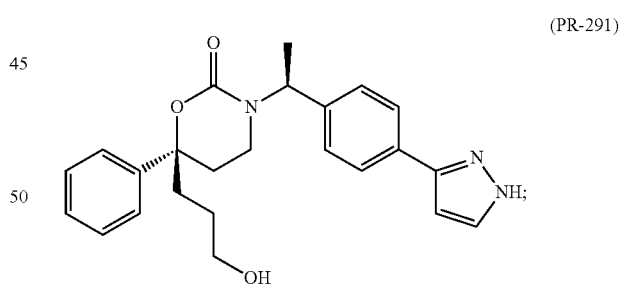

and (R)-3-((S)-1-(4-(1H-pyrazol-3-yl)phenyl)ethyl)-6-(3-
hydroxypropyl)-6-phenyl-1,3-oxazinan-2-one (PR-291)

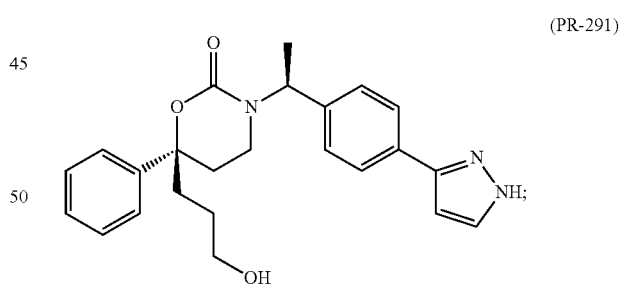

or a pharmaceutically acceptable salt, enantiomer or diastereomer thereof.

For each of the embodiments described in the previous paragraph, $R^1$ is preferably methyl or ethyl.

For each of the embodiments described in the paragraph immediately following Formulas $Iq^{1-21}$, $R^1$ is preferably methyl or ethyl; and $R^3$ is $MeSO_2NHCH_2CH_2CH_2$, $H_2NC(=O)CH_2CH_2$, $H_2NC(=O)CMe_2CH_2$, 3-hydroxypropyl, 3-hydroxy-3-methylbutyl, 2-hydroxyethyl, 2-hydroxy-2-methylpropyl or 2-cyano-2-methylpropyl.

For each of the embodiments described in the paragraph immediately following Formulas $Iq^{1-21}$, $R^1$ is preferably methyl or ethyl; and $R^3$ is $H_2NC(=O)CMe_2CH_2$, hydroxy-3-methylbutyl, 2-hydroxy-2-methylpropyl or 2-cyano-2-methylpropyl.

For each of the embodiments described in the paragraph immediately following Formulas $Iq^{1-21}$, $R^1$ is preferably methyl or ethyl; $R^2$ is phenyl optionally substituted with 1, 2 or 3 substituents selected from halo, cyano, $CONH_2$, $(C_1-C_4)$alkyl, $(C_1-C_4)$haloalkyl and $SO_2Me$; and $R^3$ is $MeSO_2NHCH_2CH_2CH_2$, $H_2NC(=O)CH_2CH_2$, $H_2NC(=O)CMe_2CH_2$, 3-hydroxypropyl, 3-hydroxy-3-methylbutyl, 2-hydroxyethyl, 2-hydroxy-2-methylpropyl or 2-cyano-2-methylpropyl.

For each of the embodiments described in the paragraph immediately following Formulas $Iq^{1-21}$, $R^1$ is preferably methyl or ethyl; $R^2$ is phenyl optionally substituted with 1, 2 or 3 substituents selected from halo, cyano, $CONH_2$, $(C_1-C_4)$alkyl, $(C_1-C_4)$haloalkyl and $SO_2Me$; and $R^3$ is $H_2NC(=O)CMe_2CH_2$, 3-hydroxy-3-methylbutyl, 2-hydroxy-2-methylpropyl or 2-cyano-2-methylpropyl.

For each of the embodiments described in the paragraph immediately following Formulas $Iq^{1-21}$, $R^1$ is preferably methyl or ethyl; and $R^3$ is 2-hydroxy-2-methylpropyl or 2-cyano-2-methylpropyl.

For each of the embodiments described in the paragraph immediately following Formulas $Iq^{1-21}$, $R^1$ is preferably methyl or ethyl; $R^2$ is phenyl or fluorophenyl; and $R^3$ is 2-hydroxy-2-methylpropyl or 2-cyano-2-methylpropyl.

For each of the embodiments described in the paragraph immediately following Formulas $Iq^{1-21}$, $R^1$ is preferably methyl or ethyl; $R^2$ is phenyl or fluorophenyl; $R^3$ is 2-hydroxy-2-methylpropyl or 2-cyano-2-methylpropyl; one or two ring carbon atoms in the pyridine, pyridazine, pyrimidine, pyrazine, pyrazole, thiazole and thiadiazole rings in Formulas $Iq^{1-21}$ are optionally substituted with fluoro, chloro, cyano, $CONH_2$, $CONHMe$, $CONMe_2$, $CONHc$-Pr, methoxy, ethoxy, methyl, ethyl or $CF_3$. the substitutable ring nitrogen atom in the pyrazole rings in Formulas $Iq^{18}$, $Iq^{20}$ and $Iq^{21}$ are optionally substituted with $(C_1-C_4)$alkyl, $(C_3-C_4)$cycloalkyl, $(C_3-C_4)$cycloalkyl$(C_1-C_2)$alkyl, or $(C_1-C_2)$haloalkyl, the ring nitrogen in the pyridine rings in Formulas $Iq^{1-4}$ is optionally substituted by oxo.

Another embodiment of the invention is a compound of any one of Formulas $Ir^{1-21}$, or a pharmaceutically acceptable salt, enantiomer or diastereomer thereof:

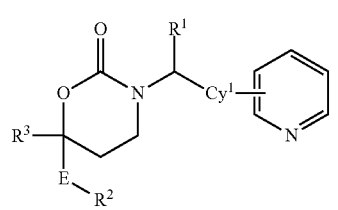

$Ir^1$

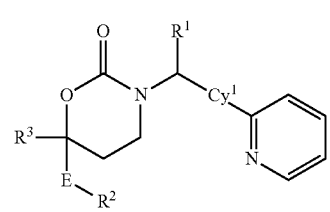

$Ir^2$

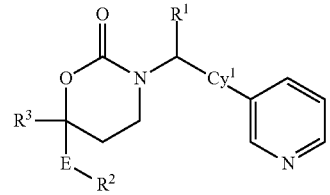

$Ir^3$

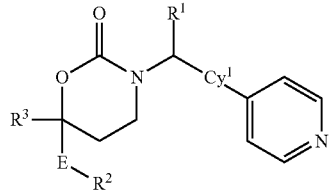

$Ir^4$

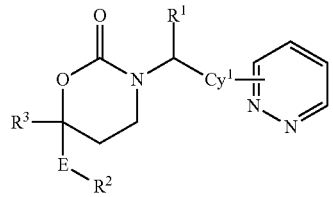

$Ir^5$

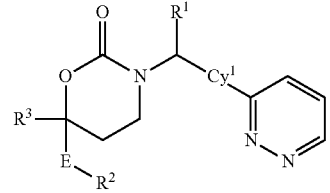

$Ir^6$

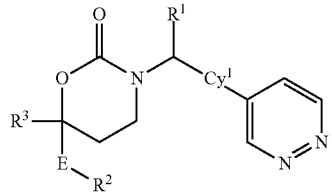

$Ir^7$

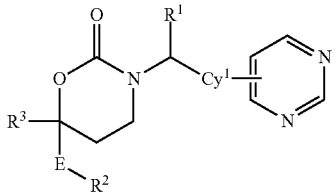

$Ir^8$

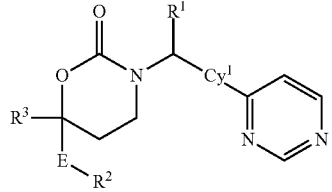

$Ir^9$

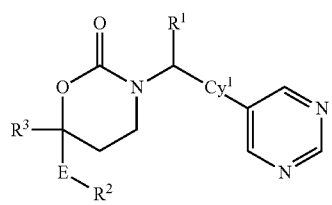
Ir¹⁰

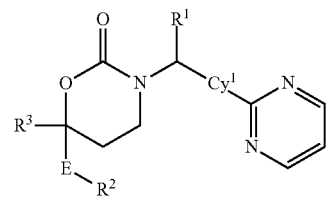
Ir¹¹

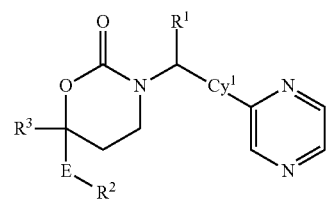
Ir¹²

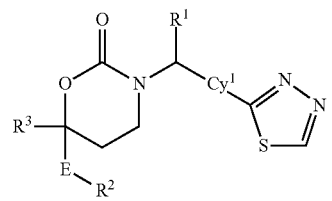
Ir¹³

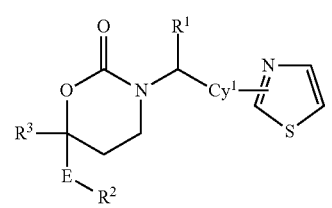
Ir¹⁴

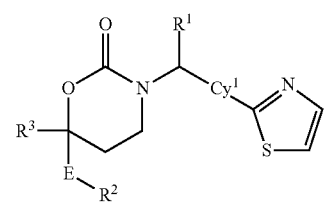
Ir¹⁵

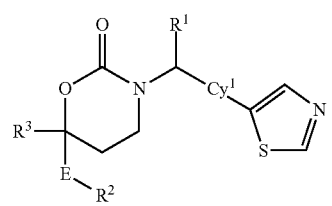
Ir¹⁶

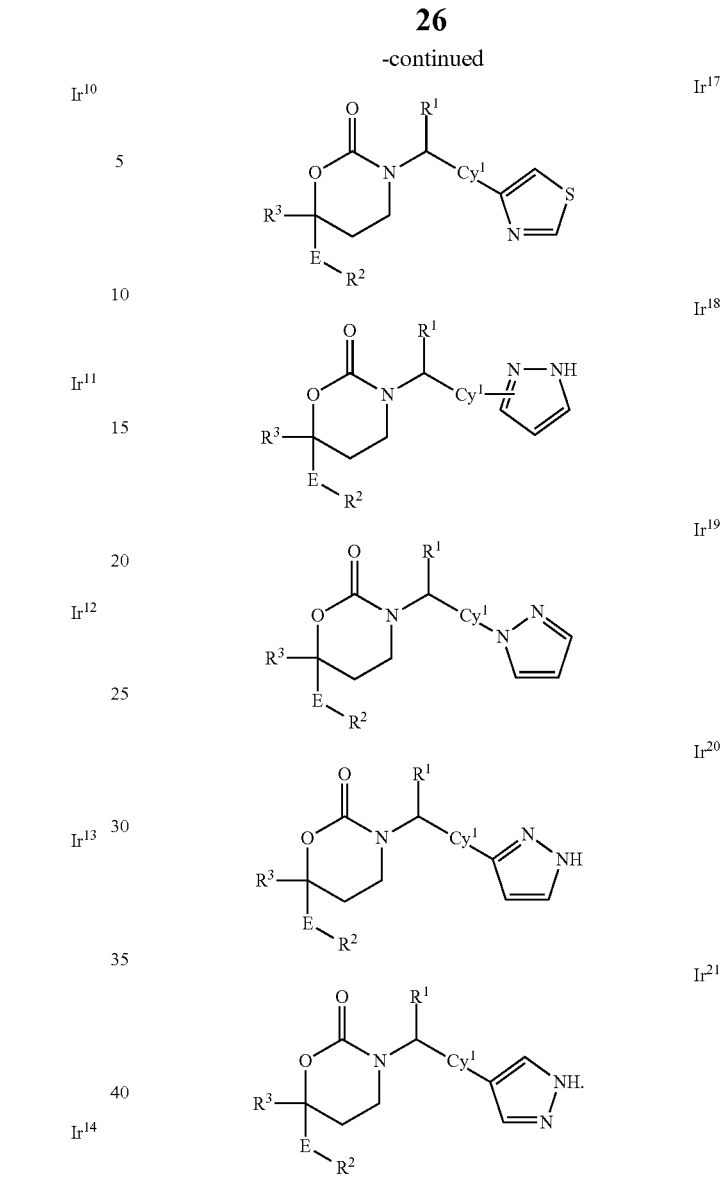

In Formulas Ir$^{1-21}$, the pyridine, pyridazine, pyrimidine, pyrazine, pyrazole, thiazole and thiadiazole rings are optionally substituted (substitution at ring carbons bonded to hydrogen and ring nitrogen atoms bonded to hydrogen atoms are encompassed, i.e., a "substitutable ring nitrogen atom") with up to four substituents as described for Cy² in the first embodiment. Suitable substituents for Cy² and suitable values for R¹, R², R³, Cy¹ and E are as defined above in the first embodiment. Alternatively, suitable substituents for Cy¹ and the pyridine, pyridazine, pyrimidine, pyrazine, pyrazole, thiazole and thiadiazole rings in Formulas Ir$^{1-21}$ are independently fluorine, chlorine, bromine, iodine, cyano, nitro, amino, hydroxy, carboxy, $(C_1-C_6)$alkyl, hydroxy$(C_1-C_6)$alkyl, $(C_3-C_6)$cycloalkyl, hydroxy$(C_3-C_6)$cycloalkyl, $(C_4-C_7)$cycloalkylalkyl, $(C_2-C_6)$alkenyl, halo$(C_2-C_6)$alkenyl, hydroxy$(C_2-C_6)$alkenyl, $(C_2-C_6)$alkynyl, $(C_3-C_6)$cycloalkyl$(C_2-C_4)$alkynyl, halo$(C_1-C_6)$alkyl, halo$(C_3-C_6)$cycloalkyl, halo$(C_4-C_7)$cycloalkylalkyl, $(C_1-C_6)$alkoxy, $(C_3-C_6)$cycloalkoxy, $(C_4-C_7)$cycloalkylalkoxy, halo$(C_1-C_6)$alkoxy, halo$(C_3-C_6)$cycloalkoxy, halo$(C_4-C_7)$cycloalkylalkoxy, $(C_1-C_6)$alkylthio, $(C_3-C_6)$cycloalkythio, $(C_4-C_7)$cycloalkylalkylthio, halo$(C_1-C_6)$alkylthio, halo$(C_3-C_6)$cycloalkythio, halo ($C_4$-$C_7$)cycloalkylalkylthio, ($C_1$-$C_6$)alkanesulfinyl, ($C_3$-$C_6$)cycloalkanesulfinyl, ($C_4$-$C_7$)cycloalkylalkanesulfinyl, halo($C_1$-$C_6$)alkanesulfinyl, halo($C_3$-$C_6$)cycloalkanesulfinyl, halo($C_4$-$C_7$)cycloalkylalkanesulfinyl, ($C_1$-$C_6$)alkanesulfonyl, ($C_3$-$C_6$)cycloalkanesulfonyl, ($C_4$-$C_7$)cycloalkyl-alkanesulfonyl, halo($C_1$-$C_6$)alkanesulfonyl, halo($C_3$-$C_6$)cycloalkanesulfonyl, halo($C_4$-$C_7$)cyclo-alkylalkanesulfonyl, ($C_1$-$C_6$)alkylamino, di($C_1$-$C_6$)alkylamino, ($C_1$-$C_6$)alkoxy($C_1$-$C_6$)alkoxy, halo($C_1$-$C_6$)alkoxy($C_1$-$C_6$)alkoxy, ($C_1$-$C_6$)alkoxycarbonyl, $H_2$NCO, $H_2$NSO$_2$, ($C_1$-$C_6$)alkylaminocarbonyl, di($C_1$-$C_6$)alkylaminocarbonyl, ($C_1$-$C_3$)alkoxy($C_1$-$C_3$)alkylaminocarbonyl, heterocyclylcarbonyl, ($C_1$-$C_6$)alkylaminosulfonyl, di($C_1$-$C_6$)alkylaminosulfonyl, heterocyclylsulfonyl, ($C_1$-$C_6$)alkylcarbonylamino, ($C_1$-$C_6$)alkylcarbonylamino($C_1$-$C_6$)alkyl, ($C_1$-$C_6$)alkylsulfonylamino, ($C_1$-$C_6$)alkylsulfonylamino($C_1$-$C_6$)alkyl, ($C_1$-$C_6$)alkoxycarbonyl($C_1$-$C_6$)alkoxy, ($C_1$-$C_6$)alkoxy($C_1$-$C_6$)alkyl, halo($C_1$-$C_6$)alkoxy($C_1$-$C_6$)alkyl, hydroxy($C_1$-$C_6$)alkoxy, heteroaryl, amino($C_1$-$C_6$)alkyl, ($C_1$-$C_6$)alkylamino($C_1$-$C_6$)alkyl, di($C_1$-$C_6$)alkylamino($C_1$-$C_6$)alkyl amino($C_2$-$C_6$)alkoxy, ($C_1$-$C_6$)alkylamino($C_2$-$C_6$)alkoxy, di($C_1$-$C_6$)alkylamino($C_2$-$C_6$)alkoxy, ($C_1$-$C_6$)alkylcarbonyl, ($C_3$-$C_6$)cycloalkylcarbonyl, ($C_3$-$C_6$)cycloalkylaminocarbonyl, {($C_3$-$C_6$)cycloalkyl}{($C_1$-$C_6$)alkyl}aminocarbonyl, di($C_3$-$C_6$)cycloalkylaminocarbonyl, ($C_3$-$C_6$)cycloalkylaminosulfonyl, {($C_3$-$C_6$)cycloalkyl}{($C_1$-$C_6$)alkyl}aminosulfonyl, di($C_3$-$C_6$)cycloalkylaminosulfonyl, cyano($C_1$-$C_6$)alkyl, aminocarbonyl($C_1$-$C_6$)alkyl, ($C_1$-$C_6$)alkylaminocarbonyl($C_1$-$C_6$)alkyl, di($C_1$-$C_6$)alkylaminocarbonyl($C_1$-$C_6$)alkyl, ($C_3$-$C_6$)cycloalkylaminocarbonyl($C_1$-$C_6$)alkyl, {($C_3$-$C_6$)cycloalkyl}{($C_1$-$C_6$)alkyl}aminocarbonyl($C_1$-$C_6$)alkyl and di($C_3$-$C_6$)cycloalkylaminocarbonyl($C_1$-$C_6$)alkyl; and values for $R^1$, $R^2$, $R^3$, $Cy^1$ and E are as defined above in the first embodiment. Alternatively, suitable substituents for $Cy^1$ include ($C_1$-$C_4$)alkyl, ($C_1$-$C_4$)alkoxy, ($C_1$-$C_4$)haloalkyl, ($C_1$-$C_4$)haloalkoxy, halogen, cyano and nitro; suitable substituents for a substitutable ring nitrogen atom in the pyrazole rings in Formulas Ir$^{18}$, Ir$^{20}$ and Ir$^{21}$ include ($C_1$-$C_4$)alkyl, ($C_3$-$C_4$)cycloalkyl, ($C_3$-$C_4$)cycloalkyl($C_1$-$C_2$)alkyl, and ($C_1$-$C_4$) haloalkyl; suitable substituents for a ring carbon atom in the pyridine, pyridazine, pyrimidine, pyrazine, pyrazole, thiazole and thiadiazole rings in Formulas Ir$^{1-21}$ include fluorine, chlorine, cyano, hydroxy, amino, ($C_1$-$C_4$)alkyl, ($C_3$-$C_4$)cycloalkyl, ($C_3$-$C_4$)cycloalkyl($C_1$-$C_2$)alkyl, halo($C_1$-$C_4$)alkyl, ($C_1$-$C_4$)alkoxy, ($C_1$-$C_4$)haloalkoxy, CONH$_2$, ($C_1$-$C_4$)alkylaminocarbonyl, di($C_1$-$C_4$)alkylaminocarbonyl, ($C_3$-$C_4$)cycloalkylaminocarbonyl, {($C_1$-$C_4$)alkyl}{($C_3$-$C_4$)cycloalkyl}aminocarbonyl and ($C_1$-$C_4$)alkylcarbonylamino; the ring nitrogen in pyridines Ir$^{1-4}$ is optionally substituted by oxo; and suitable values for $R^1$, $R^2$, $R^3$, $Cy^1$ and E are as defined above in the first embodiment. In another alternative, the embodiments described in this paragraph exclude the compounds PR-205, PR-211, PR-214, PR-222, PR-225, PR-235, PR-236, PR-281, PR-292, PR-295, PR-298, PR-300, PR-302, PR-305, PR-304, PR-306, PR-307, PR-210, PR-296, PR-311, PR-230, PR-244, PR-258 and PR-291 or a pharmaceutically acceptable salt, enantiomer or diastereomer thereof.

Alternatively, the first embodiment above excludes the compounds of structural formulas PR-205, PR-211, PR-214, PR-222, PR-225, PR-235, PR-236, PR-281, PR-292, PR-295, PR-298, PR-300, PR-302, PR-305, PR-304, PR-306, PR-307, PR-210, PR-296, PR-311, PR-230, PR-244, PR-258 and PR-291, or a pharmaceutically acceptable salt, enantiomer or diastereomer thereof, and the compound of Example 32, Example 33, (R)-6-allyl-3-((S)-1-(4-(6-aminopyridin-3-yl)phenyl)ethyl)-6-phenyl-1,3-oxazinan-2-one, (R)-3-((S)-1-(4-(6-aminopyridin-3-yl)phenyl)ethyl)-6-(3-hydroxypropyl)-6-phenyl-1,3-oxazinan-2-one, (R)-6-(3-hydroxypropyl)-3-((S)-1-(4-(6-oxo-1,6-dihydropyridin-3-yl)phenyl)ethyl)-6-phenyl-1,3-oxazinan-2-one, (R)-6-allyl-6-(4-fluorophenyl)-3-((S)-1-(4-(pyridin-3-yl)phenyl)ethyl)-1,3-oxazinan-2-one, (R)-6-(2-aminoethyl)-6-phenyl-3-((S)-1-(4-(pyridin-3-yl)phenyl)ethyl)-1,3-oxazinan-2-one and (R)-6-(3-hydroxypropyl)-3-((S)-1-(4-(1-methyl-6-oxo-1,6-dihydropyridin-3-yl)phenyl)ethyl)-6-phenyl-1,3-oxazinan-2-one, (R)-6-allyl-6-phenyl-3-((S)-1-(4-(pyridin-3-yl)phenyl)ethyl)-1,3-oxazinan-2-one, (R)-6-allyl-6-(4-fluorophenyl)-3-((S)-1-(4-(pyridin-3-yl)phenyl)ethyl)-1,3-oxazinan-2-one, 3-((R)-6-(4-fluorophenyl)-2-oxo-3-((S)-1-(4-(pyridin-3-yl)phenyl)ethyl)-1,3-oxazinan-6-yl)propanoic acid, 3-((R)-2-oxo-6-phenyl-3-((S)-1-(4-(pyridin-4-yl)phenyl)ethyl)-1,3-oxazinan-6-yl)propanoic acid, (R)-6-allyl-6-phenyl-3-((S)-1-(4-(pyridin-4-yl)phenyl)ethyl)-1,3-oxazinan-2-one, (R)-6-allyl-3-((S)-1-(4-(6-methoxypyridin-3-yl)phenyl)ethyl)-6-phenyl-1,3-oxazinan-2-one, (R)-3-((S)-1-(4-(1H-pyrazol-3-yl)phenyl)ethyl)-6-allyl-6-phenyl-1,3-oxazinan-2-one, or a pharmaceutically acceptable salt, enantiomer or diastereomer thereof.

For each of the embodiment described in the previous paragraph, $R^1$ is preferably methyl or ethyl.

For each of the embodiment described in the paragraph immediately following Formulas Ir$^{1-21}$, $R^1$ is preferably methyl or ethyl; and $R^3$ is MeSO$_2$NHCH$_2$CH$_2$CH$_2$, H$_2$NC(=O)CH$_2$CH$_2$, H$_2$NC(=O)CMe$_2$CH$_2$, 3-hydroxypropyl, 3-hydroxy-3-methylbutyl, 2-hydroxyethyl, 2-hydroxy-2-methylpropyl or 2-cyano-2-methylpropyl.

For each of the embodiment described in the paragraph immediately following Formulas Ir$^{1-21}$, $R^1$ is preferably methyl or ethyl; and $R^3$ is H$_2$NC(=O)CMe$_2$CH$_2$, 3-hydroxy-3-methylbutyl, 2-hydroxy-2-methylpropyl or 2-cyano-2-methylpropyl.

For each of the embodiment described in the paragraph immediately following Formulas Ir$^{1-21}$, $R^1$ is preferably methyl or ethyl; $R^2$ is phenyl optionally substituted with 1, 2 or 3 substituents selected from halo, cyano, CONH$_2$, ($C_1$-$C_4$)alkyl, ($C_1$-$C_4$)haloalkyl and SO$_2$Me; and $R^3$ is MeSO$_2$NHCH$_2$CH$_2$CH$_2$, H$_2$NC(=O)CH$_2$CH$_2$, H$_2$NC(=O)CMe$_2$CH$_2$, 3-hydroxypropyl, 3-hydroxy-3-methylbutyl, 2-hydroxyethyl, 2-hydroxy-2-methylpropyl or 2-cyano-2-methylpropyl.

For each of the embodiment described in the paragraph immediately following Formulas Ir$^{1-21}$, $R^1$ is preferably methyl or ethyl; $R^2$ is phenyl optionally substituted with 1, 2 or 3 substituents selected from halo, cyano, CONH$_2$, ($C_1$-$C_4$)alkyl, ($C_1$-$C_4$)haloalkyl and SO$_2$Me; and $R^3$ is H$_2$NC(=O)CMe$_2$CH$_2$, 3-hydroxy-3-methylbutyl, 2-hydroxy-2-methylpropyl or 2-cyano-2-methylpropyl.

For each of the embodiment described in the paragraph immediately following Formulas Ir$^{1-21}$, $R^1$ is preferably methyl or ethyl; and $R^3$ is 2-hydroxy-2-methylpropyl or 2-cyano-2-methylpropyl.

For each of the embodiment described in the paragraph immediately following Formulas Ir$^{1-21}$, $R^1$ is preferably methyl or ethyl; $R^2$ is phenyl or fluorophenyl; and $R^3$ is 2-hydroxy-2-methylpropyl or 2-cyano-2-methylpropyl.

For each of the embodiment described in the paragraph immediately following Formulas Ir$^{1-21}$, $R^1$ is preferably methyl or ethyl; $R^2$ is phenyl or fluorophenyl; $R^3$ is 2-hydroxy-2-methylpropyl or 2-cyano-2-methylpropyl; one or two ring carbon atoms in the pyridine, pyridazine, pyrimidine, pyrazine, pyrazole, thiazole and thiadiazole rings in Formulas Ir$^{1-21}$ are optionally substituted with fluoro, chloro, cyano, CONH$_2$, CONHMe, CONMe$_2$, CONHc-Pr, methoxy, ethoxy, methyl, ethyl or CF₃. the substitutable ring nitrogen atom in the pyrazole rings in Formulas Ir¹⁸, Ir²⁰ and Ir²¹ are optionally substituted with $(C_1-C_4)$alkyl, $(C_3-C_4)$cycloalkyl, $(C_3-C_4)$cycloalkyl$(C_1-C_2)$alkyl, or $(C_1-C_2)$haloalkyl, the ring nitrogen in the pyridine rings in Formulas Ir¹⁻⁴ is optionally substituted by oxo.

Another embodiment of the invention is a compound of any one of Formulas Is¹⁻²¹, or a pharmaceutically acceptable salt thereof:

Is¹
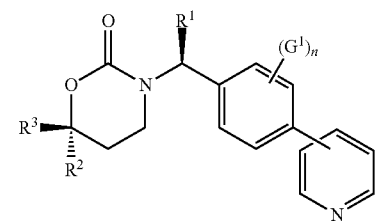

Is²
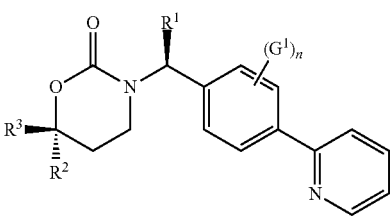

Is³
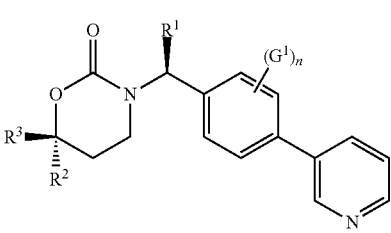

Is⁴
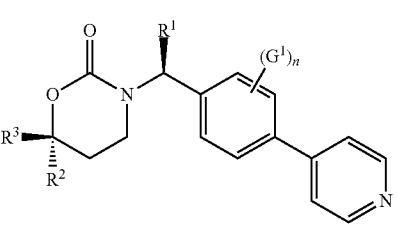

Is⁵
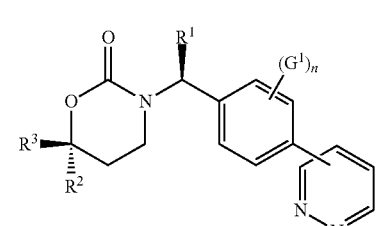

Is⁶
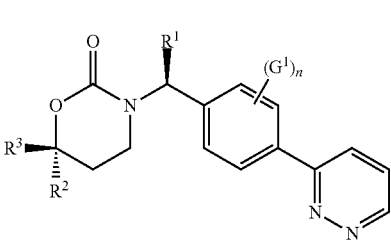

-continued

Is⁷
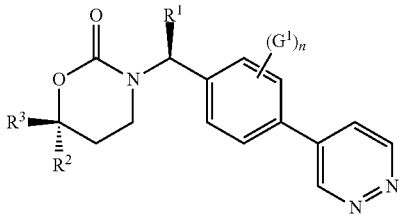

Is⁸
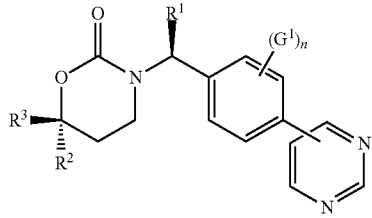

Is⁹
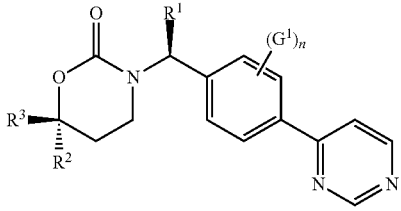

Is¹⁰
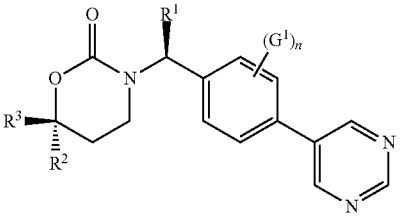

Is¹¹
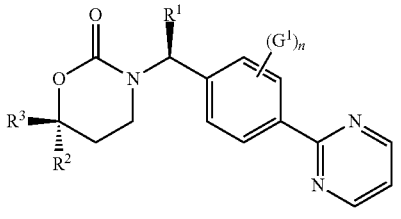

Is¹²
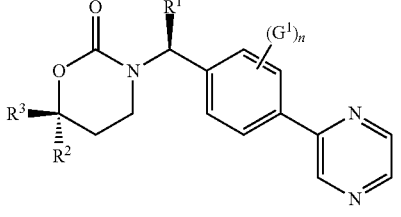

Is¹³
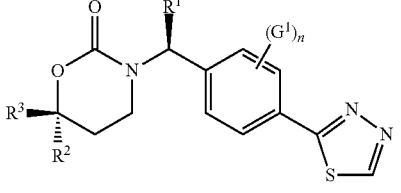

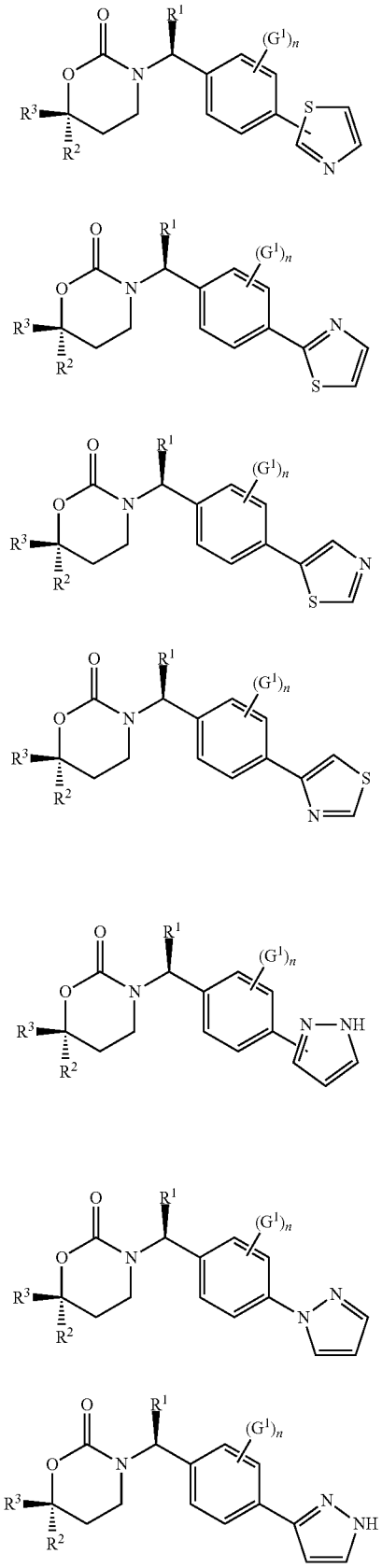

In Formulas $Is^{1-21}$, the pyridine, pyridazine, pyrimidine, pyrazine, pyrazole, thiazole and thiadiazole rings in Formulas $Is^{1-21}$ are optionally substituted (substitution at ring carbons bonded to hydrogen and ring nitrogen atoms bonded to hydrogen atoms are encompassed, i.e., a "substitutable ring nitrogen atom") with up to four substituents as described for $Cy^2$ in the first embodiment. Suitable values for $G^1$ are fluorine, chlorine, bromine, iodine, cyano, nitro, amino, hydroxy, carboxy, $(C_1-C_6)$alkyl, hydroxy$(C_1-C_6)$alkyl, $(C_3-C_6)$cycloalkyl, hydroxy$(C_3-C_6)$cycloalkyl, $(C_4-C_7)$cycloalkylalkyl, $(C_2-C_6)$alkenyl, halo$(C_2-C_6)$alkenyl, hydroxy$(C_2-C_6)$alkenyl, $(C_2-C_6)$alkynyl, $(C_3-C_6)$cycloalkyl$(C_2-C_4)$alkynyl, halo$(C_1-C_6)$alkyl, halo$(C_3-C_6)$cycloalkyl, halo$(C_4-C_7)$cycloalkylalkyl, $(C_1-C_6)$alkoxy, $(C_3-C_6)$cycloalkoxy, $(C_4-C_7)$cycloalkylalkoxy, halo$(C_1-C_6)$alkoxy, halo$(C_3-C_6)$cycloalkoxy, halo$(C_4-C_7)$cycloalkylalkoxy, $(C_1-C_6)$alkylthio, $(C_3-C_6)$cycloalkythio, $(C_4-C_7)$cycloalkylalkylthio, halo$(C_1-C_6)$alkylthio, halo$(C_3-C_6)$cycloalkythio, halo$(C_4-C_7)$cycloalkylalkylthio, $(C_1-C_6)$alkanesulfinyl, $(C_3-C_6)$cycloalkanesulfinyl, $(C_4-C_7)$cycloalkylalkanesulfinyl, halo$(C_1-C_6)$alkanesulfinyl, halo$(C_3-C_6)$cycloalkanesulfinyl, halo$(C_4-C_7)$cycloalkylalkanesulfinyl, $(C_1-C_6)$alkanesulfonyl, $(C_3-C_6)$cycloalkanesulfonyl, $(C_4-C_7)$cycloalkyl-alkanesulfonyl, halo$(C_1-C_6)$alkanesulfonyl, halo$(C_3-C_6)$cycloalkanesulfonyl, halo$(C_4-C_7)$cycloalkyl-alkanesulfonyl, $(C_1-C_6)$alkylamino, di$(C_1-C_6)$alkylamino, $(C_1-C_6)$alkoxy$(C_1-C_6)$alkoxy, halo$(C_1-C_6)$alkoxy$(C_1-C_6)$alkoxy, $(C_1-C_6)$alkoxycarbonyl, $H_2NCO$, $H_2NSO_2$, $(C_1-C_6)$alkylaminocarbonyl, di$(C_1-C_6)$alkylaminocarbonyl, $(C_1-C_3)$alkoxy$(C_1-C_3)$alkylaminocarbonyl, heterocyclylcarbonyl, $(C_1-C_6)$alkylaminosulfonyl, di$(C_1-C_6)$alkylaminosulfonyl, heterocyclylsulfonyl, $(C_1-C_6)$alkylcarbonylamino, $(C_1-C_6)$alkylcarbonylamino$(C_1-C_6)$alkyl, $(C_1-C_6)$alkylsulfonylamino, $(C_1-C_6)$alkylsulfonylamino$(C_1-C_6)$alkyl, $(C_1-C_6)$alkoxycarbonyl$(C_1-C_6)$alkoxy, $(C_1-C_6)$alkoxy$(C_1-C_6)$alkyl, halo$(C_1-C_6)$alkoxy$(C_1-C_6)$alkyl, hydroxy$(C_1-C_6)$alkoxy, heteroaryl, amino$(C_1-C_6)$alkyl, $(C_1-C_6)$alkylamino$(C_1-C_6)$alkyl, di$(C_1-C_6)$alkylamino$(C_1-C_6)$alkylamino$(C_2-C_6)$alkoxy, $(C_1-C_6)$alkylamino$(C_2-C_6)$alkoxy, di$(C_1-C_6)$alkylamino$(C_2-C_6)$alkoxy, $(C_1-C_6)$alkylcarbonyl, $(C_3-C_6)$cycloalkylcarbonyl, $(C_3-C_6)$cycloalkylaminocarbonyl, {$(C_3-C_6)$cycloalkyl}{$(C_1-C_6)$alkyl}aminocarbonyl, di$(C_3-C_6)$cycloalkylaminocarbonyl, $(C_3-C_6)$cycloalkylaminosulfonyl, {$(C_3-C_6)$cycloalkyl}{$(C_1-C_6)$alkyl}aminosulfonyl, di$(C_3-C_6)$cycloalkylaminosulfonyl, cyano$(C_1-C_6)$alkyl, aminocarbonyl$(C_1-C_6)$alkyl, $(C_1-C_6)$alkylaminocarbonyl$(C_1-C_6)$alkyl, di$(C_1-C_6)$alkylaminocarbonyl$(C_1-C_6)$alkyl, $(C_3-C_6)$cycloalkylaminocarbonyl$(C_1-C_6)$alkyl, {$(C_3-C_6)$cycloalkyl}{$(C_1-C_6)$alkyl}aminocarbonyl$(C_1-C_6)$alkyl and di$(C_3-C_6)$cycloalkylaminocarbonyl$(C_1-C_6)$alkyl; n is 0, 1 or 2; substituents for $Cy^2$ and suitable values for $R^1$, $R^2$ and $R^3$ are as defined above in the first embodiment. Alternatively, n is 0, 1 or 2, suitable values for $G^1$ in Formulas $Is^{1-21}$ and suitable substituents for the pyridine, pyridazine, pyrimidine, pyrazine, pyrazole, thiazole and thiadiazole rings in Formulas $Is^{1-21}$ are independently fluorine, chlorine, bromine, iodine, cyano, nitro, amino, hydroxy, carboxy, $(C_1-C_6)$alkyl, hydroxy$(C_1-C_6)$alkyl, $(C_3-C_6)$cycloalkyl, hydroxy$(C_3-C_6)$cycloalkyl, $(C_4-C_7)$cycloalkylalkyl, $(C_2-C_6)$alkenyl, halo$(C_2-C_6)$alkenyl, hydroxy$(C_2-C_6)$alkenyl, $(C_2-C_6)$alkynyl, $(C_3-C_6)$cycloalkyl$(C_2-C_4)$alkynyl, halo$(C_1-C_6)$alkyl, halo$(C_3-C_6)$cycloalkyl, halo$(C_4-C_7)$cycloalkylalkyl, $(C_1-C_6)$alkoxy, $(C_3-C_6)$cycloalkoxy, $(C_4-C_7)$cycloalkylalkoxy, halo$(C_1-C_6)$alkoxy, halo$(C_3-C_6)$cycloalkoxy, halo$(C_4-C_7)$cycloalkylalkoxy, $(C_1-C_6)$alkylthio, $(C_3-C_6)$cycloalkythio, $(C_4-C_7)$cycloalkylalkylthio, halo$(C_1-C_6)$alkylthio, halo$(C_3-C_6)$cycloalkythio, halo$(C_4-C_7)$cycloalkylalkylthio, $(C_1-C_6)$alkanesulfinyl, $(C_3-C_6)$cycloalkanesulfinyl, $(C_4-C_7)$cycloalkylalkanesulfinyl, halo$(C_1-C_6)$alkanesulfinyl, halo$(C_3-C_6)$cycloalkanesulfinyl, halo$(C_4-C_7)$cycloalkylalkanesulfinyl, $(C_1-C_6)$alkanesulfonyl, $(C_3-C_6)$cycloalkanesulfonyl, $(C_4-C_7)$cycloalkyl-alkanesulfonyl, halo$(C_1-C_6)$alkanesulfonyl, halo$(C_3-C_6)$cycloalkanesulfonyl, halo$(C_4-C_7)$cycloalkyl-alkanesulfonyl, $(C_1-C_6)$alkylamino, di$(C_1-C_6)$alkylamino, $(C_1-C_6)$alkoxy$(C_1-C_6)$alkoxy, halo$(C_1-C_6)$alkoxy$(C_1-C_6)$alkoxy, $(C_1-C_6)$alkoxycarbonyl, $H_2NCO$, $H_2NSO_2$, $(C_1-C_6)$alkylaminocarbonyl, di$(C_1-C_6)$alkylaminocarbonyl, $(C_1-C_3)$alkoxy$(C_1-C_3)$alkylaminocarbonyl, heterocyclylcarbonyl, $(C_1-C_6)$alkylaminosulfonyl, di$(C_1-C_6)$alkylaminosulfonyl, heterocyclylsulfonyl, $(C_1-C_6)$alkylcarbonylamino, $(C_1-C_6)$alkylcarbonylamino$(C_1-C_6)$alkyl, $(C_1-C_6)$alkylsulfonylamino, $(C_1-C_6)$alkylsulfonylamino$(C_1-C_6)$alkyl, $(C_1-C_6)$alkoxycarbonyl$(C_1-C_6)$alkoxy, $(C_1-C_6)$alkoxy$(C_1-C_6)$alkyl, halo$(C_1-C_6)$alkoxy$(C_1-C_6)$alkyl, hydroxy$(C_1-C_6)$alkoxy, heteroaryl, amino$(C_1-C_6)$alkyl, $(C_1-C_6)$alkylamino$(C_1-C_6)$alkyl, di$(C_1-C_6)$alkylamino$(C_1-C_6)$alkylamino$(C_2-C_6)$alkoxy, $(C_1-C_6)$alkylamino$(C_2-C_6)$alkoxy, di$(C_1-C_6)$alkylamino$(C_2-C_6)$alkoxy and $(C_1-C_6)$alkylcarbonyl; and values for $R^1$, $R^2$, $R^3$ and E are as defined above in the first embodiment. Alternatively, n is 0, 1 or 2; suitable values for $G^1$ include $(C_1-C_4)$alkyl, $(C_1-C_4)$alkoxy, $(C_1-C_4)$haloalkyl, $(C_1-C_4)$haloalkoxy, halogen, cyano and nitro; suitable substituents for a substitutable ring nitrogen atom in the pyrazole rings in Formulas $Is^{18}$, $Is^{20}$ and $Is^{21}$ include $(C_1-C_4)$alkyl, $(C_3-C_4)$cycloalkyl, $(C_3-C_4)$cycloalkyl$(C_1-C_2)$alkyl, and $(C_1-C_4)$haloalkyl; suitable substituents for a ring carbon atom in the pyridine, pyridazine, pyrimidine, pyrazine, pyrazole, thiazole and thiadiazole rings in Formulas $Is^{1-21}$ include fluorine, chlorine, cyano, amino, $(C_1-C_4)$alkyl, $(C_3-C_4)$cycloalkyl, $(C_3-C_4)$cycloalkyl$(C_1-C_2)$alkyl, halo$(C_1-C_4)$alkyl, $(C_1-C_4)$alkoxy, $(C_1-C_4)$haloalkoxy, $CONH_2$, $(C_1-C_4)$alkylaminocarbonyl, di$(C_1-C_4)$alkylaminocarbonyl, $(C_3-C_4)$cycloalkylaminocarbonyl, $\{(C_1-C_4)$alkyl$\}\{(C_3-C_4)$cycloalkyl$\}$aminocarbonyl and $(C_1-C_4)$alkylcarbonylamino; the ring nitrogen in pyridines $Is^{1-4}$ is optionally substituted by oxo; and suitable values for $R^1$, $R^2$ and $R^3$ are as defined above in the first embodiment. In another alternative, the embodiments described in this paragraph exclude the compounds PR-205, PR-211, PR-214, PR-222, PR-225, PR-235, PR-236, PR-281, PR-292, PR-295, PR-298, PR-300, PR-302, PR-305, PR-304, PR-306, PR-307, PR-210, PR-296, PR-311, PR-230, PR-244, PR-258 and PR-291, or a pharmaceutically acceptable salt, enantiomer or diastereomer thereof.

Alternatively, the first embodiment above excludes the compounds of structural formulas PR-205, PR-211, PR-214, PR-222, PR-225, PR-235, PR-236, PR-281, PR-292, PR-295, PR-298, PR-300, PR-302, PR-305, PR-304, PR-306, PR-307, PR-210, PR-296, PR-311, PR-230, PR-244, PR-258 and PR-291, or a pharmaceutically acceptable salt, enantiomer or diastereomer thereof, and the compound of Example 32, Example 33, (R)-6-allyl-3-((S)-1-(4-(6-aminopyridin-3-yl)phenyl)ethyl)-6-phenyl-1,3-oxazinan-2-one, (R)-3-((S)-1-(4-(6-aminopyridin-3-yl)phenyl)ethyl)-6-(3-hydroxypropyl)-6-phenyl-1,3-oxazinan-2-one, (R)-6-(3-hydroxypropyl)-3-((S)-1-(4-(6-oxo-1,6-dihydropyridin-3-yl)phenyl)ethyl)-6-phenyl-1,3-oxazinan-2-one, (R)-6-allyl-6-(4-fluorophenyl)-3-((S)-1-(4-(pyridin-3-yl)phenyl)ethyl)-1,3-oxazinan-2-one, (R)-6-(2-aminoethyl)-6-phenyl-3-((S)-1-(4-(pyridin-3-yl)phenyl)ethyl)-1,3-oxazinan-2-one and (R)-6-(3-hydroxypropyl)-3-((S)-1-(4-(1-methyl-6-oxo-1,6-dihydropyridin-3-yl)phenyl)ethyl)-6-phenyl-1,3-oxazinan-2-one, (R)-6-allyl-6-phenyl-3-((S)-1-(4-(pyridin-3-yl)phenyl)ethyl)-1,3-oxazinan-2-one, (R)-6-allyl-6-(4-fluorophenyl)-3-((S)-1-(4-(pyridin-3-yl)phenyl)ethyl)-1,3-oxazinan-2-one, 3-((R)-6-(4-fluorophenyl)-2-oxo-3-((S)-1-(4-(pyridin-3-yl)phenyl)ethyl)-1,3-oxazinan-6-yl)propanoic acid, 3-((R)-2-oxo-6-phenyl-3-((S)-1-(4-(pyridin-4-yl)phenyl)ethyl)-1,3-oxazinan-6-yl)propanoic acid, (R)-6-allyl-6-phenyl-3-((S)-1-(4-(pyridin-4-yl)phenyl)ethyl)-1,3-oxazinan-2-one, (R)-6-allyl-3-((S)-1-(4-(6-methoxypyridin-3-yl)phenyl)ethyl)-6-phenyl-1,3-oxazinan-2-one, (R)-3-((S)-1-(4-(1H-pyrazol-3-yl)phenyl)ethyl)-6-allyl-6-phenyl-1,3-oxazinan-2-one, or a pharmaceutically acceptable salt, enantiomer or diastereomer thereof.

For each of the embodiment described in the previous paragraph, $R^1$ is preferably methyl or ethyl.

For each of the embodiment described in the paragraph immediately following Formulas $Is^{1-21}$, $R^1$ is preferably methyl or ethyl; and $R^3$ is $MeSO_2NHCH_2CH_2CH_2$, $H_2NC(=O)CH_2CH_2$, $H_2NC(=O)CMe_2CH_2$, 3-hydroxypropyl, 3-hydroxy-3-methylbutyl, 2-hydroxyethyl, 2-hydroxy-2-methylpropyl or 2-cyano-2-methylpropyl.

For each of the embodiment described in the paragraph immediately following Formulas $Is^{1-21}$, $R^1$ is preferably methyl or ethyl; and $R^3$ is $H_2NC(=O)CMe_2CH_2$, 3-hydroxy-3-methylbutyl, 2-hydroxy-2-methylpropyl or 2-cyano-2-methylpropyl.

For each of the embodiment described in the paragraph immediately following Formulas $Is^{1-21}$, $R^1$ is preferably methyl or ethyl; $R^2$ is phenyl optionally substituted with 1, 2 or 3 substituents selected from halo, cyano, $CONH_2$, $(C_1-C_4)$alkyl, $(C_1-C_4)$haloalkyl and $SO_2Me$; and $R^3$ is $MeSO_2NHCH_2CH_2CH_2$, $H_2NC(=O)CH_2CH_2$, $H_2NC(=O)CMe_2CH_2$, 3-hydroxypropyl, 3-hydroxy-3-methylbutyl, 2-hydroxyethyl, 2-hydroxy-2-methylpropyl or 2-cyano-2-methylpropyl.

For each of the embodiment described in the paragraph immediately following Formulas $Is^{1-21}$, $R^1$ is preferably methyl or ethyl; $R^2$ is phenyl optionally substituted with 1, 2 or 3 substituents selected from halo, cyano, $CONH_2$, $(C_1-C_4)$alkyl, $(C_1-C_4)$haloalkyl and $SO_2Me$; and $R^3$ is $H_2NC(=O)CMe_2CH_2$, 3-hydroxy-3-methylbutyl, 2-hydroxy-2-methylpropyl or 2-cyano-2-methylpropyl.

For each of the embodiment described in the paragraph immediately following Formulas $Is^{1-21}$, $R^1$ is preferably methyl or ethyl; and $R^3$ is 2-hydroxy-2-methylpropyl or 2-cyano-2-methylpropyl.

For each of the embodiment described in the paragraph immediately following Formulas $Is^{1-21}$, $R^1$ is preferably methyl or ethyl; $R^2$ is phenyl or fluorophenyl; and $R^3$ is 2-hydroxy-2-methylpropyl or 2-cyano-2-methylpropyl.

For each of the embodiment described in the paragraph immediately following Formulas $Is^{1-21}$, $R^1$ is preferably methyl or ethyl; $R^2$ is phenyl or fluorophenyl; $R^3$ is 2-hydroxy-2-methylpropyl or 2-cyano-2-methylpropyl; one or two ring carbon atoms in the pyridine, pyridazine, pyrimidine, pyrazine, pyrazole, thiazole and thiadiazole rings in Formulas $Is^{1-21}$ are optionally substituted with fluoro, chloro, cyano, $CONH_2$, $CONHMe$, $CONMe_2$, $CONHc-Pr$, methyl, ethyl or CF$_3$; the substitutable ring nitrogen atom in the pyrazole rings in Formulas Is$^{18}$, Is$^{20}$ and Is$^{21}$ is optionally substituted with (C$_1$-C$_4$)alkyl, (C$_3$-C$_4$)cycloalkyl, (C$_3$-C$_4$)cycloalkyl(C$_1$-C$_2$)alkyl, or (C$_1$-C$_2$)haloalkyl, the ring nitrogen in the pyridine rings in Formulas Is$^{1-4}$ is optionally substituted by oxo.

Another embodiment of the invention (referred to herein as the "First Alternate Embodiment") is a compound represented by Structural Formulas Is$^{1-21}$, wherein: n is 0 or 1, preferably 0; each G$^1$ is independently (C$_1$-C$_4$)alkyl, (C$_1$-C$_4$)alkoxy, (C$_1$-C$_4$)haloalkyl, (C$_1$-C$_4$)haloalkoxy, halogen, cyano or nitro; the substitutable ring nitrogen atom in the pyrazole rings in Formulas Is$^{18}$, Is$^{20}$ and Is$^{21}$ is substituted with hydroxy(C$_1$-C$_6$)alkyl, (C$_1$-C$_6$)alkylcarbonylamino(C$_1$-C$_6$)alkyl, (C$_1$-C$_6$)alkylsulfonylamino(C$_1$-C$_6$)alkyl, (C$_1$-C$_6$)alkoxy(C$_1$-C$_6$)alkyl, amino(C$_1$-C$_6$)alkyl, (C$_1$-C$_6$)alkylamino(C$_1$-C$_6$)alkyl, di(C$_1$-C$_6$)alkylamino(C$_1$-C$_6$)alkyl, cyano(C$_1$-C$_6$)alkyl, aminocarbonyl(C$_1$-C$_6$)alkyl, (C$_1$-C$_6$)alkylaminocarbonyl(C$_1$-C$_6$)alkyl, di(C$_1$-C$_6$)alkylaminocarbonyl(C$_1$-C$_6$)alkyl, (C$_3$-C$_6$)cycloalkylaminocarbonyl(C$_1$-C$_6$)alkyl, {(C$_3$-C$_6$)cycloalkyl}{(C$_1$-C$_6$)alkyl}aminocarbonyl(C$_1$-C$_6$)alkyl or di(C$_3$-C$_6$)cycloalkylaminocarbonyl(C$_1$-C$_6$)alkyl; the pyridine, pyridazine, pyrimidine, pyrazine, pyrazole, thiazole and thiadiazole rings in Formulas Is$^{1-21}$ are optionally substituted at one or more substitutable ring carbon atoms with a group independently selected from fluorine, chlorine, cyano, hydroxy, amino, (C$_1$-C$_4$)alkyl, (C$_3$-C$_4$)cycloalkyl, (C$_3$-C$_4$)cycloalkyl(C$_1$-C$_2$)alkyl, halo(C$_1$-C$_4$)alkyl, (C$_1$-C$_4$)alkoxy, (C$_1$-C$_4$)haloalkoxy, CONH$_2$, (C$_1$-C$_4$)alkylaminocarbonyl, di(C$_1$-C$_4$)alkylaminocarbonyl and (C$_1$-C$_4$)alkylcarbonylamino; R$^1$ is methyl or ethyl; R$^2$ is phenyl, thienyl, pyridyl or isopropyl each optionally substituted with up to three groups independently selected from halo, methyl, methylthio or (4-morpholino)methyl; and R$^3$ is methyl, ethyl, propyl, butyl, vinyl, allyl or ethoxyethyl each optionally substituted with up to two groups independently selected from methyl, HO—, MeO—, H$_2$N—, MeC(=O)NH—, MeS(=O)$_2$NH—, H$_2$NC(=O)—, MeNHC(=O)—, HO$_2$C—, (HO)$_2$P(=O)O—, H$_2$NS(=O)$_2$O—, H$_2$NS(=O)$_2$NH—, MeNHC(=O)NH—, MeNHC(=O)O—, oxo, cyano, HO$_2$C—, HOCH$_2$CH$_2$NH—, 4-morpholino, HOCH$_2$C(=O)NH—, H$_2$NCH$_2$C(=O)NH—, EtNHC(=O)NH, MeOC(=O)NH—, MeNHC(=NC=N)NH—, Me-, MeS—, MeSO$_2$—, MeSO$_2$N(Me)—, MeS(=O)$_2$NHC(=O)—, imidazolylamino-, imidazolyl, tetrazolyl, H$_2$NCONH—, H$_2$NCO$_2$—, HOCH$_2$CH$_2$O—, MeNH—, Me$_2$N— and MeCONMe.

Alternatively for Structural Formulas Is$^{1-21}$, R$^2$ is phenyl optionally substituted with 1, 2 or 3 substituents independently selected from halo, cyano, CONH$_2$, (C$_1$-C$_4$)alkyl, (C$_1$-C$_4$)haloalkyl and SO$_2$Me; and R$^3$ is MeSO$_2$NHCH$_2$CH$_2$, H$_2$NC(=O)CH$_2$CH$_2$, H$_2$NC(=O)CMe$_2$CH$_2$, 3-hydroxypropyl, 3-hydroxy-3-methylbutyl, 2-hydroxyethyl, 2-hydroxy-2-methylpropyl or 2-cyano-2-methylpropyl; and the remainder of the variables are as described above for the First Alternate Embodiment.

Alternatively for Structural Formulas Is$^{1-21}$, R$^3$ is H$_2$NC(=O)CMe$_2$CH$_2$, 3-hydroxy-3-methylbutyl, 2-hydroxy-2-methylpropyl or 2-cyano-2-methylpropyl; and the remainder of the variables are as described above for the First Alternate Embodiment.

Alternatively for Structural Formulas Is$^{1-21}$, R$^2$ is phenyl optionally substituted with 1, 2 or 3 substituents independently selected from halo, cyano, CONH$_2$, (C$_1$-C$_4$)alkyl, (C$_1$-C$_4$)haloalkyl and SO$_2$Me; and R$^3$ is H$_2$NC(=O)CMe$_2$CH$_2$, 3-hydroxy-3-methylbutyl, 2-hydroxy-2-methylpropyl or 2-cyano-2-methylpropyl; and the remainder of the variables are as described in the First Alternate Embodiment.

Alternatively for Structural Formulas Is$^{1-21}$, R$^3$ is 2-hydroxy-2-methylpropyl or 2-cyano-2-methylpropyl; and the remainder of the variables are as described in the First Alternate Embodiment.

Alternatively for Structural Formulas Is$^{1-21}$, R$^2$ is phenyl or fluorophenyl; and R$^3$ is 2-hydroxy-2-methylpropyl or 2-cyano-2-methylpropyl; and the remainder of the variables are as described in the First Alternate Embodiment.

Alternatively for Structural Formulas Is$^{1-21}$, R$^2$ is phenyl or fluorophenyl; R$^3$ is 2-hydroxy-2-methylpropyl or 2-cyano-2-methylpropyl; one or two substitutable ring carbon atoms in the pyridine, pyridazine, pyrimidine, pyrazine, pyrazole, thiazole and thiadiazole rings in Formulas Is$^{1-21}$ are optionally substituted with methyl or ethyl; and the remainder of the variables are as described in the First Alternate Embodiment.

For the embodiment described in the previous seven paragraphs, n is 0 and all of the substitutable ring carbons in the pyridine, pyridazine, pyrimidine, pyrazine, pyrazole, thiazole and thiadiazole rings in Formulas Is$^{1-21}$ are preferably unsubstituted.

Another embodiment of the invention is a compound represented by any one of Formulas It$^{1-6}$, or a pharmaceutically acceptable salt thereof:

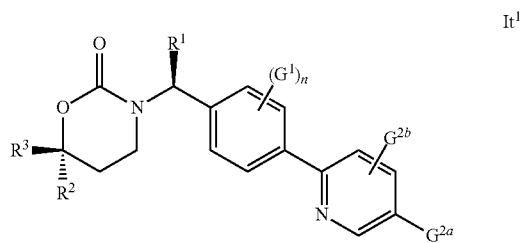

It$^1$

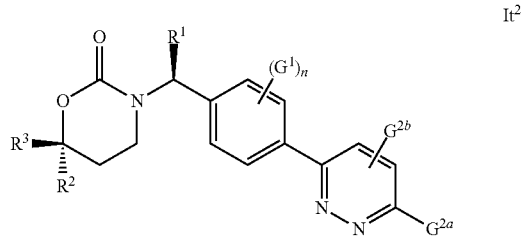

It$^2$

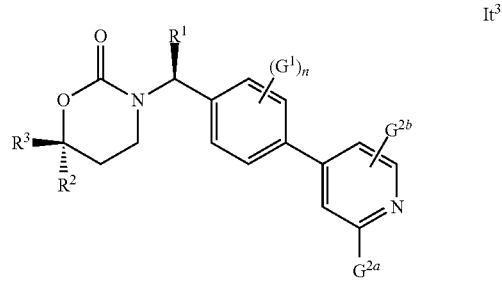

It$^3$

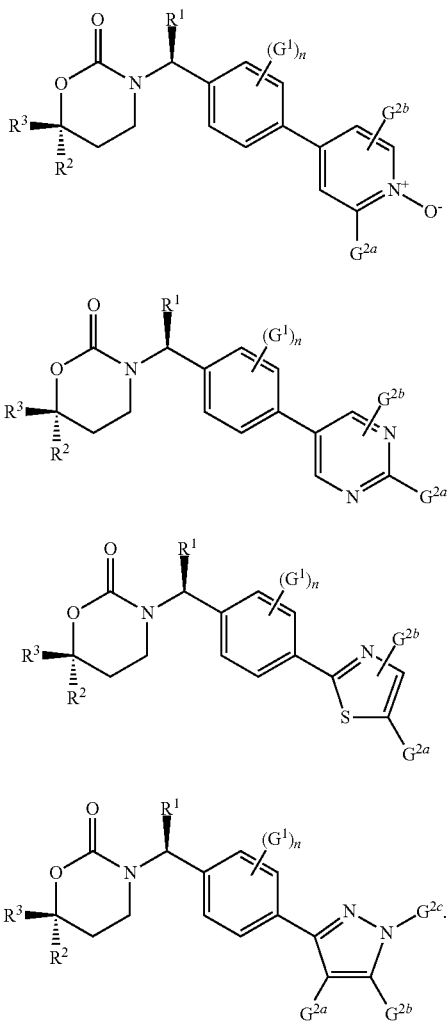

In Formulas $It^{1-7}$, $G^1$ is $(C_1-C_4)$alkyl, $(C_1-C_4)$alkoxy, $(C_1-C_4)$haloalkyl, $(C_1-C_4)$haloalkoxy, halogen, cyano and nitro; n is 0 1 or 2; $G^{2a}$ and $G^{2b}$ are independently selected from hydrogen, fluorine, chlorine, cyano, amino, $(C_1-C_4)$alkyl, $(C_3-C_4)$cycloalkyl, $(C_3-C_4)$cycloalkyl$(C_1-C_2)$alkyl, halo$(C_1-C_4)$alkyl, $(C_1-C_4)$alkoxy, $(C_1-C_4)$haloalkoxy, $CONH_2$, $(C_1-C_4)$alkylaminocarbonyl, di$(C_1-C_4)$alkylaminocarbonyl, $(C_3-C_4)$cycloalkylaminocarbonyl, $\{(C_1-C_4)alkyl\}\{(C_3-C_4)cycloalkyl\}$aminocarbonyl and $(C_1-C_4)$alkylcarbonylamino; $G^2$ is $(C_1-C_4)$alkyl, $(C_3-C_4)$cycloalkyl or $(C_1-C_4)$haloalkyl; and suitable values for $R^1$, $R^2$ and $R^3$ are as defined above in the first embodiment. In another alternative, the embodiments in the this paragraph exclude the compounds PR-205, PR-211, PR-214, PR-222, PR-225, PR-235, PR-236, PR-281, PR-292, PR-295, PR-298, PR-300, PR-302, PR-305, PR-304, PR-306, PR-307, PR-210, PR-296, PR-311, PR-230, PR-244, PR-258, and PR-291, or a pharmaceutically acceptable salt, enantiomer or diastereomer thereof.

Alternatively, the first embodiment above excludes the compounds of structural formulas PR-205, PR-211, PR-214, PR-222, PR-225, PR-235, PR-236, PR-281, PR-292, PR-295, PR-298, PR-300, PR-302, PR-305, PR-304, PR-306, PR-307, PR-210, PR-296, PR-311, PR-230, PR-244, PR-258 and PR-291, or a pharmaceutically acceptable salt, enantiomer or diastereomer thereof, and the compound of Example 32, Example 33, (R)-6-allyl-3-((S)-1-(4-(6-aminopyridin-3-yl)phenyl)ethyl)-6-phenyl-1,3-oxazinan-2-one, (R)-3-((S)-1-(4-(6-aminopyridin-3-yl)phenyl)ethyl)-6-(3-hydroxypropyl)-6-phenyl-1,3-oxazinan-2-one, (R)-6-(3-hydroxypropyl)-3-((S)-1-(4-(6-oxo-1,6-dihydropyridin-3-yl)phenyl)ethyl)-6-phenyl-1,3-oxazinan-2-one, (R)-6-allyl-6-(4-fluorophenyl)-3-((S)-1-(4-(pyridin-3-yl)phenyl)ethyl)-1,3-oxazinan-2-one, (R)-6-(2-aminoethyl)-6-phenyl-3-((S)-1-(4-(pyridin-3-yl)phenyl)ethyl)-1,3-oxazinan-2-one and (R)-6-(3-hydroxypropyl)-3-((S)-1-(4-(1-methyl-6-oxo-1,6-dihydropyridin-3-yl)phenyl)ethyl)-6-phenyl-1,3-oxazinan-2-one, (R)-6-allyl-6-phenyl-3-((S)-1-(4-(pyridin-3-yl)phenyl)ethyl)-1,3-oxazinan-2-one, (R)-6-allyl-6-(4-fluorophenyl)-3-((S)-1-(4-(pyridin-3-yl)phenyl)ethyl)-1,3-oxazinan-2-one, 3-((R)-6-(4-fluorophenyl)-2-oxo-3-((S)-1-(4-(pyridin-3-yl)phenyl)ethyl)-1,3-oxazinan-6-yl)propanoic acid, 3-((R)-2-oxo-6-phenyl-3-((S)-1-(4-(pyridin-4-yl)phenyl)ethyl)-1,3-oxazinan-6-yl)propanoic acid, (R)-6-allyl-6-phenyl-3-((S)-1-(4-(pyridin-4-yl)phenyl)ethyl)-1,3-oxazinan-2-one, (R)-6-allyl-3-((S)-1-(4-(6-methoxypyridin-3-yl)phenyl)ethyl)-6-phenyl-1,3-oxazinan-2-one, (R)-3-((S)-1-(4-(1H-pyrazol-3-yl)phenyl)ethyl)-6-allyl-6-phenyl-1,3-oxazinan-2-one, or a pharmaceutically acceptable salt, enantiomer or diastereomer thereof.

For each of the embodiment described in the previous paragraph, $R^1$ is preferably methyl or ethyl.

For each of the embodiment described in the paragraph immediately following Formulas $It^{1-7}$, $R^1$ is preferably methyl or ethyl; and $R^3$ is $MeSO_2NHCH_2CH_2CH_2$, $H_2NC(=O)CH_2CH_2$, $H_2NC(=O)CMe_2CH_2$, 3-hydroxypropyl, 3-hydroxy-3-methylbutyl, 2-hydroxyethyl, 2-hydroxy-2-methylpropyl or 2-cyano-2-methylpropyl.

For each of the embodiment described in the paragraph immediately following Formulas $It^{1-7}$, $R^1$ is preferably methyl or ethyl; and $R^3$ is $H_2NC(=O)CMe_2CH_2$, 3-hydroxy-3-methylbutyl, 2-hydroxy-2-methylpropyl or 2-cyano-2-methylpropyl.

For each of the embodiment described in the paragraph immediately following Formulas $It^{1-7}$, $R^1$ is preferably methyl or ethyl; $R^2$ is phenyl optionally substituted with 1, 2 or 3 substituents selected from halo, cyano, $CONH_2$, $(C_1-C_4)$alkyl, $(C_1-C_4)$haloalkyl and $SO_2Me$; and $R^3$ is $MeSO_2NHCH_2CH_2CH_2$, $H_2NC(=O)CH_2CH_2$, $H_2NC(=O)CMe_2CH_2$, 3-hydroxypropyl, 3-hydroxy-3-methylbutyl, 2-hydroxyethyl, 2-hydroxy-2-methylpropyl or 2-cyano-2-methylpropyl.

For each of the embodiment described in the paragraph immediately following Formulas $It^{1-7}$, $R^1$ is preferably methyl or ethyl; $R^2$ is phenyl optionally substituted with 1, 2 or 3 substituents selected from halo, cyano, $CONH_2$, $(C_1-C_4)$alkyl, $(C_1-C_4)$haloalkyl and $SO_2Me$; and $R^3$ is $H_2NC(=O)CMe_2CH_2$, 3-hydroxy-3-methylbutyl, 2-hydroxyethyl, 2-hydroxy-2-methylpropyl or 2-cyano-2-methylpropyl.

For each of the embodiment described in the paragraph immediately following Formulas $It^{1-7}$, $R^1$ is preferably methyl or ethyl; and $R^3$ is 2-hydroxy-2-methylpropyl or 2-cyano-2-methylpropyl.

For each of the embodiment described in the paragraph immediately following Formulas $It^{1-7}$, $R^1$ is preferably methyl or ethyl; $R^2$ is phenyl or fluorophenyl; and $R^3$ is 2-hydroxy-2-methylpropyl or 2-cyano-2-methylpropyl.

Alternatively, —CHO, $NH_2$—$SO_2NH_2$, —COON, and —$CONH_2$ are excluded as permissible substituents for the pyridine and thiazole rings at the position corresponding to $Cy^2$ for all of the specific embodiments described above for Formulas $Iq^{1-21}$, $Ip^{1-21}$, $Ir^{1-21}$, $Is^{1-21}$, and $It^{1-7}$.

Another embodiment of the invention (referred to herein as the "Second Alternate Embodiment") is a compound represented by Structural Formulas $It^{1-7}$, wherein: n is 0 or 1, preferably 0; each $G^1$ is independently ($C_1$-$C_4$)alkyl, ($C_1$-$C_4$)alkoxy, ($C_1$-$C_4$)haloalkyl, ($C_1$-$C_4$)haloalkoxy, halogen, cyano or nitro; $G^{1a}$ is hydroxy($C_1$-$C_6$)alkyl, ($C_1$-$C_6$)alkylcarbonylamino($C_1$-$C_6$)alkyl, ($C_1$-$C_6$)alkylsulfonylamino($C_1$-$C_6$)alkyl, ($C_1$-$C_6$)alkoxy($C_1$-$C_6$)alkyl, amino($C_1$-$C_6$)alkyl, ($C_1$-$C_6$)alkylamino($C_1$-$C_6$)alkyl, di($C_1$-$C_6$)alkylamino($C_1$-$C_6$)alkyl, cyano($C_1$-$C_6$)alkyl, aminocarbonyl($C_1$-$C_6$)alkyl, ($C_1$-$C_6$)alkylaminocarbonyl($C_1$-$C_6$)alkyl, di($C_1$-$C_6$)alkylaminocarbonyl($C_1$-$C_6$)alkyl, ($C_3$-$C_6$)cycloalkylaminocarbonyl($C_1$-$C_6$)alkyl, {($C_3$-$C_6$)cycloalkyl}{($C_1$-$C_6$)alkyl}aminocarbonyl($C_1$-$C_6$)alkyl or di($C_3$-$C_6$)cycloalkylaminocarbonyl($C_1$-$C_6$)alkyl; $G^{2b}$ and $G^{2c}$ are independently selected from hydrogen, fluorine, chlorine, cyano, hydroxy, amino, ($C_1$-$C_4$)alkyl, ($C_3$-$C_4$)cycloalkyl, ($C_3$-$C_4$)cycloalkyl($C_1$-$C_2$)alkyl, halo($C_1$-$C_4$)alkyl, ($C_1$-$C_4$)alkoxy, ($C_1$-$C_4$)haloalkoxy, $CONH_2$, ($C_1$-$C_4$)alkylaminocarbonyl, di($C_1$-$C_4$)alkylaminocarbonyl and ($C_1$-$C_4$)alkylcarbonylamino; $R^1$ is methyl or ethyl; $R^2$ is phenyl, thienyl, pyridyl or isopropyl each optionally substituted with up to three groups independently selected from halo, methyl, methylthio or (4-morpholino)methyl; and $R^3$ is methyl, ethyl, propyl, butyl, vinyl, allyl or ethoxyethyl each optionally substituted with up to two groups independently selected from methyl, HO—, MeO—, $H_2N$—, MeC(=O)NH—, MeS(=O)$_2$NH—, $H_2$NC(=O)—, MeNHC(=O)—, $HO_2C$—, (HO)$_2$P(=O)O—, $H_2$NS(=O)$_2$O—, $H_2$NS(=O)$_2$NH—, MeNHC(=O)NH—, MeNHC(=O)O—, oxo, cyano, $HO_2C$—, $HOCH_2CH_2NH$—, 4-morpholino, $HOCH_2C$(=O)NH—, $H_2NCH_2C$(=O)NH—, EtNHC(=O)NH, MeOC(=O)NH—, MeNHC(=NC≡N)NH—, Me-, MeS—, $MeSO_2$—, $MeSO_2N(Me)$—, MeS(=O)$_2$NHC(=O)—, imidazolylamino-, imidazolyl, tetrazolyl, $H_2NCONH$—, $H_2NCO_2$—, $HOCH_2CH_2O$—, MeNH—, $Me_2N$— and MeCONMe.

Alternatively for Structural Formulas $It^{1-7}$, $R^2$ is phenyl optionally substituted with 1, 2 or 3 substituents independently selected from halo, cyano, $CONH_2$, ($C_1$-$C_4$)alkyl, ($C_1$-$C_4$)haloalkyl and $SO_2Me$; and $R^3$ is $MeSO_2NHCH_2CH_2CH_2$, $H_2NC$(=O)$CH_2CH_2$, $H_2NC$(=O)$CMe_2CH_2$, 3-hydroxypropyl, 3-hydroxy-3-methylbutyl, 2-hydroxyethyl, 2-hydroxy-2-methylpropyl or 2-cyano-2-methylpropyl; and the remainder of the variables are as described above for the Second Alternate Embodiment.

Alternatively for Structural Formulas $It^{1-7}$, $R^3$ is $H_2NC$(=O)$CMe_2CH_2$, 3-hydroxy-3-methylbutyl, 2-hydroxy-2-methylpropyl or 2-cyano-2-methylpropyl; and the remainder of the variables are as described above for the Second Alternate Embodiment.

Alternatively for Structural Formulas $It^{1-7}$, $R^2$ is phenyl optionally substituted with 1, 2 or 3 substituents independently selected from halo, cyano, $CONH_2$, ($C_1$-$C_4$)alkyl, ($C_1$-$C_4$)haloalkyl and $SO_2Me$; and $R^3$ is $H_2NC$(=O)$CMe_2CH_2$, 3-hydroxy-3-methylbutyl, 2-hydroxy-2-methylpropyl or 2-cyano-2-methylpropyl; and the remainder of the variables are as described in the Second Alternate Embodiment.

Alternatively for Structural Formulas $It^{1-7}$, $R^3$ is 2-hydroxy-2-methylpropyl or 2-cyano-2-methylpropyl; and the remainder of the variables are as described in the Second Alternate Embodiment.

Alternatively for Structural Formulas $It^{1-7}$, $R^2$ is phenyl or fluorophenyl; and $R^3$ is 2-hydroxy-2-methylpropyl or 2-cyano-2-methylpropyl; and the remainder of the variables are as described in the Second Alternate Embodiment.

Alternatively for Structural Formulas $It^{1-7}$, $R^2$ is phenyl or fluorophenyl; $R^3$ is 2-hydroxy-2-methylpropyl or 2-cyano-2-methylpropyl; one or two substitutable ring carbon atoms in the oxodihydropyridyl rings are optionally substituted with methyl or ethyl; and the remainder of the variables are as described in the Second Alternate Embodiment.

For the embodiment described in the previous seven paragraphs, n is 0 and $G^{2b}$ and $G^{2c}$ are preferably —H.

Compounds of the invention are also disclosed in INHIBITORS OF 11β-HYDROXYSTEROID DEHYDOGENASE I, U.S. Provisional Application No. 61/61/135,933, filed Jul. 25, 2008; Cyclic Inhibitors Of 11β-Hydroxysteroid Dehydrogenase 1, U.S. Provisional Application No. 61/135,933, filed May 1, 2008; Cyclic Inhibitors Of 11β-Hydroxysteroid Dehydrogenase 1, U.S. Provisional Application No. 61/137,148, filed Jul. 25, 2008; and Cyclic Inhibitors Of 11β-Hydroxysteroid Dehydrogenase 1, International Application No. PCT/US2008/009017, filed Jul. 25, 2008; the entire teachings of these applications are incorporated herein by reference in their entirety.

Definitions

The term "alkyl" means a straight or branched hydrocarbon radical having 1-10 carbon atoms and includes, for example, methyl, ethyl, n-propyl, isopropyl, n-butyl, sec-butyl, isobutyl, tert-butyl, n-pentyl, n-hexyl, n-heptyl, n-octyl, n-nonyl, n-decyl and the like.

The term "cycloalkyl" means a monocyclic, bicyclic or tricyclic, saturated hydrocarbon ring having 3-10 carbon atoms and includes, for example, cyclopropyl (c-Pr), cyclobutyl, cyclopentyl, cyclohexyl, cycloheptyl, cyclooctyl, bicyclo[2.2.2]octyl, bicyclo[2.2.1]heptyl, spiro[4.4]nonane, adamantyl and the like.

The term "aryl" means an aromatic radical which is a phenyl group, a naphthyl group, an indanyl group or a tetrahydronaphthalene group. An aryl group is optionally substituted with 1-4 substituents. Exemplary substituents include alkyl, alkoxy, alkylthio, alkylsulfonyl, halogen, trifluoromethyl, dialkylamino, nitro, cyano, $CO_2H$, $CONH_2$, N-monoalkyl-substituted amido and N,N-dialkyl-substituted amido.

The term "heteroaryl" means a 5- and 6-membered heteroaromatic radical which may optionally be fused to a saturated or unsaturated ring containing 0-4 heteroatoms selected from N, O, and S and includes, for example, a heteroaromatic radical which is 2- or 3-thienyl, 2- or 3-furanyl, 2- or 3-pyrrolyl, 2-, 3-, or 4-pyridyl, 2-pyrazinyl, 2-, 4-, or 5-pyrimidinyl, 3- or 4-pyridazinyl, 1H-indol-6-yl, 1H-indol-5-yl, 1H-benzimidazol-6-yl, 1H-benzimidazol-5-yl, 2-, 4-, 5-, 6-, 7- or 8-quinazolinyl, 2-, 3-, 5-, 6-, 7- or 8-quinoxalinyl, 2-, 3-, 4-, 5-, 6-, 7- or 8-quinolinyl, 1-, 3-, 4-, 5-, 6-, 7- or 8-isoquinolinyl, 2-, 4-, or 5-thiazolyl, 2-, 3-, 4-, or 5-pyrazolyl, 2-, 3-, 4-, or 5-imidazolyl. A heteroaryl is optionally substituted. Exemplary substituents include alkyl, alkoxy, alkylthio, alkylsulfonyl, halogen, trifluoromethyl, dialkylamino, nitro, cyano, $CO_2H$, $CONH_2$, N-monoalkyl-substituted amido and N,N-dialkyl-substituted amido, or by oxo to form an N-oxide.

The term "heterocyclyl" means a 4-, 5-, 6- and 7-membered saturated or partially unsaturated heterocyclic ring containing 1 to 4 heteroatoms independently selected from N, O, and S. Exemplary heterocyclyls include pyrrolidine, pyrrolidin-2-one, 1-methylpyrrolidin-2-one, piperidine, piperidin-2-one, dihydropyridine, tetrahydropyridine, piperazine, 1-(2,2,2-trifluoroethyl)piperazine, 1,2-dihydro-2-oxopyridine, 1,4-dihydro-4-oxopyridine, piperazin-2-one, 3,4,5,6-tetrahydro-4-oxopyrimidine, 3,4-dihydro-4-oxopyrimidine, tetrahydrofuran, tetrahydropyran, tetrahydrothiophene, tetrahydrothiopyran, isoxazolidine, 1,3-dioxolane, 1,3-dithiolane, 1,3-dioxane, 1,4-dioxane, 1,3-dithiane, 1,4-dithiane, oxazolidin-2-one, imidazolidin-2-one, imidazolidine-2,4-dione, tetrahydropyrimidin-2(1H)-one, morpholine, N-methylmorpholine, morpholin-3-one, 1,3-oxazinan-2-one, thiomorpholine, thiomorpholine 1,1-dioxide, tetrahydro-1,2,5-thiaoxazole 1,1-dioxide, tetrahydro-2H-1,2-thiazine 1,1-dioxide, hexahydro-1,2,6-thiadiazine 1,1-dioxide, tetrahydro-1,2,5-thiadiazole 1,1-dioxide isothiazolidine 1,1-dioxide, 6-oxo-1, 6-dihydropyridazin-3-yl, 6-oxo-1,6-dihydropyridazin-4-yl, 5-oxo-4,5-dihydro-1H-1,2,4-triazol-3-yl and 5-oxo-4,5-dihydro-1H-imidazol-2-yl. A heterocyclyl can be optionally substituted with 1-4 substituents. Exemplary substituents include alkyl, haloalkyl, halogen and oxo.

The term "spirocycloalkyl" means a cycloalkyl group which shares one ring carbon with another alkyl or cycloalkyl group.

As used herein the terms "subject" and "patient" may be used interchangeably, and means a mammal in need of treatment, e.g., companion animals (e.g., dogs, cats, and the like), farm animals (e.g., cows, pigs, horses, sheep, goats and the like) and laboratory animals (e.g., rats, mice, guinea pigs and the like). Typically, the subject is a human in need of treatment.

When a disclosed compound or its pharmaceutically acceptable salt is named or depicted by structure, it is to be understood that solvates or hydrates of the compound or its pharmaceutically acceptable salts are also included. "Solvates" refer to crystalline forms wherein solvent molecules are incorporated into the crystal lattice during crystallization. Solvate may include water or nonaqueous solvents such as ethanol, isopropanol, DMSO, acetic acid, ethanolamine, and EtOAc. Solvates, wherein water is the solvent molecule incorporated into the crystal lattice, are typically referred to as "hydrates." Hydrates include stoichiometric hydrates as well as compositions containing variable amounts of water. Some of the compounds disclosed in the exemplification may be in the anhydrous form.

The term "compound" also includes labeling at one or more positions with deuterium. "Labeled with deuterium at a position" means that the amount deuterium at the position is greater than the amount that is present at natural abundance. In certain instances, the deuterium at each position in a "compound" is at natural abundance.

Certain of the disclosed compounds may exist in various stereoisomeric forms. Stereoisomers are compounds that differ only in their spatial arrangement. Enantiomers are pairs of stereoisomers whose mirror images are not superimposable, most commonly because they contain an asymmetrically substituted carbon atom that acts as a chiral center. "Enantiomer" means one of a pair of molecules that are mirror images of each other and are not superimposable. Diastereomers are stereoisomers that are not related as mirror images, most commonly because they contain two or more asymmetrically substituted carbon atoms. The symbol "*" in a structural formula represents the presence of a chiral carbon center. "R" and "S" represent the configuration of substituents around one or more chiral carbon atoms. Thus, "R*" and "S*" denote the relative configurations of substituents around one or more chiral carbon atoms.

"Racemate" or "racemic mixture" means a compound of equimolar quantities of two enantiomers, wherein such mixtures exhibit no optical activity; i.e., they do not rotate the plane of polarized light.

"Geometric isomer" means isomers that differ in the orientation of substituent atoms in relationship to a carbon-carbon double bond, to a cycloalkyl ring, or to a bridged bicyclic system. Atoms (other than H) on each side of a carbon-carbon double bond may be in an E (substituents are on opposite sides of the carbon-carbon double bond) or Z (substituents are oriented on the same side) configuration.

"R," "S," "S*," "R*," "E," "Z," "cis," and "trans," indicate configurations relative to the core molecule.

The compounds of the invention may be prepared as individual isomers by either isomer-specific synthesis or resolved from an isomeric mixture. Conventional resolution techniques include forming the salt of a free base of each isomer of an isomeric pair using an optically active acid (followed by fractional crystallization and regeneration of the free base), forming the salt of the acid form of each isomer of an isomeric pair using an optically active amine (followed by fractional crystallization and regeneration of the free acid), forming an ester or amide of each of the isomers of an isomeric pair using an optically pure acid, amine or alcohol (followed by chromatographic separation and removal of the chiral auxiliary), or resolving an isomeric mixture of either a starting material or a final product using various well known chromatographic methods.

When the stereochemistry of a disclosed compound is named or depicted by structure, the named or depicted stereoisomer is at least 60%, 70%, 80%, 90%, 99% or 99.9% by weight pure relative to the other stereoisomers. When a single enantiomer is named or depicted by structure, the depicted or named enantiomer is at least 60%, 70%, 80%, 90%, 99% or 99.9% by weight optically pure. Percent optical purity by weight is the ratio of the weight of the enantiomer over the weight of the enantiomer plus the weight of its optical isomer.

When a disclosed compound is named or depicted by structure without indicating the stereochemistry, and the compound has at least one chiral center, it is to be understood that the name or structure encompasses one enantiomer of compound free from the corresponding optical isomer, a racemic mixture of the compound and mixtures enriched in one enantiomer relative to its corresponding optical isomer.

When a disclosed compound is named or depicted by structure without indicating the stereochemistry and has at least two chiral centers, it is to be understood that the name or structure encompasses a diastereomer free of other diastereomers, a pair of diastereomers free from other diastereomeric pairs, mixtures of diastereomers, mixtures of diastereomeric pairs, mixtures of diastereomers in which one diastereomer is enriched relative to the other diastereomer(s) and mixtures of diastereomeric pairs in which one diastereomeric pair is enriched relative to the other diastereomeric pair(s).

The compounds of the invention may be present in the form of pharmaceutically acceptable salts. For use in medicines, the salts of the compounds of the invention refer to non-toxic "pharmaceutically acceptable salts." Pharmaceutically acceptable salt forms include pharmaceutically acceptable acidic/anionic or basic/cationic salts.

Pharmaceutically acceptable basic/cationic salts include, the sodium, potassium, calcium, magnesium, diethanolamine, n-methyl-D-glucamine, L-lysine, L-arginine, ammonium, ethanolamine, piperazine and triethanolamine salts.

Pharmaceutically acceptable acidic/anionic salts include, the acetate, benzenesulfonate, benzoate, bicarbonate, bitartrate, bromide, calcium edetate, camsylate, carbonate, chloride, citrate, dihydrochloride, edetate, edisylate, estolate, esylate, fumarate, glyceptate, gluconate, glutamate, glycollylarsanilate, hexylresorcinate, hydrobromide, hydrochloride, hydroxynaphthoate, iodide, isethionate, lactate, lactobionate, malate, maleate, malonate, mandelate, mesylate, methylsulfate, mucate, napsylate, nitrate, pamoate, pantothenate, phosphate/diphosphate, polygalacturonate, salicylate, stearate, subacetate, succinate, sulfate, hydrogensulfate, tannate, tartrate, teoclate, tosylate, and triethiodide salts.

The following abbreviations have the indicated meanings:

| Abbreviation | Meaning |
|---|---|
| A % | Area percentage |
| Boc | tert-butoxy carbonyl or t-butoxy carbonyl |
| (Boc)$_2$O | di-tert-butyl dicarbonate |
| Cbz | Benzyloxycarbonyl |
| CbzCl | Benzyl chloroformate |
| c-Pr | cyclopropyl |
| DAST | diethylaminosulfur trifluoride |
| DBU | 1,8-diazabicyclo[5.4.0]undec-7-ene |
| DCC | N,N'-dicyclohexylcarbodiimide |
| DCU | N,N'-dicyclohexylurea |
| DIAD | diisopropyl azodicarboxylate |
| DIBAL-H | diisobutylaluminum hydride |
| DIEA | N,N-diisopropylethylamine |
| DMAP | 4-(dimethylamino)pyridine |
| DMF | N,N-dimethylformamide |
| DMPU | 1,3-dimethyl-3,4,5,6-tetrahydro-2(1H)-pyrimidinone |
| 2,4-DNP | 2,4-dinitrophenylhydrazine |
| DPTBS | Diphenyl-t-butylsilyl |
| dr | diastereomer ratio |
| EDC•HCl, EDCl | 1-[3-(dimethylamino)propyl]-3-ethylcarbodiimide hydrochloride |
| Equiv | equivalents |
| EtOAc | Ethyl acetate |
| Fmoc | 1-[[(9H-fluoren-9-ylmethoxy)carbonyl]oxy]- |
| Fmoc-OSu | 1-[[(9H-fluoren-9-ylmethoxy)carbonyl]oxy]-2,5-pyrrolidinedione |
| h, hr | hour(s) |
| HOBt | 1-hydroxybenzotriazole |
| HATU | 2-(7-Aza-1H-benzotriazole-1-yl)-1,1,3,3-tetramethyluronium hexafluorophosphate |
| HBTU | 2-(1 H-Benzotriazol-1-yl)-1,1,3,3-tetramethyluronium hexafluorophosphate |
| KHMDS | potassium hexamethyldisilazane |
| LAH or LiAlH$_4$ | lithium aluminum hydride |
| LC-MS | liquid chromatography-mass spectroscopy |
| LHMDS | lithium hexamethyldisilazane |
| m-CPBA | meta-chloroperoxybenzoic acid |
| Me | methyl |
| MsCl | methanesulfonyl chloride |
| Min | minute |
| MS | mass spectrum |
| NaH | sodium hydride |
| NaHCO$_3$ | sodium bicarbonate |
| NaN$_3$ | sodium azide |
| NaOH | sodium hydroxide |
| Na$_2$SO$_4$ | sodium sulfate |
| NMM | N-methylmorpholine |
| NMP | N-methylpyrrolidinone |
| Pd$_2$(dba)$_3$ | tris(dibenzylideneacetone)dipalladium(0) |
| PE | petroleum ether |
| Quant | quantitative yield |
| rt | room temperature |
| Satd | saturated |
| SOCl$_2$ | thionyl chloride |
| SFC | supercritical fluid chromatography |
| SPA | scintillation proximity assay |
| SPE | solid phase extraction |
| TBAF | tetrabutylammonium fluoride |
| TBS | t-butyldimethylsilyl |
| TBDPS | t-butyldiphenylsilyl |
| TBSCl | t-butyldimethylsilyl chloride |
| TBDPSCl | t-butyldiphenylsilyl chloride |
| TEA | triethylamine or Et$_3$N |
| TEMPO | 2,2,6,6-tetramethyl-1-piperidinyloxy free radical |
| Teoc | 1-[2-(trimethylsilyl)ethoxycarbonyloxy]- |
| Teoc-OSu | 1-[2-(trimethylsilyl)ethoxycarbonyloxy]pyrrolidin-2,5-dione |
| T$_{ext}$ | External temperature |
| T$_{int}$ | Internal temperature |
| TFA | trifluoroacetic acid |
| Tlc, TLC | thin layer chromatography |
| TMS | trimethylsilyl |
| TMSCl | chlorotrimethylsilane or trimethylsilyl chloride |
| t$_R$ | retention time |
| TsOH | p-toluenesulfonic acid |

General Description of Synthetic Methods

Compounds of Formula I* can be prepared by several processes. In the discussion below, $A^1$, $Cy^1$, E, $R^1$, $R^2$, $R^3$, Y and n have the meanings indicated above unless otherwise noted. $Cy^2$ is an optionally substituted pyridyl, pyridazinyl, pyrimidinyl, pyrazinyl, thiadiazolyl, thiazolyl or pyrazolyl group. In cases where the synthetic intermediates and final products of Formula I* described below contain potentially reactive functional groups, for example amino, hydroxyl, thiol and carboxylic acid groups, that may interfere with the desired reaction, it may be advantageous to employ protected forms of the intermediate. Methods for the selection, introduction and subsequent removal of protecting groups are well known to those skilled in the art. (T. W. Greene and P. G. M. Wuts "Protective Groups in Organic Synthesis" John Wiley & Sons, Inc., New York 1999). Such protecting group manipulations are assumed in the discussion below and not described explicitly. Generally, reagents in the reaction schemes are used in equimolar amounts; however, in certain cases it may be desirable to use an excess of one reagent to drive a reaction to completion. This is especially the case when the excess reagent can be readily removed by evaporation or extraction. Bases employed to neutralize HCl in reaction mixtures are generally used in slight to substantial excess (1.05-5 equivalents).

In a first process a compound of Formula I*, can be prepared by reaction of an aminoalcohol intermediate of Formula II with a reagent of Formula III, wherein $Z^1$ and $Z^2$ are leaving groups such as chloride, 1-imidazolyl or aryloxide in an inert solvent such as THF, CH$_2$Cl$_2$, toluene or MeCN, usually in the presence of an organic or inorganic base such as triethylamine or NaHCO$_3$ respectively, at −10° C. to 120° C.:

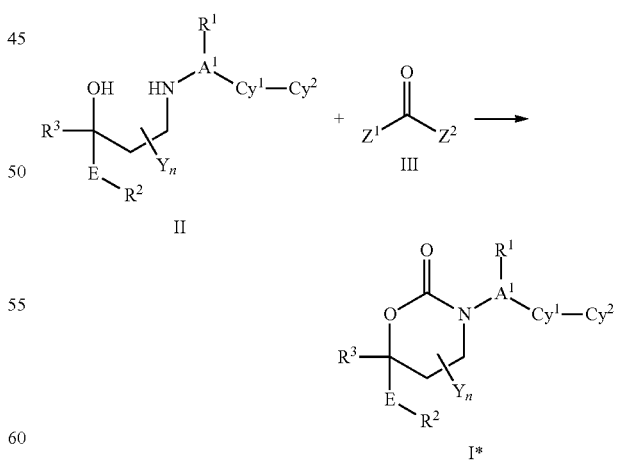

Certain instances of reagent III are especially convenient because they are commercially available. For example when $Z^1$ and $Z^2$ are both chloride, III is phosgene. When $Z^1$ and $Z^2$ are both 1-imidazolyl, III is carbonyl diimidazole. When $Z^1$ is chloride and $Z^2$ is p-nitrophenoxide, III is p-nitrophenyl chloroformate. When $Z^1$ and $Z^2$ are both $OCCl_3$, III is triphosgene and as little as one third of molar equivalent can be used.

Aminoalcohol intermediates of Formula II can be prepared by reduction of amides of Formula IV using a hydride reagent such as $BH_3$.THF solution, $BH_3$.$Me_2S$ or $LiAlH_4$ in an inert solvent ethereal such as THF or DME at 20° C. to 100° C. for between 1 h and 48 h:

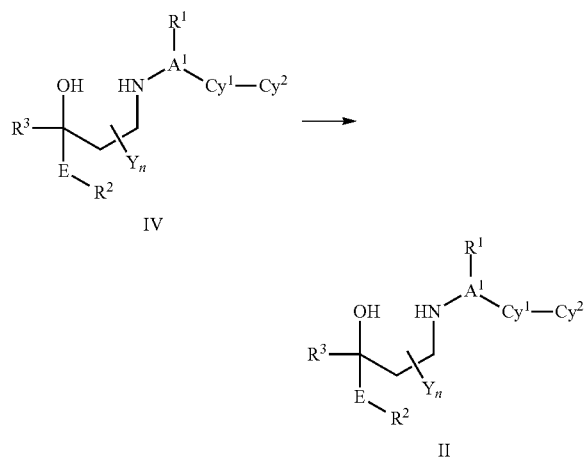

Intermediates of Formula IV can be prepared by coupling of a β-hydroxyacid of Formula V with an amine of Formula VI using standard peptide coupling reagents such as EDC in the presence of HOBt and N,N-diisopropylethylamine in an inert solvent such as $CH_2Cl_2$ at 0-30° C. for between 1 h and 24 h:

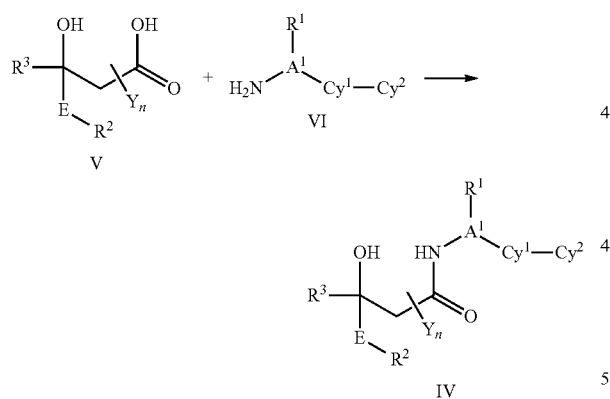

Amine intermediates of Formula VI, wherein $A^1$=$CH_2$ and $R^1$ is absent, can be prepared by reduction of amides of Formula VII using a hydride reagent such as $BH_3$.THF solution, $BH_3$.$Me_2S$ or $LiAlH_4$ in an inert solvent ethereal such as THF or DME at 20° C. to 100° C. for between 1 h and 48 h:

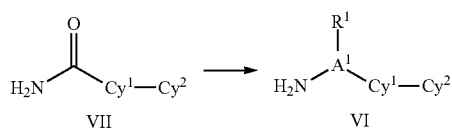

Amine intermediates of Formula VI, wherein $A^1$ is a bond, $R^1$ is absent and $Cy^1$ is not an aromatic or heteroaromatic ring, can be prepared from ketones of formula VIII via oximes of Formula IX or by reductive amination of a ketone of Formula VIII with ammonia:

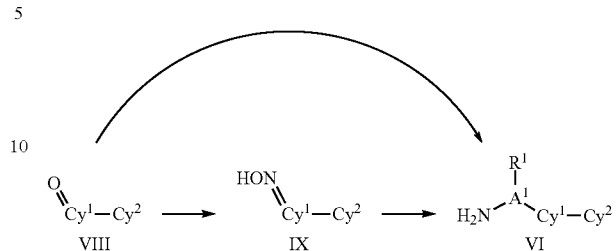

Methods for the conversion of ketones to oximes are described in Smith, M. B. and March, J. "March's Advanced Organic Chemistry" pp 1194-1195, $5^{th}$ Edition, Wiley, New York, N.Y., 2001. Methods for the reduction of oximes to primary amines are described in Smith, M. B. and March, J. "March's Advanced Organic Chemistry" p 1555, $5^{th}$ Edition, Wiley, New York, N.Y., 2001. Methods for the reductive amination of ketones are described in Baxter, E. W. and Reitz, A. B. "Organic Reactions" Volume 59, Ed. Overman, L. E., Wiley Interscience, 2002.

Similarly amine intermediates of Formula VI, wherein $A^1$ is CH and $R^1$ is methyl or ethyl, can be prepared by reduction t-butylsulfinylimines of Formula VIIIb which can be prepared from ketones of Formula VIIIa and t-butylsulfinamide or by addition of organometallic reagents of Formula $R^1M$, wherein $R^1$ is Me or Et and M is Li, MgCl, MgBr or MgI, to t-butylsulfinylimines of Formula VIIId which can be prepared from aldehydes of Formula VIIIc.

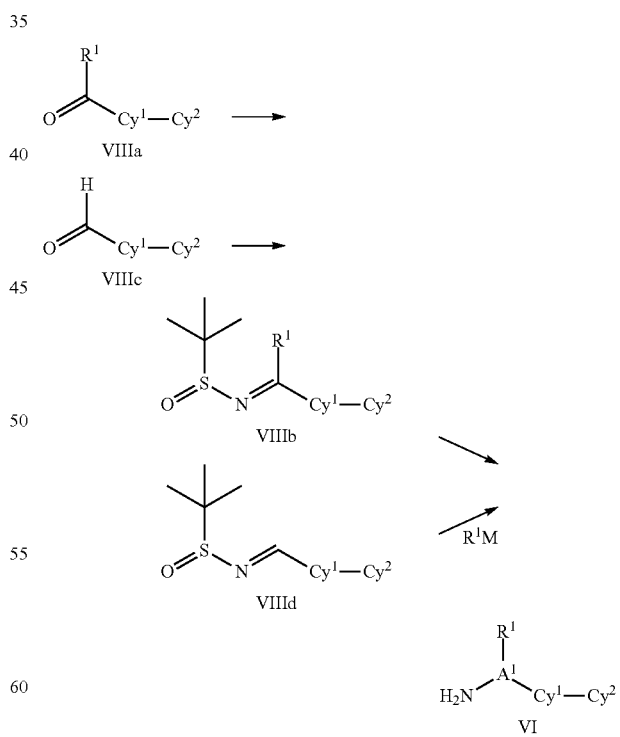

High stereoselectivity is often achieved in such reactions using chiral t-butylsulfinylimines.

Intermediates of Formula II, wherein n=0, can be prepared by reaction of oxetanes of Formula X with amines of Formula VI as described in Smith, M. B. and March, J. "March's Advanced Organic Chemistry" p 505, 5$^{th}$ Edition, Wiley, New York, N.Y. 2001:

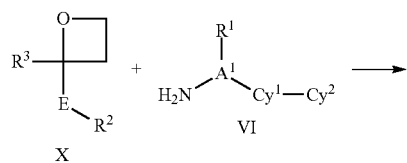

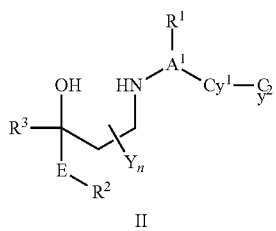

Aldehydes of Formula Xa can be prepared from homoallylic alcohols of Formula XXI by treatment with Os$_4$ and NalO$_4$.

Intermediates of Formula II can also be prepared by reaction of amines of Formula VI with haloalcohols of Formula XXX or sulfonates of Formula XVII.

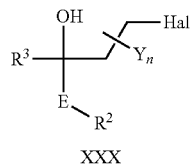

XXX or

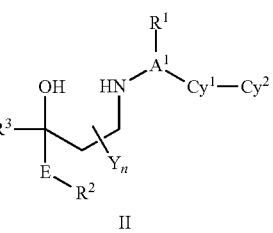

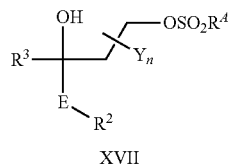

XVII

-continued

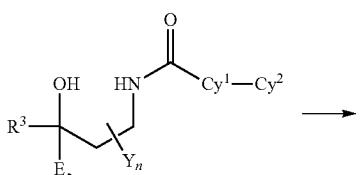

II

Intermediates of Formula II can also be prepared by reductive amination of β-hydroxyaldehydes of Formula Xa with amines of Formula VI. Methods for the reductive amination of aldehydes are described in Baxter, E. W. and Reitz, A. B. "Organic Reactions" Volume 59, Ed. Overman, L. E., Wiley Interscience, 2002.

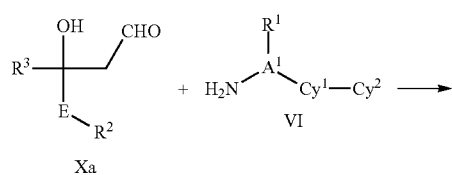

Xa

Intermediates of Formula II, wherein A$^1$=CH$_2$ and R$^1$ is absent, can be prepared by reduction of amide intermediates of formula XI using a hydride reagent such as BH$_3$.THF solution, BH$_3$.Me$_2$S or LiAlH$_4$ in an inert solvent ethereal such as THF or DME at 20° C. to 100° C. for between 1 h and 48 h:

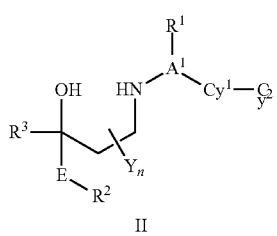

Amide intermediates of Formula XI can be prepared by reaction of an aminoalcohol intermediate of Formula XII with activated carboxylic acid of Formula XIII wherein $Z^3$=chloride or an activated ester, such as an N-hydroxysuccinimide ester:

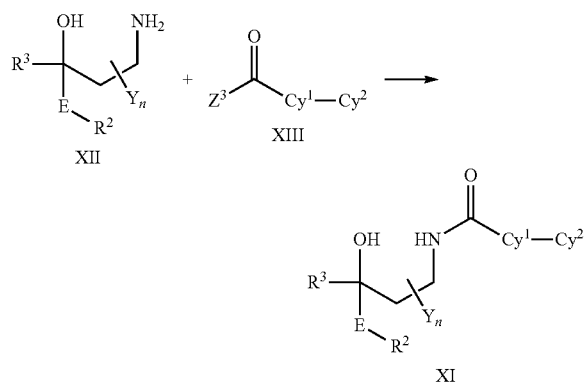

Amino-alcohol intermediates of Formula XII, wherein n=0, can be prepared by reaction of an epoxide of Formula XIV with cyanide ion followed by reduction of the resulting hydroxynitrile of Formula XV with hydrogen gas in the presence of a catalyst or with a hydride source such as LiAlH$_4$:

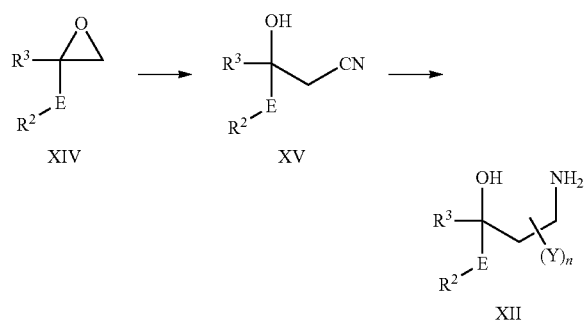

Epoxide compounds of formula XIV can, in turn, be prepared in a number of ways including, as described in Aube, J. "Epoxidation and Related Processes" Chapter 3.2 in Volume 1 of "Comprehensive Organic Synthesis" Edited by B. M. Trost, I. Fleming and Stuart L. Schreiber, Pergamon Press, New York, 1992.

Hydroxynitrile intermediates of Formula XV can be prepared by treatment of ketones of Formula XVI with acetonitrile anion, formed by treatment of acetonitrile with n-BuLi or LDA, in an inert, anhydrous solvent such as THF at low temperature:

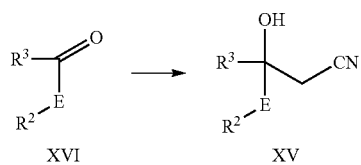

Amino-alcohol intermediates of Formula XII, wherein n is 0, can be prepared by treatment of sulfonate intermediates of Formula XVII, wherein $R^4$ is for example methyl, trifluoromethyl or p-methylphenyl, with ammonia:

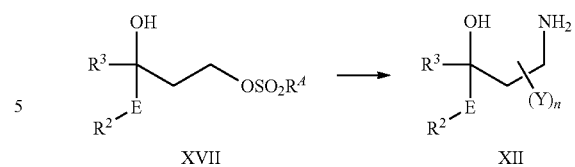

Amino-alcohol intermediates of Formula XII can be prepared by treatment of sulfonate intermediates of Formula XVII with sodium azide to give an azide intermediate of Formula XVIII, followed by catalytic hydrogenation or by Staudinger reduction with PPh$_3$ in wet THF:

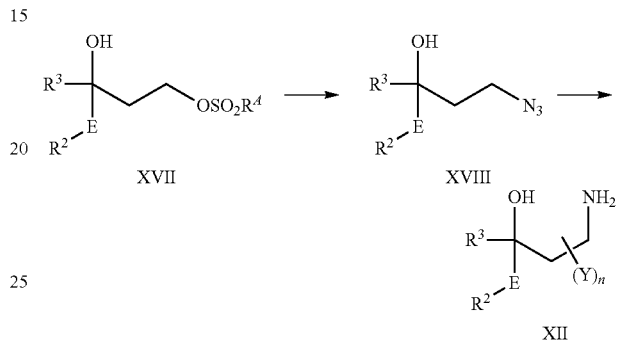

Sulfonate intermediates of Formula XVII can be prepared from diol intermediates of Formula XIX with a sulfonyl chloride $R^4SO_2Cl$:

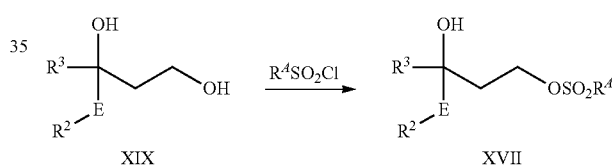

Diol intermediates of Formula XIX can be prepared by hydroboration of allyl alcohols of Formula XX:

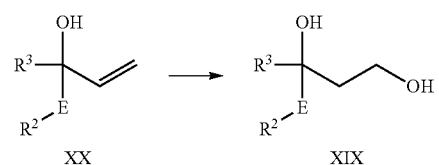

Diol intermediates of Formula XIX can be prepared by ozonolysis and reduction of homoallyl alcohols of Formula XXI:

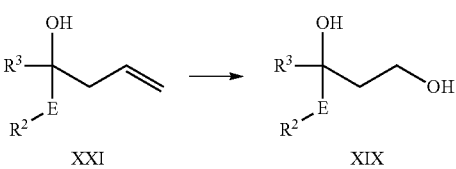

Aminoalcohol intermediates of Formula II, wherein $A^1$ is a bond, $R^1$ is absent, and $Cy^1$ is a heteroaryl group or an aryl group bearing at least one strongly electron withdrawing group such as $CF_3$, can be prepared by reaction of an aminoalcohol intermediate of Formula XII with a compound of Formula XXII, wherein $Cy^1$ is a heteroaryl group or an aryl group bearing at least one strongly electron withdrawing group such as $CF_3$ and $R^B$ is a leaving group such a fluoro, chloro, bromo or iodo:

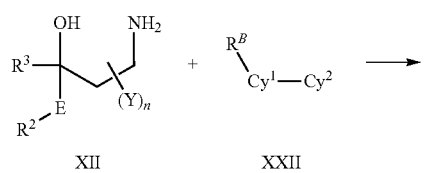

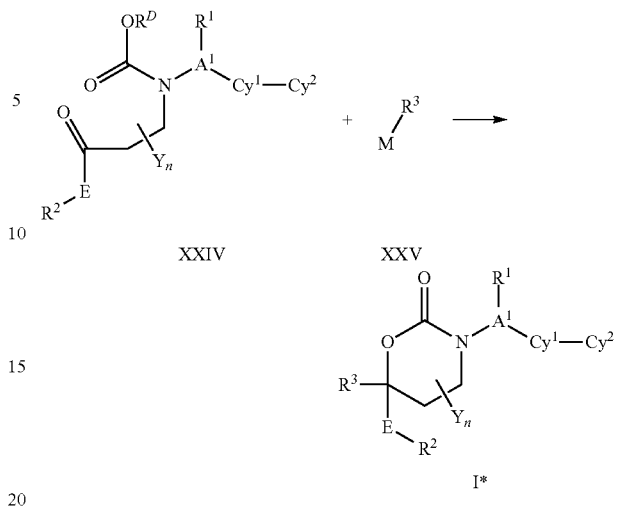

In specific examples, organometallic reagent XXV is allylmagnesium bromide, allylzinc(II) bromide, (2-methylallyl)magnesium chloride or (2-methoxy-2-oxoethyl)zinc(II) bromide. In certain cases when M is MgCl, MgBr or MgI, it is advantageous to add $CeCl_3$ to the reaction mixture.

Ketocarbamates of Formula XXIV can be prepared by reaction of aminoketones of Formula XXVI with intermediates of Formula XXVII wherein $R^E$ is a leaving group such as chloride, succinyloxy, imidazolyl or t-butoxycarboxycarbonyl:

Aminoalcohol intermediates of Formula II, wherein $A^1$ is $(C_1)$alkylene can be prepared by reaction of an aminoalcohol of Formula XII with an aldehyde or methyl ketone of Formula XII in the presence of a reducing agent such as $NaCNBH_3$ or $Na(OAc)_3BH$:

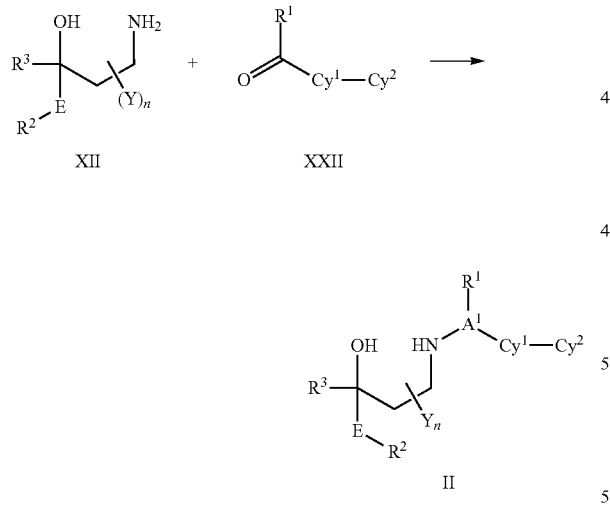

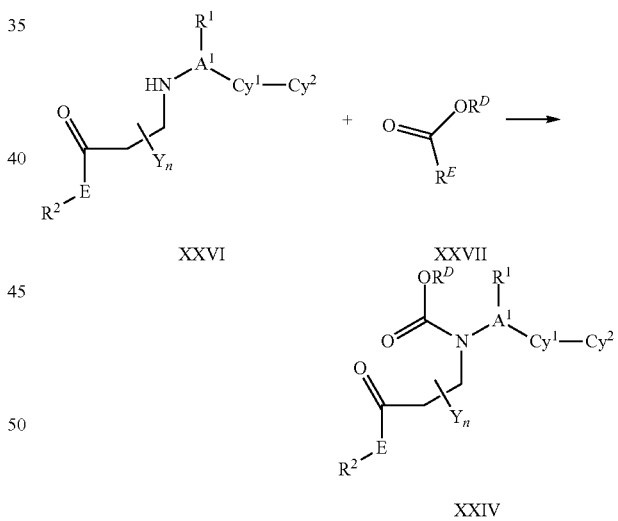

Methods for the reductive amination of aldehydes and ketones are described in Baxter, E. W. and Reitz, A. B. "Organic Reactions" Volume 59, Ed. Overman, L. E., Wiley Interscience, 2002.

In a second process a compound of Formula I* can be prepared by reaction of a ketocarbamate of Formula XXIV, wherein $R^D$ is alkyl or arylalkyl group such as methyl, t-butyl or benzyl, with an organometallic reagent of Formula XXV wherein M includes, but is not limited to, MgCl, MgBr, MgI or Li:

Aminoketones of Formula XXVI, wherein n=0, can be prepared by reaction of α,β-unsaturated ketones of Formula XXVIII with amines of Formula VI:

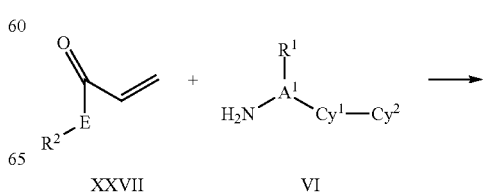

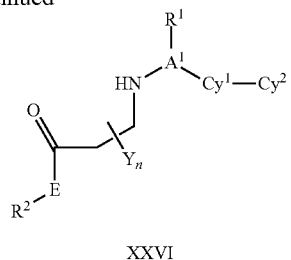

XXVI

Aminoketones of Formula XXVI, wherein n=0, can be prepared by reaction of β-dialkylaminoketones of Formula XXVIII, wherein $R^F$ is lower alkyl especially methyl, with amines of Formula VI:

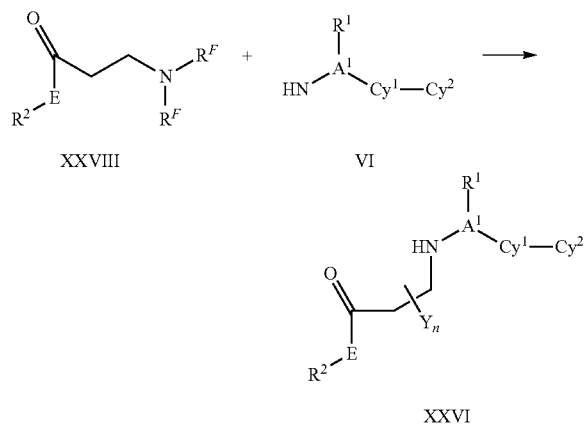

XXVIII      VI

XXVI

β-Dialkylaminoketones of Formula XXVIII are in turn derived from α,β-unsaturated ketones of Formula XXVII with dialkylamines of Formula $R^FNHR^F$.

In a third process a compound of Formula I* can be prepared by reaction of a compound of Formula XVII with an isocyanate of Formula XXIX in the presence of a base:

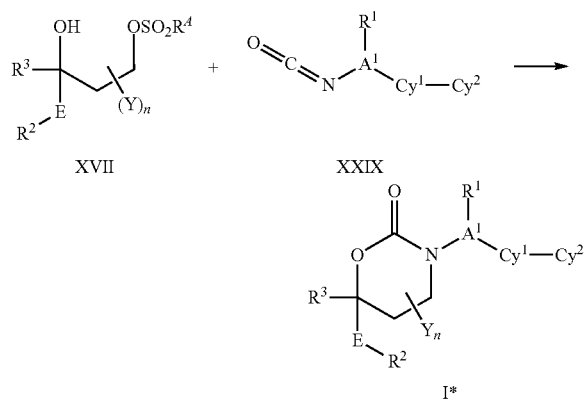

XVII      XXIX

I*

Isocyanates of Formula XXIX can be prepared from amines of Formula VI by treatment with phosgene, diphosgene or triphosgene. This third process is described in greater detail in U.S. Provisional Application Ser. No. 61/137,013, filed Jul. 25, 2008 entitled SYNTHESIS OF INHIBITORS OF 11β-HYDROXYSTEROID DEHYDROGENASE TYPE 1, the entire teachings of which are incorporated herein by reference.

In a fourth process a compound of Formula I* can be prepared by reaction of a halo compound of Formula, wherein Hal is chlorine or bromine, with an isocyanate of Formula XXIX in the presence of a base:

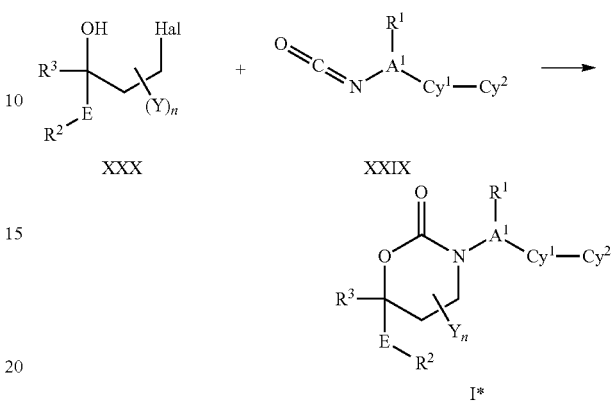

XXX      XXIX

I*

Halo compounds of Formula XXX can be prepared by reaction of β-haloketones of Formula XXXI with organometallic reagents of Formula XXV wherein M is a metal containing radical including MgCl, MgBr, MgI or Li. The reaction is optionally carried out in the presence of anhydrous cerium trichloride:

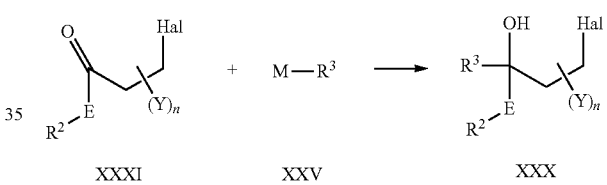

XXXI      XXV      XXX

In a fifth process a compound of Formula I*, wherein $A^1$ is $CH_2$ or $CH_2CH_2$ and $R^1$ is absent, can be prepared by reaction of a compound of Formula XXXII, with a compound of Formula XXXIII, wherein $A^1$ is $CH_2$ or $CH_2CH_2$ and $R^G$ is a leaving group such as Br, I, $OSO_2Me$, $OSO_2CF_3$ or $OSO_2Ph$, in the presence of a base such as NaH or $K_2CO_3$:

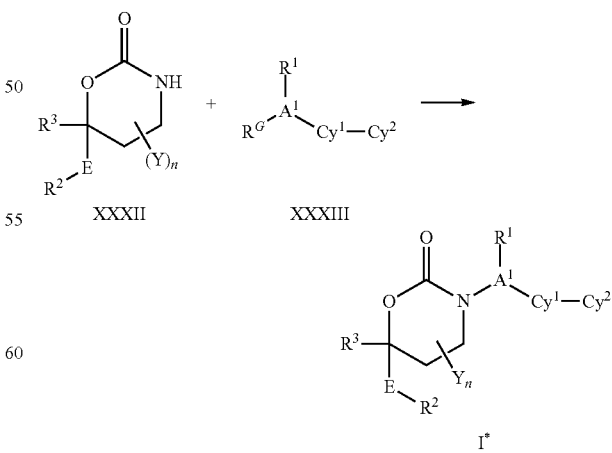

XXXII      XXXIII

I*

Compounds of Formula XXXII can be prepared by treatment of compounds of Formula XII with various reagents of Formula III, wherein $Z^1$ and $Z^2$ are leaving groups such as chloride, 1-imidazolyl or aryloxide in an inert solvent such as THF, $CH_2Cl_2$, toluene or MeCN, usually in the presence of an organic or inorganic base such as triethylamine or $NaHCO_3$ respectively, at $-10°$ C. to $120°$ C.:

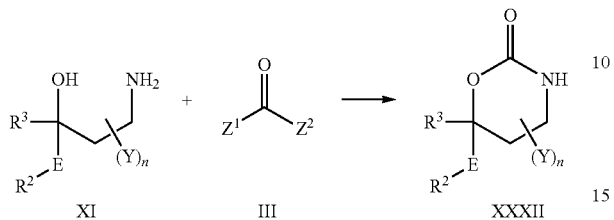

In a sixth process a compound of Formula I*, wherein $A^1$ is a bond and R1 is absent, can be prepared by reaction of a compound of Formula XXXII, with a compound of Formula XXII, wherein $R^B$ is a leaving group such as chloro, bromo, iodo or $OSO_2CF_3$, in the presence of a base such as $K_2CO_3$ and a copper or palladium catalyst in an inert solvent such as dioxane, DMF or NMP at elevated temperature:

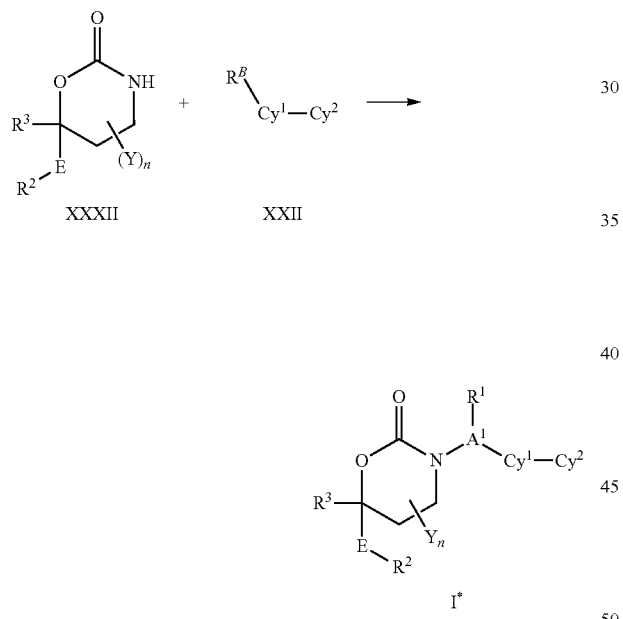

In a seventh process a compound of Formula I* can be prepared by Suzuki coupling of a compound of Formula XXXIV, wherein $Cy^1$ is aryl or heteroaryl and $R^X$ is bromo, iodo, or trifluoromethanesulfonyloxy, with a boronic acid ($R^Y$ is hydrogen) or a boronate ester of Formula XXXV ($R^Y$ is $(C_1-C_6)$alkyl and the two groups $R^Y$ taken together form a $(C_1-C_{12})$alkylene group). Alternatively, a compound of Formula XXXIV can be combined with $Cy^2$-H, wherein the H is replaced with the residue of Formula XXXIV by a transition metal mediated C—H activation process, to yield a compound of general formula 1*. These reactions are particularly suited for heteroaromatic $Cy^2$-H as detailed in e.g. *Chem Sus Chem* 2008, 1, 404-407, *Eur. J. Inorg. Chem.* 2008, 2550-59, *J. Am. Chem. Soc.* 2008, 130, 15185-92, and references quoted therein.

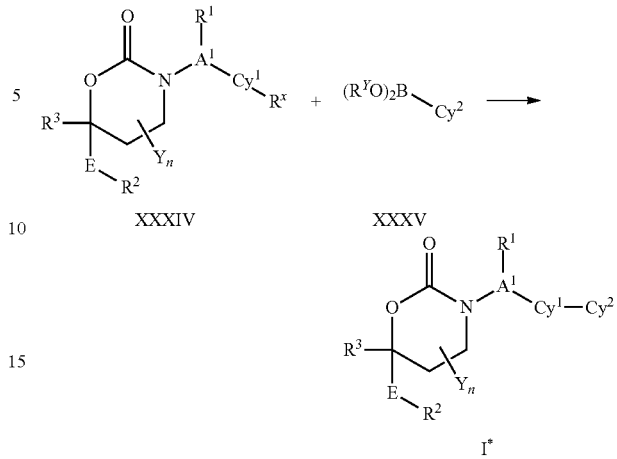

In an eighth process a compound of Formula XXXIV, wherein $Cy^1$ is aryl or heteroaryl and $R^X$ is bromo, iodo, or trifluoromethanesulfonyloxy, can be reacted with bis(pinacolato)diboron in the presence of a palladium catalyst to give a boronate ester of Formula XXXVI which can be further reacted with a heterocyclic compound of Formula XXXVII, wherein $R^X$ is bromo, iodo, or trifluoromethanesulfonyloxy, again in the presence of a palladium catalyst, to give a compound of Formula I*.

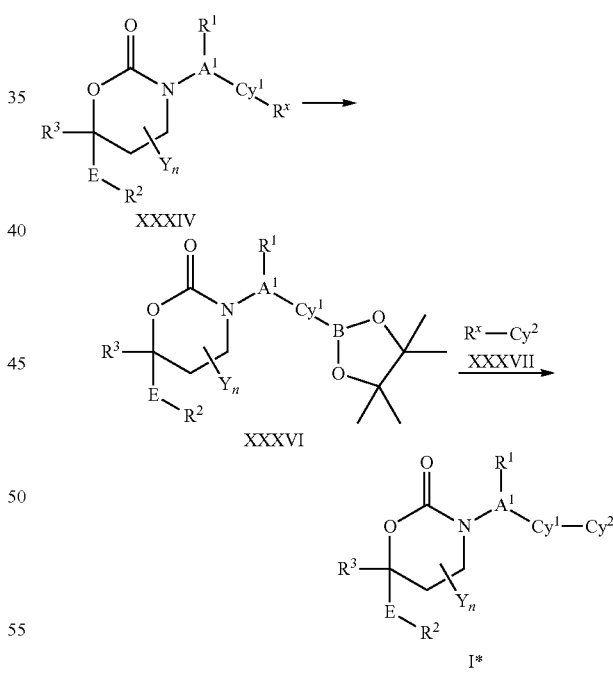

In a ninth process a compound of Formula I* can be prepared from another compound of Formula I*. For example:

(1) a compound of Formula I*, wherein $R^1$ or $R^3$ is ω-hydroxy($C_2$-$C_6$)alkyl, can be oxidized to a compound of Formula I*, wherein $R^1$ or $R^3$ is ω-carboxy($C_1$-$C_5$)alkyl, using Jones reagent.

(2) a compound of Formula I*, wherein $R^1$ or $R^3$ is ω-carboxy($C_1$-$C_6$)alkyl, can be coupled with ammonia or a ($C_1$-$C_6$)alkylamine using a standard peptide coupling reagent such as EDC to afford a compound of Formula I*, wherein $R^1$ or $R^3$ is ω-$H_2NC(=O)(C_1-C_6)$alkyl or ω-{$(C_1-C_6)$alkylNHC$(=O)$}$(C_1-C_6)$alkyl.

(3) a compound of Formula I*, wherein $R^1$ or $R^3$ is ω-hydroxy$(C_1-C_6)$alkyl, can be converted to its methanesulfonate or trifluoromethanesulfonate, treated with sodium azide and reduced to give a compound of Formula I*, wherein $R^1$ or $R^3$ is ω-amino$(C_1-C_6)$alkyl.

(4) a compound of Formula I*, wherein $R^1$ or $R^3$ is amino$(C_1-C_6)$alkyl, can be reacted with acetic anhydride or acetyl chloride to give a compound of Formula I*, wherein $R^1$ or $R^3$ is {acetylamino}$(C_1-C_6)$alkyl.

(5) a compound of Formula I*, wherein $R^1$ or $R^3$ is amino$(C_1-C_6)$alkyl, can be reacted with methanesulfonyl chloride to give a compound of Formula I*, wherein $R^1$ or $R^3$ is {methanesulfonylamino}$(C_1-C_6)$alkyl.

(6) a compound of Formula I*, wherein $R^1$ is $(C_2-C_6)$ alkenyl, is hydroborated to afford a compound of Formula I*, wherein $R^1$ is hydroxy$(C_2-C_6)$alkyl.

(7) a compound of Formula I*, wherein $R^3$ is $(C_2-C_6)$ alkenyl, is hydroborated to afford a compound of Formula I*, wherein $R^3$ is hydroxy$(C_2-C_6)$alkyl.

(8) a compound of Formula I*, wherein $R^1$ is $(C_2-C_6)$ alkenyl, can be reacted with osmium tetroxide and N-methylmorpholine-N-oxide to afford a compound of Formula I*, wherein $R^1$ is vicinal dihydroxy$(C_2-C_6)$alkyl, (9) a compound of Formula I*, wherein $R^3$ is $(C_2-C_6)$ alkenyl, can be reacted with osmium tetroxide and N-methylmorpholine-N-oxide to afford a vicinal diol compound of Formula I*, wherein $R^3$ is vicinal dihydroxy$(C_2-C_6)$alkyl,

(10) a compound of Formula I*, wherein $R^1$ is $(C_2-C_6)$ alkenyl, can be reacted with ozone followed by $NaBH_4$ to give a compound of Formula I*, wherein $R^1$ is ω-hydroxy$(C_1-C_5)$ alkyl.

(11) a compound of Formula I*, wherein $R^3$ is $(C_2-C_6)$ alkenyl, can be reacted with ozone followed by $NaBH_4$ to give a compound of Formula I*, wherein $R^3$ is ω-hydroxy$(C_1-C_5)$ alkyl.

(12) a compound of Formula I*, wherein $R^1$ or $R^3$ is amino$(C_1-C_6)$alkyl, can be reacted with an $(C_1-C_6)$alkyl isocyanate to give a compound of Formula I*, wherein $R^1$ or $R^3$ is $(C_1-C_6)$alkylaminocarbonylamino$(C_1-C_6)$alkyl.

(13) a compound of Formula I*, wherein $R^1$ or $R^3$ is amino$(C_1-C_6)$alkyl, can be reacted with an $(C_1-C_6)$alkyl chloroformate to give a compound of Formula I*, wherein $R^1$ or $R^3$ is $(C_1-C_6)$alkoxycarbonylamino$(C_1-C_6)$alkyl.

(14) a compound of Formula I*, wherein $R^1$ or $R^3$ is amino$(C_1-C_6)$alkyl, can be reacted with chlorosulfonyl isocyanate or sulfamide to give a compound of Formula I*, wherein $R^1$ or $R^3$ is aminosulfonylamino$(C_1-C_6)$alkyl.

(15) a compound of Formula I*, wherein $R^1$ or $R^3$ is amino$(C_1-C_6)$alkyl, can be reacted with a $(C_1-C_6)$alkylsulfamoyl chloride to give a compound of Formula I*, wherein $R^1$ or $R^3$ is $(C_1-C_6)$alkylaminosulfonylamino$(C_1-C_6)$alkyl.

(16) a compound of Formula I*, wherein $R^1$ or $R^3$ is hydroxy$(C_1-C_6)$alkyl, can be reacted with chlorosulfonyl isocyanate to give a compound of Formula I*, wherein $R^1$ or $R^3$ is aminosulfonyloxy$(C_1-C_6)$alkyl.

(17) a compound of Formula I*, wherein $R^1$ or $R^3$ is hydroxy$(C_1-C_6)$alkyl, can be reacted with p-nitrophenyl chloroformate, pentafluorophenyl chloroformate or carbonyl diimidazole, followed by ammonia, a $(C_1-C_6)$alkylamine or a di$(C_1-C_6)$alkylamine to give a compound of Formula I*, wherein $R^1$ or $R^3$ is aminocarboxy$(C_1-C_6)$alkyl, $(C_1-C_6)$alkyl aminocarboxy$(C_1-C_6)$alkyl or di$(C_1-C_6)$alkyl aminocarboxy $(C_1-C_6)$alkyl.

(18) a compound of Formula I*, wherein $R^1$ or $R^3$ is hydroxy$(C_1-C_6)$alkyl, can be reacted with $POCl_3$ to give a compound of Formula I*, wherein $R^1$ or $R^3$ is $(HO)_2P(=O)$ $O(C_1-C_6)$alkyl.

(19) a compound of Formula I*, wherein $R^3$ is allyl or homoallyl, can be reacted with oxygen in the presence of $PdCl_2$ and CuCl to afford a compound of Formula I*, wherein $R^3$ is 2-oxopropyl or 3-oxobutyl respectively.

(20) a compound of Formula I*, wherein $R^3$ is 2-oxopropyl or 3-oxobutyl, can be reacted with MeMgX, wherein X is Cl, Br or I, to give a compound of Formula I*, wherein $R^3$ is 2-hydroxy-2-methylpropyl or 3-hydroxy-3-methylpropyl respectively.

(21) a compound of Formula I*, wherein $R^3$ is —$CH_2CO_2Me$ can be treated with MeMgX, wherein X is Cl, Br or I, to give a compound of Formula I*, wherein $R^3$ is 2-hydroxy-2-methylpropyl.

(22) a compound of Formula I*, wherein $R^3$ is allyl or —$CH_2C(Me)=CH_2$, can be hydrocyanated with TsCN in the presence of triphenylsilane and various cobalt catalysts to afford compounds of Formula I*, wherein $R^3$ is —$CH_2CH$(CN)Me or —$CH_2CMe_2CN$ respectively.

(23) a compound of Formula I*, wherein $R^3$ is $CH_2C(Me)_2$ CN, can be treated with acetamide in the presence of $PdCl_2$ to give a compound of Formula I*, wherein $R^3$ is $CH_2CMe_2CONH_2$.

(24) a compound of Formula I*, wherein $R^3$ is —$CH_2C$(Me)=$CH_2$ can be treated with m-CPBA followed by lithium triethylborohydride to afford a compound of Formula I*, wherein $R^3$ is 2-hydroxy-2-methylpropyl.

In a tenth process, certain compounds of the invention of Formula I** are prepared as follows:

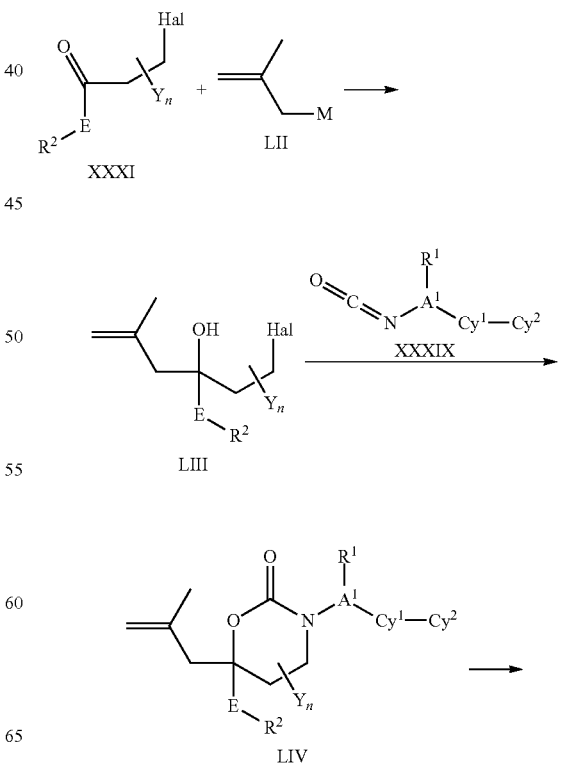

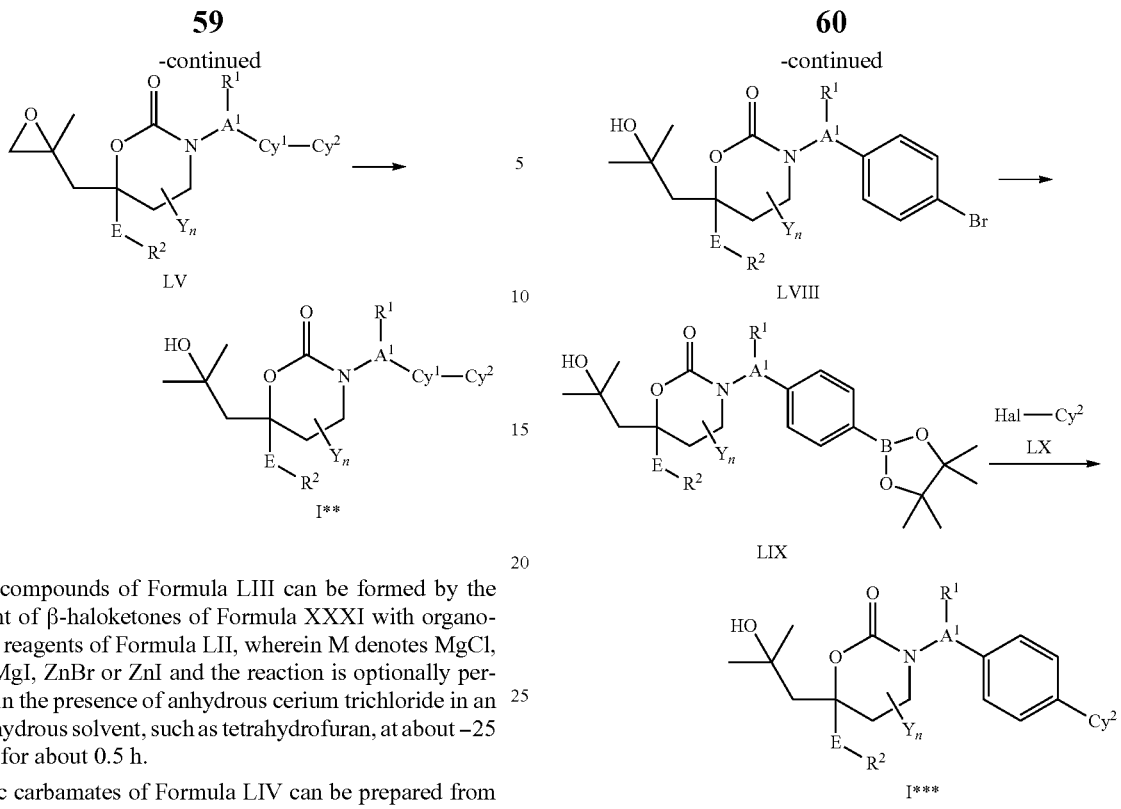

Halo compounds of Formula LIII can be formed by the treatment of β-haloketones of Formula XXXI with organometallic reagents of Formula LII, wherein M denotes MgCl, MgBr, MgI, ZnBr or ZnI and the reaction is optionally performed in the presence of anhydrous cerium trichloride in an inert anhydrous solvent, such as tetrahydrofuran, at about −25 to 0° C. for about 0.5 h.

Cyclic carbamates of Formula LIV can be prepared from the reaction between β-haloalcohols of Formula LIII where Hal is a chloride and isocyanates of Formula XXXIX in the presence of a base, such as but not limited to DBU (1,8-diazabicyclo[5.4.0]undec-7-ene), in a refluxing inert solvent, such as but not limited to tetrahydrofuran.

Tertiary alcohols of Formula LVII can be derived from trisubstituted alkenes of Formula LIV by first epoxidizing the alkene with an epoxidation reagent, such as m-CPBA (3-chloroperbenzoic acid), in an inert solvent, such as dichloromethane to produce the corresponding epoxides of Formula LV. The resulting epoxide is then reductively ring opened to provide the corresponding tertiary alcohol I* via treatment with a strong hydride reagent, such as lithium triethylborohydride, in an anhydrous inert solvent, such as tetrahydrofuran.

In a variation of the tenth process, a compound of the invention of Formula I*** is prepared by using a "Suzuki" coupling reaction of a boronate ester of Formula LIX with a haloheterocycle of Formula LX.

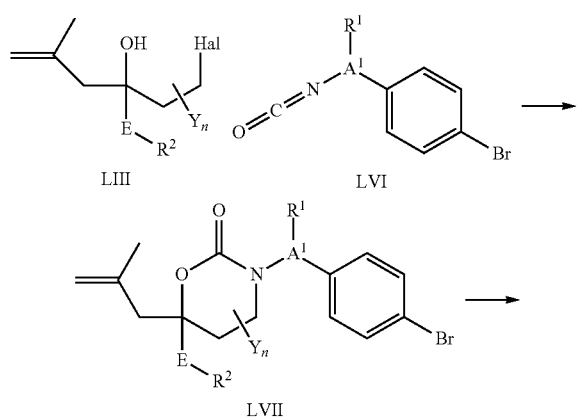

The boronate ester of Formula LIX is prepared by reaction of a bromide of Formula LVIII with bis(pinacolato)diboron. LVIII is prepared by epoxidation of alkene LVII, followed by reductive epoxide opening as described above, for 2-methyl-2-hydroxypropyl group is introduced via epoxidation and hydride ring opening as described above for conversion of LIV to I**.

This tenth process is described in greater detail in U.S. Provisional Application Ser. No. 61/137,013, filed Jul. 25, 2008 entitled SYNTHESIS OF INHIBITORS OF 11β-HYDROXYSTEROID DEHYDROGENASE TYPE 1, the entire teachings of which are incorporated herein by reference.

LC-MS Methods

Method 1 [LC-MS (3 min)]

Column: Chromolith SpeedRod, RP-18e, 50×4.6 mm; Mobil phase: A: 0.01% TFA/water, B: 0.01% TFA/CH$_3$CN; Flow rate: 1 mL/min; Gradient:

| Time (min) | A % | B % |
| --- | --- | --- |
| 0.0 | 90 | 10 |
| 2.0 | 10 | 90 |
| 2.4 | 10 | 90 |
| 2.5 | 90 | 10 |
| 3.0 | 90 | 10 |

Method 2 (10-80)

| Column | YMC-PACK ODS-AQ, 50 × 2.0 mm 5 μm |  |  |
|---|---|---|---|
| Mobile Phase | A: water (4 L) + TFA (1.5 mL)) |  |  |
|  | B: acetonitrile (4 L) + TFA (0.75 mL)) |  |  |
|  | TIME(min) | A % | B % |
|  | 0 | 90 | 10 |
|  | 2.2 | 20 | 80 |
|  | 2.5 | 20 | 80 |
| Flow Rate | 1 mL/min |  |  |
| Wavelength | UV 220 nm |  |  |
| Oven Temp | 50° C. |  |  |
| MS ionization | ESI |  |  |

Method 3 (30-90)

| Column | YMC-PACK ODS-AQ , 50 × 2.0 mm 5 μm |  |  |
|---|---|---|---|
| Mobile | A: water (4 L) + TFA (1.5 mL)) |  |  |
| Phase | B: acetonitrile (4 L) + TFA (0.75 mL)) |  |  |
|  | TIME(min) | A % | B % |
|  | 0 | 70 | 30 |
|  | 2.2 | 10 | 90 |
|  | 2.5 | 10 | 90 |
| Flow Rate | 1 mL/min |  |  |
| Wavelength | UV220 |  |  |
| Oven Temp | 50° C. |  |  |
| MS ionization | ESI |  |  |

Preparation 1

(S)-3-((S)-1-(4-bromophenyl)ethyl)-6-(2-hydroxy-2-methylpropyl)-6-phenyl-1,3-oxazinan-2-one Method 1

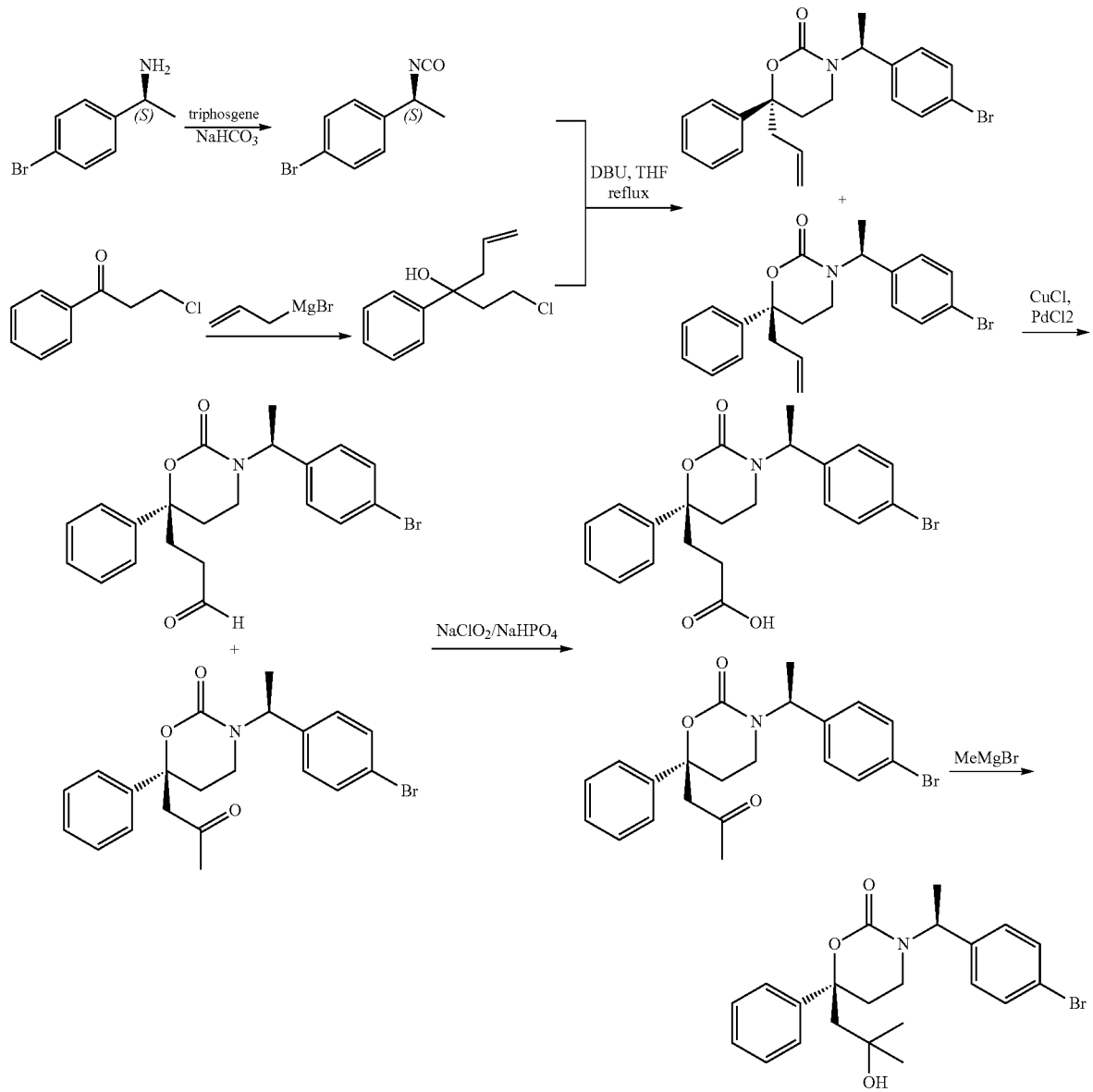

Step 1: (S)-1-bromo-4-(1-isocyanatoethyl)benzene

To a solution of (S)-1-(4-bromophenyl)ethanamine (240 g, 1.2 mol) in methylene chloride (3 L) and satd aq NaHCO$_3$ (3 L) solution was added triphosgene (118 g, 0.396 mol) at 0° C. The mixture was stirred for 15 min. The organic phase was separated, dried over Na$_2$SO$_4$ and concentrated to give 1-bromo-4-(1-isocyanato-ethyl)-benzene (170 g, 63%).

Step 2: 1-chloro-3-phenylhex-5-en-3-ol

To a solution of 3-chloro-1-phenylpropan-1-one (170 g, 1.01 mol) in anhydrous THF (1200 mL) was added allylmagnesium bromide (1.2 L, 1 mol/L) at −78° C. under nitrogen. The formed mixture was stirred for 30 min at −78° C. The reaction was quenched with aqueous NaHCO$_3$ solution. The organic phase was separated, dried over Na$_2$SO$_4$ and concentrated to give the crude product, which was purified by column chromatography (petroleum ether/EtOAc=100:1) to afford 1-chloro-3-phenylhex-5-en-3-ol (180 g, 86%). $^1$H NMR (CDCl$_3$): 2.27 (m, 2H), 2.51 (m, 1H), 2.74 (m, 1H), 3.22 (m, 1H), 3.58 (m, 1H), 5.16 (m, 2H), 5.53 (m, 1H), 7.23 (m, 1H), 7.39 (m, 4H).

Step 3: (R)-6-allyl-3-((S)-1-(4-bromophenyl)ethyl)-6-phenyl-1,3-oxazinan-2-one A mixture of 1-chloro-3-phenyl-hex-5-en-3-ol (105 g, 0.050 mmol), (S)-(−)-1-(-bromophenyl)ethyl isocyanate (170 g, 0.752 mol), and DBU (228 g, 1.5 mol) in THF (1700 mL) was heated to reflux overnight. The mixture was diluted with EtOAc and washed with 1N aq HCl. The aqueous phase was extracted with EtOAc (3×). The combined organic phase was dried over Na$_2$SO$_4$. After the solvents were evaporated, the crude product was purified by column chromatography (petroleum ether/EtOAc=20:1 to 5:1) to give (R)-6-allyl-3-((S)-1-(4-bromophenyl)ethyl)-6-phenyl-1,3-oxazinan-2-one (100 g, 34%). $^1$H NMR (CDCl$_3$): 1.39 (d, 3H), 2.14 (m, 1H), 2.24 (m, 2H), 2.48-2.61 (m, 3H), 2.82 (m, 2H), 5.01 (m, 2H), 5.52 (q, 1H), 5.73 (m, 1H), 6.62 (d, 2H), 7.12 (m, 2H), 7.28 (m, 2H).

Step 4: (S)-3-((S)-1-(4-bromophenyl)ethyl)-6-(2-oxopropyl)-6-phenyl-1,3-oxazinan-2-one and 3-((R)-3-((S)-1-(4-bromophenyl)ethyl)-2-oxo-6-phenyl-1,3-oxazinan-6-yl)propanal To a solution of (R)-6-allyl-3-((S)-1-(4-bromophenyl) ethyl)-6-phenyl-1,3-oxazinan-2-one (31 g, 78 mmol) and CuCl (19.3 g, 195 mmol) in dry DMF (150 mL) was added H$_2$O (50 mL) and PdCl$_2$ (4.10 g, 23 mmol) at rt. After addition, the mixture was stirred overnight under oxygen. After TLC showed the starting material had disappeared, the solid was filtered off. Water (200 mL) and EtOAc (200 mL) was added, the organic layers were separated and the aqueous layer was extracted with EtOAc (3×40 mL). The combined organic layer was washed with brine, dried over Na$_2$SO$_4$, filtered and concentrated to give a residue which was purified by column chromatography (petroleum ether/EtOAc=5:1 to 1:1) to give a mixture of (S)-3-((S)-1-(4-bromophenyl)ethyl)-6-(2-oxopropyl)-6-phenyl-1,3-oxazinan-2-one and 3-((R)-3-((S)-1-(4-bromophenyl)ethyl)-2-oxo-6-phenyl-1,3-oxazinan-6-yl)propanal, (26 g, 81%).

Step 5: (S)-3-((S)-1-(4-bromophenyl)ethyl)-6-(2-oxopropyl)-6-phenyl-1,3-oxazinan-2-one To a mixture of (S)-3-((S)-1-(4-bromophenyl)ethyl)-6-(2-oxopropyl)-6-phenyl-1,3-oxazinan-2-one and 3-((R)-3-((S)-1-(4-bromophenyl)ethyl)-2-oxo-6-phenyl-1,3-oxazinan-6-yl)propanal (20 g, 48.2 mmol) in t-BuOH (250 mL) and 2-methyl-2-butene (50 mL) was added a solution of NaClO$_2$ (19.3 g, 0.213 mol) and NaH$_2$PO$_4$ (28 g, 0.179 mol) in H$_2$O (300 mL) at 0° C. The formed mixture was stirred for 1 h at 0° C. The mixture was treated with water (100 mL) and extracted with CH$_2$Cl$_2$. The combined organic layer was dried over Na$_2$SO$_4$, filtered and concentrated to leave a residue, which was purified by column chromatography (petroleum ether/EtOAc=5:1 to 2.5:1) to afford (S)-3-((S)-1-(4-bromophenyl) ethyl)-6-(2-oxopropyl)-6-phenyl-1,3-oxazinan-2-one (10.0 g, 83%). $^1$H NMR (CDCl$_3$): 1.49 (d, 3H), 2.12 (s, 3H), 2.33 (m, 2H), 2.63 (m, 1H), 2.86-3.08 (m, 3H), 5.57 (q, 1H), 6.66 (d, 2H), 7.19 (m, 2H), 7.33 (m, 5H).

Step 6: (S)-3-((S)-1-(4-bromophenyl)ethyl)-6-(2-hydroxy-2-methylpropyl)-6-phenyl-1,3-oxazinan-2-one To a solution of (S)-3-((S)-1-(4-bromophenyl)ethyl)-6-(2-oxopropyl)-6-phenyl-1,3-oxazinan-2-one (20 g, 46.4 mmol) in anhydrous THF (200 mL) was added dropwise methylmagnesium bromide (31 mL, 144 mmol) at −78° C. under nitrogen. Then the mixture was stirred at rt for 1 h. The reaction mixture was quenched with aq NaHCO$_3$ (50 mL) under ice water bath. The organic layers were separated. The aqueous layer was extracted with EtOAc (150 mL). The combined organic layers were washed with brine, dried over Na$_2$SO$_4$ and concentrated in vacuo to give the crude product, which was purified column chromatography (petroleum ether/EtOAc=5:1 to 2:1) to afford (S)-3-((S)-1-(4-bromophenyl) ethyl)-6-(2-hydroxy-2-methylpropyl)-6-phenyl-1,3-oxazinan-2-one (13 g, 65%). After re-crystallization from EtOH, 4 g of the pure compound was obtained. $^1$H NMR (CDCl$_3$): 1.06 (s, 3H), 1.12 (s, 3H), 1.44 (d, 3H), 2.14 (m, 3H), 2.21 (m, 1H), 2.33 (m, 1H), 2.76 (m, 1H), 5.54 (q, 1H), 6.74 (d, 2H), 7.16 (d, 2H), 7.28 (m, 5H).

Alternative Procedure for Method 1 Step 2

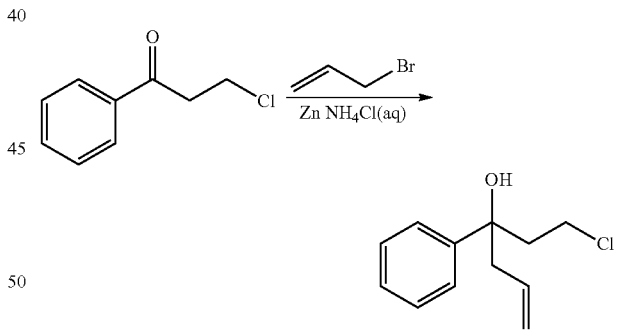

A solution of 3-chloro-1-phenylpropan-1-one (100 g, 0.595 mol) in THF (280 ml) was added dropwise to a well-stirred mixture of zinc powder (need not be activated) (40 g, 1.231 mol, satd aq NH$_4$Cl solution (1500 ml) and THF (400 ml). Allyl bromide (143 g, 1.19 mol) was dissolved in THF (200 ml) was slowly added to the reaction mixture. The reaction was mildly exothermic, and the mixture began to reflux spontaneously. After refluxing had ceased, the mixture was stirred for 1 h. The mixture was extracted with EtOAc, dried over anhydrous Na$_2$SO$_4$, and concentrated to give 1-chloro-3-phenylhex-5-en-3-ol (122 g, 97%). $^1$H NMR: (400 MHz, CDCl$_3$): δ=2.24 (s, 1H), 2.34 (m, 2H), 2.53 (m, 1H), 2.75 (m, 1H), 3.20 (m, 1H), 3.58 (m, 1H), 5.18 (t, 1H), 5.51 (m, 1H), 7.26 (m, 1H), 7.26-7.39 (m, 3H).

(R)-6-allyl-3-((S)-1-(4-bromophenyl)propyl)-6-phenyl-1,3-oxazinan-2-one was prepared from (S)-1-(4-bromophenyl)propan-1-amine following procedures analogous to those described in Preparation 1 Method 1 Steps 1 to 3 above.

(S)-3-((S)-1-(4-bromophenyl)ethyl)-6-(4-fluorophenyl)-6-(2-hydroxy-2-methylpropyl)-1,3-oxazinan-2-one was prepared from (R)-6-allyl-3-((S)-1-(4-bromophenyl)ethyl)-6-(4-fluorophenyl)-1,3-oxazinan-2-one following procedures analogous to those described in Preparation 1 Method 1 Steps 4 and 6.

Method 2 with brine and dried over sodium sulfate. Removal of the solvent under vacuum produced crude 1-chloro-5-methyl-3-phenyl-hex-5-en-3-ol, which was chased with THF to achieve $H_2O$ <500 ppm based on Karl Fischer titration. The crude product (306 g, 83 wt %, 95% yield) was used directly in Step 3. $^1$H-NMR spectroscopy (500 MHz, CDCl$_3$) δ 7.38-7.37 (d. J=7.8 Hz, 2H), 7.33 (t, J=7.9 Hz, 2H), 7.24 (t, J=7.4 Hz, 1H), 4.91 (s, 1H), 4.76 (s, 1H), 3.57 (ddd, J=5.6, 10.7, and 10.7, 1H), 3.13 (ddd, J=4.7, 10.7 and 10.7 Hz, 1H), 2.66 (d, J=13.3 Hz, 1H), 2.54 (d, J=11.3 Hz, 1H), 2.53 (s, 1H), 2.36 (ddd, J=5.4, 10.6 and 13.9 Hz. 1H), 2.29 (ddd, J=5.6, 11.3 and 13.3

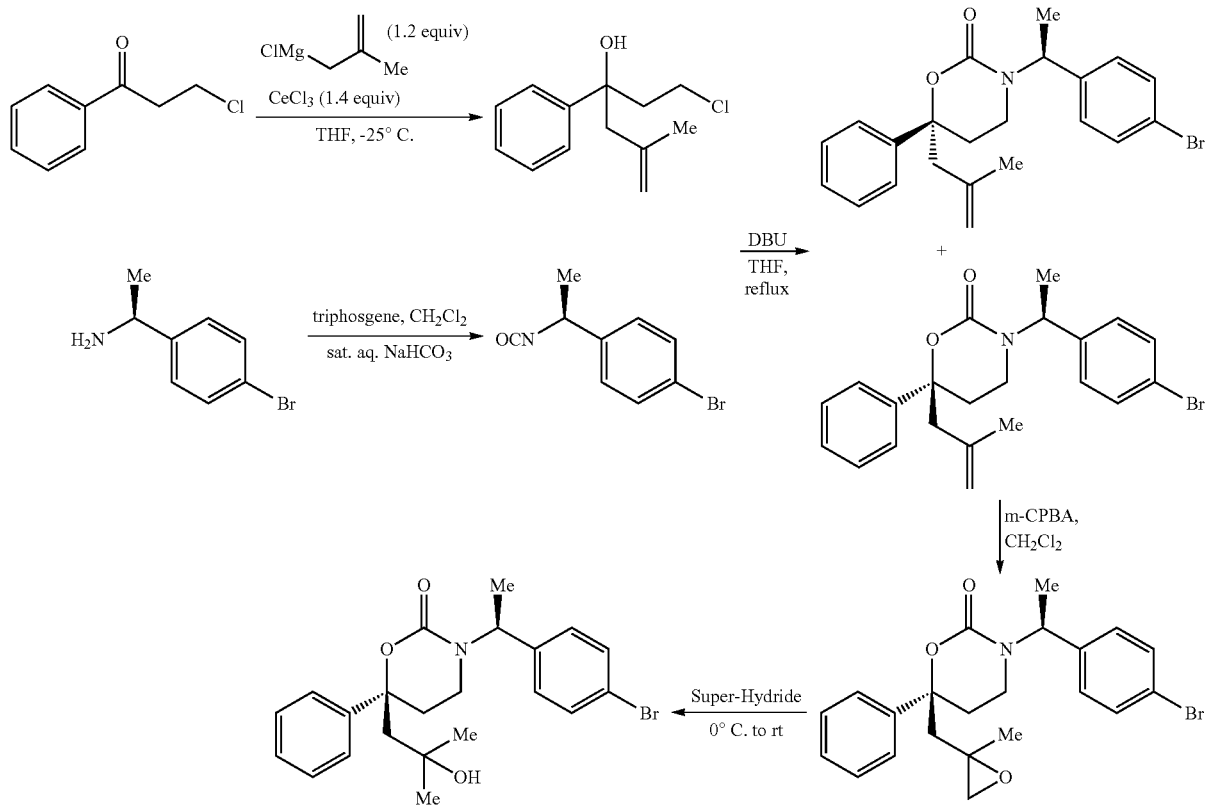

Step 1. 1-Chloro-5-methyl-3-phenyl-hex-5-en-3-ol

To a stirred suspension of magnesium turnings (46.7 g, 1.94 mol) in 1500 mL of THF ($H_2O$ <100 ppm based on Karl Fischer titration) was charged 53.0 mL of 1 M DIBAL-H in hexane under nitrogen at rt. Then 3-chloro-2-methylprop-1-ene (160 g, 1.77 mol) was introduced while maintaining the internal temperature below 30° C. The resulting solution was agitated for 2 h at rt. The solution was titrated in the presence of 1.1'-bipyridine to indicate 0.8 M of the corresponding Grignard reagent. To a dry flask containing 307.0 g of anhydrous CeCl$_3$ (1.25 mol) at rt under nitrogen was added 1556.8 mL of the Grignard reagent (0.8 M, 1.25 mol). The resulting slurry was cooled to −10° C. and agitated for 0.5 h. To the slurry was added 200 g of 3-chloro-1-phenylpropan-1-one (1.19 mol) in 200 mL of THF while maintaining the internal temperature below 0° C. After the mixture was stirred for 0.5 h, 1200 mL of 1 M aq HCl was added to obtain a clear solution while maintaining the internal temperature below 30° C. After the phase cut, the aqueous layer was extracted with EtOAc (500 mL). The combined organic layers were washed Hz, 1H), 1.29 (s, 3H). $^{13}$C-NMR spectroscopy (125 MHz, CDCl$_3$) δ 144.3, 141.4, 128.0, 126.6, 124.8, 116.1, 74.2, 51.2, 46.0, 39.9, 23.9.

Step 2. 1-Bromo-4-((S)-1-isocyanato-ethyl)-benzene

To a 10 L jacketed reactor was charged 241 g of sodium bicarbonate (2.87 mol, 2.30 equiv) and 5 L of deionized water. The resulting solution was agitated for 10-20 min, until the solids dissolved (homogeneous). To the clear solution was charged 250 g (1.25 mol, 1.00 equiv) of (S)-(−)-1-(4-bromophenyl)ethylamine as a solution in 1.00 L of dichloromethane. An additional 4 L of dichloromethane was charged to the reactor. The biphasic solution was agitated and cooled to $T_{int}$=2-3° C. Triphosgene (126 g, 424 mmol, 0.340 equiv) was charged to the reactor in approximately two equal portions ~6 min apart. It should be noted that a slight exotherm was noted upon the addition of triphosgene. The resulting murky solution was agitated at $T_{int}$=2-5° C. for 30 min, at which point HPLC analysis indicates >99 A % conversion (220 nm). The dichloromethane layer was cut and dried with anhydrous sulfate. The resulting solution was passed through a celite plug and concentrated to ~1.5 L which fine particles of a white solid developed. The solution was filtered and concentrated to a thick oil via reduced pressure to produce 239 g of 1-bromo-4-((S)-1-isocyanato-ethyl)-benzene (93.7 wt %, 79.4% yield). $^1$H-NMR spectroscopy (400 MHz, $CD_2Cl_2$) δ 7.53 (d, J=11.4 Hz, 2H), 7.26 (d, J=8.2 Hz, 2H), 4.80 (q, J=6.7 Hz, 1H), 1.59 (d, J=6.7 Hz, 3H). The material was used in Step 3 without further purification.

Step 3. (R)-3-((S)-1-(4-bromophenyl)ethyl)-6-(2-methylallyl)-6-phenyl-1,3-oxazinan-2-one To a dried 10 L jacketed reactor under a nitrogen atmosphere was charged 1-chloro-5-methyl-3-phenyl-hex-5-en-3-ol (167 g, 81.7 wt %, 610 mmol, 1.00 equiv), 1-bromo-4-((S)-1-isocyanato-ethyl)-benzene (219 g, 93.7 wt %, 911 mmol, 1.50 equiv), anhydrous tetrahydrofuran (3.00 L), and then 1,8-diazabicyclo[5.4.0]undec-7-ene (DBU, 409 mL, 2.73 mol, 4.50 equiv). The resulting solution was agitated and refluxed ($T_{int}$=67-69° C., $T_{ext}$=75° C.) for 19 h, at which point HPLC analysis indicated ~1 A % (220 nm) of the 1-chloro-5-methyl-3-phenyl-hex-5-en-3-ol remained. The dark solution was cooled to $T_{int}$=20-25° C. Two liters of tetrahydrofuran were removed by distillation under reduced pressure. The remaining dark solution was diluted with 4.0 L of ethyl acetate and 1.0 L of hexanes. The resulting solution was washed with 4.0 L of a 1.0 M aqueous solution of hydrogen chloride (note: the wash is slightly exothermic). The aqueous solution was cut and the remaining organic solution was dried with anhydrous sodium sulfate, filtered and then concentrated to an oil via reduced pressure. The resulting material was subjected to flash silica chromatography (5-30% ethyl acetate/hexanes, 1.74 kg of silica) to produce 137.8 g of material (59 wt %, 3.1:1 diastereomeric ratio favoring the desired diastereomer (R)-3-((S)-1-(4-bromophenyl)ethyl)-6-(2-methylallyl)-6-phenyl-1,3-oxazinan-2-one, 32.3% yield). The material was used in Step 4 without further purification.

Analytical data for (R)-3-((S)-1-(4-bromophenyl)ethyl)-6-(2-methylallyl)-6-phenyl-1,3-oxazinan-2-one: $^1$H-NMR spectroscopy (500 MHz, $CD_2Cl_2$) δ 7.42-7.35 (m, 3H), 7.33-7.31 (m, 2H), 7.25-7.23 (m, 2H), 6.80-6.74 (m, 2), 5.55 (q, J=7.1 Hz, 1H), 5.37-5.36 (m, 1H), 4.89 (s, 1H), 4.69 (s, 1H), 2.96-2.93 (m, 1H), 2.61 (dd, J=13.8 and 26.4 Hz, 2H), 2.37-2.25 (m, 3H), 1.68 (s, 3H), 1.50 (d, J=7.1 Hz, 3H). $^{13}$C-NMR spectroscopy (125 MHz, $CD_2Cl_2$) δ 152.5, 141.5, 140.1, 138.3, 130.6, 128.1, 128.0, 126.9, 124.4, 120.2, 115.3, 82.4, 52.1, 50.1, 35.6, 29.8, 23.4, 14.5.

Analytical data for (S)-3-((S)-1-(4-bromophenyl)ethyl)-6-(2-methylallyl)-6-phenyl-1,3-oxazinan-2-one: $^1$H-NMR spectroscopy (400 MHz, $CD_2Cl_2$) δ 7.50-7.48 (m, 2H), 7.43-7.39 (m, 2H), 7.35-7.32 (m, 3H), 7.20-7.18 (m, 2H), 5.60 (q, J=7.1 Hz, 1H), 4.85 (s, 1H), 4.66 (s, 1H), 2.73-2.67 (m, 2H), 2.60 (dd, J=13.9 and 19.4 Hz, 2H), 2.28 (dt, J=3.3 and 13.7 Hz, 1H), 2.14-2.05 (m, 1H), 1.66 (s, 3H), 1.24 (d, J=7.2 Hz, 3H). $^{13}$C-NMR spectroscopy (100 MHz, $CD_2Cl_2$) δ 153.4, 142.5, 141.0, 140.1, 131.8, 129.3, 128.9, 127.8, 125.3, 121.5, 116.3, 83.9, 53.2, 51.0, 36.6, 31.3, 24.3, 15.4.

Step 4. (6S)-3-((S)-1-(4-bromophenyl)ethyl)-6-((2-methyloxiran-2-yl)methyl)-6-phenyl-1,3-oxazinan-2-one To a 1.0 L 2-neck RBF was charged (R)-3-((S)-1-(4-bromophenyl)ethyl)-6-(2-methylallyl)-6-phenyl-1,3-oxazinan-2-one (135.8 g, 59 wt %, 3.1:1 dr, 193 mmol, 1.00 equiv), dichloromethane (700 mL), and then 3-chloroperbenzoic acid (m-CPBA, 70%, 95.3 g, 386 mmol, 2.0 equiv). The resulting solution was agitated at rt ($T_{int}$=20-25° C.) for 1 h, which HPLC analysis indicates >99 A % (220 nm) conversion. The resulting solution was diluted with 700 mL of methyl tert-butyl ether (MTBE) and washed with 1×500 mL of 30 wt % solution of sodium thiosulfate and 1×500 mL of saturated aqueous solution of sodium bicarbonate. The wash sequence was repeated until the peak on an HPLC trace of the organic solution that corresponds to a HPLC sample peak of m-CPBA is <2.5 A % (220 nm), which in this example the wash sequence was repeated 3 times. The resulting organic layer was dried with anhydrous sodium sulfate, filtered and then concentrated to an oil via reduced pressure. The resulting material was diluted with 200 mL of anhydrous tetrahydrofuran and then concentrated to a thick oil via reduced pressure to provide (6S)-3-((S)-1-(4-bromophenyl)ethyl)-6-((2-methyloxiran-2-yl)methyl)-6-phenyl-1,3-oxazinan-2-one which was used directly in Step 5.

Step 5. (S)-3-((S)-1-(4-bromophenyl)ethyl)-6-(2-hydroxy-2-methylpropyl)-6-phenyl-1,3-oxazinan-2-one To a 2.0 L 3-neck oven-dried RBF was charged the crude (6S)-3-((S)-1-(4-bromophenyl)ethyl)-6-((2-methyloxiran-2-yl)methyl)-6-phenyl-1,3-oxazinan-2-one and 750 mL of anhydrous THF. The resulting solution was agitated and cooled to $T_{int}$=2-3° C. To the agitated clear solution was charged 1.0 M lithium triethylborohydride in tetrahydrofuran (Super Hydride, 348 mL, 348 mmol, 1.8 equiv). The addition is exothermic and addition was controlled to maintain $T_{int}$=<8° C. The resulting solution was agitated at $T_{int}$=2-3° C. for 1.5 h and then allowed to warm to $T_{int}$=10-13° C. over a 2.5 h, which HPLC analysis indicates ~94 A % (220 nm) conversion. To the agitated solution was charged a solution of hydrogen peroxide (95.7 mL of a 35 wt % aqueous solution diluted with 400 mL of water, 1.08 mol, 5.60 equiv). The addition is highly exothermic and addition was controlled to maintain $T_{int}$=<25° C. The resulting solution was diluted with 1.00 L of methyl tert-butyl ether (MTBE) and washed with 1.00 L of water followed by 500 mL of a ~30 wt % solution of sodium thiosulfate. The organic solution was dried with anhydrous sodium sulfate, filtered, and then concentrated via reduced pressure. The resulting material was subjected to flash silica chromatography (10-60% ethyl acetate, 600 g of silica) to produce 68 g of material consisting of both diastereomers (1.98:1 dr) and 41 g of the desired diastereomer, (>99:1 dr). The material consisting of the mixed fractions was recrystallized from 250 mL of isopropyl acetate (IPAC) and 200 mL of heptane (anti-solvent) to produce upon filtration 31.3 g of product (95.7 A % at 220 nm, 74:1 dr). The two samples were combined to produce 72.3 g of (S)-3-((S)-1-(4-bromophenyl)ethyl)-6-(2-hydroxy-2-methylpropyl)-6-phenyl-1,3-oxazinan-2-one (83.6% yield for the two step operation). $^1$H-NMR spectroscopy (400 MHz, $CDCl_3$) δ 7.37-7.29 (m, 5H), 7.25-7.21 (m, 2H), 6.82-6.79 (m, 2H), 5.61 (q, J=6.9 Hz, 1H), 2.83 (ddd, J=2.5, 5.4 and 11.6 Hz, 1H), 2.39 (ddd, J=5.7, 12.0 and 14.1 Hz, 1H), 2.27 (ddd, J=2.6, 4.8 and 14.0 Hz, 1H), 2.21-2.14 (m, 3H), 2.08 (s, 1H), 1.49 (d, J=7.0 Hz, 3H), 1.18 (s, 3H), 1.13 (s, 3H). $^{13}$C-NMR spectroscopy (100

MHz, CDCl₃) δ 153.2, 142.6, 138.5, 131.6, 129.13, 129.10, 128.0, 125.3, 121.6, 84.2, 71.4, 54.1, 53.3, 36.4, 33.6, 32.1, 30.8, 15.6.

Preparation 2

(S)-6-(2-hydroxy-2-methylpropyl)-6-phenyl-3-((S)-1-(4-(4,4,5,5-tetramethyl-1,3,2-dioxaborol-an-2-yl)phenyl)ethyl)-1,3-oxazinan-2-one

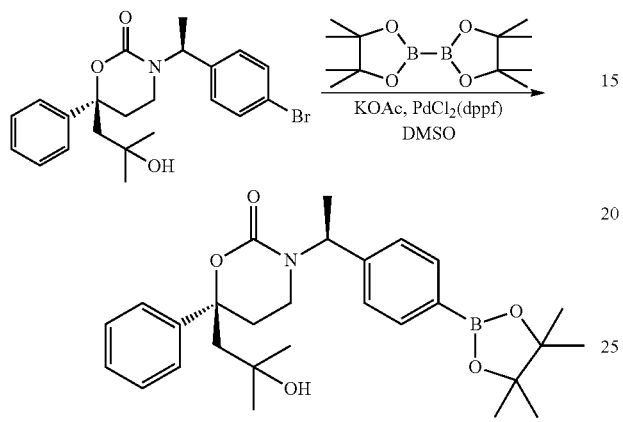

To a solution of (S)-3-((S)-1-(4-bromophenyl)ethyl)-6-(2-hydroxy-2-methylpropyl)-6-phenyl-1,3-oxazinan-2-one (6.6 g, 15.2 mmol) and 4,4,4',4',5,5,5',5'-octamethyl-2,2'-bi(1,3,2-dioxaborolane) (6.1 g, 24.3 mmol) in dry DMSO (20 mL) was added KOAc (4.8 g, 48.6 mmol) and Pd(dppf)cl₂ (372 mg, 0.46 mmol). After addition, the mixture was allowed to warm to 100° C. for 20 h. After TLC showed the starting material had disappeared, the solid was filtered off. Water (60 mL) and EtOAc (20 mL) were added. The layers were separated and the aqueous layer was extracted with EtOAc (3×15 mL). The combined organic layer was washed with brine, dried over Na₂SO₄, filtered and concentrated to give a residue, which was purified by column chromatography to give (S)-6-(2-hydroxy-2-methylpropyl)-6-phenyl-3-((S)-1-(4-(4,4,5,5-tetramethyl-1,3,2-dioxaborol-an-2-yl)phenyl)ethyl)-1,3-oxazinan-2-one (4.4 g, 60%).

(S)-6-(4-fluorophenyl)-6-(2-hydroxy-2-methylpropyl)-3-((S)-1-(4-(4,4,5,5-tetramethyl-1,3,2-dioxaborolan-2-yl)phenyl)ethyl)-1,3-oxazinan-2-one was prepared from (S)-3-((S)-1-(4-bromophenyl)ethyl)-6-(2-hydroxy-2-methylpropyl)-6-(4-fluorophenyl)-1,3-oxazinan-2-one following an analogous procedure.

(S)-6-(2-hydroxy-2-methylpropyl)-6-phenyl-3-((S)-1-(4-(4,4,5,5-tetramethyl-1,3,2-dioxaborolan-2-yl)phenyl)propyl)-1,3-oxazinan-2-one was prepared from (S)-3-((S)-1-(4-bromophenyl)propyl)-6-(2-hydroxy-2-methylpropyl)-6-phenyl-1,3-oxazinan-2-one following an analogous procedure.

(R)-6-Methoxymethyl-6-phenyl-3-{(S)-1-[4-(4,4,5,5-tetramethyl-[1,3,2]dioxaborolan-2-yl)-phenyl]-ethyl}-[1,3]oxazinan-2-one was prepared from 3-[1-(4-bromo-phenyl)-ethyl]-6-methoxymethyl-6-phenyl-[1,3]oxazinan-2-one following an analogous procedure.

Preparation 3

3-((R)-3-((S)-1-(4-bromophenyl)ethyl)-2-oxo-6-phenyl-1,3-oxazinan-6-yl)-2,2-dimethylpropanenitrile

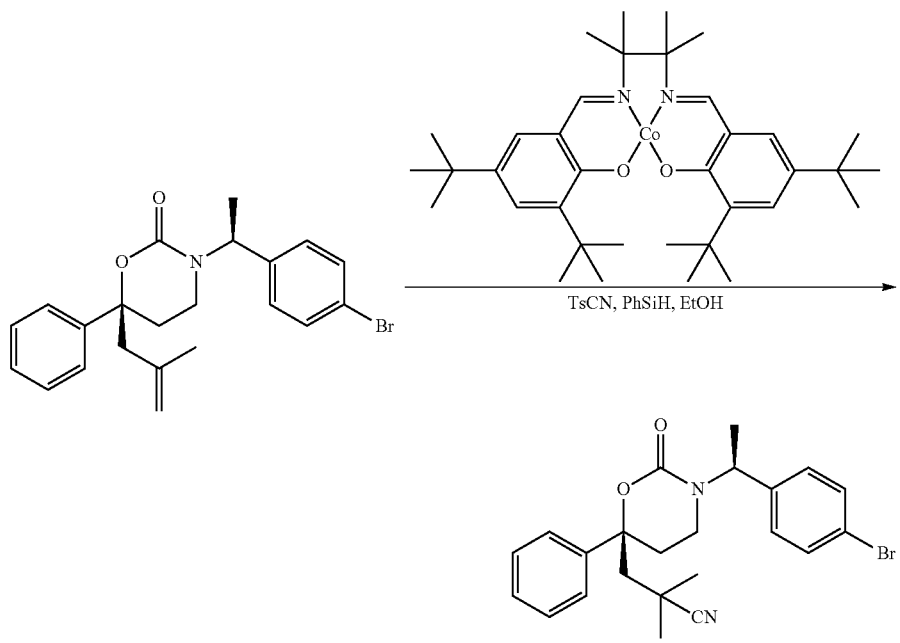

Preparation of Cobalt(II) Complex

A 50 mL flask was charged with N,N'-bis(3,5-di-tert-butylsalicylidene)-1,1,2,2-tetramethylethenediamine (0.430 g, 0.78 mmol, 1.0 equiv), EtOH (17 mL), and Co(OAc)₂ (0.139 g, 0.78 mmol, 1.0 equiv). The mixture was degassed and then heated to reflux under nitrogen for 3 h, cooled to room temperature. The precipitate was filtered and the purple solid was washed with EtOH (10 mL) and dried under high vacuum to give 0.353 g (75%) of the cobalt(II) complex.

A mixture of (R)-3-((S)-1-(4-bromophenyl)ethyl)-6-(2-methylallyl)-6-phenyl-1,3-oxazinan-2-one (490 mg, 1.18 mmol), the cobalt(II) complex whose preparation is described immediately above (8 mg, 0.01 equiv), TsCN (257 mg, 1.2 equiv), and PhSiH$_3$ (137 mg, 157 μL, 1.07 equiv) in ethanol (10 mL) was stirred 4 h at rt. After removing the solvent under reduced pressure, the residue was purified by chromatography on a 40 g silica gel column, eluted with a 25-80% EtOAc in hexanes gradient to afford 3-((R)-3-((S)-1-(4-bromophenyl)ethyl)-2-oxo-6-phenyl-1,3-oxazinan-6-yl)-2,2-dimethylpropanenitrile (267 mg, 51% yield). LC-MS (3 min. method) t$_R$=1.89 min., m/z 441, 443 (M+1)

Preparation 4

2,2-dimethyl-3-((R)-2-oxo-6-phenyl-3-((S)-1-(4-(4,4,5,5-tetramethyl-1,3,2-dioxaborolan-2-yl)phenyl)ethyl)-1,3-oxazinan-6-yl)propanenitrile

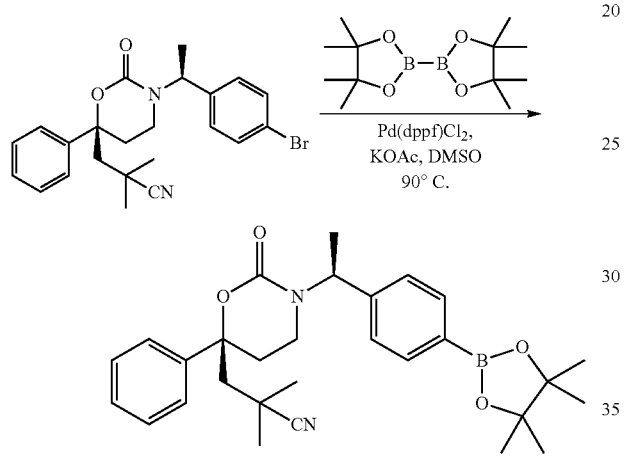

3-((R)-3-((S)-1-(4-bromophenyl)ethyl)-2-oxo-6-phenyl-1,3-oxazinan-6-yl)-2,2-dimethylpropanenitrile (467 mg, 1.06 mmol), 4,4,4',4',5,5,5',5'-octamethyl-2,2'-bi(1,3,2-dioxaborolane) (538 mg, 2 equiv), KOAc (333 mg, 3.2 equiv), PdCl$_2$(dppf)CH$_2$Cl$_2$ (27 mg, 0.033 equiv) were mixed with dry DMSO (6 mL). The mixture was degassed and refilled with N$_2$ gas 3 times. The mixture was then heated overnight at 90° C. under protection of N$_2$ gas. After being cooled to rt, the mixture was diluted with EtOAc (30 mL), washed with water (20 mL). The aqueous layer was extracted with EtOAc (2×15 mL). The combined organic layers were washed by water (15 mL), brine (2×10 mL) and dried over Na$_2$SO$_4$. After filtration and concentration, the residue was purified chromatography on a 40 g silica gel column, eluted with a 20-50% EtOAc in Hexanes gradient, to afford 2,2-dimethyl-3-((R)-2-oxo-6-phenyl-3-((S)-1-(4-(4,4,5,5-tetramethyl-1,3,2-dioxaborolan-2-yl)phenyl)ethyl)-1,3-oxazinan-6-yl)propanenitrile (393 mg, 76% yield).

Preparation 5

3-((R)-3-((S)-1-(4-bromophenyl)ethyl)-6-(4-fluorophenyl)-2-oxo-1,3-oxazinan-6-yl)-2-methylpropanenitrile Method 1

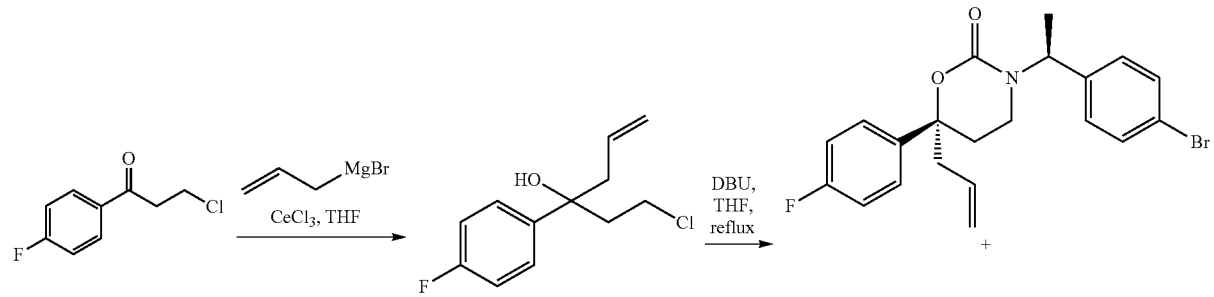

-continued

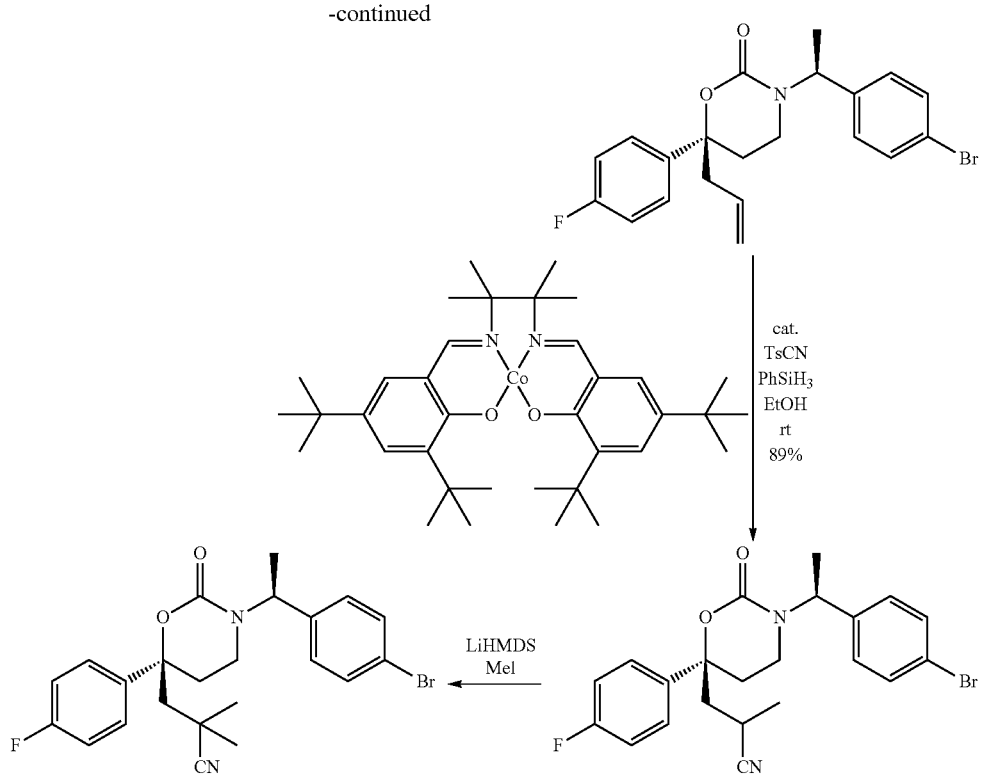

Step 1. 1-chloro-3-(4-fluorophenyl)hex-5-en-3-ol

A 250-mL flask was charged with anhydrous CeCl$_3$ (5.58 g, 22.6 mmol) and THF (40 mL). The mixture was vigorously stirred for 3.5 h at rt. The suspension was then cooled to −78° C. and a solution of allylmagnesium bromide (1.0 M in THF, 21 mL, 21.0 mmol) was added. After stirring for 2 h at −78° C., a solution of 3-chloro-1-(4-fluorophenyl)propan-1-one (2.522 g, 13.5 mmol) in THF (30 mL) was added via cannula. The reaction mixture was allowed to slowly warm to 8° C. while stirring overnight (18 h). The reaction was then quenched with satd aq NaHCO$_3$, extracted with EtOAc, and dried over Na$_2$SO$_4$. After the solvents were evaporated, the residue was purified by chromatography on silica gel eluted with hexanes/EtOAc to afford of 1-chloro-3-(4-fluorophenyl) hex-5-en-3-ol (3.0049 g, 97%) as an oil. LC-MS Method 1 $t_R$=1.79 min, m/z 213, 211 (M–OH)$^+$; $^1$H NMR (400 MHz, CDCl$_3$) δ 7.37-7.32 (m, 2H), 7.07-7.02 (m, 2H), 5.57-5.47 (m, 1H), 5.20-5.19 (m, 1H), 5.16 (m, 1H), 3.59-3.52 (m, 1H), 3.24-3.18 (m, 1H), 2.70 (dd, J=13.8, 5.9 Hz, 1H), 2.50 (dd, J=13.8, 8.5 Hz, 1H), 2.29 (t, J=7.9 Hz, 2H), 2.22 (s, 1H); $^{19}$F NMR (376 MHz, CDCl$_3$) δ −116.52 (m).

Step 2. (R)-6-allyl-3-((S)-1-(4-bromophenyl)ethyl)-6-(4-fluorophenyl)-1,3-oxazinan-2-one and (S)-6-allyl-3-((S)-1-(4-bromophenyl)ethyl)-6-(4-fluorophenyl)-1,3-oxazinan-2-one A mixture of 1-chloro-3-(4-fluorophenyl)hex-5-en-3-ol (0.413 g, 1.8 mmol, 1.0 equiv), (S)-(−)-1-(4-bromophenyl) ethyl isocyanate (0.501 g, 2.2 mmol, 1.2 equiv), and DBU (0.738 g, 4.8 mmol, 2.7 equiv) in THF (10 mL) was heated to reflux for 25 h. The mixture was diluted with EtOAc and washed with 1 N aq HCl. The aqueous phase was extracted with EtOAc (2×). The combined organic phase was dried over Na$_2$SO$_4$. After the solvents were evaporated, the crude product was directly used in the next step without further purification.

An analytical sample was purified by chromatography on silica gel eluted with hexanes/EtOAc to afford the two diastereomers of 6-allyl-3-((S)-1-(4-bromo-phenyl)ethyl)-6-(4-fluorophenyl)-1,3-oxazinan-2-one.

Isomer 1: (S)-6-allyl-3-((S)-1-(4-bromophenyl)ethyl)-6-(4-fluorophenyl)-1,3-oxazinan-2-one. LC-MS Method 1 $t_R$=2.03 min, m/z 420, 418 (MH$^+$); $^1$H NMR (400 MHz, CDCl$_3$) δ 7.46 (d, J=8.2 Hz, 2H), 7.31-7.28 (m, 2H), 7.17 (d, J=8.2 Hz, 2H), 7.07 (t, J=8.5 Hz, 2H), 5.76-5.66 (m, 2H), 5.10-4.99 (m, 2H), 2.75-2.52 (m, 4H), 2.23-2.19 (m, 1H), 2.08-2.00 (m, 1H), 1.24 (d, J=7.0 Hz, 3H); $^{19}$F NMR (376 MHz, CDCl$_3$) δ −115.07 (m).

Isomer 2: (R)-6-allyl-3-((S)-1-(4-bromophenyl)ethyl)-6-(4-fluorophenyl)-1,3-oxazinan-2-one. LC-MS Method 1 $t_R$=1.98 min, m/z 420, 418 (MH$^+$); $^1$H NMR (400 MHz, CDCl$_3$) δ 7.25-7.20 (m, 4H), 7.05-7.01 (m, 2H), 6.71 (d, J=8.5 Hz, 2H), 5.74-5.64 (m, 1H), 5.58 (q, J=7.0 Hz, 1H), 5.09-4.99 (m, 2H), 2.92-2.87 (m, 1H), 2.63-2.50 (m, 2H), 2.33-2.16 (m, 3H), 1.47 (d, J=7.0 Hz, 3H); $^{19}$F NMR (376 MHz, CDCl$_3$) δ −114.91 (m).

Step 3

A mixture of (R)-6-allyl-3-((S)-1-(4-bromophenyl)ethyl)-6-(4-fluorophenyl)-1,3-oxazinan-2-one (1.067 g, 2.55 mmol, 1.0 equiv), the cobalt(II) catalyst described in Preparation 3 (0.016 g, 0.0264 mmol, 0.010 equiv), TsCN (0.555 g, 3.06 mmol, 1.2 equiv), and PhSiH$_3$ (0.294 g, 2.72 mmol, 1.07 equiv) in EtOH (5 mL) was stirred at room temperature for 4 h. After the solvent was removed under reduced pressure, the residue was purified by chromatography on silica gel eluted with hexanes/ethyl acetate to afford 1.013 g (89%) of 3-((R)-

3-((S)-1-(4-bromophenyl)ethyl)-6-(4-fluorophenyl)-2-oxo-1,3-oxazinan-6-yl)-2-methylpropanenitrile as a solid. LC-MS $t_R$=1.83, 1.86 min in 3 min chromatography, m/z 445, 447 (MH$^+$); $^1$H NMR (400 MHz, CDCl$_3$) δ 7.32-7.22 (m, 4H), 7.13-7.05 (m, 2H), 6.80-6.73 (m, 2H), 5.60-5.56 (m, 1H), 3.00-1.94 (m, 7H), 1.51-1.49 (m, 3H), 1.35-1.32 (m, 1.5H), 1.27-1.24 (m, 1.5H); $^{19}$F NMR (376 MHz, CDCl$_3$) δ −113.08 (m), −113.69 (m).

Step 4

To a solution of 3-((R)-3-((S)-1-(4-bromophenyl)ethyl)-6-(4-fluorophenyl)-2-oxo-1,3-oxazinan-6-yl)-2-methylpropanenitrile (0.332 g, 0.746 mmol) and MeI (1.40 g, 13 equiv) in THF (12 mL) at −78° C. was added 2.4 mL (2.4 mmol, 3.2 equiv) of a 1.0 M LiHMDS solution in THF. The resulting mixture was stirred overnight, with the temperature slowly rising to ambient. The reaction mixture was quenched with brine (1 mL), diluted with CH$_2$Cl$_2$, and dried over Na$_2$SO$_4$. After the solvents were evaporated, the residue was purified by reversed-phase HPLC (SunFire™ Prep C$_{18}$ OBD™ 5 µm 19×50 mm column, 10%→90% CH$_3$CN/H$_2$O, 0.1% CF$_3$COOH over 8 min and then 90% CH$_3$CN/H$_2$O, 0.1% CF$_3$COOH over 2 min, flow rate 20 mL/min) to afford 0.2547 g (74%) of 3-((R)-3-((S)-1-(4-bromophenyl)ethyl)-6-(4-fluorophenyl)-2-oxo-1,3-oxazinan-6-yl)-2,2-dimethylpropanenitrile. LC-MS Method 1 $t_R$=1.89 min, m/z 459, 461 (MH$^+$); $^1$H NMR (400 MHz, CD$_3$OD) δ 7.31-7.27 (m, 2H), 7.22-7.18 (m, 2H), 7.04-6.99 (m, 2H), 6.83 (d, J=8.2 Hz, 2H), 5.41 (q, J=7.0 Hz, 1H), 3.02-2.97 (m, 1H), 2.42-2.36 (m, 1H), 2.29-2.08 (m, 4H), 1.42 (d, J=7.0 Hz, 3H), 1.30 (s, 3H), 1.22 (s, 3H); $^{19}$F NMR (376 MHz, CD$_3$OD) δ −116.50 (m).
Method 2

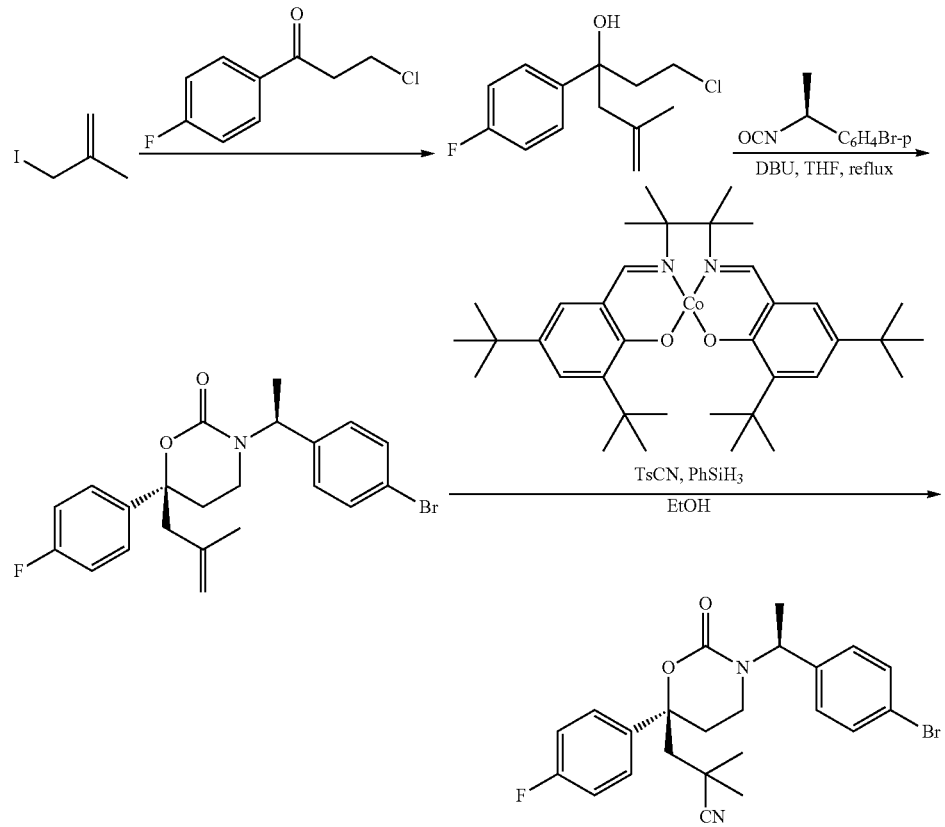

Step 1

A solution of 3-chloro-1-(4-fluorophenyl)-propan-1-one (18.6 g, 0.1 mol) in THF (50 mL) was added to a well-stirred suspension of zinc power (13 g, 0.2 mol) in a mixture of aqueous saturated NH$_4$Cl solution (260 mL) and THF (65 mL). A solution of 3-iodo-2-methylprop-1-ene (36.4 g, 0.2 mol) in THF (50 mL) was added dropwise. The reaction mixture was mildly exothermic, and began to reflux spontaneously. After the refluxing had ceased, the mixture was stirred for 1 h. TLC showed the 3-chloro-1-(4-fluorophenyl)propan-1-one not reacted completely. A solution of 3-iodo-2-methylprop-1-ene (18.2 g, 0.1 mol) in THF (30 mL) was added, and the mixture was stirred at rt overnight. The mixture was extracted with EtOAc (2×500 mL). The combined organic layer was dried and concentrated. The residue was purified by column chromatography on silica gel eluted with petroleum ether/EtOAc 50:1→430:1→5:1, to give 1-chloro-3-(4-fluorophenyl)-5-methylhex-5-en-3-ol (17 g, yield 76%) as an oil.

Step 2

A mixture of 1-chloro-3-(4-fluorophenyl)-5-methylhex-5-en-3-ol (3.15 g, 13 mmol), (S)-(–)-1-(-bromophenyl)ethyl isocyanate (3.5 g, 16 mmol), and DBU (8 g, 33 mmol) in THF (80 mL) was heated to reflux for 25 h. The mixture was diluted with EtOAc and washed with 1N aq HCl. The aqueous phase was extracted with EtOAc (3×). The combined organic phase was dried over Na₂SO₄. After the solvents were evaporated, the crude product was purified by column to give (R)-3-((S)-1-(4-bromophenyl)-ethyl)-6-(4-fluorophenyl)-6-(2-methylallyl)-1,3-oxazinan-2-one (2.13 g, yield: 38%).

Step 3

A mixture of (R)-3-((S)-1-(4-bromophenyl)ethyl)-6-(4-fluorophenyl)-6-(2-methylallyl)-1,3-oxazinan-2-one (2.13 g, 4.9 mmol), the cobalt(II) catalyst described in Preparation 3 (0.032 g, 0.053 mmol), TsCN (1.11 g, 6.12 mmol), and PhSiH₃ (0.6 g, 5.54 mmol) in EtOH (10 mL) was stirred at room temperature for 8 h. After the solvent was removed under reduced pressure, the residue was purified by column chromatography to give 3-((R)-3-((S)-1-(4-bromophenyl)ethyl)-6-(4-fluorophenyl)-2-oxo-1,3-oxazinan-6-yl)-2,2-dimethylpropanenitrile (1.84 g, 81.1%).

Preparation 6

3-((R)-6-(4-fluorophenyl)-2-oxo-3-((S)-1-(4-(4,4,5,5-tetramethyl-1,3,2-dioxaborolan-2-yl)phenyl)ethyl)-1,3-oxazinan-6-yl)-2,2-dimethylpropanenitrile

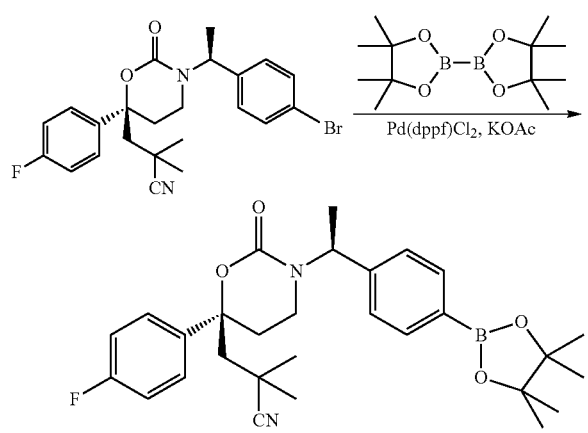

To a solution of 3-((R)-3-((S)-1-(4-bromophenyl)ethyl)-6-(4-fluorophenyl)-2-oxo-1,3-oxazinan-6-yl)-2,2-dimethylpropanenitrile (730 mg, 1.59 mmol) in DMSO (8 mL) was added bis(pinacolato)diboron (480 mg, 1.89 mmol), KOAc (480 mg, 4.89 mmol) and Pd(dppf)Cl₂ (45 mg, 0.042 mmol) under nitrogen atmosphere. The formed mixture was stirred at 90° C. for 20 h. The reaction was quenched with water and extracted with EtOAc. The combined organic phase was dried over anhydrous Na₂SO₄ and concentrated to give the crude product, which was purified by column chromatography to give 3-((R)-6-(4-fluorophenyl)-2-oxo-3-((S)-1-(4-(4,4,5,5-tetramethyl-1,3,2-dioxaborolan-2-yl)phenyl)ethyl)-1,3-oxazinan-6-yl)-2,2-dimethylpropanenitrile (191 mg, 23.7%).

Preparation 7

(R)-6-allyl-6-(4-fluorophenyl)-3-((S)-1-(4-(4,4,5,5-tetramethyl-1,3,2-dioxaborolan-2-yl)phenyl)ethyl)-1,3-oxazinan-2-one

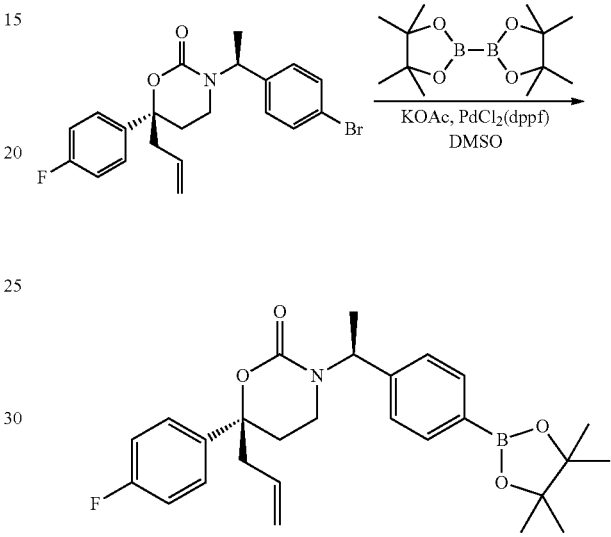

A mixture of (R)-6-allyl-3-((S)-1-(4-bromophenyl)ethyl)-6-(4-fluorophenyl)-1,3-oxazinan-2-one (0.4910 g, 1.17 mmol, 1.0 equiv), bis(pinacolato)diboron (0.3925 g, 1.55 mmol, 1.3 equiv), KOAc (0.3696 g, 3.76 mmol, 3.2 equiv), and PdCl₂(dppf).CH₂Cl₂ (0.0316 g, 0.0386 mmol, 0.033 equiv) in DMSO (6 mL) was heated at 90° C. under N₂ for 20 h. After cooling, the reaction mixture was partitioned between EtOAc and water. The organic phase was washed with brine, and dried over Na₂SO₄. After the solvents were evaporated, the residue was purified by chromatography on silica gel eluted with hexanes/ethyl acetate to give 0.4776 g (87%) of (R)-6-allyl-6-(4-fluorophenyl)-3-((S)-1-(4-(4,4,5,5-tetramethyl-1,3,2-dioxaborolan-2-yl)phenyl)ethyl)-1,3-oxazinan-2-one as a white solid.

Preparation 8

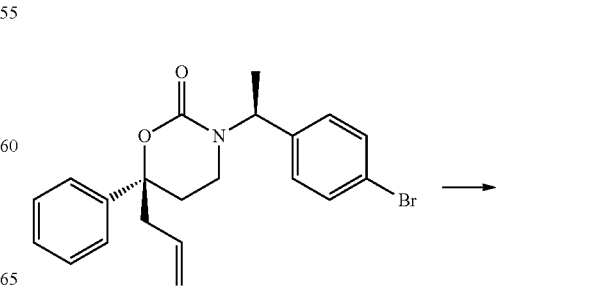

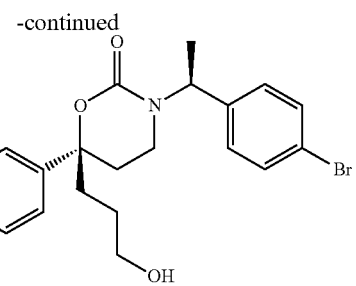
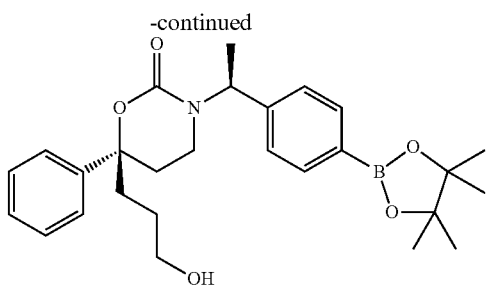

To a solution of (R)-6-allyl-3-((S)-1-(4-bromophenyl)ethyl)-6-phenyl-1,3-oxazinan-2-one (5 g, 12.5 mmol) in tetrahydrofuran (60 mL) was added $BH_3$ THF (25 mL, 1 mol/L, 25 mmol) at 0° C. under nitrogen atmosphere. The formed mixture was stirred for 2 h. The reaction was quenched with water. Then NaOH (3 mol/L, 10 mL) and $H_2O_2$ (15 mL) were added to the above mixture. When the reaction was over, the mixture was extracted with EtOAc. The combined organic phase was concentrated to give the crude product, which was purified by column chromatography to give (R)-3-((S)-1-(4-bromophenyl)ethyl)-6-(3-hydroxypropyl)-6-phenyl-1,3-oxazinan-2-one (2.5 g, 40%). $^1$H NMR: (400 MHz, $CDCl_3$): δ=1.48 (t, 3H), 1.53 (m, 1H), 1.73 (m, 1H), 1.93-1.98 (m, 2H), 2.17-2.28 (m, 3H), 3.57 (t, 2H), 5.59 (m, 1H), 6.72 (m, 2H), 7.20 (m, 2H), 7.25-7.37 (m, 5H).

(R)-3-((S)-1-(4-bromophenyl)ethyl)-6-(4-fluorophenyl)-6-(3-hydroxypropyl)-1,3-oxazinan-2-one was prepared from (R)-6-allyl-3-((S)-1-(4-bromophenyl)ethyl)-6-(4-fluorophenyl)-1,3-oxazinan-2-one following an analogous procedure.

(R)-3-((S)-1-(4-bromophenyl)propyl)-6-(3-hydroxypropyl)-6-phenyl-1,3-oxazinan-2-one was prepared from (R)-6-allyl-3-((S)-1-(4-bromophenyl)propyl)-6-phenyl-1,3-oxazinan-2-one following an analogous procedure.

Preparation 9

(R)-6-(3-hydroxypropyl)-6-phenyl-3-((S)-1-(4-(4,4,5,5-tetramethyl-1,3,2-dioxaborolan-2-yl)phenyl)ethyl)-1,3-oxazinan-2-one To a solution of ((R)-3-((S)-1-(4-bromophenyl)ethyl)-6-(3-hydroxypropyl)-6-phenyl-1,3-oxazinan-2-one (2 g, 4.8 mmol) in DMSO (30 mL) were added bis(pinacolato)diboron (1.58 g, 6.3 mmol), KOAc (1.51 g, 15.4 mmol) and $PdCl_2$ (130 mg, 0.16 mmol) under nitrogen atmosphere. The formed mixture was stirred at 90° C. for 20 h. The reaction was quenched with water and extracted with EtOAc. The combined organic phase was concentrated to give the crude product, which was purified by column chromatography to give (R)-6-(3-hydroxypropyl)-6-phenyl-3-((S)-1-(4-(4,4,5,5-tetramethyl-1,3,2-dioxaborolan-2-yl)phenyl)ethyl)-1,3-oxazinan-2-one (1.7 g, 77%). $^1$H NMR: (400 MHz, $CDCl_3$): δ=1.18 (t, 1H), 1.33 (S, 11H), 1.43 (m, 2H), 1.48 (m, 3H), 1.71 (m, 1H), 1.88 (m, 2H), 2.1-2.3 (t, 3H), 2.7 (m, 1H), 3.5 (m, 2H), 5.5 (m, 1H), 6.72 (m, 2H), 7.25-7.37 (m, 5H), 7.48 (m, 2H).

(R)-6-(4-fluorophenyl)-6-(3-hydroxypropyl)-3-((S)-1-(4-(4,4,5,5-tetramethyl-1,3,2-dioxaborolan-2-yl)phenyl)ethyl)-1,3-oxazinan-2-one was prepared from (R)-3-((S)-1-(4-bromophenyl)ethyl)-6-(4-fluorophenyl)-6-(3-hydroxypropyl)-1,3-oxazinan-2-one following an analogous procedure.

(R)-6-(3-hydroxypropyl)-6-phenyl-3-((S)-1-(4-(4,4,5,5-tetramethyl-1,3,2-dioxaborolan-2-yl)phenyl)propyl)-1,3-oxazinan-2-one was prepared from (R)-3-((S)-1-(4-bromophenyl)propyl)-6-(3-hydroxypropyl)-6-phenyl-1,3-oxazinan-2-one following an analogous procedure.

Preparation 10

(R)-3-((S)-1-(4-bromophenyl)ethyl)-6-(methoxymethyl)-6-phenyl-1,3-oxazinan-2-one

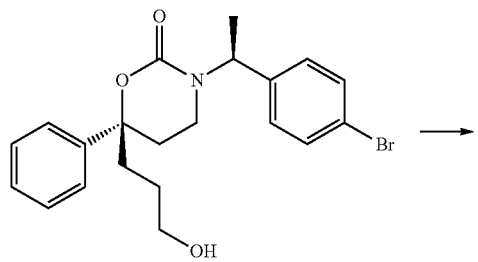

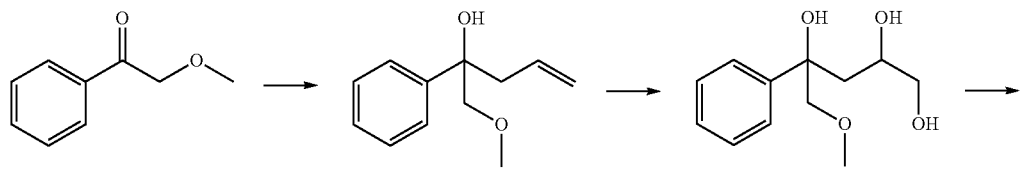

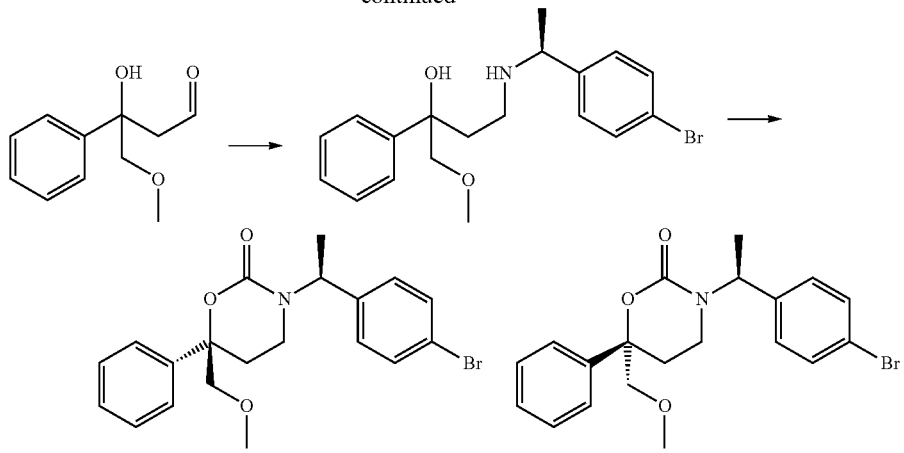

-continued

Step 1. 1-Methoxy-2-phenyl-pent-4-en-2-ol

2-Methoxy-1-phenyl-ethanone (5.00 g) dissolved in tetrahydrofuran (50 mL) was added to 2 M allylmagnesium chloride in tetrahydrofuran (21 mL) at room temperature. The solution was stirred at room temperature for 3 h and then 10% aqueous $NH_4Cl$ solution (50 mL) was added. The resulting mixture was extracted with tert-butyl methyl ether (3×50 mL) and the combined extracts were washed with water (50 mL) and brine (50 mL). The solvent was evaporated to afford the title compound as a colorless oil. Yield: 6.40 g (quantitative). Mass spectrum (ESI$^+$): m/z=175 [M+H−H$_2$O]$^+$ Step 2. 5-Methoxy-4-phenyl-pentane-1,2,4-triol $OsO_4$ (4% in water, 2 mL; alternatively, $K_2OsO_4$ may be used) followed by N-methyl-morpholine-N-oxide (5.20 g) was added to a solution of 1-methoxy-2-phenyl-pent-4-en-2-ol (1.10 g) in tetrahydrofuran (10 mL) chilled in an ice bath. The cooling bath was removed and the solution was stirred at room temperature overnight. Then, 10% aqueous $Na_2S_2O_5$ solution (10 mL) was added and the resulting mixture was stirred at room temperature for another 1.5 h. After removal of the organic solvent under reduced pressure, the remaining mixture was extracted with ethyl acetate. The combined extracts were washed with brine and dried ($MgSO_4$). The solvent was evaporated to afford the title compound in good purity (ca. 95%). Yield: 1.20 g (96% of theory). Mass spectrum (ESI$^-$): m/z=225 [M−H]$^-$ Step 3.
3-Hydroxy-4-methoxy-3-phenyl-butyraldehyde $NaIO_4$ (5.20 g) was added to a mixture of 5-methoxy-4-phenyl-pentane-1,2,4-triol (1.10 g), dichloromethane (10 mL), and water (5 mL) chilled in an ice bath. The mixture was stirred vigorously while warming to ambient temperature in the cooling bath and further stirred at this temperature overnight. Then, water (20 mL) and dichloromethane (50 mL) were added, the organic layer was separated, and the aqueous layer was extracted with dichloromethane (2×25 mL). The combined organic phases were washed with water and dried ($MgSO_4$). After removal of the solvent, the title compound was yielded which was directly submitted to the next reaction step (glycol cleavage)

Yield: 0.94 g (quantitative).

Step 4. 4-[(S)-1-(4-Bromo-phenyl)-ethylamino]-1-methoxy-2-phenyl-butan-2-ol (S)-1-(4-Bromo-phenyl)-ethylamine (0.93 g), $NaB(OAc)_3$ (0.98 g), and acetic acid (0.27 mL) were added in the given order to a solution of 3-hydroxy-4-methoxy-3-phenyl-butyraldehyde (0.90 g) in tetrahydrofuran (20 mL) at ca. 10-15° C. The cooling bath was removed and the mixture was stirred at room temperature for 2 h. Then, water (50 mL) and 1 M aqueous NaOH solution (20 mL) were added and the resulting mixture was stirred for another 30 min. The mixture was extracted with ethyl acetate and the combined extracts were washed with water and brine. After drying ($MgSO_4$), the solvent was removed to give the title compound which was submitted to the subsequent reaction step without further purification. Yield: 1.80 g (quantitative). Mass spectrum (ESI$^+$): m/z=378/380 (Br) [M+H]$^+$ Step 5. 3-[(S)-1-(4-Bromo-phenyl)-ethyl]-(R)-6-methoxymethyl-6-phenyl-[1,3]oxazinan-2-one and 3-[(S)-1-(4-Bromo-phenyl)-ethyl]-(S)-6-methoxymethyl-6-phenyl-[1,3]oxazinan-2-one Triphosgene (157 mg) was added to an ice-cold solution of 4-[(S)-1-(4-bromo-phenyl)-ethylamino]-1-methoxy-2-phenyl-butan-2-ol (1:1 diastereomeric mixture, 200 mg) and EtNiPr$_2$ (91 µL) in dichloromethane (5 mL). The resulting solution was stirred with cooling for 2 h and at room temperature overnight. Then, the solution was concentrated under reduced pressure and the residue was purified by HPLC on reversed phase (MeCN/H$_2$O/NH$_3$) to afford the title compounds in separate fractions.

Isomer 1: 3-[(S)-1-(4-Bromo-phenyl)-ethyl]-(R)-6-methoxymethyl-6-phenyl-[1,3]oxazinan-2-one. Yield: 45 mg (21% of theory). Mass spectrum (ESI$^+$): m/z=404 [M+H]$^+$ $^1$H NMR (400 MHz, DMSO-d$_6$) δ 1.41 (d, J=7.1 Hz, 3H), 2.19 (td, J=11.2, 5.2 Hz, 1H), 2.24-2.34 (m, 1H), 2.34-2.41 (m, 1H), 3.02-3.09 (m, 1H), 3.27 (s, 3H), 3.49 (d, B part of an AB signal, J=10.6 Hz, 1H), 3.53 (d, A part of an AB signal, J=10.6 Hz, 1H), 5.34 (q, J=7.0 Hz, 1H), 6.80 (dm, J=8.4 Hz, 2H), 7.27 (dm, J=8.4 Hz, 2H), 7.32-7.42 (m, 5H).

Isomer 2: 3-[(S)-1-(4-Bromo-phenyl)-ethyl]-(S)-6-methoxymethyl-6-phenyl-[1,3]oxazinan-2-one. Yield: 45 mg (21% of theory). Mass spectrum (ESI$^+$): m/z=404 [M+H]$^+$ $^1$H NMR (400 MHz, DMSO-d$_6$) δ 1.20 (d, J=7.2 Hz, 3H), 2.13-

2.23 (m, 1H), 2.32-2.40 (m, 1H), 2.63-2.72 (m, 1H), 2.73-2.81 (m, 1H), 3.26 (s, 3H), 3.48 (d, B part of an AB signal, J=10.6 Hz, 1H), 3.55 (d, A part of an AB signal, J=10.6 Hz, 1H), 5.35 (q, J=7.2 Hz, 1H), 7.19 (dm, J=8.4 Hz, 2H), 7.32-7.45 (m, 5H), 7.53 (dm, J=8.4 Hz, 2H).

Preparation 11

N-(3-((R)-3-((S)-1-(4-bromophenyl)ethyl)-2-oxo-6-phenyl-1,3-oxazinan-6-yl)propyl)-N-methylacetamide

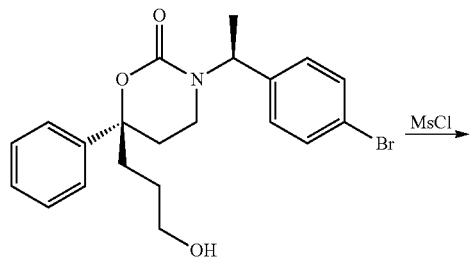

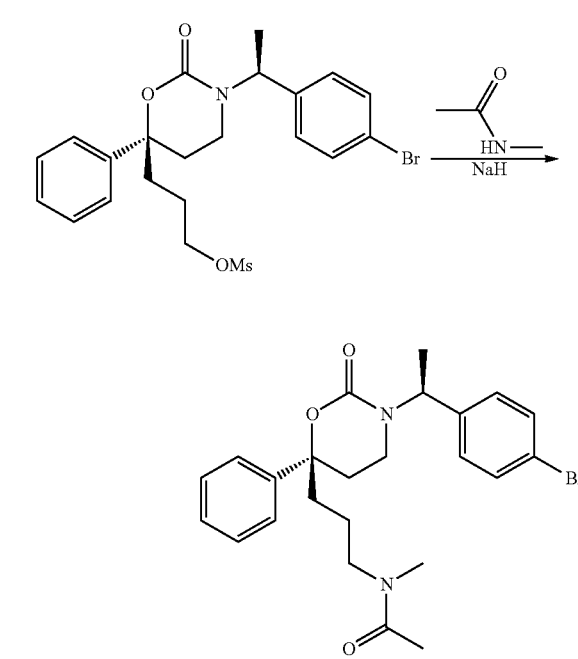

Step 1

To a solution of (R)-3-((S)-1-(4-bromophenyl)ethyl)-6-(3-hydroxypropyl)-6-phenyl-1,3-oxazinan-2-one (200 mg, 0.48 mmol) in CH$_2$Cl$_2$ (5 mL) was added Et$_3$N (240 mg, 2.4 mmol) and methanesulfonyl chloride (164 mg, 1.4 mmol) at 0° C. The reaction solution was stirred at rt for 1 h. The reaction was quenched with H$_2$O and the mixture was extracted with CH$_2$Cl$_2$. The organic phase was concentrated to give 3-((R)-3-((S)-1-(4-bromophenyl)ethyl)-2-oxo-6-phenyl-1,3-oxazinan-6-yl)propyl methanesulfonate (234 mg, 98%), which was used for the next step without further purification.

Step 2

To a solution of 3-((R)-3-((S)-1-(4-bromophenyl)ethyl)-2-oxo-6-phenyl-1,3-oxazinan-6-yl)propyl methanesulfonate (234 mg, 0.24 mmol) in CH$_2$Cl$_2$ (3 mL) was added NaH (82 mg, 3.4 mmol) at 0° C. The mixture was stirred at rt for 30 min. Then N-methylacetamide (204 mg, 2.8 mmol) was added the above mixture. The formed mixture was stirred at 80° C. for 5 h. After the reaction was over, the reaction was quenched with water and the mixture was extracted with EtOAc. The combined organic phase was concentrated to give the crude product, which was purified by preparative TLC to give N-(3-((R)-3-((S)-1-(4-bromophenyl)ethyl)-2-oxo-6-phenyl-1,3-oxazinan-6-yl)propyl)-N-methylacetamide (150 mg, 68%). LC-MS Method 2 tR=1.50 min, m/z=497, 495, 475, 473. $^1$H NMR (400 MHz, CDCl$_3$): δ=1.41 (m, 1H), 1.48 (t, 3H), 1.73 (m, 1H), 1.83-1.95 (m, 2H), 2.01 (m, 3H), 2.1-2.3 (m, 3H), 2.71 (m, 1H), 2.81 (s, 3H), 3.1 (m, 1H), 3.2 (m, 1H), 5.5 (m, 1H), 6.72 (m, 2H), 7.10 (m, 2H), 7.20 (m, 2H), 7.37 (m, 3H).

(R)-3-((S)-1-(4-bromophenyl)ethyl)-6-(3-(2-oxopyrrolidin-1-yl)propyl)-6-phenyl-1,3-oxazinan-2-one was prepared from (R)-3-((S)-1-(4-bromophenyl)ethyl)-6-(3-hydroxypropyl)-6-phenyl-1,3-oxazinan-2-one following an analogous procedure using pyrrolidin-2-one in Step 2.

Preparation 12

(S)-3-((S)-1-(4-bromophenyl)ethyl)-6-(2-(1-dioxoisothiazolidin-2-yl)ethyl)-6-phenyl-1,3-oxazinan-2-one

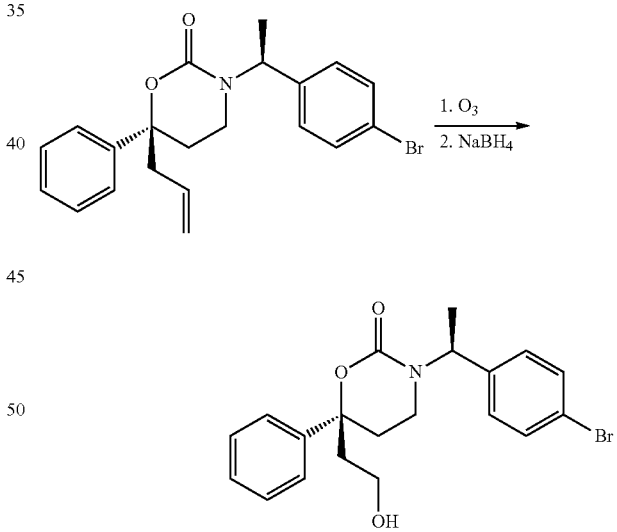

To a solution of (R)-6-allyl-3-((S)-1-(4-bromophenyl)ethyl)-6-phenyl-1,3-oxazinan-2-one (3 g, 7.5 mmol) in CH$_2$Cl$_2$ (50 mL) was treated with O$_3$ at −78° C. till the mixture turned blue. Then NaBH$_4$ (285 mg, 75 mmol) was added to the solution at 0° C., and the reaction solution was stirred at room temperature for 3 hours. The reaction was quenched by H$_2$O, and the mixture was extracted with EtOAc. The combined organic phase was concentrated to give the crude product, which was purified by preparative TLC to give (S)-3-((S)-1-(4-bromo-phenyl)ethyl)-6-(2-hydroxyethyl)-6-phenyl-1,3-oxazinan-2-one (2.5 g, 84%). $^1$H NMR (CDCl$_3$): 1.48 (t, 3H), 2.05-2.41 (m, 4H), 2.71-2.92 (m, 2H), 3.51 (m, 1H), 3.71 (m, 1H), 5.58 (m, 1H), 6.73 (d, 2H), 7.12 (m, 2H), 7.23-7.45 (m, 6H).

Preparation 13

(S)-3-((S)-1-(4-bromophenyl)ethyl)-6-(2-(1,1-dioxo-isothiazolidin-2-yl)ethyl)-6-phenyl-1,3-oxazinan-2-one

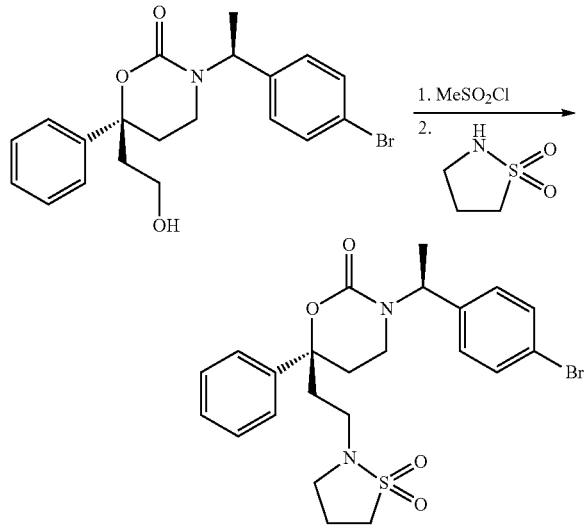

Step 1

To a solution of (S)-3-((S)-1-(4-bromophenyl)ethyl)-6-(2-hydroxyethyl)-6-phenyl-1,3-oxazinan-2-one (300 mg, 0.75 mmol) in dichloromethane (20 mL) were added Et₃N (390 mg, 3.75 mmol) and methanesulfonyl chloride (256 mg, 2.25 mmol) at 0° C. The reaction solution was stirred at rt for 1 h. The reaction was quenched with H₂O and the mixture was extracted with dichloromethane. The organic phase was concentrated to give 2-((S)-3-((S)-1-(4-bromophenyl)ethyl)-2-oxo-6-phenyl-1,3-oxazinan-6-yl)ethyl-methane sulfonate (352.8 mg, 98%), which was used for the next step without further purification.

Step 2

To a solution of 2-((S)-3-((S)-1-(4-bromophenyl)ethyl)-2-oxo-6-phenyl-1,3-oxazinan-6-yl)ethyl-methanesulfonate (360 mg, 0.75 mmol) and K₂CO₃ (207 mg, 1.5 mmol) in acetonitrile (10 mL) was added isothiazolidine 1,1-dioxide (121 mg, 4.6 mmol), and the mixture was refluxed overnight. The mixture was filtered and the filtrate was concentrated to give the crude product, which was purified by preparative HPLC to afford compound (S)-3-((S)-1-(4-bromophenyl)ethyl)-6-(2-(1,1-dioxo-isothiazolidin-2-yl)ethyl)-6-phenyl-1,3-oxazinan-2-one (2.43 mg, 1%). LC-MS Method 2 $t_R$=1.37 min, m/z=509, 507. ¹H NMR (CDCl₃): 1.48 (t, 3H), 2.05-2.41 (m, 7H), 2.71-2.92 (m, 2H), 3.11 (m, 3H), 3.21 (m, 2H), 5.58 (m, 1H), 6.73 (d, 2H), 7.18 (m, 1H), 7.23 (m, 3H); 7.35 (m, 3H).

(R)-3-((S)-1-(4-bromophenyl)ethyl)-6-(3-(1,1-dioxo-isothiazolidin-2-yl)propyl)-6-phenyl-1,3-oxazinan-2-one was prepared from (R)-3-((S)-1-(4-bromophenyl)ethyl)-6-(3-hydroxypropyl)-6-phenyl-1,3-oxazinan-2-one following an analogous procedure.

Preparation 14

(S)-3-((S)-1-(4-bromophenyl)ethyl)-6-(4-fluorophenyl)-6-((1-hydroxycyclopropyl)methyl)-1,3-oxazinan-2-one

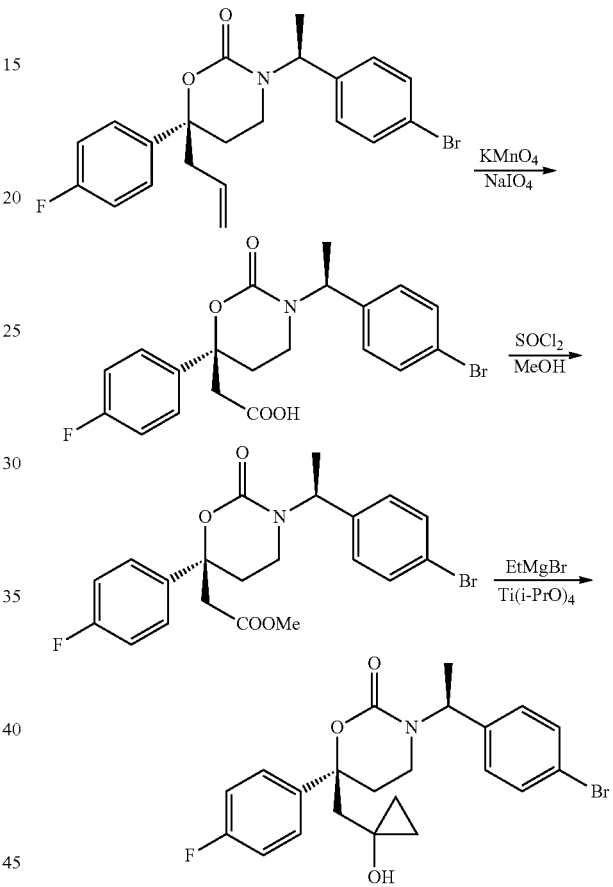

Step 1

To a solution of (R)-6-allyl-3-((S)-1-(4-bromophenyl)ethyl)-6-(4-fluorophenyl)-1,3-oxazinan-2-one (450 mg, 1.01 mmol) in acetone (10 mL) was added a solution of KMnO₄ (190 mg, 1.2 mmol) and NaIO₄ (1.5 g, 7.2 mmol) in water (10 mL). The mixture was stirred for 2 h at 0° C. The mixture was filtered and the filtrate was adjusted to pH 5-6 with aqueous 1 N aq HCl solution. The mixture was extracted with EtOAc. The organic phase washed with brine, dried over anhydrous Na₂SO₄ and concentrated to give 2-((S)-3-((S)-1-(4-bromophen-yl)ethyl)-6-(4-fluorophenyl)-2-oxo-1,3-oxazinan-6-yl)acetic acid (540 mg, crude), which was used for the next step without purification.

Step 2

To a solution of 2-((S)-3-((S)-1-(4-bromophen-yl)ethyl)-6-(4-fluorophenyl)-2-oxo-1,3-oxazinan-6-yl)acetic acid (540 mg, 1.24 mol) in MeOH (20 mL) was added SOCl$_2$ (5 mL) at 0° C., and the reaction mixture was stirred at rt for 2 h. The reaction mixture was concentrated and the residue was purified by preparative TLC to give methyl 2-((S)-6-(4-fluorophenyl)-3-((S)-1-(4-(1-methyl-6-oxo-1,6-dihydropyridin-3-yl)phenyl)-ethyl)-2-oxo-1,3-oxazinan-6-yl)acetate (150 mg, 27%). $^1$H NMR (CDCl$_3$): δ=1.49 (d, 3H), 2.19 (m, 1H), 2.44 (m, 1H), 2.60 (m, 1H), 2.77-3.08 (m, 3H), 3.51 (s, 3H), 5.52 (m, 2H), 6.62 (d, 2H), 6.98 (t, 2H), 7.23 (t, 2H), 7.28 (m, 2H).

Step 3

To a solution of methyl 2-((S)-6-(4-fluorophenyl)-3-((S)-1-(4-(1-methyl-6-oxo-1,6-dihydropyridin-3-yl)phenyl)-ethyl)-2-oxo-1,3-oxazinan-6-yl)acetate (150 mg, 0.33 mmol), and tetraisopropoxytitanium (189 mg, 0.66 mmol) in THF (20 mL) was added 3.0 M ethylmagnesium bromide (4 mL, 12 mmol) at rt under nitrogen. Then the mixture was stirred for 2 h. The reaction was quenched with aqueous NH$_4$Cl solution, and the mixture was filtered. The filtrate was extracted with EtOAc. The combined organic phase was washed with brine, dried over anhydrous Na$_2$SO$_4$, and concentrated to give the crude product, which was purified by preparative HPLC to give (S)-3-((S)-1-(4-bromophenyl) ethyl)-6-(4-fluorophenyl)-6-((1-hydroxycyclopropyl)methyl)-1,3-oxazinan-2-one (2.51 mg, 2%). $^1$H NMR (CDCl$_3$): 0.03 (m, 1H), 0.18 (m, 1H), 0.49 (m, 1H), 0.60 (m, 1H), 1.43 (m, 3H), 2.08 (s, 2H), 2.26 (m, 1H), 2.37 (m, 2H), 2.88 (m, 1H), 5.53 (m, 1H), 6.66 (d, 2H), 6.97 (t, 2H), 7.16 (m, 2H), 7.26 (m, 2H).

Preparation 15

N-(3-((R)-3-((S)-1-(4-bromophenyl)ethyl)-2-oxo-6-phenyl-1,3-oxazinan-6-yl)propyl)-N-methylmethane-sulfonamide

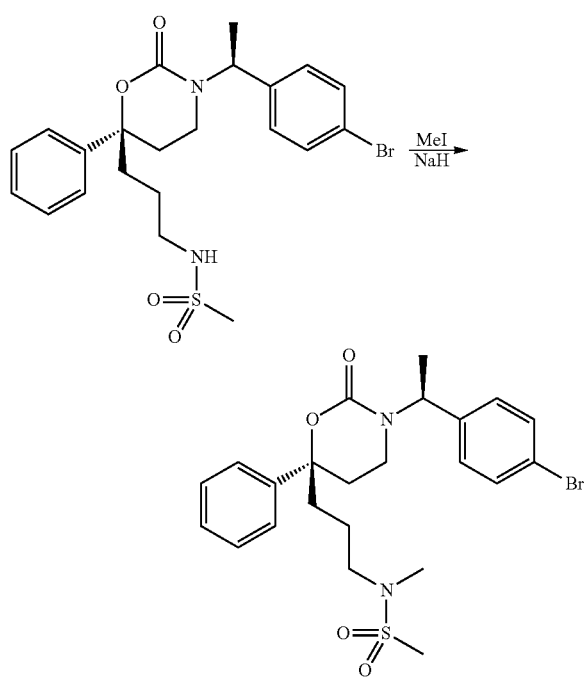

To a solution of 3-((R)-3-((S)-1-(4-bromophenyl)ethyl)-2-oxo-6-phenyl-1,3-oxazinan-6-yl) propyl methanesulfonate (180 mg, 0.36 mmol) in DMF (5 mL) was added NaH (14.6 mg, 0.36 mmol) at 0° C. The mixture was stirred at rt for 30 min. Then iodomethane (153 mg, 1.1 mmol) was added to the above mixture. The formed mixture was stirred at 40° C. for 3 h. After the reaction was over, the reaction was quenched with NH$_4$Cl solution and the mixture was extracted with EtOAc. The combined organic phase was concentrated to give the crude product, which was purified by preparative TLC to give N-(3-((R)-3-((S)-1-(4-bromophenyl)ethyl)-2-oxo-6-phenyl-1,3-oxazinan-6-yl)propyl)-N-methylmethane-sulfonamide (100 mg, 55%). LC-MS Method 2 t$_R$=1.41 min, m/z=511, 509. $^1$H NMR (400 MHz, CDCl$_3$): δ=1.45 (m, 1H), 1.48 (t, 3H), 1.83-1.97 (m, 3H), 2.1-2.2 (m, 3H), 2.61 (s, 3H), 2.71 (s, 3H), 2.91 (m, 1H), 3.0 (m, 2H), 5.5 (m, 1H), 6.72 (m, 2H), 7.10 (m, 2H), 7.20 (m, 2H), 7.37 (m, 3H).

EXAMPLE 1

6-(4-((S)-1-((S)-6-(2-hydroxy-2-methylpropyl)-2-oxo-6-phenyl-1,3-oxazinan-3-yl)ethyl)phenyl)-2-methylnicotinonitrile

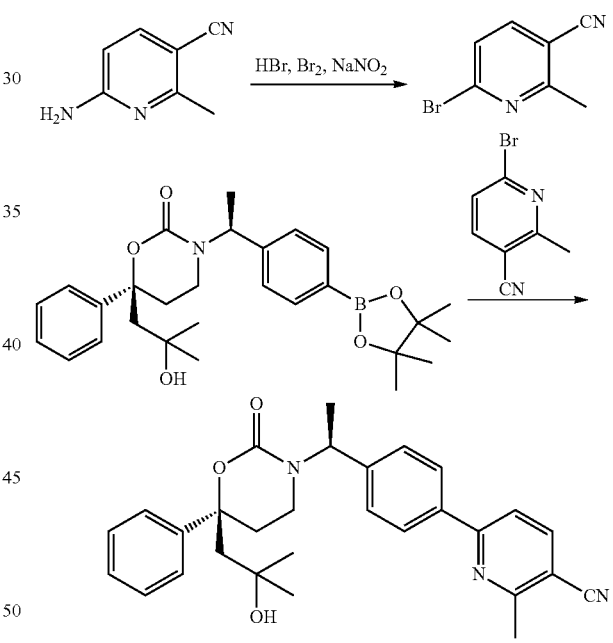

Step 1

To a solution of 6-amino-2-methyl-nicotinonitrile (1 g, 7.5 mmol) in aqueous HBr solution (48%, 1.25 g, 7.5 mmol) was added bromine (2.4 g, 15 mmol) at 0° C. A solution of NaNO$_2$ (1.3 g, 19 mmol) in water (5 mL) was added dropwise. The mixture was warmed to rt and stirred for 1.5 h. The solution was poured into iced water (20 mL). The aqueous mixture was neutralized with NaOH (1N, 5 mL), and extracted with EtOAc (4×10 mL). The combined organic layers were dried (Na$_2$SO$_4$), filtered, and concentrated under reduced pressure. The residue was purified by flash chromatography on silica gel to give a white solid (500 mg, 34%).

Step 2

To a solution of (S)-6-(2-hydroxy-2-methylpropyl)-6-phenyl-3-(S-1-(4-(4,4,5,5-tetramethyl-1,3,2-dioxaborolan-2-yl)-phenyl)-ethyl)-1,3-oxazinan-2-one (400 mg, 0.84 mmol) and 6-bromo-2-methylnicotinonitrile (164 mg, 0.84 mmol) in dry 1,4-dioxane (5 mL) was added $Cs_2CO_3$ (1 mL, 2M) and $Pd(PPh_3)_2Cl_2$ (40 mg). The mixture was heated at 110° C. for 2 h. After TLC showed the starting material had disappeared, the solid was filtered off. Water (5 mL) and EtOAc (5 mL) were added, the aqueous layer was extracted with EtOAc (3×8 mL). The combined organic layer was washed with brine, dried over $Na_2SO_4$, filtered, and concentrated. After HPLC purification, 6-(4-((S)-1-((S)-6-(2-hydroxy-2-methylpropyl)-2-oxo-6-phenyl-1,3-oxazinan-3-yl)ethyl)phenyl)-2-methylnicotinonitrile was obtained (100 mg, 26%). LC-MS Method 2 $t_R$=1.363 min, m/z=412; $^1$H NMR ($CDCl_3$): δ1.02 (s, 3H), 1.14 (s, 3H), 1.51 (d, 3H), 2.10-2.22 (m, 4H), 2.30-2.40 (m, 1H), 2.73 (s, 3H), 2.85 (m, 1H), 3.53 (m, 2H), 3.60-3.80 (m, 2H), 5.65 (m, 1H), 7.01 (d, 2H), 7.15-7.32 (m, 5H), 7.50 (d, 1H), 7.70 (d, 2H), 7.80 (d, 1H).

EXAMPLE 2

6-(4-((S)-1-((R)-6-(2-cyano-2-methylpropyl)-2-oxo-6-phenyl-1,3-oxazinan-3-yl)ethyl)phenyl)-N-cyclopropylnicotinamide

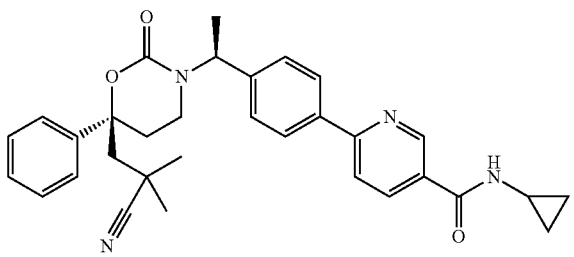 [SMILES: C[C@@H](c1ccc(-c2ccc(C(=O)NC3CC3)cn2)cc1)N1CC[C@](CC(C)(C)C#N)(c2ccccc2)OC1=O]

The title compound was prepared from (S)-6-(2-hydroxy-2-methylpropyl)-6-phenyl-3-(S-1-(4-(4,4,5,5-tetramethyl-1,3,2-dioxaborolan-2-yl)-phenyl)-ethyl)-1,3-oxazinan-2-one and 6-bromo-N-cyclopropylnicotinamide following a procedure analogous to that described in Example 1 Step 2. LC-MS Method 2 $t_R$=1.223 min, m/z=523.3; $^1$H NMR ($CDCl_3$) 0.66-0.71 (m, 2H), 0.93 (m, 2H), 1.24 (s, 3H), 1.47 (s, 3H), 1.57 (m, 3H), 2.19 (s, 2H), 2.23-2.34 (m, 2H), 2.48 (m, 2H), 2.92 (m, 2H), 5.67 (m, 1H), 6.36 (d, 1H), 6.97 (d, 2H), 7.34-7.40 (m, 5H), 7.72 (m, 3H), 8.18 (m, 1H), 8.97 (s, 1H)

EXAMPLE 3

N-tert-butyl-6-(4-((S)-1-((R)-6-(2-cyano-2-methylpropyl)-2-oxo-6-phenyl-1,3-oxazinan-3-yl)ethyl)phenyl)nicotinamide

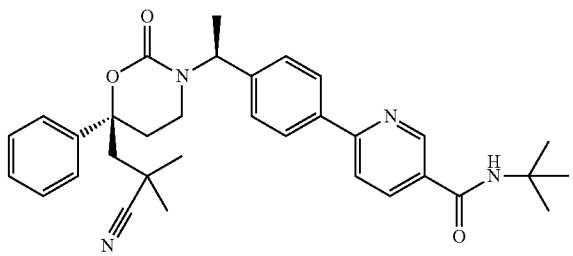 [SMILES: C[C@@H](c1ccc(-c2ccc(C(=O)NC(C)(C)C)cn2)cc1)N1CC[C@](CC(C)(C)C#N)(c2ccccc2)OC1=O]

The title compound was prepared from 2,2-dimethyl-3-((R)-2-oxo-6-phenyl-3-((S)-1-(4-(4,4,5,5-tetramethyl-1,3,2-dioxaborolan-2-yl)phenyl)ethyl)-1,3-oxazinan-6-yl)propanenitrile and 6-bromo-N-tert-butylnicotinamide following a procedure analogous to that described in Example 1 Step 2. LC-MS Method 2 $t_R$=1.323 min, m/z=539.3; $^1$H NMR ($CDCl_3$) 1.35 (s, 3H), 1.49 (s, 3H), 1.53 (s, 9H), 1.56 (m, 3H), 2.18 (m, 2H), 2.33 (m, 1H), 2.49 (m, 2H), 2.93 (m, 1H), 5.70 (m, 1H), 6.00 (m, 1H), 6.98 (d, 2H), 7.38 (m, 5H), 7.34-7.40 (m, 5H), 7.69-7.74 (m, 3H), 8.13 (m, 1H), 9.00 (s, 1H)

EXAMPLE 4

(S)-3-((S)-1-(4-(6-cyclopropylpyridazin-3-yl)phenyl)ethyl)-6-(2-hydroxy-2-methylpropyl)-6-phenyl-1,3-oxazinan-2-one

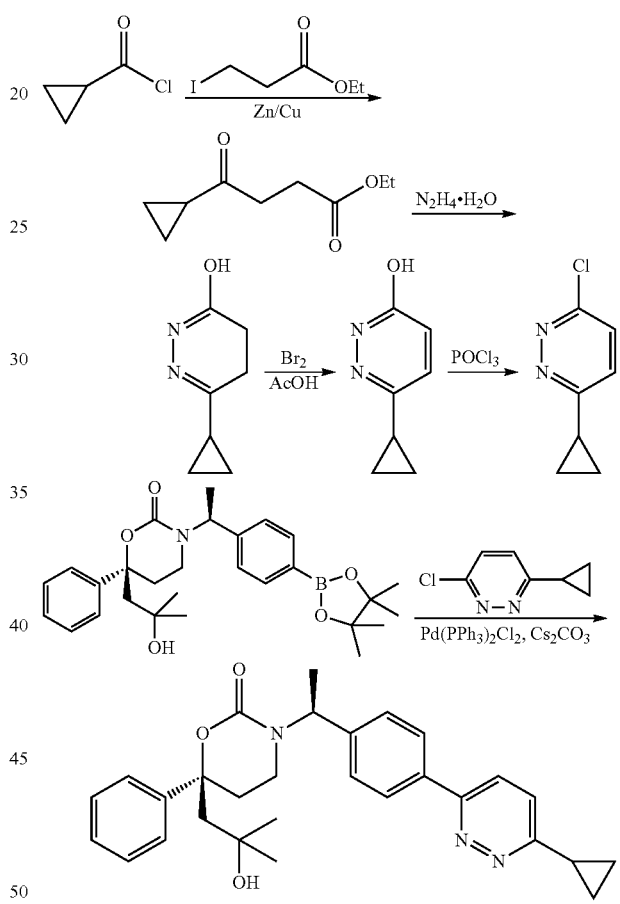

Step 1

A mixture of ethyl 3-iodopropanoate (8 g, 35 mmol) and zinc-copper (4.5 g, 70 mmol) in a mixture of benzene (80 mL) and DMA (8 mL) was heated at 60° C. for 4.5 hours under $N_2$. $Pd(PPh_3)_2Cl_2$ (1.2 g, 1.8 mmol) was added, followed by addition of cyclopropanecarbonyl chloride (3.7 g, 35 mmol). The mixture was stirred at 60° C. for another 30 minutes. The reaction mixture was diluted with ethyl acetate (300 mL), and washed with 1N HCl (50 mL), satd aq $NaHCO_3$ (80 mL) and brine (30 mL). The organic layer was dried over $Na_2SO_4$ and concentrated to afford the ethyl 4-cyclopropyl-4-oxobutanoate (4.2 g), which was used for next step directly without purification.

Step 2

A mixture of ethyl 4-cyclopropyl-4-oxobutanoate (2.2 g, 13 mmol, crude) and $N_2H_4 \cdot H_2O$ (3.3 mL, 85%, 56 mmol) in EtOH (20 mL) was refluxed for 4 h. The mixture was concentrated, and the residue was treated with a mixture of ethyl acetate (100 mL) and water (20 mL). The organic layer was dried over $Na_2SO_4$ and concentrated to give the crude product, which was purified by preparative TLC to give 6-cyclopropyl-4,5-dihydropyridazin-3-ol (200 mg, 11%). $^1H$ NMR (400 MHz, $CD_3OD$): δ0.79 (m, 4H), 1.62 (m, 1H), 2.26 (m, 4H).

Step 3

To a solution of 6-cyclopropyl-4,5-dihydropyridazin-3-ol (200 mg, 1.5 mmol) in AcOH (6 mL) was added $Br_2$ (695 mg, 4.4 mmol) at 70° C. The mixture was stirred at 70° C. for 15 minutes, and more $Br_2$ (695 mg, 4.4 mmol) was added. The mixture was refluxed for 2 hours, and concentrated. The residue was diluted with ethyl acetate (60 mL), the organic layer was washed with satd aq $NaHCO_3$ solution (20 mL). The organic layer was dried over $Na_2SO_4$ and concentrated to give 6-cyclopropyl-4,5-dihydropyridazin-3-ol (182 mg, 91%). $^1H$ NMR (400 MHz, $CD_3OD$): δ0.75 (m, 2H), 0.85 (m, 2H), 1.85 (m, 1H), 6.79 (d, 2H), 7.25 (d, 1H).

Step 4

A mixture of 6-cyclopropylpyridazin-3-ol (182 mg, 1.3 mmol) in $POCl_3$ (15 mL) was refluxed for 1 hour, and concentrated. The residue was treated with ethyl acetate (60 mL) and sat. $NaHCO_3$ aqueous solution (10 mL) at 0° C. The organic layer was dried over $Na_2SO_4$ and concentrated to afford 3-chloro-6-cyclopropylpyridazine (185 mg, 89%). $^1H$ NMR (400 MHz, $CD_3OD$): δ1.11 (m, 2H), 1.20 (m, 2H), 2.25 (m, 1H), 7.52 (d, 1H), 7.67 (d, 1H).

Step 5

A mixture of S-6-(2-hydroxy-2-methylpropyl)-6-phenyl-3-((S)-1-(4-(4,4,5,5-tetramethyl-1,3,2-dioxaborolan-2-yl)phenyl)-ethyl)-1,3-oxazinan-2-one (868 mg, 1.8 mmol), 3-chloro-6-cyclopropylpyridazine (350 mg, 2.26 mmol), $PdCl_2(PPh_3)_2$ (509 mg, 0.7 mmol) and 2 M aq $Cs_2CO_3$ solution (4.6 mL) in 1,4-dioxane (9 mL) was heated to reflux for 2 h. The reaction mixture was concentrated. The residue was treated with water (60 mL), and extracted with ethyl acetate (360 mL×3). The combined organic phase was dried over $Na_2SO_4$ and concentrated to give the crude product, which was purified by preparative TLC and preparative HPLC to afford (S)-3-((S)-1-(4-(6-cyclopropylpyridazin-3-yl)phenyl)ethyl)-6-(2-hydroxy-2-methylpropyl)-6-phenyl-1,3-oxazinan-2-one (104.5 mg, 12%). LC-MS Method 2 $t_R$=1.068 min, m/z=472.3; $^1H$ NMR (400 MHz, $CD_3OD$): δ1.06 (s, 3H), 1.08 (m, 2H), 1.13 (s, 3H), 1.19 (m, 2H), 1.50 (d, 3H), 2.10 (m, 1H), 2.12 (s, 2H), 2.20 (m, 2H), 2.30 (m, 1H), 2.78 (m, 1H), 5.65 (m, 1H), 6.96 (d, 2H), 7.25 (m, 6H), 7.55 (d, 1H), 7.74 (d, 2H).

EXAMPLE 5

(S)-3-((S)-1-(4-(5-chloro-6-methylpyridazin-3-yl)phenyl)ethyl)-6-(2-hydroxy-2-methylpropyl)-6-phenyl-1,3-oxazinan-2-one and (S)-3-((S)-1-(4-(6-chloro-3-methylpyridazin-4-yl)phenyl)ethyl)-6-(2-hydroxy-2-methylpropyl)-6-phenyl-1,3-oxazinan-2-one

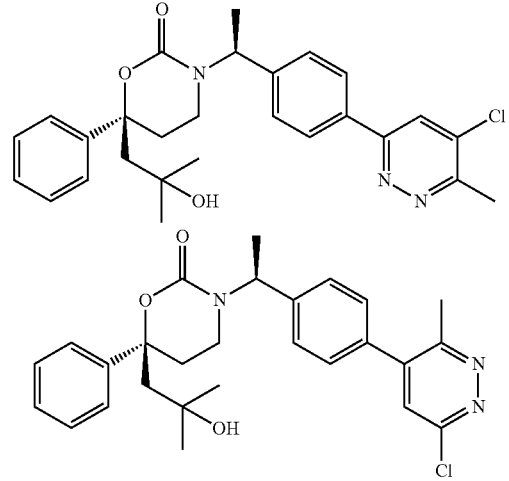

The isomeric title compounds were prepared by reaction of (S)-6-(2-hydroxy-2-methylpropyl)-6-phenyl-3-((S)-1-(4-(4,4,5,5-tetramethyl-1,3,2-dioxaborol-an-2-yl)phenyl)ethyl)-1,3-oxazinan-2-one and 4,6-dichloro-3-methylpyridazine following a procedure analogous to that described in Example 14.

Isomer 1: LC-MS Method 1 $t_R$=1.6 min, m/z=480, 482 (M+1); $^1H$ NMR ($CD_3OD$) 8.19 (s, 1H), 7.85 (d, 2H), 7.35 (m, 5H), 7.13 (d, 2H), 5.61 (q, 1H), 3.08 (m, 1H), 2.79 (s, 3H), 2.48 (m, 3H), 2.26 (td, 1H), 2.15 (s, 2H), 1.58 (d, 3H), 1.26 (s, 3H), 0.95 (s, 3H).

Isomer 2: LC-MS Method 1 $t_R$=1.53 min, m/z=480, 482 (M+1); $^1H$ NMR ($CD_3OD$) 7.58 (s, 1H), 7.35 (m, 4H), 7.31-7.22 (m, 3H), 7.13 (d, 2H), 3.11 (m, 1H), 2.53 (s, 3H), 2.23 (td, 1H), 2.16 (s, 2H), 1.57 (d, 3H), 1.27 (s, 3H), 0.96 (s, 3H).

4,6-dichloro-3-methylpyridazine was prepared following the procedure described in WO 2003/041712 (Intermediate A3, p 12).

EXAMPLE 6

(S)-3-((S)-1-(4-(6-tert-butylpyridazin-3-yl)phenyl)ethyl)-6-(2-hydroxy-2-methylpropyl)-6-phenyl-1,3-oxazinan-2-one

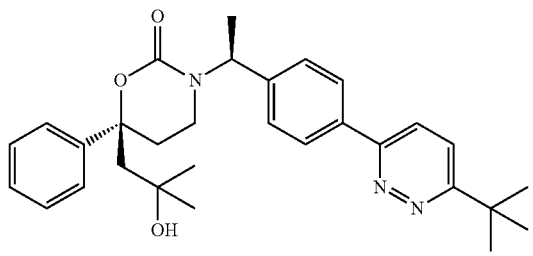 [SMILES: C[C@@H](c1ccc(-c2ccc(C(C)(C)C)nn2)cc1)N1CC[C@](CC(C)(C)O)(c2ccccc2)OC1=O]

The title compound was prepared from (S)-6-(2-hydroxy-2-methylpropyl)-6-phenyl-3-((S)-1-(4-(4,4,5,5-tetramethyl- 1,3,2-dioxaborol-an-2-yl)phenyl)ethyl)-1,3-oxazinan-2-one and 3-bromo-6-tert-butylpyridazine following a procedure analogous to that described in Example Step 2. 3-bromo-6-tert-butylpyridazine was prepared from pivaloyl chloride following procedures analogous to those described in Example 4 Steps 1-4 using POBr$_3$ in place of POCl$_3$ in Step 4. LC-MS Method 2 t$_R$=1.208 min, m/z=488.3; $^1$H NMR (CD$_3$OD) 0.94 (s, 3H), 1.25 (s, 3H), 1.48 (s, 9H), 1.57 (d, 3H), 2.15 (s, 2H), 2.29 (m, 1H), 2.50 (m, 2H), 3.10 (m, 1H), 5.60 (m, 1H), 7.14 (d, 2H), 7.30 (m, 5H), 7.81 (d, 2H), 8.07 (d, 1H), 8.20 (d, 1H)

EXAMPLE 7

(S)-6-(2-hydroxy-2-methylpropyl)-3-((S)-1-(4-(6-(2-hydroxypropan-2-yl)pyridazin-3-yl)phenyl)ethyl)-6-phenyl-1,3-oxazinan-2-one

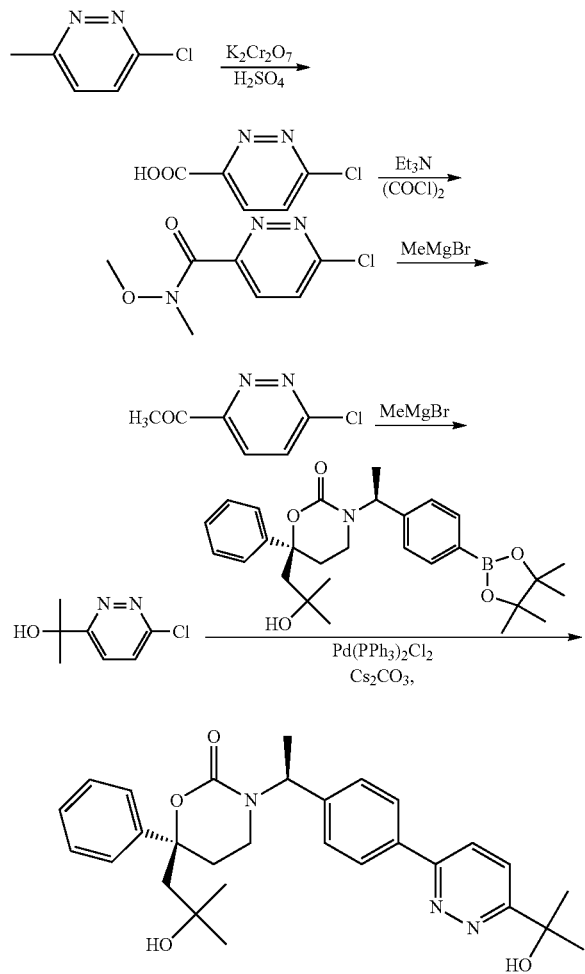

Step 1

To a stirred solution of 3-chloro-6-methylpyridazine (12.8 g, 100 mol) in concentrated H$_2$SO$_4$ (100 mL) was added powered K$_2$Cr$_2$O$_7$ (35.3 g, 120 mmol) slowly at 50° C. The reaction mixture was stirred at 50° C. for 4 h, and poured into the iced water carefully. The mixture was extracted with EtOAc. The combined organic layer was washed with brine, dried over Na$_2$SO$_4$, and filtered. The solvent was removed under vacuum to afford the 6-chloropyridazine-3-carboxylic acid (9.25 g, 59%), which was used directly in the next step. $^1$H NMR (DMSO-d$_6$, 400 MHz): δ8.21 (d, J=4.8 Hz, 1H), 8.06 (d, J=4.8 Hz, 1H).

Step 2

To a stirred solution of 6-chloropyridazine-3-carboxylic acid (12.5 g, 0.078 mol) in CH$_2$Cl$_2$ (80 mL) at 0° C. were added triphosgene (11.6 g, 0.039 mol), Et$_3$N (55 mL, 0.4 mol), and N,O-dimethylhydroxylamine hydrochloride (7.6 g, 0.078 mol). The reaction mixture was stirred at room temperature for 2 h. The salt was filtered, after removal of the solvent in vacuo, the residue was purified by column chromatography to afford 6-chloro-N-methoxy-N-methylpyridazine-3-carboxamide (13.5 g, 86%). $^1$H NMR (DMSO-d$_6$, 400 MHz): δ 8.08 (d, J=9.2 Hz, 1H), 8.06 (d, J=9.2 Hz, 1H), 3.33 (s, 3H), 8.06 (s, 3H).

Step 3

To a solution of 6-chloro-N-methoxy-N-methylpyridazine-3-carboxamide (13.5 g, 0.0659 mol) in THF (600 mL) was added CH$_3$MgBr (43.2 ml, 0.13 mol) at −78° C. under N$_2$. The reaction mixture was stirred at −78° C. for 2 h, quenched by addition of aq NH$_4$Cl and filtered. The filtrate was extracted with EtOAc. The combined organic layer was washed with brine, dried over Na$_2$SO$_4$, and filtered. The solvent was removed under vacuum, and the residue was purified by column chromatography to afford 1-(6-chloropyridazin-3-yl)ethanone. (9.3 g, 90% yield). $^1$H NMR (CDCl$_3$, 400 MHz): δ 8.03 (d, J=8.8 Hz, 1H), 7.60 (d, J=8.8 Hz, 1H), 2.81 (s, 3H).

Step 4

To a solution of 1-(6-chloropyridazin-3-yl)ethanone (120 mg, 0.757 mol) in THF (5 mL) was added MeMgBr (0.38 mL, 1.14 mol), and stirred at −78° C. for 30 min and at rt for 30 minutes. The reaction mixture was quenched with satd aq NH$_4$Cl, and extracted with EtOAc. The combined organic layer was dried over Na$_2$SO$_4$ and concentrated to give an oil, which was purified by prep TLC to give the product (1:2 PE/EtOAcA). $^1$H NMR (CD$_3$OD): δ1.61 (s, 6H), 3.30 (m, 1H), 7.76 (d, 1H), 8.00 (d, 2H).

Step 5

A solution of (S)-6-(2-hydroxy-2-methylpropyl)-6-phenyl-3-((S)-1-(4-(4,4,5,5-tetramethyl-1,3,2-dioxaborolan-2-yl)phenyl)ethyl)-1,3-oxazinan-2-one (50 mg, 0.104 mmol), 2-(6-chloropyridazin-3-yl)-propan-2-ol (20 mg, 0.151 mmol), Pd(PPh$_3$)$_2$Cl$_2$ (30 mg, 0.046 mmol), 2 M aq Cs$_2$CO$_3$ (0.4 mL) in dioxane (5 mL) was heated at reflux for 2 h. The reaction mixture was concentrated, and the residue was treated with water (20 mL) and extracted with EtOAc (3×10 mL). The combined organic layer was washed with satd aq NaCl solution, dried with anhydrous Na$_2$SO$_4$, and concentrated to give an oil, which was purified by preparative TLC and HPLC to give the product. LC-MS Method 2 t$_R$=1.031 min, m/z=490.3; $^1$H NMR (CD$_3$OD): δ0.89 (s, 1H), 0.96 (s, 3H), 1.28 (m, 6H), 1.57 (d, 3H), 1.66 (m, 6H), 2.15 (s, 2H), 2.28 (m, 1H), 2.56 (m, 2H), 3.08 (m, 1H), 5.62 (m, 1H), 7.13 (d, 2H), 7.38 (m, 5H), 7.82 (m, 2H), 8.05 (m, 2H).

EXAMPLE 8

N-tert-butyl-6-(4-((S)-1-((S)-6-(2-hydroxy-2-methyl-propyl)-2-oxo-6-phenyl-1,3-oxazinan-3-yl)ethyl)phenyl)pyridazine-3-carboxamide

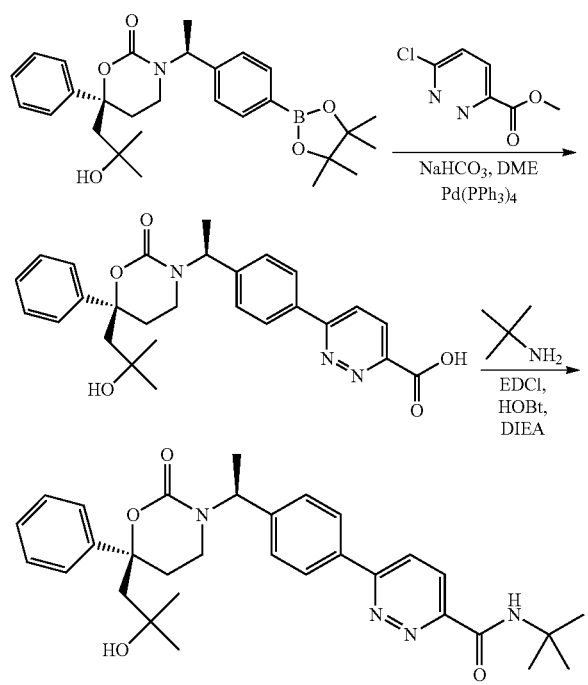

Step 1

To a solution of methyl 6-chloropyridazine-3-carboxylate (36 mg, 0.2 mmol) in DME (6 mL) was added Pd(PPh$_3$)$_4$ (20 mg, 0.02 mmol) under N$_2$. The mixture was stirred at room temperature for 1 h. (S)-6-(2-hydroxy-2-methylpropyl)-6-phenyl-3-((S)-1-(4-(4,4,5,5-tetramethyl-1,3,2-dioxaborolan-2-yl)phenyl)-ethyl)-1,3-oxazinan-2-one (96 mg, 0.2 mmol) in EtOH (2 mL) and satd aq NaHCO$_3$ (2 mL) were added. The mixture was stirred at 100° C. for another 2 h under N$_2$. The reaction mixture was quenched by addition of H$_2$O, and extracted by EtOAc. The combined organic phase was dried and concentrated to give the crude product, which was purified by preparative TLC to give 6-(4-((S)-1-((S)-6-(2-hydroxy-2-methylpropyl)-2-oxo-6-phenyl-1,3-oxazinan-3-yl)-ethyl)-phenyl)-pyridazine-3-carboxylic acid (63 mg, 60%).

Step 2

To a solution of 6-(4-(S-1-(S-6-(2-hydroxy-2-methylpropyl)-2-oxo-6-phenyl-1,3-oxazinan-3-yl)ethyl)phenyl)pyridazine-3-carboxylic acid (479 mg, 1.0 mmol) in CH$_2$Cl$_2$ (50 mL) was added DIEA (2 mL, 10 mmol), HOBt (675 mg, 5 mmol), EDCl (985 mg, 5 mmol), and 2-methylpropan-2-amine (438 mg, 6 mmol) at 0° C. under N$_2$. The mixture was stirred at rt overnight. The reaction was quenched by addition of HCl (1 N), and extracted with CH$_2$Cl$_2$. The combined organic phase was dried over Na$_2$SO$_4$ and concentrated to give the crude product, which was purified by preparative TLC to give N-tert-butyl-6-(4-((S)-1-((S)-6-(2-hydroxy-2-methylpropyl)-2-oxo-6-phenyl-1,3-oxazinan-3-yl)-ethyl)-phenyl)-pyridazine-3-carboxamide (230 mg, 51%). LC-MS Method 2 t$_R$=1.372 min, m/z=473.1; $^1$H NMR (CDCl$_3$): δ1.07 (s, 3H), 1.12 (s, 3H), 1.48 (m, 9H), 1.52 (d, 3H), 2.04 (m, 1H), 2.20 (s, 2H), 2.22 (m, 2H), 2.36 (m, 1H), 2.87 (m, 1H), 5.68 (m, 1H), 7.08 (m, 2H), 7.20-7.30 (m, 5H), 7.8 (m, 2H), 8.09 (m, 1H), 8.25 (m, 1H).

EXAMPLE 9

N-tert-butyl-6-(4-((S)-1-((R)-6-(2-cyano-2-methyl-propyl)-2-oxo-6-phenyl-1,3-oxazinan-3-yl)ethyl)phenyl)pyridazine-3-carboxamide

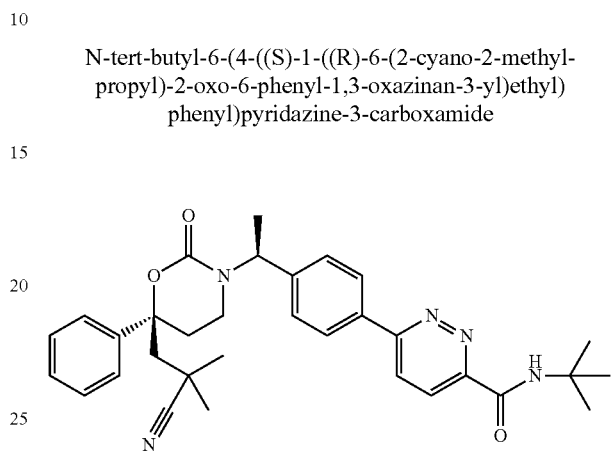

The title compound was prepared from 2,2-dimethyl-3-((R)-2-oxo-6-phenyl-3-((S)-1-(4-(4,4,5,5-tetramethyl-1,3,2-dioxaborolan-2-yl)phenyl)ethyl)-1,3-oxazinan-6-yl)propanenitrile and methyl 6-chloropyridazine-3-carboxylate following procedures analogous to those described in Example 8. LC-MS Method 2 t$_R$=1.404 min, m/z=540.3; $^1$H NMR (CDCl$_3$) 1.33 (s, 3H), 1.46 (s, 3H), 1.51 (s, 9H), 1.59 (m, 3H), 2.13 (m, 2H), 2.36 (m, 1H), 2.51 (m, 2H), 2.95 (m, 1H), 5.70 (m, 1H), 6.99 (m, 2H), 7.38 (m, 5H), 7.83 (m, 2H), 7.92 (m, 1H), 8.16 (m, 1H), 8.32 (m, 1H)

EXAMPLE 10

N-cyclopropyl-6-(4-((S)-1-((S)-6-(2-hydroxy-2-methylpropyl)-2-oxo-6-phenyl-1,3-oxazinan-3-yl)ethyl)phenyl)pyridazine-3-carboxamide

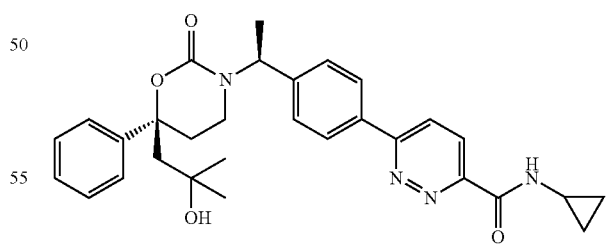

The title compound was prepared from (S)-6-(2-hydroxy-2-methylpropyl)-6-phenyl-3-((S)-1-(4-(4,4,5,5-tetramethyl-1,3,2-dioxaborolan-2-yl)phenyl)-ethyl)-1,3-oxazinan-2-one and methyl 6-chloropyridazine-3-carboxylate following procedures analogous to those described in Example 8 using cyclopropylamine in Step 2. LC-MS Method 2 t$_R$=1.221 min, m/z=457.1; $^1$H NMR (CDCl$_3$) 0.67 (m, 2H), 0.88 (m, 2H), 1.20 (s, 3H), 1.23 (s, 3H), 1.54 (d, 3H), 2.20 (m, 4H), 2.3 (s, 1H), 2.9 (m, 1H), 3.0 (m, 2H), 5.7 (m, 1H), 7.0 (m, 2H), 7.28-7.34 (m, 5H), 7.8 (m, 2H), 7.90 (m, 1H), 8.2 (m, 1H), 8.3 (m, 1H)

EXAMPLE 11

6-(4-((S)-1-((R)-6-(2-cyano-2-methylpropyl)-2-oxo-6-phenyl-1,3-oxazinan-3-yl)ethyl)phenyl)-N-cyclopropylpyridazine-3-carboxamide

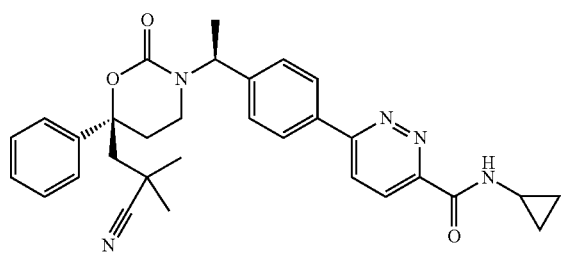 [SMILES: C[C@@H](c1ccc(-c2ccc(C(=O)NC3CC3)nn2)cc1)N1CC[C@](CC(C)(C)C#N)(c2ccccc2)OC1=O]

The title compound was prepared from 2,2-dimethyl-3-((R)-2-oxo-6-phenyl-3-((S)-1-(4-(4,4,5,5-tetramethyl-1,3,2-dioxaborolan-2-yl)phenyl)ethyl)-1,3-oxazinan-6-yl)propanenitrile and methyl 6-chloropyridazine-3-carboxylate following procedures analogous to those described in Example 8 using cyclopropylamine in Step 2. LC-MS Method 2 $t_R$=1.17 min, m/z=524.3; $^1$H NMR (CDCl$_3$) 0.71 (m, 2H), 0.94 (m, 2H), 1.34 (s, 3H), 1.48 (s, 3H), 1.59 (m, 3H), 2.18 (m, 2H), 2.36 (m, 1H), 2.53 (m, 2H), 2.94 (m, 1H), 3.02 (m, 1H), 5.72 (m, 1H), 7.03 (m, 2H), 7.39 (m, 5H), 7.84 (m, 2H), 7.93 (m, 1H), 7.25 (m, 1H), 8.34 (m, 1H)

EXAMPLE 12

(R)-6-(2-(5-methyl-1,3,4-oxadiazol-2-yl)ethyl)-3-((S)-1-(4-(6-methylpyridazin-3-yl)phenyl)ethyl)-6-phenyl-1,3-oxazinan-2-one

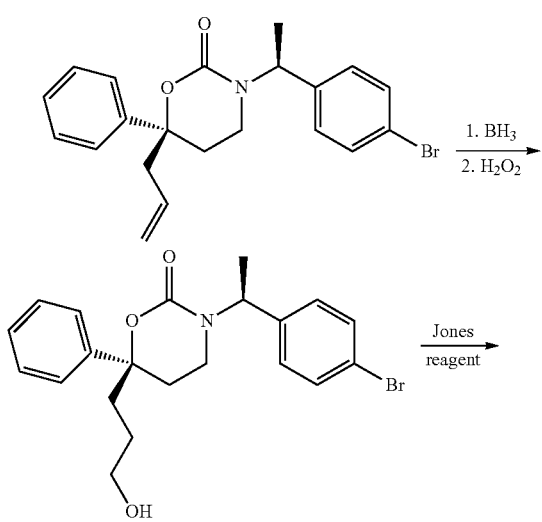

-continued

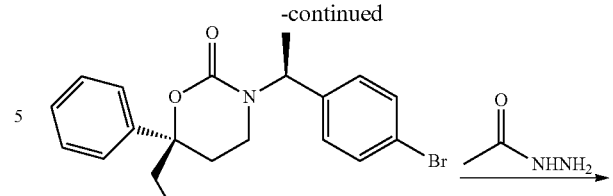

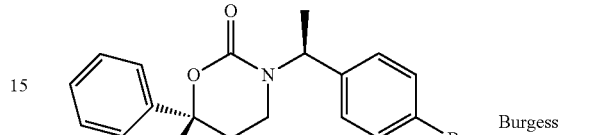

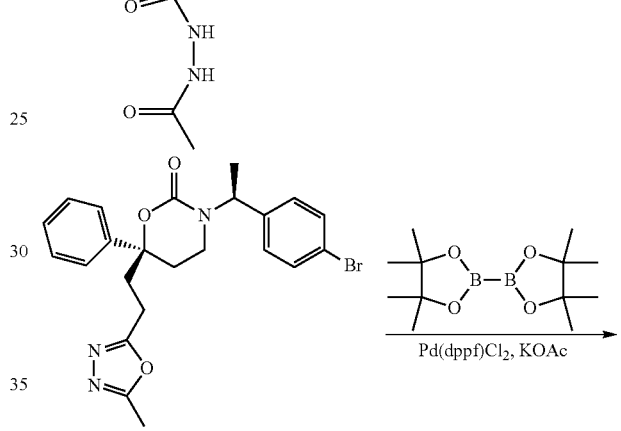

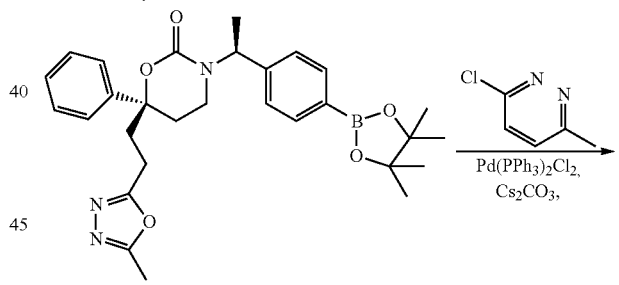

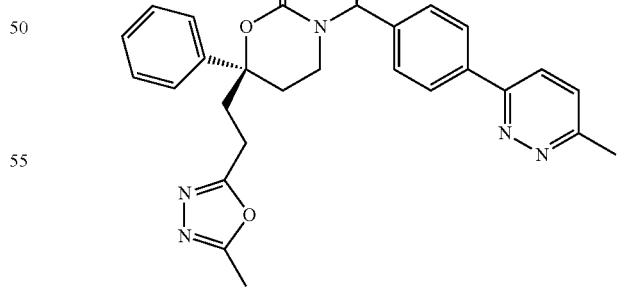

Step 1

To a solution of (R)-6-allyl-3-((S)-1-(4-bromophenyl)ethyl)-6-phenyl-1,3-oxazinan-2-one (11.37 g, 28.5 mmol) in tetrahydrofuran (250 mL) was added BH$_3$ THF (80 mL, 1 mol/L, 4 mmol) at 0° C. under nitrogen atmosphere. The mixture was stirred for 2 h, quenched by addition of water. NaOH solution (3 mol/L, 16 mL) and $H_2O_2$ (45 mL) were added to the above mixture. When reaction was over, the mixture was extracted with EtOAc. The combined organic layer was concentrated to give the crude product, which was purified by column chromatography to give (R)-3-((S)-1-(4-bromophenyl)ethyl)-6-(3-hydroxypropyl)-6-phenyl-1,3-oxazinan-2-one (4.32 g, 36.4%). $^1$H NMR: (400 MHz, $CDCl_3$): δ1.48 (t, 3H), 1.53 (m, 1H), 1.73 (m, 1H), 1.93-1.98 (m, 2H), 2.17-2.28 (m, 3H), 3.57 (t, 2H), 5.59 (m, 1H), 6.72 (m, 2H), 7.20 (m, 2H), 7.25-7.37 (m, 5H).

Step 2

(R)-3-(S-1-(4-bromophenyl)-ethyl)-6-(3-hydroxypropyl)-6-phenyl-1,3-oxazinan-2-one (500 mg, 1.2 mmol) was dissolved in 20 mL of acetone, and cooled in an ice bath. The mixture was added Jones reagent (0.7 mL, 1.8 mmol) slowly, and stirred for 1 h. Solvents were removed in vacuum, and the residue was dissolved in a mixture of dichloromethane (30 mL) and water (30 mL). The aqueous layer was extracted with dichloromethane. The combined organic layers were washed with brine, dried over $Na_2SO_4$, and concentrated to give the crude product, which was purified by preparative TLC to give the 3-((R)-3-((S)-1-(4-bromophenyl)ethyl)-2-oxo-6-phenyl-1,3-oxazinan-6-yl)propanoic acid (300 mg, 60%).

Step 3

To a solution of 3-((R)-3-((S)-1-(4-bromophenyl)ethyl)-2-oxo-6-phenyl-1,3-oxazinan-6-yl)propanoic acid (1 g, 2.23 mmol) in $CH_2Cl_2$ (10 mL) was added $SOCl_2$ (1.37 g, 11.5 mmol) at 0° C. The mixture was heated to reflux for 2 h. The solvent was removed to afford 3-(R-3-(S-1-(4-bromophenyl)ethyl)-2-oxo-6-phenyl-1,3-oxazinan-6-yl)-propanoyl chloride (0.85 g, 82%).

To a mixture of 3-(R-3-(S-1-(4-bromophenyl)ethyl)-2-oxo-6-phenyl-1,3-oxazinan-6-yl)-propanoyl chloride (0.85 g, 1.9 mmol) and acetohydrazide (0.74 g, 10 mmol) in $CH_2Cl_2$ (5 mL) was added $Et_3N$ (1.01 g, 10 mmol) at 0° C. The mixture was stirred at 0° C. for 1 h and washed with satd aq $NaHCO_3$. The organic layer was dried over $Na_2SO_4$ and concentrated to afford N'-acetyl-3-((R)-3-((S)-1-(4-bromophenyl)ethyl)-2-oxo-6-phenyl-1,3-oxazinan-6-yl)propanehydrazide (0.9 g, 97%).

Step 4

To a solution of N'-acetyl-3-((R)-3-((S)-1-(4-bromophenyl)ethyl)-2-oxo-6-phenyl-1,3-oxazinan-6-yl)propanehydrazide (0.1 g, 0.21 mmol) in THF (2 mL) was added Burgess Reagent (75 mg, 0.315 mmol). The sealed vial was irradiated in the microwave at 100° C. for 15 min. The mixture was extracted with EtOAc (3×30 mL). The combined organic layer was washed with brine (50 mL), dried over $Na_2SO_4$, filtered, and concentrated. The residue was purified by preparative TLC to afford (R)-3-((S)-1-(4-bromophenyl)ethyl)-6-(2-(5-methyl-1,3,4-oxadiazol-2-yl)ethyl)-6-phenyl-1,3-oxazinan-2-one (58 mg, yield: 59%). $^1$H NMR ($CDCl_3$): δ1.49-1.51 (m, 3H), 2.23-2.26 (m, 2H), 2.30-2.33 (m, 2H), 2.42 (s, 3H), 2.43-2.45 (m, 1H), 2.49-2.54 (m, 1H), 2.87-2.91 (m, 1H), 3.06-3.09 (m, 1H), 5.61-5.63 (m, 1H), 6.76-6.78 (d, 2H), 7.20-7.22 (m, 2H), 7.26-7.33 (m, 2H), 7.35-7.37 (m, 3H).

Step 5

To a solution of (R)-3-((S)-1-(4-bromophenyl)ethyl)-6-(2-(5-methyl-1,3,4-oxadiazol-2-yl)ethyl)-6-phenyl-1,3-oxazinan-2-one (490 mg, 1.04 mmol), and 4,4,4',4',5,5,5',5'-octamethyl-2,2'-bi(1,3,2-dioxaborolane) (424 mg, 1.67 mmol) in dry DMSO (20 mL) was added KOAc (326 mg, 3.33 mmol) and Pd(dppf)$Cl_2$ (25.3 mg, 0.031 mmol) under $N_2$ atmosphere. The mixture was warmed at 100° C. for 3 h. After TLC showed the starting material had disappeared, the solid was filtered off, water (50 mL) and EtOAc (50 mL) were added, and the mixture was extracted with EtOAc (3×50 mL). The combined organic layer was washed with brine (50 mL), dried over $Na_2SO_4$, filtered, and concentrated. The residue was purified by prep TLC to afford (R)-6-(2-(5-methyl-1,3,4-oxadiazol-2-yl)ethyl)-6-phenyl-3-((S)-1-(4-(4,4,5,5-tetramethyl-1,3,2-dioxaborolan-2-yl)phenyl)ethyl)-1,3-oxazinan-2-one (0.395 g, yield: 73.6%).

Step 6

(R)-6-(2-(5-methyl-1,3,4-oxadiazol-2-yl)ethyl)-6-phenyl-3-((S)-1-(4-(4,4,5,5-tetramethyl-1,3,2-dioxaborolan-2-yl)phenyl)ethyl)-1,3-oxazinan-2-one and 3-chloro-6-methylpyridazine were reacted following a procedure analogous to that described in Example 1 Step 2 to afford (R)-6-(2-(5-methyl-1,3,4-oxadiazol-2-yl)ethyl)-3-((S)-1-(4-(6-methylpyridazin-3-yl)phenyl)ethyl)-6-phenyl-1,3-oxazinan-2-one. LC-MS Method 2 $t_R$=0.984 min, m/z=499.1; $^1$H NMR ($CD_3OD$) 1.50 (m, 3H), 2.25 (m, 2H), 2.42 (m, 1H), 2.35 (s, 3H), 2.38 (m, 1H), 2.42 (m, 1H), 2.49-2.55 (m, 1H), 2.65 (s, 3H), 2.90 (m, 1H), 3.05 (m, 1H), 5.52 (m, 1H), 7.07 (m, 2H), 7.25 (m, 3H), 7.32 (m, 2H), 7.69-7.76 (m, 3H), 8.06 (m, 1H)

EXAMPLE 13

(S)-3-((S)-1-(4-(5-fluoropyrimidin-2-yl)phenyl)ethyl)-6-(2-hydroxy-2-methylpropyl)-6-phenyl-1,3-oxazinan-2-one

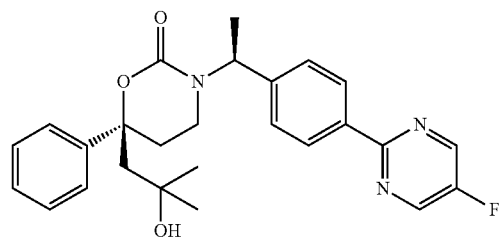

The title compound was prepared from (S)-6-(2-hydroxy-2-methylpropyl)-6-phenyl-3-((S)-1-(4-(4,4,5,5-tetramethyl-1,3,2-dioxaborolan-2-yl)phenyl)-ethyl)-1,3-oxazinan-2-one and 2-chloro-5-fluoropyrimidine a procedure analogous to that described in Example 1 Step 2. LC-MS Method 2 $t_R$=1.327 min, m/z=391.9; $^1$H NMR ($CDCl_3$) 1.11 (s, 3H), 1.18 (s, 3H), 1.52 (d, 3H), 2.20 (m, 4H), 2.38 (m, 1H), 2.85 (m, 1H), 5.72 (m, 1H), 7.08 (m, 2H), 7.20-7.40 (m, 5H), 8.12 (m, 2H), 8.61 (m, 2H)

EXAMPLE 14

(S)-3-((S)-1-(4-(2-(1H-imidazol-1-yl)pyrimidin-5-yl)phenyl)ethyl)-6-(2-hydroxy-2-methylpropyl)-6-phenyl-1,3-oxazinan-2-one

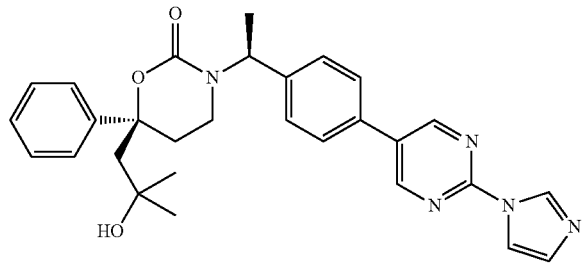 [SMILES: C[C@@H](c1ccc(-c2cnc(-n3ccnc3)nc2)cc1)N1CC[C@](CC(C)(C)O)(c2ccccc2)OC1=O]

A microwave vial equipped with a flea stir bar was charged with (S)-6-(2-hydroxy-2-methylpropyl)-6-phenyl-3-((S)-1-(4-(4,4,5,5-tetramethyl-1,3,2-dioxaborolan-2-yl)phenyl)-ethyl)-1,3-oxazinan-2-one (20 mg, 0.042 mmol), 5-bromo-2-(1H-imidazol-1-yl)pyrimidine (19 mg, 0.083 mmol), $Cs_2CO_3$ (27 mg, 0.083 mmol), water (0.1 mL) and dioxane (1 mL). The mixture was sparge with $N_2$ for 10 min and $PdCl_2$(dppf) (2 mg, 0.003 mmol) was added. The mixture was sparged with $N_2$ for 10 min and heated at 110° C. for 10 min in the microwave. The mixture was diluted with MeOH (1 mL), filtered and the filtrate was purified directly by prep HPLC to afford the title compound (12.1 mg, 58%) as an oil. LC-MS Method 1 $t_R$=1.27 min, m/z=498; $^1$H NMR ($CD_3OD$) 0.96 (s, 3H), 1.27 (s, 3H), 1.58 (d, 3H), 2.17 (s, 2H), 2.26 (m, 1H), 2.50 (2H), 3.12 (m, 1H), 5.60 (q, 1H), 7.18 (d, 2H), 7.25-7.40 (5H), 7.58 (d, 2H), 7.77 (s, 1H), 8.47 (s, 1H), 9.12 (s, 2H), 9.88 (s, 1H)

EXAMPLE 15

N-cyclopropyl-5-(4-((S)-1-((S)-6-(2-hydroxy-2-methylpropyl)-2-oxo-6-phenyl-1,3-oxazinan-3-yl)ethyl)phenyl)pyrimidine-2-carboxamide

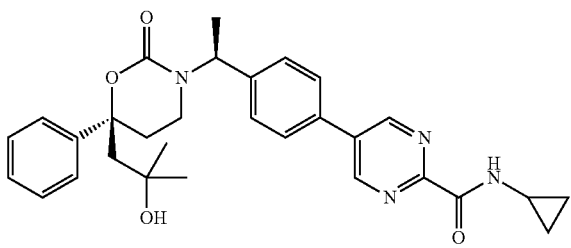 [SMILES: C[C@@H](c1ccc(-c2cnc(C(=O)NC3CC3)nc2)cc1)N1CC[C@](CC(C)(C)O)(c2ccccc2)OC1=O]

The title compound was prepared from (S)-6-(2-hydroxy-2-methylpropyl)-6-phenyl-3-((S)-1-(4-(4,4,5,5-tetramethyl-1,3,2-dioxaborolan-2-yl)phenyl)-ethyl)-1,3-oxazinan-2-one and 5-bromo-N-cyclopropylpyrimidine-2-carboxamide following a procedure analogous to that described in Example 1 Step 2. LC-MS Method 2 $t_R$=1.167 min, m/z=515.2; $^1$H NMR ($CDCl_3$) 0.65 (m, 2H), 0.87 (m, 2H), 1.09 (m, 6H), 1.51 (m, 3H), 2.26 (m, 2H), 2.31 (m, 2H), 2.43 (m, 3H), 2.83 (m, 1H), 2.98 (m, 1H), 5.67 (m, 1H), 7.06 (m, 1H), 7.25 (m, 7H), 8.02 (m, 1H), 8.89 (m, 2H)

EXAMPLE 16

5-(4-((S)-1-((R)-6-(2-cyano-2-methylpropyl)-2-oxo-6-phenyl-1,3-oxazinan-3-yl)ethyl)phenyl)-N-cyclopropylpyrimidine-2-carboxamide

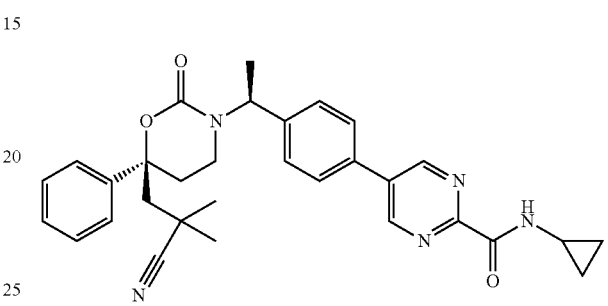

The title compound was prepared from 2,2-dimethyl-3-((R)-2-oxo-6-phenyl-3-((S)-1-(4-(4,4,5,5-tetramethyl-1,3,2-dioxaborolan-2-yl)phenyl)ethyl)-1,3-oxazinan-6-yl)propanenitrile and 5-bromo-N-cyclopropylpyrimidine-2-carboxamide following a procedure analogous to that described in Example 1 Step 2. LC-MS Method 2 $t_R$=1.237 min, m/z=524.3; $^1$H NMR ($CDCl_3$) 0.62 (m, 2H), 0.83 (m, 2H), 1.32 (s, 3H), 1.44 (s, 3H), 1.49 (d, 3H), 2.08 (m, 2H), 2.24 (m, 1H), 2.42 (m, 2H), 2.90 (m, 2H), 5.61 (m, 1H), 6.93 (m, 2H), 7.20-7.36 (m, 7H), 8.00 (s, 1H), 8.88 (s, 2H).

EXAMPLE 17

N-tert-butyl-5-(4-((S)-1-((S)-6-(2-hydroxy-2-methylpropyl)-2-oxo-6-phenyl-1,3-oxazinan-3-yl)ethyl)phenyl)pyrimidine-2-carboxamide

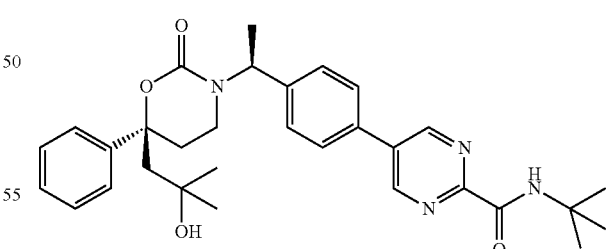

The title compound was prepared from (S)-6-(2-hydroxy-2-methylpropyl)-6-phenyl-3-((S)-1-(4-(4,4,5,5-tetramethyl-1,3,2-dioxaborolan-2-yl)phenyl)-ethyl)-1,3-oxazinan-2-one and 5-bromo-N-tert-butylpyrimidine-2-carboxamide following a procedure analogous to that described in Example 1 Step 2. LC-MS Method 2 $t_R$=1.287 min, m/z=531.3; $^1$H NMR ($CDCl_3$) 1.11 (s, 3H), 1.18 (s, 3H), 1.49 (s, 9H), 1.54 (m, 3H), 2.04 (s, 1H), 2.11 (m, 2H), 2.21 (m, 2H), 2.34 (m, 1H), 2.78

(m, 1H), 5.67 (m, 1H), 7.06 (m, 2H), 7.19 (m, 1H), 7.25 (m, 6H), 7.84 (s, 1H), 8.85 (s, 2H).

EXAMPLE 18

(R)-6-(2-(5-methyl-1,3,4-oxadiazol-2-yl)ethyl)-3-((S)-1-(4-(2-methylpyrimidin-5-yl)phenyl)ethyl)-6-phenyl-1,3-oxazinan-2-one

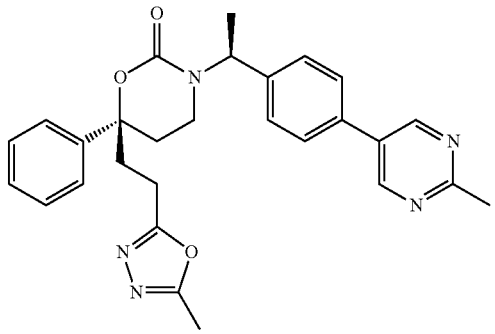 [SMILES: Cc1ncc(-c2ccc([C@H](C)N3CC[C@](CCc4nnc(C)o4)(c4ccccc4)OC3=O)cc2)cn1]

The title compound was prepared from (R)-6-(2-(5-methyl-1,3,4-oxadiazol-2-yl)ethyl)-6-phenyl-3-((S)-1-(4-(4,4,5,5-tetramethyl-1,3,2-dioxaborolan-2-yl)phenyl)ethyl)-1,3-oxazinan-2-one and 5-bromo-2-methylpyrimidine following a procedure analogous to that described in Example 1 Step 2. LC-MS Method 2 $t_R$=1.035 min, m/z=484.1; $^1$H NMR (CD$_3$OD) 1.57 (m, 3H), 2.29 (m, 2H), 2.38 (m, 1H), 2.41 (s, 3H), 2.47 (m, 1H), 2.50 (m, 1H), 2.63 (m, 1H), 2.72 (s, 3H), 2.96 (m, 1H), 3.15 (m, 1H), 5.58 (m, 1H), 7.12 (m, 2H), 7.33 (m, 3H), 7.38 (m, 2H), 7.47 (m, 2H), 8.88 (s, 2H).

EXAMPLE 19

N-cyclopropyl-2-(4-((S)-1-((S)-6-(2-hydroxy-2-methylpropyl)-2-oxo-6-phenyl-1,3-oxazinan-3-yl)ethyl)phenyl)thiazole-4-carboxamide

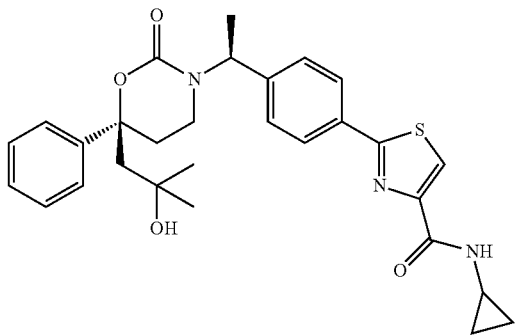 [SMILES: C[C@@H](c1ccc(-c2nc(C(=O)NC3CC3)cs2)cc1)N1CC[C@](CC(C)(C)O)(c2ccccc2)OC1=O]

The title compound was prepared from (S)-6-(2-hydroxy-2-methylpropyl)-6-phenyl-3-((S)-1-(4-(4,4,5,5-tetramethyl-1,3,2-dioxaborolan-2-yl)phenyl)ethyl)-1,3-oxazinan-2-one and 2-bromo-N-cyclopropylthiazole-4-carboxamide following a procedure analogous to that described in Example 1 Step 2. LC-MS Method 2 $t_R$=1.252 min, m/z=542.1; $^1$H NMR (CDCl$_3$) 0.61 (m, 2H), 0.81 (m, 2H), 1.04 (s, 3H), 1.12 (s, 3H), 1.49 (d, 3H), 2.06-2.24 (m, 5H), 2.29-2.40 (m, 1H), 2.71-2.89 (m, 2H), 5.62 (m, 1H), 6.94-7.01 (m, 2H), 7.19-7.31 (m, 5H), 7.35 (s, 1H), 7.61 (m, 2H), 8.01 (s, 1H).

EXAMPLE 20

N-cyclopropyl-2-(4-((S)-1-((S)-6-(2-hydroxy-2-methylpropyl)-2-oxo-6-phenyl-1,3-oxazinan-3-yl)ethyl)phenyl)thiazole-5-carboxamide

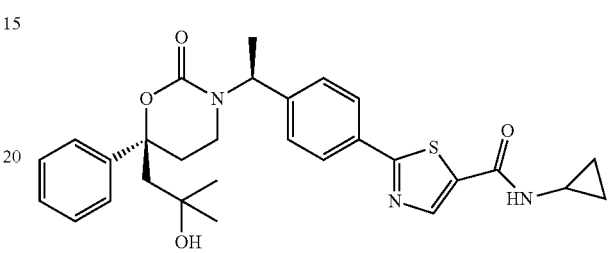

The title compound was prepared from (S)-6-(2-hydroxy-2-methylpropyl)-6-phenyl-3-((S)-1-(4-(4,4,5,5-tetramethyl-1,3,2-dioxaborolan-2-yl)phenyl)ethyl)-1,3-oxazinan-2-one and 2-bromo-N-cyclopropylthiazole-5-carboxamide following a procedure analogous to that described in Example 1 Step 2. LC-MS Method 2 $t_R$=1.219 min, m/z=462.1; $^1$H NMR (CDCl$_3$) 0.51 (m, 2H), 0.81 (m, 2H), 1.04 (s, 3H), 1.12 (s, 3H), 1.47 (d, 3H), 2.06-2.24 (m, 5H), 2.29-2.40 (m, 1H), 2.71-2.89 (m, 2H), 5.62 (m, 1H), 6.09 (s, 1H), 6.94 (m, 2H), 7.21-7.39 (m, 5H), 7.61 (m, 2H), 8.01 (s, 1H)

EXAMPLE 21

2-(4-((S)-1-((R)-6-(2-cyano-2-methylpropyl)-2-oxo-6-phenyl-1,3-oxazinan-3-yl)ethyl)phenyl)-N-cyclopropylthiazole-5-carboxamide

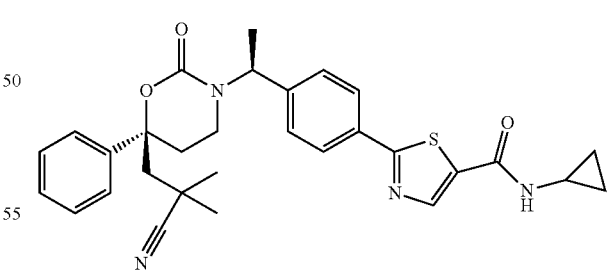

The title compound was prepared from 2,2-dimethyl-3-((R)-2-oxo-6-phenyl-3-((S)-1-(4-(4,4,5,5-tetramethyl-1,3,2-dioxaborolan-2-yl)phenyl)ethyl)-1,3-oxazinan-6-yl)propanenitrile and 2-bromo-N-cyclopropylthiazole-5-carboxamide following a procedure analogous to that described in Example 1 Step 2. LC-MS Method 2 $t_R$=1.262 min, m/z=529.3; $^1$H NMR (CDCl$_3$) 0.63 (m, 2H), 0.86 (m, 2H), 1.30 (s, 3H), 1.43 (s, 3H), 1.52 (d, 3H), 2.02 (s, 2H), 2.29

(m, 1H), 2.81-2.99 (m, 2H), 5.62 (m, 1H), 6.50 (s, 1H), 6.89 (d, 2H), 7.37 (m, 5H), 7.60 (m, 2H), 8.14 (s, 1H)

EXAMPLE 22

N-tert-butyl-2-(4-((S)-1-((S)-6-(2-hydroxy-2-methyl-propyl)-2-oxo-6-phenyl-1,3-oxazinan-3-yl)ethyl)phenyl)thiazole-4-carboxamide

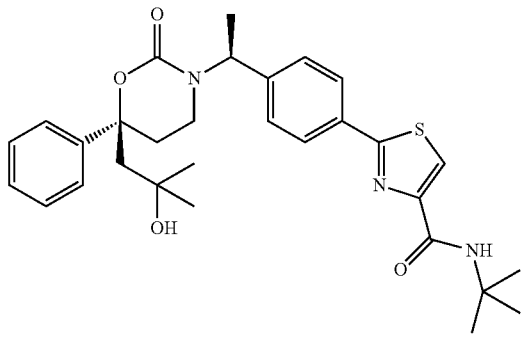 [SMILES: C[C@@H](c1ccc(-c2nc(C(=O)NC(C)(C)C)cs2)cc1)N1CC[C@](CC(C)(C)O)(c2ccccc2)OC1=O]

The title compound was prepared from (S)-6-(2-hydroxy-2-methylpropyl)-6-phenyl-3-((S)-1-(4-(4,4,5,5-tetramethyl-1,3,2-dioxaborolan-2-yl)phenyl)ethyl)-1,3-oxazinan-2-one and 2-bromo-N-tert-butylthiazole-4-carboxamide following a procedure analogous to that described in Example 1 Step 2. LC-MS Method 2 $t_R$=1.315 min, m/z=478.3; $^1$H NMR (CDCl$_3$) 1.18 (s, 3H), 1.36 (s, 3H), 1.49 (s, 9H), 2.11 (d, 3H), 2.14 (s, 4H), 2.33 (m, 1H), 2.80 (m, 1H), 5.64 (m, 1H), 7.19 (m, 2H), 7.28-7.39 (m, 5H), 7.60 (m, 2H), 7.94 (s, 1H)

EXAMPLE 23

N-tert-butyl-2-(4-((S)-1-((S)-6-(2-hydroxy-2-methyl-propyl)-2-oxo-6-phenyl-1,3-oxazinan-3-yl)ethyl)phenyl)thiazole-5-carboxamide

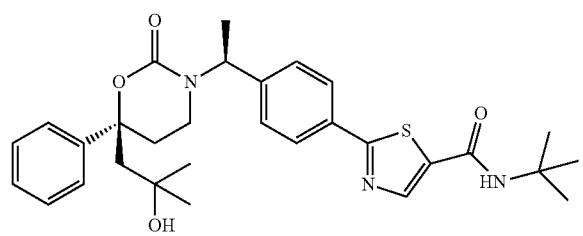 [SMILES: C[C@@H](c1ccc(-c2ncc(C(=O)NC(C)(C)C)s2)cc1)N1CC[C@](CC(C)(C)O)(c2ccccc2)OC1=O]

The title compound was prepared from (S)-6-(2-hydroxy-2-methylpropyl)-6-phenyl-3-((S)-1-(4-(4,4,5,5-tetramethyl-1,3,2-dioxaborolan-2-yl)phenyl)ethyl)-1,3-oxazinan-2-one and 2-bromo-N-tert-butylthiazole-5-carboxamide following a procedure analogous to that described in Example 1 Step 2. LC-MS Method 2 $t_R$=1.351 min, m/z=558.1; $^1$H NMR (CDCl$_3$) 1.13 (s, 3H), 1.16 (s, 3H), 1.49 (s, 9H), 1.51 (d, 3H), 2.15-2.32 (m, 5H), 2.41 (m, 1H), 2.89 (m, 1H), 3.72 (m, 1H), 5.70 (m, 1H), 5.78 (m, 1H), 7.02 (m, 2H), 7.34 (m, 5H), 7.70 (m, 2H), 8.08 (m, 1H)

EXAMPLE 24

N-tert-butyl-2-(4-((S)-1-((R)-6-(2-cyano-2-methyl-propyl)-2-oxo-6-phenyl-1,3-oxazinan-3-yl)ethyl)phenyl)thiazole-5-carboxamide

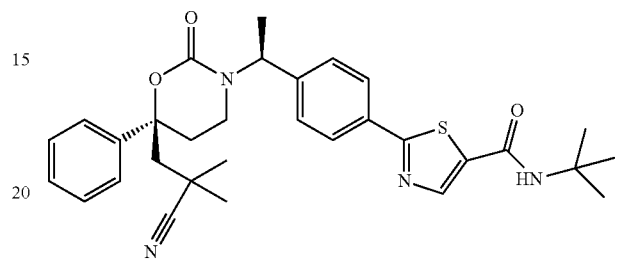

The title compound was prepared from 2,2-dimethyl-3-((R)-2-oxo-6-phenyl-3-((S)-1-(4-(4,4,5,5-tetramethyl-1,3,2-dioxaborolan-2-yl)phenyl)ethyl)-1,3-oxazinan-6-yl)propanenitrile and 2-bromo-N-tert-butylthiazole-5-carboxamide following a procedure analogous to that described in Example 1 Step 2. LC-MS Method 2 $t_R$=1.292 min, m/z=545.4; $^1$H NMR (CDCl$_3$) 1.25 (s, 3H), 1.40 (s, 3H), 1.49 (d, 3H), 2.11 (s, 2H), 2.26 (m, 1H), 2.42 (m, 2H), 2.88 (m, 1H), 5.61 (m, 1H), 5.73 (s, 1H), 6.85 (m, 2H), 7.31 (m, 5H), 7.60 (m, 2H), 8.00 (m, 1H).

EXAMPLE 25

N-tert-butyl-3-(4-((S)-1-((S)-6-(2-hydroxy-2-methyl-propyl)-2-oxo-6-phenyl-1,3-oxazinan-3-yl)ethyl)phenyl)-1-methyl-1H-pyrazole-5-carboxamide and N-tert-butyl-5-(4-((S)-1-((S)-6-(2-hydroxy-2-methyl-propyl)-2-oxo-6-phenyl-1,3-oxazinan-3-yl)ethyl)phenyl)-1-methyl-1H-pyrazole-3-carboxamide

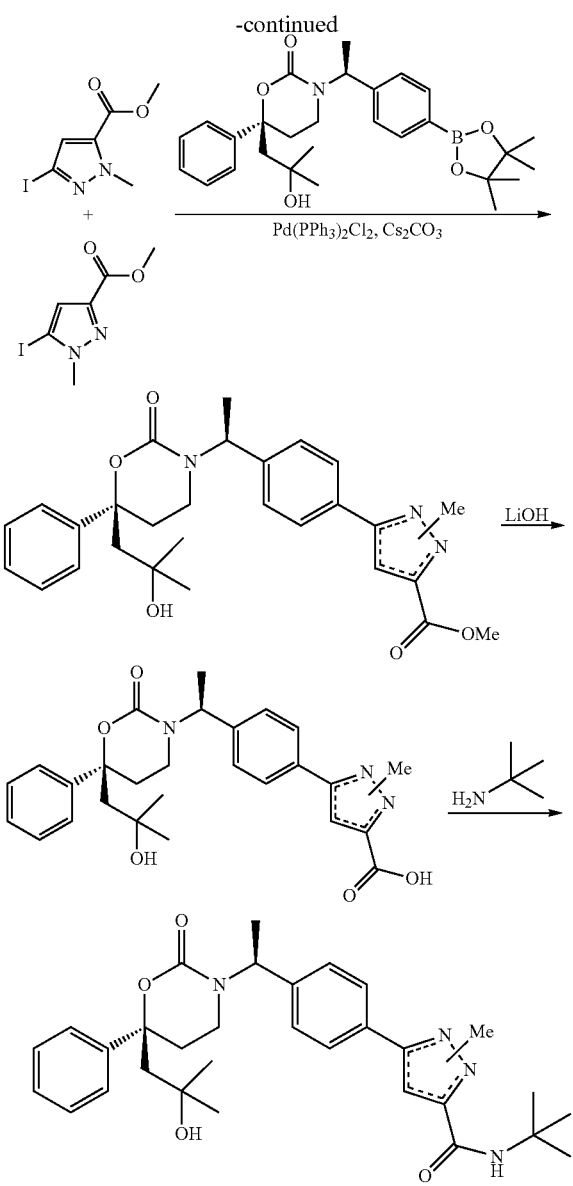

filtrate was concentrated to give 1-tert-butyl 5-ethyl 3-amino-1H-pyrazole-1,5-dicarboxylate (1.2 g, 37%), which was purified by preparative TLC. $^1$H NMR: δ 1.34 (m, 3H), 1.66 (s, 9H), 4.36 (m, 2H), 5.84 (s, 1H), Step 3

To a solution of t-butyl 5-ethyl 3-amino-1H-pyrazole-1,5-dicarboxylate (1.1 g, 3.0 mmol) in conc HCl solution (18 mL) was added a solution of $NaNO_2$ (414 mg, 6.0 mmol) in water (2 mL) over 3 min at 0° C. A solution of KI (1.26 g, 7.5 mmol) in water (3 mL) was added to the reaction mixture over 5 min, resulting in nitrogen evolution. The reaction mixture was stirred for 5 min. Water was added, the aqueous mixture was extracted with EA, washed with $NaS_2O_3$ (2×), dried over $Na_2SO_4$, and concentrated to give ethyl 3-iodo-1H-pyrazole-5-carboxylate (600 mg, 75%), which was purified by preparative TLC. $^1$H NMR: δ 1.31 (m, 3H), 4.32 (m, 2H), 6.90 (s, 1H).

Step 4

To a solution of ethyl 3-iodo-1H-pyrazole-5-carboxylate (600 mg, 2.56 mmol) and $K_2CO_3$ (609 mg, 4.51 mmol) in dry $CH_3CN$ (10 mL) was added MeI (974 mg, 6.77 mmol). The mixture was stirred at room temperature overnight under $N_2$. After TLC showed that starting material had disappeared, the solid was filtered. Solvent was removed and the residue was purified to give methyl 3-iodo-1-methyl-1H-pyrazole-5-carboxylate and methyl 5-iodo-1-methyl-1H-pyrazole-3-carboxylate.

Isomer 1: $^1$H NMR: δ 1.29 (m, 3H), 4.10 (s, 3H), 4.29 (m, 2H), 6.88 (s, 1H).
Isomer 2:

Step 5

To a solution of isomer 1 of the product from Step 4 (200 mg, 0.71 mmol) and (S)-6-(2-hydroxy-2-methylpropyl)-6-phenyl-3-((S)-1-(4-(4,4,5,5-tetramethyl-1,3,2-dioxaborolan-2-yl)phenyl)ethyl)-1,3-oxazinan-2-one (285 mg, 0.60 mmol) in dry dioxane (6 mL) was added $Cs_2CO_3$ (0.6 mL, 1.2 mmol) and $Pd(PPh_3)_2Cl_2$ (30 mg). After addition, the mixture was stirred at 110° C. for 2 h under nitrogen. After TLC showed the starting material had disappeared, the solid was filtered off. Water (20 mL) and EtOAc (20 mL) were added, the aqueous layer was extracted with EtOAc (3×10 mL). The combined organic layer was washed with brine, dried over $Na_2SO_4$, filtered, and concentrated to give methyl 3-(4-(S-1-(S-6-(2-hydroxy-2-methylpropyl)-2-oxo-6-phenyl-1,3-oxazinan-3-yl)-ethyl)-phenyl)-methyl-pyrazole-5-carboxylate isomer 1 (280 mg, 92%), which was purified by preparative TLC. $^1$H NMR ($CDCl_3$): δ1.09 (s, 3H), 1.18 (s, 3H), 1.36 (m, 3H), 1.50 (d, 3H), 2.19 (m, 6H), 2.34 (m, 1H), 2.80 (m, 1H), 4.19 (s, 3H), 4.33 (m, 2H), 5.66 (m, 1H), 7.31 (m, 6H), 7.52 (m, 3H).

Step 1

Sodium (23 g, 1 mol) was dissolved in a mixture of dry EtOH (250 mL) and dry $Et_2O$ (200 mL) under nitrogen. The mixture was cooled to 0° C. in an iced water bath. Diethyl oxalate (73 g, 0.5 mol) was dissolved in $Et_2O$ (25 mL) was added dropwise, the reaction mixture was stirred for 30 min, a solution of $CH_3CN$ (20.5 g, 0.5 mol) in $Et_2O$ (25 mL) was added, and the mixture was stirred for 1 h. The solid was collected by filtration to give sodium (Z)-1-cyano-3-ethoxy-3-oxoprop-1-en-2-olate (90 g) which was used without purification.

Step 2

To a suspension of sodium (Z)-1-cyano-3-ethoxy-3-oxoprop-1-en-2-olate (1.44 g, 8.78 mmol) in $CHCl_3$ (80 mL) was added HCl (5 mL) in ethyl ether. t-butyl hydrazinecarboxylate (1.16 g, 8.78 mmol) was added, the mixture was stirred for 24 h at rt, the precipitate was removed by filtration, and the Step 6

To a solution of methyl 3-(4-(S-1-(S-6-(2-hydroxy-2-methylpropyl)-2-oxo-6-phenyl-1,3-oxazinan-3-yl)-ethyl)-phenyl)-methyl-pyrazole-5-carboxylate isomer 1 (280 mg, 0.55 mmol) in dry MeOH (6 mL) was added LiOH (1.10 mmol) at 0° C. The mixture was stirred at rt overnight. After TLC showed the stating material had disappeared, MeOH was removed in vacuo. 1N aq HCl and EtOAc were added to adjust the pH=6~7, the aqueous layer was extracted with EtOAc (3×15 mL). The combined organic layer was washed with brine, dried over Na₂SO₄, filtered, and concentrated to give 3-(4-((S)-1-((S)-6-(2-hydroxy-2-methylpropyl)-2-oxo-6-phenyl-1,3-oxazinan-3-yl)-ethyl)-phenyl)-methyl-pyrazole-5-carboxylic acid isomer 1 (200 mg, 74%), which was purified by preparative TLC.

Step 7

A mixture of 3-(4-((S)-1-((S)-6-(2-hydroxy-2-methylpropyl)-2-oxo-6-phenyl-1,3-oxazinan-3-yl)-ethyl)-phenyl)-methyl-pyrazole-5-carboxylic acid isomer 1 (100 mg, 0.21 mmol), 2-methylpropan-2-amine (31 mg, 0.42 mmol), EDCl (83 mg, 0.42 mmol), HOBt (57 mg, 0.42 mmol), and DIEA (1 mL) in dry CH₂Cl₂ (6 mL) at 0° C. was stirred at it overnight under nitrogen. After TLC showed the starting material had disappeared, the solvent was removed in vacuo to give N-tert-butyl-3-(4-((S)-1-((S)-6-(2-hydroxy-2-methylpropyl)-2-oxo-6-phenyl-1,3-oxazinan-3-yl)ethyl)phenyl)-methyl-pyrazole-5-carboxamide isomer 1 (21 mg, 19%), which was purified by preparative HPLC. LC-MS Method 2 $t_R$=1.35 min, m/z=475.3; ¹H NMR (CDCl₃): δ 1.09 (s, 3H), 1.18 (s, 3H), 1.43 (s, 9H), 1.52 (d, 3H), 2.22 (m, 4H), 2.38 (m, 1H), 2.87 (m, 1H), 4.16 (s, 3H), 5.68 (m, 1H), 5.82 (s, 1H), 6.60 (s, 1H), 6.99 (d, 2H), 7.27-7.40 (m, 5H), 7.50 (d, 2H).

N-tert-butyl-3-(4-((S)-1-((S)-6-(2-hydroxy-2-methylpropyl)-2-oxo-6-phenyl-1,3-oxazinan-3-yl)ethyl)phenyl)-methyl-pyrazole-5-carboxamide isomer 2 was prepared from isomer 2 of the product of Step 4 following procedures analogous to those described in Step 5-7. LC-MS Method 2 $t_R$=1.335 min, m/z=475.3; 1H NMR (CDCl3) 1.12 (s, 3H), 1.19 (s, 3H), 1.48 (s, 9H), 1.54 (d, 3H), 2.12 (m, 1H), 2.18-2.39 (m, 4H), 2.53 (m, 1H), 2.91 (m, 1H), 3.80 (s, 3H), 5.71 (m, 1H), 6.70 (s, 1H), 6.76 (m, 1H), 7.02 (d, 2H), 7.13 (m, 2H), 7.30 (m, 1H), 7.34 (m, 4H)

EXAMPLE 26

(S)-3-((S)-1-(4-(2-(2,4-dimethyl-1H-imidazol-1-yl)pyrimidin-5-yl)phenyl)ethyl)-6-(2-hydroxy-2-methylpropyl)-6-phenyl-1,3-oxazinan-2-one

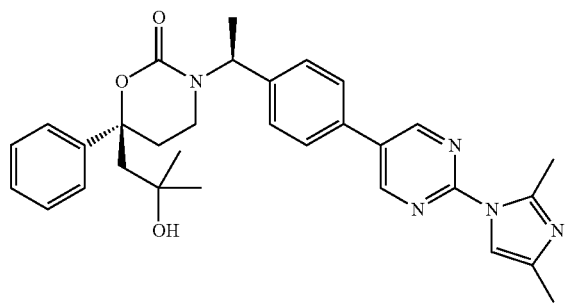 [SMILES: Cc1cn(-c2ncc(-c3ccc([C@H](C)N4CC[C@](CC(C)(C)O)(c5ccccc5)OC4=O)cc3)cn2)c(C)n1]

The title compound was prepared from (S)-6-(2-hydroxy-2-methylpropyl)-6-phenyl-3-((S)-1-(4-(4,4,5,5-tetramethyl-1,3,2-dioxaborolan-2-yl)phenyl)ethyl)-1,3-oxazinan-2-one and 5-bromo-2-(2,4-dimethyl-1H-imidazol-1-yl)-pyrimidine following a procedure analogous to that described in Example 1 Step 2. LC-MS Method 2 $t_R$=0.962 min, m/z=526.3; ¹H NMR (CD₃OD) 0.86 (s, 3H), 1.16 (s, 3H), 1.49 (m, 3H), 2.06 (m, 2H), 2.12 (m, 1H), 2.20 (s, 3H), 2.35-2.48 (m, 2H), 2.82 (s, 3H), 3.03 (m, 1H), 5.53 (m, 1H), 7.07 (m, 2H), 7.19-7.32 (m, 6H), 7.45 (m, 2H), 7.80 (m, 1H), 8.96 (s, 2H).

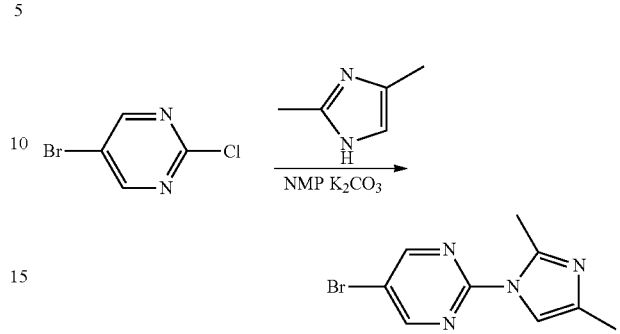

To a solution of 5-bromo-2-chloropyrimidine (0.3 g, 1.55 mmol) in NMP (15 mL) were added 2,4-dimethyl-1H-imidazole (0.224 g, 2.2 mmol) and K₂CO₃ (0.43 g, 3.1 mmol). The resulting solution was stirred at 80° C. overnight. After water (50 mL) and EtOAc (50 mL) were added, the mixture was extracted with EtOAc (3×50 mL). The combined organic layer was washed with brine (50 mL), dried over Na₂SO₄, filtered, and concentrated. The residue was purified by pre-TLC to afford 5-bromo-2-(2,4-dimethyl-1H-imidazol-1-yl)-pyrimidine (0.2 g, 51%).

EXAMPLE 27

(S)-6-(2-hydroxy-2-methylpropyl)-3-((S)-1-(4-(2-(2-methyl-1H-imidazol-1-yl)pyrimidin-5-yl)phenyl)ethyl)-6-phenyl-1,3-oxazinan-2-one

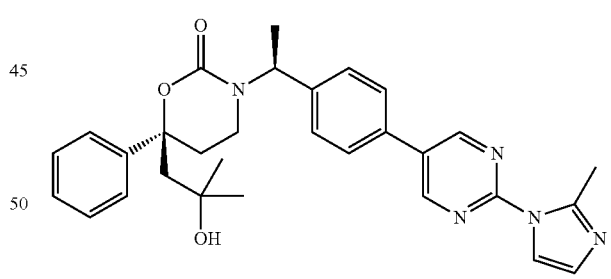

The title compound was prepared from (S)-6-(2-hydroxy-2-methylpropyl)-6-phenyl-3-((S)-1-(4-(4,4,5,5-tetramethyl-1,3,2-dioxaborolan-2-yl)phenyl)ethyl)-1,3-oxazinan-2-one and 5-bromo-2-(2-methyl-1H-imidazol-1-yl)-pyrimidine following a procedure analogous to that described in Example 1 Step 2. LC-MS Method 2 $t_R$=0.932 min, m/z=512.3; ¹H NMR (CD₃OD) 0.86 (s, 3H), 1.16 (s, 3H), 1.49 (m, 3H), 2.15 (m, 2H), 2.18 (m, 1H), 2.37-2.49 (m, 2H), 2.79 (s, 3H), 3.03 (m, 1H), 5.53 (m, 1H), 7.01-7.06 (m, 3H), 7.21-7.29 (m, 5H), 7.44 (m, 2H), 7.97 (m, 1H), 8.95 (s, 2H).

5-bromo-2-(2-methyl-1H-imidazol-1-yl)-pyrimidine was prepared 5-bromo-2-chloropyrimidine and 2-methylimidazole following a procedure analogous to that described for 5-bromo-2-(2,4-dimethyl-1H-imidazol-1-yl)-pyrimidine in Example 26.

EXAMPLE 28

(S)-3-((S)-1-(4-(6-(cyclopentyloxy)pyridin-2-yl)phenyl)ethyl)-6-(2-hydroxy-2-methylpropyl)-6-phenyl-1,3-oxazinan-2-one

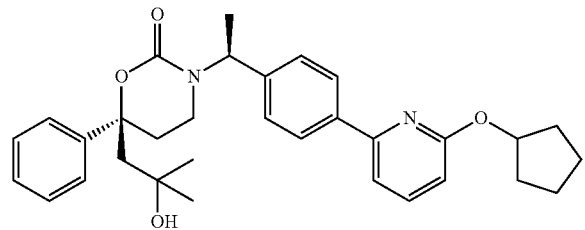 [SMILES: C[C@@H](c1ccc(-c2cccc(OC3CCCC3)n2)cc1)N1CC[C@](CC(C)(C)O)(c2ccccc2)OC1=O]

The title compound was prepared from (S)-3-((S)-1-(4-bromophenyl)ethyl)-6-(2-hydroxy-2-methylpropyl)-6-phenyl-1,3-oxazinan-2-one and 2-(cyclopentyloxy)-6-(4,4,5,5-tetramethyl-1,3,2-dioxaborolan-2-yl)pyridine following a procedure analogous to that described in Example 14. LC-MS Method 1 $t_R$=2.23 min, m/z=515, 457; $^1$H NMR (CD$_3$OD) 0.96 (s, 3H), 1.27 (s, 3H), 1.56 (d, 3H), 1.70 (2H), 1.85 (4H), 2.05 (2H), 2.17 (s, 2H), 2.24 (m, 1H), 2.46 (2H), 3.05 (m, 1H), 5.47 (m, 1H), 5.58 (q, 1H), 6.70 (d, 1H), 7.00 (d, 2H), 7.25-7.40 (6H), 7.70 (t, 1H), 7.77 (d, 2H).

EXAMPLE 29

(S)-6-(2-hydroxy-2-methylpropyl)-3-((S)-1-(4-(5-(2-hydroxypropan-2-yl)pyrimidin-2-yl)phenyl)ethyl)-6-phenyl-1,3-oxazinan-2-one

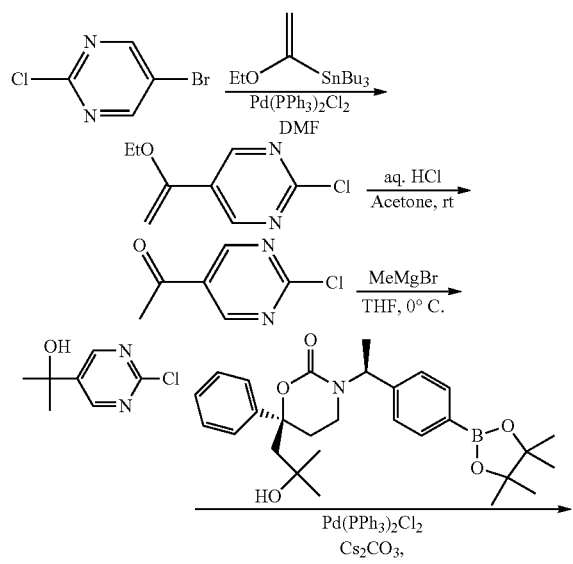

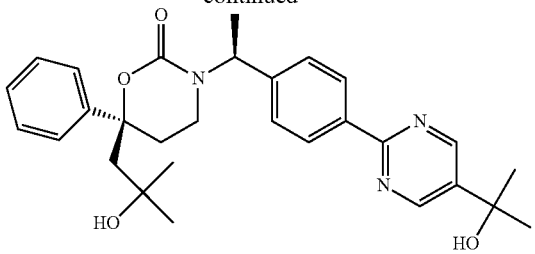

Step 1

To a solution of 5-bromo-2-chloropyrimidine (600 mg, 3.13 mmol) in dry DMF (10 mL) under N$_2$ were added tributyl(1-ethoxyvinyl)stannane (1.09 mL, 3.23 mmol) and Pd(PPh$_3$)$_2$Cl$_2$ (113 mg, 0.161 mmol). The mixture was stirred at 100° C. for 3 h and at rt for 16 h. The mixture was diluted with ether (20 mL), and treated with aqueous KF solution (5 g of KF in 3 mL of water). The mixture was stirred vigorously for 1 h at room temperature before being filtered through diatomaceous earth. The filtrate was washed with satd aq NaHCO$_3$ and brine. The aqueous phase was extracted with EtOAc. The combined organic layer was dried over anhydrous Na$_2$SO$_4$ and concentrated to give 2-chloro-5-(1-ethoxyvinyl)pyrimidine (350 mg, yield 61%).

Step 2

To a solution of 2-chloro-5-(1-ethoxyvinyl)pyrimidine (350 mg, 1.9 mmol) in THF (15 mL) was, added aqueous HCl (1N, 15 mL). The mixture was stirred at rt for 4 h, extracted with EtOAc. The organic phase was washed with satd aq NaHCO$_3$ and brine. The combined organic layer was dried over anhydrous Na$_2$SO$_4$ and concentrated to give the crude product, which was purified by prep TLC (PE:EA 3:1) to give 1-(2-chloropyrimidin-5-yl)ethanone (268 mg, yield 90%).

Step 3

To a solution of 1-(2-chloropyrimidin-5-yl)ethanone (268 mg, 1.7 mmol) in THF (20 mL) was added MeMgBr (2.68 mL, 8.04 mmol) at −78° C. under nitrogen. The solution was stirred at −78° C. for 20 min, quenched with satd aq NH$_4$Cl, and extracted with EtOAc. The combined organic layer was dried over anhydrous Na$_2$SO$_4$ and concentrated to give an oil, which was purified by prep TLC (PE:EA 3:1) to give 2-(2-chloropyrimidin-5-yl)propan-2-ol (150 mg, yield 51%).

Step 4

To a solution of 2-(2-chloropyrimidin-5-yl)propan-2-ol (30 mg, 0.17 mmol) in DME (6 mL) was added Pd(PPh$_3$)$_4$ (10 mg, 0.01 mmol) under nitrogen. The mixture was stirred at room temperature for 1 hour. (S)-6-(2-hydroxy-2-methylpropyl)-6-phenyl-3-((S)-1-(4-(4,4,5,5-tetramethyl-1,3,2-dioxaborolan-2-yl)phenyl)ethyl)-1,3-oxazinan-2-one (60 mg, 0.125 mmol) in EtOH (2 mL) was added, followed by addition of satd aq NaHCO$_3$ (2 mL). The mixture was stirred at 100° C. for 2 h. The reaction was quenched with water, and extracted with EtOAc. The combined organic layer was dried over anhydrous Na$_2$SO$_4$ and concentrated to give (S)-6-(2-hydroxy-2-methylpropyl)-3-((S)-1-(4-(5-(2-hydroxypropan-2-yl)pyrimidin-2-yl)phenyl)ethyl)-6-phenyl-1,3-oxazinan-2-one (21 mg, yield 25%). LC-MS Method 2 $t_R$=0.98 min, m/z=512, 490, 472, 432; ¹H NMR (CD₃OD): δ 1.02 (s, 3H), 1.13 (s, 3H), 1.50 (d, 3H), 1.61 (s, 6H), 2.02 (s, 1H), 2.18 (m, 5H), 2.30 (m, 1H), 2.75 (m, 1H), 5.66 (m, 1H), 7.00 (m, 2H), 7.20-7.33 (m, 5H), 8.10 (m, 2H), 8.92 (s, 2H).

EXAMPLE 30

(S)-3-((S)-1-(4-(6-(dimethylamino)pyridin-2-yl)phenyl)ethyl)-6-(2-hydroxy-2-methylpropyl)-6-phenyl-1,3-oxazinan-2-one

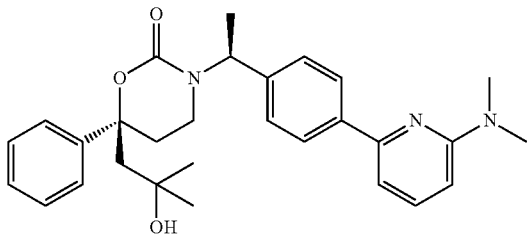 [SMILES: C[C@@H](c1ccc(-c2cccc(N(C)C)n2)cc1)N1CC[C@](CC(C)(C)O)(c2ccccc2)OC1=O]

The title compound was prepared from (S)-6-(2-hydroxy-2-methylpropyl)-6-phenyl-3-((S)-1-(4-(4,4,5,5-tetramethyl-1,3,2-dioxaborolan-2-yl)phenyl)ethyl)-1,3-oxazinan-2-one and 2-bromo-6-(dimethylamino)pyridine following a procedure analogous to that described in Example 14. LC-MS Method 1 t_R=1.39 min, m/z=474; ¹H NMR (CD₃OD) 0.96 (s, 3H), 1.26 (s, 3H), 1.58 (d, 3H), 2.18 (s, 2H), 2.28 (m, 1H), 2.50 (2H), 3.12 (m, 1H), 3.34 (s, 6H), 5.59 (q, 1H), 6.99 (d, 1H), 7.18 (3H), 7.25-7.40 (5H), 7.57 (d, 2H), 7.98 (m, 1H).

EXAMPLE 31

(S)-6-(2-hydroxy-2-methylpropyl)-3-((S)-1-(4-(2-(2-hydroxypropan-2-yl)pyrimidin-5-yl)phenyl)ethyl)-6-phenyl-1,3-oxazinan-2-one

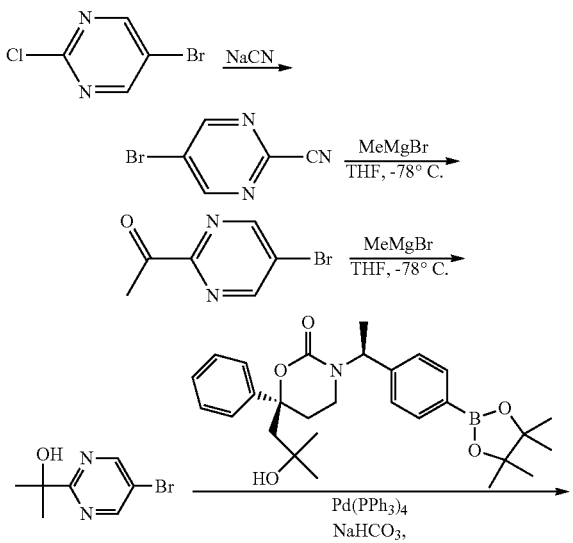

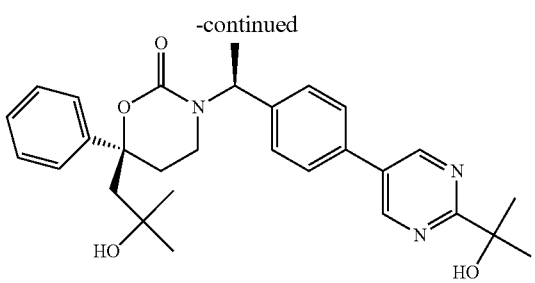

Step 1

To a solution of sodium cyanide (168.35 mg, 3.36 mmol), triethylenediamine (60 mg, 0.52 mmol) in a mixture of DMSO (0.7 mL) and water (1.4 mL) was added a solution of 5-bromo-2-chloropyrimidine (500 mg, 2.59 mmol) in DMSO (1.3 mL). The solution was stirred at rt overnight, diluted with water, and extracted with EtOAc. The combined organic layer was dried over anhydrous Na₂SO₄ and concentrated to give 5-bromopyrimidine-2-carbonitrile (500 mg, yield 100%, crude).

Step 2

To a solution of 5-bromopyrimidine-2-carbonitrile (300 mg, 1.63 mmol) in THF (20 mL) was added MeMgBr (5.43 mL, 16.3 mmol) at −78° C. under nitrogen. The solution was stirred at −78° C. for 20 min., quenched with satd aq NH₄Cl, and extracted with EtOAc. The combined organic layer was dried over anhydrous Na₂SO₄ and concentrated to give an oil, which was purified by prep TLC (3:1 PE/EtOAc) to give 1-(5-bromopyrimidin-2-yl)ethanone (99 mg, yield 30.2%). ¹H NMR (CDCl₃): δ2.70 (s, 3H), 8.90 (m, 2H).

Step 3

To a solution of 1-(5-bromopyrimidin-2-yl)ethanone (99 mg, 0.50 mmol) in THF (10 mL) was added MeMgBr (1.65 mL, 4.95 mmol) at −78° C. under nitrogen. The formed solution was stirred at −78° C. for 20 min, quenched with satd aq NH₄Cl, and extracted with EtOAc. The combined organic layer was dried over anhydrous Na₂SO₄ and concentrated to give an oil, which was purified by prep TLC (3:1 PE/EtOAc) to give 2-(5-bromopyrimidin-2-yl)propan-2-ol (50 mg, yield: 46.77%).

Step 4

To a solution of 2-(5-bromopyrimidin-2-yl)propan-2-ol (30 mg, 0.14 mmol) in DME (6 mL) was added Pd(PPh₃)₄ (10 mg, 0.01 mmol) under nitrogen. The mixture was stirred at room temperature for 1 h. (S)-6-(2-hydroxy-2-methylpropyl)-6-phenyl-3-((S)-1-(4-(4,4,5,5-tetramethyl-1,3,2-dioxaborolan-2-yl)phenyl)ethyl)-1,3-oxazinan-2-one (60 mg, 0.125 mmol) in EtOH (2 mL) was added, followed by addition of satd aq NaHCO₃ (2 mL). The mixture was stirred at 100° C. for 2 h, quenched with water, and extracted with EtOAc. The combined organic layer was dried over anhydrous Na₂SO₄ and concentrated to give (S)-6-(2-hydroxy-2-methylpropyl)-3-((S)-1-(4-(2-(2-hydroxypropan-2-yl)pyrimidin-5-yl)phenyl)ethyl)-6-phenyl-1,3-oxazinan-2-one (17 mg, yield 25.12%). LC-MS Method 2 t_R=1.00 min, m/z=490; ¹H NMR (CD₃OD): δ0.95 (s, 3H), 1.27 (s, 3H), 1.57 (d, 3H), 1.61 (s, 6H), 2.22 (s, 2H), 2.25 (m, 1H), 2.50 (m, 2H), 3.06 (m, 1H), 5.61 (m, 1H), 7.10 (m, 2H), 7.34 (m, 5H), 7.45 (m, 2H), 8.92 (s, 2H).

EXAMPLE 32

4108.1002-007 Example 20

6-methyl-6-phenyl-3-(3-(pyridin-3-yl)phenyl)-1,3-oxazinan-2-one

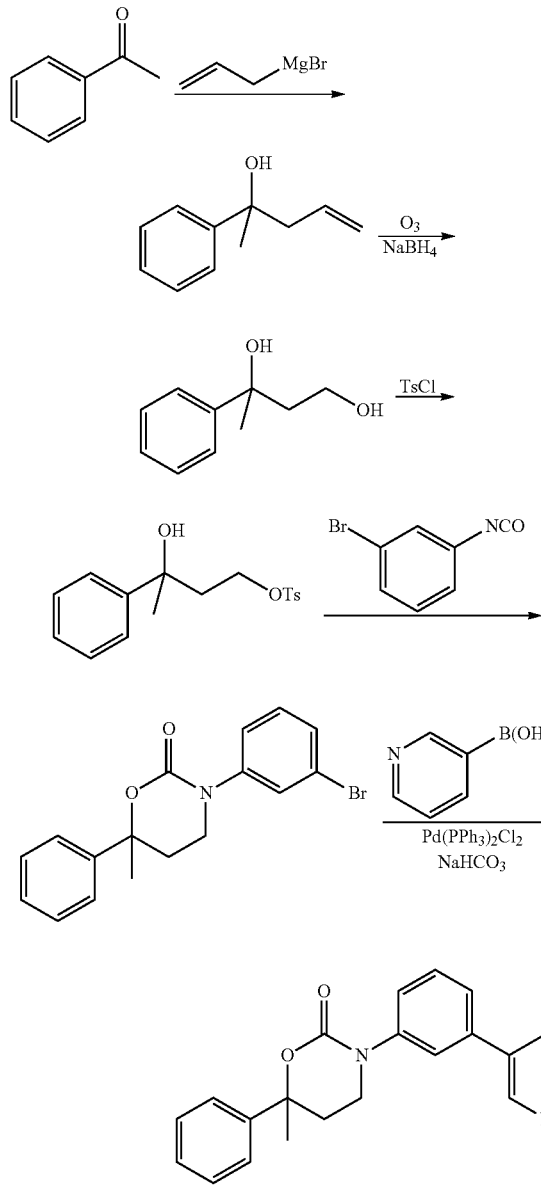

The title compound was prepared from 3-(3-bromophenyl)-6-methyl-6-phenyl-1,3-oxazinan-2-one and 3-pyridylboronic acid following procedures analogous to those in Example 1 Step 2. LC-MS Method 2, $t_R$=1.819 min, m/z=345.1. $^1$H NMR (CDCl$_3$) 1.80 (s, 3H), 2.45-2.65 (m, 2H), 3.40 (m, 1H), 3.62 (m, 1H), 7.30-7.60 (m, 8H), 7.85 (m, 1H), 8.40 (m, 1H), 8.75 (m, 1H), 9.00 (m, 1H), 9.30-9.50 (b, 2H).

EXAMPLE 33

4108.1002-007 Example 33

6-methyl-6-phenyl-3-(3-(pyridin-4-yl)phenyl)-1,3-oxazinan-2-one

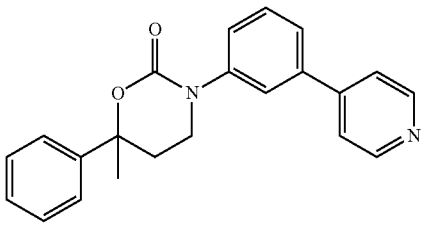 [SMILES: CC1(c2ccccc2)CCN(c2cccc(-c3ccncc3)c2)C(=O)O1]

The title compound was prepared from 3-(3-bromophenyl)-6-methyl-6-phenyl-1,3-oxazinan-2-one and 4-pyridylboronic acid following procedures analogous to those in Example 1 Step 2. LC-MS Method 2, $t_R$=1.329 min, m/z=345.1. $^1$H NMR (CDCl$_3$) 1.70 (s, 3H), 2.30-2.50 (m, 2H), 3.30 (m, 1H), 3.50 (m, 1H), 4.10 (m, 2H), 7.27-7.50 (m, 9H), 8.60 (b, 1H).

EXAMPLE 34

4108.1002-007 Example 205

(S)-6-(2-hydroxyethyl)-6-phenyl-3-((S)-1-(4-(pyridin-3-yl)phenyl)ethyl)-1,3-oxazinan-2-one

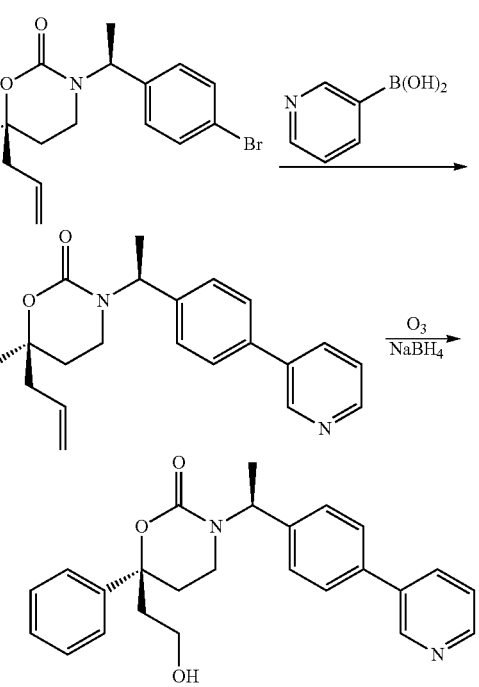

The title compound was prepared from (R)-6-allyl-3-((S)-1-(4-bromophenyl)ethyl)-6-phenyl-1,3-oxazinan-2-one and pyridine-3-boronic acid using a procedure analogous to that described in Example 1 Step 2 followed by treatment with (i) ozone and (ii) NaBH$_4$. LC-MS Method 2 $t_R$=1.44, min, m/z=403; $^1$H NMR (CDCl$_3$) 1.50 (t, 3H), 1.68 (m, 2H), 1.91 (m, 2H), 2.05 (m, 1H), 2.26 (m, 2H), 2.83 (m, 1H), 3.53 (m, 2H), 5.62 (q, 1H), 6.93 (d, 2H), 7.20-7.32 (m, 8H), 7.73 (m, 1H), 8.51 (s, 1H), 8.72 (s, 1H).

EXAMPLE 35

4108.1002-007 Example 210

(R)-6-(3-hydroxypropyl)-6-phenyl-3-((S)-1-(4-(pyridin-4-yl)phenyl)ethyl)-1,3-oxazinan-2-one

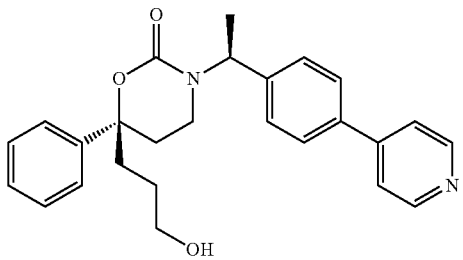 [SMILES: C[C@@H](c1ccc(-c2ccncc2)cc1)N1CC[C@](CCCO)(c2ccccc2)OC1=O]

The title compound was prepared from (R)-6-allyl-3-((S)-1-(4-bromophenyl)ethyl)-6-phenyl-1,3-oxazinan-2-one and pyridine-4-boronic acid using a procedure analogous to that described in Example 1 Step 2 followed by a procedure analogous to that described in Example 12 Step 1. LC-MS Method 2 $t_R$=2.2, min, m/z=417; $^1$H NMR (CDCl$_3$) 1.48 (m, 2H), 1.50 (t, 2H), 1.92 (m, 2H), 2.28 (m, 3H), 2.89 (m, 1H), 3.53 (m, 3H), 5.66 (m, 1H), 6.99 (m, 2H), 7.28 (q, 8H), 7.52 (d, 2H), 8.51 (m, 1H), 8.63 (m, 1H).

EXAMPLE 36

4108.1002-007 Example 211

(R)-6-(3-hydroxypropyl)-6-phenyl-3-((S)-1-(4-(pyridin-3-yl)phenyl)ethyl)-1,3-oxazinan-2-one

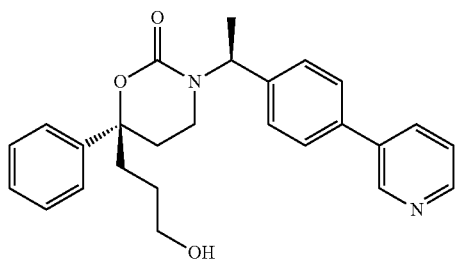 [SMILES: C[C@@H](c1ccc(-c2cccnc2)cc1)N1CC[C@](CCCO)(c2ccccc2)OC1=O]

The title compound was prepared from (R)-6-allyl-3-((S)-1-(4-bromophenyl)ethyl)-6-phenyl-1,3-oxazinan-2-one and pyridine-3-boronic acid using a procedure analogous to that described in Example 1 Step 2 followed by a procedure analogous to that described in Example 12 Step 1. LC-MS Method 2 $t_R$=1.5, min, m/z=417; $^1$H NMR (CDCl$_3$) 1.32 (m, 2H), 1.50 (t, 3H), 1.68 (m, 2H), 1.91 (m, 2H), 2.15 (m, 1H), 2.26 (m, 2H), 2.83 (m, 1H), 3.51 (m, 2H), 5.62 (q, 1H), 6.93 (d, 2H), 7.20-7.32 (m, 8H), 7.73 (m, 1H), 8.51 (s, 1H), 8.72 (s, 1H).

EXAMPLE 37

4108.1002-007 Example 214

(S)-6-(4-fluorophenyl)-6-(2-hydroxyethyl)-3-((S)-1-(4-(pyridin-3-yl)phenyl)ethyl)-1,3-oxazinan-2-one

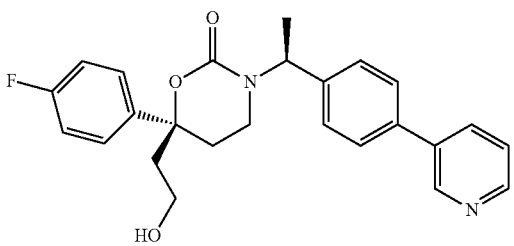 [SMILES: C[C@@H](c1ccc(-c2cccnc2)cc1)N1CC[C@](CCO)(c2ccc(F)cc2)OC1=O]

The title compound was prepared from (R)-6-allyl-3-((S)-1-(4-bromophenyl)ethyl)-6-(4-fluorophenyl)-1,3-oxazinan-2-one and pyridine-3-boronic acid using a procedure analogous to that described in Example 1 Step 2 followed by treatment with (i) ozone and (ii) NaBH$_4$. LC-MS Method 2 $t_R$=1.412, min, m/z=421.2; $^1$H NMR (CDCl$_3$) 1.52 (d, 3H), 2.03-2.17 (m, 3H), 2.22-2.32 (m, 3H), 2.81 (m, 1H), 3.47-3.52 (m, 1H), 3.72 (m, 1H), 5.63 (m, 1H), 6.93-7.01 (m, 4H), 7.21-7.26 (m, 2H), 7.28-7.33 (m, 3H), 7.73 (m, 1H), 8.51 (m, 1H), 8.68 (m, 1H).

EXAMPLE 38

4108.1002-007 Example 222

3-(4-((S)-1-((R)-6-(3-hydroxypropyl)-2-oxo-6-phenyl-1,3-oxazinan-3-yl)ethyl)phenyl)pyridine 1-oxide

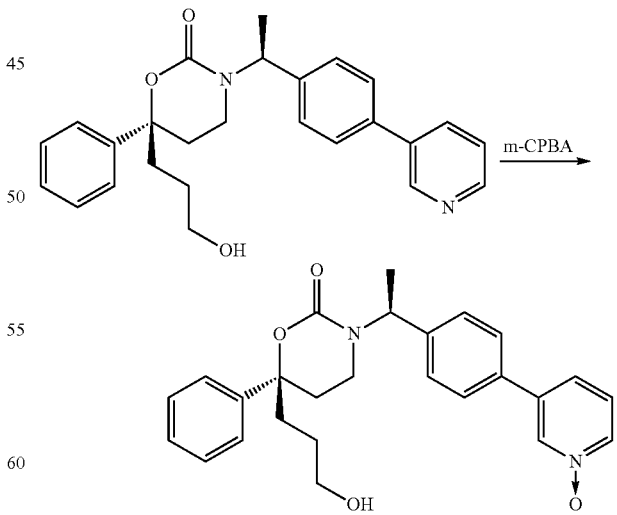

A mixture of (R)-1-((S)-1-(4'-fluorobiphenyl-4-yl)ethyl)-4-(4-fluorophenyl)-4-(3-hydroxypropyl)tetra-hydropyrimidin-2(1H)-one (30 mg, 0.07 mmol) and 3-chloro-perbenzoic acid (84 mg, 0.49 mmol) in THF (1.5 mL) was stirred at rt for 3 h. Satd aq NaHCO₃ was added to the reaction mixture, and the organic layer was separated. The organic layer was washed with brine, dried over Na₂SO₄ and concentrated to give the crude product, which was purified by preparative HPLC to give 3-(4-((S)-1-((R)-6-(3-hydroxypropyl)-2-oxo-6-phenyl-1,3-oxazinan-3-yl)ethyl)phenyl)pyridine 1-oxide (2.83 mg, 9%). LC-MS Method 2 $t_R$=1.623, min, m/z=433.2; ¹H NMR (400 MHz, CDCl₃): δ=1.54 (t, 3H), 1.94 (m, 2H), 2.21-2.24 (m, 2H), 2.35-2.39 (m, 2H), 2.49 (m, 1H), 3.1 (m, 1H), 3.44 (m, 1H), 5.57 (m, 1H), 7.07 (m, 2H), 7.28-7.42 (m, 6H), 7.58 (m, 1H), 7.77 (m, 1H), 8.19 (m, 1H), 8.28 (m, 1H), 8.49 (m, 1H).

EXAMPLE 39

4108.1002-007 Example 230

(R)-6-allyl-6-(4-fluorophenyl)-3-((S)-1-(4-(5-methyl-1,3,4-thiadiazol-2-yl)phenyl)ethyl)-1,3-oxazinan-2-one

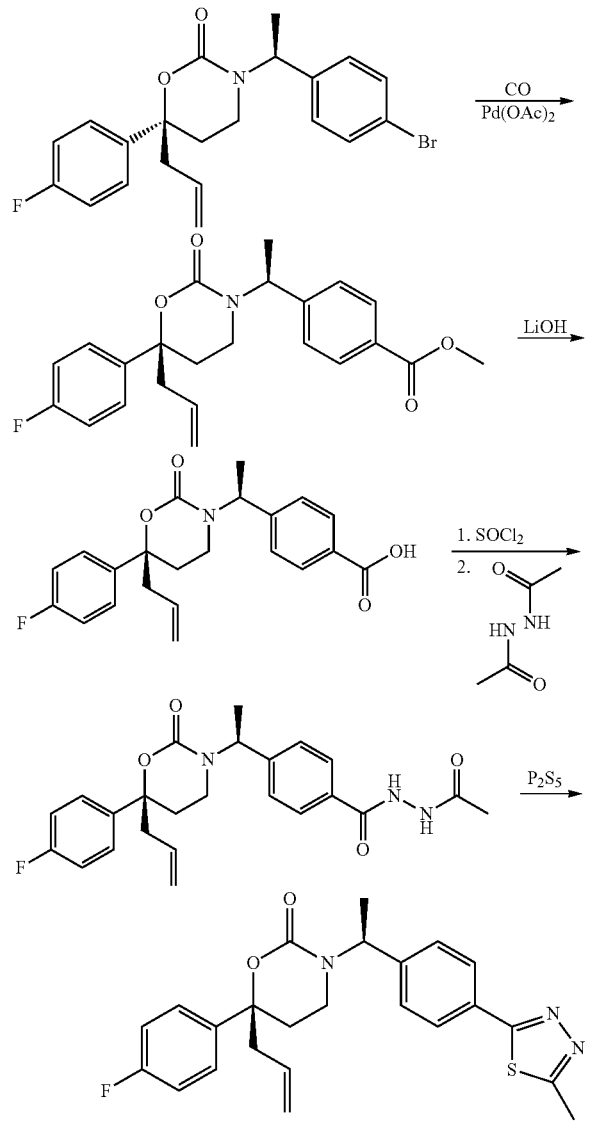

Step 1

To a 16 mm culture tube with a Teflon-coated stirring bar, a solution of (R)-6-allyl-3-((S)-1-(4-bromophenyl)ethyl)-6-(4-fluorophenyl)-1,3-oxazinan-2-one (87 mg, 0.209 mmol) in dry DMSO (4 mL) and dry methanol (1.5 mL), triethylamine (60 μL, 2 equiv), Pd(OAc)₂ (10 mg, 0.2 equiv) and 1,3-bis(diphenylphosphino)propane (35 mg, 0.4 equiv) were added. The tube was sealed with a septum and Parafilm tape. The reaction mixture was purged with CO gas through a long needle for 1 min. A balloon filled with CO gas was attached to maintain a CO atmosphere. The reaction mixture was submerged in an oil bath preheated to 85° C. and stirred vigorously. After 12 h, LC-MS showed the reaction was complete. The mixture was filtered through a thin pad of Celite. The Celite was washed with EtOAc (35 mL). The filtrate was washed with 3% aq HCl (10 mL), water (2×8 mL) and brine (2×7 mL), and dried over Na₂SO₄. After filtration and concentration, the residue was purified by chromatography on a 12-g silica gel cartridge eluted with a 10-60% EtOAc in hexanes gradient to afford methyl 4-((S)-1-((R)-6-allyl-6-(4-fluorophenyl)-2-oxo-1,3-oxazinan-3-yl)ethyl)benzoate (68.4 mg, 83%). LC-MS Method 1, $t_R$=1.79 min, m/z=398. ¹H NMR (CDCl₃) 7.79 (d, 2H), 7.26 (m, 2H), 7.04 (t, 2H), 6.94 (d, 2H), 5.69 (m, m, 2H), 5.07 (dd, 2H), 3.89 (s, 3H), 2.94 (m, 1H), 2.58 (m, 2H), 1.54 (d, 3H).

Step 2 methyl 4-((S)-1-((R)-6-allyl-6-(4-fluorophenyl)-2-oxo-1,3-oxazinan-3-yl)ethyl)benzoate was treated with LiOH to afford 4-((S)-1-((R)-6-allyl-6-(4-fluorophenyl)-2-oxo-1,3-oxazinan-3-yl)ethyl)benzoic acid.

Step 3

4-((S)-1-((R)-6-allyl-6-(4-fluorophenyl)-2-oxo-1,3-oxazinan-3-yl)ethyl)benzoic acid (40 mg, 0.104 mmol) was dissolved in CH₂Cl₂ (6 mL). At 0° C., thionyl chloride (1 mL, excess) was added slowly. After 10 min., the mixture was warmed up to rt and stirred 1 h at rt The mixture was concentrated and redissolved in CH₂Cl₂ (6 mL). NaHCO₃ (22 mg, 2.5 equiv.) and acetohydrazide (12 mg, 1.5 equiv.) were added slowly. After stirring 1 h at rt, LC-MS found reaction completed. The mixture was diluted with CH₂Cl₂ (10 mL), filtered NaHCO₃ and washed by water (5 mL), 5% aq HCl (2×5 mL), satd aq NaHCO₃ (4 mL), brine (4 mL) and dried over Na₂SO₄. After filtration and concentration, the crude N'-acetyl-4-((S)-1-((R)-6-allyl-6-(4-fluorophenyl)-2-oxo-1,3-oxazinan-3-yl)ethyl)benzohydrazide (34 mg, 74%) was used for next step without further purification.

Step 4

N'-acetyl-4-((S)-1-((R)-6-allyl-6-(4-fluorophenyl)-2-oxo-1,3-oxazinan-3-yl)ethyl)benzohydrazide (4 mg, 0.009 mmol) was dissolved in 5:1 toluene/pyridine (1.5 mL). Phosphorus pentasulfide (8.1 mg, 2 equiv.) was added and the mixture was heated in Microwave Oven for 25 min at 130° C. LC-MS found reaction completed. The mixture was diluted with EtOAc (8 mL), washed with 5% HCl (2×5 mL), satd aq NaHCO₃ solution (4 mL), brine (4 mL) and dried over Na₂SO₄. After filtration and concentration, the residue was purified by prep HPLC to afford 2.43 mg (61% yield). LC-MS Method 1 $t_R$=1.7, min, m/z=438; ¹H NMR (CDCl₃) 7.66 (d, 2H), 7.26 (t, 2H), 7.02 (t, 2H), 6.97 (d, 2H), 5.69 (m, 2H), 5.07 (dd, 2H), 2.98 (m, 1H), 2.83 (s, 3H), 1.56 (d, 3H).

EXAMPLE 40

4108.1002-007 Example 235

(R)-6-(3-hydroxypropyl)-3-((S)-1-(4-(6-methoxypyridin-3-yl)phenyl)ethyl)-6-phenyl-1,3-oxazinan-2-one

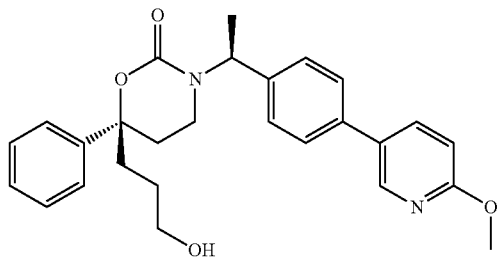 [SMILES: COc1ccc(-c2ccc([C@H](C)N3CC[C@](CCCO)(c4ccccc4)OC3=O)cc2)cn1]

The title compound was prepared from (R)-6-allyl-3-((S)-1-(4-bromophenyl)ethyl)-6-phenyl-1,3-oxazinan-2-one and 2-methoxypyridine-5-boronic acid using a procedure analogous to that described in Example 1 Step 2 followed by a procedure analogous to that described in Example 12 Step 1. LC-MS Method 3 $t_R$=1.22, min, m/z=447; $^1$H NMR (CDCl$_3$) 1.01 (d, 1H), 1.10 (d, 1H), 1.49 (s, 3H), 1.85-1.95 (m, 1H), 2.00-2.07 (m, 1H), 2.21-2.30 (m, 2H), 2.40 (m, 1H), 2.35 (m, 1H), 3.87 (m, 1H), 3.90 (s, 3H), 3.95 (m, 1H), 5.61 (m, 1H), 6.71 (d, 1H), 6.83 (d, 1H), 6.91 (m, 1H), 7.16 (m, 2H), 7.25 (m, 2H), 7.31 (m, 3H), 7.61 (d, 1H), 8.22 (s, 1H).

EXAMPLE 41

4108.1002-007 Example 236

3-((R)-6-(4-fluorophenyl)-2-oxo-3-((S)-1-(4-(pyridin-3-yl)phenyl)ethyl)-1,3-oxazinan-6-yl)propanamide

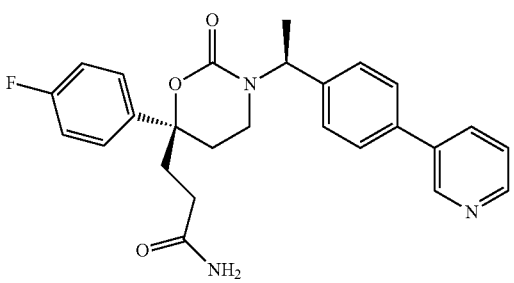 [SMILES: C[C@@H](c1ccc(-c2cccnc2)cc1)N1CC[C@](CCC(N)=O)(c2ccc(F)cc2)OC1=O]

The title compound was prepared from (R)-6-(4-fluorophenyl)-6-(3-hydroxypropyl)-3-((S)-1-(4-(pyridin-3-yl)phenyl)ethyl)-1,3-oxazinan-2-one using a procedure analogous to that described in Example 12 Step 2, followed by a procedure analogous to that described in Example 8 Step 2 using ammonia. LC-MS Method 2 $t_R$=1.372, min, m/z=448.3; $^1$H NMR (CDCl$_3$) 1.52 (d, 3H), 1.97 (m, 2H), 2.27-2.33 (m, 4H), 2.43 (m, 1H), 2.97 (m, 1H), 5.13 (s, 1H), 5.24 (s, 1H), 5.66 (m, 1H), 6.92-7.08 (m, 4H), 7.22 (m, 2H), 7.31 (m, 2H), 7.48 (m, 1H), 7.97 (m, 1H), 8.57 (m, 1H), 8.74 (m, 1H).

EXAMPLE 42

4108.1002-007 Example 244

(R)-6-allyl-3-((S)-1-(4-(2,4-dimethylthiazol-5-yl)phenyl)ethyl)-6-(4-fluorophenyl)-1,3-oxazinan-2-one

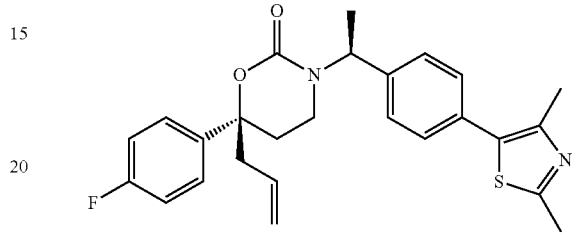

The title compound was prepared from (R)-6-allyl-3-((S)-1-(4-bromophenyl)ethyl)-6-(4-fluorophenyl)-1,3-oxazinan-2-one and 2,4-dimethylthiazole-5-boronic acid following a procedure analogous to that described in Example 14. LC-MS Method 1 $t_R$=1.82, min, m/z=451; $^1$H NMR (CDCl$_3$) 7.26 (t, 2H), 7.13 (d, 2H), 7.03 (t, 2H), 6.91 (d, 2H), 5.76-5.64 (m, 2H), 5.06 (dd, 2H), 2.98 (m, 1H), 2.74 (s, 3H), 2.42 (s, 3H), 1.53 (d, 3H).

EXAMPLE 43

4108.1002-007 Example 258

(R)-6-allyl-6-(4-fluorophenyl)-3-((S)-1-(4-(3-(trifluoromethyl)-1H-pyrazol-1-yl)phenyl)ethyl)-1,3-oxazinan-2-one

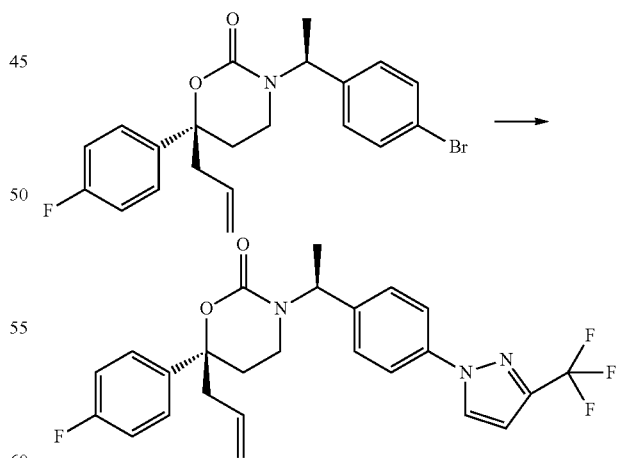

(R)-6-Allyl-3-((S)-1-(4-bromophenyl)ethyl)-6-(4-fluorophenyl)-1,3-oxazinan-2-one (20 mg, 0.048 mmol), 3-(trifluoromethyl)-1H-pyrazole (20 mg, 3 equiv.), CuI (1.4 mg, 15% mol), (1R,2R)-(−)-1,2-transcyclohexanediamine (2 mg, 30% mol), K$_3$PO$_4$ (20 mg, 2 equiv.) were mixed with dry toluene (2 mL) and heated in Microwave Oven for 1 h at 130°

C. LC-MS found product peak. The mixture was diluted with EtOAc (8 mL), washed by water (2 mL), brine (3 mL) and dried over $Na_2SO_4$. After filtration and concentration, the residue was purified chromatography on a 4-g silica gel cartridge eluted with a gradient from 5 to 55% EtOAc in gexanes to afford (R)-6-allyl-6-(4-fluorophenyl)-3-((S)-1-(4-(3-(trifluoromethyl)-1H-pyrazol-1-yl)phenyl)ethyl)-1,3-oxazinan-2-one (9.7 mg, 43%) product. LC-MS Method 1 $t_R$=2.05, min, m/z=474; $^1$H NMR ($CDCl_3$) 7.86 (s, 1H), 7.43 (d, 2H), 7.26 (t, 2H), 7.01 (dd, 2H), 6.69 (d, 1H), 5.76-5.64 (m, 2H), 5.05 (dd, 2H), 2.95 (m, 1H), 2.65-2.51 (m, 2H), 1.54 (d, 3H).

EXAMPLE 44

4108.1002-007 Example 281

(R)-6-(4-fluorophenyl)-6-(3-hydroxypropyl)-3-((S)-1-(4-(6-(trifluoromethyl)pyridin-3-yl)phenyl)ethyl)-1,3-oxazinan-2-one

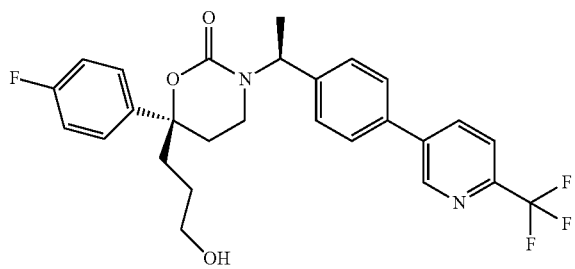 [SMILES: C[C@@H](c1ccc(-c2ccc(C(F)(F)F)nc2)cc1)N1CC[C@](CCCO)(c2ccc(F)cc2)OC1=O]

The title compound was prepared from (R)-3-((S)-1-(4-bromophenyl)ethyl)-6-(4-fluorophenyl)-6-(3-hydroxypropyl)-1,3-oxazinan-2-one and 2-trifluoromethylpyridine-3-boronic acid following a procedure analogous to that described in Example 1 Step 2. LC-MS Method 3 $t_R$=1.36 min, m/z=459.3; $^1$H NMR ($CDCl_3$) 1.40 (m, 1H), 1.51 (m, 3H), 1.63 (m, 1H), 1.70-1.98 (m, 3H), 2.11-2.33 (m, 3H), 2.95 (m, 1H), 3.50-3.63 (m, 2H), 5.66 (m, 1H), 6.97 (m, 4H), 7.20 (m, 2H), 7.29 (m, 2H), 7.67 (m, 1H), 7.87-7.90 (m, 1H), 8.78 (m, 1H).

EXAMPLE 45

4108.1002-007 Example 291

(R)-3-((S)-1-(4-(1H-pyrazol-3-yl)phenyl)ethyl)-6-(3-hydroxypropyl)-6-phenyl-1,3-oxazinan-2-one

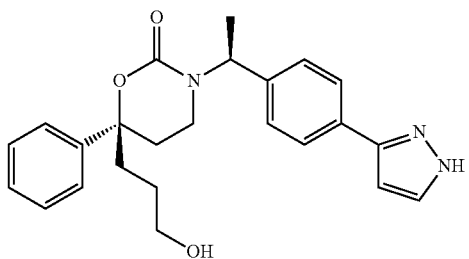 [SMILES: C[C@@H](c1ccc(-c2cc[nH]n2)cc1)N1CC[C@](CCCO)(c2ccccc2)OC1=O]

The title compound was prepared from (R)-6-allyl-3-((S)-1-(4-bromophenyl)ethyl)-6-phenyl-1,3-oxazinan-2-one and pyrazole-3-boronic acid using a procedure analogous to that described in Example 1 Step 2 followed by a procedure analogous to that described in Example 12 Step 1. LC-MS Method 2 $t_R$=1.808 min, m/z=362.2; $^1$H NMR ($CDCl_3$) 1.48 (d, 3H), 1.60-1.72 (m, 2H), 1.90 (m, 2H), 2.22 (m, 3H), 2.84 (m, 1H), 3.46-3.54 (m, 2H), 5.61 (q, 1H), 6.48 (s, 1H), 6.89 (d, 2H), 7.19-7.30 (m, 6H), 7.43 (d, 2H), 7.52 (s, 1H).

EXAMPLE 46

4108.1002-007 Example 292

(R)-6-allyl-3-((S)-1-(4-(5-fluoropyridin-3-yl)phenyl)ethyl)-6-phenyl-1,3-oxazinan-2-one

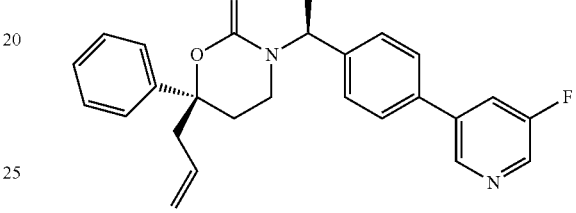

The title compound was prepared from (R)-6-allyl-3-((S)-1-(4-bromophenyl)ethyl)-6-phenyl-1,3-oxazinan-2-one and 5-fluoropyridine-3-boronic acid using a procedure analogous to that described in Example 14. LC-MS Method 1 $t_R$=1.84 min, m/z=417 (M+1); $^1$H NMR ($CDCl_3$) 8.58 (s, 1H), 8.45 (d, 1H, J=3 Hz), 7.57-7.54 (m, 1H), 7.39-7.30 (m, 5H), 7.27-7.25 (m, 2H), 6.93 (d, 2H, J=8 Hz), 5.80-5.68 (m, 2H), 5.11-5.03 (m, 2H), 2.97-2.91 (m, 1H), 2.69-2.55 (m, 2H), 2.41-2.21 (m, 3H), 1.55 (d, 3H, J=7 Hz).

EXAMPLE 47

4108.1002-007 Example 295

3-((R)-2-oxo-6-phenyl-3-((S)-1-(4-(pyridin-3-yl)phenyl)ethyl)-1,3-oxazinan-6-yl)propanamide

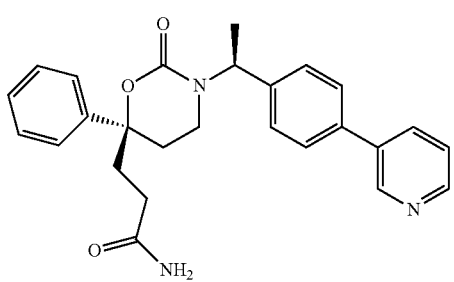 [SMILES: C[C@@H](c1ccc(-c2cccnc2)cc1)N1CC[C@](CCC(N)=O)(c2ccccc2)OC1=O]

The title compound was prepared from (R)-6-(3-hydroxypropyl)-6-phenyl-3-((S)-1-(4-(pyridin-3-yl)phenyl)ethyl)-1,3-oxazinan-2-one using a procedure analogous to that described in Example 12 Step 2, followed by a procedure analogous to that described in Example 8 Step 2 using ammonia. LC-MS Method 2 $t_R$=1.381 min, m/z=430.2; $^1$H NMR ($CDCl_3$) 1.56 (m, 3H), 1.92-2.03 (m, 3H), 2.18-2.37 (m, 5H), 2.51 (m, 1H), 2.94 (m, 1H), 5.29-5.61 (m, 2H), 5.71 (m, 1H), 7.03 (m, 2H), 7.21-7.38 (m, 8H), 7.77 (m, 1H), 8.53 (m, 1H), 8.72 (s, 1H).

EXAMPLE 48

4108.1002-007 Example 296

3-((R)-2-oxo-6-phenyl-3-((S)-1-(4-(pyridin-4-yl)phenyl)ethyl)-1,3-oxazinan-6-yl)propanamide

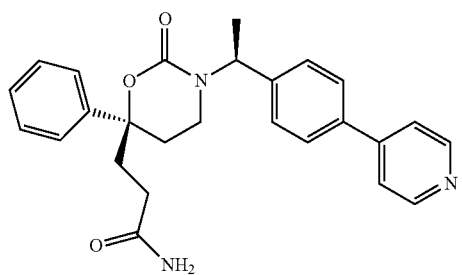 [SMILES: C[C@@H](c1ccc(-c2ccncc2)cc1)N1CC[C@](CCC(N)=O)(c2ccccc2)OC1=O]

The title compound was prepared from (R)-6-(3-hydroxypropyl)-6-phenyl-3-((S)-1-(4-(pyridin-4-yl)phenyl)ethyl)-1,3-oxazinan-2-one employing a procedure analogous to that described in Example 12 Step 2, followed by a procedure analogous to that described in Example 8 Step 2 using ammonia. LC-MS Method 2 $t_R$=1.327 min, m/z=430.2; $^1$H NMR (CDCl$_3$) 1.49 (m, 3H), 1.93 (m, 1H), 2.12-2.34 (m, 5H), 2.44 (m, 1H), 2.94 (m, 1H), 5.46 (m, 2H), 5.67 (m, 1H), 7.08 (m, 2H), 7.19-7.42 (m, 5H), 7.45 (m, 2H), 7.80 (m, 2H), 8.76 (m, 2H).

EXAMPLE 49

4108.1002-007 Example 298

(R)-3-((S)-1-(4-(5-fluoropyridin-3-yl)phenyl)ethyl)-6-(3-hydroxypropyl)-6-phenyl-1,3-oxazinan-2-one

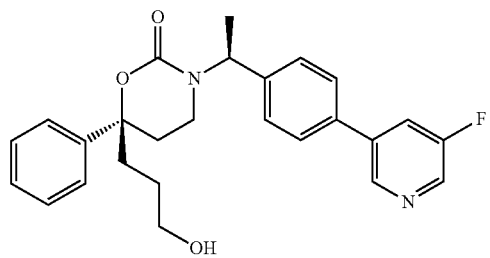 [SMILES: C[C@@H](c1ccc(-c2cncc(F)c2)cc1)N1CC[C@](CCCO)(c2ccccc2)OC1=O]

The title compound was prepared from (R)-6-allyl-3-((S)-1-(4-(5-fluoropyridin-3-yl)phenyl)ethyl)-6-phenyl-1,3-oxazinan-2-one following a procedure analogous to that described in Example 12 Step 1. LC-MS Method 1 $t_R$=1.5 min, m/z=457 (M+Na); $^1$H NMR (CDCl$_3$) 8.64 (s, 1H), 8.50 (s, 1H), 7.74-7.71 (dd, 1H, J=2, 9 Hz), 7.41-7.27 (m, 7H), 7.05 (dd, 2H, J=3, 8 Hz), 5.74-5.68 (m, 1H), 4.27-4.24 (t, 1H, J=6, 6 Hz), 3.60-3.57 (t, 1H, J=6, 6 Hz), 2.98-2.93 (m, 1H), 2.38-2.20 (m, 3H), 2.10-1.93 (m, 3H), 1.73-1.70 (1H, m), 1.57 (d, 3H, J=7 Hz), 1.41-1.37 (m, 1H).

EXAMPLE 50

4108.1002-007 Example 300

3-(4-((S)-1-((R)-6-(3-amino-3-oxopropyl)-2-oxo-6-phenyl-1,3-oxazinan-3-yl)ethyl)phenyl)pyridine 1-oxide

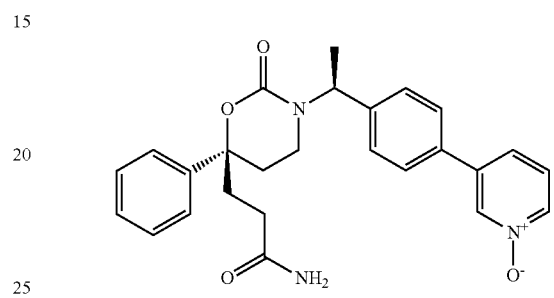

The title compound was prepared from 3-((R)-2-oxo-6-phenyl-3-((S)-1-(4-(pyridin-3-yl)phenyl)ethyl)-1,3-oxazinan-6-yl)propanamide following a procedure analogous to that described 38. LC-MS Method 2 $t_R$=1.476 min, m/z=445.2; $^1$H NMR (CDCl$_3$) 1.56 (d, 3H), 1.98-2.15 (m, 1H), 2.18-2.37 (m, 5H), 2.47-2.58 (m, 1H), 2.96 (m, 1H), 5.51 (s, 1H), 5.57 (s, 1H), 5.70 (q, 1H), 7.03 (q, 2H), 7.26-7.38 (m, 9H), 8.20 (d, 1H), 8.49 (s, 1H).

EXAMPLE 51

4108.1002-007 Example 302

(R)-6-allyl-6-(4-fluorophenyl)-3-((S)-1-(4-(5-fluoropyridin-3-yl)phenyl)ethyl)-1,3-oxazinan-2-one

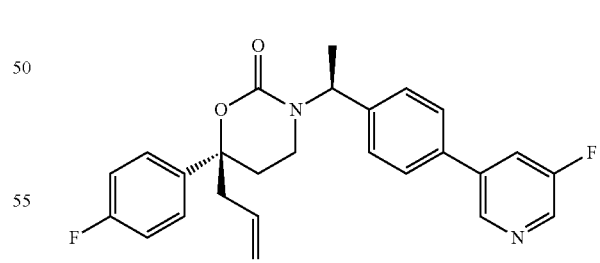

The title compound was prepared from (R)-6-allyl-3-((S)-1-(4-bromophenyl)ethyl)-6-(4-fluorophenyl)-1,3-oxazinan-2-one and 5-fluoropyridine-3-boronic acid following a procedure analogous to that described in Example 14. LC-MS Method 1 $t_R$=1.84 min, m/z=435 (M+1); $^1$H NMR (CDCl$_3$) 8.58 (t, 1H, J=1.5, 1.5 Hz), 8.44 (d, 1H, J=3 Hz), 7.51-7.48 (ddd, 1H, J=9, 4, 2 Hz), 7.33-7.262 (m, 4H), 7.04 (at, J=9, 9 Hz), 6.98 (d, 2H, 8 Hz), 5.76-5.66 (m, 2H), 5.11-5.00 (m, 2H), 3.00-2.95 (m, 1H), 2.65-2.5 (m, 2H), 2.41-2.33 (m, 1H) 2.31-2.18 (m, 2H), 1.55 (d, 3H, J=7 Hz).

EXAMPLE 52

4108.1002-007 Example 304

3-((R)-3-((S)-1-(4-(6-methoxypyridin-3-yl)phenyl)ethyl)-2-oxo-6-phenyl-1,3-oxazinan-6-yl)propanamide

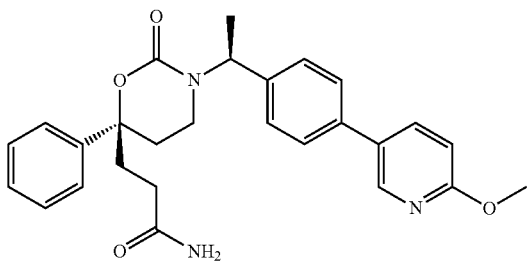 [SMILES: COc1ccc(-c2ccc([C@H](C)N3CC[C@](CCC(N)=O)(c4ccccc4)OC3=O)cc2)cn1]

The title compound was prepared from 3-((R)-3-((S)-1-(4-bromophenyl)ethyl)-2-oxo-6-phenyl-1,3-oxazinan-6-yl)propanamide and 6-methoxypyridine-3-boronic acid following a procedure analogous to that described in Example 14. LC-MS Method 3 $t_R$=1.106 min, m/z=460.2; $^1$H NMR (CD$_3$OD) 1.54 (m, 3H), 1.95 (m, 1H), 2.16-2.29 (m, 4H), 2.40 (m, 2H), 2.44 (m, 1H), 3.10 (m, 1H), 3.99 (s, 3H), 5.56 (m, 1H), 6.94 (m, 1H), 7.03 (m, 2H), 7.28-7.39 (m, 8H), 7.93 (m, 1H), 8.28 (m, 1H).

EXAMPLE 53

4108.1002-007 Example 305

(R)-6-(4-fluorophenyl)-6-(3-hydroxypropyl)-3-((S)-1-(4-(5-methoxypyridin-3-yl)phenyl)ethyl)-1,3-oxazinan-2-one

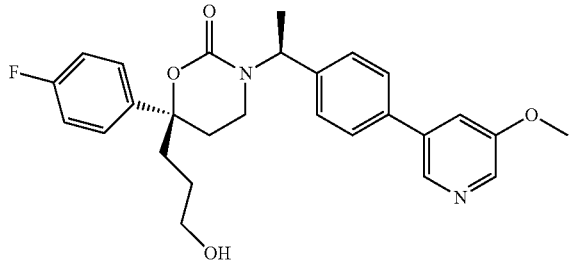 [SMILES: COc1cncc(-c2ccc([C@H](C)N3CC[C@](CCCO)(c4ccc(F)cc4)OC3=O)cc2)c1]

The title compound was prepared from (R)-3-((S)-1-(4-bromophenyl)ethyl)-6-(4-fluorophenyl)-6-(3-hydroxypropyl)-1,3-oxazinan-2-one and 5-methoxypyridine-3-boronic acid following a procedure analogous to that described in Example 1 Step 2. LC-MS Method 2 $t_R$=1.694 min, m/z=465.2; $^1$H NMR (CDCl$_3$) 1.34 (m, 1H), 1.53 (m, 3H), 1.68 (m, 1H), 1.94 (m, 3H), 2.18-2.32 (m, 3H), 2.95 (m, 1H), 3.56 (m, 2H), 3.88 (s, 3H), 5.69 (m, 1H), 7.01 (m, 4H), 7.24 (m, 3H), 7.31 (m, 2H), 8.25 (m, 1H), 8.34 (m, 1H).

EXAMPLE 54

4108.1002-007 Example 306

(R)-6-allyl-3-((S)-1-(4-(5-chloropyridin-3-yl)phenyl)ethyl)-6-(4-fluorophenyl)-1,3-oxazinan-2-one

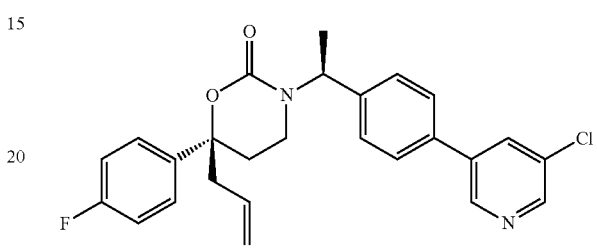

The title compound was prepared from (R)-3-((S)-1-(4-bromophenyl)ethyl)-6-(4-fluorophenyl)-6-(3-hydroxypropyl)-1,3-oxazinan-2-one and 5-chloropyridine-3-boronic acid following a procedure analogous to that described in Example 14. LC-MS Method 1 $t_R$=1.97 min, m/z=451 (M+1); $^1$H NMR (CDCl$_3$) 8.68 (d, 1H, J=2 Hz), 8.59 (d, 1H, J=2 Hz), 7.94 (t, 1H, J=2.2 Hz), 7.33-7.27 (m, 4H), 7.04 (ap q, 2H, J=9, 17 Hz), 5.75-5.65 (m, 2H), 5.12-5.02 (m, 2H), 3.03-2.98 (m, 1H), 2.66-2.54 (m, 2H), 2.41-2.17 (m, 3H), 1.56 (d, 3H, J=7 Hz).

EXAMPLE 55

4108.1002-007 Example 307

N-(2-((S)-2-oxo-6-phenyl-3-((S)-1-(4-(pyridin-3-yl)phenyl)ethyl)-1,3-oxazinan-6-yl)ethyl)methanesulfonamide

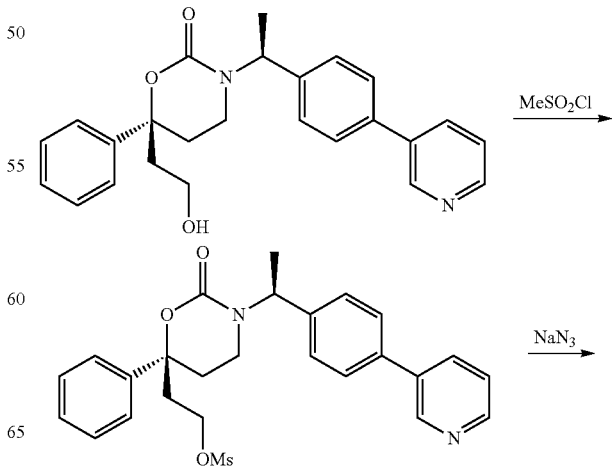

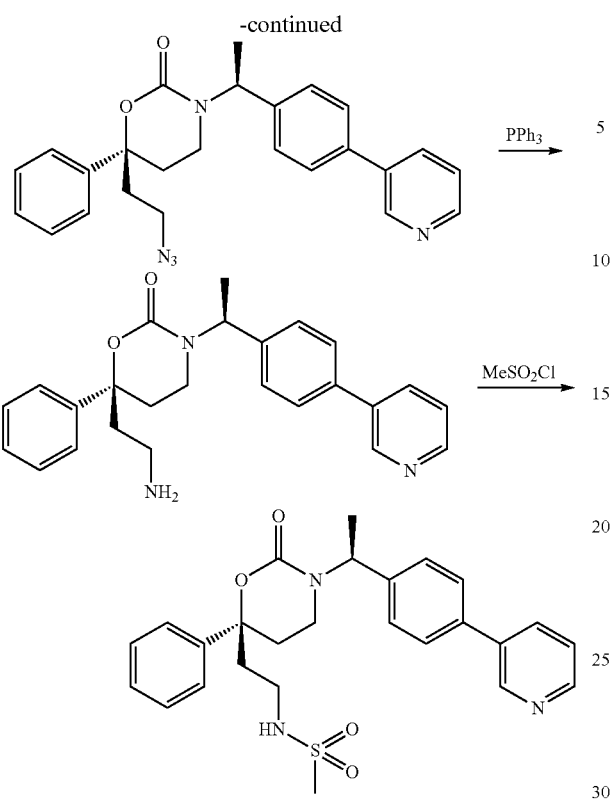

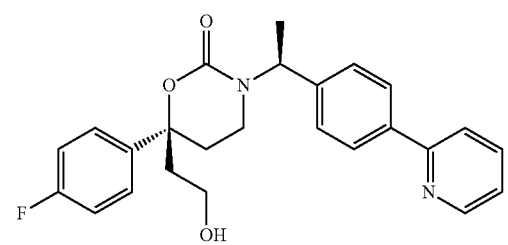

7.7 (s, 1H), 7.49 (t, 2H, J=7, 7 Hz), 7.27-7.24 (m, 2H), 7.17 (m, 2H), 7.09-7.02 (aq, 2H, J=9, 17 Hz), 5.73 (q, 1H, J=7, 14 Hz), 4.27 (t, 1H, J=6, 6 Hz), 3.60 (t, 1H, J=6, 6 Hz), 3.09-3.03 (m, 1H), 2.95 (s, 3H), 2.41-2.25 (m, 3H), 2.06-1.90 (m, 2H) 1.73-1.64 (m, 1H), 1.58 (d, 3H, J=7 Hz), 1.40-1.33 (m, 1H).

EXAMPLE 57

4108.1002-007 Example 430

(S)-6-(4-fluorophenyl)-6-(2-hydroxyethyl)-3-((S)-1-(4-(pyridin-2-yl)phenyl)ethyl)-1,3-oxazinan-2-one

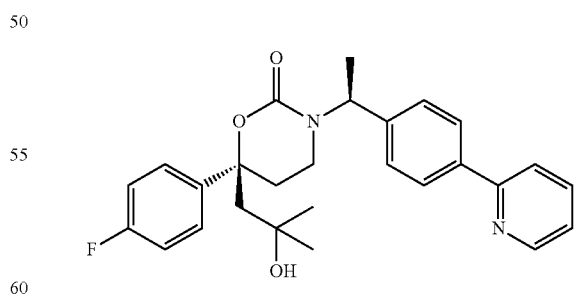

The title compound was prepared from (S)-3-((S)-1-(4-bromophenyl)ethyl)-6-(4-fluorophenyl)-6-(2-hydroxyethyl)-1,3-oxazinan-2-one and pyridine-2-boronic acid following a procedure analogous to that described in Example 1 Step 2. LC-MS Method 2 $t_R$=1.462 min, m/z=420.18; $^1$H NMR (CDCl$_3$) 1.48 (d, 3H), 2.03-2.30 (m, 5H), 2.85 (m, 1H), 3.50 (m, 1H), 3.72 (m, 1H), 5.65 (m, 1H), 6.98 (m, 4H), 7.24 (m, 2H), 7.60 (m, 1H), 7.74 (m, 3H), 8.62 (m, 1H).

The title compound was prepared from (R)-6-(2-aminoethyl)-6-phenyl-3-((S)-1-(4-(pyridin-3-yl)phenyl)ethyl)-1,3-oxazinan-2-one by treatment with MeSO$_2$Cl. LC-MS Method 2 $t_R$=1.525 min, m/z=480.2; $^1$H NMR (CDCl$_3$) 1.52 (d, 3H), 2.05-2.32 (m, 6H), 2.81 (s, 3H), 2.86 (m, 1H), 2.93-3.04 (m, 1H), 3.06-3.20 (m, 1H), 4.73 (s, 1H), 5.63 (q, 1H), 6.95 (d, 2H), 7.05-7.22 (m, 2H), 7.23-7.40 (m, 6H), 7.71 (d, 1H), 8.50 (d, 1H), 8.66 (s, 1H).

EXAMPLE 56

4108.1002-007 Example 311

(R)-6-(4-fluorophenyl)-6-(3-hydroxypropyl)-3-((S)-1-(4-(2-methylpyridin-4-yl)phenyl)ethyl)-1,3-oxazinan-2-one

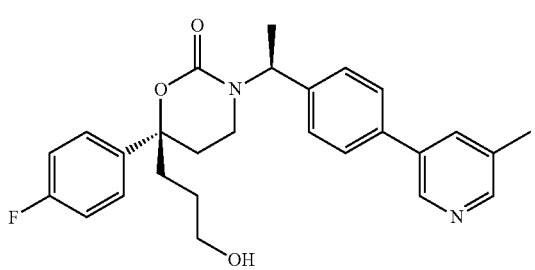 [SMILES: Cc1cncc(-c2ccc([C@H](C)N3CC[C@](CCCO)(c4ccc(F)cc4)OC3=O)cc2)c1]

The title compound was prepared from (R)-3-((S)-1-(4-bromophenyl)ethyl)-6-(4-fluorophenyl)-6-(3-hydroxypropyl)-1,3-oxazinan-2-one and 2-methylpyridine-4-boronic acid following a procedure analogous to that described in Example 14. LC-MS Method 1 $t_R$=1.29 min, m/z=431 (M+1); $^1$H NMR (CDCl$_3$) 8.71 (d, 1H, J=6 Hz), 7.78 (d, 1H, J=6 Hz),

EXAMPLE 58

4108.1002-007 Example 431

(S)-6-(4-fluorophenyl)-6-(2-hydroxy-2-methylpropyl)-3-((S)-1-(4-(pyridin-2-yl)phenyl)ethyl)-1,3-oxazinan-2-one The title compound was prepared from (S)-3-((S)-1-(4-bromophenyl)ethyl)-6-(4-fluorophenyl)-6-(2-hydroxy-2-methylpropyl)-1,3-oxazinan-2-one and pyridine-2-boronic acid following a procedure analogous to that described in Example 1 Step 2. LC-MS Method 2 $t_R$=1.049 min, m/z=391; $^1$H NMR (CDCl$_3$) 1.06-1.19 (d, 6H), 1.50 (s, 3H), 2.11-2.38

(m, 6H), 2.80 (m, 1H), 5.66 (m, 1H), 6.97 (m, 2H), 7.04 (d, 2H), 7.18 (m, 1H), 7.23 (m, 2H), 7.58 (m, 1H), 7.73 (m, 3H), 8.60 (d, 1H).

EXAMPLE 59

4108.1002-007 Example 432

(R)-6-(4-fluorophenyl)-6-(3-hydroxypropyl)-3-((S)-1-(4-(pyridin-2-yl)phenyl)ethyl)-1,3-oxazinan-2-one

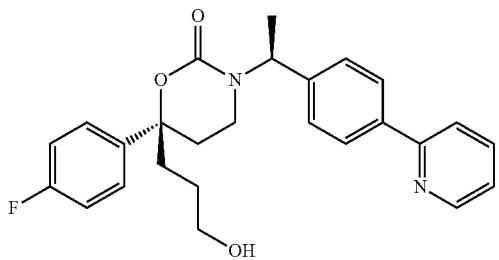 [SMILES: C[C@@H](c1ccc(-c2ccccn2)cc1)N1CC[C@](CCCO)(c2ccc(F)cc2)OC1=O]

The title compound was prepared from (R)-3-((S)-1-(4-bromophenyl)ethyl)-6-(4-fluorophenyl)-6-(3-hydroxypropyl)-1,3-oxazinan-2-one and pyridine-2-boronic acid following a procedure analogous to that described in Example 1 Step 2. LC-MS Method 2 $t_R$=0.905 min, m/z=435.2; $^1$H NMR (CDCl$_3$) 1.22-1.37 (m, 1H), 1.49 (d, 3H), 1.60-1.70 (m, 2H), 1.80-1.97 (m, 2H), 2.07-2.31 (m, 3H), 2.85 (m, 1H), 3.50 (m, 2H), 5.65 (m, 1H), 6.97 (m, 4H), 7.20 (m, 3H), 7.57-7.70 (m, 4H), 8.60 (m, 1H).

EXAMPLE 60

4108.1002-007 Example 433

3-((R)-6-(4-fluorophenyl)-2-oxo-3-((S)-1-(4-(pyridin-2-yl)phenyl)ethyl)-1,3-oxazinan-6-yl)propanamide

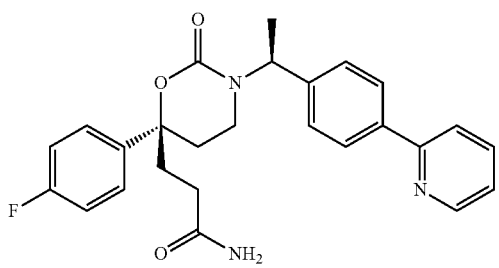 [SMILES: C[C@@H](c1ccc(-c2ccccn2)cc1)N1CC[C@](CCC(N)=O)(c2ccc(F)cc2)OC1=O]

The title compound was prepared from 3-((R)-3-((S)-1-(4-bromophenyl)ethyl)-6-(4-fluorophenyl)-2-oxo-1,3-oxazinan-6-yl)propanamide and pyridine-2-boronic acid following a procedure analogous to that described in Example 1 Step 2. LC-MS Method 2 $t_R$=0.976 min, m/z=448; $^1$H NMR (CDCl$_3$) 1.50 (d, 3H), 1.91 (m, 1H), 2.17-2.23 (m, 5H), 2.41 (m, 1H), 2.86 (m, 1H), 5.18 (m, 1H), 5.32 (m, 1H), 5.66 (m, 1H), 7.00 (m, 4H), 7.18 (m, 3H), 7.57 (d, 1H), 7.69 (m, 3H), 8.58 (d, 1H).

EXAMPLE 61

4108.1002-007 Example 434

N-(3-((R)-6-(4-fluorophenyl)-2-oxo-3-((S)-1-(4-(pyridin-2-yl)phenyl)ethyl)-1,3-oxazinan-6-yl)propyl)methanesulfonamide

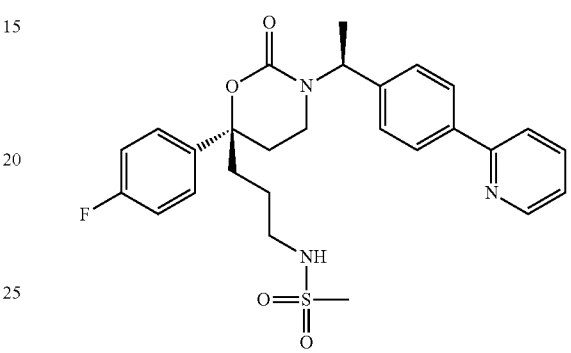

The title compound was prepared from N-(3-((R)-3-((S)-1-(4-bromophenyl)ethyl)-6-(4-fluorophenyl)-2-oxo-1,3-oxazinan-6-yl)propyl)methanesulfonamide and pyridine-2-boronic acid following a procedure analogous to that described in Example 1 Step 2. LC-MS Method 2 $t_R$=1.036 min, m/z=512.1; $^1$H NMR (CDCl$_3$) 1.49 (d, 3H), 1.60-1.70 (m, 1H), 1.84 (m, 1H), 1.89-1.99 (m, 2H), 2.10-2.20 (m, 2H), 2.25 (m, 1H), 2.74 (s, 3H), 3.01 (m, 2H), 4.22 (m, 1H), 5.64 (m, 1H), 6.97 (m, 4H), 7.16 (m, 3H), 7.58 (d, 1H), 7.70 (m, 3H), 8.60 (m, 1H).

EXAMPLE 62

4108.1002-007 Example 435

(R)-6-(4-fluorophenyl)-6-(3-hydroxypropyl)-3-((S)-1-(4-(6-methylpyridin-2-yl)phenyl)ethyl)-1,3-oxazinan-2-one

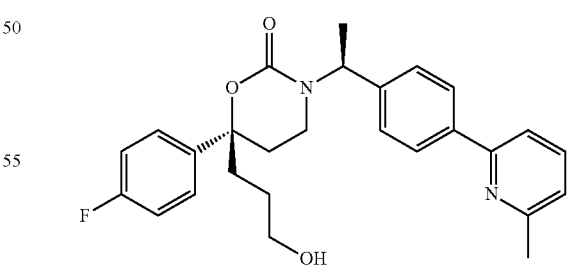

The title compound was prepared from (R)-3-((S)-1-(4-bromophenyl)ethyl)-6-(4-fluorophenyl)-6-(3-hydroxypropyl)-1,3-oxazinan-2-one and 6-methylpyridine-2-boronic acid following a procedure analogous to that described in Example 1 Step 2. LC-MS Method 2 $t_R$=0.868 min, m/z=449.2; $^1$H NMR (CD$_3$OD) 1.28 (m, 1H), 1.56 (d, 3H), 1.61 (m, 1H), 1.95 (m, 2H), 2.23 (m, 1H), 2.34 (m, 1H), 2.46

(m, 1H), 2.55 (s, 3H), 3.11 (m, 1H), 3.46 (m, 2H), 5.50 (m, 1H), 7.06 (m, 4H), 7.19 (d, 1H), 7.31 (m, 2H), 7.51 (d, 1H), 7.73 (m, 3H).

EXAMPLE 63

4108.1002-007 Example 436

(S)-6-(4-fluorophenyl)-6-(2-hydroxyethyl)-3-((S)-1-(4-(6-methoxypyridin-3-yl)phenyl)ethyl)-1,3-oxazinan-2-one

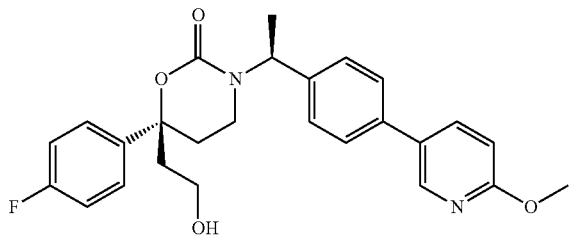 [SMILES: COc1ccc(-c2ccc([C@H](C)N3CC[C@](CCO)(c4ccc(F)cc4)OC3=O)cc2)cn1]

The title compound was prepared from (S)-3-((S)-1-(4-bromophenyl)ethyl)-6-(4-fluorophenyl)-6-(2-hydroxyethyl)-1,3-oxazinan-2-one and 6-methoxypyridine-3-boronic acid following a procedure analogous to that described in Example 1 Step 2. LC-MS Method 2 $t_R$=1.887 min, m/z=450.2; $^1$H NMR (CDCl$_3$) 1.54 (d, 3H), 2.07-2.29 (m, 2H), 2.34 (m, 3H), 2.97 (m, 1H), 3.55 (m, 1H), 3.74 (m, 1H), 4.06 (d, 3H), 5.64 (m, 1H), 6.93 (m, 1H), 6.95-7.11 (m, 2H), 7.26-7.37 (m, 2H), 7.90 (m, 1H), 8.38 (m, 1H).

EXAMPLE 64

4108.1002-007 Example 437

(S)-6-(4-fluorophenyl)-6-(2-hydroxy-2-methylpropyl)-3-((S)-1-(4-(6-methoxypyridin-3-yl)phenyl)ethyl)-1,3-oxazinan-2-one

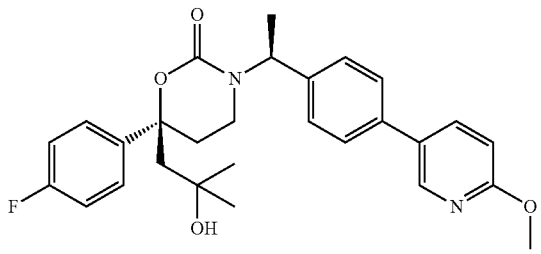

The title compound was prepared from (S)-3-((S)-1-(4-bromophenyl)ethyl)-6-(4-fluorophenyl)-6-(2-hydroxy-2-methylpropyl)-1,3-oxazinan-2-one and 6-methoxypyridine-3-boronic acid following a procedure analogous to that described in Example 1 Step 2. LC-MS Method 3 $t_R$=1.111 min, m/z=478.23; $^1$H NMR (CDCl$_3$) 1.15 (d, 6H), 1.55 (d, 3H), 2.17-2.29 (m, 4H), 2.42 (m, 1H), 2.91 (m, 1H), 3.95 (s, 3H), 5.70 (m, 1H) 6.80 (d, 1H), 7.03 (m, 4H), 7.30 (m, 4H), 7.71 (m, 1H), 8.30 (s, 1H).

EXAMPLE 65

4108.1002-007 Example 438

(R)-6-(4-fluorophenyl)-6-(3-hydroxypropyl)-3-((S)-1-(4-(6-methoxypyridin-3-yl)phenyl)ethyl)-1,3-oxazinan-2-one

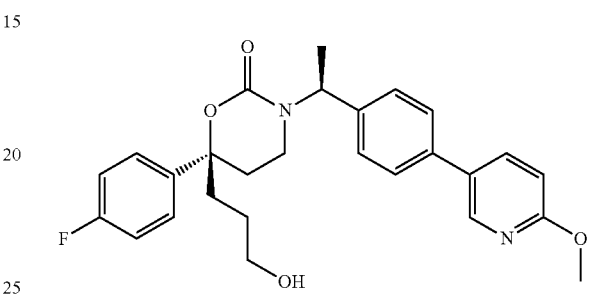

The title compound was prepared from (R)-3-((S)-1-(4-bromophenyl)ethyl)-6-(4-fluorophenyl)-6-(3-hydroxypropyl)-1,3-oxazinan-2-one and 6-methoxypyridine-3-boronic acid following a procedure analogous to that described in Example 1 Step 2. LC-MS Method 2 $t_R$=1.3 min, m/z=487.1; $^1$H NMR (CD$_3$OD) 1.25-1.37 (m, 1H), 1.55 (d, 3H), 1.61 (m, 1H), 1.95 (m, 2H), 2.17-2.28 (m, 1H), 2.36 (m, 1H), 2.48 (m, 1H), 3.12 (m, 1H), 3.48 (m, 2H), 3.94 (s, 3H), 5.58 (m, 1H), 6.86 (d, 1H), 7.07 (m, 4H), 7.35 (m, 4H), 7.86 (dd, 1H), 8.28 (s, 1H).

EXAMPLE 66

4108.1002-007 Example 439

3-((R)-6-(4-fluorophenyl)-3-((S)-1-(4-(6-methoxypyridin-3-yl)phenyl)ethyl)-2-oxo-1,3-oxazinan-6-yl)propanamide

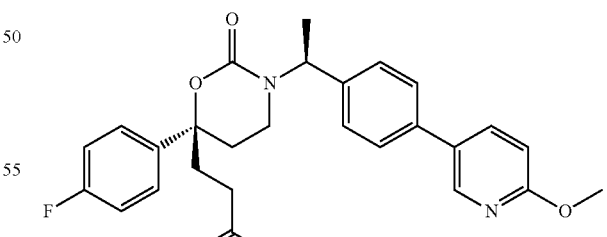

The title compound was prepared from 3-((R)-3-((S)-1-(4-bromophenyl)ethyl)-6-(4-fluorophenyl)-2-oxo-1,3-oxazinan-6-yl)propanamide and 6-methoxypyridine-3-boronic acid following a procedure analogous to that described in Example 1 Step 2. LC-MS Method 2 $t_R$=1.254 min, m/z=477.21; $^1$H NMR (CDCl$_3$) 1.55 (d, 3H), 2.01 (m, 1H), 2.15-2.34 (m, 5H), 2.46 (m, 1H), 2.96 (m, 1H), 4.00 (s, 3H), 5.66 (m, 1H), 5.80 (s, 1H), 6.19 (s, 1H), 6.86 (d, 1H), 7.03 (m, 4H), 7.23 (m, 2H), 7.79 (dd, 1H), 8.36 (s, 1H).

EXAMPLE 67

4108.1002-007 Example 440

N-(3-((R)-6-(4-fluorophenyl)-3-((S)-1-(4-(6-methoxypyridin-3-yl)phenyl)ethyl)-2-oxo-1,3-oxazinan-6-yl)propyl)methanesulfonamide

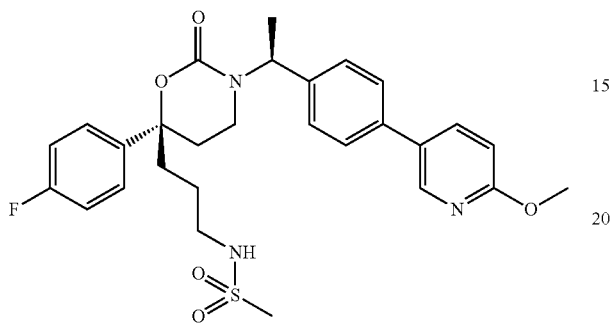

The title compound was prepared from N-(3-((R)-3-((S)-1-(4-bromophenyl)ethyl)-6-(4-fluorophenyl)-2-oxo-1,3-oxazinan-6-yl)propyl)methanesulfonamide and 6-methoxypyridine-3-boronic acid following a procedure analogous to that described in Example 1 Step 2. LC-MS Method 2 $t_R$=1.327 min, m/z=542.1; $^1$H NMR (CD$_3$OD) 1.33 (m, 1H), 1.58 (d, 3H), 1.66 (m, 1H), 1.98 (m, 2H), 2.20-2.39 (m, 2H), 2.47 (m, 1H), 2.87 (s, 3H), 2.99 (m, 2H), 3.15 (m, 1H), 3.96 (s, 3H), 5.60 (m, 1H), 6.87 (d, 1H), 7.12 (m, 4H), 7.36 (m, 4H), 7.87 (d, 1H), 8.29 (s, 1H).

EXAMPLE 68

4108.1002-007 Example 441

3-(4-((S)-1-((R)-6-(3-amino-3-oxopropyl)-6-(4-fluorophenyl)-2-oxo-1,3-oxazinan-3-yl)ethyl)phenyl)pyridine 1-oxide

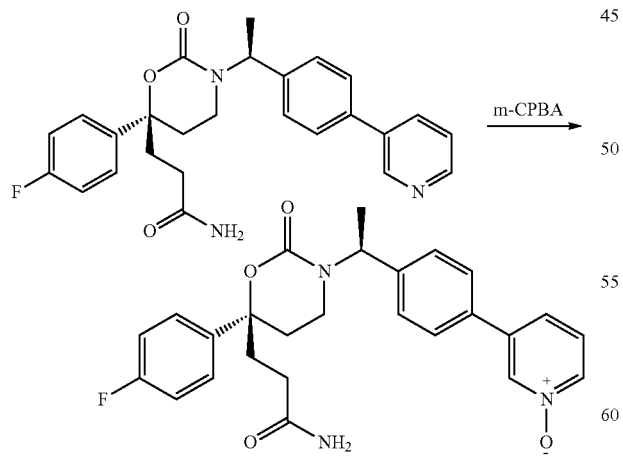

To a solution of 3-((R)-6-(4-fluorophenyl)-2-oxo-3-((S)-1-(4-(pyridin-3-yl)phenyl)ethyl)-1,3-oxazinan-6-yl) propanamide (70 mg, 0.16 mmol) in CH$_2$Cl$_2$ (10 mL), was added m-CPBA (135 mg, 0.79 mmol), and the reaction mixture was stirred at rt for 3 h. After the solvent was removed under reduced pressure, the residue was purified by preparative TLC to afford 3-((R)-6-(4-fluorophenyl)-2-oxo-3-((S)-1-(4-(pyridin-3-yl)phenyl)ethyl)-1,3-oxazinan-6-yl)propanoic acid (10 mg, 15%). LC-MS Method 2 $t_R$=0.987 min, m/z=464.17; $^1$H NMR (CDCl$_3$): 1.51 (m, 3H), 1.92 (m, 1H), 2.12-2.28 (m, 5H), 2.43 (m, 1H), 2.95 (m, 1H), 5.56 (m, 1H), 5.65 (m, 1H), 5.31 (m, 1H), 6.95 (m, 2H), 7.08 (m, 2H), 7.15 (m, 1H), 7.20 (m, 1H), 7.25 (m, 2H), 7.56 (m, 1H), 7.24 (m, 1H), 8.35 (m, 1H), 8.65 (m, 1H).

EXAMPLE 69

4108.1002-007 Example 442

(R)-3-((S)-1-(4-(5-chloropyridin-3-yl)phenyl)ethyl)-6-(4-fluoroPhenyl)-6-(3-hydroxypropyl)-1,3-oxazinan-2-one

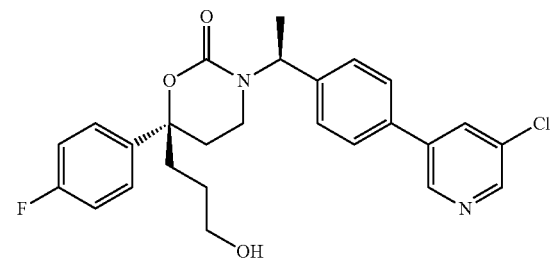 [SMILES: C[C@@H](c1ccc(-c2cncc(Cl)c2)cc1)N1CC[C@](CCCO)(c2ccc(F)cc2)OC1=O]

The title compound was prepared from (R)-3-((S)-1-(4-bromophenyl)ethyl)-6-(4-fluorophenyl)-6-(3-hydroxypropyl)-1,3-oxazinan-2-one and 5-chloropyridine-3-boronic acid following a procedure analogous to that described in Example 14. LC-MS Method 1 $t_R$=1.64 min, m/z=469.

EXAMPLE 70

4108.1002-007 Example 443

3-((R)-6-(4-fluorophenyl)-3-((S)-1-(4-(5-fluoropyridin-3-yl)phenyl)ethyl)-2-oxo-1,3-oxazinan-6-yl)propanoic acid

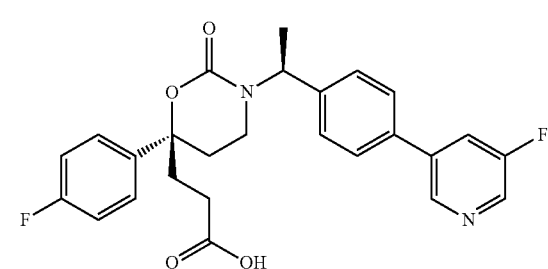 [SMILES: C[C@@H](c1ccc(-c2cncc(F)c2)cc1)N1CC[C@](CCC(=O)O)(c2ccc(F)cc2)OC1=O]

The title compound was prepared from (R)-6-(4-fluorophenyl)-3-((S)-1-(4-(5-fluoropyridin-3-yl)phenyl)ethyl)-6-(3-hydroxypropyl)-1,3-oxazinan-2-one following a procedure analogous to that described in Example 14. LC-MS Method 1 $t_R$=1.52 min, m/z=467.

EXAMPLE 71

4108.1002-007 Example 444

5-(4-((S)-1-((R)-6-(4-fluorophenyl)-6-(3-hydroxypropyl)-2-oxo-1,3-oxazinan-3-yl)ethyl)phenyl)nicotinamide

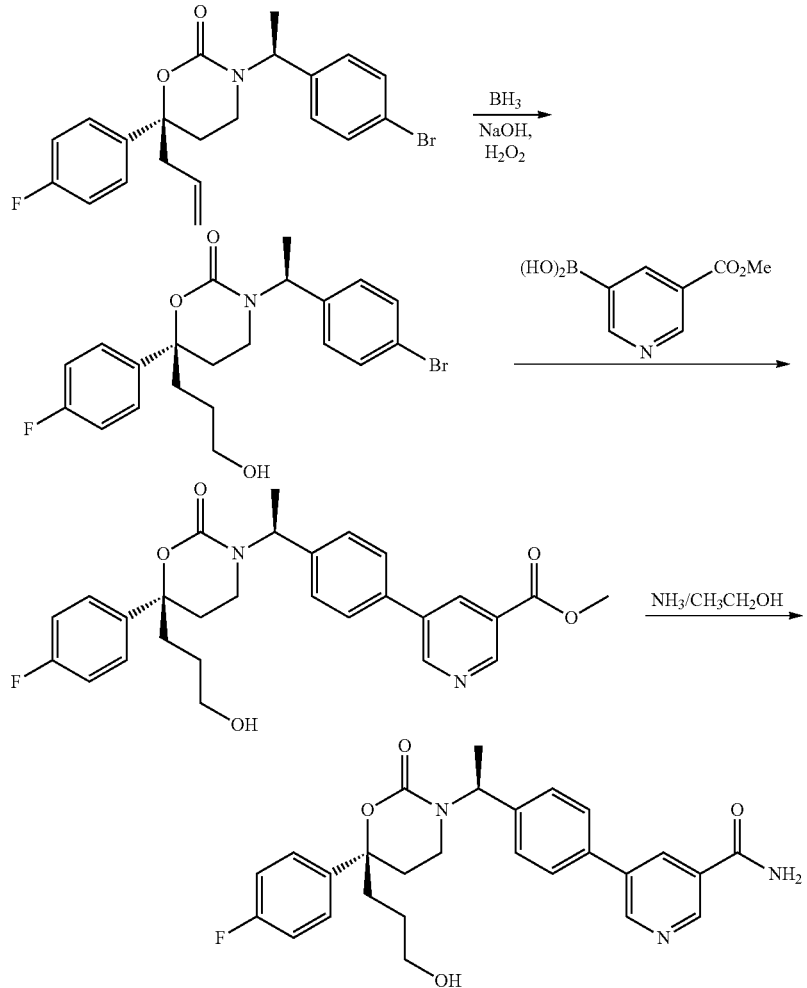

Step 1

To a solution of (R)-6-allyl-3-((S)-1-(4-bromophenyl)ethyl)-6-(4-fluorophenyl)-1,3-oxazinan-2-one (1 g, 2.4 mmol) in dry THF (15 mL) was added dropwise $BH_3$.THF (5 mL, 1 M) at 0° C. After stirring for 2 h at rt, the reaction mixture was cooled to 0° C. and water (1 mL), aqueous NaOH (0.5 mL, 3 M) and $H_2O_2$ (0.5 mL, 30%) were successively added. The mixture was stirred for 2-3 h at rt and diluted with water (8 mL). The pH was adjusted to 6-7 with 0.5 N HCl. The layers were separated, and the aqueous phase was extracted with EtOAc (3×10 mL). The combined organic layers were washed with a satd aq $NaHCO_3$ (20 mL) and brine (20 mL), dried over $Na_2SO_4$, and concentrated in vacuo to give the crude product, which was purified by preparative TLC to afford (R)-3-((S)-1-(4-bromophenyl)ethyl)-6-(4-fluorophenyl)-6-(3-hydroxypropyl)-1,3-oxazinan-2-one (400 mg, 38%).

Step 2

A mixture of (R)-3-((S)-1-(4-bromophenyl)ethyl)-6-(4-fluorophenyl)-6-(3-hydroxypropyl)-1,3-oxazinan-2-one (250 mg, 0.6 mmol), 5-(methoxycarbonyl)pyridin-3-ylboronic acid (163 mg, 0.9 mmol), $PdCl_2(PPh_3)_2$ (50 mg, 20%) and aqueous $Cs_2CO_3$ solution (2 M, 2 mL) in 1,4-dioxane (6 mL) was heated to reflux at 100° C. overnight under $N_2$. The mixture was filtered, and the filtrate was extracted with EtOAc for 3 times. The combined organic layer was washed with brine, dried over $Na_2SO_4$ and concentrated to the crude product, which was purified by preparative HPLC to give methyl 5-(4-((S)-1-((R)-6-(4-fluorophenyl)-6-(3-hydroxypropyl)-2-oxo-1,3-oxazinan-3-yl)ethyl)phenyl)nicotinate (220 mg, crude).

Step 3

Methyl 5-(4-((S)-1-((R)-6-(4-fluorophenyl)-6-(3-hydroxypropyl)-2-oxo-1,3-oxazinan-3-yl)ethyl)phenyl)nicotinate (30 mg, 0.1 mmol) was dissolved in anhydrous $NH_3$ in EtOH (5 mL). Then the mixture was stirred at rt overnight. The solvent was removed in vacuo to give the crude product, which was purified by preparative HPLC to provide 5-(4-((S)-1-((R)-6-(4-luorophenyl)-6-(3-hydroxypropyl)-2-oxo-1,3-oxazinan-3-yl)ethyl)phenyl)nicotinamide (10 mg, 34%). LC-MS Method 2 t$_R$=1.022 min, m/z=478; $^1$H NMR (CD$_3$OD): 1.31 (m, 1H), 1.56 (m, 3H), 1.59 (m, 1H), 1.91 (m, 2H), 2.17-2.28 (m, 1H), 2.33 (m, 1H), 2.44 (m, 1H), 3.14 (m, 1H), 3.44 (m, 2H), 5.60 (m, 1H), 7.04-7.17 (m, 4H), 7.29 (m, 2H), 7.49 (m, 2H), 8.41 (m, 1H), 8.86 (m, 1H), 8.97 (m, 1H).

EXAMPLE 72

4108.1002-007 Example 445

5-(4-((S)-1-((R)-6-(4-fluorophenyl)-6-(3-hydroxypropyl)-2-oxo-1,3-oxazinan-3-yl)ethyl)phenyl)-N,N-dimethylnicotinamide

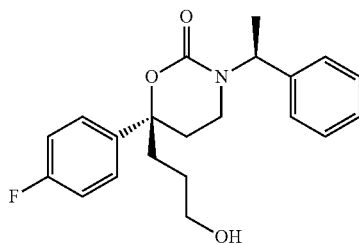

The title compound was prepared methyl 5-(4-((S)-1-((R)-6-(4-fluorophenyl)-6-(3-hydroxypropyl)-2-oxo-1,3-oxazinan-3-yl)ethyl)phenyl)nicotinate following a procedure analogous to that described in Example 71 Step 3 using dimethylamine in place of ammonia. LC-MS Method 2 t$_R$=1.086 min, m/z=506.3; $^1$H NMR (CDCl$_3$) 0.87 (m, 1H), 1.21-1.37 (m, 4H), 1.64 (m, 1H), 1.98 (m, 2H), 2.22 (m, 1H), 2.35 (m, 1H), 2.54 (m, 1H), 2.65 (m, 1H), 3.05 (m, 3H), 3.15 (m, 4H), 3.45 (m, 2H), 5.63 (m, 1H), 7.03-7.18 (m, 4H), 7.34 (m, 2H), 7.49 (m, 2H), 8.06 (m, 1H), 8.58 (m, 1H), 8.81 (m, 1H).

EXAMPLE 73

Example 4108.1002-007 Example 446

5-(4-((S)-1-((R)-6-(4-fluorophenyl)-6-(3-hydroxypropyl)-2-oxo-1,3-oxazinan-3-yl)ethyl)phenyl)-N-methylnicotinamide

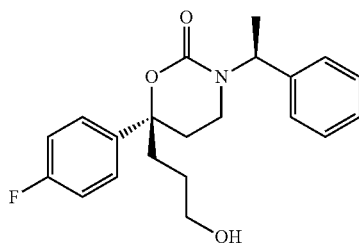

The title compound was prepared methyl 5-(4-((S)-1-((R)-6-(4-fluorophenyl)-6-(3-hydroxypropyl)-2-oxo-1,3-oxazinan-3-yl)ethyl)phenyl)nicotinate following a procedure analogous to that described in Example 71 Step 3 using methylamine in place of ammonia. LC-MS Method 2 t$_R$=1.055 min, m/z=491.12; $^1$H NMR (CD$_3$OD) 1.18 (m, 1H), 1.48 (d, 3H), 1.51 (m, 1H), 1.85 (m, 2H), 2.13 (m, 1H), 2.25 (m, 1H), 2.48 (m, 1H), 2.88 (s, 3H), 3.09 (m, 1H), 3.38 (m, 2H), 5.51 (m, 1H), 6.98-7.07 (m, 4H), 7.22 (m, 2H), 7.42 (m, 2H), 8.28 (m, 1H), 8.75 (s, 1H), 8.82 (s, 1H).

EXAMPLE 74

4108.1002-007 Example 447

3-((R)-6-(4-fluorophenyl)-2-oxo-3-((S)-1-(4-(pyridin-4-yl)phenyl)ethyl)-1,3-oxazinan-6-yl)propanamide

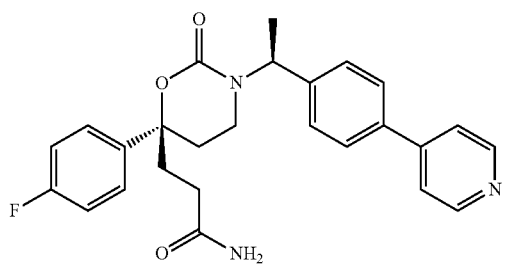 [SMILES: C[C@@H](c1ccc(-c2ccncc2)cc1)N1CC[C@](CCC(N)=O)(c2ccc(F)cc2)OC1=O]

The title compound was prepared from 3-((R)-3-((S)-1-(4-bromophenyl)ethyl)-6-(4-fluorophenyl)-2-oxo-1,3-oxazinan-6-yl)propanamide and pyridine-4-boronic acid following a procedure analogous to that described in Example 1 Step 2. LC-MS Method 2 t$_R$=0.906 min, m/z=448.1; $^1$H NMR (CDCl$_3$) 1.59 (d, 3H), 2.15 (m, 1H), 2.24-2.32 (m, 4H), 2.45 (m, 1H), 3.07 (m, 2H), 5.66 (m, 1H), 5.71 (m, 1H), 5.84 (m, 1H), 7.03 (m, 2H), 7.05 (m, 2H), 7.22 (m, 1H), 7.25 (m, 1H), 7.50 (d, 2H), 7.93 (d, 2H), 8.84 (d, 2H).

EXAMPLE 75

4108.1002-007 Example 448

(S)-6-(4-fluorophenyl)-6-(2-hydroxyethyl)-3-((S)-1-(4-(2-methylpyridin-4-yl)phenyl)ethyl)-1,3-oxazinan-2-one

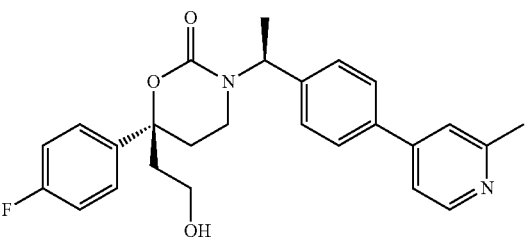 [SMILES: Cc1cc(-c2ccc([C@H](C)N3CC[C@](CCO)(c4ccc(F)cc4)OC3=O)cc2)ccn1]

The title compound was prepared from (S)-3-((S)-1-(4-bromophenyl)ethyl)-6-(4-fluorophenyl)-6-(2-hydroxyethyl)-1,3-oxazinan-2-one and 2-methylpyridine-4-boronic acid following a procedure analogous to that described in Example 1 Step 2. LC-MS Method 2 t$_R$=0.945 min, m/z=435.5; $^1$H NMR (CD$_3$OD) 1.56 (d, 3H), 1.92 (m, 1H), 2.01 (m, 1H), 2.17 (m, 2H), 2.36 (m, 2H), 2.48 (m, 1H), 2.56

(m, 3H), 3.12 (m, 1H), 3.62 (m, 1H), 5.62 (m, 1H), 7.05 (m, 4H), 7.30 (m, 2H), 7.44 (m, 1H), 7.54 (m, 3H), 8.39 (s, 2H).

EXAMPLE 76

4108.1002-007 Example 449

(S)-6-(4-fluorophenyl)-6-(2-hydroxy-2-methylpropyl)-3-((S)-1-(4-(2-methylpyridin-4-yl)phenyl)ethyl)-1,3-oxazinan-2-one

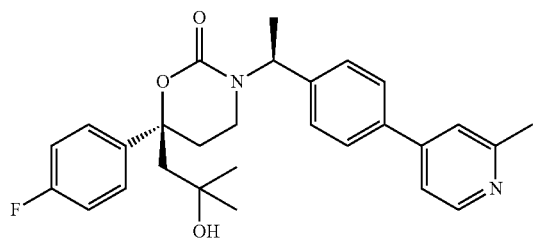 [SMILES: Cc1cc(-c2ccc([C@H](C)N3CC[C@](CC(C)(C)O)(c4ccc(F)cc4)OC3=O)cc2)ccn1]

The title compound was prepared from (S)-3-((S)-1-(4-bromophenyl)ethyl)-6-(4-fluorophenyl)-6-(2-hydroxy-2-methylpropyl)-1,3-oxazinan-2-one and 2-methylpyridine-4-boronic acid following a procedure analogous to that described in Example 1 Step 2. LC-MS Method 2 $t_R$=0.976 min, m/z=463.8; $^1$H NMR (CDCl$_3$) 1.09 (d, 6H), 1.49 (d, 3H), 2.16 (m, 4H), 2.35 (m, 1H), 2.56 (d, 3H), 2.85 (m, 1H), 5.65 (m, 1H), 6.94-7.05 (m, 4H), 7.17-7.26 (m, 4H), 7.34 (d, 2H), 8.47 (d, 1H).

EXAMPLE 77

4108.1002-007 Example 450

3-((R)-6-(4-fluorophenyl)-3-((S)-1-(4-(2-methylpyridin-4-yl)phenyl)ethyl)-2-oxo-1,3-oxazinan-6-yl)propanoic acid

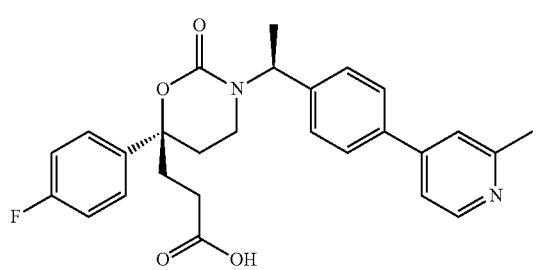 [SMILES: Cc1cc(-c2ccc([C@H](C)N3CC[C@](CCC(=O)O)(c4ccc(F)cc4)OC3=O)cc2)ccn1]

The title compound was prepared from (R)-6-(4-fluorophenyl)-6-(3-hydroxypropyl)-3-((S)-1-(4-(2-methylpyridin-4-yl)phenyl)ethyl)-1,3-oxazinan-2-one following procedures analogous to those described in Example 12 Step 2. LC-MS Method 1 $t_R$=1.05 min, m/z=463.

EXAMPLE 78

4108.1002-007 Example 451

3-((R)-6-(4-fluorophenyl)-3-((S)-1-(4-(2-methylpyridin-4-yl)phenyl)ethyl)-2-oxo-1,3-oxazinan-6-yl)propanamide

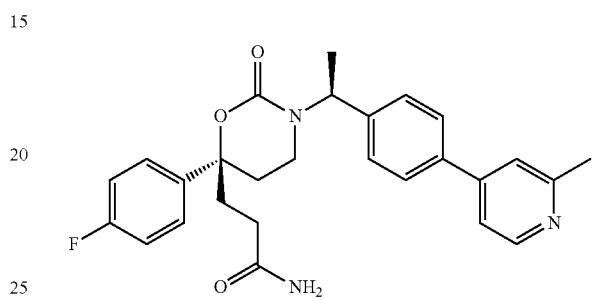

The title compound was prepared from 3-((R)-6-(4-fluorophenyl)-3-((S)-1-(4-(2-methylpyridin-4-yl)phenyl)ethyl)-2-oxo-1,3-oxazinan-6-yl)propanoic acid following procedures analogous to those described in Example 1 Step 2. LC-MS Method 2 $t_R$=0.793 min, m/z=462.2; $^1$H NMR (CDCl$_3$) 1.51 (d, 3H), 2.12-2.38 (m, 6H), 2.43 (m, 1H), 2.61 (s, 3H), 2.89 (m, 1H), 5.10-5.34 (d, 2H), 5.66 (m, 1H), 6.99 (m, 4H), 7.17-7.27 (m, 4H), 7.36 (d, 2H), 8.46 (d, 1H).

EXAMPLE 79

4108.1002-007 Example 452

(R)-6-(4-fluorophenyl)-6-(3-hydroxy-3-methylbutyl)-3-((S)-1-(4-(2-methylpyridin-4-yl)phenyl)ethyl)-1,3-oxazinan-2-one

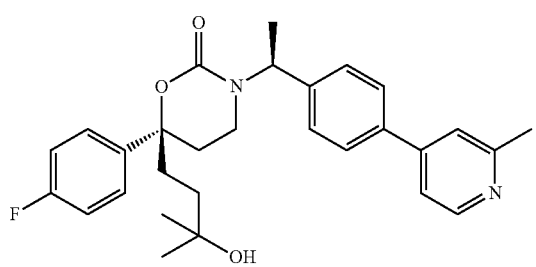 [SMILES: Cc1cc(-c2ccc([C@H](C)N3CC[C@](CCC(C)(C)O)(c4ccc(F)cc4)OC3=O)cc2)ccn1]

The title compound was prepared from (R)-6-(4-fluorophenyl)-6-(3-hydroxypropyl)-3-((S)-1-(4-(2-methylpyridin-4-yl)phenyl)ethyl)-1,3-oxazinan-2-one by treatment with (i) Jones reagent, (ii) MeOH, SOCl$_2$ and (iii) MeMgBr. LC-MS Method 2 $t_R$=0.992 min, m/z=477.5; $^1$H NMR (CDCl$_3$) 1.08 (d, 6H), 1.15 (m, 1H), 1.52 (d, 3H), 1.59 (m, 1H), 1.84-2.01 (m, 2H), 2.15-2.34 (m, 3H), 2.83 (s, 3H), 2.98

(m, 1H), 5.67 (m, 1H), 6.96 (t, 2H), 7.09 (d, 2H), 7.20 (m, 2H), 7.41 (d, 2H), 7.65 (d, 2H), 8.75 (s, 1H).

EXAMPLE 80

4108.1002-007 Example 453

N-(3-((R)-6-(4-fluorophenyl)-3-((S)-1-(4-(2-methylpyridin-4-yl)phenyl)ethyl)-2-oxo-1,3-oxazinan-6-yl)propyl)methanesulfonamide

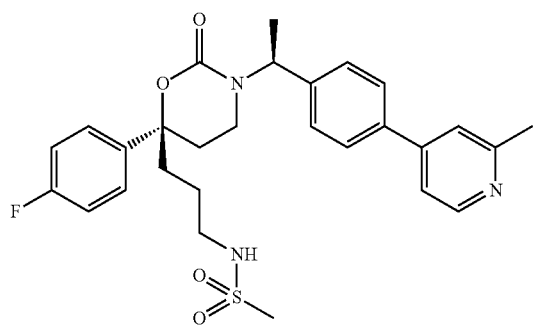 [SMILES: Cc1cc(-c2ccc([C@H](C)N3CC[C@](CCCNS(C)(=O)=O)(c4ccc(F)cc4)OC3=O)cc2)ccn1]

The title compound was prepared from N-(3-((R)-3-((S)-1-(4-bromophenyl)ethyl)-6-(4-fluorophenyl)-2-oxo-1,3-oxazinan-6-yl)propyl)methanesulfonamide and 2-methylpyridine-4-boronic acid Example 1 Step 2. LC-MS Method 2 $t_R$=0.964 min, m/z=525.21; $^1$H NMR (CDCl$_3$) 1.31-1.43 (m, 1H), 1.50 (d, 3H), 1.62 (m, 2H), 1.07-2.09 (m, 2H), 2.13-2.47 (m, 3H), 2.83 (d, 6H), 3.01 (m, 3H), 4.35 (s, 1H), 5.66 (m, 1H) 7.07 (m, 2H), 7.14 (m, 2H), 7.29 (m, 5H), 7.44 (m, 2H), 7.65 (m, 1H), 7.73 (d, 1H), 8.78 (d, 1H).

EXAMPLE 81

4108.1002-007 Example 454

(R)-3-((S)-1-(4-(2,6-dimethylpyridin-4-yl)phenyl)ethyl)-6-(4-fluorophenyl)-6-(3-hydroxypropyl)-1,3-oxazinan-2-one

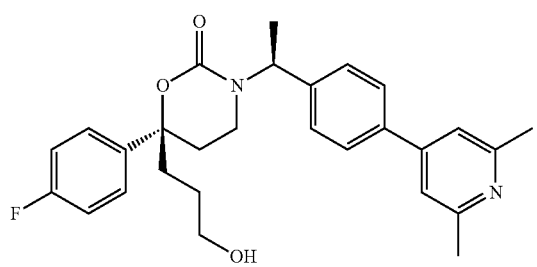

The title compound was prepared from (R)-6-(4-fluorophenyl)-6-(3-hydroxypropyl)-3-((S)-1-(4-(4,4,5,5-tetramethyl-1,3,2-dioxaborolan-2-yl)phenyl)ethyl)-1,3-oxazinan-2-one and 4-bromo-2,6-dimethylpyridine-N-oxide using a procedure analogous to that described in Example 14, followed by treatment with disiamyl borane. LC-MS Method 1 $t_R$=1.1 min, m/z=463 (M+1); $^1$H NMR (CDCl$_3$) 7.50 (s, 2H), 7.45 (d, 1H), 7.25 (m, 3H), 7.17-6.99 (m, 4H), 5.73 (q, 1H), 4.28 (t, 1H), 3.04 (m, 1H), 2.82 (s, 6H), 2.31 (m, 3H), 1.91 (m, 3H), 1.58 (d, 3H).

EXAMPLE 82

4108.1002-007 Example 455

(R)-6-(4-fluorophenyl)-6-(3-hydroxypropyl)-3-((S)-1-(4-(thiazol-2-yl)phenyl)ethyl)-1,3-oxazinan-2-one

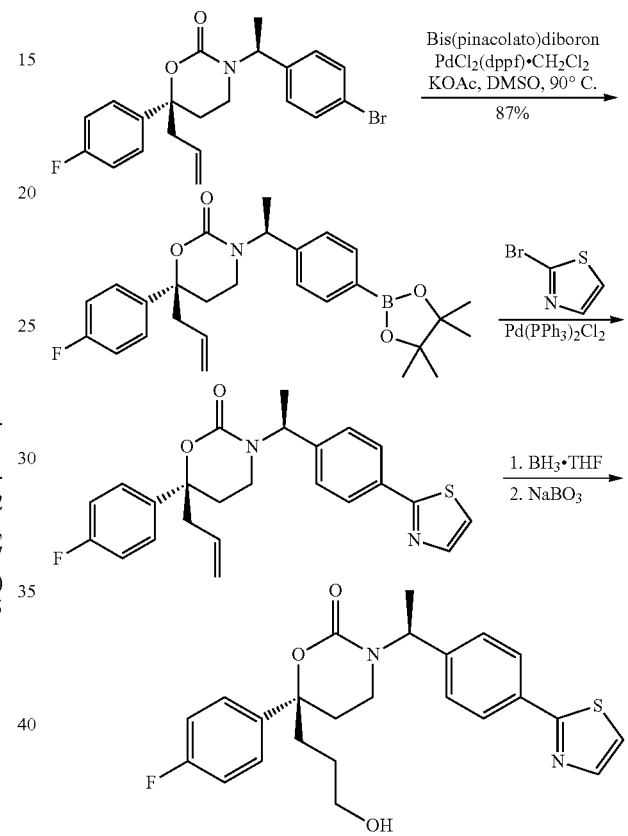

Step 1

A mixture of (R)-6-allyl-3-((S)-1-(4-bromophenyl)ethyl)-6-(4-fluorophenyl)-1,3-oxazinan-2-one (0.4910 g, 1.17 mmol, 1.0 equiv), bis(pinacolato)diboron (0.3925 g, 1.55 mmol, 1.3 equiv), KOAc (0.3696 g, 3.76 mmol, 3.2 equiv), and PdCl$_2$(dppf).CH$_2$Cl$_2$ (0.0316 g, 0.0386 mmol, 0.033 equiv) in DMSO (6 mL) was heated at 90° C. under N$_2$ for 20 h. After cooling, the reaction mixture was partitioned between EtOAc and water. The organic phase was washed with brine, and dried over Na$_2$SO$_4$. After the solvents were evaporated, the residue was purified by chromatography on silica gel eluted with hexanes/ethyl acetate to give 0.4776 g (87%) of (R)-6-allyl-6-(4-fluorophenyl)-3-((S)-1-(4-(4,4,5,5-tetramethyl-1,3,2-dioxaborolan-2-yl)phenyl)ethyl)-1,3-oxazinan-2-one as a white solid.

Step 2

(R)-6-allyl-6-(4-fluorophenyl)-3-((S)-1-(4-(4,4,5,5-tetramethyl-1,3,2-dioxaborolan-2-yl)phenyl)ethyl)-1,3-oxazinan-2-one (20 mg, 0.043 mmol), 2-bromothiazole (14 mg, 2 equiv), 2M aq Na₂SO₄ solution (0.5 mL) and Pd(PPh₃)₂Cl₂ were mixed with THF (0.6 mL) and heated in a microwave oven for 2 h at 140° C. LC-MS found reaction completed. The mixture was diluted with EtOAc (8 mL), washed with water (2 mL), 1% aq HCl (2 mL) and brine (1.5 mL). After concentration, the residue was purified by preparative HPLC to afford (R)-6-allyl-6-(4-fluorophenyl)-3-((S)-1-(4-(thiazol-2-yl)phenyl)ethyl)-1,3-oxazinan-2-one (6.0 mg, 33%). LC-MS (3 min) $t_R$=1.86 min, m/z=423 (M+1).

Step 3

(R)-6-allyl-6-(4-fluorophenyl)-3-((S)-1-(4-(thiazol-2-yl)phenyl)ethyl)-1,3-oxazinan-2-one (6.0 mg, 0.014 mmol) was dissolved in dry THF (2 mL) and cooled to 0° C. BH₃-THF (1.0M, 100 µL, excess) was added slowly. After 10 min, the mixture was warmed to it and stirred for 3 h. LC-MS found reaction completed. The mixture was quenched with water (1 mL). NaBO₃ (ca 4 mg) was added. The mixture was stirred 40 min, filtered, concentrated and purified by preparative HPLC to afford (R)-3-((S)-1-(4-(2,6-dimethylpyridin-4-yl)phenyl)ethyl)-6-(4-fluorophenyl)-6-(3-hydroxypropyl)-1,3-oxazinan-2-one (3.4 mg, 54%), LC-MS (3 min) $t_R$=1.86 min, m/z=423 (M+1). LC-MS Method 1 $t_R$=1.86 min, m/z=423 (M+1); ¹H NMR (CDCl₃) 7.71 (m, 2H), 7.40-7.22 (m, 4H), 7.16-7.03 (m, 3H), 6.96 (m, 1H), 5.66 (m, 1H), 2.96 (m, 1H), 1.54 (d, 3H).

EXAMPLE 83

4108.1002-007 Example 456

(R)-3-((S)-1-(4-(2,4-dimethylthiazol-5-yl)phenyl)ethyl)-6-(4-fluorophenyl)-6-(3-hydroxypropyl)-1,3-oxazinan-2-one

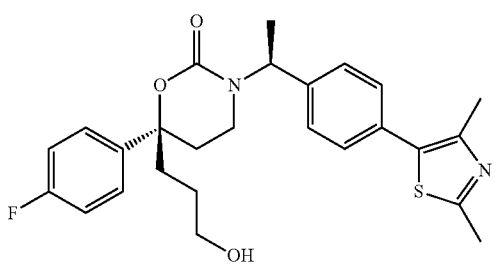 [SMILES: Cc1nc(C)c(-c2ccc([C@H](C)N3CC[C@](CCCO)(c4ccc(F)cc4)OC3=O)cc2)s1]

The title compound was prepared from (R)-6-allyl-3-((S)-1-(4-bromophenyl)ethyl)-6-(4-fluorophenyl)-1,3-oxazinan-2-one and 2,4-dimethylthiazole-5-boronic acid using a procedure analogous to that described in Example 14, followed by a procedure analogous to that described in Example 12. LC-MS Method 1 $t_R$=1.49 min, m/z=469; ¹H NMR (CDCl₃) 7.28 (m, 2H), 7.15 (d, 2H), 7.03 (q, 4H), 5.68 (q, 1H), 3.59 (t, 1H), 3.02 (m, 1H), 2.91 (s, 3H), 2.48 (s, 3H), 1.55 (d, 3H).

EXAMPLE 84

4108.1002-007 Example 457

3-((R)-3-((S)-1-(4-(2,4-dimethylthiazol-5-yl)phenyl)ethyl)-6-(4-fluorophenyl)-2-oxo-1,3-oxazinan-6-yl)propanamide

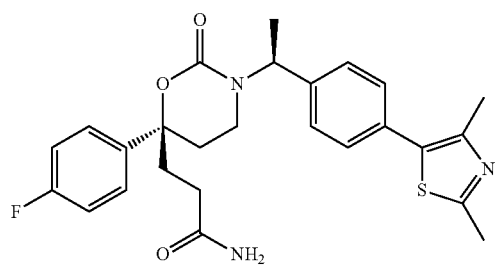 [SMILES: Cc1nc(C)c(-c2ccc([C@H](C)N3CC[C@](CCC(N)=O)(c4ccc(F)cc4)OC3=O)cc2)s1]

The title compound was prepared from (R)-3-((S)-1-(4-(2,4-dimethylthiazol-5-yl)phenyl)ethyl)-6-(4-fluorophenyl)-6-(3-hydroxypropyl)-1,3-oxazinan-2-one employing a procedure analogous to that described in Example 12 Step 2, followed by a procedure analogous to that described in Example 8 Step 2 using ammonia. LC-MS Method 1 $t_R$=1.38 min, m/z=482 (M+1); ¹H NMR (CDCl₃) 7.32 (m, 5H), 7.18 (d, 2H), 7.04 (m, 4H), 5.69 (q, 1H), 2.84 (s, 3H), 2.45 (s, 3H), 2.02 (m, 1H), 1.55 (d, 3H).

EXAMPLE 85

4108.1002-007 Example 468

(S)-6-(2-hydroxyethyl)-6-phenyl-3-((S)-1-(4-(pyridin-2-yl)phenyl)ethyl)-1,3-oxazinan-2-one

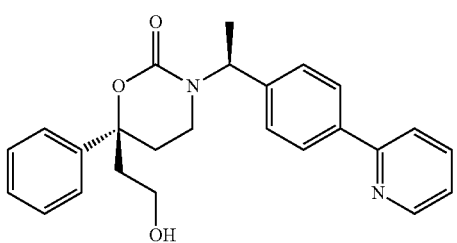 [SMILES: C[C@@H](c1ccc(-c2ccccn2)cc1)N1CC[C@](CCO)(c2ccccc2)OC1=O]

The title compound was prepared from (S)-3-((S)-1-(4-bromophenyl)ethyl)-6-(2-hydroxyethyl)-6-phenyl-1,3-oxazinan-2-one and pyridine-2-boronic acid following procedures analogous to those described in Example 1 Step 2. LC-MS Method 2 $t_R$=0.976 min, m/z=805.3; ¹H NMR (CDCl₃) 1.50 (d, 2H), 2.06-2.19 (m, 2H), 2.26 (m, 3H), 2.83

(m, 1H), 3.53 (m, 1H), 3.71 (m, 1H), 5.64 (m, 1H), 6.94 (d, 2H), 7.14 (m, 1H), 7.24 (m, 3H), 7.28 (m, 2H), 7.56 (d, 2H), 7.67 (m, 3H), 8.59 (d, 1H).

EXAMPLE 86

4108.1002-007 Example 469

(S)-6-(2-hydroxy-2-methylpropyl)-6-phenyl-3-((S)-1-(4-(pyridin-2-yl)phenyl)ethyl)-1,3-oxazinan-2-one

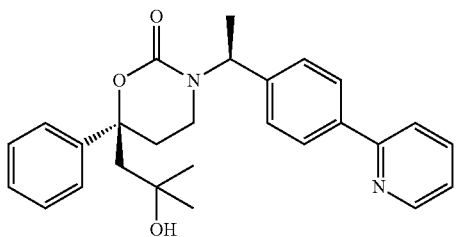 [SMILES: C[C@@H](c1ccc(-c2ccccn2)cc1)N1CC[C@](CC(C)(C)O)(c2ccccc2)OC1=O]

The title compound was prepared from (S)-3-((S)-1-(4-bromophenyl)ethyl)-6-(2-hydroxy-2-methylpropyl)-6-phenyl-1,3-oxazinan-2-one and pyridine-2-boronic acid following procedures analogous to those described in Example 1 Step 2. LC-MS Method 2 $t_R$=1.542 min, m/z=430.23; $^1$H NMR (CDCl$_3$) 1.02-1.15 (d, 6H), 1.50 (d, 3H), 2.09-2.21 (m, 6H), 2.32 (m, 1H), 2.78 (m, 1H), 5.65 (m, 1H), 6.98 (d, 2H), 7.15-7.30 (m, 6H), 7.55 (m, 1H), 7.70 (d, 1H), 8.60 (d, 1H).

EXAMPLE 87

4108.1002-007 Example 470

(R)-6-(3-hydroxypropyl)-6-phenyl-3-((S)-1-(4-(pyridin-2-yl)phenyl)ethyl)-1,3-oxazinan-2-one

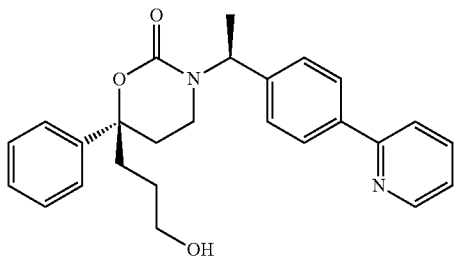 [SMILES: C[C@@H](c1ccc(-c2ccccn2)cc1)N1CC[C@](CCCO)(c2ccccc2)OC1=O]

The title compound was prepared from (R)-3-((S)-1-(4-bromophenyl)ethyl)-6-(3-hydroxypropyl)-6-phenyl-1,3-oxazinan-2-one and pyridine-2-boronic acid following procedures analogous to those described in Example 1 Step 2. LC-MS Method 2 $t_R$=1.01 min, m/z=416.21; $^1$H NMR (CD$_3$OD) 1.30 (m, 1H), 1.55 (d, 3H), 1.62 (m, 1H), 1.94 (m, 2H), 2.20 (m, 1H), 2.32 (m, 1H), 2.48 (m, 1H), 3.09 (m, 1H), 3.44 (m, 2H), 5.57 (m, 1H), 7.03 (d, 2H), 7.29-7.40 (m, 6H), 7.67 (d, 2H), 7.73 (d, 1H), 7.84 (t, 1H), 8.55 (d, 1H).

EXAMPLE 88

4108.1002-007 Example 471

3-((R)-2-oxo-6-phenyl-3-((S)-1-(4-(pyridin-2-yl)phenyl)ethyl)-1,3-oxazinan-6-yl)propanamide

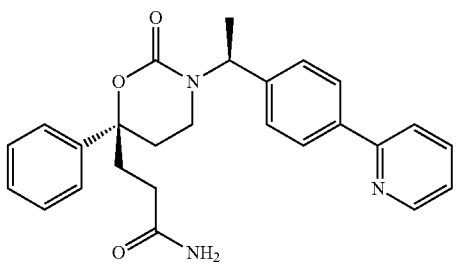 [SMILES: C[C@@H](c1ccc(-c2ccccn2)cc1)N1CC[C@](CCC(N)=O)(c2ccccc2)OC1=O]

The title compound was prepared from 3-((R)-3-((S)-1-(4-bromophenyl)ethyl)-2-oxo-6-phenyl-1,3-oxazinan-6-yl)propanamide and pyridine-2-boronic acid following procedures analogous to those described in Example 1 Step 2. LC-MS Method 2 $t_R$=0.932 min, m/z=430.1; $^1$H NMR (CDCl$_3$) 1.52 (d, 3H), 1.90 (m, 1H), 2.13 (m, 1H), 2.21 (m, 4H), 2.45 (m, 1H), 2.82 (m, 1H), 5.15 (s, 1H), 5.35 (s, 1H), 5.65 (m, 1H), 6.98 (d, 2H), 7.13-7.32 (m, 6H), 7.56 (m, 1H), 7.65 (m, 3H), 8.57 (d, 1H).

EXAMPLE 89

4108.1002-007 Example 472

N-(3-((R)-2-oxo-6-phenyl-3-((S)-1-(4-(pyridin-2-yl)phenyl)ethyl)-1,3-oxazinan-6-yl)propyl)methanesulfonamide

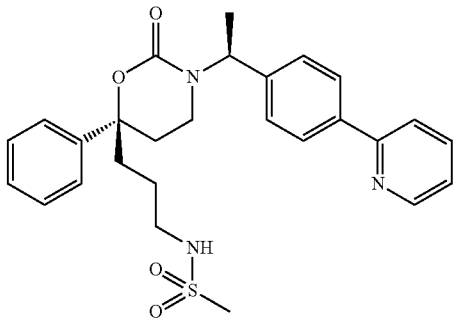 [SMILES: C[C@@H](c1ccc(-c2ccccn2)cc1)N1CC[C@](CCCNS(C)(=O)=O)(c2ccccc2)OC1=O]

The title compound was prepared from N-(3-((R)-3-((S)-1-(4-bromophenyl)ethyl)-2-oxo-6-phenyl-1,3-oxazinan-6-yl)propyl)methanesulfonamide and pyridine-2-boronic acid following procedures analogous to those described in Example 1 Step 2. LC-MS Method 2 $t_R$=1.017 min, m/z=494.1; $^1$H NMR (CDCl$_3$) 1.37-1.48 (m, 1H), 1.49 (d, 3H), 1.67 (m, 1H), 1.82-1.99 (m, 2H), 2.05-2.18 (m, 1H), 2.12-2.23 (m, 2H), 2.82 (m, 4H), 3.00 (m, 2H), 4.25 (m, 1H), 5.65 (m, 1H), 6.96 (d, 2H), 7.14-7.29 (m, 6H), 7.55 (d, 1H), 7.65 (m, 3H), 8.58 (d, 1H).

EXAMPLE 90

4108.1002-007 Example 473

(R)-6-(3-hydroxypropyl)-3-((S)-1-(4-(6-methylpyridin-2-yl)phenyl)ethyl)-6-phenyl-1,3-oxazinan-2-one

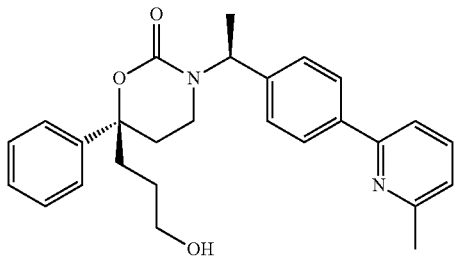 [SMILES: Cc1cccc(-c2ccc([C@H](C)N3CC[C@](CCCO)(c4ccccc4)OC3=O)cc2)n1]

The title compound was prepared from (R)-3-((S)-1-(4-bromophenyl)ethyl)-6-(3-hydroxypropyl)-6-phenyl-1,3-oxazinan-2-one and 6-methylpyridine-2-boronic acid following procedures analogous to those described in Example 1 Step 2. LC-MS Method 2 $t_R$=0.986 min, m/z=431.1; $^1$H NMR (CDCl$_3$) 1.33 (m, 2H), 1.52 (d, 3H), 1.69 (m, 1H), 1.97 (m, 2H), 2.12-2.30 (m, 3H), 2.56 (s, 3H), 2.85 (m, 1H), 3.52 (t, 2H), 5.67 (m, 1H), 6.95 (d, 2H), 7.03 (d, 1H), 7.22-7.37 (m, 6H), 7.55 (t, 1H), 7.64 (d, 2H).

EXAMPLE 91

4108.1002-007 Example 474

N-(3-((R)-2-oxo-6-phenyl-3-((S)-1-(4-(pyridin-3-yl)phenyl)ethyl)-1,3-oxazinan-6-yl)propyl)methanesulfonamide

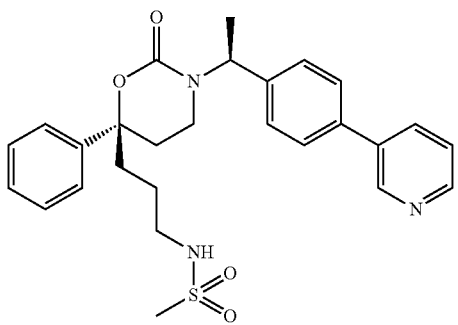 [SMILES: C[C@@H](c1ccc(-c2cccnc2)cc1)N1CC[C@](CCCNS(C)(=O)=O)(c2ccccc2)OC1=O]

The title compound was prepared from N-(3-((R)-3-((S)-1-(4-bromophenyl)ethyl)-2-oxo-6-phenyl-1,3-oxazinan-6-yl)propyl)methanesulfonamide and pyridine-3-boronic acid following procedures analogous to those described in Example 1 Step 2. LC-MS Method 2 $t_R$=1.466 min, m/z=497.3; $^1$H NMR (CDCl$_3$) 1.33 (m, 1H), 1.53 (d, 3H), 1.63 (m, 1H), 1.84-2.03 (m, 2H), 2.18 (m, 1H), 2.30 (m, 2H), 2.84 (s, 3H), 2.93 (m, 1H), 3.02 (t, 2H), 4.30 (s, 1H), 5.64 (m, 1H), 7.02 (d, 2H), 7.22 (m, 2H), 7.31 (m, 5H), 7.77 (m, 1H), 7.80 (d, 1H), 8.71 (d, 1H), 8.93 (s, 1H).

EXAMPLE 92

4108.1002-007 Example 475

(S)-6-(2-hydroxyethyl)-3-((S)-1-(4-(6-methoxypyridin-3-yl)phenyl)ethyl)-6-phenyl-1,3-oxazinan-2-one

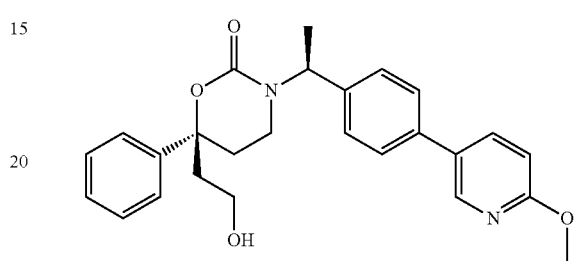

The title compound was prepared from (S)-3-((S)-1-(4-bromophenyl)ethyl)-6-(2-hydroxyethyl)-6-phenyl-1,3-oxazinan-2-one and 6-methoxypyridine-3-boronic acid following procedures analogous to those described in Example 1 Step 2. LC-MS Method 2 $t_R$=1.269 min, m/z=432.2; $^1$H NMR (CDCl$_3$) 1.50 (d, 3H), 2.05-2.35 (m, 5H), 2.90 (m, 1H), 3.51 (m, 1H), 3.70 (m, 1H), 3.97 (s, 3H), 5.63 (m, 1H), 6.85 (d, 1H), 6.92 (m, 2H), 7.17-7.35 (m, 6H), 7.81 (d, 1H), 8.32 (s, 1H).

EXAMPLE 93

4108.1002-007 Example 476

(S)-6-(2-hydroxy-2-methylpropyl)-3-((S)-1-(4-(6-methoxypyridin-3-yl)phenyl)ethyl)-6-phenyl-1,3-oxazinan-2-one

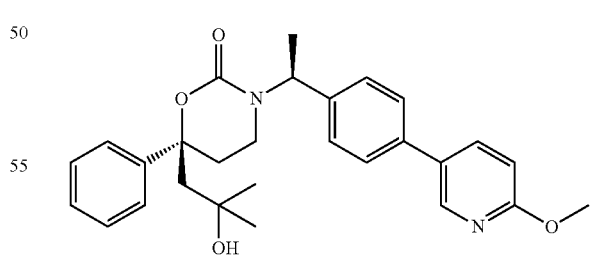

The title compound was prepared from (S)-3-((S)-1-(4-bromophenyl)ethyl)-6-(2-hydroxy-2-methylpropyl)-6-phenyl-1,3-oxazinan-2-one and 6-methoxypyridine-3-boronic acid following procedures analogous to those described in Example 1 Step 2. LC-MS Method 2 $t_R$=1.989 min, m/z=403.1; $^1$H NMR (CDCl$_3$) 1.10 (s, 3H), 1.17 (s, 3H), 1.52 (d, 3H), 2.13-2.28 (m, 6H), 2.47 (m, 1H), 2.87 (m, 1H), 3.95

(s, 3H), 5.70 (m, 1H), 6.79 (d, 1H), 7.02 (d, 2H), 7.21-7.38 (m, 6H), 7.58 (d, 1H), 8.27 (d, 1H).

EXAMPLE 94

Example 4108.1002-007 Example 477

N-(3-((R)-3-((S)-1-(4-(6-methoxypyridin-3-yl)phenyl)ethyl)-2-oxo-6-phenyl-1,3-oxazinan-6-yl)propyl)methanesulfonamide

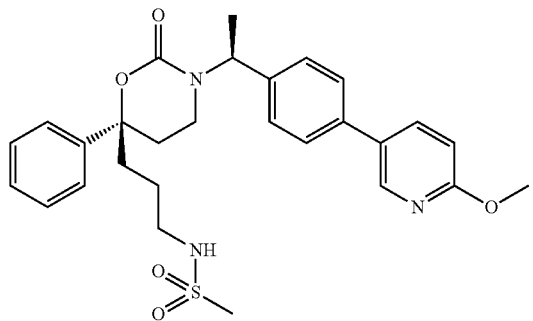 [SMILES: COc1ccc(-c2ccc([C@H](C)N3CC[C@](CCCNS(C)(=O)=O)(c4ccccc4)OC3=O)cc2)cn1]

The title compound was prepared from N-(3-((R)-3-((S)-1-(4-bromophenyl)ethyl)-2-oxo-6-phenyl-1,3-oxazinan-6-yl)propyl)methanesulfonamide and 6-methoxypyridine-3-boronic acid following procedures analogous to those described in Example 1 Step 2. LC-MS Method 2 $t_R$=1.316 min, m/z=524.1; $^1$H NMR (CDCl$_3$) 1.28-1.38 (m, 1H), 1.48 (d, 3H), 1.67 (m, 1H), 1.81-1.98 (m, 2H), 2.13 (m, 1H), 2.24 (m, 2H), 2.83 (m, 4H), 3.01 (m, 2H), 3.91 (s, 3H), 4.15 (m, 1H), 5.62 (m, 1H), 6.73 (d, 1H), 6.91 (d, 2H), 7.18-7.32 (m, 7H), 7.62 (dd, 1H), 8.21 (s, 1H).

EXAMPLE 95

4108.1002-007 Example 478

(R)-3-((S)-1-(4-(6-aminopyridin-3-yl)phenyl)ethyl)-6-(3-hydroxypropyl)-6-phenyl-1,3-oxazinan-2-one

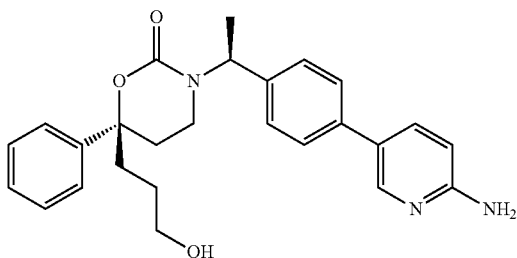 [SMILES: C[C@@H](c1ccc(-c2ccc(N)nc2)cc1)N1CC[C@](CCCO)(c2ccccc2)OC1=O]

The title compound was prepared from (R)-3-((S)-1-(4-bromophenyl)ethyl)-6-(3-hydroxypropyl)-6-phenyl-1,3-oxazinan-2-one and 6-aminopyridine-3-boronic acid following procedures analogous to those described in Example 1 Step 2. LC-MS Method 2 $t_R$=0.963 min, m/z=431.8; $^1$H NMR (CDCl$_3$) 1.36 (d, 3H), 1.75 (m, 1H), 1.98 (m, 3H), 2.21 (m, 1H), 2.38 (m, 2H), 2.89 (m, 1H), 3.56 (m, 2H), 5.05 (s, 1H), 5.65 (m, 1H), 6.62 (d, 1H), 6.97 (d, 2H), 7.17 (d, 2H), 7.20-7.39 (m, 5H), 7.63 (d, 1H), 8.12 (s, 1H).

EXAMPLE 96

4108.1002-007 Example 479

(S)-6-(2-hydroxyethyl)-3-((S)-1-(4-(2-methylpyridin-4-yl)phenyl)ethyl)-6-phenyl-1,3-oxazinan-2-one

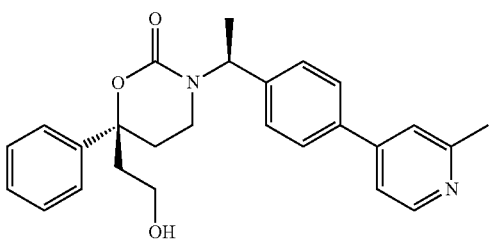 [SMILES: Cc1cc(-c2ccc([C@H](C)N3CC[C@](CCO)(c4ccccc4)OC3=O)cc2)ccn1]

The title compound was prepared from (S)-3-((S)-1-(4-bromophenyl)ethyl)-6-(2-hydroxyethyl)-6-phenyl-1,3-oxazinan-2-one and 2-methylpyridine-4-boronic acid following procedures analogous to those described in Example 1 Step 2. LC-MS Method 2 $t_R$=0.928 min, m/z=444.4; $^1$H NMR (CDCl$_3$) 1.50 (d, 3H), 2.05-2.18 (m, 2H), 2.26-2.39 (m, 6H), 2.82 (s, 3H), 2.94 (m, 1H), 3.51 (m, 1H), 3.72 (m, 1H), 5.54 (m, 1H), 7.00 (d, 2H), 7.24-7.38 (m, 7H), 7.57 (s, 1H), 7.64 (d, 1H), 8.75 (d, 1H).

EXAMPLE 97

4108.1002-007 Example 480

(S)-6-(2-hydroxy-2-methylpropyl)-3-((S)-1-(4-(2-methylpyridin-4-yl)phenyl)ethyl)-6-phenyl-1,3-oxazinan-2-one

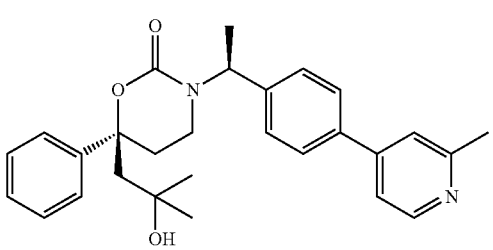 [SMILES: Cc1cc(-c2ccc([C@H](C)N3CC[C@](CC(C)(C)O)(c4ccccc4)OC3=O)cc2)ccn1]

The title compound was prepared from (S)-3-((S)-1-(4-bromophenyl)ethyl)-6-(2-hydroxy-2-methylpropyl)-6-phenyl-1,3-oxazinan-2-one and 2-methylpyridine-4-boronic acid following procedures analogous to those described in Example 1 Step 2. LC-MS Method 2 $t_R$=0.866 min, m/z=444.2; $^1$H NMR (CDCl$_3$) 1.04-1.16 (d, 6H), 1.50 (d, 3H), 2.14-2.25 (m, 4H), 2.45 (m, 1H), 2.57 (s, 3H), 2.83 (m, 1H), 5.65 (m, 1H), 7.04 (d, 2H), 7.20-7.33 (m, 9H), 8.45 (d, 1H).

EXAMPLE 98

4108.1002-007 Example 481

3-((R)-3-((S)-1-(4-(2-methylpyridin-4-yl)phenyl)ethyl)-2-oxo-6-phenyl-1,3-oxazinan-6-yl)propanamide

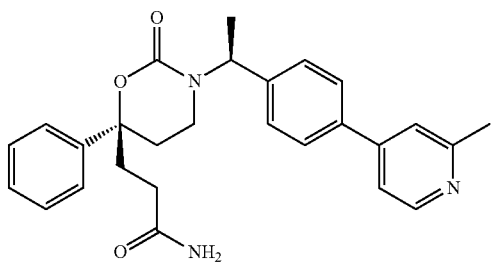 [SMILES: Cc1cc(-c2ccc([C@H](C)N3CC[C@](CCC(N)=O)(c4ccccc4)OC3=O)cc2)ccn1]

The title compound was prepared from 3-((R)-3-((S)-1-(4-bromophenyl)ethyl)-2-oxo-6-phenyl-1,3-oxazinan-6-yl)propanamide and 2-methylpyridine-4-boronic acid following procedures analogous to those described in Example 1 Step 2. LC-MS Method 2 $t_R$=0.917 min, m/z=444.4; $^1$H NMR (CDCl$_3$) 1.51 (d, 3H), 1.92 (m, 1H), 2.13-2.32 (m, 5H), 2.44 (m, 1H), 2.82 (s, 3H), 2.93 (m, 1H), 5.50-5.68 (m, 3H), 7.06 (d, 2H), 7.19-7.35 (m, 5H), 7.39 (d, 2H), 7.58 (s, 1H), 7.65 (d, 1H), 8.74 (d, 1H).

EXAMPLE 99

4108.1002-007 Example 482

N-(3-((R)-3-((S)-1-(4-(2-methylpyridin-4-yl)phenyl)ethyl)-2-oxo-6-phenyl-1,3-oxazinan-6-yl)propyl)methanesulfonamide

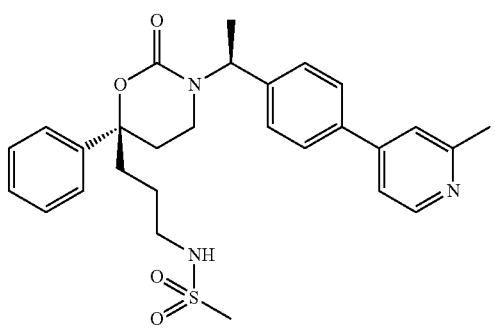 [SMILES: Cc1cc(-c2ccc([C@H](C)N3CC[C@](CCCNS(C)(=O)=O)(c4ccccc4)OC3=O)cc2)ccn1]

The title compound was prepared from N-(3-((R)-3-((S)-1-(4-bromophenyl)ethyl)-2-oxo-6-phenyl-1,3-oxazinan-6-yl)propyl)methanesulfonamide and 2-methylpyridine-4-boronic acid following procedures analogous to those described in Example 1 Step 2. LC-MS Method 2 $t_R$=0.988 min, m/z=508.2; $^1$H NMR (CDCl$_3$) 1.36 (m, 1H), 1.51 (d, 3H), 1.70 (m, 1H), 1.96 (m, 2H), 2.17 (m, 1H), 2.26 (m, 2H), 2.59 (s, 3H), 2.86 (m, 4H), 3.02 (m, 2H), 4.19 (m, 1H), 5.62 (m, 1H), 6.96 (d, 2H), 7.19 (m, 3H), 7.26 (d, 2H), 7.29 (m, 4H), 8.47 (d, 1H).

EXAMPLE 100

4108.1002-007 Example 483

(R)-6-(3-hydroxypropyl)-3-((S)-1-(4-(1-methyl-1H-pyrazol-3-yl)phenyl)ethyl)-6-phenyl-1,3-oxazinan-2-one

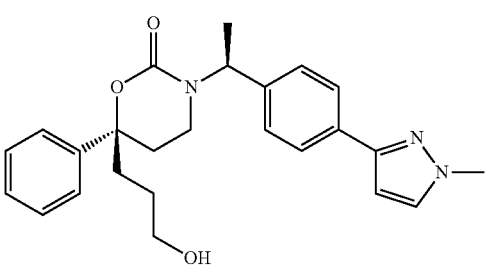 [SMILES: C[C@@H](c1ccc(-c2ccn(C)n2)cc1)N1CC[C@](CCCO)(c2ccccc2)OC1=O]

The title compound was prepared from (R)-6-allyl-3-((S)-1-(4-bromophenyl)ethyl)-6-phenyl-1,3-oxazinan-2-one and pyrazole-3-boronic acid using a procedure analogous to that described in Example 1 Step 2, followed by treatment with NaH and MeI, and hydroboration using a procedure analogous to that described in Example 12 Step 1. LC-MS Method 3 $t_R$=1.18 min, m/z=442.1; $^1$H NMR (CDCl$_3$) 1.29 (m, 1H), 1.47 (d, 3H), 1.65 (m, 1H), 1.83-2.03 (m, 3H), 2.11 (m, 1H), 2.18-2.37 (m, 3H), 2.75-2.96 (m, 1H), 3.52 (m, 2H), 3.78 (m, 1H), 3.91 (s, 1H), 5.63 (m, 1H), 6.41 (s, 1H), 6.87 (d, 2H), 6.94 (d, 1H), 7.08 (d, 1H), 7.19-7.37 (m, 7H), 7.43 (d, 2H).

EXAMPLE 101

4108.1002-007 Example 502

6-(4-((S)-1-((R)-6-(4-fluorophenyl)-6-(3-hydroxypropyl)-2-oxo-1,3-oxazinan-3-yl)ethyl)phenyl)nicotinonitrile

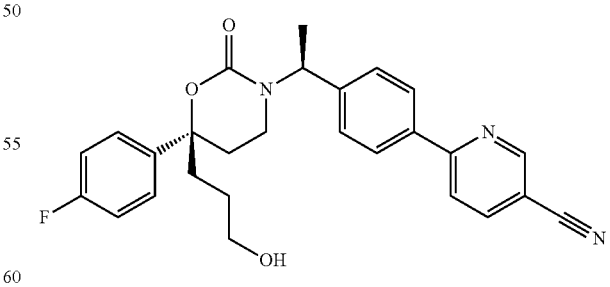

The title compound was prepared from (R)-6-allyl-6-(4-fluorophenyl)-3-((S)-1-(4-(4,4,5,5-tetramethyl-1,3,2-dioxaborolan-2-yl)phenyl)ethyl)-1,3-oxazinan-2-one and 2-bromo-5-cyanopyridine following a procedure analogous to that described in Example 14. LC-MS Method 1 tR=1.58, m/z=482 (M+Na); 1H NMR (CDCl3) 8.93 (d, 1H), 8.01 (dt, 1H), 7.79 (m, 3H), 7.25 (m, 1H), 7.07 (m, 5H), 5.74 (q, 1H), 4.28 (t, 1H), 3.59 (t, 1H), 2.98 (m, 1H), 1.58 (d, 3H), 1.53 (m, 1H).

EXAMPLE 102

4108.1002-007 Example 510

N-methyl-N-(3-((R)-3-((S)-1-(4-(2-methylpyridin-4-yl)phenyl)ethyl)-2-oxo-6-phenyl-1,3-oxazinan-6-yl)propyl)acetamide

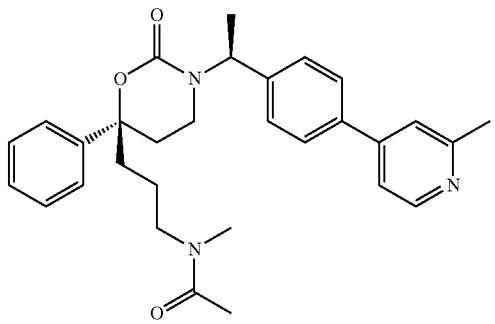 [SMILES: CC(=O)N(C)CCC[C@]1(c2ccccc2)CCN([C@@H](C)c2ccc(-c3ccnc(C)c3)cc2)C(=O)O1]

The title compound was prepared from N-(3-((R)-3-((S)-1-(4-bromophenyl)ethyl)-2-oxo-6-phenyl-1,3-oxazinan-6-yl)propyl)-N-methylacetamide and 2-methylpyridine-4-boronic acid following a procedure analogous to that described in Example 1 Step 2. LC-MS Method 2 $t_R$=0.98, m/z=486.2; $^1$H NMR (CDCl$_3$) 1.21-1.38 (m, 1H), 1.52 (d, 3H), 1.61-1.90 (m, 3H), 2.05 (d, 3H), 2.17 (m, 1H), 2.42 (m, 2H), 2.78 (s, 1H), 2.83 (s, 3H), 2.85 (s, 2H), 2.92 (m, 1H), 3.11-3.33 (m, 2H), 5.65 (m, 1H), 7.05 (d, 2H), 7.21 (m, 2H), 7.30 (m, 3H), 7.38 (d, 2H), 7.60 (s, 1H), 7.71 (d, 1H), 8.72 (d, 1H).

EXAMPLE 103

4108.1002-007 Example 511

N-(2-((S)-3-((S)-1-(4-(2-methylpyridin-4-yl)phenyl)ethyl)-2-oxo-6-phenyl-1,3-oxazinan-6-yl)ethyl)methanesulfonamide

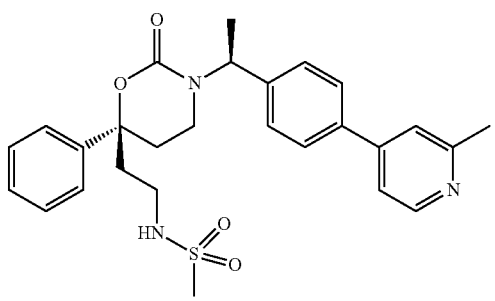 [SMILES: Cc1cc(-c2ccc([C@H](C)N3CC[C@](CCNS(C)(=O)=O)(c4ccccc4)OC3=O)cc2)ccn1]

The title compound was prepared from N-(2-((S)-3-((S)-1-(4-bromophenyl)ethyl)-2-oxo-6-phenyl-1,3-oxazinan-6-yl)ethyl)methanesulfonamide and 2-methylpyridine-4-boronic acid following a procedure analogous to that described in Example 1 Step 2. LC-MS Method 2 $t_R$=1.12, m/z=494; $^1$H NMR (CDCl$_3$) 1.48 (d, 3H), 2.10 (m, 2H), 2.20-2.41 (m, 2H), 2.43 (m, 1H), 2.71 (s, 3H), 2.73 (s, 3H), 3.11 (m, 2H), 5.52 (m, 1H), 7.13 (d, 2H), 7.25 (m, 3H), 7.34 (m, 2H), 7.62 (d, 2H), 7.91 (m, 1H), 8.08 (s, 1H), 8.56 (d, 1H).

EXAMPLE 104

Example 4108.1002-007 Example 512

(R)-3-((S)-1-(4-(2-methylpyridin-4-yl)phenyl)ethyl)-6-(3-(2-oxopyrrolidin-1-yl)propyl)-6-phenyl-1,3-oxazinan-2-one

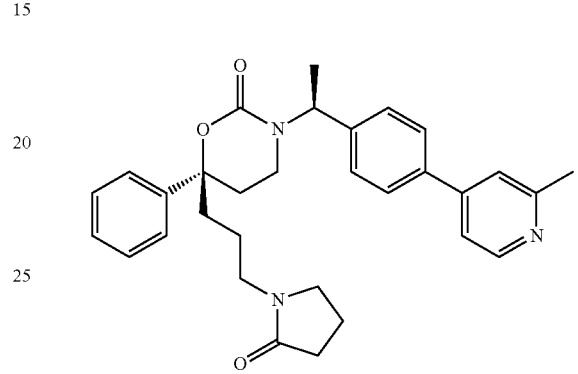

The title compound was prepared from (R)-3-((S)-1-(4-bromophenyl)ethyl)-6-(3-(2-oxopyrrolidin-1-yl)propyl)-6-phenyl-1,3-oxazinan-2-one and 2-methylpyridine-4-boronic acid following a procedure analogous to that described in Example 1 Step 2. LC-MS Method 2 $t_R$=0.992, m/z=498.1; $^1$H NMR (CDCl$_3$) 1.21 (m, 3H), 1.48 (d, 3H), 1.61-1.95 (m, 5H), 2.12 (m, 1H), 2.26 (m, 4H), 2.52 (s, 3H), 2.83 (m, 1H), 3.11 (m, 3H), 3.22 (m, 1H), 5.67 (m, 1H), 6.95 (d, 2H), 7.18 (m, 1H), 7.21 (m, 1H), 7.23 (m, 2H), 7.29 (m, 3H), 7.30 (m, 2H), 8.41 (d, 1H).

EXAMPLE 105

Example 4108.1002-007 Example 515

(S)-6-(2-(1,1-dioxo-isothiazolidin-2-yl)ethyl)-3-((S)-1-(4-(2-methylpyridin-4-yl)phenyl)ethyl)-6-phenyl-1,3-oxazinan-2-one

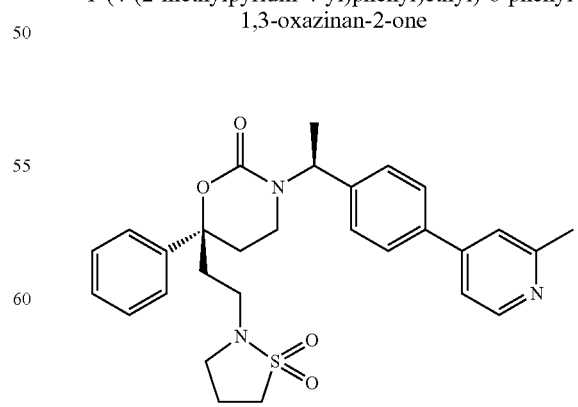

The title compound was prepared from (S)-3-((S)-1-(4-bromophenyl)ethyl)-6-(2-(1,1-dioxo-isothiazolidin-2-yl)

ethyl)-6-phenyl-1,3-oxazinan-2-one and 2-methylpyridine-4-boronic acid following a procedure analogous to that described in Example 1 Step 2. LC-MS Method 2 $t_R$=0.984, m/z=520.1; $^1$H NMR (CDCl$_3$) 1.52 (d, 3H), 2.11-2.29 (m, 5H), 2.32 (m, 2H), 2.81 (s, 3H), 2.83-2.96 (m, 2H), 2.98-3.08 (m, 3H), 3.11-3.22 (m, 2H), 5.67 (m, 1H), 7.06 (d, 2H), 7.24-7.36 (m, 5H), 7.38 (d, 2H), 7.61 (s, 1H), 7.69 (m, 1H), 8.73 (d, 1H).

EXAMPLE 106

4108.1002-007 Example 517

(R)-6-(3-(1,1-dioxo-isothiazolidin-2-yl)propyl)-3-((S)-1-(4-(2-methylpyridin-4-yl)phenyl)ethyl)-6-phenyl-1,3-oxazinan-2-one

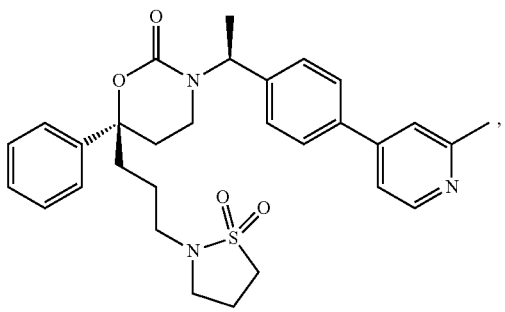 [SMILES: Cc1cc(-c2ccc([C@H](C)N3CC[C@](CCCN4CCCS4(=O)=O)(c4ccccc4)OC3=O)cc2)ccn1]

The title compound was prepared from (R)-3-((S)-1-(4-bromophenyl)ethyl)-6-(3-(1,1-dioxo-isothiazolidin-2-yl)propyl)-6-phenyl-1,3-oxazinan-2-one and 2-methylpyridine-4-boronic acid following a procedure analogous to that described in Example 1 Step 2. LC-MS Method 2 $t_R$=1.001, m/z=534.1; $^1$H NMR (CDCl$_3$) 1.22-1.33 (m, 1H), 1.52 (d, 3H), 1.68-1.81 (m, 1H), 1.83-2.03 (m, 2H), 2.12-2.38 (m, 5H), 2.83-2.91 (m, 5H), 2.93-3.13 (m, 5H), 5.68 (m, 1H), 7.09 (d, 2H), 7.18-7.32 (m, 5H), 7.36 (d, 2H), 7.61 (s, 1H), 7.68 (s, 1H), 8.24 (s, 1H).

EXAMPLE 107

4108.1002-007 Example 519

6-(4-fluorophenyl)-6-methyl-3-((S)-1-(4-(2-methylpyridin-4-yl)phenyl)ethyl)-1,3-oxazinan-2-one

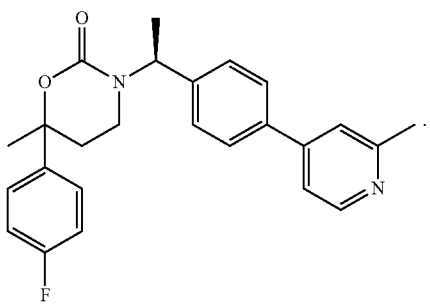

Isomer 1 of the title compound, (S)-6-(4-fluorophenyl)-6-methyl-3-((S)-1-(4-(2-methylpyridin-4-yl)phenyl)ethyl)-1,3-oxazinan-2-one, was prepared from (S)-3-((S)-1-(4-bromophenyl)ethyl)-6-(4-fluorophenyl)-6-methyl-1,3-oxazinan-2-one and 2-methylpyridine-4-boronic acid following a procedure analogous to that described in Example 14. LC-MS Method 1 $t_R$=1.28, m/z=405 (M+1); $^1$H NMR (CDCl$_3$) 8.84 (d, 1H, J=6.1 Hz), 7.81 (d, 1H, J=5.9 Hz), 7.75 (s, 1H), 7.70 (d, 2H, J=8.2 Hz), 7.52 (d, 2H, J=8.20 Hz), 7.34-7.31 (m, 2H), 7.09 (t, 2H, J=8.6 Hz), 5.81 (q, 1H, J=7.2 Hz), 2.89 (s, 3H), 2.84-2.72 (m, 2H), 2.31 (dt, 1H, J=13.9, 3.7 Hz), 2.11-2.03 (m, 1H), 1.64 (s, 3H), 1:38 (d, 3H, J=7 Hz).

Isomer 2 of the title compound, (R)-6-(4-fluorophenyl)-6-methyl-3-((S)-1-(4-(2-methylpyridin-4-yl)phenyl)ethyl)-1,3-oxazinan-2-one, was prepared from (R)-3-((S)-1-(4-bromophenyl)ethyl)-6-(4-fluorophenyl)-6-methyl-1,3-oxazinan-2-one and 2-methylpyridine-4-boronic acid following a procedure analogous to that described in Example 14. LC-MS Method 1 $t_R$=1.18, m/z=405 (M+1); $^1$H NMR (CDCl$_3$) 8.83 (s, 1H), 7.72 (s, 1H), 7.66 (s, 1H), 7.48 (d, 2H, J=7.3 Hz), 7.32 (br m, 2H), 7.16 (d, 2H, J=6.7), 7.04 (t, 2H, J=7.6 Hz), 5.77 (q, 1H, J=6.7 Hz), 3.05 (br m, 1H), 2.89 (s, 3H, 2.42-2.32 (m, 2H), 2.23 (br m, 1H), 1.64 (s, 3H), 1.59 (d, 3H, J=6.7 Hz).

EXAMPLE 108

4108.1002-007 Example 542

(R)-6-(4-fluorophenyl)-6-(3-hydroxypropyl)-3-((S)-1-(4-(pyrazin-2-yl)phenyl)ethyl)-1,3-oxazinan-2-one

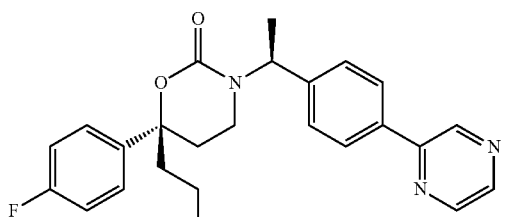

The title compound was prepared from (R)-6-(4-fluorophenyl)-6-(3-hydroxypropyl)-3-((S)-1-(4-(4,4,5,5-tetramethyl-1,3,2-dioxaborolan-2-yl)phenyl)ethyl)-1,3-oxazinan-2-one and 2-bromopyrazine following a procedure analogous to that described in Example 1 Step 2. LC-MS Method 2 $t_R$=1.157, m/z=458; $^1$H NMR (CDCl$_3$) 1.31 (m, 1H), 1.52 (d, 3H), 1.63 (m, 1H), 1.81-1.95 (m, 2H), 2.09-2.32 (m, 3H), 2.91

(m, 1H), 3.68 (t, 2H), 5.69 (m, 1H), 6.91 (m, 4H), 7.21 (m, 2H), 7.73 (m, 2H), 8.43 (s, 1H), 8.56 (s, 1H), 8.89 (s, 1H).

EXAMPLE 109

4108.1002-007 Example 543

(R)-6-(4-fluorophenyl)-6-(3-hydroxypropyl)-3-((S)-1-(4-(5-(trifluoromethyl)pyridin-2-yl)phenyl)ethyl)-1,3-oxazinan-2-one

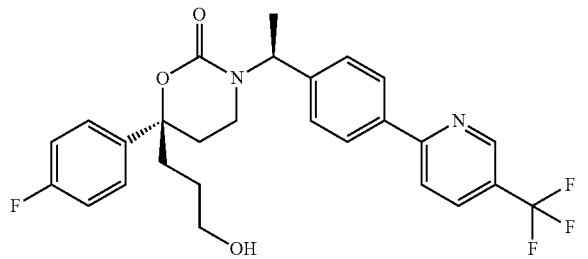 [SMILES: C[C@@H](c1ccc(-c2ccc(C(F)(F)F)cn2)cc1)N1CC[C@](CCCO)(c2ccc(F)cc2)OC1=O]

The title compound was prepared from (R)-6-(4-fluorophenyl)-6-(3-hydroxypropyl)-3-((S)-1-(4-(4,4,5,5-tetramethyl-1,3,2-dioxaborolan-2-yl)phenyl)ethyl)-1,3-oxazinan-2-one and 2-bromo-5-(trifluoromethyl)pyridine following a procedure analogous to that described in Example 14. LC-MS Method 1 $t_R$=1.86, m/z=503 (M+1); $^1$H NMR (CDCl$_3$) 8.87 (s, 1H), 7.93 (dd, 1H), 7.72 (t, 3H), 7.18 (m, 2H), 6.98 (m, 4H), 5.67 (m, 1H), 3.52 (t, 1H), 2.89 (m, 1H), 1.49 (d, 3H).

EXAMPLE 110

4108.1002-007 Example 544

6-(4-((S)-1-((R)-6-(3-hydroxypropyl)-2-oxo-6-phenyl-1,3-oxazinan-3-yl)ethyl)phenyl)nicotinonitrile

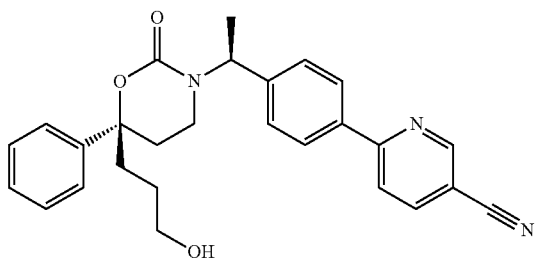 [SMILES: C[C@@H](c1ccc(-c2ccc(C#N)cn2)cc1)N1CC[C@](CCCO)(c2ccccc2)OC1=O]

The title compound was prepared from (R)-6-(3-hydroxypropyl)-6-phenyl-3-((S)-1-(4-(4,4,5,5-tetramethyl-1,3,2-dioxaborolan-2-yl)phenyl)ethyl)-1,3-oxazinan-2-one and 2-bromo-5-cyanopyridine following a procedure analogous to that described in Example 1 Step 2. LC-MS Method 2 $t_R$=1.159, m/z=442.4; $^1$H NMR (CD$_3$OD) 1.21 (m, 1H), 1.48 (d, 3H), 1.53 (m, 1H), 1.85 (m, 2H), 2.15 (m, 1H), 2.22 (m, 1H), 2.42 (m, 1H), 3.05 (m, 1H), 3.38 (m, 2H), 5.50 (m, 1H), 6.98 (d, 2H), 7.25 (m, 3H), 7.28 (m, 2H), 7.79 (d, 2H), 7.89 (d, 1H), 8.08 (m, 1H), 8.82 (s, 1H).

EXAMPLE 111

Example 4108.1002-007 Example 545

6-(4-((S)-1-((S)-6-(4-fluorophenyl)-6-(2-hydroxy-2-methylpropyl)-2-oxo-1,3-oxazinan-3-yl)ethyl)phenyl)nicotinonitrile

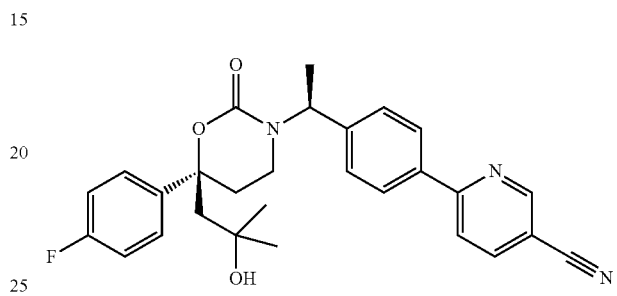

The title compound was prepared from (S)-6-(4-fluorophenyl)-6-(2-hydroxy-2-methylpropyl)-3-((S)-1-(4-(4,4,5,5-tetramethyl-1,3,2-dioxaborolan-2-yl)phenyl)ethyl)-1,3-oxazinan-2-one and 2-bromo-5-cyanopyridine following procedures analogous to those described in Example 1 Step 2. LC-MS Method 2 $t_R$=1.301, m/z=416; $^1$H NMR (CDCl$_3$) 1.09 (d, 6H), 1.49 (d, 3H), 2.09-2.22 (m, 4H), 2.37 (m, 1H), 2.87 (m, 1H), 5.68 (m, 1H), 6.92-7.01 (t, 2H), 7.06 (m, 2H), 7.23 (m, 2H), 7.71 (d, 1H), 7.78 (d, 2H), 7.91 (d, 1H), 8.88 (s, 1H). The compound was dissolved in refluxing isopropyl acetate and allowed to cool slowly to afford a solid with mp 155-157° C.

EXAMPLE 112

4108.1002-007 Example 546

(R)-3-((S)-1-(4-(5-fluoropyridin-2-yl)phenyl)ethyl)-6-(3-hydroxpropyl)-6-Phenyl-1,3-oxazinan-2-one

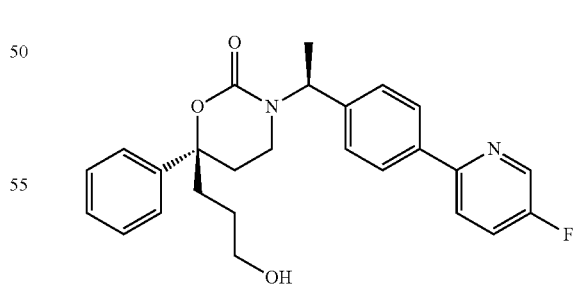

The title compound was prepared from (R)-6-(3-hydroxypropyl)-6-phenyl-3-((S)-1-(4-(4,4,5,5-tetramethyl-1,3,2-dioxaborolan-2-yl)phenyl)ethyl)-1,3-oxazinan-2-one and 2-bromo-5-fluoropyridine following a procedure analogous to that described in Example 1 Step 2. LC-MS Method 2 $t_R$=1.197, m/z=435.1; $^1$H NMR (CDCl$_3$) 1.21-1.37 (m, 2H), 1.48 (d, 3H), 1.81-1.95 (m, 2H), 2.18 (m, 1H), 2.20-2.31 (m, 2H), 2.85 (m, 1H), 3.52 (t, 2H), 5.65 (m, 1H), 6.95 (d, 2H), 7.22 (m, 3H), 7.28 (m, 2H), 7.40 (m, 1H), 7.58 (m, 3H), 8.42 (d, 1H).

EXAMPLE 113

4108.1002-007 Example 547

(R)-6-(4-fluorophenyl)-6-(3-hydroxypropyl)-3-((S)-1-(4-(pyrimidin-2-yl)phenyl)ethyl)-1,3-oxazinan-2-one

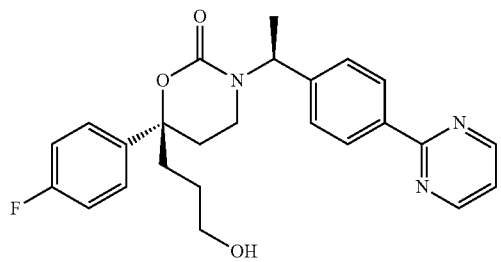 [SMILES: C[C@@H](c1ccc(-c2ncccn2)cc1)N1CC[C@](CCCO)(c2ccc(F)cc2)OC1=O]

The title compound was prepared (R)-6-(4-fluorophenyl)-6-(3-hydroxypropyl)-3-((S)-1-(4-(4,4,5,5-tetramethyl-1,3,2-dioxaborolan-2-yl)phenyl)ethyl)-1,3-oxazinan-2-one and 2-chloropyrimidine following procedures analogous to those described in Example 1 Step 2. LC-MS Method 2 $t_R$=1.401, m/z=436.1; $^1$H NMR (CDCl$_3$) 1.53 (d, 3H), 1.62 (m, 1H), 1.81-1.98 (m, 3H), 2.15 (m, 2H), 2.31 (m, 1H), 2.76 (m, 1H), 3.51 (t, 2H), 5.67 (m, 1H), 6.92 (m, 4H), 7.11 (m, 1H), 7.19 (m, 1H), 8.15 (d, 2H), 8.71 (d, 2H).

EXAMPLE 114

4108.1002-007 Example 548

(R)-6-(4-fluorophenyl)-6-(3-hydroxypropyl)-3-((S)-1-(4-(6-methylpyridazin-3-yl)phenyl)ethyl)-1,3-oxazinan-2-one

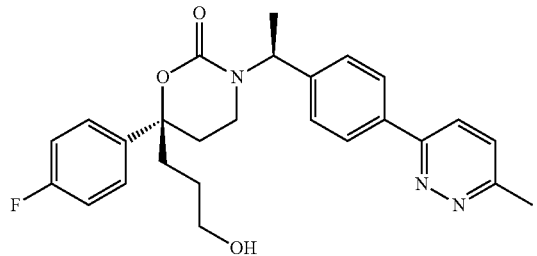 [SMILES: Cc1ccc(-c2ccc([C@H](C)N3CC[C@](CCCO)(c4ccc(F)cc4)OC3=O)cc2)nn1]

The title compound was prepared from (R)-6-(4-fluorophenyl)-6-(3-hydroxypropyl)-3-((S)-1-(4-(4,4,5,5-tetramethyl-1,3,2-dioxaborolan-2-yl)phenyl)ethyl)-1,3-oxazinan-2-one and 3-chloro-6-methylpyridazine following a procedure analogous to that described in Example 1 Step 2. LC-MS Method 2 $t_R$=1.09, m/z=450; $^1$H NMR (CDCl$_3$) 1.26-1.39 (m, 1H), 1.50 (d, 3H), 1.59-1.70 (m, 1H), 1.81-1.99 (m, 3H), 2.09-2.20 (m, 2H), 2.22-2.34 (m, 1H), 2.71 (s, 3H), 2.90 (m, 1H), 3.50 (t, 2H), 5.67 (m, 1H), 6.90-7.08 (m, 4H), 7.19 (m, 1H), 7.21 (m, 1H), 7.33 (d, 1H), 7.62 (d, 1H), 7.77 (d, 2H).

EXAMPLE 115

4108.1002-007 Example 549

(S)-6-(4-fluorophenyl)-6-((1-hydroxycyclopropyl)methyl)-3-((S)-1-(4-(2-methylpyridin-4-yl)phenyl)ethyl)-1,3-oxazinan-2-one

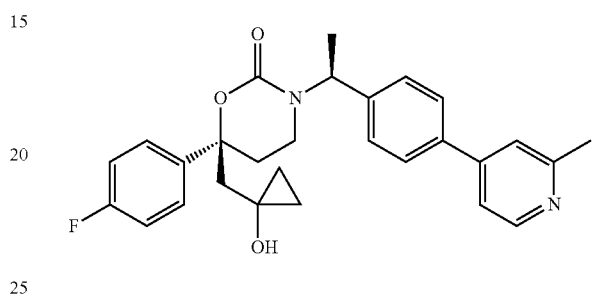

The title compound was prepared from (S)-3-((S)-1-(4-bromophenyl)ethyl)-6-(4-fluorophenyl)-6-((1-hydroxycyclopropyl)methyl)-1,3-oxazinan-2-one and 2-methylpyridine-4-boronic acid following a procedure analogous to that described in Example 1 Step 2. LC-MS Method 2 $t_R$=0.996, m/z=461.1; $^1$H NMR (CDCl$_3$) 0.35 (m, 1H), 0.17 (m, 3H), 0.51 (m, 1H), 0.61 (m, 1H), 1.48 (d, 3H), 2.11 (s, 2H), 2.28 (m, 1H), 2.42 (m, 2H), 2.56 (s, 3H), 2.71 (s, 1H), 2.95 (m, 1H), 5.63 (m, 1H), 6.91 (m, 2H), 6.98 (m, 2H), 7.19 (m, 1H), 7.26-7.38 (m, 5H), 8.49 (d, 1H).

EXAMPLE 116

4108.1002-007 Example 550

3-((R)-6-(4-fluorophenyl)-3-((S)-1-(4-(2-methylpyridin-4-yl)phenyl)ethyl)-2-oxo-1,3-oxazinan-6-yl)-2,2-dimethylpropanenitrile

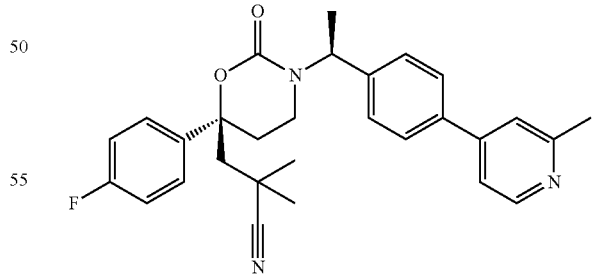

The title compound was prepared from 3-((R)-3-((S)-1-(4-bromophenyl)ethyl)-6-(4-fluorophenyl)-2-oxo-1,3-oxazinan-6-yl)-2,2-dimethylpropanenitrile and 2-methylpyridine-4-boronic acid following a procedure analogous to that described in Example 1 Step 2. LC-MS Method 2 $t_R$=0.926, m/z=472.2; $^1$H NMR (CD$_3$OD) 1.31 (s, 3H), 1.41 (s, 1H), 1.58 (d, 3H), 2.30 (m, 2H), 2.34 (m, 1H), 2.43 (m, 1H), 2.61

(d, 2H), 2.81 (s, 3H), 3.21 (m, 1H), 5.62 (m, 1H), 7.08 (m, 2H), 7.29 (d, 2H), 7.41 (m, 2H), 7.79 (d, 2H), 8.09 (m, 1H), 8.19 (s, 1H), 8.68 (d, 1H).

EXAMPLE 117

4108.1002-007 Example 551

N-methyl-N-(2-((S)-3-((S)-1-(4-(2-methylpyridin-4-yl)phenyl)ethyl)-2-oxo-6-phenyl-1,3-oxazinan-6-yl)ethyl)methanesulfonamide

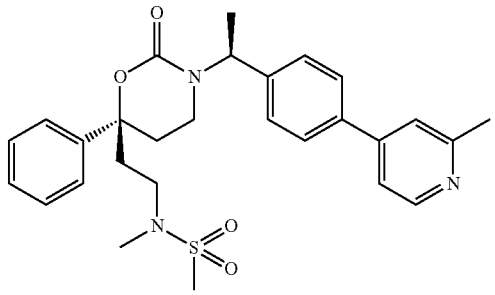 [SMILES: Cc1cc(-c2ccc([C@H](C)N3CC[C@](CCN(C)S(C)(=O)=O)(c4ccccc4)OC3=O)cc2)ccn1]

The title compound was prepared from N-(2-((S)-3-((S)-1-(4-bromophenyl)ethyl)-2-oxo-6-phenyl-1,3-oxazinan-6-yl)ethyl)-N-methylmethanesulfonamide and 2-methylpyridine-4-boronic acid following a procedure analogous to that described in Example 1 Step 2. LC-MS Method 2 $t_R$=0.989, m/z=508.1; $^1$H NMR (CDCl$_3$) 1.53 (d, 3H), 2.17-2.32 (m, 5H), 2.63 (s, 3H), 2.71 (s, 3H), 2.81 (s, 3H), 2.93 (m, 2H), 3.22 (m, 1H), 5.67 (m, 1H), 7.08 (m, 2H), 7.21 (s, 2H), 7.25 (m, 3H), 7.33 (m, 2H), 7.61 (s, 1H), 7.71 (d, 1H), 8.72 (d, 1H).

EXAMPLE 118

4108.1002-007 Example 552

(R)-3-((S)-1-(4-(2-methylpyridin-4-yl)phenyl)ethyl)-6-phenyl-6-(2-(1,1-dioxoisothiazolidin-2-yl)ethyl)-1,3-oxazinan-2-one

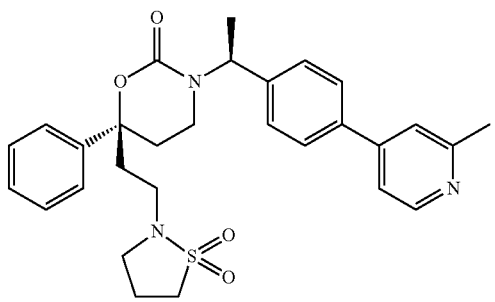 [SMILES: Cc1cc(-c2ccc([C@H](C)N3CC[C@](CCN4CCCS4(=O)=O)(c4ccccc4)OC3=O)cc2)ccn1]

The title compound was prepared from (S)-3-((S)-1-(4-bromophenyl)ethyl)-6-(2-(1,1-dioxo-isothiazolidin-2-yl)ethyl)-6-phenyl-1,3-oxazinan-2-one and 2-methylpyridine-4-boronic acid following a procedure analogous to that described in Example 1 Step 2.

EXAMPLE 119

Example 4108.1002-007 Example 553

N-methyl-N-(3-((R)-3-((S)-1-(4-(2-methylpyridin-4-yl)phenyl)ethyl)-2-oxo-6-phenyl-1,3-oxazinan-6-yl)propyl)methanesulfonamide

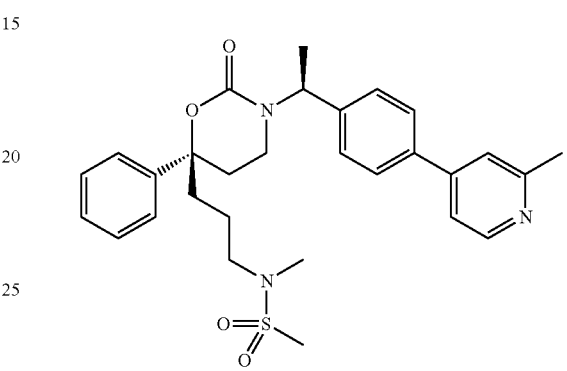

The title compound was prepared from N-(3-((R)-3-((S)-1-(4-bromophenyl)ethyl)-2-oxo-6-phenyl-1,3-oxazinan-6-yl)propyl)-N-methylmethanesulfonamide and 2-methylpyridine-4-boronic acid following a procedure analogous to that described in Example 1 Step 2. LC-MS Method 2 $t_R$=1, m/z=522.1; $^1$H NMR (CDCl$_3$) 1.23 (m, 1H), 1.48 (d, 3H), 1.68-1.99 (m, 3H), 2.11-2.31 (m, 3H), 2.56 (s, 3H), 2.66 (s, 3H), 2.68 (s, 3H), 2.84-3.08 (m, 3H), 5.68 (m, 1H), 6.92 (d, 1H), 7.15 (d, 1H), 7.25 (m, 4H), 7.31 (m, 4H), 8.43 (d, 1H).

EXAMPLE 120

4108.1002-007 Example 554

4-(4-((S)-1-((R)-6-(3-hydroxypropyl)-2-oxo-6-phenyl-1,3-oxazinan-3-yl)ethyl)phenyl)-2,6-dimethylpyridine 1-oxide

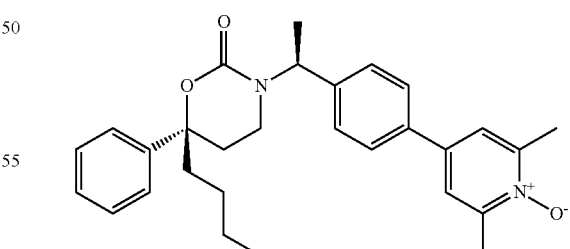

The title compound was prepared from (R)-6-(3-hydroxypropyl)-6-phenyl-3-((S)-1-(4-(4,4,5,5-tetramethyl-1,3,2-dioxaborolan-2-yl)phenyl)ethyl)-1,3-oxazinan-2-one and 4-bromo-2,6-dimethylpyridine-N-oxide following a procedure analogous to that described in Example 1 Step 2. LC-MS Method 2 $t_R$=1.086, m/z=461.1; $^1$H NMR (CDCl$_3$) 1.34 (m, 1H), 1.50 (d, 3H), 1.61-1.72 (m, 2H), 1.88-2.00 (m, 2H), 2.18

(m, 1H), 2.22-2.34 (m, 2H), 2.62 (s, 6H), 2.88 (m, 1H), 3.51 (t, 2H), 5.65 (m, 1H), 6.93 (d, 2H), 7.21 (m, 1H), 7.26 (m, 4H), 7.29-7.38 (m, 4H).

EXAMPLE 121

4108.1002-007 Example 555

4-(4-((S)-1-((S)-6-(2-hydroxy-2-methylpropyl)-2-oxo-6-phenyl-1,3-oxazinan-3-yl)ethyl)phenyl)-2,6-dimethylpyridine 1-oxide

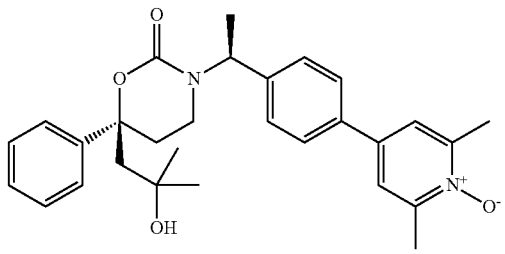 [SMILES: Cc1cc(-c2ccc([C@H](C)N3CC[C@](CC(C)(C)O)(c4ccccc4)OC3=O)cc2)cc(C)[n+]1[O-]]

The title compound was prepared from (S)-6-(2-hydroxy-2-methylpropyl)-6-phenyl-3-((S)-1-(4-(4,4,5,5-tetramethyl-1,3,2-dioxaborolan-2-yl)phenyl)ethyl)-1,3-oxazinan-2-one and 4-bromo-2,6-dimethylpyridine-N-oxide following a procedure analogous to that described in Example 1 Step 2. LC-MS Method 2 $t_R$=1.185, m/z=459.1; $^1$H NMR (CDCl$_3$) 1.11 (s, 3H), 1.18 (s, 3H), 1.57 (d, 3H), 2.20 (s, 2H), 2.22-2.35 (m, 2H), 2.38-2.49 (m, 1H), 2.72 (s, 6H), 2.91 (m, 1H), 5.70 (m, 1H), 7.08 (d, 2H), 7.31 (m, 3H), 7.37 (m, 4H), 7.43 (s, 2H).

EXAMPLE 122

4108.1002-007 Example 556

4-(4-((S)-1-((R)-6-(4-fluorophenyl)-6-(3-hydroxypropyl)-2-oxo-1,3-oxazinan-3-yl)ethyl)phenyl)-2,6-dimethylpyridine 1-oxide

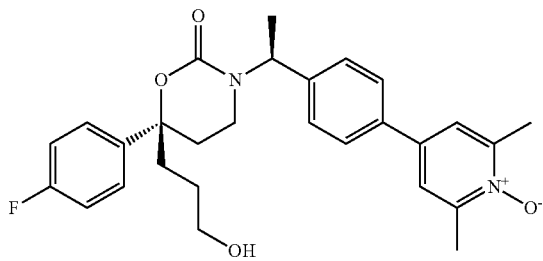 [SMILES: Cc1cc(-c2ccc([C@H](C)N3CC[C@](CCCO)(c4ccc(F)cc4)OC3=O)cc2)cc(C)[n+]1[O-]]

The title compound was prepared from (R)-6-(4-fluorophenyl)-6-(3-hydroxypropyl)-3-((S)-1-(4-(4,4,5,5-tetramethyl-1,3,2-dioxaborolan-2-yl)phenyl)ethyl)-1,3-oxazinan-2-one and 4-bromo-2,6-dimethylpyridine-N-oxide following a procedure analogous to that described in Example 1 Step 2. LC-MS Method 2 $t_R$=1.092, m/z=479.1; $^1$H NMR (CDCl$_3$) 1.38 (m, 1H), 1.56 (d, 3H), 1.71 (m, 1H), 1.95 (m, 2H), 2.19-2.31 (m, 3H), 2.58 (s, 3H), 2.61 (s, 3H), 2.95 (m, 1H), 3.58 (m, 1H), 5.71 (m, 1H), 7.05 (m, 4H), 7.21-7.32 (m, 4H), 7.38 (m, 2H).

EXAMPLE 123

4108.1002-007 Example 557

4-(4-((S)-1-((S)-6-(4-fluorophenyl)-6-(2-hydroxy-2-methylpropyl)-2-oxo-1,3-oxazinan-3-yl)ethyl)phenyl)-2,6-dimethylpyridine 1-oxide

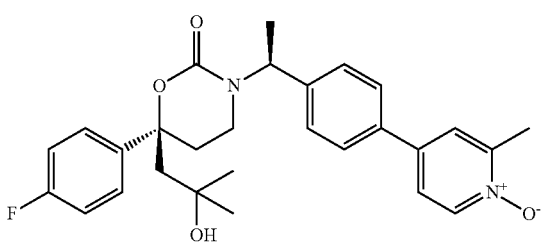 [SMILES: Cc1cc(-c2ccc([C@H](C)N3CC[C@](CC(C)(C)O)(c4ccc(F)cc4)OC3=O)cc2)cc[n+]1[O-]]

The title compound was prepared from (S)-6-(4-fluorophenyl)-6-(2-hydroxy-2-methylpropyl)-3-((S)-1-(4-(4,4,5,5-tetramethyl-1,3,2-dioxaborolan-2-yl)phenyl)ethyl)-1,3-oxazinan-2-one one and 4-bromo-2,6-dimethylpyridine-N-oxide following a procedure analogous to that described in Example 1 Step 2. LC-MS Method 2 $t_R$=1.354, m/z=493; $^1$H NMR (CDCl$_3$) 1.18 (d, 6H), 1.48 (d, 3H), 2.08-2.21 (m, 5H), 2.36 (m, 1H), 2.53 (s, 6H), 2.82 (m, 1H), 5.65 (m, 1H), 6.98 (m, 4H), 7.18 (m, 4H), 7.28 (m, 2H).

EXAMPLE 124

4108.1002-007 Example 558

4-(4-((S)-1-((S)-6-(4-fluorophenyl)-6-(2-hydroxy-2-methylpropyl)-2-oxo-1,3-oxazinan-3-yl)ethyl)phenyl)-2-methylpyridine 1-oxide The title compound was prepared from (S)-6-(4-fluorophenyl)-6-(2-hydroxy-2-methylpropyl)-3-((S)-1-(4-(2-methylpyridin-4-yl)phenyl)ethyl)-1,3-oxazinan-2-one following a procedure analogous to that described in Example 38. LC-MS Method 1 $t_R$=1.28, m/z=479 (M+1); $^1$H NMR (CDCl$_3$) 8.52 (d, J=6.2 Hz, 1H), 7.56-7.27 (m, 6H), 7.11-7.00 (m, 4H), 5.70 (q, J=7.0 Hz, 1H), 2.97-2.93 (m, 1H), 2.69 (s, 3H), 2.50-2.42 (m, 1H), 2.31-2.16 (m, 4H), 1.55 (d, J=7.0 Hz, 3H), 1.14 (s, 6H).

EXAMPLE 125

4108.1002-007 Example 559

(R)-3-((S)-1-(4-(2-aminopyridin-4-yl)phenyl)ethyl)-6-(3-hydroxypropyl)-6-phenyl-1,3-oxazinan-2-one

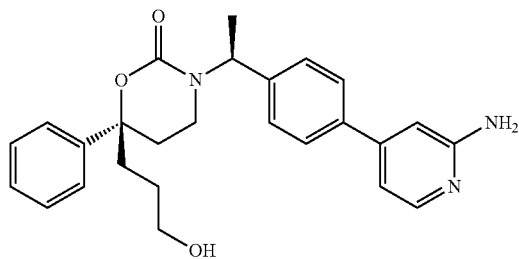 [SMILES: C[C@@H](c1ccc(-c2ccnc(N)c2)cc1)N1CC[C@](CCCO)(c2ccccc2)OC1=O]

The title compound was prepared from (R)-6-(3-hydroxypropyl)-6-phenyl-3-((S)-1-(4-(4,4,5,5-tetramethyl-1,3,2-dioxaborolan-2-yl)phenyl)ethyl)-1,3-oxazinan-2-one and 2-amino-4-bromopyridine following a procedure analogous to that described in Example 1 Step 2. LC-MS Method 2 $t_R$=0.951, m/z=432; $^1$H NMR (CDCl$_3$) 1.26-1.40 (m, 1H), 1.48 (d, 3H), 1.59-1.63 (m, 1H), 1.83-1.95 (m, 2H), 2.09-2.20 (m, 1H), 2.21-2.37 (m, 2H), 2.86 (m, 1H), 3.50 (m, 2H), 4.54-4.75 (s, 2H), 5.62 (m, 1H), 6.56 (s, 1H), 6.71 (d, 1H), 6.90 (d, 2H), 7.21-7.33 (m, 7H), 8.00 (m, 1H).

EXAMPLE 126

4108.1002-007 Example 561

(R)-6-(4-fluorophenyl)-6-(3-hydroxypropyl)-3-((S)-1-(4-(2-methylpyrimidin-4-yl)phenyl)ethyl)-1,3-oxazinan-2-one

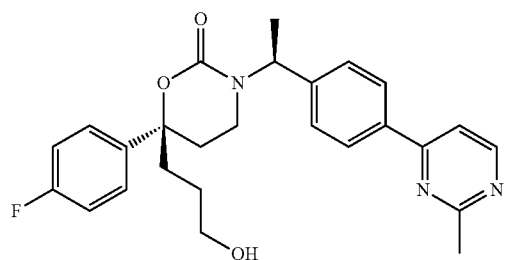 [SMILES: Cc1nccc(-c2ccc([C@H](C)N3CC[C@](CCCO)(c4ccc(F)cc4)OC3=O)cc2)n1]

The title compound was prepared from (R)-6-(4-fluorophenyl)-6-(3-hydroxypropyl)-3-((S)-1-(4-(4,4,5,5-tetramethyl-1,3,2-dioxaborolan-2-yl)phenyl)ethyl)-1,3-oxazinan-2-one and 4-bromo-2-methylpyrimidine following a procedure analogous to that described in Example 1 Step 2. LC-MS Method 2 $t_R$=1.159, m/z=450; $^1$H NMR (CDCl$_3$) 1.33 (m, 3H), 1.52 (m, 3H), 1.63 (m, 3H), 1.80-1.95 (m, 2H), 2.15-2.30 (m, 3H), 2.75 (s, 3H), 2.90 (m, 1H), 3.51 (m, 2H), 5.68 (m, 1H), 6.99 (m, 4H), 7.20 (m, 2H), 7.41 (m, 1H), 7.79 (d, 2H), 8.60 (m, 1H).

EXAMPLE 127

4108.1002-007 Example 562

(R)-3-((S)-1-(4-(2,6-dimethylpyrimidin-4-yl)phenyl)ethyl)-6-(4-fluorophenyl)-6-(3-hydroxypropyl)-1,3-oxazinan-2-one

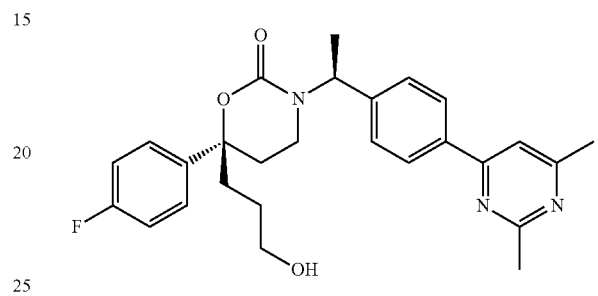

The title compound was prepared from (R)-6-(4-fluorophenyl)-6-(3-hydroxypropyl)-3-((S)-1-(4-(4,4,5,5-tetramethyl-1,3,2-dioxaborolan-2-yl)phenyl)ethyl)-1,3-oxazinan-2-one and 4-bromo-2,6-dimethylpyrimidine following a procedure analogous to that described in Example 1 Step 2. LC-MS Method 2 tR=1.073, m/z=464.1; $^1$H NMR (CD$_3$OD) 1.21 (m, 1H), 1.48 (d, 3H), 1.82 (m, 2H), 2.15 (m, 1H), 2.23 (m, 2H), 2.38 (m, 1H), 2.46 (s, 3H), 2.62 (s, 3H), 3.08 (m, 1H), 3.39 (m, 2H), 5.51 (m, 1H), 6.95-7.08 (m, 4H), 7.21 (m, 2H), 7.51 (s, 1H), 7.83 (d, 2H).

EXAMPLE 128

4108.1002-007 Example 563

(R)-6-(4-fluorophenyl)-6-(3-hydroxypropyl)-3-((S)-1-(4-(pyrimidin-4-yl)phenyl)ethyl)-1,3-oxazinan-2-one

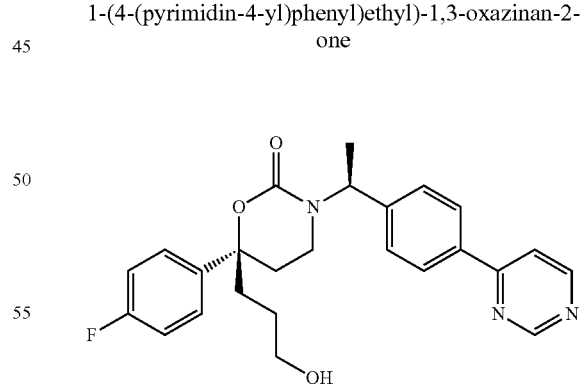

The title compound was prepared from (R)-6-(4-fluorophenyl)-6-(3-hydroxypropyl)-3-((S)-1-(4-(4,4,5,5-tetramethyl-1,3,2-dioxaborolan-2-yl)phenyl)ethyl)-1,3-oxazinan-2-one and 4-chloropyrimidine following a procedure analogous to that described in Example 1 Step 2. LC-MS Method 2 $t_R$=1.172, m/z=392.1; $^1$H NMR (CDCl$_3$) 1.28-1.40 (m, 1H), 1.52 (m, 3H), 1.64 (m, 2H), 1.81-1.99 (m, 2H), 2.09-2.37 (m, 3H), 2.90 (m, 1H), 3.51 (t, 2H), 5.68 (m, 1H), 6.88-7.07 (m, 3H), 7.16-7.28 (m, 3H), 7.58 (m, 1H), 7.79 (d, 2H), 8.61-8.80 (d, 1H), 9.18 (s, 1H).

EXAMPLE 129

4108.1002-007 Example 564

(R)-6-(4-fluorophenyl)-6-(3-hydroxypropyl)-3-((S)-1-(4-(pyrimidin-5-yl)phenyl)ethyl)-1,3-oxazinan-2-one

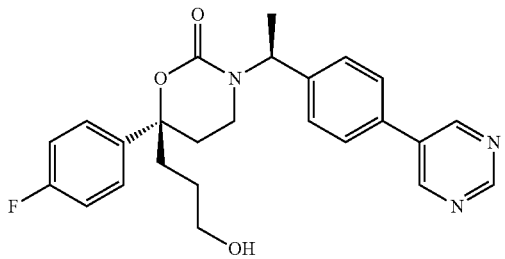 [SMILES: C[C@@H](c1ccc(-c2cncnc2)cc1)N1CC[C@](CCCO)(c2ccc(F)cc2)OC1=O]

The title compound was prepared from (R)-6-(4-fluorophenyl)-6-(3-hydroxypropyl)-3-((S)-1-(4-(4,4,5,5-tetramethyl-1,3,2-dioxaborolan-2-yl)phenyl)ethyl)-1,3-oxazinan-2-one and 5-bromopyrimidine following a procedure analogous to that described in Example 1 Step 2. LC-MS Method 2 $t_R$=1.332, m/z=436.1; $^1$H NMR (CD$_3$OD) 1.49 (d, 3H), 1.83 (m, 2H), 2.14-2.28 (m, 4H), 2.42 (m, 1H), 3.08 (m, 1H), 3.49 (m, 2H), 5.52 (m, 1H), 6.99 (t, 2H), 7.08 (d, 2H), 7.23 (m, 2H), 7.42 (d, 2H), 8.91 (s, 2H), 9.06 (s, 1H).

EXAMPLE 130

4108.1002-007 Example 569

(S)-6-(2-hydroxy-2-methylpropyl)-6-phenyl-3-((S)-1-(4-(pyrazin-2-yl)phenyl)ethyl)-1,3-oxazinan-2-one

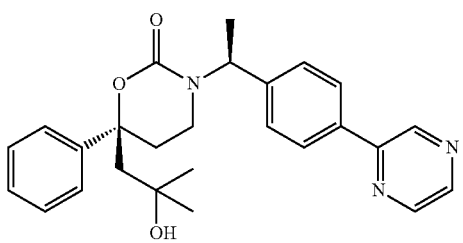 [SMILES: C[C@@H](c1ccc(-c2cnccn2)cc1)N1CC[C@](CC(C)(C)O)(c2ccccc2)OC1=O]

The title compound was prepared from (S)-6-(2-hydroxy-2-methylpropyl)-6-phenyl-3-((S)-1-(4-(4,4,5,5-tetramethyl-1,3,2-dioxaborolan-2-yl)phenyl)ethyl)-1,3-oxazinan-2-one and 2-bromopyrazine following a procedure analogous to that described in Example 1 Step 2. LC-MS Method 2 $t_R$=1.249, m/z=374; $^1$H NMR (CDCl$_3$) 1.12 (s, 3H), 1.28 (s, 3H), 1.58 (m, 3H), 2.19-2.20 (m, 4H), 2.39 (m, 1H), 2.89 (m, 1H), 5.74 (m, 1H), 7.09 (m, 2H), 7.28-7.40 (m, 5H), 7.78 (m, 2H), 8.48 (m, 1H), 8.59 (m, 1H), 8.94 (m, 1H).

EXAMPLE 131

4108.1002-007 Example 570

(S)-6-(2-hydroxy-2-methylpropyl)-6-phenyl-3-((S)-1-(4-(pyrimidin-4-yl)phenyl)ethyl)-1,3-oxazinan-2-one

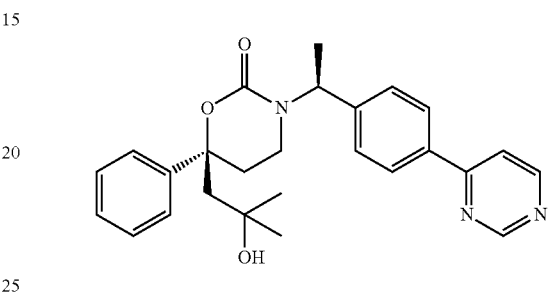

The title compound was prepared from (S)-6-(2-hydroxy-2-methylpropyl)-6-phenyl-3-((S)-1-(4-(4,4,5,5-tetramethyl-1,3,2-dioxaborolan-2-yl)phenyl)ethyl)-1,3-oxazinan-2-one and 4-chloropyrimidine following a procedure analogous to that described in Example 1 Step 2. LC-MS Method 2 $t_R$=1.167, m/z=374; $^1$H NMR (CDCl$_3$) 1.06 (s, 3H), 1.11 (s, 3H), 1.49 (d, 3H), 2.11 (s, 1H), 2.17 (s, 2H), 2.21 (m, 1H), 2.35 (m, 1H), 2.80 (m, 1H), 5.66 (m, 1H), 7.02 (d, 2H), 7.21-7.36 (m, 5H), 7.54 (d, 1H), 7.78 (d, 2H), 8.68 (d, 1H), 9.16 (s, 1H).

EXAMPLE 132

4108.1002-007 Example 571

(R)-6-(4-fluorophenyl)-6-(3-hydroxypropyl)-3-((S)-1-(4-(pyridazin-3-yl)phenyl)ethyl)-1,3-oxazinan-2-one

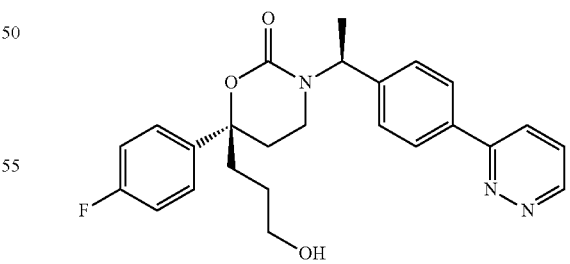

The title compound was prepared from (R)-6-(4-fluorophenyl)-6-(3-hydroxypropyl)-3-((S)-1-(4-(4,4,5,5-tetramethyl-1,3,2-dioxaborolan-2-yl)phenyl)ethyl)-1,3-oxazinan-2-one and 3-chloropyridazine following a procedure analogous to that described in Example 1 Step 2. LC-MS Method 2 $t_R$=1.067, m/z=436.1; $^1$H NMR (CDCl$_3$) 0.82 (m, 3H), 1.52 (d, 3H), 1.65 (m, 1H), 1.80-1.98 (m, 2H), 2.11-2.28

(m, 3H), 2.91 (m, 1H), 3.51 (t, 3H), 5.68 (m, 1H), 6.94-7.04 (m, 4H), 7.18 (m, 2H), 7.47 (m, 1H), 7.71 (d, 1H), 7.78 (d, 2H), 9.08 (d, 1H).

EXAMPLE 133

4108.1002-007 Example 572

(R)-3-((S)-1-(4-(2,6-dimethylpyridin-4-yl)phenyl)ethyl)-6-(3-hydroxypropyl)-6-phenyl-1,3-oxazinan-2-one

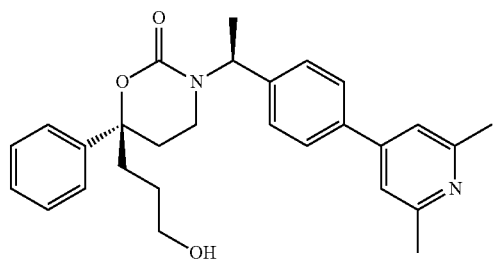 [SMILES: Cc1cc(-c2ccc([C@H](C)N3CC[C@](CCCO)(c4ccccc4)OC3=O)cc2)cc(C)n1]

The title compound was prepared from (R)-6-(3-hydroxypropyl)-6-phenyl-3-((S)-1-(4-(4,4,5,5-tetramethyl-1,3,2-dioxaborolan-2-yl)phenyl)ethyl)-1,3-oxazinan-2-one and 4-bromo-2,6-dimethylpyridine following a procedure analogous to that described in Example 1 Step 2. LC-MS Method 2 $t_R$=1.228, m/z=445; $^1$H NMR (CDCl$_3$) 1.32 (m, 1H) 1.51 (d, 3H), 1.60-1.72 (m, 1H), 1.86-2.02 (m, 2H), 2.19 (m, 1H), 2.25-2.39 (m, 2H), 2.79 (s, 6H), 2.93 (m, 1H), 3.50 (t, 2H), 5.64 (m, 1H), 7.00 (d, 2H), 7.21 (m, 2H), 7.29 (m, 2H), 7.32 (m, 3H), 7.40 (m, 2H).

EXAMPLE 134

4108.1002-007 Example 573

(S)-6-(2-hydroxy-2-methylpropyl)-3-((S)-1-(4-(6-methylpyridazin-3-yl)phenyl)ethyl)-6-phenyl-1,3-oxazinan-2-one Method 1

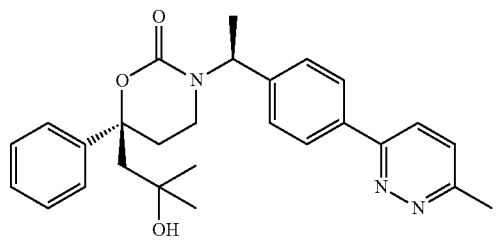 [SMILES: Cc1ccc(-c2ccc([C@H](C)N3CC[C@](CC(C)(C)O)(c4ccccc4)OC3=O)cc2)nn1]

The title compound was prepared from (S)-6-(2-hydroxy-2-methylpropyl)-6-phenyl-3-((S)-1-(4-(4,4,5,5-tetramethyl-1,3,2-dioxaborolan-2-yl)phenyl)ethyl)-1,3-oxazinan-2-one and 3-chloro-6-methyl-pyridazine following a procedure analogous to that described in Example 1 Step 2. LC-MS Method 2 $t_R$=1.118, m/z=446; $^1$H NMR (CD$_3$OD) 0.96 (s, 3H), 1.26 (s, 3H), 1.58 (d, 3H), 2.17 (s, 2H), 2.26 (m, 1H), 2.50 (m, 2H), 2.69 (s, 3H), 3.08 (m, 1H), 5.59 (m, 1H), 7.11 (m, 2H), 7.25-7.40 (5H), 7.63 (m, 1H), 7.82 (m, 2H), 7.98 (d, 1H). The compound was dissolved in refluxing methyl acetate and allowed to cool slowly to rt to afford a solid with mp 149.5-151.5° C.

Method 2

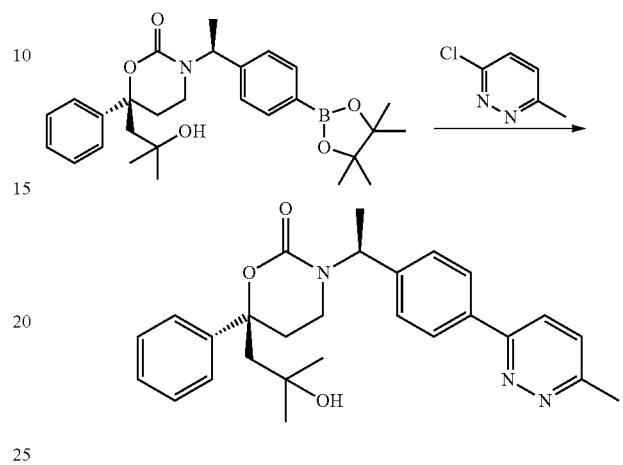

(S)-6-(2-Hydroxy-2-methyl-propyl)-3-{(S)-1-[4-(6-methyl-pyridazin-3-yl)-phenyl]-ethyl}-6-phenyl-[1,3]oxazinan-2-one was prepared from (S)-6-(2-hydroxy-2-methyl-propyl)-6-phenyl-3-[(S)-1-(4-(4,4,5,5-tetramethyl-1,3,2-dioxaborolan-2-yl)phenyl)ethyl]-1,3-oxazinan-2-one and 3-chloro-6-methyl-pyridazine following a procedure analogous to that described in Example 138 Method 2. Yield: 3.09 g (62% of theory). Mass spectrum (ESI+): m/z=446 [M+H]$^+$.

EXAMPLE 135

4108.1002-007 Example 574

(S)-6-(2-hydroxy-2-methylpropyl)-3-((S)-1-(4-(2-methylpyrimidin-4-yl)phenyl)ethyl)-6-phenyl-1,3-oxazinan-2-one

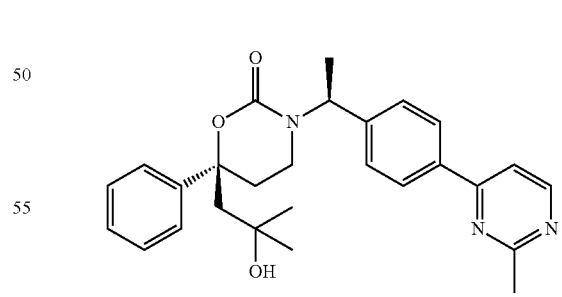

The title compound was prepared from (S)-6-(2-hydroxy-2-methylpropyl)-6-phenyl-3-((S)-1-(4-(4,4,5,5-tetramethyl-1,3,2-dioxaborolan-2-yl)phenyl)ethyl)-1,3-oxazinan-2-one and 4-chloro-2-methylpyrimidine following a procedure analogous to that described in Example 1 Step 2. LC-MS Method 2 $t_R$=1.196, m/z=446; $^1$H NMR (CD$_3$OD) 0.92 (s, 3H), 1.27 (s, 3H), 1.58 (d, 3H), 2.12 (s, 2H), 2.23 (m, 1H), 2.51-2.66 (m, 2H), 2.70 (s, 3H), 3.07 (m, 1H), 5.59 (m, 1H), 7.09 (d, 2H), 7.16-7.42 (m, 5H), 7.65 (d, 1H), 7.89 (d, 2H), 8.61 (d, 1H).

EXAMPLE 136

4108.1002-007 Example 575

(S)-3-((S)-1-(4-(5-fluoropyridin-2-yl)phenyl)ethyl)-6-(2-hydroxy-2-methylpropyl)-6-phenyl-1,3-oxazinan-2-one

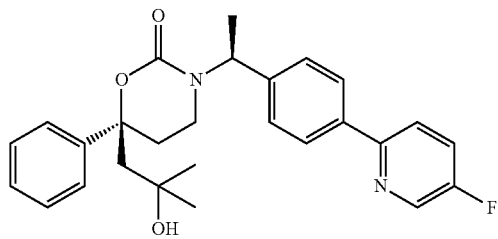 [SMILES: C[C@@H](c1ccc(-c2ccc(F)cn2)cc1)N1CC[C@](CC(C)(C)O)(c2ccccc2)OC1=O]

The title compound was prepared from (S)-6-(2-hydroxy-2-methylpropyl)-6-phenyl-3-((S)-1-(4-(4,4,5,5-tetramethyl-1,3,2-dioxaborolan-2-yl)phenyl)ethyl)-1,3-oxazinan-2-one and 2-bromo-5-fluoropyridine following a procedure analogous to that described in Example 1 Step 2. LC-MS Method 2 $t_R$=1.363, m/z=390.9; $^1$H NMR (CDCl$_3$) 1.11 (s, 3H), 1.19 (s, 3H), 1.53 (d, 3H), 2.16-2.30 (m, 4H), 2.32-2.43 (m, 1H), 2.86 (m, 1H), 5.71 (m, 1H), 7.03 (d, 2H), 7.30 (m, 1H), 7.36 (m, 4H), 7.44 (m, 1H), 7.69 (dd, 1H), 7.68 (d, 2H), 8.43 (d, 1H). The compound was dissolved in refluxing ethyl acetate and allowed to cool slowly to rt to afford a solid with mp 159-160° C.

EXAMPLE 137

4108.1002-007 Example 576

(R)-6-(4-fluorophenyl)-6-(3-hydroxypropyl)-3-((S)-1-(4-(2-methylpyrimidin-5-yl)phenyl)ethyl)-1,3-oxazinan-2-one

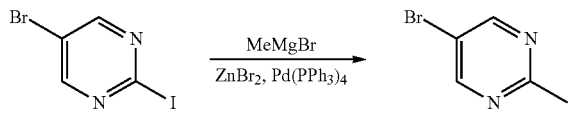

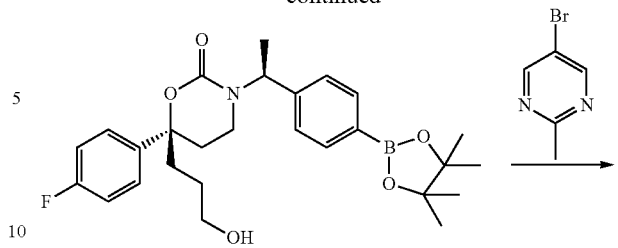

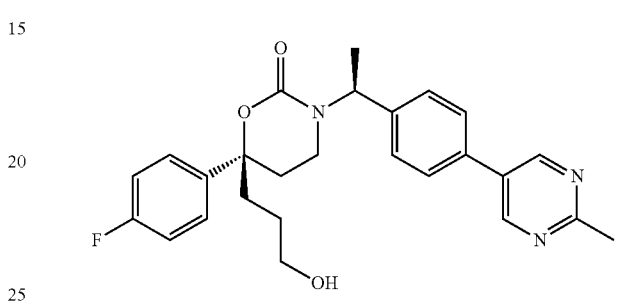

Step 1

To a solution of ZnBr$_2$ (1.33 g, 6 mmol) in THF (15 mL) was added MeMgBr (0.69 g, 6 mmol) under N$_2$ at −78° C. The mixture was stirred for 1 h and used for next step. To a solution of 5-bromo-2-iodo-pyrimidine (1.42 g, 5 mmol) in THF (15 mL) was added Pd(PPh$_3$)$_4$ (0.366 g, 0.33 mmol) and the prepared MeZnBr solution (10 mL) under N$_2$ at 0° C. The mixture was heated to 60° C. for 5 h during which time a second portion of MeZnBr solution (5 mL) was added. After cooling to room temperature, the reaction was poured into aqueous NH$_4$Cl solution. The mixture was extracted with EtOAc. The organic phase was separated and dried over Na$_2$SO$_4$, concentrated to give 5-bromo-2-methylpyrimidine (60 mg, 7%). $^1$H NMR (CDCl$_3$): 1.63 (s, 3H), 8.82 (s, 2H).

Step 2

To a solution of (R)-6-(4-fluorophenyl)-6-(3-hydroxypropyl)-3-((S)-1-(4-(4,4,5,5-tetramethyl-1,3,2-dioxaborolan-2-yl)phenyl)ethyl)-1,3-oxazinan-2-one (61 mg, 0.13 mmol), 5-bromo-2-methylpyrimidine (18 mg, 0.11 mmol), PdCl$_2$(PPh$_3$)$_2$ (6 mg, 10%) and aqueous solution of Cs$_2$CO$_3$ (2 mol/L, 0.13 mL) in 1,4-dioxane (1 mL) was heated to reflux overnight. The reaction was quenched with water. The organic layer was separated, dried and concentrated to give the residue, which was purified by column chromatography to give (R)-6-(4-fluorophenyl)-6-(3-hydroxypropyl)-3-((S)-1-(4-(2-methylpyrimidin-5-yl)phenyl)ethyl)-1,3-oxazinan-2-one (22 mg, 39%). $^1$H NMR (CDCl$_3$): 1.42 (m, 1H), 1.48 (d, 3H), 1.67 (m, 1H), 1.71-1.99 (m, 4H), 2.11-2.41 (m, 3H), 2.52 (s, 3H), 2.72 (m, 1H), 3.53 (m, 2H), 5.62 (m, 1H), 6.89-7.04 (m, 4H), 7.15-7.33 (m, 4H), 8.70 (s, 2H). LC-MS Method 2 $t_R$=1.184, m/z=450; $^1$H NMR (CDCl$_3$) 1.20 (d, 1H), 1.27-1.40 (m, 1H), 1.49 (d, 3H), 1.59-1.70 (m, 1H), 1.71-2.07 (m, 4H), 2.11-2.33 (m, 3H), 2.70 (s, 3H), 2.90 (m, 1H), 3.46-3.61 (t, 2H), 5.67 (m, 1H), 6.90-7.11 (m, 4H), 7.26 (m, 4H), 8.57-8.83 (s, 2H).

EXAMPLE 138

4108.1002-007 Example 583

6-(4-((S)-1-((S)-6-(2-hydroxy-2-methylpropyl)-2-oxo-6-phenyl-1,3-oxazinan-3-yl)ethyl)phenyl)nicotinonitrile Method 1

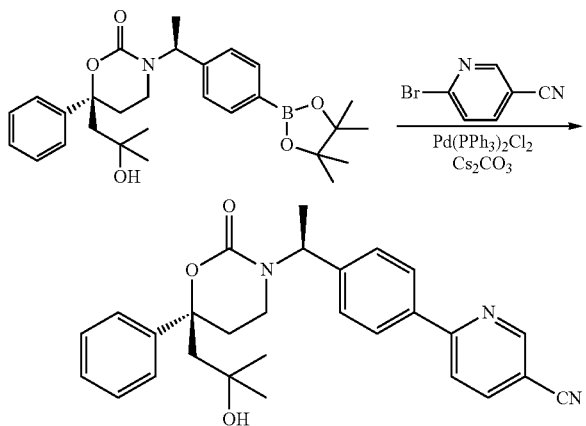

To a solution of (S)-6-(2-hydroxy-2-methylpropyl)-6-phenyl-3-((S)-1-(4-(4,4,5,5-tetramethyl-1,3,2-dioxaborolan-2-yl)phenyl)ethyl)-1,3-oxazinan-2-one (200 mg, 0.42 mmol) in 1,4-dioxane (1.5 mL) was added 6-bromonicotinonitrile (123 mg, 0.67 mmol), Pd(PPh$_3$)$_2$Cl$_2$ (30 mg, 0.042 mmol), and Cs$_2$CO$_3$ (1 mL, 2 M) were added. The vessel was sealed with a septum and placed into the microwave cavity. Microwave irradiation of 100 W was used, and the temperature being ramped from rt to 120° C. Once this temperature was reached, the reaction mixture was held at this temperature for 30 min. After the mixture was cooled to rt, the mixture was filtered. The filtrate was extracted with EtOAc (4×20 mL). The organic layer was washed with brine, dried over Na$_2$SO$_4$ and concentrated to give the crude product, which was purified by preparative TLC to give 6-(4-((S)-1-((S)-6-(2-hydroxy-2-methylpropyl)-2-oxo-6-phenyl-1,3-oxazinan-3-yl)ethyl)phenyl)nicotinonitrile (120 mg, 62%). LC-MS Method 2 t$_R$=1.33, m/z=398; $^1$H NMR (CDCl$_3$): 1.13 (s, 3H), 1.19 (s, 3H), 1.58 (d, 3H), 2.22 (m, 2H), 2.27 (m, 2H), 2.40 (m, 1H), 2.89 (m, 1H), 3.49 (s, 1H), 5.73 (m, 1H), 7.11 (d, 2H), 7.28-7.38 (m, 5H), 7.80 (m, 3H), 8.00 (d, 1H), 8.93 (s, 1H).

Method 2

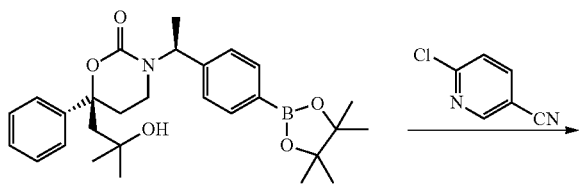

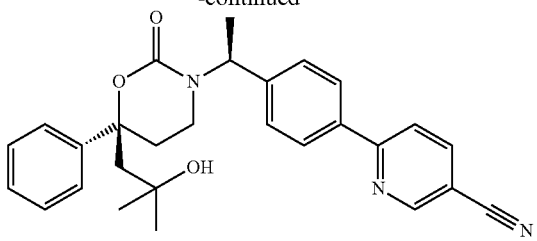

2 M aqueous Na$_2$CO$_3$ solution (1.04 mL) was added to a solution of (S)-6-(2-hydroxy-2-methylpropyl)-6-phenyl-3-[(S)-1-(4-(4,4,5,5-tetramethyl-1,3,2-dioxaborolan-2-yl)phenyl)ethyl]-1,3-oxazinan-2-one (0.50 g) and 6-chloro-nicotinonitrile (0.22 g) in dimethylformamide (3 mL). The resulting mixture was sparged with argon for 5 min, before [1,1'-bis(diphenylphosphino)ferrocene]-dichloropalladium (II) dichloromethane complex (51 mg) is added. The mixture was heated to 100° C. and stirred at this temperature overnight. After cooling to ambient temperature, water was added and the resulting mixture was extracted with ethyl acetate. The combined organic extracts were washed with brine, dried (MgSO$_4$), and concentrated. The residue was purified by chromatography on silica gel (CH$_2$Cl$_2$/MeOH 98:2->80:20) to afford (S)-6-(4-{(S)-1-[6-(2-Hydroxy-2-methyl-propyl)-2-oxo-6-phenyl-[1,3]oxazinan-3-yl]-ethyl}-phenyl)-nicotinonitrile as an oil (0.50 g) which was crystallized from a mixture of EtOAc (15 mL) and iPr$_2$O (5 mL) by scratching to yield a solid, mp 160-162° C. Yield: 0.32 g (67% of theory). Mass spectrum (ESI$^+$): m/z=456 [M+H]$^+$. mp=160-162° C.

EXAMPLE 139

4108.1002-007 Example 585

(S)-3-((S)-1-(4-(2,6-dimethylpyridin-4-yl)phenyl)ethyl)-6-(2-hydroxy-2-methylpropyl)-6-phenyl-1,3-oxazinan-2-one

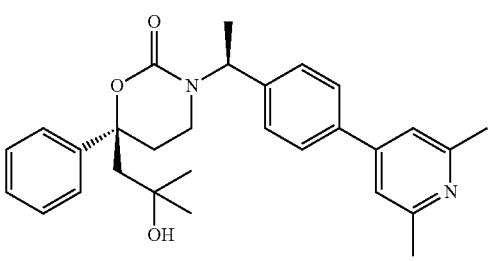 [SMILES: Cc1cc(-c2ccc([C@H](C)N3CC[C@](CC(C)(C)O)(c4ccccc4)OC3=O)cc2)cc(C)n1]

The title compound was prepared from (S)-6-(2-hydroxy-2-methylpropyl)-6-phenyl-3-((S)-1-(4-(4,4,5,5-tetramethyl-1,3,2-dioxaborolan-2-yl)phenyl)ethyl)-1,3-oxazinan-2-one and 4-bromo-2,6-dimethylpyridine following a procedure analogous to that described in Example 1 Step 2. LC-MS Method 2 t$_R$=1.049, m/z=459.1; $^1$H NMR (CD$_3$OD) 0.94 (s, 3H), 1.24 (s, 3H), 1.55 (d, 3H), 2.15 (s, 2H), 2.23 (m, 1H), 2.45 (m, 1H), 2.51 (s, 6H), 3.05 (m, 1H), 5.57 (m, 1H), 7.04 (d, 2H), 7.24 (s, 2H), 7.26-7.38 (m, 5H), 7.45 (m, 1H).

EXAMPLE 140

4108.1002-007 Example 587

6-(4-((S)-1-((R)-6-(3-hydroxypropyl)-2-oxo-6-phenyl-1,3-oxazinan-3-yl)ethyl)phenyl)nicotinamide

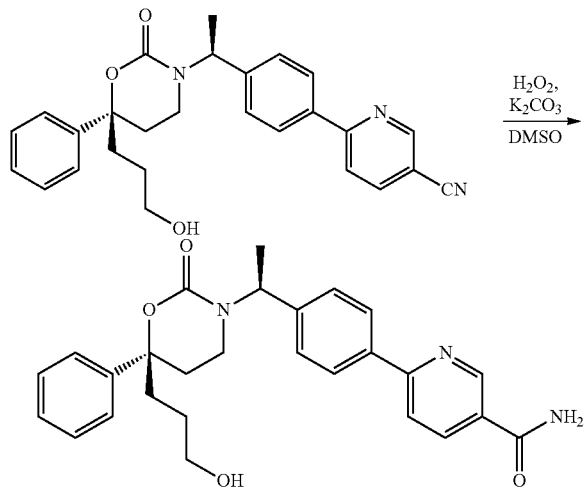

6-(4-((S)-1-((R)-6-(3-hydroxypropyl)-2-oxo-6-phenyl-1,3-oxazinan-3-yl)ethyl)phenyl)nicotinonitrile (50 mg, 0.11 mmol) and H$_2$O$_2$ (0.04 mL, 30%), K$_2$CO$_3$ (6.27 mg, 0.046 mmol) in DMSO (0.39 mL) was stirred overnight at room temperature. The reaction was added water and EtOAc. The layer was separated. The organic phase was washed with brine and dried, concentrated to give the product (9.95 mg, 19%) LC-MS Method 2 $t_R$=1.083, m/z=460.1; $^1$H NMR (CD$_3$OD) 1.21 (m, 1H), 1.51 (d, 3H), 1.53-1.64 (m, 1H), 1.85-1.94 (m, 2H), 2.10-2.21 (m, 1H), 2.29 (m, 1H), 2.42 (m, 1H), 3.03 (m, 1H), 3.39 (t, 2H), 5.52 (m, 1H), 6.99 (d, 2H), 7.21-7.34 (m, 5H), 7.22 (d, 2H), 7.31 (d, 1H), 8.22 (d, 1H), 8.98 (s, 1H).

EXAMPLE 141

4108.1002-007 Example 589

(R)-3-((S)-1-(4-(2,6-dimethylpyridin-3-yl)phenyl)ethyl)-6-(4-fluorophenyl)-6-(3-hydroxypropyl)-1,3-oxazinan-2-one

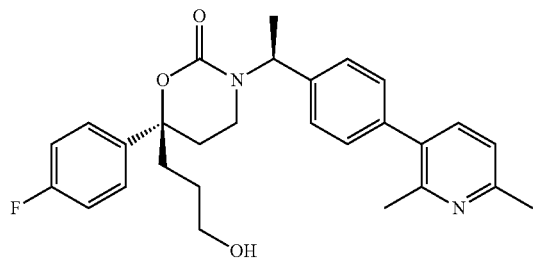 [SMILES: Cc1ccc(-c2ccc([C@H](C)N3CC[C@](CCCO)(c4ccc(F)cc4)OC3=O)cc2)c(C)n1]

The title compound was prepared from (R)-6-(4-fluorophenyl)-6-(3-hydroxypropyl)-3-((S)-1-(4-(4,4,5,5-tetramethyl-1,3,2-dioxaborolan-2-yl)phenyl)ethyl)-1,3-oxazinan-2-one and 3-bromo-2,6-dimethylpyridine following a procedure analogous to that described in Example 1 Step 2. LC-MS Method 2 $t_R$=1.012, m/z=463.1; $^1$H NMR (CDCl$_3$) 1.32 (m, 2H), 1.49 (d, 3H), 1.62 (m, 2H), 1.86-1.96 (m, 2H), 2.17-2.29 (m, 3H), 2.31 (s, 3H), 2.49 (s, 3H), 2.93 (m, 1H), 3.51 (m, 2H), 5.68 (m, 1H), 6.88-7.03 (m, 7H), 7.25 (m, 3H).

EXAMPLE 142

4108.1002-007 Example 597

3-((R)-6-(4-fluorophenyl)-3-((S)-1-(4-(2-methylpyrimidin-4-yl)phenyl)ethyl)-2-oxo-1,3-oxazinan-6-yl)-2,2-dimethylpropanenitrile

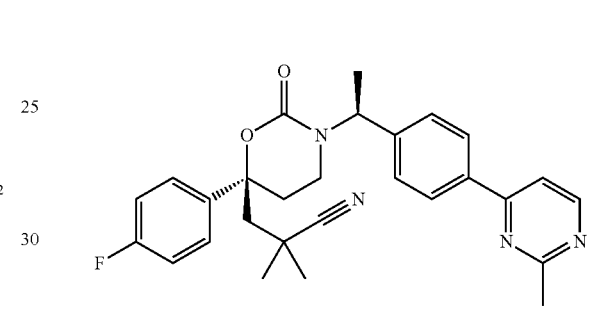

The title compound was prepared from 3-((R)-6-(4-fluorophenyl)-2-oxo-3-((S)-1-(4-(4,4,5,5-tetramethyl-1,3,2-dioxaborolan-2-yl)phenyl)ethyl)-1,3-oxazinan-6-yl)-2,2-dimethylpropanenitrile and 4-chloro-2-methylpyrimidine following a procedure analogous to that described in Example 1 Step 2. LC-MS Method 1 $t_R$=1.55, m/z=473 (M+1); $^1$H NMR (CDCl$_3$) 8.96 (s, 1H), 7.98 (d, 2H), 7.84 (s, 1H), 7.29 (m, 2H), 7.10 (m, 4H), 5.72 (d, 1H), 3.05 (d, 1H), 2.97 (s, 3H), 2.91 (m, 1H), 2.51 (d, 1H), 1.61 (d, 3H), 1.38 (d, 3H), 1.27 (d, 3H).

EXAMPLE 143

4108.1002-007 Example 598

6-(4-((S)-1-((S)-6-(2-hydroxy-2-methylpropyl)-2-oxo-6-phenyl-1,3-oxazinan-3-yl)ethyl)phenyl)nicotinamide

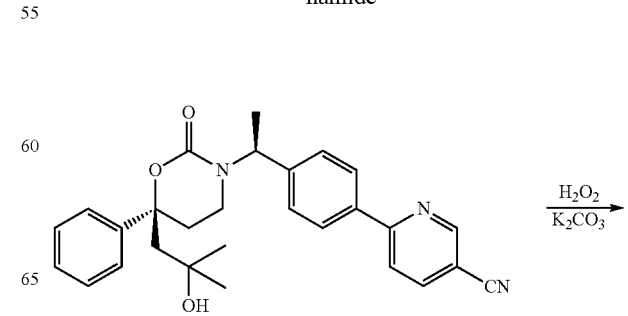

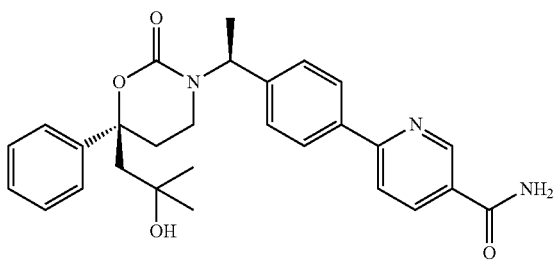

To a solution of 6-(4-((S)-1-((S)-6-(2-hydroxy-2-methylpropyl)-2-oxo-6-phenyl-1,3-oxazinan-3-yl)ethyl)phenyl)nicotinonitrile (120 mg, 0.26 mmol) in DMSO (8 mL) were added $H_2O_2$ (0.5 mL, 30%) and $K_2CO_3$ (35 mg, 0.26 mmol), and the mixture was stirred at rt for 3 h. The reaction was quenched with $H_2O$ (10 mL) and the mixture was extracted with EtOAc (4×20 mL). The organic layer was washed with brine, dried over $Na_2SO_4$ and concentrated to give the crude product, which was purified by preparative HPLC to give 6-(4-((S)-1-((S)-6-(2-hydroxy-2-methylpropyl)-2-oxo-6-phenyl-1,3-oxazinan-3-yl)ethyl)phenyl)nicotinamide (55.46 mg, 45%). LC-MS Method 2 $t_R$=1.12 min, m/z=474, 416. $^1$H NMR (CDCl$_3$): 1.03 (s, 3H), 1.09 (s, 3H), 1.46 (d, 3H), 2.13-2.26 (m, 5H), 2.30 (m, 1H), 2.44 (s, 1H), 2.79 (d, 1H), 5.61 (m, 1H), 6.15-6.38 (s, 1H), 6.97 (d, 2H), 7.13-7.29 (m, 5H), 7.60 (d, 2H), 7.70 (d, 2H), 8.15 (d, 1H), 9.05 (s, 1H).

EXAMPLE 144

4108.1002-007 Example 599

(S)-3-((S)-1-(4-(2,6-dimethylpyridin-4-yl)phenyl)ethyl)-6-(4-fluorophenyl)-6-(2-hydroxy-2-methylpropyl)-1,3-oxazinan-2-one

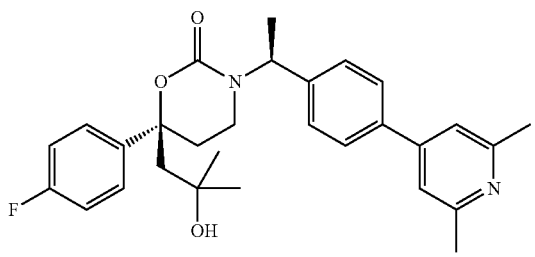 [SMILES: Cc1cc(-c2ccc([C@H](C)N3CC[C@](CC(C)(C)O)(c4ccc(F)cc4)OC3=O)cc2)cc(C)n1]

The title compound was prepared (S)-6-(4-fluorophenyl)-6-(2-hydroxy-2-methylpropyl)-3-((S)-1-(4-(4,4,5,5-tetramethyl-1,3,2-dioxaborolan-2-yl)phenyl)ethyl)-1,3-oxazinan-2-one and 4-bromo-2,6-dimethylpyridine following a procedure analogous to that described in Example 1 Step 2. LC-MS Method 2 $t_R$=1.001, m/z=477.1; $^1$H NMR (CDCl$_3$) 1.05-1.23 (d, 6H), 1.49 (d, 3H), 2.10-2.23 (m, 4H), 2.31-2.42 (m, 1H), 2.56 (s, 6H), 2.89 (m, 1H), 5.67 (m, 1H), 6.92-7.07 (m, 4H), 7.08 (s, 2H), 7.22 (m, 2H), 7.33 (d, 2H).

EXAMPLE 145

4108.1002-007 Example 604

6-(4-((S)-1-((R)-6-(2-(5-methyl-1,3,4-oxadiazol-2-yl)ethyl)-2-oxo-6-phenyl-1,3-oxazinan-3-yl)ethyl)phenyl)nicotinonitrile

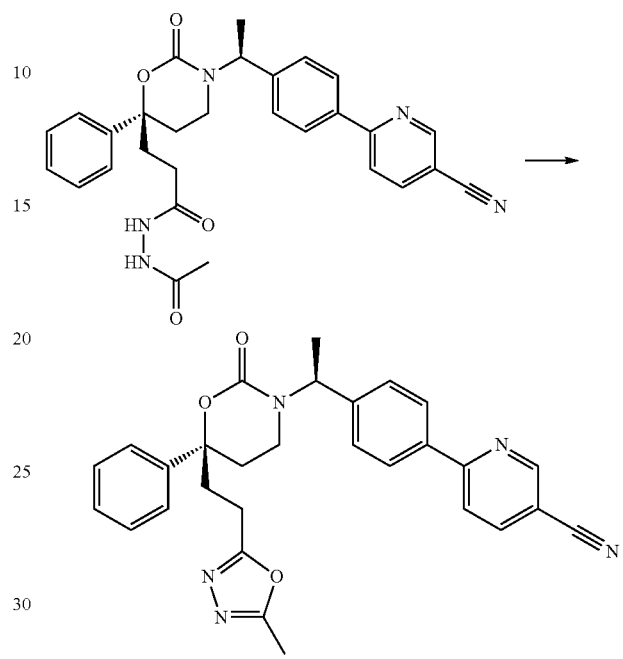

The title compound was prepared from N'-acetyl-3-((R)-3-((S)-1-(4-(5-cyanopyridin-2-yl)phenyl)ethyl)-2-oxo-6-phenyl-1,3-oxazinan-6-yl)propanehydrazide following procedures analogous to those described in Example 12 Step 6. LC-MS Method 2 $t_R$=1.265, m/z=494.1; $^1$H NMR (CDCl$_3$) 1.59 (d, 3H), 2.06 (m, 1H), 2.33 (m, 5H), 2.48 (s, 2H), 2.52-2.71 (m, 2H), 2.97 (m, 1H), 3.09 (m, 1H), 5.72 (m, 1H), 7.08 (d, 2H), 7.29 (m, 2H), 7.32 (m, 2H), 7.34-7.58 (m, 2H), 7.77 (m, 2H), 7.99 (d, 1H), 8.89 (s, 1H).

EXAMPLE 146

4108.1002-007 Example 607

6-(4-((S)-1-((R)-6-(2-(5-methyl-1,3,4-thiadiazol-2-yl)ethyl)-2-oxo-6-phenyl-1,3-oxazinan-3-yl)ethyl)phenyl)nicotinonitrile

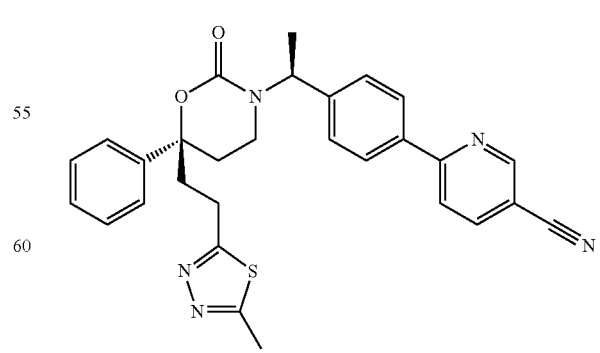

The title compound was prepared from N'-acetyl-3-((R)-3-((S)-1-(4-(5-cyanopyridin-2-yl)phenyl)ethyl)-2-oxo-6- phenyl-1,3-oxazinan-6-yl)propanehydrazide following a procedure analogous to that described in Example 39 Step 4. LC-MS Method 2 $t_R$=1.306, m/z=511.1; $^1$H NMR (CDCl$_3$) 1.59 (d, 3H), 2.25 (m, 1H), 2.43 (m, 2H), 2.49 (m, 2H), 2.74 (s, 3H), 2.82 (m, 1H), 2.99 (m, 1H), 3.31 (m, 1H), 5.72 (m, 1H), 7.09 (d, 2H), 7.31 (m, 3H), 7.40 (m, 2H), 7.72-7.87 (m, 3H), 8.00 (d, 1H), 8.91 (s, 1H).

EXAMPLE 147

4108.1002-007 Example 609

(R)-6-(4-fluorophenyl)-6-(3-hydroxypropyl)-3-((S)-1-(4-(2-methoxypyridin-4-yl)phenyl)ethyl)-1,3-oxazinan-2-one

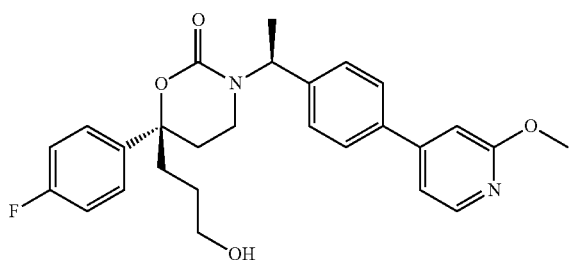 [SMILES: COc1cc(-c2ccc([C@H](C)N3CC[C@](CCCO)(c4ccc(F)cc4)OC3=O)cc2)ccn1]

The title compound was prepared from (R)-3-((S)-1-(4-bromophenyl)ethyl)-6-(4-fluorophenyl)-6-(3-hydroxypropyl)-1,3-oxazinan-2-one and 2-methoxypyridin-4-ylboronic acid following a procedure analogous to that described in Example 14. LC-MS Method 1 $t_R$=1.9 min, m/z=447 (M+1); $^1$H NMR (CDCl$_3$) 8.29 (1H, d, J=5.5 Hz), 7.34 (2H, m), 7.21-7.15 (m, 3H), 7.02-6.93 (5H, m), 5.67-5.61 (1H, m), 4.05 (3H, s), 3.53 (1H, t, J=6.41 Hz), 2.97-2.93 (1H, m), 2.33-2.11 (3H, m), 2.06-1.83 (3H, m), 1.67-1.57 (1H, m), 1.50 (3H, d, J=7.03), 1.36-1.26 (1H, m).

EXAMPLE 148

4108.1002-007 Example 610

(R)-6-(4-fluorophenyl)-3-((S)-1-(4-(5-fluoropyridin-3-yl)phenyl)ethyl)-6-(3-hydroxypropyl)-1,3-oxazinan-2-one

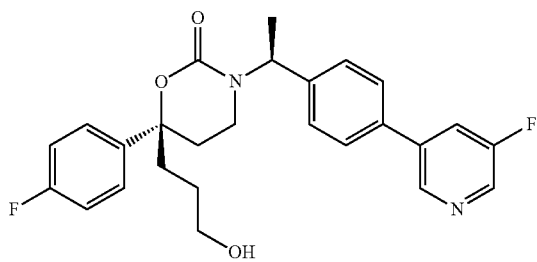 [SMILES: C[C@@H](c1ccc(-c2cncc(F)c2)cc1)N1CC[C@](CCCO)(c2ccc(F)cc2)OC1=O]

The title compound was prepared from (R)-3-((S)-1-(4-bromophenyl)ethyl)-6-(4-fluorophenyl)-6-(3-hydroxypropyl)-1,3-oxazinan-2-one and 5-fluoropyridin-3-ylboronic acid following a procedure analogous to that described in Example 14. LC-MS Method 1 $t_R$=1.5 min, m/z=453 (M+1).

EXAMPLE 149

4108.1002-007 Example 619

(S)-6-(2-hydroxy-2-methylpropyl)-3-((S)-1-(4-(2-methylpyrimidin-5-yl)phenyl)ethyl)-6-phenyl-1,3-oxazinan-2-one Method 1

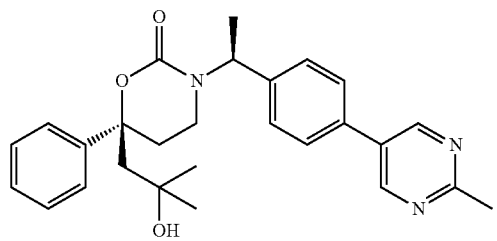

The title compound was prepared from (S)-6-(2-hydroxy-2-methylpropyl)-6-phenyl-3-((S)-1-(4-(4,4,5,5-tetramethyl-1,3,2-dioxaborolan-2-yl)phenyl)ethyl)-1,3-oxazinan-2-one and 2-methyl-5-bromopyrimidine following a procedure analogous to that described in Example 1 Step 2. LC-MS Method 2 $t_R$=1.221 min, m/z=468.2; $^1$H NMR (CDCl$_3$) 1.06 (s, 3H), 1.12 (s, 3H), 1.49 (d, 3H), 2.11-2.28 (m, 4H), 2.31-2.42 (m, 1H), 2.70 (s, 3H), 2.82 (m, 1H), 5.65 (m, 1H), 7.00 (d, 2H), 7.21-7.34 (m, 7H), 8.19 (s, 2H).

Method 2

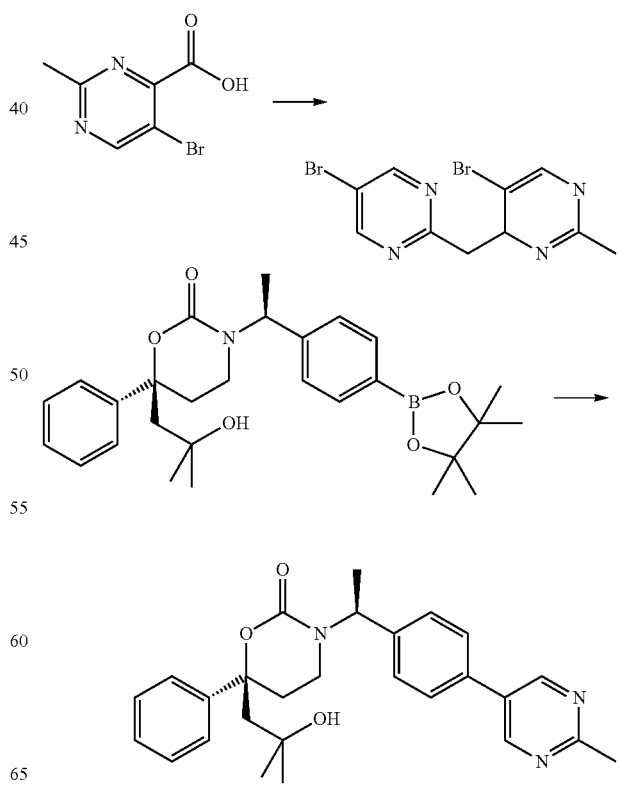

Step 1. 5-Bromo-2-(5-bromo-2-methyl-1,4-dihydro-pyrimidin-4-ylmethyl)-pyrimidine 5-Bromo-2-methyl-pyrimidine-4-carboxylic acid (5.0 g) was heated above its melting point ($m_p$ 176° C.) during which decarboxylation takes place. After cooling to ambient temperature, the tar-like substance was purified by chromatography on silica gel (CH$_2$Cl$_2$/MeOH 90:10->70:30) to afford the title compound as a black liquid. Yield: 0.45 g (6% of theory). Mass spectrum (ESI$^+$): m/z=345/347/349 (2 Br) [M+H]$^+$

Step 2. (S)-6-(2-Hydroxy-2-methyl-propyl)-3-{(S)-1-[4-(2-methyl-pyrimidin-5-yl)-phenyl]-ethyl}-6-phenyl-[1,3]oxazinan-2-one 2 M aqueous Na$_2$CO$_3$ solution (1.67 mL) was added to a solution of (S)-6-(2-hydroxy-2-methylpropyl)-6-phenyl-3-[(S)-1-(4-(4,4,5,5-tetramethyl-1,3,2-dioxaborolan-2-yl)phenyl)ethyl]-1,3-oxazinan-2-one (0.80 g) and 5-bromo-2-(5-bromo-2-methyl-1,4-dihydro-pyrimidin-4-ylmethyl)-pyrimidine (0.40 g) in dimethylformamide (5 mL). The resulting mixture was sparged with argon for 5 min, before [1,1'-bis(diphenylphosphino)ferrocene]-dichloropalladium (II) dichloromethane complex (82 mg) was added. The mixture was heated to 100° C. and stirred at this temperature overnight. After cooling to ambient temperature, water was added, and the resulting mixture was extracted with ethyl acetate. The combined organic extracts were washed with brine, dried (MgSO$_4$), and concentrated. The residue was purified by chromatography on silica gel (CH$_2$Cl$_2$/MeOH 95:5->80:20) followed by HPLC (MeCN/H$_2$O/NH$_4$OH) to afford the title compound (340 mg) which was crystallized from 1:3 EtOAc/diisopropylether by scratching to yield a solid, mp 112-115° C. Yield: 0.25 g (34% of theory). Mass spectrum (ESI$^+$): m/z=446 [M+H]$^+$

EXAMPLE 150

4108.1002-007 Example 627

6-(4-{1-[6-(2-Hydroxy-2-methyl-propyl)-2-oxo-6-phenyl-[1,3]oxazinan-3-yl]-ethyl}-phenyl)-N-methyl-nicotinamide

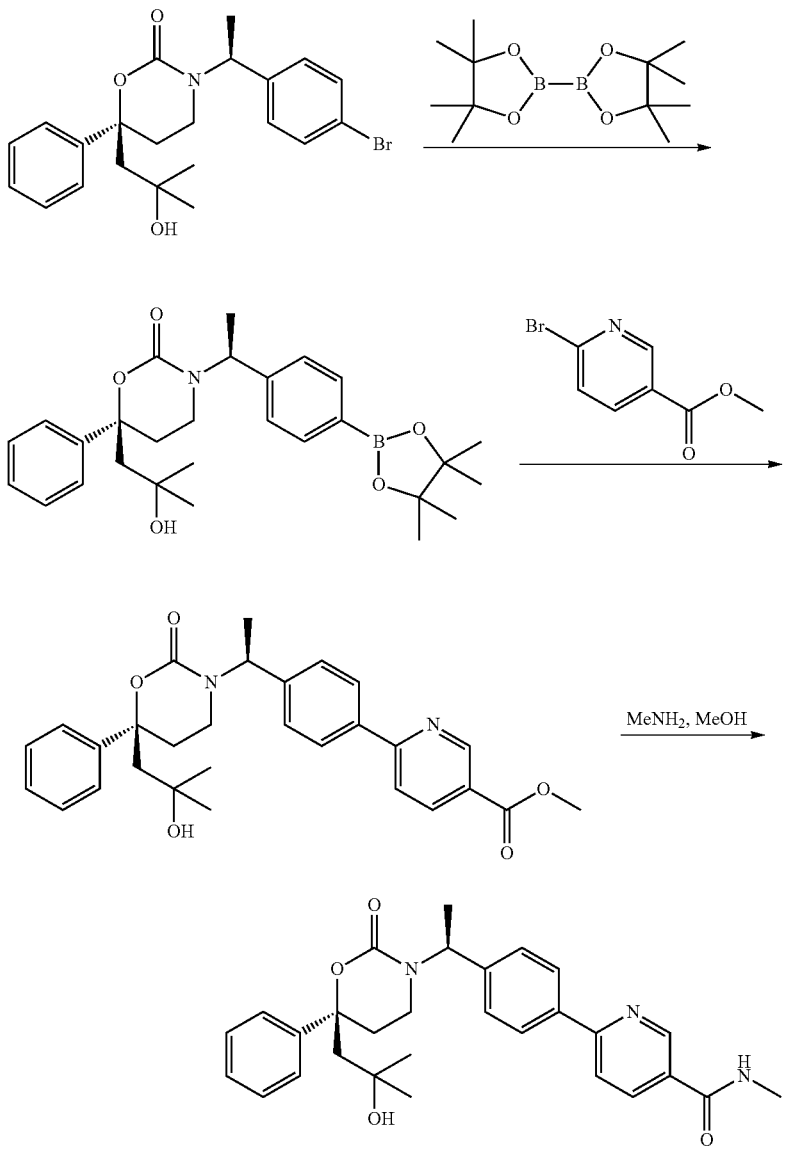

Step 1

To a solution of (S)-3-((S)-1-(4-bromophenyl)ethyl)-6-(2-hydroxy-2-methylpropyl)-6-phenyl-1,3-oxazinan-2-one (6.6 g, 15.2 mmol) and 4,4,4',4',5,5,5',5'-octamethyl-2,2'-bi(1,3,2-dioxaborolane) (6.1 g, 24.3 mmol) in dry DMSO (20 mL) was added KOAc (4.8 g, 48.6 mmol) and Pd(dppf)Cl$_2$ (372 mg, 0.46 mmol). After addition, the mixture was warmed to 100° C. for 20 h. After TLC showed the starting material had disappeared, the solid was filtered off. Water (60 mL) and EtOAc (20 mL) were added, the layers were separated and the aqueous layer was extracted with EtOAc (3×15 mL). The combined organic layer was washed with brine, dried over Na$_2$SO$_4$, filtered and concentrated to give (S)-6-(2-hydroxy-2-methylpropyl)-6-phenyl-3-((S)-1-(4-(4,4,5,5-tetramethyl-1,3,2-dioxaborolan-2-yl)phenyl)ethyl)-1,3-oxazinan-2-one (4.4 g, 60%), which was purified by column. $^1$H NMR (CDCl$_3$): 1.03 (s, 3H), 1.12 (s, 3H), 1.22 (s, 12H), 1.49 (d, 3H), 2.13 (m, 4H), 2.26 (m, 1H), 2.73 (m, 1H), 5.64 (q, 1H), 6.91 (d, 2H), 7.38 (m, 5H), 7.51 (d, 2H).

Step 2

To a solution of (S)-6-(2-hydroxy-2-methylpropyl)-6-phenyl-3-((S)-1-(4-(4,4,5,5-tetramethyl-1,3,2-dioxaborolan-2-yl)phenyl)ethyl)-1,3-oxazinan-2-one (500 mg, 1.04 mmol) and methyl 6-bromonicotinate (292 mg, 1.35 mmol) in dry 1,4-dioxane (5 mL) was added CsCO$_3$ (1 mL, 2 mmol) and Pd(PPh$_3$)$_2$Cl$_2$ (50 mg). After addition, the mixture was warmed to 110° C. for 30 min under microwave. After TLC showed the starting material had disappeared, the solid was filtered off. Water (20 mL) and EtOAc (10 mL) was added, the layers were separated and the aqueous layer was extracted with EtOAc (3×10 mL). The combined organic layer was washed with brine, dried over Na$_2$SO$_4$, filtered and concentrated to give methyl 6-(4-((S)-1-((S)-6-(2-hydroxy-2-methylpropyl)-2-oxo-6-phenyl-1,3-oxazinan-3-yl)ethyl)phenyl)nicotinate (507 mg, 89%), which was purified by preparative TLC. $^1$H NMR (CDCl$_3$): 1.13 (s, 3H), 1.19 (s, 3H), 1.61 (d, 3H), 2.24 (m, 4H), 2.37 (m, 1H), 2.88 (m, 1H), 4.02 (s, 3H), 5.76 (q, 1H), 7.11 (d, 2H), 7.29-7.47 (m, 6H), 7.78 (m, 1H), 7.82 (m, 2H), 8.38 (d, 1H), 9.31 (s, 1H).

Step 3

Methyl 6-(4-((S)-1-((S)-6-(2-hydroxy-2-methylpropyl)-2-oxo-6-phenyl-1,3-oxazinan-3-yl)ethyl)phenyl)nicotinate (150 mg, 0.307 mmol) was dissolved in NH$_2$Me/MeOH (10 mL). The mixture was stirred at rt overnight. The solvent was removed in vacuo to give the crude product, which was purified by preparative HPLC and chiral HPLC to afford 6-(4-((S)-1-((S)-6-(2-hydroxy-2-methylpropyl)-2-oxo-6-phenyl-1,3-oxazinan-3-yl)ethyl)phenyl)-N-methylnicotinamide (54 mg, 36%). LC-MS Method 2 t$_R$=1.117 min, m/z=430.1; $^1$H NMR (CD$_3$OD) 0.93 (s, 3H), 1.27 (s, 3H), 1.59 (d, 3H), 2.16 (s, 2H), 2.22-2.37 (m, 1H), 2.41-2.60 (m, 2H), 2.99 (s, 3H), 3.11 (m, 1H), 5.60 (m, 1H), 7.12 (d, 1H), 7.29 (m, 5H), 7.80 (m, 2H), 8.01 (d, 1H), 8.41 (d, 1H), 9.03 (s, 1H).

EXAMPLE 151

4108.1002-007 Example 629

(S)-6-(2-hydroxy-2-methylpropyl)-3-((S)-1-(4-(5-methylpyrazin-2-yl)phenyl)ethyl)-6-phenyl-1,3-oxazinan-2-one

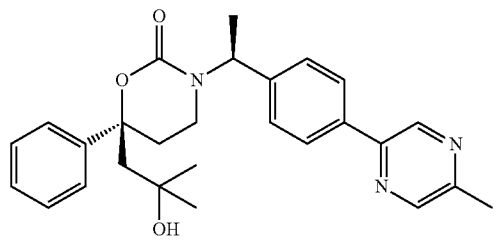 [SMILES: Cc1cnc(-c2ccc([C@H](C)N3CC[C@](CC(C)(C)O)(c4ccccc4)OC3=O)cc2)cn1]

The title compound was prepared from (S)-6-(2-hydroxy-2-methylpropyl)-6-phenyl-3-((S)-1-(4-(4,4,5,5-tetramethyl-1,3,2-dioxaborolan-2-yl)phenyl)ethyl)-1,3-oxazinan-2-one and 2-bromo-5-methylpyrazine following a procedure analogous to that described in Example 1 Step 2. LC-MS Method 2 t$_R$=1.257 min, m/z=388; $^1$H NMR (CDCl$_3$) 1.07 (s, 3H), 1.12 (s, 3H), 1.49 (d, 3H), 2.01-2.13 (m, 4H), 2.28-2.39 (m, 1H), 2.57 (s, 3H), 2.80 (m, 1H), 5.68 (m, 1H), 7.02 (d, 2H), 7.21-7.33 (m, 5H), 7.67 (d, 2H), 8.41 (s, 1H), 8.76 (s, 1H).

EXAMPLE 152

4108.1002-007 Example 631

5-fluoro-2-(4-((S)-1-((S)-6-(2-hydroxy-2-methylpropyl)-2-oxo-6-phenyl-1,3-oxazinan-3-yl)ethyl)phenyl)pyridine 1-oxide

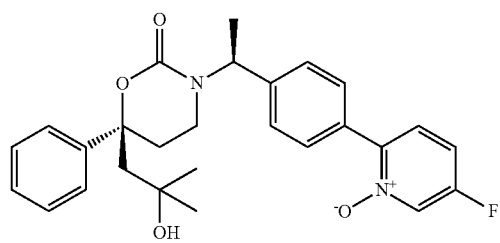

The title compound was prepared from (S)-3-((S)-1-(4-(5-fluoropyridin-2-yl)phenyl)ethyl)-6-(2-hydroxy-2-methylpropyl)-6-phenyl-1,3-oxazinan-2-one following a procedure analogous to that described in Example 38. LC-MS Method 1 t$_R$=1.29 min, m/z=465 (M+1), 407; $^1$H NMR (CD$_3$OD) 8.37 (m, 1H), 7.50-7.37 (m, 4H), 7.29-7.19 (m, 5H), 6.97 (d, J=7.9 Hz, 2H), 5.48 (q, J=7.0 Hz, 1H), 2.99-2.94 (m, 1H), 2.46-2.33

(m, 2H), 2.22-2.14 (m, 1H), 2.06 (s, 2H), 1.46 (d, J=7.0 Hz, 3H), 1.16 (s, 3H), 0.85 (s, 3H).

EXAMPLE 153

4108.1002-007 Example 632

5-(4-((S)-1-((S)-6-(4-fluorophenyl)-6-(2-hydroxy-2-methylpropyl)-2-oxo-1,3-oxazinan-3-yl)ethyl)phenyl)pyrazine-2-carbonitrile

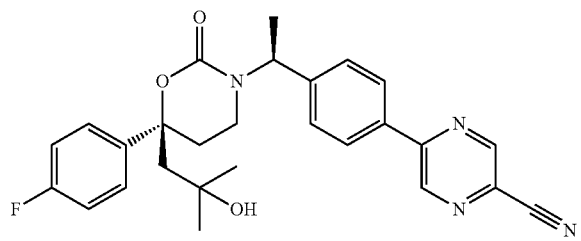 [SMILES: C[C@@H](c1ccc(-c2cnc(C#N)cn2)cc1)N1CC[C@](CC(C)(C)O)(c2ccc(F)cc2)OC1=O]

The title compound was prepared from (S)-6-(4-fluorophenyl)-6-(2-hydroxy-2-methylpropyl)-3-((S)-1-(4-(4,4,5,5-tetramethyl-1,3,2-dioxaborolan-2-yl)phenyl)ethyl)-1,3-oxazinan-2-one and 5-chloropyrazine-2-carbonitrile following a procedure analogous to that described in Example 14. LC-MS Method 1 $t_R$=1.64 min, m/z=497 (M+Na); $^1$H NMR (CDCl$_3$) 8.98 (d, 2H), 7.89 (d, 2H), 7.27 (m, 1H), 7.17 (m, 2H), 7.04 (m, 3H), 5.72 (q, 1H), 4.40 (br s, 1H), 2.98 (m, 1H), 1.59 (d, 3H), 1.13 (d, 6H).

EXAMPLE 154

4108.1002-007 Example 633

4-(4-((S)-1-((S)-6-(2-hydroxy-2-methylpropyl)-2-oxo-6-phenyl-1,3-oxazinan-3-yl)propyl)phenyl)-2,6-dimethylpyridine 1-oxide

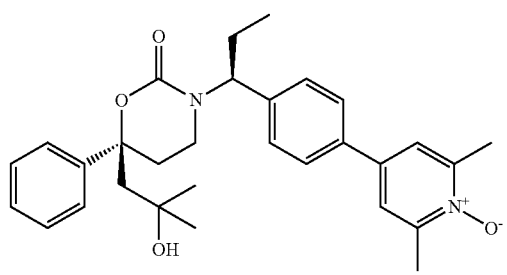 [SMILES: CC[C@@H](c1ccc(-c2cc(C)[n+]([O-])c(C)c2)cc1)N1CC[C@](CC(C)(C)O)(c2ccccc2)OC1=O]

The title compound was prepared from (S)-6-(2-hydroxy-2-methylpropyl)-6-phenyl-3-((S)-1-(4-(4,4,5,5-tetramethyl-1,3,2-dioxaborolan-2-yl)phenyl)propyl)-1,3-oxazinan-2-one and 4-bromo-2,6-dimethylpyridine-N-oxide following a procedure analogous to that described in Example 1 Step 2. LC-MS Method 2 $t_R$=1.185 min, m/z=489.2; $^1$H NMR (CDCl$_3$) 0.96 (t, 3H), 1.03 (s, 3H), 1.12 (s, 3H), 1.81-2.00 (m, 4H), 2.11-2.22 (m, 5H), 2.30-2.42 (m, 1H), 2.57 (s, 6H), 2.87 (m, 1H), 5.43 (m, 1H), 7.09 (d, 2H), 7.18 (m, 1H), 7.22 (m, 4H), 7.26 (m, 2H), 7.31 (m, 2H).

EXAMPLE 155

4108.1002-007 Example 634

(S)-6-(4-fluorophenyl)-6-(2-hydroxy-2-methylpropyl)-3-((S)-1-(4-(6-methylpyridazin-3-yl)phenyl)ethyl)-1,3-oxazinan-2-one

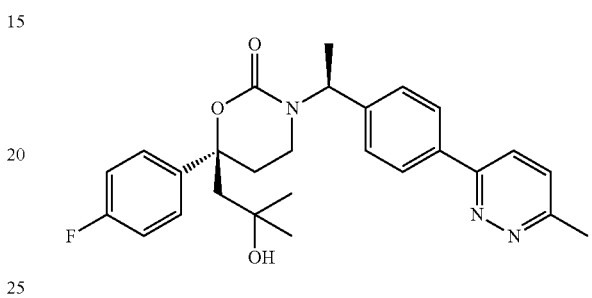

The title compound was prepared from (S)-6-(4-fluorophenyl)-6-(2-hydroxy-2-methylpropyl)-3-((S)-1-(4-(4,4,5,5-tetramethyl-1,3,2-dioxaborolan-2-yl)phenyl)ethyl)-1,3-oxazinan-2-one and 3-chloro-6-methylpyridazine following a procedure analogous to that described in Example 1 Step 2. LC-MS Method 2 $t_R$=1.163 min, m/z=464; $^1$H NMR (CDCl$_3$) 1.12 (d, 6H), 1.55 (d, 3H), 2.18 (s, 2H), 2.19-2.28 (m, 2H), 2.40 (m, 1H), 2.74 (s, 3H), 2.90 (m, 1H), 5.71 (m, 1H), 6.96-7.05 (t, 2H), 7.10 (d, 2H), 7.29 (m, 2H), 7.38 (d, 2H), 7.69 (d, 1H), 7.82 (d, 2H).

EXAMPLE 156

4108.1002-007 Example 635

6-(4-((S)-1-((S)-6-(2-hydroxy-2-methylpropyl)-2-oxo-6-phenyl-1,3-oxazinan-3-yl)ethyl)phenyl)-N,N-dimethylnicotinamide

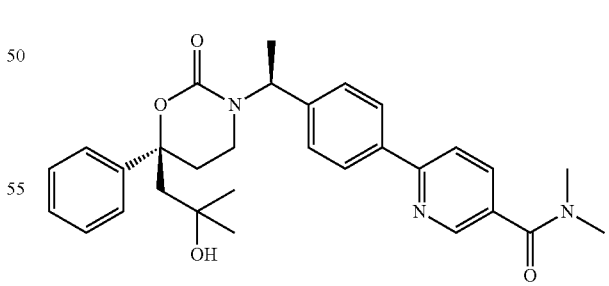

The title compound was prepared from methyl 6-(4-((S)-1-((S)-6-(2-hydroxy-2-methylpropyl)-2-oxo-6-phenyl-1,3-oxazinan-3-yl)ethyl)phenyl)nicotinate and dimethylamine following a procedure analogous to that described in Example 150 Step 3. LC-MS Method 2 $t_R$=1.708 min, m/z=444.1; $^1$H NMR (CDCl$_3$) 1.10 (s, 3H), 1.18 (s, 3H), 1.56 (d, 3H), 2.18-2.31 (m, 4H), 2.32-2.53 (m, 1H), 2.86 (m, 1H), 3.08 (s, 3H), 3.13 (s, 3H), 5.71 (m, 1H), 7.08 (d, 2H), 7.29-7.52 (m, 5H), 7.69 (d, 1H), 7.76 (d, 1H), 7.82 (d, 1H), 8.70 (s, 1H).

EXAMPLE 157

4108.1002-007 Example 640

6-(4-((S)-1-((S)-6-(4-fluorophenyl)-6-(2-hydroxy-2-methylpropyl)-2-oxo-1,3-oxazinan-3-yl)ethyl)phenyl)pyrazine-2-carbonitrile

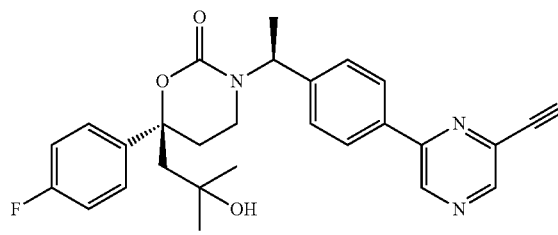

The title compound was prepared from (S)-6-(4-fluorophenyl)-6-(2-hydroxy-2-methylpropyl)-3-((S)-1-(4-(4,4,5,5-tetramethyl-1,3,2-dioxaborolan-2-yl)phenyl)ethyl)-1,3-oxazinan-2-one and 6-chloropyrazine-2-carbonitrile following a procedure analogous to that described in Example 14. LC-MS Method 1 $t_R$=1.61 min, m/z=497 (M+Na); $^1$H NMR (CDCl3) 8.98 (d, 2H), 7.87 (d, 2H), 7.26 (m, 1H), 7.18 (m, 3H), 7.04 (t, 2H), 5.72 (q, 1H), 2.99 (m, 1H), 1.59 (d, 3H), 1.14 (d, 6H).

EXAMPLE 158

4108.1002-007 Example 644

2-(4-((S)-1-((S)-6-(2-hydroxy-2-methylpropyl)-2-oxo-6-phenyl-1,3-oxazinan-3-yl)ethyl)phenyl)-N,N-dimethylthiazole-5-carboxamide

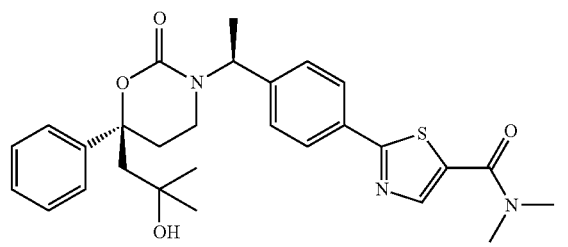 [SMILES: C[C@@H](c1ccc(-c2ncc(C(=O)N(C)C)s2)cc1)N1CC[C@](CC(C)(C)O)(c2ccccc2)OC1=O]

The title compound was prepared from (S)-6-(2-hydroxy-2-methylpropyl)-6-phenyl-3-((S)-1-(4-(4,4,5,5-tetramethyl-1,3,2-dioxaborolan-2-yl)phenyl)propyl)-1,3-oxazinan-2-one and 2-bromo-N,N-dimethylthiazole-5-carboxamide following a procedure analogous to that described in Example 1 Step 2. LC-MS Method 2 $t_R$=1.215 min, m/z=450.1; $^1$H NMR (CD$_3$OD) 0.92 (s, 3H), 1.22 (s, 3H), 1.53 (d, 3H), 2.11 (s, 2H), 2.19-2.28 (m, 1H), 2.40-2.58 (m, 2H), 3.00-3.31 (m, 4H), 5.56 (m, 1H), 7.02 (d, 2H), 7.26-7.39 (m, 5H), 7.69 (d, 2H), 8.08 (s, 1H). The compound was dissolved in refluxing isopropyl acetate and allowed to cool slowly to rt to afford a solid with mp 110-111.5° C.

EXAMPLE 159

4108.1002-007 Example 645

6-(4-{1-[6-(4-Fluoro-phenyl)-6-(2-hydroxy-2-methyl-propyl)-2-oxo-[1,3]oxazinan-3-yl]-ethyl}-phenyl)-pyrazine-2-carboxylic acid amide

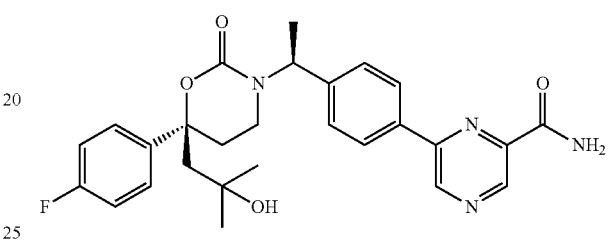

The title compound was prepared from 6-(4-((S)-1-((S)-6-(4-fluorophenyl)-6-(2-hydroxy-2-methylpropyl)-2-oxo-1,3-oxazinan-3-yl)ethyl)phenyl)pyrazine-2-carbonitrile following a procedure analogous to that described in Example 140. LC-MS Method 1 $t_R$=1.32 min, m/z=493; $^1$H NMR (CDCl$_3$) 9.24 (d, 2H), 7.88 (s, 1H), 7.83 (d, 2H), 4.29 (m, 2H), 7.16 (d, 2H), 7.06 (t, 2H), 6.62 (s, 1H), 5.74 (q, 1H), 3.00 (m, 1H), 2.48 (m, 1H), 1.60 (d, 3H), 1.17 (d, 6H).

EXAMPLE 160

4108.1002-007 Example 656

(S)-3-((S)-1-(4-(6-ethoxy-5-methylpyridin-3-yl)phenyl)ethyl)-6-(2-hydroxy-2-methylpropyl)-6-phenyl-1,3-oxazinan-2-one

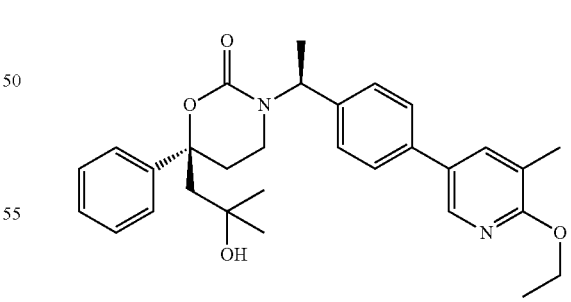

The title compound was prepared from (S)-6-(2-hydroxy-2-methylpropyl)-6-phenyl-3-((S)-1-(4-(4,4,5,5-tetramethyl-1,3,2-dioxaborolan-2-yl)phenyl)ethyl)-1,3-oxazinan-2-one and 5-bromo-2-ethoxy-3-methylpyridine following a procedure analogous to that described in Example 1 Step 2. LC-MS Method 2 $t_R$=1.314 min, m/z=489; $^1$H NMR (CDCl$_3$) 1.04 (s, 3H), 1.11 (s, 3H), 1.34 (t, 3H), 1.47 (d, 3H), 2.13-2.24 (m, 7H), 2.32 (m, 1H), 2.81 (m, 1H), 4.34 (q, 2H), 5.62 (q, 1H), 6.93 (d, 2H), 7.17-7.27 (m, 7H), 7.42 (s, 1H), 8.02 (s, 1H).

EXAMPLE 161

4108.1002-007 Example 657

N-cyclopropyl-6-(4-((S)-1-((S)-6-(2-hydroxy-2-methylpropyl)-2-oxo-6-phenyl-1,3-oxazinan-3-yl)ethyl) phenyl)nicotinamide

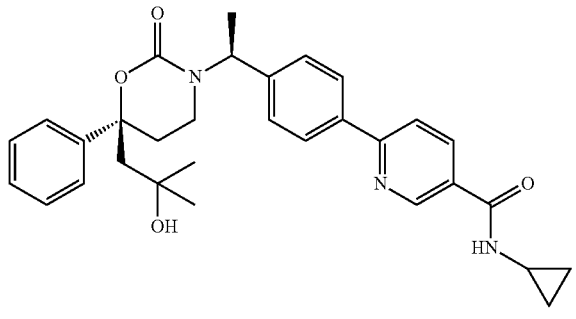 [SMILES: C[C@@H](c1ccc(-c2ccc(C(=O)NC3CC3)cn2)cc1)N1CC[C@](CC(C)(C)O)(c2ccccc2)OC1=O]

The title compound was prepared from (S)-6-(2-hydroxy-2-methylpropyl)-6-phenyl-3-((S)-1-(4-(4,4,5,5-tetramethyl-1,3,2-dioxaborolan-2-yl)phenyl)ethyl)-1,3-oxazinan-2-one and 6-bromo-N-cyclopropylnicotinamide following a procedure analogous to that described in Example 14. LC-MS Method 1 $t_R$=1.74 min, m/z=456.1; $^1$H NMR (CDCl$_3$) 0.61 (m, 2H), 0.82 (m, 2H), 1.13 (s, 3H), 1.22 (s, 3H), 1.49 (d, 3H), 2.17 (m, 3H), 2.21 (m, 1H), 2.31 (m, 1H), 2.79 (m, 1H), 2.88 (m, 1H), 5.66 (m, 1H), 6.40 (s, 1H), 6.99 (d, 1H), 7.20-7.31 (m, 5H), 7.60 (d, 1H), 7.68 (d, 2H), 8.07 (d, 1H), 8.89 (s, 1H). The compound was dissolved in refluxing isopropyl acetate and allowed to cool slowly to it to afford a solid with mp 191-194° C.

6-bromo-N-cyclopropylnicotinamide was prepared from 6-bromonicotinoyl chloride and cyclopropylamine.

EXAMPLE 162

4108.1002-007 Example 660

(S)-3-((S)-1-(4-(2-ethoxy-6-methylpyridin-4-yl)phenyl)ethyl)-6-(2-hydroxy-2-methylpropyl)-6-phenyl-1,3-oxazinan-2-one

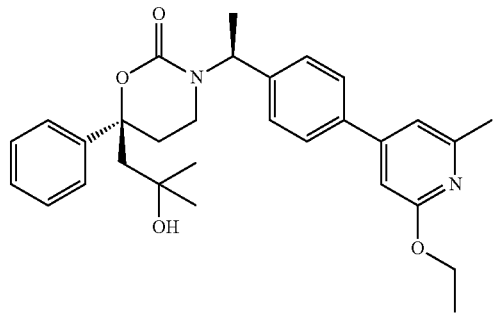 [SMILES: CCOc1cc(-c2ccc([C@H](C)N3CC[C@](CC(C)(C)O)(c4ccccc4)OC3=O)cc2)cc(C)n1]

The title compound was prepared from (S)-6-(2-hydroxy-2-methylpropyl)-6-phenyl-3-((S)-1-(4-(4,4,5,5-tetramethyl-1,3,2-dioxaborolan-2-yl)phenyl)ethyl)-1,3-oxazinan-2-one and 4-bromo-2-ethoxy-6-methylpyridine following a procedure analogous to that described in Example 1 Step 2. LC-MS Method 2 $t_R$=1.259 min, m/z=489.2; $^1$H NMR (CDCl$_3$) 1.10 (s, 3H), 1.15 (s, 3H), 1.34 (m, 3H), 1.49 (m, 3H), 2.16 (m, 3H), 2.19 (m, 1H), 2.32 (m, 1H), 2.42 (m, 3H), 2.79 (m, 1H), 4.32 (m, 2H), 5.66 (m, 1H), 6.55 (s, 1H), 6.76 (s, 1H), 6.98 (m, 2H), 7.19-7.29 (m, 7H).

EXAMPLE 163

4108.1002-007 Example 661

N-tert-butyl-6-(4-((S)-1-((S)-6-(2-hydroxy-2-methylpropyl)-2-oxo-6-phenyl-1,3-oxazinan-3-yl)ethyl) phenyl)nicotinamide

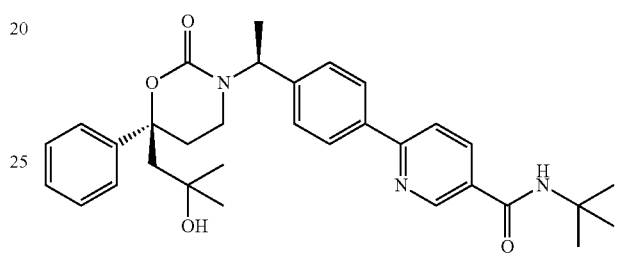

The title compound was prepared from (S)-6-(2-hydroxy-2-methylpropyl)-6-phenyl-3-((S)-1-(4-(4,4,5,5-tetramethyl-1,3,2-dioxaborolan-2-yl)phenyl)ethyl)-1,3-oxazinan-2-one and 6-bromo-N-tert-butylnicotinamide following a procedure analogous to that described in Example 1 Step 2. LC-MS Method 2 $t_R$=1.898 min, m/z=472.2; $^1$H NMR (CDCl$_3$) 1.08 (s, 3H), 1.15 (s, 3H), 1.34 (s, 9H), 1.49 (d, 3H), 2.16 (m, 3H), 2.19 (m, 1H), 2.32 (m, 1H), 2.42 (m, 3H), 2.79 (m, 1H), 4.32 (m, 2H), 5.66 (m, 1H), 6.55 (s, 1H), 6.76 (s, 1H), 6.98 (m, 2H), 7.19-7.29 (m, 7H).

6-bromo-N-tert-butylnicotinamide was prepared from 6-bromonicotinoyl chloride and tert-butylamine.

EXAMPLE 164

4108.1002-007 Example 662

2-(4-((S)-1-((S)-6-(2-hydroxy-2-methylpropyl)-2-oxo-6-phenyl-1,3-oxazinan-3-yl)ethyl)phenyl)isonicotinonitrile

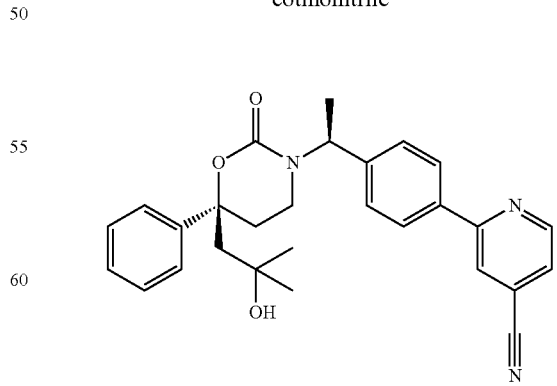

The title compound was prepared from (S)-6-(2-hydroxy-2-methylpropyl)-6-phenyl-3-((S)-1-(4-(4,4,5,5-tetramethyl- 1,3,2-dioxaborolan-2-yl)phenyl)ethyl)-1,3-oxazinan-2-one and 2-bromoisonicotinonitrile following a procedure analogous to that described in Example 138 Method 1. LC-MS Method 2 $t_R$=1.419 min, m/z=478.1; $^1$H NMR (CD$_3$OD) 0.93 (s, 3H), 1.26 (s, 3H), 1.57 (d, 3H), 2.17 (s, 2H), 2.25 (m, 1H), 2.41-2.58 (m, 2H), 3.06 (m, 1H), 5.58 (m, 1H), 7.08 (d, 2H), 7.25-7.40 (m, 5H), 7.59 (d, 1H), 7.80 (d, 2H), 8.10 (s, 1H), 8.29 (d, 1H).

EXAMPLE 165

4108.1002-007 Example 663

2-(4-((S)-1-((S)-6-(2-hydroxy-2-methylpropyl)-2-oxo-6-phenyl-1,3-oxazinan-3-yl)ethyl)phenyl)nicotinonitrile

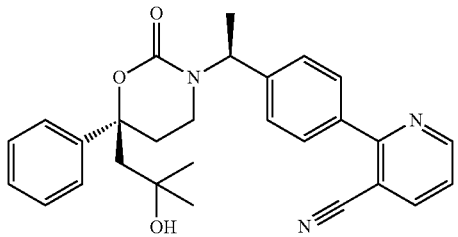 [SMILES: C[C@@H](c1ccc(-c2ncccc2C#N)cc1)N1CC[C@](CC(C)(C)O)(c2ccccc2)OC1=O]

The title compound was prepared from (S)-6-(2-hydroxy-2-methylpropyl)-6-phenyl-3-((S)-1-(4-(4,4,5,5-tetramethyl-1,3,2-dioxaborolan-2-yl)phenyl)ethyl)-1,3-oxazinan-2-one and 2-bromonicotinonitrile following a procedure analogous to that described in Example 138 Method 1. LC-MS Method 2 $t_R$=1.23 min, m/z=398.1; $^1$H NMR (CD$_3$OD) 0.93 (s, 3H), 1.26 (s, 3H), 1.57 (d, 3H), 2.17 (s, 2H), 2.28 (m, 1H), 2.50 (m, 2H), 3.09 (m, 1H), 5.58 (m, 1H), 7.08 (d, 2H), 7.22-7.41 (m, 5H), 7.50 (m, 1H), 7.62 (d, 2H), 8.23 (d, 1H), 8.81 (m, 1H). Mass spectrum (ESI$^-$): m/z=500 [M+HCOO]$^-$

EXAMPLE 166

4108.1002-007 Example 665

2,2-dimethyl-3-((R)-3-((S)-1-(4-(6-methylpyridazin-3-yl)phenyl)ethyl)-2-oxo-6-phenyl-1,3-oxazinan-6-yl)propanenitrile

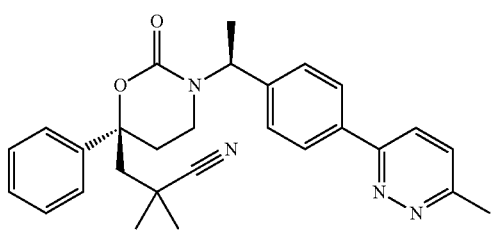 [SMILES: Cc1ccc(-c2ccc([C@H](C)N3CC[C@](CC(C)(C)C#N)(c4ccccc4)OC3=O)cc2)nn1]

The title compound was prepared from 2,2-dimethyl-3-((R)-2-oxo-6-phenyl-3-((S)-1-(4-(4,4,5,5-tetramethyl-1,3,2-dioxaborolan-2-yl)phenyl)ethyl)-1,3-oxazinan-6-yl)propanenitrile and 3-chloro-6-methylpyridazine following a procedure analogous to that described in Example 14. LC-MS Method 1 $t_R$=1.41 min, m/z=455; $^1$H NMR (CDCl$_3$) 8.20 (d, 1H), 7.92 (d, 1H), 7.74 (d, 2H), 7.37 (dt, 6H), 7.05 (d, 2H), 5.66 (q, 1H), 3.00 (dm, 1H), 2.93 (s, 3H), 2.49 (m, 2H), 2.34 (m, 1H), 2.17 (d, 2H), 1.58 (d, 3H), 1.39 (s, 3H), 1.33 (s, 3H).

EXAMPLE 167

4108.1002-007 Example 677

(R)-6-(methoxymethyl)-3-((S)-1-(4-(6-methylpyridazin-3-yl)phenyl)ethyl)-6-phenyl-1,3-oxazinan-2-one

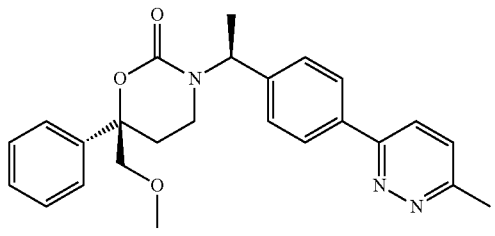

The title compound was prepared from (R)-6-(methoxymethyl)-6-phenyl-3-((S)-1-(4-(4,4,5,5-tetramethyl-1,3,2-dioxaborolan-2-yl)phenyl)ethyl)-1,3-oxazinan-2-one and 3-chloro-6-methylpyridazine following a procedure analogous to that described in Example 14. Mass spectrum (ESI$^+$): m/z=418 [M+H]$^+$.

EXAMPLE 168

4108.1002-007 Example 680

5-(4-{(S)-1-[(S)-6-(2-Hydroxy-2-methyl-propyl)-2-oxo-6-phenyl-[1,3]oxazinan-3-yl]-ethyl}-phenyl)-pyridine-2-carboxylic acid ethylamide

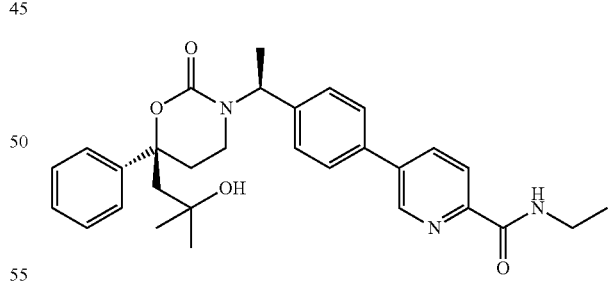

2-(1H-Benzotriazol-1-yl)-1,1,3,3-tetramethyluronium tetrafluoroborate (75 mg) was added to a solution of 5-(4-{(S)-1-[(S)-6-(2-hydroxy-2-methyl-propyl)-2-oxo-6-phenyl-[1,3]oxazinan-3-yl]ethyl}-phenyl)-pyridine-2-carboxylic acid (0.10 g) and diisopropylethylamine (50 μL) in dimethylformamide (1 mL) at room temperature. The resulting solution was stirred for 25 min, before ethylamine (70% in water, 50 μL) was added. The solution was stirred at room temperature overnight and then concentrated under reduced pressure. The crude product was purified by HPLC on reversed phase (MeCN/H₂O) to afford the title compound as a foam-like solid. Yield: 25 mg (24% of theory). Mass spectrum (ESI⁺): m/z=502 [M+H]⁺

Intermediate XXVII 5-(4-{(S)-1-[(S)-6-(2-Hydroxy-2-methyl-propyl)-2-oxo-6-phenyl-[1,3]oxazinan-3-yl]-ethyl}-phenyl)-pyridine-2-carboxylic acid

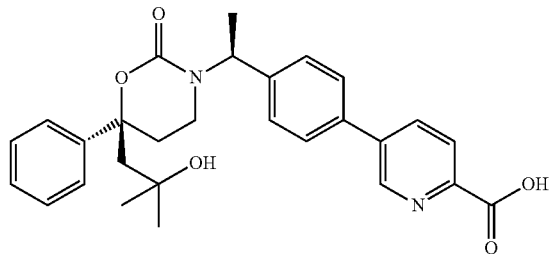

2 M aqueous Na₂CO₃ solution (1.3 mL) was added to a solution of (S)-6-(2-hydroxy-2-methylpropyl)-6-phenyl-3-{(S)-1-[4-(4,4,5,5-tetramethyl-1,3,2-dioxaborolan-2-yl)phenyl]ethyl}-1,3-oxazinan-2-one (0.60 g) and 5-bromo-pyridine-2-carboxylic acid methyl ester (0.41 g) in dimethylformamide (4 mL). The resulting mixture was sparged with argon for 10 min, before [1,1'-bis(diphenylphosphino)ferrocene]dichloropalladium(II) dichloromethane complex (61 mg) was added. The mixture was heated to 100° C. and stirred at this temperature overnight. After cooling to ambient temperature, the mixture was diluted with ethyl acetate and extracted with water and brine. The aqueous extracts were combined, acidified (pH ca. 5-6) using citric acid, and extracted with CH₂Cl₂/MeOH (ca. 10:1). The combined organic extracts were washed with brine and dried (MgSO₄). The solvent was removed and the residue was purified by chromatography on silica gel (CH₂Cl₂/MeOH 98:2->50:50) to afford the title compound as a resin-like solid. Yield: 0.44 g (73% of theory); Mass spectrum (ESI⁺): m/z=475 [M+H]⁺.

EXAMPLE 169

5-(4-{(S)-1-[(S)-6-(2-Hydroxy-2-methyl-propyl)-2-oxo-6-phenyl-[1,3]oxazinan-3-yl]-ethyl}-phenyl)-pyridine-2-carboxylic acid methylamide

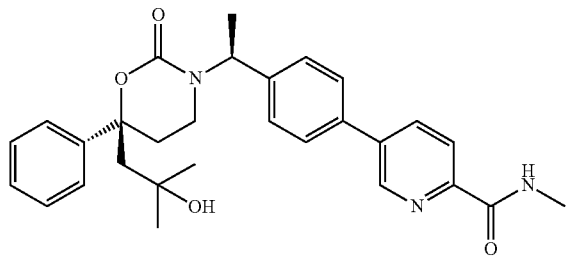

The title compound was prepared from 5-(4-{(S)-1-[(S)-6-(2-hydroxy-2-methyl-propyl)-2-oxo-6-phenyl-[1,3]oxazinan-3-yl]-ethyl}-phenyl)-pyridine-2-carboxylic acid and methylamine following a procedure analogous to that described in Example 168. Mass spectrum (ESI⁺): m/z=488 [M+H]⁺.

EXAMPLE 170

(4-{(S)-1-[(S)-6-(2-Hydroxy-2-methyl-propyl)-2-oxo-6-phenyl-[1,3]oxazinan-3-yl]-ethyl}-phenyl)-pyridine-2-carboxylic acid dimethylamide

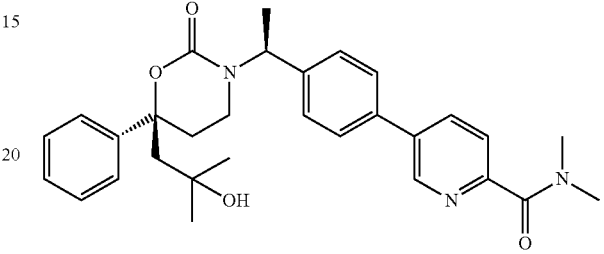

The title compound was prepared from 5-(4-{(S)-1-[(S)-6-(2-hydroxy-2-methyl-propyl)-2-oxo-6-phenyl-[1,3]oxazinan-3-yl]-ethyl}-phenyl)-pyridine-2-carboxylic acid and dimethylamine following a procedure analogous to that described in Example 168. Mass spectrum (ESI⁺): m/z=502 [M+H]⁺.

EXAMPLE 171

(S)-6-(2-Hydroxy-2-methyl-propyl)-6-phenyl-3-[(S)-1-(4-thiazol-5-yl-phenyl)-ethyl]-[1,3]oxazinan-2-one

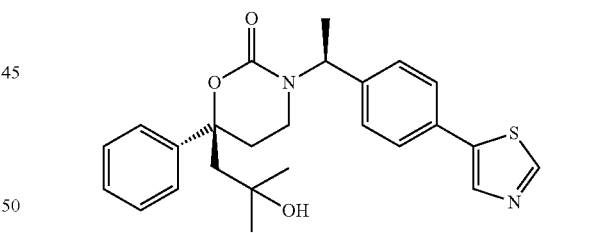

2 M aqueous Na₂CO₃ solution (0.63 mL) was added to a solution of 5-bromo-thiazole (70 μL) and (S)-6-(2-hydroxy-2-methylpropyl)-6-phenyl-3-[(S)-1-(4-(4,4,5,5-tetramethyl-1,3,2-dioxaborolan-2-yl)phenyl)ethyl]-1,3-oxazinan-2-one (0.30 g) in dimethylformamide (3 mL). The resulting mixture was sparged with argon for 10 min, before [1,1'-bis(diphenylphosphino)-ferrocene]dichloro-palladium(II) dichloromethane complex (15 mg) was added. The mixture was heated to 90° C. and stirred at this temperature for 2 h. After cooling to ambient temperature, water was added, and the resulting mixture was extracted with ethyl acetate. The combined organic extracts were washed with brine, dried (MgSO₄), and concentrated. The residue was purified by chromatography on silica gel (cyclohexane/ethyl acetate 50:50->0:100) to afford the title compound as a solid. Yield: 0.19 g (70% of theory); Mass spectrum (ESI+): m/z=437 [M+H]+.

EXAMPLE 172

(S)-6-(2-Hydroxy-2-methyl-propyl)-3-{(S)-1-[4-(5-methyl-[1,3,4]thiadiazol-2-yl)-phenyl]-ethyl}-6-phenyl-[1,3]oxazinan-2-one

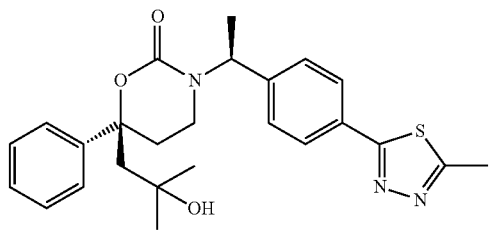

The title compound was prepared from (S)-6-(2-hydroxy-2-methylpropyl)-6-phenyl-3-[(S)-1-(4-(4,4,5,5-tetramethyl-1,3,2-dioxaborolan-2-yl)phenyl)ethyl]-1,3-oxazinan-2-one and 2-bromo-5-methyl-[1,3,4]thiadiazole following a procedure analogous to that described in Example 171. Mass spectrum (ESI−): m/z=496 [M+HCOO]−.

EXAMPLE 173

(S)-6-(2-Hydroxy-2-methyl-propyl)-6-phenyl-3-[(S)-1-(4-[1,3,4]thiadiazol-2-yl-phenyl)-ethyl]-[1,3]oxazinan-2-one

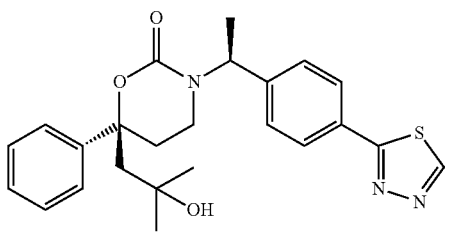

The title compound was prepared from (S)-6-(2-hydroxy-2-methylpropyl)-6-phenyl-3-[(S)-1-(4-(4,4,5,5-tetramethyl-1,3,2-dioxaborolan-2-yl)phenyl)ethyl]-1,3-oxazinan-2-one and 2-bromo-[1,3,4]thiadiazole following a procedure analogous to that described in Example 171. Mass spectrum (ESI+): m/z=438 [M+H]+.

EXAMPLE 174

(S)-6-(2-Hydroxy-2-methyl-propyl)-6-phenyl-3-[(S)-1-(4-thiazol-2-yl-phenyl)-ethyl]-[1,3]oxazinan-2-one

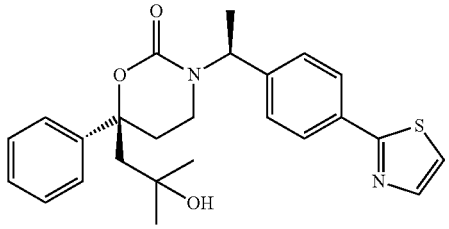

The title compound was prepared from (S)-6-(2-hydroxy-2-methylpropyl)-6-phenyl-3-[(S)-1-(4-(4,4,5,5-tetramethyl-1,3,2-dioxaborolan-2-yl)phenyl)ethyl]-1,3-oxazinan-2-one and 2-bromo-thiazole following a procedure analogous to that described in Example 171. Mass spectrum (ESI+): m/z=437 [M+H]+.

EXAMPLE 175

(S)-6-(2-Hydroxy-2-methyl-propyl)-6-phenyl-3-[(S)-1-(4-thiazol-4-yl-phenyl)-ethyl]-[1,3]oxazinan-2-one

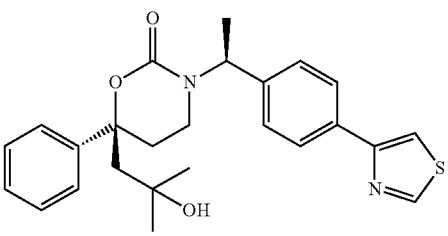

The title compound was prepared from (S)-6-(2-hydroxy-2-methylpropyl)-6-phenyl-3-[(S)-1-(4-(4,4,5,5-tetramethyl-1,3,2-dioxaborolan-2-yl)phenyl)ethyl]-1,3-oxazinan-2-one and 4-bromo-thiazole following a procedure analogous to that described in Example 171. Mass spectrum (ESI+): m/z=437 [M+H]+.

EXAMPLE 176

3-{(S)-1-[4-(2,4-Dimethyl-thiazol-5-yl)-phenyl]-ethyl}-(S)-6-(2-hydroxy-2-methyl-propyl)-6-phenyl-[1,3]oxazinan-2-one

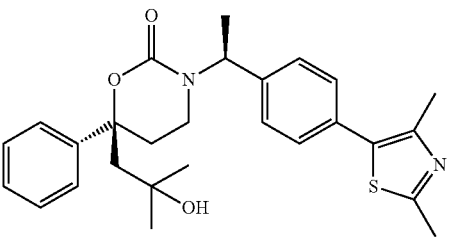

The title compound was prepared from (S)-6-(2-hydroxy-2-methylpropyl)-6-phenyl-3-[(S)-1-(4-(4,4,5,5-tetramethyl-1,3,2-dioxaborolan-2-yl)phenyl)ethyl]-1,3-oxazinan-2-one and 5-bromo-2,4-dimethyl-thiazole following a procedure analogous to that described in Example 171. Mass spectrum (ESI+): m/z=465 [M+H]+.

EXAMPLE 177

(S)-6-(2-Hydroxy-2-methyl-propyl)-6-phenyl-3-{(S)-1-[4-(1,3,5-trimethyl-1H-pyrazol-4-yl)-phenyl]-ethyl}-[1,3]oxazinan-2-one

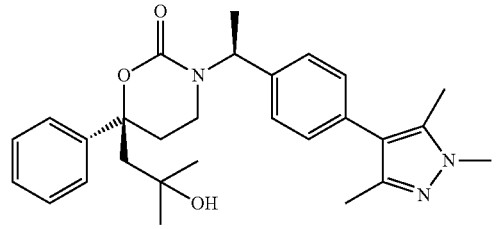

The title compound was prepared from (S)-6-(2-hydroxy-2-methylpropyl)-6-phenyl-3-[(S)-1-(4-(4,4,5,5-tetramethyl- 1,3,2-dioxaborolan-2-yl)phenyl)ethyl]-1,3-oxazinan-2-one and 4-bromo-1,3,5-trimethyl-1H-pyrazole following a procedure analogous to that described in Example 171. Mass spectrum (ESI$^+$): m/z=462 [M+H]$^+$.

EXAMPLE 178

(S)-6-(2-Hydroxy-2-methyl-propyl)-3-{(S)-1-[4-(1-methyl-1H-pyrazol-4-yl)-phenyl]-ethyl}-6-phenyl-[1,3]oxazinan-2-one

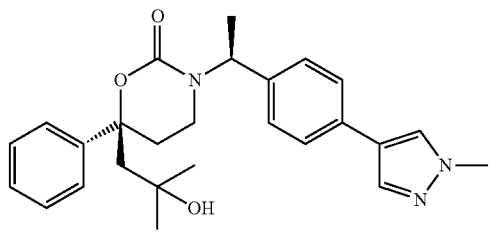

The title compound was prepared from (S)-6-(2-hydroxy-2-methylpropyl)-6-phenyl-3-[(S)-1-(4-(4,4,5,5-tetramethyl-1,3,2-dioxaborolan-2-yl)phenyl)ethyl]-1,3-oxazinan-2-one and 4-bromo-1-methyl-1H-pyrazole following a procedure analogous to that described in Example 171. Mass spectrum (ESI$^+$): m/z=434 [M+H]$^+$.

EXAMPLE 179

(S)-6-(2-Hydroxy-2-methyl-propyl)-6-phenyl-3-{(S)-1-[4-(5-trifluoromethyl-[1,3,4]thiadiazol-2-yl)-phenyl]-ethyl}-[1,3]oxazinan-2-one

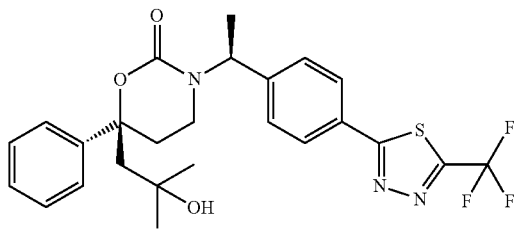

The title compound was prepared from (S)-6-(2-hydroxy-2-methylpropyl)-6-phenyl-3-[(S)-1-(4-(4,4,5,5-tetramethyl-1,3,2-dioxaborolan-2-yl)phenyl)ethyl]-1,3-oxazinan-2-one and 2-chloro-5-trifluoromethyl-[1,3,4]thiadiazole following a procedure analogous to that described in Example 171. Mass spectrum (ESI$^-$): m/z=550 [M+HCOO]$^-$.

EXAMPLE 180

(S)-6-(2-Hydroxy-2-methyl-propyl)-3-{(S)-1-[(2-methyl-4-thiazol-5-yl)-phenyl]-ethyl}-6-phenyl-[1,3]oxazinan-2-one

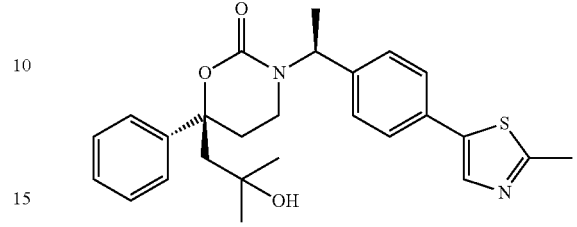

A flask charged with a stir bar, 3-[(S)-1-(4-bromo-phenyl)-ethyl]-(S)-6-(2-hydroxy-2-methyl-propyl)-6-phenyl-[1,3]oxazinan-2-one (0.30 g), 2-methyl-thiazole (0.15 g), potassium acetate (0.15 g), palladium(II) acetate (5 mg), and N,N-dimethylacetamide (5 mL) was sparged with argon for 10 min. Then, the mixture was heated to 150° C. and stirred at this temperature overnight. After cooling to ambient temperature, ethyl acetate was added and the resulting mixture was washed with water and brine. Then, the organic phase was dried (Na$_2$SO$_4$) and concentrated. The residue was purified by chromatography on silica gel (cyclohexane/ethyl acetate 80:20->0:100) to afford the title compound. Yield: 95 mg (28% of theory); Mass spectrum (ESI$^+$): m/z=451 [M+H]$^+$.

EXAMPLE 181

(S)-3-{1-[4-(4,5-Dimethyl-thiazol-2-yl)-phenyl]-ethyl}-6-(2-hydroxy-2-methyl-propyl)-6-phenyl-[1,3]oxazinan-2-one

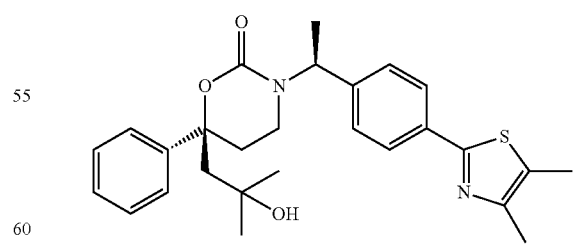

The title compound was prepared from 3-[(S)-1-(4-bromo-phenyl)-ethyl]-(S)-6-(2-hydroxy-2-methyl-propyl)-6-phenyl-[1,3]oxazinan-2-one and 4,5-dimethyl-thiazole following a procedure analogous to that described in Example 180. Mass spectrum (ESI$^+$): m/z=465 [M+H]$^+$.

EXAMPLE 182

(S)-6-(2-Hydroxy-2-methyl-propyl)-3-{(S)-1-[4-(6-methanesulfinyl-pyridin-3-yl)-phenyl]-ethyl}-6-phenyl-[1,3]oxazinan-2-one

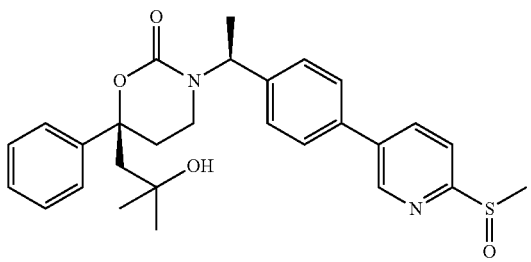 [SMILES: C[C@@H](c1ccc(-c2ccc(S(C)=O)nc2)cc1)N1CC[C@](CC(C)(C)O)(c2ccccc2)OC1=O]

The title compound was prepared from (S)-6-(2-hydroxy-2-methylpropyl)-6-phenyl-3-[(S)-1-(4-(4,4,5,5-tetramethyl-1,3,2-dioxaborolan-2-yl)phenyl)ethyl]-1,3-oxazinan-2-one and 5-bromo-2-methanesulfinyl-pyridine following a procedure analogous to that described in Example 171. Mass spectrum (ESI+): m/z=493 [M+H]+.

5-Bromo-2-methanesulfinyl-pyridine

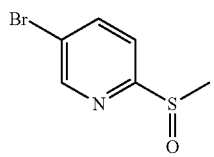

NaIO4 (0.52 g) dissolved in water (0.5 mL) was added to a solution of 5-bromo-2-methylsulfanyl-pyridine (0.25 g) in acetic acid (3 mL) at room temperature. The resulting mixture was stirred at room temperature overnight. Then, water and ethyl acetate were added and the mixture was stirred for another 10 min. The organic phase was separated and washed with 10% aqueous Na2S2O3 solution, 10% aqueous K2CO3 solution, and brine. After drying (MgSO4), the solvent was evaporated to afford the title compound. Yield: 0.20 g (72% of theory); Mass spectrum (ESI+): m/z=220/222 (Br) [M+H]+.

EXAMPLE 183

(S)-6-(2-Hydroxy-2-methyl-propyl)-3-{(S)-1-[4-(6-methanesulfonyl-pyridin-3-yl)-phenyl]-ethyl}-6-phenyl-[1,3]oxazinan-2-one

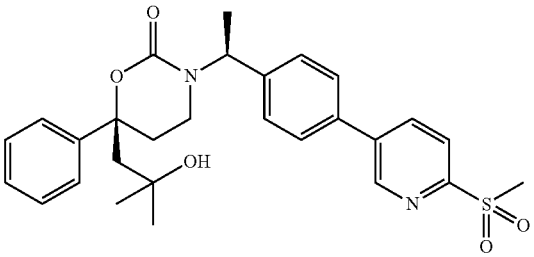 [SMILES: C[C@@H](c1ccc(-c2ccc(S(C)(=O)=O)nc2)cc1)N1CC[C@](CC(C)(C)O)(c2ccccc2)OC1=O]

The title compound was prepared from (S)-6-(2-hydroxy-2-methylpropyl)-6-phenyl-3-[(S)-1-(4-(4,4,5,5-tetramethyl-1,3,2-dioxaborolan-2-yl)phenyl)ethyl]-1,3-oxazinan-2-one and 5-bromo-2-methanesulfonyl-pyridine following a procedure analogous to that described in Example 171. Mass spectrum (ESI+): m/z=509 [M+H]+.

EXAMPLE 184

(S)-6-(2-Hydroxy-2-methyl-propyl)-3-{(S)-1-[4-(4-methanesulfinyl-pyridin-2-yl)-phenyl]-ethyl}-6-phenyl-[1,3]oxazinan-2-one

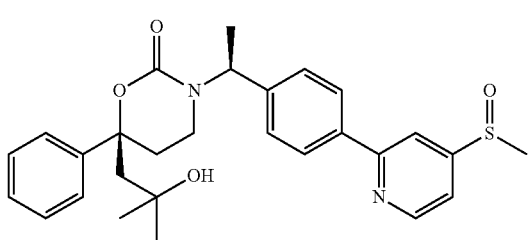 [SMILES: C[C@@H](c1ccc(-c2cc(S(C)=O)ccn2)cc1)N1CC[C@](CC(C)(C)O)(c2ccccc2)OC1=O]

The title compound was prepared from (S)-6-(2-hydroxy-2-methylpropyl)-6-phenyl-3-[(S)-1-(4-(4,4,5,5-tetramethyl-1,3,2-dioxaborolan-2-yl)phenyl)ethyl]-1,3-oxazinan-2-one and 2-bromo-4-methanesulfinyl-pyridine following a procedure analogous to that described in Example 171. Mass spectrum (ESI+): m/z=493 [M+H]+.

2-Bromo-4-methylsulfanyl-pyridine

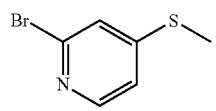

NaSCH3 (0.14 g) was added to a solution of 2-bromo-4-iodo-pyridine (0.50 g) in dimethylformamide (5 mL) at room temperature. The solution was heated to 60° C. and stirred at this temperature for 4 h. After cooling to room temperature, ethyl acetate was added and the resulting solution was washed with water and brine. The organic phase was dried (MgSO4) and the solvent was evaporated. The residue was purified by chromatography on silica gel (cyclohexane/ethyl acetate 98:2->80:20) to afford the title compound. Yield: 0.34 g (94% of theory); Mass spectrum (ESI+): m/z=204/206 (Br) [M+H]+.

2-Bromo-4-methanesulfinyl-pyridine

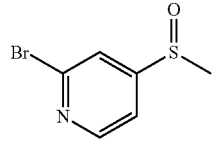

The title compound was prepared from 2-bromo-4-methylsulfanyl-pyridine following a procedure analogous to that described for 5-bromo-2-methanesulfinyl-pyridine in Example 182. Mass spectrum (ESI⁺): m/z=220/222 (Br) [M+H]⁺.

EXAMPLE 185

(S)-6-(2-Hydroxy-2-methyl-propyl)-3-{(S)-1-[4-(4-methanesulfonyl-pyridin-2-yl)-phenyl]-ethyl}-6-phenyl-[1,3]oxazinan-2-one

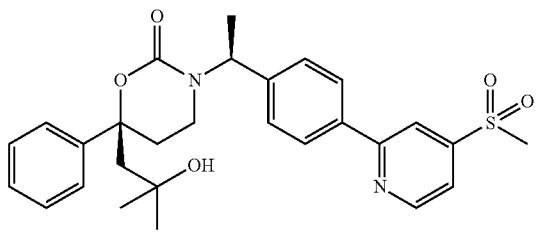 [SMILES: C[C@@H](c1ccc(-c2cc(S(C)(=O)=O)ccn2)cc1)N1CC[C@](CC(C)(C)O)(c2ccccc2)OC1=O]

The title compound was prepared from (S)-6-(2-hydroxy-2-methylpropyl)-6-phenyl-3-[(S)-1-(4-(4,4,5,5-tetramethyl-1,3,2-dioxaborolan-2-yl)phenyl)ethyl]-1,3-oxazinan-2-one and 2-bromo-4-methanesulfonyl-pyridine following a procedure analogous to that described in Example 171. Mass spectrum (ESI⁺): m/z=509 [M+H]⁺.

2-Bromo-4-methanesulfonyl-pyridine

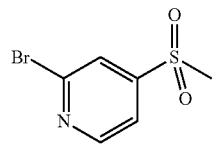

3-Chloroperoxybenzoic acid (70%, 0.72 g) was added to a solution of 2-bromo-4-methylsulfanyl-pyridine (0.20 g) in dichloromethane (2 mL) at room temperature. The resulting mixture was stirred at room temperature overnight. Then, the solution was diluted with dichloromethane and the mixture was washed with aqueous K₂CO₃ solution, aqueous Na₂S₂O₃ solution, aqueous K₂CO₃ solution again, and brine. After drying (MgSO₄) and removing the solvent, the residue was purified by HPLC on reversed phase (methanol/water) to afford the title compound. Yield: 0.12 g (52% of theory); Mass spectrum (ESI⁺): m/z=236/238 (Br) [M+H]⁺.

EXAMPLE 186

(S)-6-(2-Hydroxy-2-methyl-propyl)-3-{(S)-1-[4-(5-methanesulfonyl-pyridin-2-yl)-phenyl]-ethyl}-6-phenyl-[1,3]oxazinan-2-one

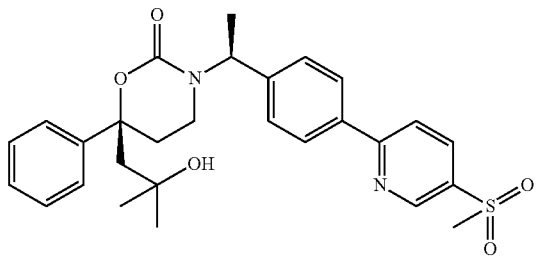 [SMILES: C[C@@H](c1ccc(-c2ccc(S(C)(=O)=O)cn2)cc1)N1CC[C@](CC(C)(C)O)(c2ccccc2)OC1=O]

The title compound was prepared from (S)-6-(2-hydroxy-2-methylpropyl)-6-phenyl-3-[(S)-1-(4-(4,4,5,5-tetramethyl-1,3,2-dioxaborolan-2-yl)phenyl)ethyl]-1,3-oxazinan-2-one and 2-bromo-5-methanesulfonyl-pyridine following a procedure analogous to that described in Example 171. Mass spectrum (ESI⁺): m/z=509 [M+H]⁺.

EXAMPLE 187

(S)-6-(2-Hydroxy-2-methyl-propyl)-3-{(S)-1-[4-(2-methanesulfonyl-pyridin-4-yl)-phenyl]-ethyl}-6-phenyl-[1,3]oxazinan-2-one

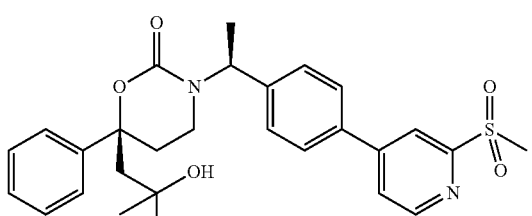

The title compound was prepared from (S)-6-(2-hydroxy-2-methylpropyl)-6-phenyl-3-[(S)-1-(4-(4,4,5,5-tetramethyl-1,3,2-dioxaborolan-2-yl)phenyl)ethyl]-1,3-oxazinan-2-one and 4-iodo-2-methanesulfonyl-pyridine following a procedure analogous to that described in Example 171. Mass spectrum (ESI⁺): m/z=509 [M+H]⁺.

4-Iodo-2-methylsulfanyl-pyridine

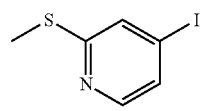

The title compound was prepared from 2-fluoro-4-iodo-pyridine following a procedure analogous to that described for 2-bromo-4-methylsulfanyl-pyridine in Example 184. Mass spectrum (ESI⁺): m/z=252 [M+H]⁺.

4-Iodo-2-methanesulfonyl-pyridine

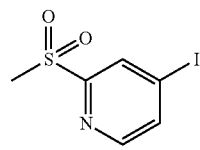

The title compound was prepared from 4-iodo-2-methylsulfanyl-pyridine following a procedure analogous to that described for 2-bromo-4-methanesulfonyl-pyridine in Example 185. Mass spectrum (ESI⁺): m/z=284 [M+H]⁺.

EXAMPLE 188

(S)-6-(2-Hydroxy-2-methyl-propyl)-3-{(S)-1-[4-(5-methanesulfonyl-pyridin-3-yl)-phenyl]-ethyl}-6-phenyl-[1,3]oxazinan-2-one

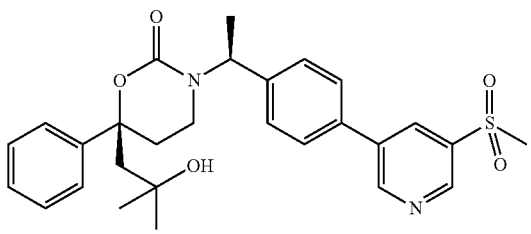 [SMILES: C[C@@H](c1ccc(-c2cncc(S(C)(=O)=O)c2)cc1)N1CC[C@](CC(C)(C)O)(c2ccccc2)OC1=O]

The title compound was prepared from (S)-6-(2-hydroxy-2-methylpropyl)-6-phenyl-3-[(S)-1-(4-(4,4,5,5-tetramethyl-1,3,2-dioxaborolan-2-yl)phenyl)ethyl]-1,3-oxazinan-2-one and 3-bromo-5-methanesulfonyl-pyridine following a procedure analogous to that described in Example 171. Mass spectrum (ESI⁺): m/z=509 [M+H]⁺.

EXAMPLE 189

(S)-6-(2-Hydroxy-2-methyl-propyl)-3-{(S)-1-[4-(5-methanesulfinyl-pyridin-3-yl)-phenyl]-ethyl}-6-phenyl-[1,3]oxazinan-2-one

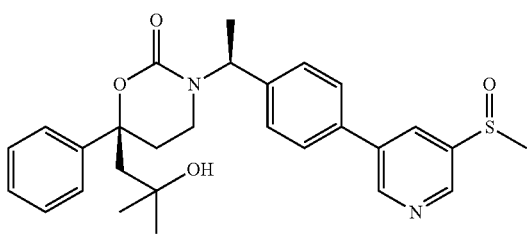 [SMILES: C[C@@H](c1ccc(-c2cncc(S(C)=O)c2)cc1)N1CC[C@](CC(C)(C)O)(c2ccccc2)OC1=O]

The title compound was prepared from (S)-6-(2-hydroxy-2-methylpropyl)-6-phenyl-3-[(S)-1-(4-(4,4,5,5-tetramethyl-1,3,2-dioxaborolan-2-yl)phenyl)ethyl]-1,3-oxazinan-2-one and 3-bromo-5-methanesulfinyl-pyridine following a procedure analogous to that described in Example 171. Mass spectrum (ESI⁺): m/z=493 [M+H]⁺.

3-Bromo-5-methanesulfinyl-pyridine

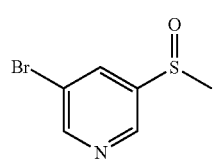

The title compound was prepared from 3-bromo-5-methylsulfanyl-pyridine following a procedure analogous to that described for 5-bromo-2-methanesulfinyl-pyridine in Example 182.

EXAMPLE 190

(S)-6-(2-Hydroxy-2-methyl-propyl)-3-{(S)-1-[4-(6-methanesulfonyl-pyridin-2-yl)-phenyl]-ethyl}-6-phenyl-[1,3]oxazinan-2-one

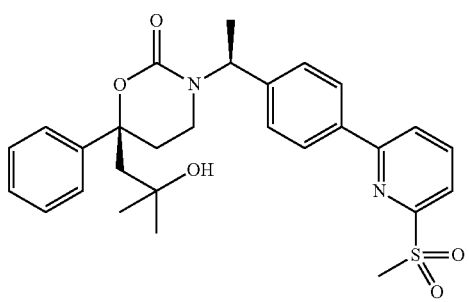 [SMILES: C[C@@H](c1ccc(-c2cccc(S(C)(=O)=O)n2)cc1)N1CC[C@](CC(C)(C)O)(c2ccccc2)OC1=O]

The title compound was prepared from (S)-6-(2-hydroxy-2-methylpropyl)-6-phenyl-3-[(S)-1-(4-(4,4,5,5-tetramethyl-1,3,2-dioxaborolan-2-yl)phenyl)ethyl]-1,3-oxazinan-2-one and 2-bromo-6-methanesulfonyl-pyridine following a procedure analogous to that described in Example 171. Mass spectrum (ESI⁺): m/z=526 [M+NH₄]⁺.

2-Bromo-6-methanesulfonyl-pyridine

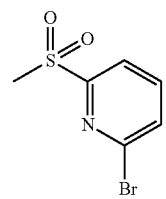

The title compound was prepared from 2-bromo-6-methylsulfanyl-pyridine following a procedure analogous to that described for 2-bromo-4-methanesulfonyl-pyridine in Example 185. Mass spectrum (ESI⁺): m/z=236/238 (Br) [M+H]⁺.

EXAMPLE 191

(S)-6-(2-Hydroxy-2-methyl-propyl)-3-{(S)-1-[4-(6-methanesulfinyl-pyridin-2-yl)-phenyl]-ethyl}-6-phenyl-[1,3]oxazinan-2-one

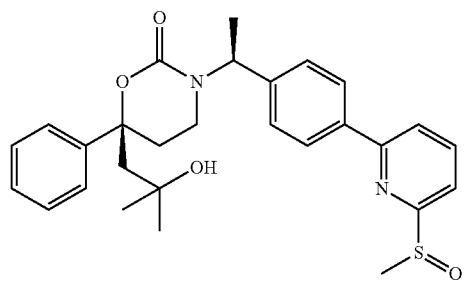 [SMILES: C[C@@H](c1ccc(-c2cccc(S(C)=O)n2)cc1)N1CC[C@](CC(C)(C)O)(c2ccccc2)OC1=O]

The title compound was prepared from (S)-6-(2-hydroxy-2-methylpropyl)-6-phenyl-3-[(S)-1-(4-(4,4,5,5-tetramethyl- 1,3,2-dioxaborolan-2-yl)phenyl)ethyl]-1,3-oxazinan-2-one and 2-bromo-6-methanesulfinyl-pyridine following a procedure analogous to that described in Example 171. Mass spectrum (ESI⁺): m/z=493 [M+H]⁺.

2-Bromo-6-methanesulfinyl-pyridine

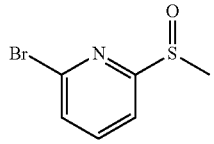

The title compound was prepared from 2-bromo-6-methylsulfanyl-pyridine following a procedure analogous to that described for 5-bromo-2-methanesulfinyl-pyridine in Example 182. Mass spectrum (ESI⁺): m/z=220/222 (Br) [M+H]⁺.

EXAMPLE 192

3-{(S)-1-[4-(2-Cyclopropyl-pyrimidin-5-yl)-phenyl]-ethyl}-(S)-6-(2-hydroxy-2-methyl-propyl)-6-phenyl-[1,3]oxazinan-2-one

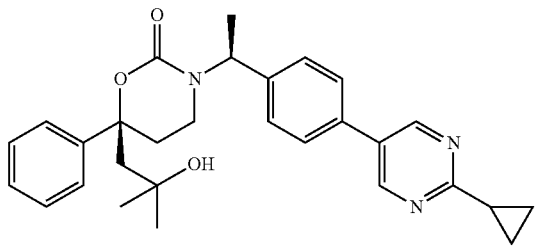 [SMILES: C[C@@H](c1ccc(-c2cnc(C3CC3)nc2)cc1)N1CC[C@](CC(C)(C)O)(c2ccccc2)OC1=O]

The title compound was prepared from (S)-6-(2-hydroxy-2-methylpropyl)-6-phenyl-3-[(S)-1-(4-(4,4,5,5-tetramethyl-1,3,2-dioxaborolan-2-yl)phenyl)ethyl]-1,3-oxazinan-2-one and 5-bromo-2-cyclopropyl-pyrimidine (for preparation see WO 2006004532) following a procedure analogous to that described in Example 171. Mass spectrum (ESI⁺): m/z=472 [M+H]⁺.

EXAMPLE 193

3-{(S)-1-[4-(1,3-Dimethyl-1H-pyrazol-4-yl)-phenyl]-ethyl}-(S)-6-(2-hydroxy-2-methyl-propyl)-6-phenyl-[1,3]oxazinan-2-one

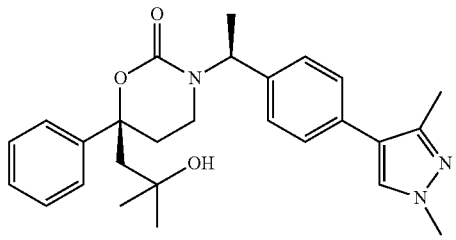 [SMILES: Cc1nn(C)cc1-c1ccc([C@H](C)N2CC[C@](CC(C)(C)O)(c3ccccc3)OC2=O)cc1]

The title compound was prepared from (S)-6-(2-hydroxy-2-methylpropyl)-6-phenyl-3-[(S)-1-(4-(4,4,5,5-tetramethyl-1,3,2-dioxaborolan-2-yl)phenyl)ethyl]-1,3-oxazinan-2-one and 4-bromo-1,3-dimethyl-1H-pyrazole following a procedure analogous to that described in Example 171. Mass spectrum (ESI⁺): m/z=448 [M+H]⁺.

EXAMPLE 194

2-[5-(4-{(S)-1-[(S)-6-(2-Hydroxy-2-methyl-propyl)-2-oxo-6-phenyl-[1,3]oxazinan-3-yl]-ethyl}-phenyl)-pyridin-2-yl]-2-methyl-propionitrile

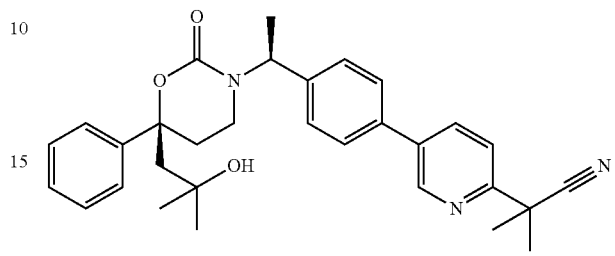

The title compound was prepared from (S)-6-(2-hydroxy-2-methylpropyl)-6-phenyl-3-[(S)-1-(4-(4,4,5,5-tetramethyl-1,3,2-dioxaborolan-2-yl)phenyl)ethyl]-1,3-oxazinan-2-one and 2-(5-bromo-pyridin-2-yl)-2-methyl-propionitrile following a procedure analogous to that described in Example 171. Mass spectrum (ESI⁺): m/z=498 [M+H]⁺.

2-(5-Bromo-pyridin-2-yl)-2-methyl-propionitrile

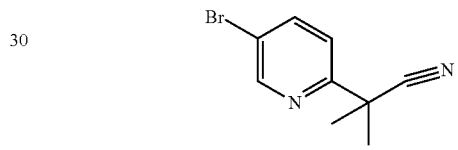

NaN[(SiCH₃)₃]₂ (1 M in tetrahydrofuran, 6.3 mL) was added dropwise to a solution of 2,5-dibromo-pyridine (1.50 g) and isobutyronitrile (0.58 mL) in toluene (15 mL) chilled in an ice bath and kept under argon atmosphere. The resulting mixture was further stirred with cooling for 1 h and then at room temperature overnight. The mixture was filtered and the filtrate was washed with water, 10% aqueous K₂CO₃ solution, and brine. The organic phase was dried (MgSO₄) and the solvent was evaporated. The residue was purified by chromatography on silica gel (dichloromethane/methanol 99:1->95:5) to furnish the title compound. Yield: 0.26 g (18% of theory); Mass spectrum (ESI⁺): m/z=220/222 (Br) [M+H]⁺.

EXAMPLE 195

(S)-6-(2-Hydroxy-2-methyl-propyl)-3-{(S)-1-[4-(5-methanesulfinyl-pyridin-2-yl)-phenyl]-ethyl}-6-phenyl-[1,3]oxazinan-2-one

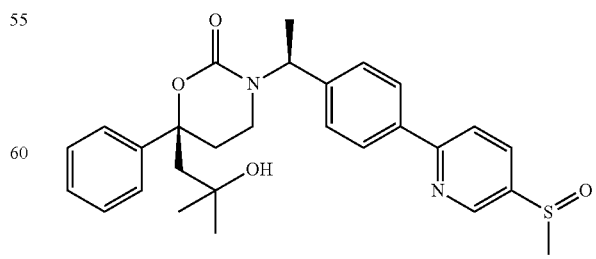

The title compound was prepared from (S)-6-(2-hydroxy-2-methylpropyl)-6-phenyl-3-[(S)-1-(4-(4,4,5,5-tetramethyl- 1,3,2-dioxaborolan-2-yl)phenyl)ethyl]-1,3-oxazinan-2-one and 2-bromo-5-methanesulfinyl-pyridine following a procedure analogous to that described in Example 171. Mass spectrum (ESI⁺): m/z=493 [M+H]⁺.

2-Bromo-5-methanesulfinyl-pyridine

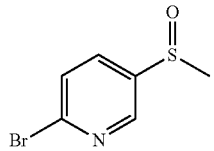

The title compound was prepared from 2-bromo-5-methylsulfanyl-pyridine following a procedure analogous to that described for 5-bromo-2-methanesulfinyl-pyridine in Example 182. Mass spectrum (ESI⁺): m/z=220/222 (Br) [M+H]⁺.

EXAMPLE 196

2-[5-(4-{(S)-1-[(S)-6-(2-Hydroxy-2-methyl-propyl)-2-oxo-6-phenyl-[1,3]oxazinan-3-yl]-ethyl}-phenyl)-pyridin-2-yl]-isobutyramide

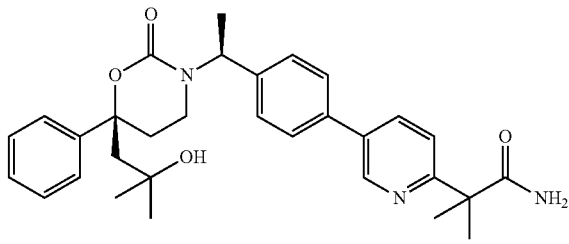 [SMILES: C[C@@H](c1ccc(-c2ccc(C(C)(C)C(N)=O)nc2)cc1)N1CC[C@](CC(C)(C)O)(c2ccccc2)OC1=O]

Hydrogen peroxide (35% in water, 0.1 mL) was added to a mixture of 2-[5-(4-{(S)-1-[(S)-6-(2-hydroxy-2-methyl-propyl)-2-oxo-6-phenyl-[1,3]oxazinan-3-yl]-ethyl}-phenyl)-pyridin-2-yl]-2-methyl-propionitrile (0.21 g; for preparation see Example 194) and K₂CO₃ (0.03 g) in ddimethyl sulfoxide (2 mL) at room temperature. After stirring the mixture for 3 h at room temperature, another portion of hydrogen peroxide (35% in water, 0.1 mL) and K₂CO₃ (0.03 g) were added. The mixture was further stirred at room temperature for 1 h and at 40° C. overnight. After cooling to room temperature, little aqueous Na₂S₂O₃ solution was added and then the mixture was concentrated. The residue was purified by HPLC on reversed phase (methanol/water/ammonia) to furnish the title compound. Yield: 0.03 g (14% of theory); Mass spectrum (ESI⁺): m/z=516 [M+H]⁺.

EXAMPLE 197

4108.1002-007 Example 225

(R)-6-(4-fluorophenyl)-6-(3-hydroxypropyl)-3-((S)-1-(4-(pyridin-3-yl)phenyl)ethyl)-1,3-oxazinan-2-one

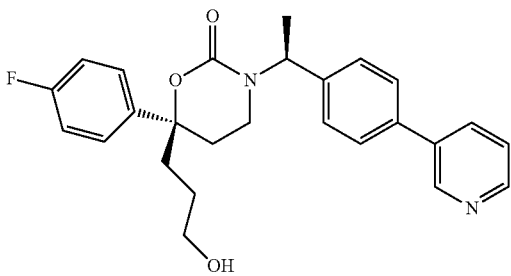 [SMILES: C[C@@H](c1ccc(-c2cccnc2)cc1)N1CC[C@](CCCO)(c2ccc(F)cc2)OC1=O]

The title compound was prepared from (R)-6-allyl-6-(4-fluorophenyl)-3-((S)-1-(4-(pyridin-3-yl)phenyl)ethyl)-1,3-oxazinan-2-one employing a procedure analogous to that described in Example 1 Step 2, followed by a procedure analogous to that described in Example 71 Step 1. LC-MS Method 2 t_R=1.463, min, m/z=435.2; ¹H NMR (CDCl₃) 1.51 (d, 3H), 1.82-1.98 (m, 3H), 2.11-2.21 (m, 2H), 2.22-2.32 (m, 2H), 2.93 (m, 1H), 3.53 (m, 2H), 5.66 (m, 1H), 6.93-7.01 (m, 4H), 7.22 (m, 1H), 7.28 (m, 2H), 7.33 (m, 1H), 7.79 (m, 1H), 8.52 (m, 1H), 8.68 (m, 1H).

EXAMPLE 198

(S)-3-((S)-1-(4-(6-(2-hydroxy-2-methylpropoxy)pyridin-3-yl)phenyl)ethyl)-6-(2-hydroxy-2-methyl-propyl)-6-phenyl-1,3-oxazinan-2-one

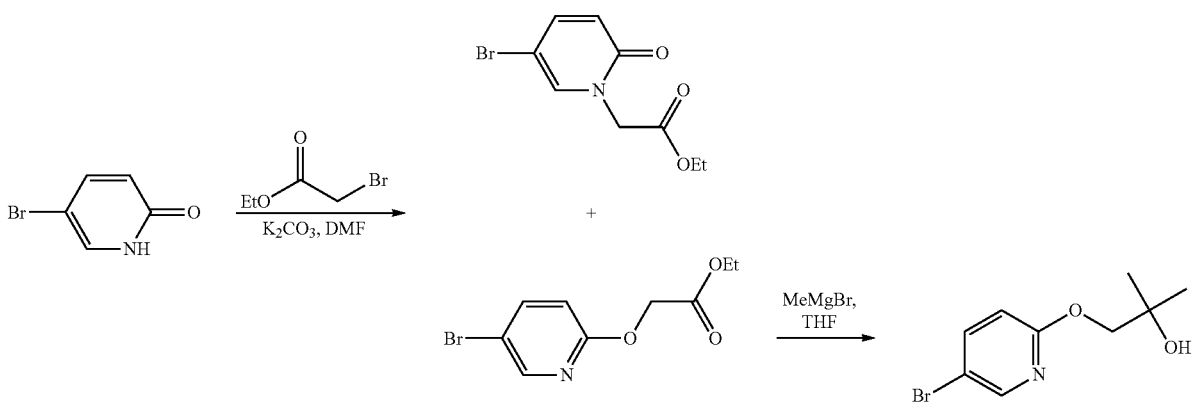

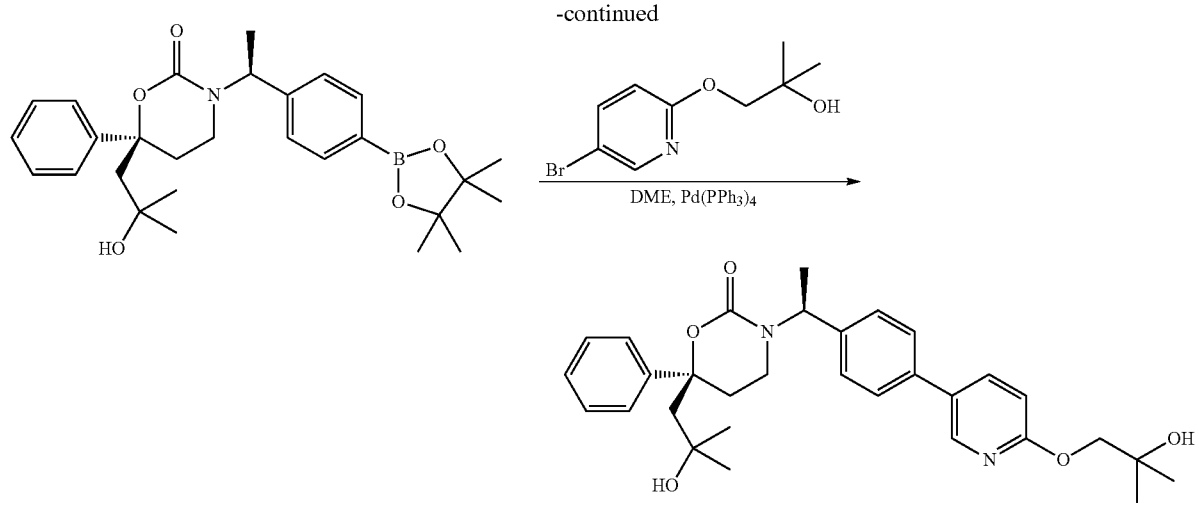

Step 1

To a solution of compound 1 (348 mg, 2.0 mmol) and $K_2CO_3$ (830 mg, 6.0 mmol) in DMF (15 mL) was added ethyl 2-bromoacetate (668 mg, 4.0 mmol). The mixture was stirred at rt for 2 h, filtered, and the filtrate was concentrated in vacuo to give the crude final product, which was purified by preparative TLC (1:1 PE/EtOAc) to afford ethyl 2-(5-bromopyridin-2-yloxy)acetate (100 mg, 19.2%). $^1$H NMR (CDCl$_3$): δ 8.13 (s, 1H), 7.69-6.67 (d, 1H), 6.80-6.78 (d, 1H), 4.84 (s, 2H), 4.25-4.20 (q, 2H), 1.28-1.25 (t, 3H) and ethyl 2-(5-bromo-2-oxopyridin-1(2H)-yl)acetate (300 mg, 57.7%), $^1$H NMR (CDCl$_3$): δ 7.41-7.26 (m, 2H), 6.53-6.5 (d, 1H), 4.59 (s, 2H), 4.28-4.21 (q, 2H), 1.32-1.23 (q, 3H).

Step 2

To a solution of ethyl 2-(5-bromopyridin-2-yloxy)acetate (65 mg, 0.25 mmol) in anhydrous THF (2 mL) was added MeMgBr (2.5 mL, 2.5 mmol) dropwise at −78° C. The reaction mixture was stirred at −78° C. for 1 h, quenched with satd aq NH$_4$Cl (5 mL), and extracted with EtOAc (3×10 mL). The combined organic layer was dried over anhydrous Na$_2$SO$_4$, concentrated, and purified by preparative TLC (1:1 PE/EtOAc) to afford 1-(5-bromopyridin-2-yloxy)-2-methylpropan-2-ol (30 mg, 48.8%).

Step 3

To a solution of 1-(5-bromopyridin-2-yloxy)-2-methylpropan-2-ol (30 mg, 0.122 mmol) in DME (6 mL) was added Pd(PPh$_3$)$_4$ (10 mg) under nitrogen. The mixture was stirred for 1 h at rt. A solution of (S)-6-(2-hydroxy-2-methylpropyl)-6-phenyl-3-((S)-1-(4-(4,4,5,5-tetramethyl-1,3,2-dioxaborolan-2-yl)phenyl)ethyl)-1,3-oxazinan-2-one (58.4 mg, 0.122 mmol) in EtOH (2 mL) and satd aq NaHCO$_3$ (2 mL) were added. The mixture was stirred at 100° C. for 2 h, quenched with water, and extracted with EtOAc (3×10 mL). The combined organic layer was dried over anhydrous Na$_2$SO$_4$, concentrated, and purified by preparative TLC (1:1 PE/EtOAc) and HPLC to afford the title compound (7.6 mg, 12.1%). $^1$H NMR (CDCl$_3$): δ 8.23 (d, 1H), 7.72 (q, 1H), 7.74-6.68 (m, 10H), 5.70 (m, 1H), 4.24 (s, 2H), 3.43 (s, 1H), 2.85 (m, 1H), 2.40 (m, 1H), 2.27-2.14 (m, 5H), 1.54 (d, 3H), 1.33-1.29 (d, 3H), 1.18-1.12 (d, 3H).

EXAMPLE 199

N-cyclopropyl-5-(4-((S)-1-((S)-6-(2-hydroxy-2-methylpropyl)-6-isopropyl-2-oxo-1,3-oxazinan-3-yl)ethyl)phenyl)pyrimidine-2-carboxamide

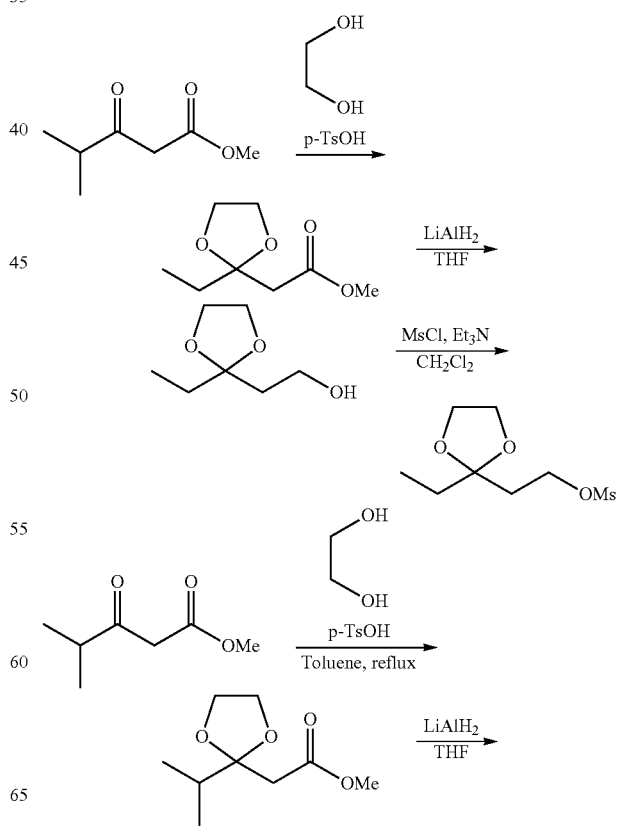

213
-continued

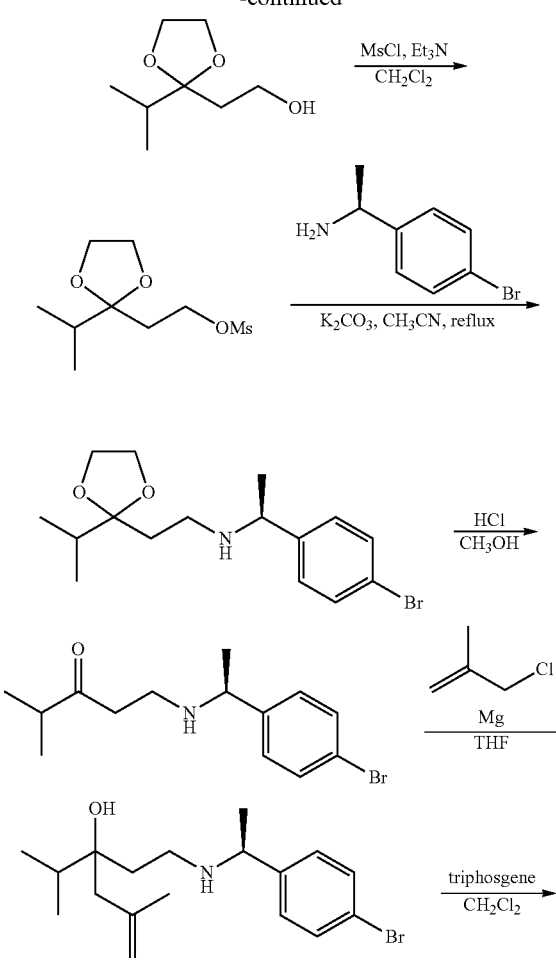

214
-continued

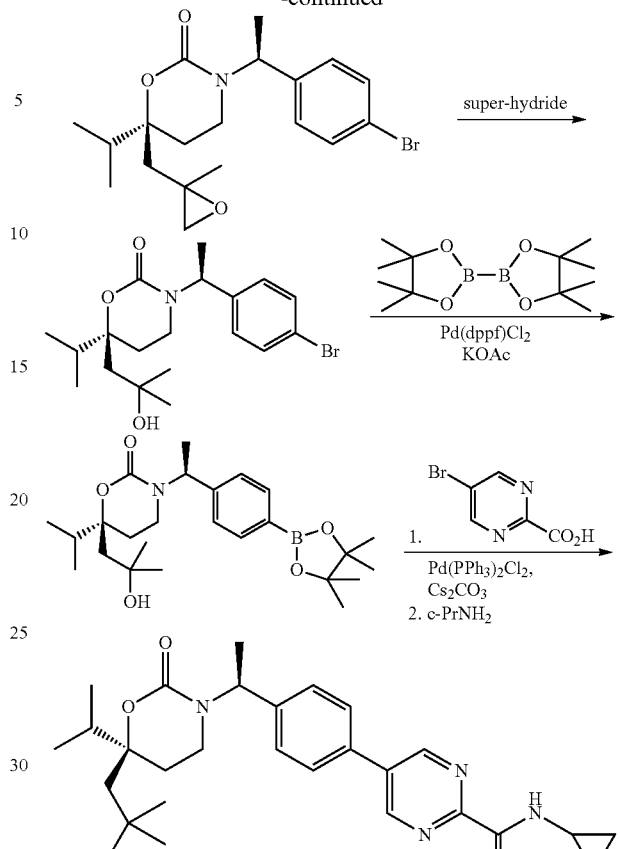

Step 1

To a solution of methyl 4-methyl-3-oxopentanoate (72 g, 0.5 mol), and ethylene glycol (56 g, 1 mol) in toluene (500 mL) was added 4-methylbenzenesulfonic acid (1.9 g, 0.01 mol). The mixture was stirred at reflux with a Dean-Stark trap to remove water. The reaction mixture was washed with a small amount of water and brine, dried over anhydrous $Na_2SO_4$, and concentrated in vacuum to give the crude methyl 2-(2-isopropyl-1,3-dioxolan-2-yl)-acetate (67 g 71% yield), which was used for the next step without further purification.

Step 2

In a flame-dried three neck flask equipped with an addition funnel, magnetic stirring bar, rubber septum, and a nitrogen inlet, was placed $LiAlH_4$ (3.12 g, 82.1 mmol) and THF (700 mL). After being cooled at 0° C., a solution of methyl 2-(2-isopropyl-1,3-dioxolan-2-yl)acetate (12 g, 63.8 mmol) in THF (160 mL) was added dropwise with stirring. The mixture was warmed to rt, and stirred for 24 hours. The reaction was quenched by adding water (5 mL), 15% aqueous NaOH (10 mL), and water (5 mL) slowly. The organic layer was separated, and the residue was extracted with EtOAc (3×100 mL). The combined organic phase was dried over $Na_2SO_4$, and concentrated to afford the crude product, which was purified by column chromatography to give 2-(2-isopropyl-1,3-dioxolan-2-yl)-ethanol (6.8 g, 67%). $^1$H NMR ($CDCl_3$): δ 0.90 (d, J=6.8 Hz, 6H), 1.87-1.96 (m, 3H), 2.81 (br, 1H), 3.69-3.72 (m, 2H), 3.92-4.01 (m, 4H).

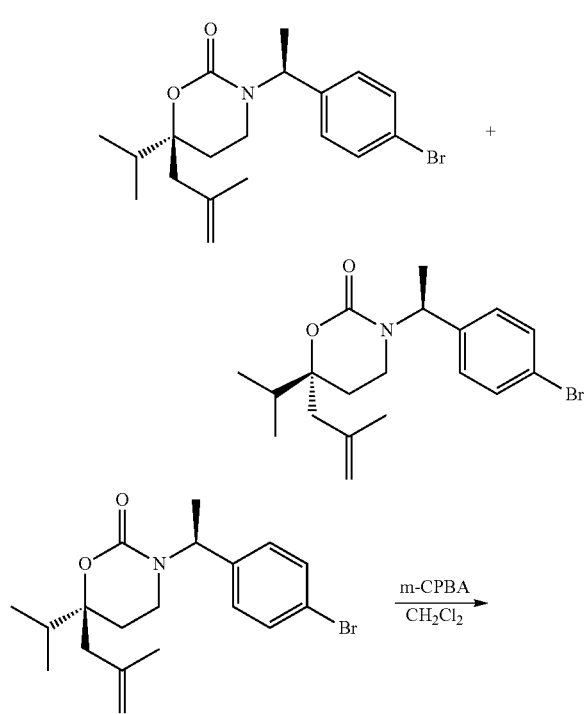

Step 3

To a solution of 2-(2-isopropyl-1,3-dioxolan-2-yl)-ethanol (8.0 g, 50 mmol) and triethylamine (23.5 mL, 170 mmol) in anhydrous $CH_2Cl_2$ (120 mL) was added methanesulfonyl chloride (11.6 mL, 150 mmol) at 0° C., and the reaction mixture was stirred at rt till the reaction was finished. The reaction mixture was washed with water and brine, dried over $Na_2SO_4$, filtered, and concentrated to give the crude 2-(2-isopropyl-1,3-dioxolan-2-yl)ethyl methanesulfonate (12 g, crude), which was used for the next step without further purification.

Step 4

To a solution of 2-(2-isopropyl-1,3-dioxolan-2-yl)ethyl methanesulfonate (12 g, 50 mmol) and (S)-1-(4-methoxyphenyl)-ethyl amine (19.9 g, 100 mmol) in $CH_3CN$ (250 mL) was added $K_2CO_3$ (8 g, 58 mmol), and the mixture was refluxed for 10 h. The solution was filtered, and the filtrate was concentrated to afford the crude product, which was purified by column chromatography to give (S)-1-(4-bromophenyl)-N-(2-(2-isopropyl-1,3-dioxolan-2-yl)ethyl)ethanamine (6.5 g, 38% yield).

Step 5

To a solution of (5)-1-(4-bromophenyl)-N-(2-(2-isopropyl-1,3-dioxolan-2-yl)ethyl)ethanamine (6.5 g, 19 mmol) in MeOH (60 mL) was added conc HCl (60 mL). The mixture was stirred at 65° C. till the reaction was finished. The mixture was cooled to 0° C., and the pH of the mixture was adjusted to 7 by adding the satd aq $NaHCO_3$. The mixture was concentrated, and the residue was extracted with EtOAc (3×100 mL). The organic layer was washed with brine, dried over $Na_2SO_4$, and concentrated to give (S)-1-(1-(4-bromophenyl)ethylamino)-4-methylpentan-3-one (5.5 g, 97% yield), which was used for the next step without further purification. $^1$H NMR ($CDCl_3$): δ 1.07 (d, J=6.8 Hz, 6H), 1.29 (d, J=6.4 Hz, 3H), 1.89 (br, 1H), 2.54-2.62 (m, 4H), 2.66-2.69 (m, 1H), 3.68-3.72 (m, 1H), 7.18-7.20 (m, 2H), 7.41-7.44 (m, 2H).

Step 6

To a suspension of Mg (11 g, 458 mmol) and $I_2$ (0.5 g) in anhydrous THF (50 mL) was added 3-chloro-2-methylprop-1-ene (1 mL) to initiate the reaction. THF (300 mL) was added, more solution of 3-chloro-2-methylprop-1-ene (15 mL) in THF (20 mL) was dropped into the reaction at 0° C. under $N_2$ over 30 min. A solution of (S)-1-(1-(4-bromophenyl)-ethyl amino)-4-methylpentan-3-one (5 g) in THF (50 mL) was added dropwise at −78° C. over 45 min. The reaction was stirred at rt for 2 h, cautiously quenched with satd aq $NH_4Cl$, and filtered. The filtrate was extracted with EtOAc (3×100 mL), washed with brine, dried over anhydrous $Na_2SO_4$, and concentrated in vacuo to give 1-(S-1-(4-bromophenylamino)-3-isopropyl-5-methylhex-5-en-3-ol (6.4 g, 90% yield), which was used for the next step without further purification.

Step 7

To a solution of 1-(S-1-(4-bromophenylamino)-3-isopropyl-5-methylhex-5-en-3-ol (6.4 g, 16.8 mmol) and triethylamine (5.34 g, 52 mmol) in $CH_2Cl_2$ (260 mL) was added triphosgene (2.52 g, 8.5 mmol) at 0° C. under $N_2$, and the mixture was stirred at rt overnight. The reaction mixture was quenched with water, and extracted with $CH_2Cl_2$ (3×50 mL). The combined organic layer was washed with brine, dried over $Na_2SO_4$, filtered, and concentrated to afford the crude product, which was purified by column chromatography to give two isomers of 3-((S)-1-(4-bromophenyl)ethyl)-6-isopropyl-6-(2-methylallyl)-1,3-oxazinan-2-one.

Isomer 1: (1.85 g, 27% yield) $^1$H NMR ($CDCl_3$): δ0.83 (d, J=7.2 Hz, 3H), 0.89 (d, J=7.2 Hz, 3H), 1.45 (d, J=6.8 Hz, 3H), 1.64-1.70 (m, 2H), 1.79 (s, 3H), 1.88-1.95 (m, 1H), 2.20-2.34 (m, 2H), 2.59-2.65 (m, 1H), 3.01-3.08 (m, 1H), 4.70 (s, 1H), 4.87 (s, 1H), 5.68-5.77 (m, 1H), 7.14 (d, J=8.4 Hz, 2H), 7.41 (d, J=8.4 Hz, 2H).

Isomer 2: (1.25 g, 18% yield) $^1$H NMR ($CDCl_3$): δ0.87 (d, J=6.8 Hz, 3H), 0.92 (d, J=6.8 Hz, 3H), 1.50 (d, J=7.2 Hz, 3H), 1.60-1.66 (m, 1H), 1.78 (s, 3H), 1.73-1.79 (m, 1H), 1.78-2.05 (m, 1H), 2.08 (d, J=14.0 Hz, 1H), 2.30 (d, J=14.0 Hz, 1H), 2.62-2.68 (m, 1H), 2.98-3.05 (m, 1H), 4.64 (s, 1H), 4.84 (s, 1H), 5.70-5.75 (m, 1H), 7.13 (d, J=8.4 Hz, 2H), 7.40 (d, J=8.4 Hz, 2H).

Step 8

To a solution of 3-((S)-1-(4-bromophenyl)ethyl)-6-isopropyl-6-(2-methylallyl)-1,3-oxazinan-2-one. isomer 1 (500 mg, 1.32 mmol) in dry $CH_2Cl_2$ (64 mL) was added m-CPBA (455 g, 2.64 mmol) at rt. The reaction mixture was stirred until the starting material was consumed (monitored by TLC). The mixture was diluted with $(CH_3)_3COCH_3$ (70 mL), washed with 30% $Na_2S_2O_3$, and aq $NaHCO_3$ (3×), dried over $Na_2SO_4$, filtered, and concentrated to give 3-((S)-1-(4-bromophenyl)ethyl)-6-isopropyl-6-((2-methyloxiran-2-yl)methyl)-1,3-oxazinan-2-one isomer 1 (520 mg, 99%), which was used directly for the next step without further purification.

Step 9

To a solution of 3-((S)-1-(4-bromophenyl)ethyl)-6-isopropyl-6-((2-methyloxiran-2-yl)methyl)-1,3-oxazinan-2-one isomer 1 (520 mg, 1.32 mmol) in THF (32 mL) was added dropwise $LiEt_3BH$ (Super-Hydride, 13.6 mL, 13.6 mmol) at 0° C. under $N_2$ over 30 min., the resulting solution was stirred at 10-13° C. for 21.5 h. To the mixture was added $H_2O_2$ (40 mL). The resulting solution was diluted with $(CH_3)_3COCH_3$ (380 mL), and washed with water, 30% aq $Na_2S_2O_3$, and brine. The organic phase was dried over $Na_2SO_4$, and filtered. The filtrate was concentrated to give the crude product, which was purified by column chromatography to afford 3-((S)-1-(4-bromophenyl)ethyl)-6-(2-hydroxy-2-methylpropyl)-6-isopropyl-1,3-oxazinan-2-one isomer 1 (320 mg, 61%). $^1$H NMR ($CDCl_3$): δ0.82 (d, J=6.8 Hz, 3H), 0.95 (d, J=6.8 Hz, 3H), 1.31 (s, 3H), 1.34 (s, 3H), 1.51 (d, J=10.0 Hz, 3H), 1.61 (d, J=15.2 Hz, 1H), 1.78-1.84 (m, 1H), 1.91 (d, J=15.2 Hz, 1H), 2.02-2.15 (m, 2H), 2.36 (br, 1H), 2.62-2.68 (m, 1H), 3.03-3.09 (m, 1H), 5.73 (t, J=7.2 Hz, 1H), 7.17-7.19 (m, 2H), 7.44-7.48 (m, 2H).

Step 10

To a solution of 3-((S)-1-(4-bromophenyl)ethyl)-6-(2-hydroxy-2-methylpropyl)-6-isopropyl-1,3-oxazinan-2-one isomer 1 (315 mg, 0.793 mmol) in DMSO (10 mL) was added 4,4,5,5-tetramethyl-1,3,2-dioxaborolan-2-yl)-1,3,2-dioxaborolane (602 mg, 2.38 mmol), $CH_3CO_2K$ (770 mg, 79.3 mmol), $Pd(dppf)_2Cl_2$ (50 mg, 0.06 mmol) under $N_2$, the reaction was stirred at 90° C. for 4 h. The mixture was quenched with $NH_4Cl$, and extracted with EtOAc, washed with water and brine. The organic phase was dried over Na₂SO₄ and filtered. The filtrate was concentrated to give the crude product, which was purified by preparative TLC to give 6-(2-hydroxy-2-methylpropyl)-6-isopropyl-3-((S)-1-(4-(4,4,5,5-tetramethyl-1,3,2-dioxaborolan-2-yl)phenyl)ethyl)-1,3-oxazinan-2-one isomer 1 (250 mg, 71%).

Step 11

5-(4-((S)-1-((S)-6-(2-hydroxy-2-methylpropyl)-6-isopropyl-2-oxo-1,3-oxazinan-3-yl)ethyl)phenyl)pyrimidine-2-carboxylic acid was prepared from (S)-6-(2-hydroxy-2-methylpropyl)-6-isopropyl-3-((S)-1-(4-(4,4,5,5-tetramethyl-1,3,2-dioxaborolan-2-yl)phenyl)ethyl)-1,3-oxazinan-2-one and 5-bromopyrimidine-2-carboxylic acid following a procedure analogous to that described in Example 1 Step 2.

Step 12

The title compound was prepared from 5-(4-((S)-1-((S)-6-(2-hydroxy-2-methylpropyl)-6-isopropyl-2-oxo-1,3-oxazinan-3-yl)ethyl)phenyl)pyrimidine-2-carboxylic acid and cyclopropylamine following a procedure analogous to that described in Example 25 Step 7.

EXAMPLE 200

(S)-3-((S)-1-(4-(6-(2-fluoroethoxy)pyridin-3-yl)phenyl)ethyl)-6-(2-hydroxy-2-methylpropyl)-6-phenyl-1,3-oxazinan-2-one Step 1

To a solution of 2-fluoroethanol (3.2 g, 50 mmol) and triethylamine (5.5 g, 55 mmol) in dichloromethane (60 mL) was added dropwise (CF₃SO₂)₂O (15.5 g, 55 mmol) at −78° C. under N₂. The mixture was stirred at 10-20° C. for 1 h, and treated with water (100 mL). The organic layer was washed with satd aq NaHCO₃ (100 mL) and brine (100 mL), dried, and concentrated to give 2-fluoroethyl trifluoromethanesulfonate (8 g, yield 82%).

Step 2

A solution of 5-bromopyridin-2(1H)-one (100 mg, 0.58 mmol), 2-fluoroethyl trifluoromethanesulfonate (1.1 g, 5.8 mmol), and K₂CO₃ (800 mg, 5.8 mmol) in DMF (3 mL) was stirred at rt overnight. 2-Fluoroethyl trifluoromethanesulfonate (1.1 g, 5.8 mmol) and K₂CO₃ (800 mg, 5.8 mmol) were added, and the mixture was treated with ethyl acetate (20 mL) and water (20 mL). The organic layer was washed with water (2×20 mL) and brine (20 mL), dried over Na₂SO₄, concentrated, and purified by preparative, TLC (1:1 petroleum ether/EtOAc) to give two isomers.

5-bromo-1-(2-fluoroethyl)pyridin-2(1H)-one (30 mg, yield 24%). ¹H NMR (CD₃OD): δ 4.25 (t, 1H), 4.32 (t, 1H), 4.62 (t, 1H), 4.74 (t, 1H), 6.52 (d, 1H), 7.61 (dd, 1H), 7.85 (s, 1H).

5-bromo-2-(2-fluoroethoxy)pyridine (30 mg, yield 24%). ¹H NMR (CD₃OD): δ4.46 (t, 1H), 4.53 (t, 1H), 4.64 (t, 1H), 4.76 (t, 1H), 6.79 (d, 1H), 7.79 (dd, 1H), 8.18 (s, 1H),

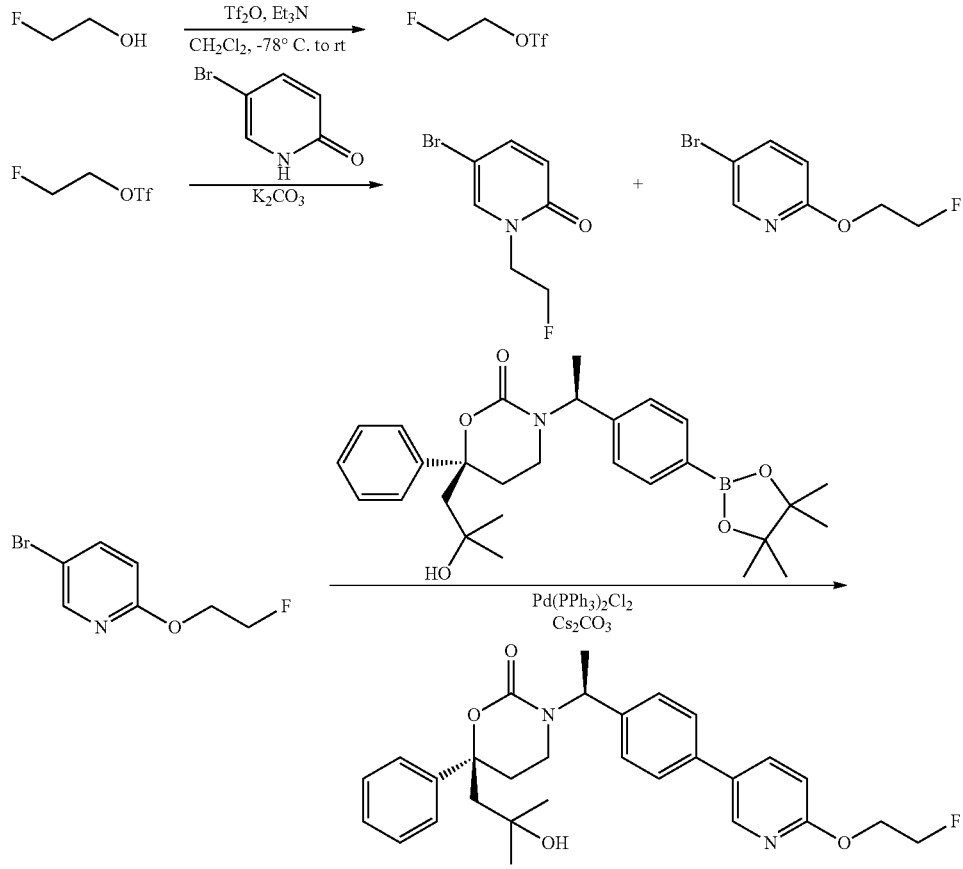

Step 3

To a solution of (S)-6-(2-hydroxy-2-methylpropyl)-6-phenyl-3-((S)-1-(4-(4,4,5,5-tetramethyl-1,3,2-dioxaborolan-2-yl)phenyl)ethyl)-1,3-oxazinan-2-one (20 mg, 0.041 mmol), 5-bromo-2-(2-fluoroethoxy)pyridine (9.2 mg, 0.041 mmol), and 2 N aq Cs$_2$CO$_3$ (0.2 mL, 0.41 mmol) in 1,4-dioxane (2 mL) was added Pd(PPh$_3$)$_2$Cl$_2$ (3 mg, 0.0041 mmol) under N$_2$. The mixture was refluxed for 2 h under N$_2$, treated with EtOAc (10 mL) and water (10 mL). The organic layer was dried over Na$_2$SO$_4$ and concentrated. The residue was purified by preparative HPLC to give (S)-3-((S)-1-(4-(6-(2-fluoroethoxy)pyridin-3-yl)phenyl)ethyl)-6-(2-hydroxy-2-methylpropyl)-6-phenyl-1,3-oxazinan-2-one (2.20 mg, 11%). LC-MS Method 2 $t_R$=1.21 min, m/z=515, 493; $^1$H NMR (CD$_3$OD): δ 0.95 (s, 3H), 1.26 (s, 3H), 1.54 (d, 3H), 2.15 (s, 2H), 2.21 (m, 1H), 2.46 (m, 2H), 3.02 (m, 1H), 4.50 (t, 1H), 4.57 (t, 1H), 4.66 (t, 1H), 4.79 (t, 1H), 5.57 (q, 1H), 6.88 (d, 1H), 7.02 (d, 2H), 7.31 (m, 7H), 7.85 (dd, 1H), 8.25 (d, 1H).

EXAMPLE 201

(S)-6-(2-Hydroxy-2-methyl-propyl)-3-{(S)-1-[4-(1-isopropyl-1H-pyrazol-4-yl)-phenyl]-ethyl}-6-phenyl-[1,3]oxazinan-2-one

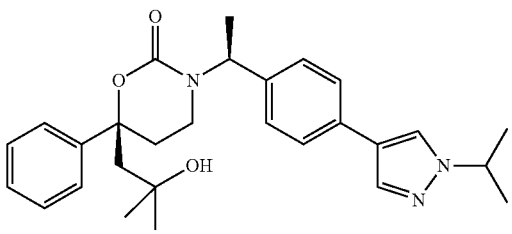 [SMILES: CC(C)n1cc(-c2ccc([C@H](C)N3CC[C@](CC(C)(C)O)(c4ccccc4)OC3=O)cc2)cn1]

2 M aqueous Na$_2$CO$_3$ solution (0.75 mL) was added to a solution of 4-bromo-1-isopropyl-1H-pyrazole (0.15 g) and (S)-6-(2-hydroxy-2-methylpropyl)-6-phenyl-3-[(S)-1-(4-(4,4,5,5-tetramethyl-1,3,2-dioxaborolan-2-yl)phenyl)ethyl]-1,3-oxazinan-2-one (0.25 g) in dimethylformamide (2 mL). The resulting mixture was sparged with argon for 10 min, before [1,1'-bis(diphenylphosphino)-ferrocene]dichloro-palladium(II) dichloromethane complex (13 mg) was added. The mixture was heated to 90° C. and stirred at this temperature for 6 h. Then another portion of [1,1'-bis(diphenyl-phosphino)-ferrocene]dichloro-palladium(II) dichloromethane complex (13 mg) was added and the mixture was further stirred at 100° C. overnight. After cooling to ambient temperature, water was added and the resulting mixture was extracted with ethyl acetate. The combined organic extracts were washed with brine, dried (MgSO$_4$), and concentrated. The residue was purified by HPLC on reversed phase (acetonitrile/water) followed by chromatography on silica gel (tert-butyl methyl ether/dichloromethane/NH$_4$OH 95:5:0.1) to afford the title compound as a solid. Yield: 23 mg (9% of theory); Mass spectrum (ESI$^+$): m/z=462 [M+H]$^+$.

EXAMPLE 202

3-{(S)-1-[4-(1-Cyclopropyl-1H-pyrazol-4-yl)-phenyl]-ethyl}-(S)-6-(2-hydroxy-2-methyl-propyl)-6-phenyl-[1,3]oxazinan-2-one

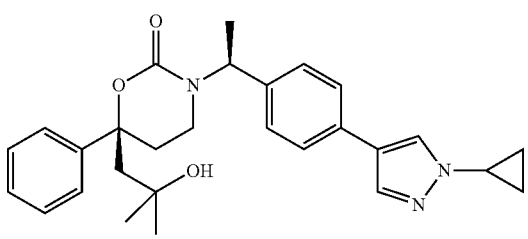 [SMILES: C[C@@H](c1ccc(-c2cnn(C3CC3)c2)cc1)N1CC[C@](CC(C)(C)O)(c2ccccc2)OC1=O]

2 M aqueous Na$_2$CO$_3$ solution (0.37 mL) was added to a solution of 4-bromo-1-isopropyl-1H-pyrazole (0.15 g) and (S)-6-(2-hydroxy-2-methylpropyl)-6-phenyl-3-[(S)-1-(4-(4,4,5,5-tetramethyl-1,3,2-dioxaborolan-2-yl)phenyl)ethyl]-1,3-oxazinan-2-one (0.35 g) in dimethylformamide (3 mL). The resulting mixture was sparged with argon for 10 min, before [1,1'-bis(diphenylphosphino)-ferrocene]dichloro-palladium(II) dichloromethane complex (20 mg) was added. The mixture was heated to 90° C. and stirred at this temperature for 2 h. After cooling to ambient temperature, water was added and the resulting mixture was extracted with ethyl acetate. The combined organic extracts were washed with brine, dried (MgSO$_4$), and concentrated. The residue was purified by chromatography on silica gel (tert-butyl methyl ether/dichloromethane/NH$_4$OH 96:4:0.1->94:6:0.1) to afford the title compound as a solid. Yield: 0.18 g (55% of theory); Mass spectrum (ESI$^+$): m/z=460 [M+H]$^+$.

4-Bromo-1-cyclopropyl-1H-pyrazole

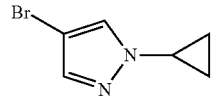

A mixture of 4-bromo-1H-pyrazole (0.50 g), cyclopropylboronic acid (0.65 g), copper(II) acetate (0.65 g), 2,2'-bipyridine (0.56 g), and sodium carbonate (0.80 g) in 1,2-dichloroethane (15 mL) was stirred at reflux temperature for 4 h. Then another portion of cyclopropylboronic acid (0.65 g) and sodium carbonate (0.80 g) were added and the mixture was further stirred at reflux temperature overnight. After cooling to room temperature, aqueous NH$_4$Cl solution was added and the resulting mixture was extracted with dichloromethane. The combined extracts were dried (Na$_2$SO$_4$) and the solvent was evaporated. The residue was purified by chromatography on silica gel (cyclohexane/ethyl acetate 95:5->80:20) to afford the title compound as a colorless oil. Yield: 0.32 g (48% of theory); Mass spectrum (ESI⁺): m/z=187/189 (Br) [M+H]⁺.

EXAMPLE 203

6-(4-{(S)-1-[(S)-6-(2-Hydroxy-2-methyl-propyl)-2-oxo-6-phenyl-[1,3]oxazinan-3-yl]-ethyl}-phenyl)-pyridazine-3-carboxylic acid dimethylamide

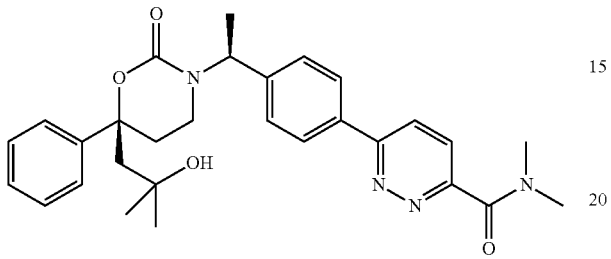

[(Benzotriazol-1-yloxy)-dimethylamino-methylene]-dimethyl-ammonium tetrafluoroborate (TBTU, 110 mg) was added to a solution of 6-(4-{(S)-1-[(S)-6-(2-hydroxy-2-methyl-propyl)-2-oxo-6-phenyl-[1,3]oxazinan-3-yl]-ethyl}-phenyl)-pyridazine-3-carboxylic acid (140 mg) and ethyldiisopropyl-amine (60 μL) in N,N-dimethylformamide (2 mL) at room temperature. The resulting solution was stirred for 20 min, before dimethylamine (2 mol/L in tetrahydrofuran, 300 μL) was added. After stirring the solution at room temperature for another 2 h, the solution was concentrated and the residue was purified by HPLC on reversed phase (methanol/water/NH₄OH) to afford the title compound. Yield: 50 mg (34% of theory); Mass spectrum (ESI⁺): m/z=503 [M+H]⁺.

6-(4-{(S)-1-[(S)-6-(2-Hydroxy-2-methyl-propyl)-2-oxo-6-phenyl-[1,3]oxazinan-3-yl]-ethyl}-phenyl)-pyridazine-3-carboxylic acid

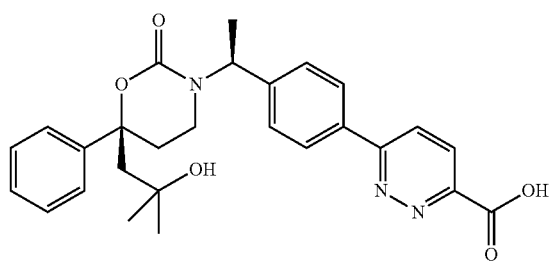 [SMILES: C[C@@H](c1ccc(-c2ccc(C(=O)O)nn2)cc1)N1CC[C@](CC(C)(C)O)(c2ccccc2)OC1=O]

2 M aqueous Na₂CO₃ solution (1.46 mL) was added to a mixture of 6-chloropyridazine-3-carboxylic acid methyl ester (0.38 g) and (S)-6-(2-hydroxy-2-methylpropyl)-6-phenyl-3-[(S)-1-(4-(4,4,5,5-tetramethyl-1,3,2-dioxaborolan-2-yl)phenyl)ethyl]-1,3-oxazinan-2-one (0.70 g) in N,N-dimethylformamide (8 mL). The resulting mixture was sparged with argon for 10 min, before [1,1'-bis(diphenylphosphino)ferrocene]dichloro-palladium(II) dichloromethane complex (72 mg) was added. The mixture was heated to 100° C. and stirred at this temperature overnight. After cooling the mixture to ambient temperature, water and 1 M hydrochloric acid were added and the resulting mixture was extracted with ethyl acetate. The combined organic extracts were washed with brine and dried (MgSO₄). The solvent was evaporated and the residue was purified by HPLC on reversed phase (methanol/water/F₃CCO₂H) to afford the title compound as an oil that solidifies while standing. Yield: 0.36 g (52% of theory); Mass spectrum (ESI⁻): m/z=474 [M−H]⁻.

EXAMPLE 204

6-(4-{(S)-1-[(S)-6-(2-Hydroxy-2-methyl-propyl)-2-oxo-6-phenyl-[1,3]oxazinan-3-yl]-ethyl}-phenyl)-pyridazine-3-carboxylic acid methylamide

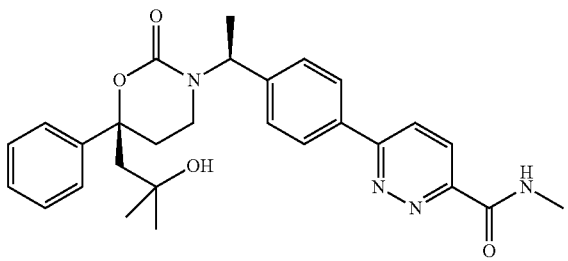 [SMILES: CNC(=O)c1ccc(-c2ccc([C@H](C)N3CC[C@](CC(C)(C)O)(c4ccccc4)OC3=O)cc2)nn1]

The title compound was prepared from 6-(4-{(S)-1-[(S)-6-(2-hydroxy-2-methyl-propyl)-2-oxo-6-phenyl-[1,3]oxazinan-3-yl]-ethyl}-phenyl)-pyridazine-3-carboxylic acid and methylamine (2 mol/L in tetrahydrofuran) following a procedure analogous to that described in Example 203. Mass spectrum (ESI⁺): m/z=489 [M+H]⁺.

EXAMPLE 205

6-(4-{(S)-1-[(S)-6-(2-Hydroxy-2-methyl-propyl)-2-oxo-6-phenyl-[1,3]oxazinan-3-yl]-ethyl}-phenyl)-pyridazine-3-carboxylic acid amide

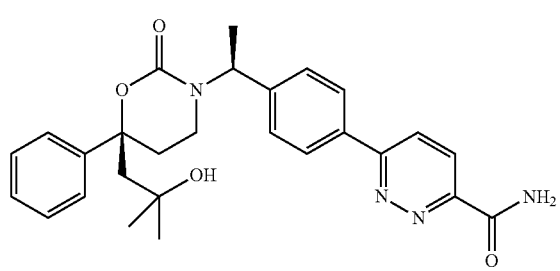 [SMILES: C[C@@H](c1ccc(-c2ccc(C(N)=O)nn2)cc1)N1CC[C@](CC(C)(C)O)(c2ccccc2)OC1=O]

The title compound was prepared from 6-(4-{(S)-1-[(S)-6-(2-hydroxy-2-methyl-propyl)-2-oxo-6-phenyl-[1,3]oxazinan-3-yl]-ethyl}-phenyl)-pyridazine-3-carboxylic acid and ammonia (32% in water) following a procedure analogous to that described in Example 203. Mass spectrum (ESI+): m/z=475 [M+H]+.

EXAMPLE 206

6-(4-{(S)-1-[(S)-6-(2-Hydroxy-2-methyl-propyl)-2-oxo-6-phenyl-[1,3]oxazinan-3-yl]-ethyl}-phenyl)-pyridine-2-carboxylic acid dimethylamide

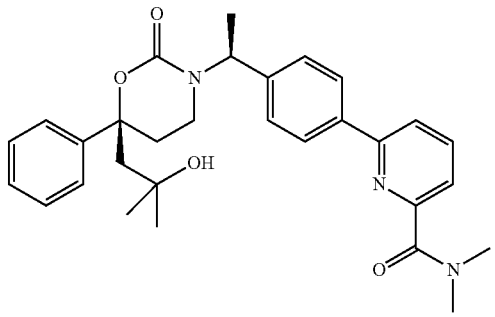 [SMILES: C[C@@H](c1ccc(-c2cccc(C(=O)N(C)C)n2)cc1)N1CC[C@](CC(C)(C)O)(c2ccccc2)OC1=O]

The title compound was prepared from (6-(4-{(S)-1-[(S)-6-(2-hydroxy-2-methyl-propyl)-2-oxo-6-phenyl-[1,3]oxazinan-3-yl]-ethyl}-phenyl)-pyridine-2-carboxylic acid and dimethylamine (2 mol/L in tetrahydrofuran) following a procedure analogous to that described in Example 203. Mass spectrum (ESI+): m/z=502 [M+H]+.

6-(4-{(S)-1-[(S)-6-(2-Hydroxy-2-methyl-propyl)-2-oxo-6-phenyl-[1,3]oxazinan-3-yl]-ethyl}-phenyl)-pyridine-2-carboxylic acid ethyl ester

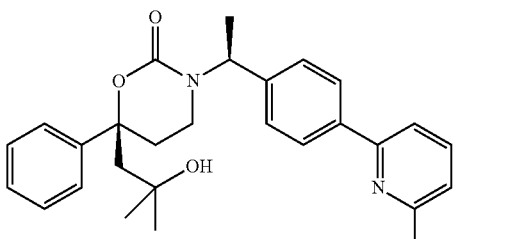

2 M aqueous Na2CO3 solution (1.46 mL) was added to a mixture of 6-bromo-pyridine-2-carboxylic acid ethyl ester (0.50 g) and (S)-6-(2-hydroxy-2-methylpropyl)-6-phenyl-3-[(S)-1-(4-(4,4,5,5-tetramethyl-1,3,2-dioxaborolan-2-yl)phenyl)ethyl]-1,3-oxazinan-2-one (0.70 g) in N,N-dimethyl-formamide (8 mL). The resulting mixture was sparged with argon for 10 min, before [1,1'-bis(diphenyl-phosphino)-ferrocene]dichloro-palladium(II) dichloromethane complex (72 mg) was added. The mixture was heated to 100° C. and stirred at this temperature overnight. After cooling to ambient temperature, water was added and the resulting mixture was extracted with ethyl acetate. The combined organic extracts were dried (MgSO4) and the solvent was evaporated. The residue was purified by HPLC on reversed phase (methanol/water/NH4OH) to afford the title compound. Yield: 0.59 g (80% of theory); Mass spectrum (ESI+): m/z=503 [M+H]+.

6-(4-{(S)-1-[(S)-6-(2-Hydroxy-2-methyl-propyl)-2-oxo-6-phenyl-[1,3]oxazinan-3-yl]-ethyl}-phenyl)-pyridine-2-carboxylic acid

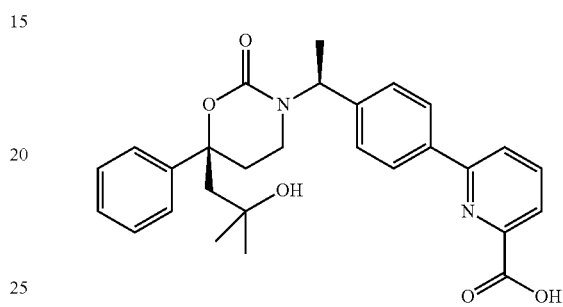

4 M aqueous NaOH solution (0.80 mL) was added to a solution of 6-(4-{(S)-1-[(S)-6-(2-hydroxy-2-methyl-propyl)-2-oxo-6-phenyl-[1,3]oxazinan-3-yl]-ethyl}-phenyl)-pyridine-2-carboxylic acid ethyl ester (0.55 g) in methanol (3 mL) and the resulting solution was stirred at room temperature overnight. Then, the solution was acidified using 1 M hydrochloric acid and the resulting mixture was extracted with ethyl acetate. The combined organic extracts were washed with brine and dried (MgSO4). The solvent was evaporated to give the title compound. Yield: 0.49 g (95% of theory); Mass spectrum (ESI−): m/z=473 [M−H]−.

EXAMPLE 207

6-(4-{(S)-1-[(S)-6-(2-Hydroxy-2-methyl-propyl)-2-oxo-6-phenyl-[1,3]oxazinan-3-yl]-ethyl}-phenyl)-pyridine-2-carboxylic acid methylamide

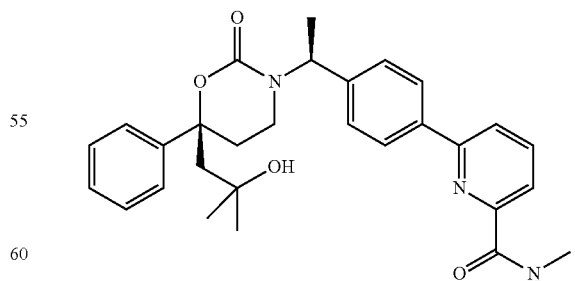

The title compound was prepared from (6-(4-{(S)-1-[(S)-6-(2-hydroxy-2-methyl-propyl)-2-oxo-6-phenyl-[1,3]oxazinan-3-yl]-ethyl}-phenyl)-pyridine-2-carboxylic acid and methylamine (2 mol/L in tetrahydrofuran) following a procedure analogous to that described in Example 203. Mass spectrum (ESI⁺): m/z=488 [M+H]⁺.

EXAMPLE 208

6-(4-{(S)-1-[(S)-6-(2-Hydroxy-2-methyl-propyl)-2-oxo-6-phenyl-[1,3]oxazinan-3-yl]-ethyl}-phenyl)-pyridine-2-carboxylic acid cyclopropylamide

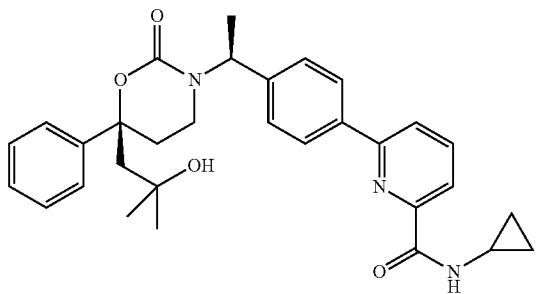 [SMILES: C[C@@H](c1ccc(-c2cccc(C(=O)NC3CC3)n2)cc1)N1CC[C@](CC(C)(C)O)(c2ccccc2)OC1=O]

The title compound was prepared from (6-(4-{(S)-1-[(S)-6-(2-hydroxy-2-methyl-propyl)-2-oxo-6-phenyl-[1,3]oxazinan-3-yl]-ethyl}-phenyl)-pyridine-2-carboxylic acid and cyclopropylamine following a procedure analogous to that described in Example 203. Mass spectrum (ESI⁺): m/z=514 [M+H]⁺.

EXAMPLE 209

6-(4-{(S)-1-[(S)-6-(2-Hydroxy-2-methyl-propyl)-2-oxo-6-phenyl-[1,3]oxazinan-3-yl]-ethyl}-phenyl)-pyridine-2-carboxylic acid amide

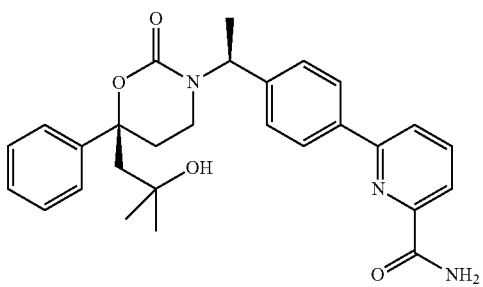 [SMILES: C[C@@H](c1ccc(-c2cccc(C(N)=O)n2)cc1)N1CC[C@](CC(C)(C)O)(c2ccccc2)OC1=O]

The title compound was prepared from (6-(4-{(S)-1-[(S)-6-(2-hydroxy-2-methyl-propyl)-2-oxo-6-phenyl-[1,3]oxazinan-3-yl]-ethyl}-phenyl)-pyridine-2-carboxylic acid and ammonia (32% in water) following a procedure analogous to that described in Example 203. Mass spectrum (ESI⁺): m/z=474 [M+H]⁺.

EXAMPLE 210

(S)-6-(2-hydroxy-2-methylpropyl)-3-((S)-1-(4-(2-methoxypyridin-4-yl)phenyl)ethyl)-6-phenyl-1,3-oxazinan-2-one

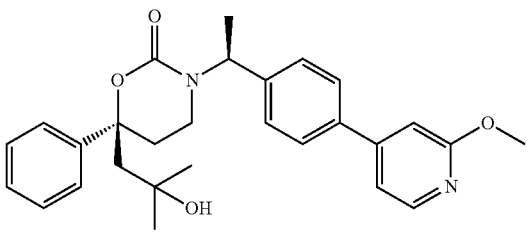 [SMILES: COc1cc(-c2ccc([C@H](C)N3CC[C@](CC(C)(C)O)(c4ccccc4)OC3=O)cc2)ccn1]

The title compound was prepared from (S)-3-((S)-1-(4-bromophenyl)ethyl)-6-(2-hydroxy-2-methylpropyl)-6-phenyl-1,3-oxazinan-2-one and 2-methoxy-4-(4,4,5,5-tetramethyl-1,3,2-dioxaborolan-2-yl)pyridine following a procedure analogous to that described in Example 14. LC-MS Method 1 $t_R$=1.66 min, m/z=461.

BIOLOGICAL TEST EXAMPLE 1

The inhibition of a microsomal preparation of 11β-HSD1 by compounds of the invention was measured essentially as previously described (K. Solly, S. S. Mundt, H. J. Zokian, G. J. Ding, A. Hermanowski-Vosatka, B. Strulovici, and W. Zheng, High-Throughput Screening of 11-Beta-Hydroxyseroid Dehydrogenase Type 1 in Scintillation Proximity Assay Format. Assay Drug Dev Technol 3 (2005) 377-384). All reactions were carried out at rt in 96 well clear flexible PET Microbeta plates (PerkinElmer). The assay begins by dispensing 49 µl of substrate solution (50 mM HEPES, pH 7.4, 100 mM KCl, 5 mM NaCl, 2 mM $MgCl_2$, 2 mM NADPH and 160 nM [³H]cortisone (1 Ci/mmol)) and mixing in 1 µL of the test compounds in DMSO previously diluted in half-log increments (8 points) starting at 0.1 mM. After a 10 minute pre-incubation, 50 µL of enzyme solution containing microsomes isolated from CHO cells overexpressing human 11β-HSD1 (10-20 µg/ml of total protein) was added, and the plates were incubated for 90 minutes at rt. The reaction was stopped by adding 50 µl of the SPA beads suspension containing 10 µM 18β-glycyrrhetinic acid, 5 mg/ml protein A coated YSi SPA beads (GE Healthcare) and 3.3 µg/ml of anti-cortisol antibody (East Coast Biologics) in Superbiock buffer (Bio-Rad). The plates were shaken for 120 minutes at rt, and the SPA signal corresponding to [³H]cortisol was measured on a Microbeta plate reader.

BIOLOGICAL TEST EXAMPLE 2

The inhibition of 11β-HSD1 by compounds of this invention was measured in whole cells as follows. Cells for the assay were obtained from two sources: fully differentiated human omental adipocytes from Zen-Bio, Inc.; and human omental pre-adipocytes from Lonza Group Ltd. Pre-differentiated omental adipocytes from Zen-Bio Inc. were purchased in 96-well plates and were used in the assay at least two weeks after differentiation from precursor preadipocytes. Zen-Bio induced differentiation of pre-adipocytes by supplementing medium with adipogenic and lipogenic hormones (human insulin, dexamethasone, isobutylmethylxanthine and PPAR-gamma agonist). The cells were maintained in full adipocyte medium (DMEM/Ham's F-12 (1:1, v/v), HEPES pH 7.4, fetal bovine serum, penicillin, streptomycin and Amphotericin B, supplied by Zen-Bio, Inc.) at 37° C., 5% $CO_2$.

Pre-adipocytes were purchased from Lonza Group Ltd. and placed in culture in Preadipocyte Growth Medium-2 supplemented with fetal bovine serum, penicillin, and streptomycin (supplied by Lonza) at 37° C., 5% $CO_2$. Pre-adipocytes were differentiated by the addition of insulin, dexamethasone, indomethacin and isobutyl-methylxanthine (supplied by Lonza) to the Preadipocyte Growth Medium-2. Cells were exposed to the differentiating factors for 7 days, at which point the cells were differentiated and ready for the assay. One day before running the assay, the differentiated omental adipocytes were transferred into serum- and phenol-red-free medium for overnight incubation. The assay was performed in a total volume of 200 μL. The cells were pre-incubated with serum-free, phenol-red-free medium containing 0.1% (v/v) of DMSO and various concentrations of the test compounds at least 1 h before [$^3$H] cortisone in ethanol (50 Ci/mmol, ARC, Inc.) was added to achieve a final concentration of cortisone of 100 nM. The cells were incubated for 3-4 hrs at 37° C., 5% $CO_2$. Negative controls were incubated without radioactive substrate and received the same amount of [$^3$H] cortisone at the end of the incubation. Formation of [$^3$H] cortisol was monitored by analyzing 25 μL of each supernatant in a scintillation proximity assay (SPA). (Solly, K.; Mundt, S. S.; Zokian, H. J.; Ding, G. J.; Hermanowski-Vosatka, A.; Strulovici, B.; Zheng, W. Assay Drug Dev. Technol. 2005, 3, 377-384). Many compounds of the invention showed significant activity in this assay.

TABLE OF BIOLOGICAL ASSAY RESULTS

Biological Test EXAMPLE 4108.1002-007 EXAMPLE 1

| Compound | $IC_{50}$ Range[a] | Average % inhibition at 100 nM |
|---|---|---|
| EXAMPLE 1 | ++ | 96.4 |
| EXAMPLE 2 | ++ | 99.0 |
| EXAMPLE 3 | ++ | 96.8 |
| EXAMPLE 4 | ++ | 96.3 |
| EXAMPLE 5 Isomer 1 | ++ | 93.8 |
| EXAMPLE 5 Isomer 2 | ++ | 88.8 |
| EXAMPLE 6 | ++ | 96.3 |
| EXAMPLE 7 | ++ | 93.3 |
| EXAMPLE 8 | ++ | 92.4 |
| EXAMPLE 9 | ++ | 92.4 |
| EXAMPLE 10 | ++ | 93.6 |
| EXAMPLE 11 | ++ | 91.6 |
| EXAMPLE 12 | ++ | 47.0 |
| EXAMPLE 13 | ++ | 92.1 |
| EXAMPLE 14 | ++ | 93.4 |
| EXAMPLE 15 | ++ | 94.1 |
| EXAMPLE 16 | ++ | 97.9 |
| EXAMPLE 17 | ++ | 94.0 |
| EXAMPLE 18 | # | 13.7 |
| EXAMPLE 19 | ++ | 94.6 |
| EXAMPLE 20 | ++ | 92.2 |
| EXAMPLE 21 | ++ | 99.2 |
| EXAMPLE 22 | ++ | 90.0 |
| EXAMPLE 23 | ++ | 89.3 |
| EXAMPLE 24 | ++ | 96.9 |
| EXAMPLE 25 Isomer 1 | ++ | 84.9 |
| EXAMPLE 25 Isomer 2 | ++ | 90.5 |
| EXAMPLE 26 | ++ | 95.2 |
| EXAMPLE 27 | ++ | 96.8 |
| EXAMPLE 28 | ++ | 89.7 |
| EXAMPLE 29 | ++ | 83.8 |
| EXAMPLE 30 | ++ | 98.1 |
| EXAMPLE 31 | ++ | 90.7 |
| EXAMPLE 32 | ++ | 54.8[b] |
| EXAMPLE 33 | + | 37.1[b] |
| EXAMPLE 34 | ++ | 98 |
| EXAMPLE 35 | ++ | 96.3 |
| EXAMPLE 36 | ++ | 93.3 |
| EXAMPLE 37 | ++ | 94.3 |
| EXAMPLE 38 | ++ | 87.3 |
| EXAMPLE 39 | ++ | 73.6 |
| EXAMPLE 40 | ++ | 93.4 |
| EXAMPLE 41 | ++ | 96.8 |
| EXAMPLE 42 | ++ | 90.9 |
| EXAMPLE 43 | ++ | 86.2 |
| EXAMPLE 44 | ++ | 100.1 |
| EXAMPLE 45 | ++ | 96.7 |
| EXAMPLE 46 | ++ | 93.4 |
| EXAMPLE 47 | ++ | 91 |
| EXAMPLE 48 | ++ | 94.3 |
| EXAMPLE 49 | ++ | 96.7 |
| EXAMPLE 50 | ++ | 81.2 |
| EXAMPLE 51 | ++ | 96.1 |
| EXAMPLE 52 | ++ | 94.5 |
| EXAMPLE 53 | ++ | 98.7 |
| EXAMPLE 54 | ++ | 97.1 |
| EXAMPLE 55 | ++ | 96.5 |
| EXAMPLE 56 | ++ | 96.7 |
| EXAMPLE 57 | ++ | 99.4 |
| EXAMPLE 58 | ++ | 97.4 |
| EXAMPLE 59 | ++ | 100.5 |
| EXAMPLE 60 | ++ | 91.9 |
| EXAMPLE 61 | ++ | 96.2 |
| EXAMPLE 62 | ++ | 97.9 |
| EXAMPLE 63 | ++ | 101.1 |
| EXAMPLE 64 | ++ | 99.6 |
| EXAMPLE 65 | ++ | 99 |
| EXAMPLE 66 | ++ | 95.6 |
| EXAMPLE 67 | ++ | 100.9 |
| EXAMPLE 68 | ++ | 50 |
| EXAMPLE 69 | ++ | 98.3 |
| EXAMPLE 70 | ++ | 49.7 |
| EXAMPLE 71 | ++ | 68.7 |
| EXAMPLE 72 | ++ | 64.8 |
| EXAMPLE 73 | ++ | 65.3 |
| EXAMPLE 74 | ++ | 95.7 |
| EXAMPLE 75 | ++ | 97.7 |
| EXAMPLE 76 | ++ | 98.7 |
| EXAMPLE 77 | ++ | 79.9 |
| EXAMPLE 78 | ++ | 95.8 |
| EXAMPLE 79 | ++ | 76.9 |
| EXAMPLE 80 | ++ | 96 |
| EXAMPLE 81 | ++ | 99.3 |
| EXAMPLE 82 | ++ | 98.1 |
| EXAMPLE 83 | ++ | 94.7 |
| EXAMPLE 84 | ++ | 93.3 |
| EXAMPLE 85 | ++ | 94.3 |
| EXAMPLE 86 | ++ | 99.6 |
| EXAMPLE 87 | ++ | 99.8 |
| EXAMPLE 88 | ++ | 98.3 |
| EXAMPLE 89 | ++ | 98.9 |
| EXAMPLE 90 | ++ | 96.7 |
| EXAMPLE 91 | ++ | 90.2 |
| EXAMPLE 92 | ++ | 97.3 |
| EXAMPLE 93 | ++ | 101.5 |
| EXAMPLE 94 | ++ | 98.7 |
| EXAMPLE 95 | ++ | 93.9 |
| EXAMPLE 96 | ++ | 99.8 |
| EXAMPLE 97 | ++ | 98.8 |
| EXAMPLE 98 | ++ | 97.8 |
| EXAMPLE 99 | ++ | 98.5 |
| EXAMPLE 100 | ++ | 93.1 |
| EXAMPLE 101 | ++ | 100.4 |

-continued

TABLE OF BIOLOGICAL ASSAY RESULTS

Biological Test EXAMPLE
4108.1002-007 EXAMPLE 1

| Compound | IC$_{50}$ Range$^a$ | Average % inhibition at 100 nM |
|---|---|---|
| EXAMPLE 102 | ++ | 94.3 |
| EXAMPLE 103 | ++ | 98.5 |
| EXAMPLE 104 | ++ | 88 |
| EXAMPLE 105 | ++ | 86.3 |
| EXAMPLE 106 | ++ | 79.6 |
| EXAMPLE 107.1 | ++ | 95.5 |
| EXAMPLE 107.2 | ++ | 93.6 |
| EXAMPLE 108 | ++ | 98.1 |
| EXAMPLE 109 | ++ | 91.5 |
| EXAMPLE 110 | ++ | 93.9 |
| EXAMPLE 111 | ++ | 97.6 |
| EXAMPLE 112 | ++ | 95.2 |
| EXAMPLE 113 | ++ | 92.4 |
| EXAMPLE 114 | ++ | 98.9 |
| EXAMPLE 115 | ++ | 95.1 |
| EXAMPLE 116 | ++ | 99.6 |
| EXAMPLE 117 | ++ | 93.9 |
| EXAMPLE 118 | ++ | 86.3 |
| EXAMPLE 119 | ++ | 90.8 |
| EXAMPLE 120 | ++ | 93.1 |
| EXAMPLE 121 | ++ | 97.3 |
| EXAMPLE 122 | ++ | 94.5 |
| EXAMPLE 123 | ++ | 93.6 |
| EXAMPLE 124 | ++ | 88.1 |
| EXAMPLE 125 | ++ | 98.6 |
| EXAMPLE 126 | ++ | 96.7 |
| EXAMPLE 127 | ++ | 93.7 |
| EXAMPLE 128 | ++ | 96.5 |
| EXAMPLE 129 | ++ | 93.9 |
| EXAMPLE 130 | ++ | 97.9 |
| EXAMPLE 131 | ++ | 98.5 |
| EXAMPLE 132 | ++ | 95.2 |
| EXAMPLE 133 | ++ | 99.2 |
| EXAMPLE 134 | ++ | 97.6 |
| EXAMPLE 135 | ++ | 97.3 |
| EXAMPLE 136 | ++ | 97.8 |
| EXAMPLE 137 | ++ | 99 |
| EXAMPLE 138 | ++ | 100 |
| EXAMPLE 139 | ++ | 97.6 |
| EXAMPLE 140 | ++ | 98.7 |
| EXAMPLE 141 | ++ | 101.9 |
| EXAMPLE 142 | ++ | 96.4 |
| EXAMPLE 143 | ++ | 97.6 |
| EXAMPLE 144 | ++ | 98.6 |
| EXAMPLE 145 | ++ | 72.4 |
| EXAMPLE 146 | ++ | 78.9 |
| EXAMPLE 147 | ++ | 98.7 |
| EXAMPLE 148 | ++ | 97.4 |
| EXAMPLE 149 | ++ | 95.5 |
| EXAMPLE 150 | ++ | 97 |
| EXAMPLE 151 | ++ | 97 |
| EXAMPLE 152 | ++ | 65.4 |
| EXAMPLE 153 | ++ | 94.7 |
| EXAMPLE 154 | ++ | 90.7 |
| EXAMPLE 155 | ++ | 94.7 |
| EXAMPLE 156 | ++ | 96.4 |
| EXAMPLE 157 | ++ | 96.3 |
| EXAMPLE 158 | ++ | 95.7 |
| EXAMPLE 159 | ++ | 94.6 |
| EXAMPLE 160 | ++ | 95 |
| EXAMPLE 161 | ++ | 95.1 |
| EXAMPLE 162 | ++ | 87.2 |
| EXAMPLE 163 | ++ | 90.3 |
| EXAMPLE 164 | ++ | 99.4 |
| EXAMPLE 165 | ++ | 94.5 |
| EXAMPLE 166 | ++ | 96.5 |
| EXAMPLE 172 | ++ | 97.9 |
| EXAMPLE 183 | ++ | 96.4 |
| EXAMPLE 186 | ++ | 95.2 |
| EXAMPLE 197 | ++ | 96.5 |
| EXAMPLE 198 | ++ | 92.4 |
| EXAMPLE 199 | ++ | 62.9 |
| EXAMPLE 200 | ++ | 98.3 |
| EXAMPLE 210 | ++ | 97.1 |

$^a$++ means IC$_{50}$ = <100 nM, + means IC$_{50}$ = 100-1000 nM, # means IC$_{50}$ > 100 nM, − means IC$_{50}$ > 1000 nM;
$^b$average % inhibition at 111 nM.

BIOLOGICAL TEST EXAMPLE 3

In vitro inhibition of 11 β-HSD1 by test compounds was determined with HTRF (Homogeneous Time-Resolved Fluorescence) technology (cisbio international, France) detecting cortisol generated from cortisterone by human liver microsomes. Briefly, compounds were incubated for 1 hour at 37° C. in Tris buffer (20 mM tris, 5 mM EDTA, pH 6.0) containing NADPH (200 µM) and cortisone (80 nM). Cortisol generated in the reaction is then detected with a competitive immunoassay, involving two HTRF conjugates: cortisol linked to XL665 and anti-cortisol antibody labeled with Europium cryptate. The incubation period for detection reaction was typically 2 hours. The amount of cortisol was determined by reading the time-resolved fluorescence of the wells (Ex 320/75 nm; Em 615/8.5 nm and 665/7.5 nm). The ratio of the two emission signals was then calculated (Em665*10000/Em615). Each assay contained incubations with vehicle controls instead of compound as controls for non-inhibited cortisol generation (100% CTL; 'high values') and incubations with carbenoxolone as controls for fully inhibited enzyme and cortisol background (0% CTL; 'low values'). Each assay also contained a calibration curve with cortisol to transform the fluorescent data into cortisol concentrations. Percent inhibition of each compound was determined relative to the carbenoxolone signal.

In the following table are compiled the 11β-HSD 1 inhibitory activities of the compounds Example 167 to Example 196, Example 201, and Example 203-209 determined as described above, wherein 100% indicates no inhibition and a value of zero or below zero indicates complete inhibition.

TABLE OF BIOLOGICAL ASSAY RESULTS
FOR BIOLOGICAL TEST 3

| Example | Average % control inhibition at 100 nM |
|---|---|
| 167 | 43 |
| 168 | −32 |
| 169 | −19 |
| 170 | −8 |
| 171 | −14 |
| 172 | 1 |
| 173 | 31 |
| 174 | 6 |
| 175 | −4 |
| 176 | 15 |
| 177 | 23 |
| 178 | −19 |
| 179 | 27 |
| 180 | 11 |

-continued

TABLE OF BIOLOGICAL ASSAY RESULTS
FOR BIOLOGICAL TEST 3

| Example | Average % control inhibition at 100 nM |
|---|---|
| 181 | 60 |
| 182 | 2 |
| 183 | −5 |
| 184 | 51 |
| 185 | 30 |
| 186 | 3 |
| 187 | 9 |
| 188 | 45 |
| 189 | 42 |
| 190 | −15 |
| 191 | −2 |
| 192 | 22 |
| 193 | 11 |
| 194 | 17 |
| 195 | −2 |
| 196 | 18 |
| 201 | −1 |
| 203 | 37 |
| 204 | 23 |
| 205 | 12 |
| 206 | 18 |
| 207 | −8 |
| 208 | 24 |
| 209 | 18 |

BIOLOGICAL TEST EXAMPLE 4

The inhibition of a microsomal preparation of 11β-HSD1 in the presence of 50% human plasma by compounds of the invention was measured as follows. Microsomes from CHO cells overexpressing human 11β-HSD1 were diluted into reaction buffer consisting of 25 mM HEPES, pH 7.4, 50 mM KCl, 2.5 mM NaCl, 1 mM MgCl2, and 50% (v/v) human plasma (BioChemed). The assay began by dispensing 49 µl of microsome solution into 96-well polypropylene plates and adding 1 µl of the test compounds in DMSO, previously diluted in half-log increments (8 points) starting at 1.0 mM. The reaction was initiated with the addition of 50 µl substrate solution consisting of reaction buffer with 2 mM NADPH and 160 nM [$^3$-H]cortisone (1 Ci/mmol). The plates were incubated for 120 minutes at rt, and the reaction was quenched with the addition of 100 µl acetonitrile with 20 mM cortisone and 20 mM cortisol. After a ten minute incubation at rt, 100 µl of each well was filtered through a MultiScreen HTS, HV filter plate (Millipore) and diluted with 100 µl of reaction buffer without human plasma. [$^3$-H]cortisone and [$^3$-H]cortisol were separated by HPLC on a Zorbax SB-C8 column (4.6×250 mm, Agilent) with an isocratic elution at 25% acetonitrile in water with 0.01% trifluoroacetic acid, and radioactivity was quantified with an in-line β-RAM (IN/US Systems, Inc.).

BIOLOGICAL TEST EXAMPLE 5

Fraction Unbound in Human Plasma

Plasma protein binding of compounds was determined with Equilibrium Dialysis of spiked plasma against compound free dextrane buffer using a dialysis membrane with mass cutoff of 5000 Da. Compound concentrations in plasma and buffer after incubation were measured using HPLC/Mass spectrometry.

BIOLOGICAL TEST EXAMPLE 6

CYP3A4 Inhibition

The assay is based on a method published by Moody et al. (Xenobiotica 1999). The inhibition of cytochrome P450 3A4-isoenzyme catalysed N-demethylation of [N-methyl-14C]-Erythromycin by the test compound was assayed at 37° C. with human recombinant cytochrome P450 3A4. All assays were carried out on a robotic system in 96 well plates. The final incubation volume of 200 µl contains TRIS buffer (0.1 M), MgCl$_2$ (5 mM), recombinant protein (40 pmol/ml), Erythromycin (50 µM) and the test compound either at four different concentrations in duplicate (e.g. highest concentration 10-50 µM with subsequent serial 1:5 dilutions) or at a concentration of 10 µM in triplicate. Following a short pre-incubation period, reactions were started with the cofactor (NADPH, 1 mM) and stopped by addition of 50 µl aqueous trichloroacetic acid (10%; w/v). An aliquot of the incubate was transferred to 96 well solid phase extraction (SPE) plates and extracted on the cartridge. The resultant [$^{14}$C]-formaldehyde/formic acid was not retained on the cartridge and was therefore separated from the unmetabolized substrate by washing the SPE plates with water. An aliquot of the eluates was transferred into well plates suitable for liquid scintillation counting. The rate of formation of [$^{14}$C]-formaldehyde/formic acid in these incubations was compared to a control activity containing no test compound. If the compound was tested at four concentrations, experimental IC$_{50}$ values were calculated.

BIOLOGICAL TEST EXAMPLE 7

CYP2C9 Inhibition

Using a procedure similar to that described in Biological Test Example 6, the inhibition of cytochrome P450 2C9-isoenzyme catalysed O-demethylation of [O-methyl-$^{14}$C]-Naproxen by the test compound was assayed at 37° C. with human recombinant cytochrome P450 2C9. The experimental IC$_{50}$ was calculated based on % control at four different concentrations.

BIOLOGICAL TEST EXAMPLE 8

CYP2C19 Inhibition

Using a procedure similar to that described in Biological Test Example 6, the inhibition of cytochrome P450 2C19-isoenzyme catalysed N-demethylation of [N-methyl-$^{14}$C]-Diazepam by the test compound was assayed at 37° C. with human recombinant cytochrome P450 2C19. The experimental IC$_{50}$ was calculated based on % control at four different concentrations.

BIOLOGICAL TEST EXAMPLE 9

CYP2C9 Inhibition

The inhibition of recombinant CYP2C9 by compounds of the invention was measured using a commercial kit from Invitrogen (cat #2859). Supplied microsomes isolated from insect cells infected with a baculovirus engineered to express human CYP2C9 were diluted to 10 mM in reaction buffer (100 mM potassium phosphate buffer, pH 8.0) with an NADPH generation system (3.33 mM glucose-6-phosphate and 0.4 U/ml glucose-6-phosphate dehydrogenase). 89 µl of this dilution were dispensed to each well of a 96-well, black, polystyrene plate and mixed with 1 μl of test compound previously diluted in DMSO in half log increments starting at 3 mM. The assay was initiated by adding 10 μl of fluorogenic substrate n-octyloxymethylresorufin (OOMR, 20 μM.) with NADP (100 μM) diluted in reaction buffer. The plate was immediately placed in a Perkin Elmer Fusion plate reader. Reaction progress was monitored by measuring fluorescence every two minutes for a total of twenty minutes (530 nM excitation filter/605 nM emission filter).

TABLE OF BIOLOGICAL ASSAY RESULTS FOR BIOLOGICAL TESTS 1 AND 4

| EXAMPLE | Biological Test Example 1 IC$_{50}$ (nM) | Biological Test Example 4[a] IC$_{50}$ (nM) | Shift[b] | Biological Test Example 5 (%) |
|---|---|---|---|---|
| 1 | 0.7 | 7.3 | 10.4 | |
| 2 | 0.8 | 2.9 | 3.8 | |
| 3 | 1.0 | 7.9 | 8.0 | |
| 4 | 0.7 | 4.0 | 5.8 | |
| 5 Isomer 1 | 1.4 | 24.8 | 17.2 | |
| 5 Isomer 2 | 8.7 | 17.0 | 1.9 | |
| 6 | 1.0 | 8.6 | 8.4 | |
| 7 | 4.9 | 4.3 | 0.9 | |
| 8 | 2.8 | 11.2 | 4.0 | |
| 9 | 1.3 | 5.1 | 3.9 | |
| 10 | 2.5 | 7.5 | 3.1 | |
| 11 | 1.0 | 3.4 | 3.5 | |
| 12 | 96.6 | nt | | |
| 13 | 1.8 | 10.5 | 5.8 | |
| 14 | 0.9 | 4.5 | 5.0 | |
| 15 | 1.7 | 4.2 | 2.4 | |
| 16 | 0.8 | 5.5 | 6.9 | |
| 17 | 2.2 | 5.7 | 2.5 | |
| 18 | >100.0 | nt | | |
| 19 | 1.9 | 19.8 | 10.4 | |
| 20 | 1.7 | 8.1 | 4.7 | |
| 21 | 0.4 | 3.4 | 7.8 | |
| 22 | 2.8 | 18.1 | 6.6 | |
| 23 | 2.7 | 13.7 | 5.1 | |
| 24 | 0.8 | 4.4 | 5.2 | |
| 25 Isomer 1 | 14.8 | nt | | |
| 25 Isomer 2 | 6.5 | nt | | |
| 26 | 1.7 | 6.8 | 4.1 | |
| 27 | 1.2 | 4.7 | 3.8 | |
| 28 | 1.4 | 185.5 | 129.7 | |
| 29 | 12.2 | nt | | |
| 30 | 0.9 | 21.8 | 24.0 | |
| 31 | 4.8 | 9.3 | 1.9 | |
| 32 | 54.0 | nt | | |
| 33 | 305.2 | nt | | |
| 34 | 1.0 | 15.9 | 16.1 | |
| 35 | 1.0 | 2.8 | 2.9 | |
| 36 | 1.0 | 19.5 | 18.6 | |
| 37 | 2.5 | 6.1 | 2.5 | |
| 38 | 3.7 | 8.1 | 2.2 | |
| 39 | 5.2 | nt | | |
| 40 | 2.3 | 28.6 | 12.4 | |
| 41 | 1.9 | 11.0 | 5.8 | |
| 42 | 1.0 | 34.3 | 33.4 | |
| 43 | 8.6 | 315.5 | 36.5 | |
| 44 | 0.7 | 4.2 | 5.7 | |
| 45 | 3.0 | 13.5 | 4.6 | |
| 46 | 0.8 | nt | | |
| 47 | 2.6 | 21.4 | 8.3 | |
| 48 | 1.0 | 3.9 | 3.8 | |
| 49 | 0.5 | 7.8 | 15.8 | |
| 50 | 29.1 | nt | | |
| 51 | 1.5 | 60.7 | 40.6 | |
| 52 | 1.1 | 10.5 | 9.3 | 1.8 |
| 53 | 1.3 | 18.5 | 14.6 | |
| 54 | 1.0 | 39.4 | 38.4 | |
| 55 | 1.5 | 8.3 | 5.6 | |
| 56 | 0.7 | 5.5 | 8.0 | |
| 57 | 1.0 | 19.2 | 18.8 | |
| 58 | 0.8 | 7.2 | 9.0 | |
| 59 | 0.5 | 5.1 | 9.9 | |
| 60 | 1.6 | 20.8 | 13.1 | |
| 61 | 0.7 | 13.6 | 18.2 | |
| 62 | 0.5 | 22.6 | 44.2 | |
| 63 | 0.8 | 15.2 | 18.4 | |
| 64 | 0.8 | 6.2 | 8.2 | |
| 65 | 0.4 | 3.8 | 8.8 | |
| 66 | 1.3 | 9.7 | 7.4 | |
| 67 | 0.7 | 6.7 | 9.9 | |
| 68 | 85.1 | nt | | |
| 69 | 0.6 | 6.3 | 9.8 | |
| 70 | 99.6 | nt | | |
| 71 | 44.1 | nt | | |
| 72 | 43.5 | nt | | |
| 73 | 46.9 | nt | | |
| 74 | 1.4 | 4.7 | 3.5 | |
| 75 | 1.1 | 9.8 | 8.6 | |
| 76 | 0.8 | 6.9 | 8.8 | |
| 77 | 38.1 | 114.1 | 3.0 | |
| 78 | 1.8 | 19.8 | 11.2 | |
| 79 | 28.3 | nt | | |
| 80 | 1.0 | 5.5 | 5.4 | |
| 81 | 0.6 | nt | | |
| 82 | 1.8 | 25.2 | 14.1 | |
| 83 | 1.0 | 8.8 | 8.9 | |
| 84 | 3.5 | 12.4 | 3.5 | |
| 85 | 0.9 | 12.9 | 13.6 | |
| 86 | 0.6 | 6.4 | 11.1 | |
| 87 | 0.7 | 8.1 | 12.0 | |
| 88 | 1.7 | 9.9 | 6.0 | |
| 89 | 0.6 | 6.2 | 10.5 | |
| 90 | 0.5 | 13.5 | 25.5 | |
| 91 | 1.4 | 13.7 | 9.9 | |
| 92 | 0.5 | 12.7 | 23.7 | |
| 93 | 0.6 | 10.2 | 18.2 | |
| 94 | 0.5 | 5.0 | 11.0 | |
| 95 | 1.2 | 120.5 | 99.6 | |
| 96 | 0.7 | 5.6 | 7.9 | |
| 97 | 1.0 | 10.8 | 11.1 | |
| 98 | 1.4 | 6.3 | 4.5 | |
| 99 | 0.5 | 7.9 | 16.6 | |
| 100 | 1.2 | 6.0 | 4.8 | |
| 101 | 1.2 | 7.5 | 6.0 | |
| 102 | 3.6 | 63.0 | 17.3 | |
| 103 | 1.9 | 8.2 | 4.3 | |
| 104 | 9.2 | nt | | |
| 105 | 19.2 | nt | | |
| 106 | 22.7 | nt | | |
| 107 Isomer 1 | 3.2 | 86.4 | 26.9 | |
| 107 Isomer 2 | 3.2 | 269.4 | 83.8 | |
| 108 | 1.8 | 7.1 | 4.0 | |
| 109 | 2.9 | 31.9 | 11.0 | |
| 110 | 0.5 | 3.7 | 7.7 | |
| 111 | 0.8 | 7.2 | 8.9 | 2 |
| 112 | 0.5 | 8.1 | 15.2 | |
| 113 | 7.4 | 22.8 | 3.1 | |
| 114 | 0.9 | 3.9 | 4.5 | |
| 115 | 1.0 | 10.3 | 10.2 | |
| 116 | 0.7 | 3.7 | 5.1 | |
| 117 | 1.7 | 12.1 | 7.3 | |
| 118 | 19.2 | nt | | |
| 119 | 2.0 | 29.7 | 15.1 | |
| 120 | 6.7 | 24.2 | 3.6 | |
| 121 | 2.3 | 7.5 | 3.3 | |
| 122 | 2.5 | 6.5 | 2.6 | |
| 123 | 6.6 | 11.1 | 1.7 | |
| 124 | 5.6 | 14.5 | 2.6 | |
| 125 | 0.6 | 6.8 | 12.3 | |
| 126 | 1.5 | 13.3 | 8.7 | |
| 127 | 6.1 | 69.8 | 11.5 | |

TABLE OF BIOLOGICAL ASSAY RESULTS FOR BIOLOGICAL TESTS 1 AND 4

| EXAMPLE | Biological Test Example 1 IC$_{50}$ (nM) | Biological Test Example 4[a] IC$_{50}$ (nM) | Shift[b] | Biological Test Example 5 (%) |
|---|---|---|---|---|
| 128 | 1.1 | 8.5 | 7.8 | |
| 129 | 4.3 | 17.3 | 4.1 | |
| 130 | 2.5 | 21.6 | 8.8 | 1.9 |
| 131 | 2.2 | 5.1 | 2.3 | |
| 132 | 6.1 | 18.9 | 3.1 | |
| 133 | 1.3 | 10.2 | 7.8 | |
| 134 | 1.3 | 5.6 | 4.3 | 10.5 |
| 135 | 1.8 | 5.4 | 3.1 | |
| 136 | 0.8 | 5.7 | 7.3 | 0.3 |
| 137 | 2.2 | 10.7 | 4.8 | |
| 138 | 1.1 | 7.5 | 7.0 | 2 |
| 139 | 2.6 | 16.1 | 6.2 | |
| 140 | 1.1 | 6.8 | 6.4 | |
| 141 | 1.0 | 6.6 | 6.3 | |
| 142 | 2.6 | 8.1 | 3.1 | |
| 143 | 1.6 | 5.5 | 3.4 | |
| 144 | 1.2 | 12.0 | 9.8 | |
| 145 | 32.8 | nt | | |
| 146 | 17.4 | nt | | |
| 147 | 0.9 | 7.9 | 9.3 | |
| 148 | 0.7 | 4.8 | 7.3 | |
| 149 | 2.5 | 32.4 | 12.9 | 2.7 |
| 150 | 1.5 | 7.4 | 5.1 | |
| 151 | 1.0 | 9.2 | 9.4 | |
| 152 | 39.6 | nt | | |
| 153 | 1.7 | 9.2 | 5.4 | |
| 154 | 3.5 | 13.2 | 3.8 | |
| 155 | 2.1 | 6.4 | 3.0 | |
| 156 | 1.1 | 10.1 | 9.2 | |
| 157 | 2.9 | 27.4 | 9.6 | |
| 158 | 2.1 | 12.9 | 6.2 | |
| 159 | 3.3 | 7.3 | 2.2 | |
| 160 | 1.0 | 17.4 | 17.5 | |
| 161 | 1.1 | 3.9 | 3.7 | |
| 162 | 1.4 | 31.7 | 21.9 | |
| 163 | 1.6 | 5.9 | 3.8 | |
| 164 | 1.2 | 22.2 | 18.2 | |
| 165 | 2.4 | 42.5 | 17.4 | |
| 166 | 1.0 | 2.3 | 2.3 | |
| 167 | nt | nt | | |
| 168 | nt | nt | | |
| 172 | 3.3 | 10.6 | 3.2 | |
| 183 | 0.93 | | | |
| 186 | 0.90 | | | |
| 197 | 1.1 | 5.7 | 5.0 | |
| 198 | 1.0 | | | |
| 199 | 63.5 | nt | | |
| 200 | 0.96 | 18.3 | 19.1 | |
| 210 | 0.6 | | | |

[a]nt means not tested;
[b]Shift is the IC$_{50}$ determined in Biological Test Example 4 divided by the IC$_{50}$ determined in Biological Test Example 1.

TABLE OF BIOLOGICAL ASSAY RESULTS FOR BIOLOGICAL TESTS 6-9

| EXAMPLE | Biological Test Example 6 CYP3A4, IC$_{50}$ [µM] | Biological Test Example 7 CYP2C9, IC$_{50}$ [µM] | Biological Test Example 8 CYP2C19, IC$_{50}$ [µM] | Biological Test Example 9 CYP2C9 IC$_{50}$ [µM] |
|---|---|---|---|---|
| 1 | 16.7 | 12.9 | 10.1 | |
| 2 | | | | |
| 3 | 2.1 | 2.5 | 3.0 | |
| 4 | 19.6 | 19.8 | 24.2 | |
| 5 Isomer 1 | | | | |
| 5 Isomer 2 | | | | 0.6 |
| 6 | | | | |
| 7 | | | | 5.3 |
| 8 | | | | |
| 9 | 48.9 | >50.0 | 0.8 | |
| 10 | 34.9 | 21.2 | 14.5 | |
| 11 | 8.7 | >50.0 | 3.7 | |
| 12 | | | | 4.0 |
| 13 | >10.0 | >10.0 | >10.0 | |
| 14 | | | | 20.1 |
| 15 | >50.0 | >50.0 | 12.5 | |
| 16 | 24.9 | >50.0 | 6.1 | |
| 17 | 45.3 | 17.8 | 5.9 | |
| 18 | | | | |
| 19 | 27.1 | 31.7 | 10.3 | |
| 20 | 49.8 | 15.4 | 47.7 | |
| 21 | | | | |
| 22 | 5.2 | 4.5 | 3.6 | |
| 23 | | | | |
| 24 | | | | |
| 25 Isomer 1 | | | | |
| 25 Isomer 2 | | | | |
| 26 | | | | |
| 27 | | | | |
| 28 | | | | |
| 29 | | | | |
| 30 | | | | |
| 31 | | | | |
| 32 | | | | |
| 33 | | | | |
| 34 | | | | 5.1 |
| 35 | | | | 2.2 |
| 36 | | | | 5.2 |
| 37 | | | | 8.5 |
| 38 | | | | >30.0 |
| 39 | | | | |
| 40 | | | | 10.0 |
| 41 | | | | 20.5 |
| 42 | | | | |
| 43 | | | | |
| 44 | | | | 1.4 |
| 45 | | | | 9.0 |
| 46 | | | | |
| 47 | | | | 27.4 |
| 48 | | | | 5.4 |
| 49 | | | | 8.4 |
| 50 | | | | |
| 51 | | | | 0.7 |
| 52 | >50.0 | 17.9 | 37.9 | 9.6 |
| 53 | | | | 6.6 |
| 54 | | | | 0.4 |
| 55 | | | | 14.1 |
| 56 | | | | 6.1 |
| 57 | | | | |
| 58 | | | | 16.9 |
| 59 | | | | 10.9 |
| 60 | | | | |
| 61 | 29.2 | 23.0 | 40.0 | 9.9 |
| 62 | | | | 10.9 |
| 63 | | | | |
| 64 | | | | 4.7 |
| 65 | | | | 4.0 |
| 66 | | | | 5.3 |
| 67 | | | | 3.8 |
| 68 | | | | |
| 69 | | | | 2.3 |
| 70 | | | | |
| 71 | | | | |
| 72 | | | | |
| 73 | | | | |
| 74 | | | | 2.9 |
| 75 | 14.9 | 12.2 | 12.2 | 9.1 |

TABLE OF BIOLOGICAL ASSAY RESULTS FOR BIOLOGICAL TESTS 6-9

| EXAMPLE | Biological Test Example 6 CYP3A4, IC$_{50}$ [μM] | Biological Test Example 7 CYP2C9, IC$_{50}$ [μM] | Biological Test Example 8 CYP2C19, IC$_{50}$ [μM] | Biological Test Example 9 CYP2C9 IC$_{50}$ [μM] |
|---|---|---|---|---|
| 76 | 5.0 | 2.9 | 8.5 | 7.9 |
| 77 | | | | |
| 78 | 7.3 | 4.8 | 5.3 | 8.7 |
| 79 | | | | |
| 80 | 13.0 | 11.2 | 13.2 | 8.9 |
| 81 | | | | |
| 82 | | | | |
| 83 | | | | 3.9 |
| 84 | | | | |
| 85 | | | | |
| 86 | | | | |
| 87 | | | | |
| 88 | | | | 23.7 |
| 89 | | | | 13.3 |
| 90 | | | | |
| 91 | | | | 17.3 |
| 92 | | | | |
| 93 | 11.6 | 8.0 | 11.4 | 8.0 |
| 94 | | | | 4.5 |
| 95 | | | | 2.4 |
| 96 | | | | |
| 97 | 8.9 | 11.2 | 19.5 | 9.7 |
| 98 | 42.2 | 36.7 | 31.3 | >30.0 |
| 99 | | | | |
| 100 | | | | 4.5 |
| 101 | >50.0 | 9.9 | >50.0 | |
| 102 | | | | |
| 103 | | | | |
| 104 | | | | |
| 105 | | | | 2.5 |
| 106 | | | | 9.5 |
| 107 Isomer 1 | | | | 2.7 |
| 107 Isomer 2 | | | | 17.5 |
| 108 | | | | |
| 109 | | | | |
| 110 | | | | |
| 111 | 9.8 | >50.0 | >50.0 | 4.7 |
| 112 | | | | 6.1 |
| 113 | | | | 2.9 |
| 114 | | | | |
| 115 | | | | 4.4 |
| 116 | | | | 5.3 |
| 117 | | | | |
| 118 | | | | |
| 119 | | | | |
| 120 | | | | 4.7 |
| 121 | | | | 4.8 |
| 122 | | | | |
| 123 | | | | 9.1 |
| 124 | | | | |
| 125 | | | | 4.3 |
| 126 | | | | |
| 127 | | | | >30.0 |
| 128 | | | | 3.3 |
| 129 | | | | 28.3 |
| 130 | 11.8 | >50.0 | 3.0 | 9.7 |
| 131 | 5.6 | 14.0 | 2.6 | 11.2 |
| 132 | | | | 18.3 |
| 133 | | | | >30.0 |
| 134 | >50.0 | >50.0 | >50.0 | >30.0 |
| 135 | 22.8 | 44.4 | 35.8 | |
| 136 | 24.1 | 20.1 | 24.7 | 9.6 |
| 137 | | | | 18.4 |
| 138 | 12.7 | 22.2 | 24.2 | |
| 139 | >50.0 | 21.4 | 18.2 | 9.9 |
| 140 | | | | 20.6 |
| 141 | | | | >30.0 |
| 142 | | | | |
| 143 | >50.0 | >50.0 | >50.0 | |
| 144 | 11.9 | 10.2 | 9.6 | |
| 145 | | | | >30.0 |
| 146 | | | | 6.1 |
| 147 | | | | 4.6 |
| 148 | | | | 1.7 |
| 149 | >50.0 | >50.0 | >50.0 | 17.4 |
| 150 | 50.0 | 28.8 | 33.8 | |
| 151 | 50.0 | 32.6 | 32.3 | |
| 152 | | | | |
| 153 | | | | |
| 154 | | | | |
| 155 | >50.0 | 38.9 | >50.0 | |
| 156 | >50.0 | >50.0 | 47.6 | |
| 157 | | | | |
| 158 | >50.0 | >50.0 | >50.0 | |
| 159 | | | | |
| 160 | 4.5 | 2.3 | 1.7 | |
| 161 | >50.0 | 36.0 | 10.5 | |
| 162 | | | | |
| 163 | 15.9 | 6.9 | 10.9 | |
| 164 | | | | |
| 165 | | | | |
| 166 | 20.7 | 9.0 | 39.5 | |
| 167 | 46.7 | 29.5 | 26.1 | |
| 168 | 16.8 | 15.1 | 7.9 | |
| 169 | 28.4 | 45.2 | 5.9 | |
| 170 | 45.6 | 48.6 | 39.4 | |
| 171 | <0.4 | 9.2 | 0.8 | |
| 172 | >50.0 | 38.1 | 44.4 | |
| 173 | 25.1 | 27.2 | 33.6 | |
| 174 | 5.4 | 7.8 | 1.0 | |
| 175 | 9.7 | 29.8 | 1.8 | |
| 176 | 7.5 | 6.0 | 7.9 | |
| 177 | >50.0 | 8.8 | 17.7 | |
| 178 | >50.0 | 21.3 | >50.0 | |
| 179 | 21.1 | 10.7 | 17.0 | |
| 180 | 9.8 | 9.2 | 14.4 | |
| 181 | 7.8 | 5.6 | 8.2 | |
| 197 | | | | 14.3 |
| 182 | >50.0 | >50.0 | >50.0 | |
| 183 | >50.0 | 45.7 | 47.4 | |
| 184 | >50.0 | >50.0 | >50.0 | |
| 185 | 42.9 | 30.0 | 25.7 | |
| 186 | >50.0 | >50.0 | 48.6 | |
| 187 | >50.0 | 25.9 | >50.0 | |
| 188 | 42.4 | 21.2 | >50.0 | |
| 189 | >50.0 | >50.0 | >50.0 | |
| 190 | 33.7 | >50.0 | >50.0 | |
| 191 | 36.4 | >50.0 | >50.0 | |
| 192 | 11.2 | 10.4 | 15.5 | |
| 193 | 26.6 | 24.2 | 33.3 | |
| 194 | | | | |
| 195 | | | | |
| 196 | | | | |
| 198 | | | | |
| 199 | | | | |
| 200 | | | | |
| 201 | | | | |

TABLE OF BIOLOGICAL ASSAY RESULTS FOR COMPARATOR COMPOUNDS IN BIOLOGICAL TESTS 1, 4 AND 5

| Comparator Compound | Biological Test Example 1 IC$_{50}$ (nM) | Biological Test Example 4[a] IC$_{50}$ (nM) | Shift[b] | Biological Test Example 5 (%) |
|---|---|---|---|---|
| 1 | 0.77 | 11.97 | | 15.51 |
| 2 | 1.80 | 14.16 | | 7.88 |

TABLE OF BIOLOGICAL ASSAY RESULTS FOR COMPARATOR COMPOUNDS IN BIOLOGICAL TESTS 1, 4 AND 5

| Comparator Compound | Biological Test Example 1 $IC_{50}$ (nM) | Biological Test Example 4[a] $IC_{50}$ (nM) | Shift[b] | Biological Test Example 5 (%) |
|---|---|---|---|---|
| 3 | 0.75 | 17.74 | 23.63 | 0.3 |
| 4 | 1.44 | 15.24 | 10.57 | |
| 5 | 0.51 | 18.50 | 36.10 | |
| 6 | 1.48 | 37.58 | 25.39 | |
| 7 | 0.99 | 41.90 | 42.43 | |
| 8 | 0.72 | 17.85 | 24.74 | |
| 9 | 0.55 | 11.86 | 21.45 | 0.3 |
| 10 | 1.79 | 53.49 | 29.91 | |
| 11 | 0.55 | 13.40 | 24.59 | 0.7 |

TABLE OF BIOLOGICAL ASSAY RESULTS FOR COMPARATOR COMPOUNDS IN BIOLOGICAL TESTS 1, 4 AND 5

| Comparator Compound | Biological Test Example 1 $IC_{50}$ (nM) | Biological Test Example 4[a] $IC_{50}$ (nM) | Shift[b] | Biological Test Example 5 (%) |
|---|---|---|---|---|
| 12 | 1.08 | 19.54 | 18.12 | 0.4 |
| 13 | 0.76 | 6.32 | 8.30 | |
| 14 | 1.30 | 8.94 | 6.90 | |
| 15 | 0.79 | 8.94 | 11.32 | |

[a] nt means not tested;
[b] Shift is the $IC_{50}$ determined in Biological Test Example 4 divided by the $IC_{50}$ determined in Biological Test Example 1.

TABLE OF BIOLOGICAL ASSAY RESULTS FOR COMPARATOR COMPOUNDS IN BIOLOGICAL TESTS 6-9

| Comparator Compound | Biological Test Example 6 CYP3A4, $IC_{50}$ [µM] | Biological Test Example 7 CYP2C9, $IC_{50}$ [µM] | Biological Test Example 8 CYP2C19, $IC_{50}$ [µM] | Biological Test Example 9 CYP2C9 $IC_{50}$ [µM] |
|---|---|---|---|---|
| 1 | | | | 27.0 |
| 2 | | | | 1.4 |
| 3 | 7.4 | 4.1 | 5.7 | 4.9 |
| 4 | | | | 5.1 |
| 5 | 9.9 | 5.1 | 8.3 | 3.7 |
| 6 | 4.4 | 2.3 | 8.6 | 5.0 |
| 7 | | | | 4.0 |
| 8 | 5.3 | 2.4 | 5.6 | 3.0 |
| 9 | 7.0 | 3.1 | 9.3 | 2.5 |
| 10 | | | | 3.6 |
| 11 | 14.1 | 6.3 | 12.5 | 5.5 |
| 12 | 4.9 | 4.6 | 9.5 | 2.5 |
| 12 | 4.9 | 3.9 | 10.1 | |
| 13 | 4.4 | 5.6 | <0.4 | 7.3 |
| 14 | 19.7 | 25.9 | 6.4 | 24.6 |
| 15 | 3.1 | 7.7 | <0.4 | 9.5 |

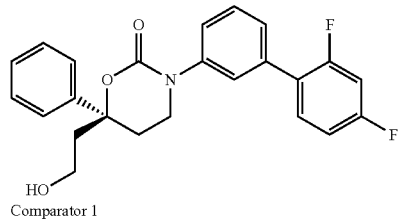

Comparator 1

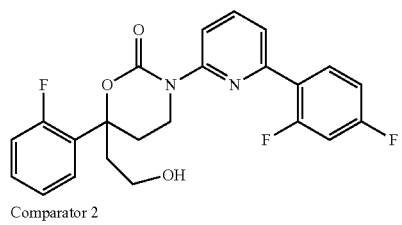

Comparator 2

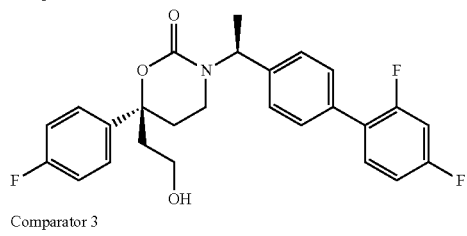

Comparator 3

-continued
TABLE OF BIOLOGICAL ASSAY RESULTS FOR COMPARATOR COMPOUNDS IN BIOLOGICAL TESTS 6-9
| Comparator Compound | Biological Test Example 6 CYP3A4, IC$_{50}$ [µM] | Biological Test Example 7 CYP2C9, IC$_{50}$ [µM] | Biological Test Example 8 CYP2C19, IC$_{50}$ [µM] | Biological Test Example 9 CYP2C9, IC$_{50}$ [µM] |
|---|---|---|---|---|
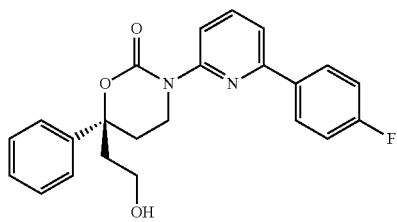 [SMILES: O=C1O[C@@](CCO)(c2ccccc2)CCN1c1cccc(-c2ccc(F)cc2)n1]
Comparator 4
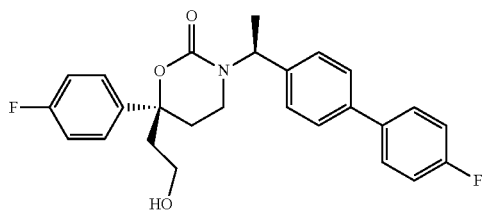 [SMILES: C[C@@H](c1ccc(-c2ccc(F)cc2)cc1)N1CC[C@](CCO)(c2ccc(F)cc2)OC1=O]
Comparator 5
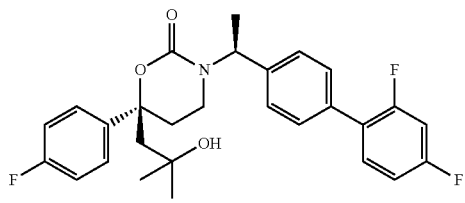 [SMILES: C[C@@H](c1ccc(-c2ccc(F)cc2F)cc1)N1CC[C@](CC(C)(C)O)(c2ccc(F)cc2)OC1=O]
Comparator 6
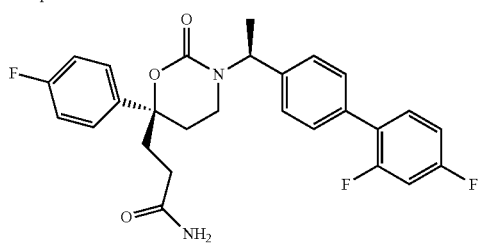
Comparator 7
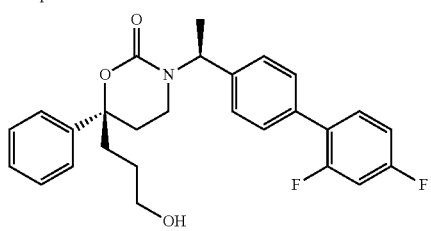
Comparator 8
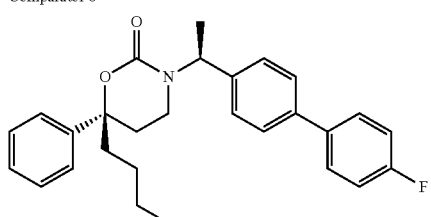
Comparator 9

TABLE OF BIOLOGICAL ASSAY RESULTS FOR COMPARATOR COMPOUNDS IN BIOLOGICAL TESTS 6-9

| Comparator Compound | Biological Test Example 6 CYP3A4, IC$_{50}$ [μM] | Biological Test Example 7 CYP2C9, IC$_{50}$ [μM] | Biological Test Example 8 CYP2C19, IC$_{50}$ [μM] | Biological Test Example 9 CYP2C9 IC$_{50}$ [μM] |
|---|---|---|---|---|

Comparator 10

Comparator 11

Comparator 12

Comparator 13

Comparator 14

Comparator 15

The compounds of the invention are useful for ameliorating or treating disorders or diseases in which decreasing the level of cortisol is effective in treating a disease state. Thus, the compounds of the invention can be used in the treatment or prevention of diabetes mellitus (e.g., type II diabetes), obesity, symptoms of metabolic syndrome, glucose intolerance, hyperglycemica, hypertension, hyperlipidemia, insulin resistance, cardiovascular disease, dyslipidemia, atherosclerosis, lipodystrophy, osteoporosis, glaucoma, Cushing's syndrome, Addison's Disease, visceral fat obesity associated with glucocorticoid therapy, depression, anxiety, Alzheimer's disease, dementia, cognitive decline (including age-related cognitive decline), polycystic ovarian syndrome, infertility and hypergonadism. The compounds of the invention can be used as therapeutic agents for pseudo Cushing's Syndrome associated with alcoholic liver disease. In addition, the compounds modulate the function of B and T cells of the immune system and can therefore be used to treat diseases such as tuberculosis, leprosy and psoriasis. They can also be used to promote wound healing, particularly in diabetic patients.

Additional diseases or disorders that are related to 11β-HSD1 activity include those selected from the group consisting of lipid disorders, hypretriglyceridemia, hypercholesterolemia, low HDL levels, high LDL levels, vascular restenosis, pancreatitis, abdominal obesity, neurodegenerative disease, retinopathy, nephropathy, neuropathy, diabetes, coronary heart disease, stroke, peripheral vascular disease, Cushing's syndrome, hyperinsulinemia, viral diseases, and Syndrome X. A further disease related to 11β-HSD1 activity is pseudo Cushing's Syndrome associated with alcoholic liver disease.

A pharmaceutical composition of the invention may, alternatively or in addition to an 11β-HSD1 inhibitor of the invention, comprise a pharmaceutically acceptable salt of a an 11β-HSD1 inhibitor of the invention and one or more pharmaceutically acceptable carriers therefore. Alternatively, a pharmaceutical composition of the invention may comprise a compound of an 11β-HSD1 inhibitor of the invention or a pharmaceutical salt thereof as the only pharmaceutically active agent in the pharmaceutical composition. The disclosed 11β-HSD1 inhibitors can be used alone or in a combination therapy with one or more additional agents for the treatment of diabetes, dyslipidemia, cardiovascular disease, hypertension, obesity, cancer or glaucoma.

The compositions of the invention are 11β-HSD1 inhibitors. Said compositions contain compounds having a mean inhibition constant ($IC_{50}$) against 11β-HSD1 of below about 1,000 nM; preferably below about 100 nM; more preferably below about 50 nM; even more preferably below about 5 nM; and most preferably below about 1 nM.

The invention includes a therapeutic method for treating or ameliorating an 11β-HSD1 mediated disorder in a subject in need thereof comprising administering to a subject in need thereof an effective amount of an 11β-HSD1 inhibitor of the invention, or an enantiomer, diastereomer, or pharmaceutically acceptable salt thereof or composition thereof. As used herein, "treating" or "treatment" includes both therapeutic and prophylactic treatment. Therapeutic treatment includes reducing the symptoms associated with a disease or condition and/or increasing the longevity of a subject with the disease or condition. Prophylactic treatment includes delaying the onset of a disease or condition in a subject at risk of developing the disease or condition or reducing the likelihood that a subject will then develop the disease or condition in a subject that is at risk for developing the disease or condition.

An embodiment of the invention includes administering an 11β-HSD1 inhibiting compound of the invention or composition thereof in a combination therapy with one or more additional agents for the treatment of diabetes, dyslipidemia, cardiovascular disease, hypertension, obesity, cancer or glaucoma. Agents for the treatment of diabetes include insulins, such as Humulin® (Eli Lilly), Lantus® (Sanofi Aventis), Novolin (Novo Nordisk), and Exubera® (Pfizer); PPAR gamma agonists, such as Avandia® (rosiglitizone maleate, GSK) and Actos® (pioglitazone hydrochloride, Takeda/Eli Lilly); sulfonylureas, such as Amaryl® (glimepiride, Sanofi Aventis), Diabeta® (glyburide, Sanofi Aventis), Micronase®/Glynase® (glyburide, Pfizer), and Glucotrol®/Glucotrol XL® and (glipizide, Pfizer); meglitinides, such as Prandin®/NovoNorm® (repaglinide, Novo Nordisk), Starlix® (nateglinide, Novartis), and Glufast® (mitiglinide, Takeda); biguanides, such as Glucophase®/Glucophase XR® (metformin HCl, Bristol Myers Squibb) and Glumetza (metformin HCl, Depomed); thiazolidinediones; amylin analogs, GLP-1 analogs; DPP-IV inhibitors; PTB-1B inhibitors; protein kinase inhibitors (including AMP-activated protein kinase inhibitors); glucagon antagonists, glycogen synthase kinase-3 beta inhibitors; glucose-6-phoshatase inhibitors; glycogen phosphorylase inhibitors; sodium glucose co-transporter inhibitors, and alpha-glucosidase inhibitors, such as Precose®/Glucobay®/Prandase®/Glucor® (acarbose, Bayer) and Glyset® (miglitol, Pfizer). Agents for the treatment of dyslipidemia and cardiovascular disease include statins, fibrates, and ezetimbe. Agents for the treatment of hypertension include alpha-blockers, beta-blockers, calcium channel blockers, diuretics, angiotensin converting enzyme (ACE) inhibitors, dual ACE and neutral endopeptidase (NEP) inhibitors, angiotensin-receptor blockers (ARBs), aldosterone synthase inhibitors, aldosterone-receptor antagonists, or endothelin receptor antagonist. Agents for the treatment of obesity include orlistat, phentermine, sibutramine and rimonabant.

An embodiment of the invention includes administering an 11β-HSD1 inhibiting compound of the invention or composition thereof in a combination therapy with one or more other 11β-HSD1 inhibitors, or with combination products, such as Avandamet® (metformin HCl and rosiglitazone maleate, GSK); Avandaryl® (glimepiride and rosiglitazone maleate, GSK); Metaglip® (glipizide and metformin HCl, Bristol Myers Squibb); and Glucovance® (glyburide and metformin HCl, Bristol Myers Squibb).

The compounds of the present invention can be prepared and administered in a wide variety of oral and parenteral dosage forms. Thus, the compounds of the present invention can be administered by injection, that is, intravenously, intramuscularly, intracutaneously, subcutaneously, intraduodenally, or intraperitoneally. Additionally, the compounds of the present invention can be administered intranasally or transdermally. It will be obvious to those skilled in the art that the following dosage forms may comprise as the active ingredient, either compounds or a corresponding pharmaceutically acceptable salt of a compound of the present invention.

For preparing pharmaceutical compositions from the compounds of the present invention, pharmaceutically acceptable carriers can either be solid or liquid. Solid form preparations include powders, tablets, pills, capsules, cachets, suppositories, and dispersible granules. A solid carrier can be one or more substances which may also act as diluents, flavoring agents, solubilizers, lubricants, suspending agents, binders, preservatives, tablet disintegrating agents, or an encapsulating material. In powders, the carrier is a finely divided solid which is in a mixture with the finely divided active ingredient.

In tablets, the active ingredient is mixed with the carrier having the necessary binding properties in suitable proportions and compacted in the shape and size desired.

The powders and tablets preferably contain from about one to about seventy percent of the active ingredient. Suitable carriers are magnesium carbonate, magnesium stearate, talc, sugar, lactose, pectin, dextrin, starch, gelatin, tragacanth, methylcellulose, sodium caboxymethylcellulose, a low-melting wax, cocoa butter, and the like. Tablets, powders, cachets, lozenges, fast-melt strips, capsules and pills can be used as solid dosage forms containing the active ingredient suitable for oral administration.

For preparing suppositories, a low-melting wax, such as a mixture of fatty acid glycerides or cocoa butter, is first-melted and the active ingredient is dispersed homogeneously therein, as by stirring. The molten homogeneous mixture is then poured into convenient sized molds, allowed to cool, and thereby to solidify.

Liquid form preparations include solutions, suspensions, retention enemas, and emulsions, for example, water or water propylene glycol solutions. For parenteral injection, liquid preparations can be formulated in solution in aqueous polyethylene glycol solution.

Aqueous solutions suitable for oral administration can be prepared by dissolving the active ingredient in water and adding suitable colorants, flavors, stabilizing, and thickening agents as desired. Aqueous suspensions for oral administration can be prepared by dispersing the finely divided active ingredient in water with viscous material, such as natural or synthetic gums, resins, methylcellulose, sodium carboxymethylcellulose, and other well-known suspending agents.

The pharmaceutical composition is preferably in unit dosage form. In such form, the composition is subdivided into unit doses containing appropriate quantities of the active ingredient. The unit dosage form can be a packaged preparation, the package containing discrete quantities of, for example, tablets, powders, and capsules in vials or ampules. Also, the unit dosage form can be a tablet, cachet, capsule, or lozenge itself, or it can be the appropriate amount of any of these in packaged form.

The quantity of active ingredient in a unit dose preparation may be varied or adjusted from about 0.1 mg to about 1000.0 mg, preferably from about 0.1 mg to about 100 mg. The dosages, however, may be varied depending upon the requirements of the patient, the severity of the condition being treated, and the compound being employed. Determination of the proper dosage for a particular situation is within the skill in the art. Also, the pharmaceutical composition may contain, if desired, other compatible therapeutic agents.

In therapeutic treatment or as a method-of-use as an inhibitor of 11β-HSD1 or an inhibitor in the production of cortisol in the cell, the active ingredient is preferably administered orally in a solid dosage form as disclosed above in an amount of about 0.1 mg to about 100 mg per daily dose where the dose is administered once or more than once daily.

All publications, patents and patent applications mentioned in this specification are herein incorporated by reference to the same extent as if each individual publication or patent application were specifically and individually designated as having been incorporated by reference. It is understood that the examples and embodiments described herein are for illustrative purposes only, and it will be appreciated that the invention is susceptible to modification, variation and change without departing from the proper scope or fair meaning of the appended claims.

While this invention has been particularly shown and described with references to example embodiments thereof, it will be understood by those skilled in the art that various changes in form and details may be made therein without departing from the scope of the invention encompassed by the appended claims.

What is claimed is:

1. A compound of Formula (Iq$^5$)

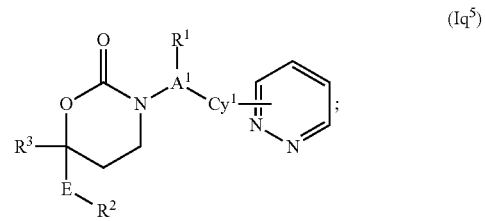

wherein:

$R^1$ is (a) absent or (b) is selected from $(C_1-C_6)$alkyl, $(C_2-C_6)$alkenyl, $(C_2-C_6)$alkynyl, $(C_1-C_3)$alkoxy$(C_1-C_3)$alkoxy, and $(C_1-C_3)$alkoxy$(C_1-C_3)$alkyl, each of which is optionally substituted with up to four groups independently selected from fluorine, cyano, oxo, $R^4$, $R^4O$—, $(R^4)_2N$—, $R^4O_2C$—, $R^4S$, $R^4S(\!=\!O)$—, $R^4S(\!=\!O)_2$—, $R^4C(\!=\!O)NR^4$—, $(R^4)_2NC(\!=\!O)$—, $(R^4)_2NC(\!=\!O)O$—, $(R^4)_2NC(\!=\!O)NR^4$—, $R^4OC(\!=\!O)NR^4$—, $(R^4)_2NC(\!=\!NCN)NR^4$—, $(R^4O)_2P(\!=\!O)O$—, $(R^4O)_2P(\!=\!O)NR^4$—, $R^4OS(\!=\!O)_2NR^4$—, $(R^4)_2NS(\!=\!O)_2O$—, $(R^4)_2NS(\!=\!O)_2NR^4$—, $R^4S(\!=\!O)_2NR^4$—, $R^4S(\!=\!O)_2NHC(\!=\!O)$—, $R^4S(\!=\!O)_2NHC(\!=\!O)O$—, $R^4S(\!=\!O)_2NHC(\!=\!O)NR^4$—, $R^4OS(\!=\!O)_2NHC(\!=\!O)$—, $R^4OS(\!=\!O)_2NHC(\!=\!O)O$—, $R^4OS(\!=\!O)_2NHC(\!=\!O)NR^4$—, $(R^4)_2NS(\!=\!O)_2NHC(\!=\!O)$—, $(R^4)_2NS(\!=\!O)_2NHC(\!=\!O)O$—, $(R^4)_2NS(\!=\!O)_2NHC(\!=\!O)NR^4$—, $R^4C(\!=\!O)NHS(\!=\!O)_2$—, $R^4C(\!=\!O)NHS(\!=\!O)_2O$—, $R^4C(\!=\!O)NHS(\!=\!O)_2NR^4$—, $R^4OC(\!=\!O)NHS(\!=\!O)_2$—, $R^4OC(\!=\!O)NHS(\!=\!O)_2O$—, $R^4OC(\!=\!O)NHS(\!=\!O)_2NR^4$—, $(R^4)_2NC(\!=\!O)NHS(\!=\!O)_2$—, $(R^4)_2NC(\!=\!O)NHS(\!=\!O)_2O$—, $(R^4)_2NC(\!=\!O)NHS(\!=\!O)_2NR^4$—, heterocyclyl, heteroaryl, arylamino and heteroarylamino;

$A^1$ is (a) a bond, or (b) $(C_1-C_3)$alkylene or $CH_2CH_2O$, wherein the oxygen is attached to $Cy^1$, or $CH_2C(\!=\!O)$, wherein the carbonyl carbon is attached to $Cy^1$;

$Cy^1$ is aryl, heteroaryl, monocyclic cycloalkyl or monocyclic heterocyclyl, each of which is optionally substituted with 1 to 4 groups independently selected from fluorine, chlorine, bromine, iodine, cyano, nitro, amino, hydroxy, carboxy, $(C_1-C_6)$alkyl, hydroxy$(C_1-C_6)$alkyl, $(C_3-C_6)$cycloalkyl, hydroxy$(C_3-C_6)$cycloalkyl, $(C_4-C_7)$cycloalkylalkyl, $(C_2-C_6)$alkenyl, halo$(C_2-C_6)$alkenyl, hydroxy$(C_2-C_6)$alkenyl, $(C_2-C_6)$alkynyl, $(C_3-C_6)$cycloalkyl$(C_2-C_4)$alkynyl, halo$(C_1-C_6)$alkyl, halo$(C_3-C_6)$cycloalkyl, halo$(C_4-C_7)$cycloalkylalkyl, $(C_1-C_6)$alkoxy, $(C_3-C_6)$cycloalkoxy, $(C_4-C_7)$cycloalkylalkoxy, halo$(C_1-C_6)$alkoxy, halo$(C_3-C_6)$cycloalkoxy, halo$(C_4-C_7)$cycloalkylalkoxy, $(C_1-C_6)$alkylthio, $(C_3-C_6)$cycloalkythio, $(C_4-C_7)$cycloalkylalkylthio, halo$(C_1-C_6)$alkylthio, halo$(C_3-C_6)$cycloalkythio, halo$(C_4-C_7)$cycloalkylalkylthio, $(C_1-C_6)$alkanesulfinyl, $(C_3-C_6)$cycloalkanesulfinyl, $(C_4-C_7)$cycloalkylalkanesulfinyl, halo$(C_1-C_6)$alkanesulfinyl, halo$(C_3-C_6)$cycloalkanesulfinyl, halo$(C_4-C_7)$cycloalkylalkanesulfinyl, $(C_1-C_6)$alkanesulfonyl, $(C_3-C_6)$cycloalkanesulfonyl, $(C_4-C_7)$cycloalkylalkanesulfonyl, halo$(C_1-C_6)$alkanesulfonyl, halo$(C_3-C_6)$cycloalkanesulfonyl, halo$(C_4-C_7)$cycloalkylalkanesulfonyl, (C$_1$-C$_6$)alkylamino, di(C$_1$-C$_6$)alkylamino, (C$_1$-C$_6$)alkoxy(C$_1$-C$_6$)alkoxy, halo(C$_1$-C$_6$)alkoxy(C$_1$-C$_6$)alkoxy, (C$_1$-C$_6$)alkoxycarbonyl, H$_2$NCO, H$_2$NSO$_2$, (C$_1$-C$_6$)alkylaminocarbonyl, di(C$_1$-C$_6$)alkylaminocarbonyl, (C$_1$-C$_3$)alkoxy(C$_1$-C$_3$)alkylaminocarbonyl, heterocyclylcarbonyl, (C$_1$-C$_6$)alkylaminosulfonyl, di(C$_1$-C$_6$)alkylaminosulfonyl, heterocyclylsulfonyl, (C$_1$-C$_6$)alkylcarbonylamino, (C$_1$-C$_6$)alkylcarbonylamino(C$_1$-C$_6$)alkyl, (C$_1$-C$_6$)alkylsulfonylamino, (C$_1$-C$_6$)alkylsulfonylamino(C$_1$-C$_6$)alkyl, (C$_1$-C$_6$)alkoxycarbonyl(C$_1$-C$_6$)alkoxy, (C$_1$-C$_6$)alkoxy(C$_1$-C$_6$)alkyl, halo(C$_1$-C$_6$)alkoxy(C$_1$-C$_6$)alkyl, hydroxy(C$_1$-C$_6$)alkoxy, heteroaryloxo, amino(C$_1$-C$_6$)alkyl, (C$_1$-C$_6$)alkylamino(C$_1$-C$_6$)alkyl, di(C$_1$-C$_6$)alkylamino(C$_1$-C$_6$)alkyl amino(C$_2$-C$_6$)alkoxy, (C$_1$-C$_6$)alkylamino(C$_2$-C$_6$)alkoxy, di(C$_1$-C$_6$)alkylamino(C$_2$-C$_6$)alkoxy, (C$_1$-C$_6$)alkylcarbonyl, (C$_3$-C$_6$)cycloalkylcarbonyl, (C$_3$-C$_6$)cycloalkylaminocarbonyl, {(C$_3$-C$_6$)cycloalkyl}{(C$_1$-C$_6$)alkyl}aminocarbonyl, di(C$_3$-C$_6$)cycloalkylaminocarbonyl, (C$_3$-C$_6$)cycloalkylaminosulfonyl, {(C$_3$-C$_6$)cycloalkyl}{(C$_1$-C$_6$)alkyl}aminosulfonyl, di(C$_3$-C$_6$)cycloalkylaminosulfonyl, cyano(C$_1$-C$_6$)alkyl, aminocarbonyl(C$_1$-C$_6$)alkyl, (C$_1$-C$_6$)alkylaminocarbonyl(C$_1$-C$_6$)alkyl, di(C$_1$-C$_6$)alkylaminocarbonyl(C$_1$-C$_6$)alkyl, (C$_3$-C$_6$)cycloalkylaminocarbonyl(C$_1$-C$_6$)alkyl, {(C$_3$-C$_6$)cycloalkyl}{(C$_1$-C$_6$)alkyl}aminocarbonyl(C$_1$-C$_6$)alkyl and di(C$_3$-C$_6$)cycloalkylaminocarbonyl(C$_1$-C$_6$)alkyl;

the pyridazine ring in Formula Iq$^5$ is optionally substituted with 1 to 4 groups independently selected from fluorine, chlorine, bromine, iodine, cyano, nitro, amino, hydroxy, carboxy, (C$_1$-C$_6$)alkyl, hydroxy(C$_1$-C$_6$)alkyl, (C$_3$-C$_6$)cycloalkyl, hydroxy(C$_3$-C$_6$)cycloalkyl, (C$_4$-C$_7$)cycloalkylalkyl, (C$_2$-C$_6$)alkenyl, halo(C$_2$-C$_6$)alkenyl, hydroxy(C$_2$-C$_6$)alkenyl, (C$_2$-C$_6$)alkynyl, (C$_3$-C$_6$)cycloalkyl(C$_2$-C$_4$)alkynyl, halo(C$_1$-C$_6$)alkyl, halo(C$_3$-C$_6$)cycloalkyl, halo(C$_4$-C$_7$)cycloalkylalkyl, (C$_1$-C$_6$)alkoxy, (C$_3$-C$_6$)cycloalkoxy, (C$_4$-C$_7$)cycloalkylalkoxy, halo(C$_1$-C$_6$)alkoxy, halo(C$_3$-C$_6$)cycloalkoxy, halo(C$_4$-C$_7$)cycloalkylalkoxy, (C$_1$-C$_6$)alkylthio, (C$_3$-C$_6$)cycloalkythio, (C$_4$-C$_7$)cycloalkylalkylthio, halo(C$_1$-C$_6$)alkylthio, halo(C$_3$-C$_6$)cycloalkythio, halo(C$_4$-C$_7$)cycloalkylalkylthio, (C$_1$-C$_6$)alkanesulfinyl, (C$_3$-C$_6$)cycloalkanesulfinyl, (C$_4$-C$_7$)cycloalkylalkanesulfinyl, halo(C$_1$-C$_6$)alkanesulfinyl, halo(C$_3$-C$_6$)cycloalkanesulfinyl, halo(C$_4$-C$_7$)cycloalkylalkanesulfinyl, (C$_1$-C$_6$)alkanesulfonyl, (C$_3$-C$_6$)cycloalkanesulfonyl, (C$_4$-C$_7$)cycloalkyl-alkanesulfonyl, halo(C$_1$-C$_6$)alkanesulfonyl, halo(C$_3$-C$_6$)cycloalkanesulfonyl, halo(C$_4$-C$_7$)cycloalkyl-alkanesulfonyl, (C$_1$-C$_6$)alkylamino, di(C$_1$-C$_6$)alkylamino, (C$_1$-C$_6$)alkoxy(C$_1$-C$_6$)alkoxy, halo(C$_1$-C$_6$)alkoxy(C$_1$-C$_6$)alkoxy, (C$_1$-C$_6$)alkoxycarbonyl, H$_2$NCO, H$_2$NSO$_2$, (C$_1$-C$_6$)alkylaminocarbonyl, di(C$_1$-C$_6$)alkylaminocarbonyl, (C$_1$-C$_3$)alkoxy(C$_1$-C$_3$)alkylaminocarbonyl, heterocyclylcarbonyl, (C$_1$-C$_6$)alkylaminosulfonyl, di(C$_1$-C$_6$)alkylaminosulfonyl, heterocyclylsulfonyl, (C$_1$-C$_6$)alkylcarbonylamino, (C$_1$-C$_6$)alkylcarbonylamino(C$_1$-C$_6$)alkyl, (C$_1$-C$_6$)alkylsulfonylamino, (C$_1$-C$_6$)alkylsulfonylamino(C$_1$-C$_6$)alkyl, (C$_1$-C$_6$)alkoxycarbonyl(C$_1$-C$_6$)alkoxy, (C$_1$-C$_6$)alkoxy(C$_1$-C$_6$)alkyl, halo(C$_1$-C$_6$)alkoxy(C$_1$-C$_6$)alkyl, hydroxy(C$_1$-C$_6$)alkoxy, heteroaryl, oxo, amino(C$_1$-C$_6$)alkyl, (C$_1$-C$_6$)alkylamino(C$_1$-C$_6$)alkyl, di(C$_1$-C$_6$)alkylamino(C$_1$-C$_6$)alkyl amino(C$_2$-C$_6$)alkoxy, (C$_1$-C$_6$)alkylamino(C$_2$-C$_6$)alkoxy, di(C$_1$-C$_6$)alkylamino(C$_2$-C$_6$)alkoxy, (C$_1$-C$_6$)alkylcarbonyl, (C$_3$-C$_6$)cycloalkylcarbonyl, (C$_3$-C$_6$)cycloalkylaminocarbonyl, {(C$_3$-C$_6$)cycloalkyl}{(C$_1$-C$_6$)alkyl}aminocarbonyl, di(C$_3$-C$_6$)cycloalkylaminocarbonyl, (C$_3$-C$_6$)cycloalkylaminosulfonyl, {(C$_3$-C$_6$)cycloalkyl}{(C$_1$-C$_6$)alkyl}aminosulfonyl, di(C$_3$-C$_6$)cycloalkylaminosulfonyl, cyano(C$_1$-C$_6$)alkyl, aminocarbonyl(C$_1$-C$_6$)alkyl, (C$_1$-C$_6$)alkylaminocarbonyl(C$_1$-C$_6$)alkyl, di(C$_1$-C$_6$)alkylaminocarbonyl(C$_1$-C$_6$)alkyl, (C$_3$-C$_6$)cycloalkylaminocarbonyl(C$_1$-C$_6$)alkyl, {(C$_3$-C$_6$)cycloalkyl}{(C$_1$-C$_6$)alkyl}aminocarbonyl(C$_1$-C$_6$)alkyl and di(C$_3$-C$_6$)cycloalkylaminocarbonyl(C$_1$-C$_6$)alkyl;

E is (a) a bond or (b) (C$_1$-C$_3$)alkylene or (C$_1$-C$_2$)alkylenyloxy, wherein the O is attached to R$^2$, each of which is optionally substituted with 1 to 4 groups independently selected from methyl, ethyl, trifluoromethyl and oxo;

R$^2$ is (C$_1$-C$_6$)alkyl, aryl, heteroaryl, cycloalkyl or heterocyclyl, each of which is optionally substituted with up to 4 groups independently selected from fluorine, chlorine, bromine, iodine, cyano, nitro, amino, hydroxy, carboxy, (C$_1$-C$_6$)alkyl, hydroxy(C$_1$-C$_6$)alkyl, (C$_3$-C$_6$)cycloalkyl, hydroxy(C$_3$-C$_6$)cycloalkyl, (C$_4$-C$_7$)cycloalkylalkyl, (C$_2$-C$_6$)alkenyl, halo(C$_2$-C$_6$)alkenyl, hydroxy(C$_2$-C$_6$)alkenyl, (C$_2$-C$_6$)alkynyl, (C$_3$-C$_6$)cycloalkyl(C$_2$-C$_4$)alkynyl, halo(C$_1$-C$_6$)alkyl, halo(C$_3$-C$_6$)cycloalkyl, halo(C$_4$-C$_7$)cycloalkylalkyl, (C$_1$-C$_6$)alkoxy, (C$_3$-C$_6$)cycloalkoxy, (C$_4$-C$_7$)cycloalkylalkoxy, halo(C$_1$-C$_6$)alkoxy, halo(C$_3$-C$_6$)cycloalkoxy, halo(C$_4$-C$_7$)cycloalkylalkoxy, (C$_1$-C$_6$)alkylthio, (C$_3$-C$_6$)cycloalkythio, (C$_4$-C$_7$)cycloalkylalkylthio, halo(C$_1$-C$_6$)alkylthio, halo(C$_3$-C$_6$)cycloalkythio, halo(C$_4$-C$_7$)cycloalkylalkylthio, (C$_1$-C$_6$)alkanesulfinyl, (C$_3$-C$_6$)cycloalkanesulfinyl, (C$_4$-C$_7$)cycloalkylalkanesulfinyl, halo(C$_1$-C$_6$)alkanesulfinyl, halo(C$_3$-C$_6$)cycloalkanesulfinyl, halo(C$_4$-C$_7$)cycloalkylalkanesulfinyl, (C$_1$-C$_6$)alkanesulfonyl, (C$_3$-C$_6$)cycloalkanesulfonyl, (C$_4$-C$_7$)cycloalkylalkanesulfonyl, halo(C$_1$-C$_6$)alkanesulfonyl, halo(C$_3$-C$_6$)cycloalkanesulfonyl, halo(C$_4$-C$_7$)cycloalkylalkanesulfonyl, (C$_1$-C$_6$)alkylamino, di(C$_1$-C$_6$)alkylamino, (C$_1$-C$_6$)alkoxy(C$_1$-C$_6$)alkoxy, halo(C$_1$-C$_6$)alkoxy(C$_1$-C$_6$)alkoxy, (C$_1$-C$_6$)alkoxycarbonyl, H$_2$NCO, H$_2$NSO$_2$, (C$_1$-C$_6$)alkylaminocarbonyl, di(C$_1$-C$_6$)alkylaminocarbonyl, (C$_1$-C$_3$)alkoxy(C$_1$-C$_3$)alkylaminocarbonyl, heterocyclylcarbonyl, (C$_1$-C$_6$)alkylaminosulfonyl, di(C$_1$-C$_6$)alkylaminosulfonyl, heterocyclylsulfonyl, (C$_1$-C$_6$)alkylcarbonylamino, (C$_1$-C$_6$)alkylcarbonylamino(C$_1$-C$_6$)alkyl, (C$_1$-C$_6$)alkylsulfonylamino, (C$_1$-C$_6$)alkylsulfonylamino(C$_1$-C$_6$)alkyl, (C$_1$-C$_6$)alkoxycarbonyl(C$_1$-C$_6$)alkoxy, (C$_1$-C$_6$)alkoxy(C$_1$-C$_6$)alkyl, halo(C$_1$-C$_6$)alkoxy(C$_1$-C$_6$)alkyl, hydroxy(C$_1$-C$_6$)alkoxy, heteroaryl, oxo, amino(C$_1$-C$_6$)alkyl, (C$_1$-C$_6$)alkylamino(C$_1$-C$_6$)alkyl, di(C$_1$-C$_6$)alkylamino(C$_1$-C$_6$)alkyl amino(C$_2$-C$_6$)alkoxy, (C$_1$-C$_6$)alkylamino(C$_2$-C$_6$)alkoxy, di(C$_1$-C$_6$)alkylamino(C$_2$-C$_6$)alkoxy, (C$_1$-C$_6$)alkylcarbonyl, (C$_3$-C$_6$)cycloalkylcarbonyl, (C$_3$-C$_6$)cycloalkylaminocarbonyl, {(C$_3$-C$_6$)cycloalkyl}{(C$_1$-C$_6$)alkyl}aminocarbonyl, di(C$_3$-C$_6$)cycloalkylaminocarbonyl, (C$_3$-C$_6$)cycloalkylaminosulfonyl, {(C$_3$-C$_6$)cycloalkyl}{(C$_1$-C$_6$)alkyl}aminosulfonyl, di(C$_3$-C$_6$)cycloalkylaminosulfonyl, cyano(C$_1$-C$_6$)alkyl, aminocarbonyl(C$_1$-C$_6$)alkyl, (C$_1$-C$_6$)alkylaminocarbonyl(C$_1$-C$_6$)alkyl, di(C$_1$-C$_6$)alkylaminocarbonyl(C$_1$-C$_6$)alkyl, (C$_3$-C$_6$)cycloalkylaminocarbonyl(C$_1$-C$_6$)alkyl, {(C$_3$-C$_6$)cycloalkyl}{(C$_1$-C$_6$)alkyl}aminocarbonyl(C$_1$-C$_6$)alkyl and di(C$_3$-C$_6$)cycloalkylaminocarbonyl(C$_1$-C$_6$)alkyl;

R$^3$ is selected from (C$_1$-C$_6$)alkyl, (C$_2$-C$_6$)alkenyl, (C$_2$-C$_6$)alkynyl, (C$_3$-C$_5$)cycloalkyl(C$_1$-C$_4$)alkyl, (C$_1$-C$_3$)alkoxy ($C_1$-$C_3$)alkoxy, and ($C_1$-$C_3$)alkoxy($C_1$-$C_3$)alkyl, each of which is optionally substituted with up to four groups independently selected from fluorine, cyano, oxo, $R^4$, $R^4O$—, $(R^4)_2N$—, $R^4O_2C$—, $R^4C(=O)O$—, $R^4S$, $R^4S(=O)$—, $R^4S(=O)_2$—, $R^4C(=O)NR^4$—, $(R^4)_2NC(=O)$—, $(R^4)_2NC(=O)O$—, $(R^4)_2NC(=O)NR^4$—, $R^4OC(=O)NR^4$—, $(R^4)_2NC(=NCN)NR^4$—, $(R^4O)_2P(=O)O$—, $(R^4O)_2P(=O)NR^4$—, $R^4OS(=O)_2NR^4$—, $(R^4)_2NS(=O)_2O$—, $(R^4)_2NS(=O)_2NR^4$—, $R^4S(=O)_2NR^4$—, $R^4S(=O)_2NHC(=O)$—, $R^4S(=O)_2NHC(=O)O$—, $R^4S(=O)_2NHC(=O)NR^4$—, $R^4OS(=O)_2NHC(=O)$—, $R^4OS(=O)_2NHC(=O)O$—, $R^4OS(=O)_2NHC(=O)NR^4$—, $(R^4)_2NS(=O)_2NHC(=O)$—, $(R^4)_2NS(=O)_2NHC(=O)O$—, $(R^4)_2NS(=O)_2NHC(=O)NR^4$—, $R^4C(=O)NHS(=O)_2$—, $R^4C(=O)NHS(=O)_2O$—, $R^4C(=O)NHS(=O)_2NR^4$—, $R^4OC(=O)NHS(=O)_2$—, $R^4OC(=O)NHS(=O)_2O$—, $R^4OC(=O)NHS(=O)_2NR^4$—, $(R^4)_2NC(=O)NHS(=O)_2$—, $(R^4)_2NC(=O)NHS(=O)_2O$—, $(R^4)_2NC(=O)NHS(=O)_2NR^4$—, spirocycloalkyl; heterocyclyl (optionally substituted with alkyl, haloalkyl, halogen or oxo), heteroaryl (optionally substituted with alkyl, haloalkyl, alkoxy, alkylthio, alkylsulfonyl, halogen, trifluoromethyl, dialkylamino, nitro, cyano, $CO_2H$, $CONH_2$, N-monoalkyl-substituted amido, N,N-dialkyl-substituted amido, or oxo), arylamino (optionally substituted with alkyl, alkoxy, alkylthio, alkylsulfonyl, halogen, trifluoromethyl, dialkylamino, nitro, cyano, $CO_2H$, $CONH_2$, N-monoalkyl-substituted amido and N,N-dialkyl-substituted amido) and heteroarylamino (optionally substituted with alkyl, haloalkyl, alkoxy, alkylthio, alkylsulfonyl, halogen, trifluoromethyl, dialkylamino, nitro, cyano, $CO_2H$, $CONH_2$, N-monoalkyl-substituted amido, N,N-dialkyl-substituted amido, or oxo); and $R^4$ is independently selected from H, ($C_1$-$C_6$)alkyl, halo($C_1$-$C_6$)alkyl, amino($C_1$-$C_6$)alkyl, ($C_1$-$C_6$)alkylamino($C_1$-$C_6$)alkyl, di($C_1$-$C_6$)alkylamino($C_1$-$C_6$)alkyl, hydroxy($C_1$-$C_6$)alkyl and ($C_1$-$C_6$)alkoxy($C_1$-$C_6$)alkyl;

or a pharmaceutically acceptable salt, enantiomer or diastereomer thereof.

2. The compound of claim 1, wherein the compound is of Formula ($Is^5$):

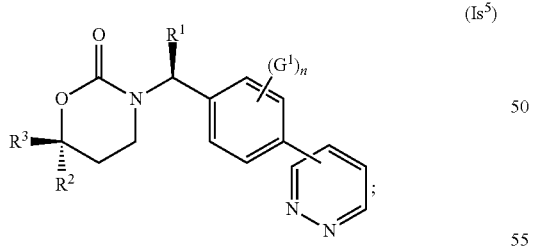

($Is^5$)

or a pharmaceutically acceptable salt thereof; wherein:

n is 0, 1, 2 or 3; and $G^1$ is fluorine, chlorine, bromine, iodine, cyano, nitro, amino, hydroxy, carboxy, ($C_1$-$C_6$)alkyl, hydroxy($C_1$-$C_6$)alkyl, ($C_3$-$C_6$)cycloalkyl, hydroxy($C_3$-$C_6$)cycloalkyl, ($C_4$-$C_7$)cycloalkylalkyl, ($C_2$-$C_6$)alkenyl, halo($C_2$-$C_6$)alkenyl, hydroxy($C_2$-$C_6$)alkenyl, ($C_2$-$C_6$)alkynyl, ($C_3$-$C_6$)cycloalkyl($C_2$-$C_4$)alkynyl, halo($C_1$-$C_6$)alkyl, halo($C_3$-$C_6$)cycloalkyl, halo($C_4$-$C_7$)cycloalkylalkyl, ($C_1$-$C_6$)alkoxy, ($C_3$-$C_6$)cycloalkoxy, ($C_4$-$C_7$)cycloalkylalkoxy, halo($C_1$-$C_6$)alkoxy, halo($C_3$-$C_6$)cycloalkoxy, halo($C_4$-$C_7$)cycloalkylalkoxy, ($C_1$-$C_6$)alkylthio, ($C_3$-$C_6$)cycloalkythio, ($C_4$-$C_7$)cycloalkylthio, halo($C_1$-$C_6$)alkylthio, halo($C_3$-$C_6$)cycloalkythio, halo($C_4$-$C_7$)cycloalkylalkylthio, ($C_1$-$C_6$)alkanesulfinyl, ($C_3$-$C_6$)cycloalkanesulfinyl, ($C_4$-$C_7$)cycloalkylalkanesulfinyl, halo($C_1$-$C_6$)alkanesulfinyl, halo($C_3$-$C_6$)cycloalkanesulfinyl, halo($C_4$-$C_7$)cycloalkylalkanesulfinyl, ($C_1$-$C_6$)alkanesulfonyl, ($C_3$-$C_6$)cycloalkanesulfonyl, ($C_4$-$C_7$)cycloalkyl-alkanesulfonyl, halo($C_1$-$C_6$)alkanesulfonyl, halo($C_3$-$C_6$)cycloalkanesulfonyl, halo($C_4$-$C_7$)cycloalkyl-alkanesulfonyl, ($C_1$-$C_6$)alkylamino, di($C_1$-$C_6$)alkylamino, ($C_1$-$C_6$)alkoxy($C_1$-$C_6$)alkoxy, halo($C_1$-$C_6$)alkoxy($C_1$-$C_6$)alkoxy, ($C_1$-$C_6$)alkoxycarbonyl, $H_2NCO$, $H_2NSO_2$, ($C_1$-$C_6$)alkylaminocarbonyl, di($C_1$-$C_6$)alkylaminocarbonyl, ($C_1$-$C_3$)alkoxy($C_1$-$C_3$)alkylaminocarbonyl, heterocyclylcarbonyl, ($C_1$-$C_6$)alkylaminosulfonyl, di($C_1$-$C_6$)alkylaminosulfonyl, heterocyclylsulfonyl, ($C_1$-$C_6$)alkylcarbonylamino, ($C_1$-$C_6$)alkylcarbonylamino($C_1$-$C_6$)alkyl, ($C_1$-$C_6$)alkylsulfonylamino, ($C_1$-$C_6$)alkylsulfonylamino($C_1$-$C_6$)alkyl, ($C_1$-$C_6$)alkoxycarbonyl($C_1$-$C_6$)alkoxy, ($C_1$-$C_6$)alkoxy($C_1$-$C_6$)alkyl, halo($C_1$-$C_6$)alkoxy($C_1$-$C_6$)alkyl, hydroxy($C_1$-$C_6$)alkoxy, heteroaryl, amino($C_1$-$C_6$)alkyl, ($C_1$-$C_6$)alkylamino($C_1$-$C_6$)alkyl, di($C_1$-$C_6$)alkylamino($C_1$-$C_6$)alkyl amino($C_2$-$C_6$)alkoxy, ($C_1$-$C_6$)alkylamino($C_2$-$C_6$)alkoxy, di($C_1$-$C_6$)alkylamino($C_2$-$C_6$)alkoxy, ($C_1$-$C_6$)alkylcarbonyl, ($C_3$-$C_6$)cycloalkylcarbonyl, ($C_3$-$C_6$)cycloalkylaminocarbonyl, {($C_3$-$C_6$)cycloalkyl}{($C_1$-$C_6$)alkyl}aminocarbonyl, di($C_3$-$C_6$)cycloalkylaminocarbonyl, ($C_3$-$C_6$)cycloalkylaminosulfonyl, {($C_3$-$C_6$)cycloalkyl}{($C_1$-$C_6$)alkyl}aminosulfonyl, di($C_3$-$C_6$)cycloalkylaminosulfonyl, cyano($C_1$-$C_6$)alkyl, aminocarbonyl($C_1$-$C_6$)alkyl, ($C_1$-$C_6$)alkylaminocarbonyl($C_1$-$C_6$)alkyl, di($C_1$-$C_6$)alkylaminocarbonyl($C_1$-$C_6$)alkyl, ($C_3$-$C_6$)cycloalkylaminocarbonyl($C_1$-$C_6$)alkyl, {($C_3$-$C_6$)cycloalkyl}{($C_1$-$C_6$)alkyl}aminocarbonyl($C_1$-$C_6$)alkyl or di($C_3$-$C_6$)cycloalkylaminocarbonyl($C_1$-$C_6$)alkyl.

3. The compound of claim 2, wherein:

n is 0, 1, 2 or 3;

$G^1$ is ($C_1$-$C_4$)alkyl, ($C_1$-$C_4$)alkoxy, ($C_1$-$C_4$)haloalkyl, ($C_1$-$C_4$)haloalkoxy, halogen, cyano or nitro;

the ring carbon atoms in the pyridazine ring in Formula $Is^5$ are independently optionally substituted with fluorine, chlorine, cyano, amino, ($C_1$-$C_4$)alkyl, ($C_3$-$C_4$)cycloalkyl, ($C_3$-$C_4$)cycloalkyl($C_1$-$C_2$)alkyl, halo($C_1$-$C_4$)alkyl, ($C_1$-$C_4$)alkoxy, ($C_1$-$C_4$)haloalkoxy, $CONH_2$, ($C_1$-$C_4$)alkylaminocarbonyl, di($C_1$-$C_4$)alkylaminocarbonyl, ($C_3$-$C_4$)cycloalkylaminocarbonyl, {($C_1$-$C_4$)alkyl}{($C_3$-$C_4$)cycloalkyl}aminocarbonyl or ($C_1$-$C_4$)alkylcarbonylamino;

$R^1$ is methyl or ethyl; and $R^2$ is phenyl optionally substituted with 1, 2 or 3 substituents selected from halo, cyano, $CONH_2$, ($C_1$-$C_4$)alkyl, ($C_1$-$C_4$)haloalkyl and $SO_2Me$; and $R^3$ is $MeSO_2NHCH_2CH_2CH_2$, $H_2NC(=O)CH_2CH_2$, $H_2NC(=O)CMe_2CH_2$, 3-hydroxypropyl, 3-hydroxy-3-methylbutyl, 2-hydroxyethyl, 2-hydroxy-2-methylpropyl and 2-cyano-2-methylpropyl.

4. The compound of claim 1, wherein the compound is selected from one of the following Formulas:

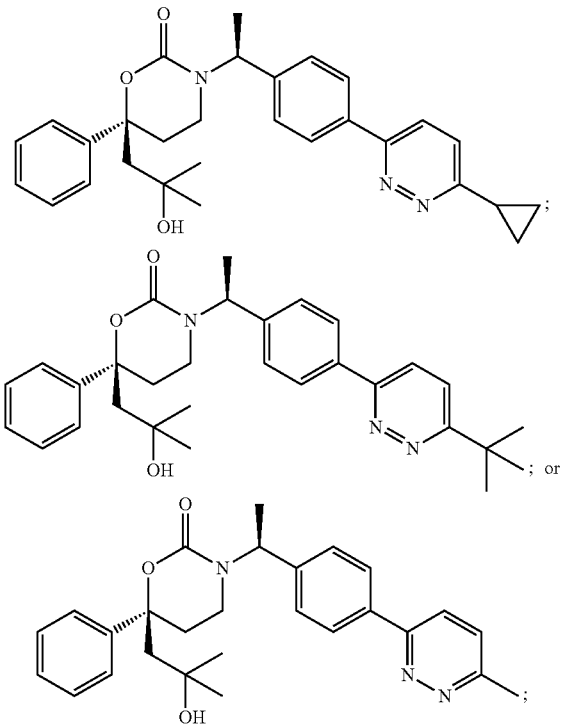

or a pharmaceutically acceptable salt thereof.

5. A method of treating a subject with a disease or disorder selected from diabetes mellitus, obesity, metabolic syndrome, prothrombotic state, proinflammatory state, glucose intolerance, hyperglycemia, hypertension, hyperlipidemia, insulin resistance, dyslipidemia, atherosclerosis, lipodystrophy, osteoporosis, glaucoma, Cushing's syndrome, Addison's disease, visceral fat obesity associated with glucocorticoid therapy, depression, anxiety, dementia, cognitive decline, polycystic ovarian syndrome, hypergonadism, tuberculosis, leprosy, psoriasis, to promote wound healing, hypertriglyceridemia, hypercholesterolemia, low HDL levels, high LDL levels, vascular restenosis, pancreatitis, abdominal obesity, coronary heart disease, peripheral vascular disease, hyperinsulinemia, viral diseases, and Syndrome X, comprising the step of administering to the subject an effective amount of the compound in claim 1.

6. A pharmaceutical composition comprising: i) a pharmaceutically acceptable carrier or diluent; and ii) the compound in claim 1; or a pharmaceutically acceptable salt, enantiomer or diastereomer thereof.

7. The compound of claim 1, wherein the compound is of the formula:
(S)-3-((S)-1-(4-(5-chloro-6-methylpyridazin-3-yl)phenyl)ethyl)-6-(2-hydroxy-2-methylpropyl)-6-phenyl-1, 3-oxazinan-2-one;
(S)-3-((S)-1-(4-(6-chloro-3-methylpyridazin-4-yl)phenyl)ethyl)-6-(2-hydroxy-2-methylpropyl)-6-phenyl-1, 3-oxazinan-2-one;
(S)-6-(2-hydroxy-2-methylpropyl)-3-((S)-1-(4-(6-(2-hydroxypropan-2-yl)pyridazin-3-yl)phenyl)ethyl)-6-phenyl-1,3-oxazinan-2-one;
N-tert-butyl-6-(4-((S)-1-((S)-6-(2-hydroxy-2-methylpropyl)-2-oxo-6-phenyl-1,3-oxazinan-3-yl)ethyl)phenyl)pyridazine-3-carboxamide;
N-tert-butyl-6-(4-((S)-1-((R)-6-(2-cyano-2-methylpropyl)-2-oxo-6-phenyl-1,3-oxazinan-3-yl)ethyl)phenyl)pyridazine-3-carboxamide;
N-cyclopropyl-6-(4-((S)-1-((S)-6-(2-hydroxy-2-methylpropyl)-2-oxo-6-phenyl-1,3-oxazinan-3-yl)ethyl)phenyl)pyridazine-3-carboxamide;
6-(4-((S)-1-((R)-6-(2-cyano-2-methylpropyl)-2-oxo-6-phenyl-1,3-oxazinan-3-yl)ethyl)phenyl)-N-cyclopropylpyridazine-3-carboxamide;
(R)-6-(2-(5-methyl-1,3,4-oxadiazol-2-yl)ethyl)-3-((S)-1-(4-(6-methylpyridazin-3-yl)phenyl)ethyl)-6-phenyl-1, 3-oxazinan-2-one;
(R)-6-(4-fluorophenyl)-6-(3-hydroxypropyl)-3-((S)-1-(4-(pyridazin-3-yl)phenyl)ethyl)-1,3-oxazinan-2-one;
(R)-6-(4-fluorophenyl)-6-(3-hydroxypropyl)-3-((S)-1-(4-(6-methylpyridazin-3-yl)phenyl)ethyl)-1,3-oxazinan-2-one;
(S)-6-(4-fluorophenyl)-6-(2-hydroxy-2-methylpropyl)-3-((S)-1-(4-(6-methylpyridazin-3-yl)phenyl)ethyl)-1,3-oxazinan-2-one;
2,2-dimethyl-3-((R)-3-((S)-1-(4-(6-methylpyridazin-3-yl)phenyl)ethyl)-2-oxo-6-phenyl-1,3-oxazinan-6-yl)propanenitrile;
(R)-6-(methoxymethyl)-3-((S)-1-(4-(6-methylpyridazin-3-yl)phenyl)ethyl)-6-phenyl-1,3-oxazinan-2-one;
6-(4-{(S)-1-[(S)-6-(2-Hydroxy-2-methyl-propyl)-2-oxo-6-phenyl-[1,3]oxazinan-3-yl]-ethyl}-phenyl)-pyridazine-3-carboxylic acid dimethylamide;
6-(4-{(S)-1-[(S)-6-(2-Hydroxy-2-methyl-propyl)-2-oxo-6-phenyl-[1,3]oxazinan-3-yl]-ethyl}-phenyl)-pyridazine-3-carboxylic acid;
6-(4-{(S)-1-[(S)-6-(2-Hydroxy-2-methyl-propyl)-2-oxo-6-phenyl-[1,3]oxazinan-3-yl]-ethyl}-phenyl)-pyridazine-3-carboxylic acid methylamide; or
6-(4-{(S)-1-[(S)-6-(2-Hydroxy-2-methyl-propyl)-2-oxo-6-phenyl-[1,3]oxazinan-3-yl]-ethyl}-phenyl)-pyridazine-3-carboxylic acid amide;
or a pharmaceutically acceptable salt thereof.

* * * * *

UNITED STATES PATENT AND TRADEMARK OFFICE
CERTIFICATE OF CORRECTION

PATENT NO. : 8,569,292 B2  Page 1 of 1
APPLICATION NO. : 12/990306
DATED : October 29, 2013
INVENTOR(S) : Claremon et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 251 days.

Signed and Sealed this
Twenty-second Day of September, 2015

Michelle K. Lee
*Director of the United States Patent and Trademark Office*